US010928403B2

(12) United States Patent
Anderberg et al.

(10) Patent No.: US 10,928,403 B2
(45) Date of Patent: Feb. 23, 2021

(54) METHODS AND COMPOSITIONS FOR DIAGNOSIS AND PROGNOSIS OF RENAL INJURY AND RENAL FAILURE

(71) Applicant: ASTUTE MEDICAL, INC., San Diego, CA (US)

(72) Inventors: Joseph Anderberg, Encinitas, CA (US); Jeff Gray, Solana Beach, CA (US); Paul McPherson, Encinitas, CA (US); Kevin Nakamura, Cardiff By The Sea, CA (US); James Patrick Kampf, San Diego, CA (US)

(73) Assignee: Astute Medical, Inc., San Diego, CA (US)

( * ) Notice: Subject to any disclaimer, the term of this patent is extended or adjusted under 35 U.S.C. 154(b) by 0 days.

(21) Appl. No.: 16/237,479

(22) Filed: Dec. 31, 2018

(65) Prior Publication Data

US 2019/0265253 A1 Aug. 29, 2019

Related U.S. Application Data

(63) Continuation of application No. 15/602,031, filed on May 22, 2017, now abandoned, which is a continuation of application No. 13/806,761, filed as application No. PCT/US2011/001125 on Jun. 23, 2011, now abandoned.

(60) Provisional application No. 61/364,305, filed on Jul. 14, 2010, provisional application No. 61/364,296, filed on Jul. 14, 2010, provisional application No. 61/357,965, filed on Jun. 23, 2010, provisional application No. 61/357,956, filed on Jun. 23, 2010, provisional application No. 61/357,966, filed on Jun. 23, 2010.

(51) Int. Cl.
*G01N 33/68* (2006.01)
*G01N 33/74* (2006.01)

(52) U.S. Cl.
CPC ......... *G01N 33/6893* (2013.01); *G01N 33/74* (2013.01); *G01N 2800/347* (2013.01); *G01N 2800/60* (2013.01)

(58) Field of Classification Search
CPC combination set(s) only.
See application file for complete search history.

(56) References Cited

U.S. PATENT DOCUMENTS

| | | | |
|---|---|---|---|
| 6,218,122 B1 | 4/2001 | Friend et al. | |
| 6,664,385 B1 | 12/2003 | Sanicola-Nadel et al. | |
| 6,784,154 B2 | 8/2004 | Westenfelder | |
| 6,861,404 B1 | 3/2005 | Cohen et al. | |
| 6,941,172 B2 | 9/2005 | Nachum | |
| 7,138,230 B2 | 11/2006 | Hu et al. | |
| 7,141,382 B1 | 11/2006 | Parikh et al. | |
| 7,235,358 B2 | 6/2007 | Wohlgemuth et al. | |
| 7,608,413 B1 | 10/2009 | Joseloff et al. | |
| 7,662,578 B2 | 2/2010 | Devarajan | |
| 7,981,684 B2 | 7/2011 | Levin et al. | |
| 7,998,744 B2 | 8/2011 | Stevenson et al. | |
| 8,008,008 B2 | 8/2011 | Parr et al. | |
| 8,071,293 B2 | 12/2011 | High et al. | |
| 8,080,394 B2 | 12/2011 | Levy et al. | |
| 8,241,861 B1 | 8/2012 | Heinecke et al. | |
| 2003/0003588 A1 | 1/2003 | Comper | |
| 2004/0053309 A1 | 3/2004 | Holt et al. | |
| 2004/0106155 A1 | 6/2004 | Comper | |
| 2004/0219603 A1 | 11/2004 | Devarajan et al. | |

(Continued)

FOREIGN PATENT DOCUMENTS

| | | |
|---|---|---|
| CN | 1791797 | 6/2006 |
| CN | 101358976 | 2/2009 |

(Continued)

OTHER PUBLICATIONS

Uliniski et al. Pediatric Nephrology, 2000; 14(7):589-97 (Year: 2000).*
Powell et al. Journal of Clinical Endocrinology and Metabolism, 1999; 84(2):596-601 (Year: 1999).*
Bohe et al. Kidney International, 1998; 54:1070-1082 (Year: 1998).*
Bohe et al.IGF-I binding proteins, IGF-I binding protein mRNA and IGF-I receptor mRNA in rats with acute renal failure given IGF-I. Kidney International, 1998; 54:1070-1082 (Year: 1998).*
"C-reactive protein," MedlinePlus Medical Encyclopedia. National Institutes of Health/US National Library of Medicine, Feb. 11, 2013. Web. Jul. 31, 2015. http://www.nlm.nih.gov/medlineplus/ency/article/003356.htm.

(Continued)

*Primary Examiner* — Vanessa L. Ford
*Assistant Examiner* — Sandra E Dillahunt
(74) *Attorney, Agent, or Firm* — Womble Bond Dickinson (US) LLP

(57) ABSTRACT

The present invention relates to methods and compositions for monitoring, diagnosis, prognosis, and determination of treatment regimens in subjects suffering from or suspected of having a renal injury. In particular, the invention relates to using a one or more assays configured to detect a kidney injury marker selected from the group consisting of Tumor necrosis factor receptor superfamily member 8, Alpha-Fetoprotein, Thyroxine-binding globulin, Prostate-specific antigen (free form), Apolipoprotein A, Apolipoprotein E, Thyrotropin subunit beta, Platelet-derived growth factor B/B dimer, C-C motif chemokine 7, C-C motif chemokine 26, Complement C4-B, Corticotropin, Interferon alpha-2, Interleukin-4 receptor alpha chain, Insulin-like growth factor-binding protein 4, Insulin-like growth factor-binding protein 5, Interleukin 21, Interleukin 23 alpha subunit, Interleukin-28A, Interleukin-33, Lutropin subunit beta, Matrix Metalloproteinase-1, Neural cell adhesion molecule 1, Pigment epithelium-derived factor, Vascular endothelial growth factor receptor 2, Vascular endothelial growth factor receptor 3, and IgG4 as diagnostic and prognostic biomarkers in renal injuries.

19 Claims, No Drawings

Specification includes a Sequence Listing.

(56) References Cited

U.S. PATENT DOCUMENTS

| | | |
|---|---|---|
| 2005/0002934 A1 | 1/2005 | Reed |
| 2005/0048033 A1 | 3/2005 | Fraser et al. |
| 2005/0112688 A1 | 5/2005 | Hu et al. |
| 2005/0137481 A1 | 6/2005 | Sheard et al. |
| 2005/0148029 A1 | 7/2005 | Buechler et al. |
| 2005/0158801 A1 | 7/2005 | Hu et al. |
| 2005/0256075 A1 | 11/2005 | Alitalo et al. |
| 2005/0272101 A1 | 12/2005 | Devarajan et al. |
| 2006/0003327 A1 | 1/2006 | Achiron et al. |
| 2006/0057066 A1 | 3/2006 | Natsoulis et al. |
| 2006/0088823 A1 | 4/2006 | Haab et al. |
| 2006/0204951 A1 | 9/2006 | Folkman et al. |
| 2006/0223077 A1 | 10/2006 | Ni et al. |
| 2006/0240437 A1 | 10/2006 | Krolewski et al. |
| 2006/0246485 A1 | 11/2006 | Sarwal et al. |
| 2007/0031905 A1 | 2/2007 | Shariat |
| 2007/0087387 A1 | 4/2007 | Devarajan |
| 2007/0093969 A1 | 4/2007 | Mendrick et al. |
| 2007/0105142 A1 | 5/2007 | Wilhelm |
| 2007/0112327 A1 | 5/2007 | Yun et al. |
| 2007/0154897 A1 | 7/2007 | Yen et al. |
| 2007/0248989 A1 | 10/2007 | Devarajan |
| 2007/0249002 A1 | 10/2007 | Hu et al. |
| 2008/0014644 A1 | 1/2008 | Barasch et al. |
| 2008/0038192 A1 | 2/2008 | Gervais |
| 2008/0038269 A1 | 2/2008 | Susan |
| 2008/0090304 A1 | 4/2008 | Barasch et al. |
| 2008/0133141 A1 | 6/2008 | Frost |
| 2008/0153092 A1 | 6/2008 | Kienle et al. |
| 2008/0206794 A1 | 8/2008 | Hu et al. |
| 2008/0254483 A1 | 10/2008 | Darbouret et al. |
| 2008/0254485 A1 | 10/2008 | Valkirs et al. |
| 2009/0022730 A1 | 1/2009 | Raulf et al. |
| 2009/0047689 A1 | 2/2009 | Kolman et al. |
| 2009/0081713 A1 | 3/2009 | Klein et al. |
| 2009/0088409 A1 | 4/2009 | Charlton |
| 2009/0090856 A1 | 4/2009 | Grant et al. |
| 2009/0148539 A1 | 6/2009 | Elias et al. |
| 2009/0176656 A1 | 7/2009 | Halloran |
| 2009/0197287 A1 | 8/2009 | Hu et al. |
| 2009/0203588 A1 | 8/2009 | Willman et al. |
| 2009/0220526 A1 | 9/2009 | Hamid |
| 2009/0258002 A1 | 10/2009 | Barrett et al. |
| 2009/0298073 A1 | 12/2009 | Gerhold et al. |
| 2009/0298106 A1 | 12/2009 | Hooper |
| 2010/0022627 A1 | 1/2010 | Scherer |
| 2010/0081148 A1 | 4/2010 | Singbartl et al. |
| 2010/0190164 A1 | 7/2010 | Tammen et al. |
| 2010/0240078 A1 | 9/2010 | Lee et al. |
| 2010/0267041 A1 | 10/2010 | Shuber et al. |
| 2011/0065608 A1 | 3/2011 | Labrie et al. |
| 2011/0104726 A1 | 5/2011 | Valkirs et al. |
| 2011/0174062 A1 | 7/2011 | Anderberg et al. |
| 2011/0195429 A1 | 8/2011 | Anderberg et al. |
| 2011/0201038 A1 | 8/2011 | Anderberg et al. |
| 2011/0207161 A1 | 8/2011 | Anderberg et al. |
| 2012/0190044 A1 | 7/2012 | Anderberg et al. |
| 2012/0190051 A1 | 7/2012 | Anderberg et al. |
| 2013/0035290 A1 | 2/2013 | Elias et al. |

FOREIGN PATENT DOCUMENTS

| | | |
|---|---|---|
| CN | 102539745 | 7/2012 |
| EP | 0828159 | 3/1998 |
| EP | 1905846 | 4/2008 |
| EP | 2261660 | 12/2010 |
| EP | 2480882 | 8/2012 |
| EP | 2513649 | 10/2012 |
| JP | 2008-537875 | 10/2008 |
| JP | 2012-508382 | 4/2012 |
| JP | 2012-510058 | 4/2012 |
| RU | 2180965 | 3/2002 |
| SU | 1429031 | 10/1988 |
| WO | WO 1998/055508 | 12/1998 |
| WO | WO 2003/054004 | 7/2003 |
| WO | WO 2003/075016 | 9/2003 |
| WO | WO 2004/005934 | 1/2004 |
| WO | WO 2005/087264 | 9/2005 |
| WO | WO 2006/044779 | 4/2006 |
| WO | WO 2006/083986 | 8/2006 |
| WO | WO 2007/013919 | 2/2007 |
| WO | WO 2007/041623 | 4/2007 |
| WO | WO 2008/060607 | 5/2008 |
| WO | WO 2008/084331 | 7/2008 |
| WO | WO 2008/104804 | 9/2008 |
| WO | WO 2008/116867 | 10/2008 |
| WO | WO 2008/122670 | 10/2008 |
| WO | WO 2008/154238 | 12/2008 |
| WO | WO 2009/038742 | 3/2009 |
| WO | WO 2010/025424 | 3/2010 |
| WO | WO 2010/025434 | 3/2010 |
| WO | WO 2010/048346 | 4/2010 |
| WO | WO 2010/048347 | 4/2010 |
| WO | WO 2010/054389 | 5/2010 |
| WO | WO 2010/059996 | 5/2010 |
| WO | WO 2010/091236 | 8/2010 |
| WO | WO 2010/111746 | 10/2010 |
| WO | WO 2010/128158 | 11/2010 |
| WO | WO 2011/025917 | 3/2011 |
| WO | WO 2011/035323 | 3/2011 |
| WO | WO 2011/075744 | 6/2011 |
| WO | WO 2011/106746 | 9/2011 |

OTHER PUBLICATIONS

Abd El Latif et al., "Urinary Epidermal Growth Factor Excretion: A Useful Prognostic Marker for Progression of Renal Damage in Children," J Med Sci, Oct. 2007;7(7):1171-1176.

Abou-Shousha and Youssef, "Interleukin-2 Regulatory Effect on P-Selectin and Interleukin-8 Production in Patients with Chronic Renal Failure," Egypt J Immunol. 2006;13(1):11-18.

Akcay et al., "Mediators of Inflammation in Acute Kidney Injury," Mediators Inflamm, 2009;2009:137072 (12 pp).

Albright, "Acute Renal Failure: A Practical Update," Mayo Clin Proc, Jan. 2001;76(1):67-74.

Alere Triage BNP Test Product Insert, 2011 (28 pp).

Allakhverdi et al., "Thymic stromal lymphopoietin is released by human epithelial cells in response to microbes, trauma, or inflammation arid potently activates mast cells," J Exp Med, Jan. 2007 (Epub);204(2):253-258.

Anders et al., "Chemokines and chemokine receptors are involved in the resolution or progression of renal disease," Kidney Int, Feb. 2003;63(2):401-415.

Anilkumar et al., "Trimeric assembly of the C-terminal region of Thrombospondin-1 or Thrombospondin-2 is necessary for cell spreading and fascin spike organisation," J Cell Sci, Jun. 1, 2002;115(Pt 11):2357-2366.

Arribas and Esselens, "ADAM17 as a Therapeutic Target in Multiple Diseases," Curr Pharm Des, 2009;15 (20):2319-2335.

Arrizabalaga et al., "Tubular and Interstitial Expression of ICAM-1 as a Marker of Renal Injury in IgA Nephropathy," Am J Nephrol Jan. 2003 (Epub):121-128.

Arthur et al., "Diagnostic and Prognostic Biomarkers in Acute Renal Failure," Contrib Nephrol, 2008;160:53-64.

Bagshaw et al., "Urinary biomarkers in septic acute kidney injury," Intensive Care Med, May 2007 (Epub);33(7):1285-1296.

Bajwa et al., "Immune Mechanisms and Novel Pharmacological Therapies of Acute Kidney Injury," Curr Drug Targets, Dec. 2009;10(12):1196-1204.

Barbano et al., "Plasma levels of soluble CD30 are increased in children with chronic renal failure and with primary grown deficiency and decrease during treatment with recomination human growth hormone," Nephrol Dial Transplant, 2001, 16:1807-1813.

Barrera-Chimal et al., "Hsp72 is an early and sensitive biomarker to detect acute kidney injury," Embo Mol Med, Dec. 2010 (Epub);3(1):5-20.

Bauer and Gawaz, "Sensitive Cardiac Troppnin Assays," New England Journal of Medicine, Dec. 2009, 361(26):2575-2577.

(56) References Cited

OTHER PUBLICATIONS

Berahovich et al., "Proteolytic activation of alternative CCR1 ligands in inflammation," J Immunol, Jun. 1, 2005;174 (11):7341-7351.
Beushausen, "NWG Biomarker Objectives," ILSI Health and Environmental Sciences Institute, ILSI-HESI Annual Meeting 2006:17 pp.
Bicik et al., "Role of Transforming Growth Factor-.beta.2 in, and a Possible Transforming Growth Factor-beta2 Gene Polymorphism as a Marker of, Renal Dysfunction in Essential Hypertension: A Study in Turkish Patients," Current Therapeutic Research, Jul./Aug. 2005;44(4):266-278.
Biotrin International, "Biotrin Biomarkers: How late do you want to detect preclinical kidney damage? Biotrin's acute kidney injury test (AKI Test)," Biotrin's Preclinical Kidney Biomarkers: 8 pp.
Bohē et al., "IGF-I binding proteins, IGF-I binding protein mRNA and IGF-I receptor mRNA in rats with acute renal failure given IGF-I," Kidn Intern, Oct. 1998;54(4):1070-1082.
Bonomini et al., "Serum Levels of Soluble Adhesion Molecules in Chronic Renal Failure and Dialysis Patients," Nephron, Aug. 1998;79(4):399-407.
Bonventre, "Dedifferentiation and Proliferation of Surviving Epithelial Cells in Acute Renal Failure," J Am Soc Nephrol, Jun. 2003;14 Suppl 1:S55-S61.
Bonventre, "Pathophysiology of Acute Kidney Injury: Roles of Potential Inhibitors of Inflammation," Contrib Nephrol, 2007;156:39-46.
Bonventre and Zuk, "Ischemic acute renal failure: An inflammatory disease?," Kidney Int, Aug. 2004;66(2):480-485.
Briasoulis et al., "A Retrospective Analysis of Serum CA 15-3 Concentrations in Patients with Localised or Metastatic Renal Cancer and its Impact on Prognosis and Follow-up. A Single-centre Experience," UroOncology, 2002;2(4):179-184.
Burne et al., "IL-1 and TNF independent pathways mediate ICAM-1NCAM-1 up-regulation in ischemia repertusion injury," J Leukoc Biol, Aug. 2001;70(2):192-198.
Burne-Taney and Rabb, "The role of adhesion molecules and T cells in ischemic renal injury," Curr Opin Nephrol Hypertens, Jan. 2003;12(1):85-90.
Bussieres et al., "Fetal urinary insulin-like growth factor I and binding protein 3 in bilateral obstructive uropathies," Prenat Diagn, Nov. 1995;15(11):1047-1055.
Cai, "Detection and Application for the biomarker of Rental Injury in Early Stage," Laboratory Med Clinic, Jun. 2005;2 (3):124-127— incl Engl transl abstract only.
Calabrese et al., "Oxidative stress and cellular stress response in diabetic nephropathy," Database Biosis [Online], Biosciences Information Service, Jan. 2007; XP002705326. Database accession No. PREV200800097004 (abstract):3 pages, Cell Stress & Chaperones. 2007 Winter;12(4):299-306.
Canani et al., "The Fatty Acid-Binding Protein-2 A54T Polymorphism Is Associated With Renal Disease in Patients With Type 2 Diabetes," Diabetes Nov. 2005;54(11):3326-3330.
Caron et al., "Ischemia injury alters endothelial cell properties of kidney cortex:stimulation of MMP-9," Exp Cell Res, Aug. 2005 (online);301(1):105-116.
Catania et al., "Role of matrix metalloproteinases in renal pathophysiologies," Am J Physiol Renal Physiol, Dec. 2006 (first published);292(3):F905-F911.
Cervelli et al., "Evaluation of Serum sCD30 in Renal Transplantation Patients With and Without Acute Rejection," Transplant Proc, May 2009, 41(4):1159-1161 (abstract only).
Choi et al., "Expression Of Vascular Endothelial Growth Factor-C And Its Receptor mRNA In The Rat Kidney With Ischemia-Reperfusion Injury," Clinical Kidney J, Jun. 2, 2011;4(Suppl 2):2 pp.
Christenson et al., "Standardization of cardiac troponin I assays: round Robin of ten candidate reference materials," Clin Chem, Mar. 2001;47(3):431-437.
Coca et al., "Biomarkers for the diagnosis and risk stratification of acute kidney injury: A systematic review," Kidney Int, Dec. 2007 (pub online);73(9):1008-1016.
Colomer et al., "Circulating CA 15-3 levels in the postsurgical follow-up of breast cancer patients and in nonmalignant diseases," Breast Cancer Res Treat, Mar. 1989;13(2):123-133.
Cooper, "Effect Of Tobacco Smoking On Renal Function," Indian J Med Res, Sep. 2006;124(3):261-268.
Correale and Fiol, "Activation of humoral immunity and eosinophils in neuromyelitis optica," Neurology, Dec. 28, 2004;63(12):2363-2370.
Cottone et al., "Endothelin-1 and F2-isoprostane relate to and predict renal dysfunction in hypertensive patients," Nephrol Dial Transpl, Sep. 2008 (advance access pub);24(2):497-503.
Cruz et al., "North East Italian Prospective Hospital Renal Outcome Survey on Acute Kidney Injury (NEiPHROS-AKI): Targeting the Problem with the RIFLE Criteria," Clin J Amer Soc Nephrol, Mar. 2007 (Epub);2(3):418-425.
Daha et al., "Is the proximal tubular cell a proinflammatory cell?," Nephrol Dial Transplant, 2000;15(Suppl 6):41-43.
De sá et al., "Leukocyte, platelet and endothelial activation in patients with acute renal failure treated by intermittent hemodialysis," Am J Nephrol, Jul.-Aug. 2001;21(4):264-273.
Devarajan, "Cellular and molecular derangements in acute tubular necrosis," Curr Opin Pediatr, Apr. 2005;17(2):193-199.
Devarajan, "Neutrophil gelatinase-associated lipocalin (NGAL): A new marker of kidney disease," Scand J Clin Lab Invest Suppl, 2008;241:89-94.
Devarajan, "Novel biomarkers for the early prediction of acute kidney injury," Cancer Therapy, Sep. 2005;3:477-488.
Devarajan, "Update on Mechanisms of Ischemic Acute Kidney Injury," J Am Soc Nephrol, May 2006 (Epub);17(6):1503-1520.
Devarajan et al., "Proteomics for Biomarker Discovery in Acute Kidney Injury," Semin Nephrol, Nov. 2007, 27(6):637-651.
Domanski et al., "Purine and Cytokine Concentrations in the Renal Vein of the Allograft During Reperfusion," Transplant Proc, Jun. 2007, 39(5):1319-1322.
Edelstein, "Biomarkers of Acute Kidney Injury," Adv Chronic Kidney Dis, Jul. 2008;15(3)222-234.
FDA, "European Medicines Agency to Consider Additional Test Results When Assessing New Drug Safety-Collaborative effort by FDA and EMEA expected to yield additional safety data," http://www.natap.org/2008/newsUpdates/071608_01.htm dated Jun. 12, 2008.
Ferguson et al., "Biomarkers of nephrotoxic acute kidney injury," Toxicology Jan. 2008 (Epub);245(3):182-193.
Flynn et al., "Urinary excretion of beta2 -glycoprotein-1 (apolipoprotein H) and other markers of tubular malfunction in "non-tubular" renal disease," J Clin Pathol, Jul. 1992;45(7):561-567.
Frangogiannis, "Chemokines in ischemia and reperfusion," Thromb Haemost, Apr. 2007 (pub online);97(5):738-747.
Fried et al., "Inflammatory and Prothrombotic Markers and the Progression of Renal Disease in Elderly Individuals," J Am Soc Nephrol, Dec. 2004;15(12):3184-3191.
Fujisaki et al., "Infusion of radiocontrast agents induces exaggerated release of urinary endothelin in patients with impaired renal function," Clin Exp Nephrol, Dec. 2003;7(4):279-283.
Furuichi et al., "Chemokine/chemokine receptor-mediated inflammation regulates pathologic changes from acute kidney injury to chronic kidney disease," Clin Exp Nephrol, Dec. 2008 (Epub);13(1):9-14.
Furuichi et al., "Roles of chemokines in renal ischemia/reperfusion injury," Front Biosci, May 1, 2008;13:4021-4028.
Galkina and Ley, "Leukocyte Recruitment and Vascular Injury in Diabetic Nephropathy," J Am Soc Nephrol, Jan. 2006 (Epub);17(2):368-377.
Garcia et al., "Adenosine A2A receptor activation and macrophagemediated experimental glomerulonephritis," FASEB J, Sep. 2007 (Epub);22(2):445-454.
Gbadegesin et al., "Plasma and urinary soluble adhesion molecule expression is increased during first documented acute pyelonephritis," Arch Dis Child, Mar. 2002;86(3):218-221.

(56) References Cited

OTHER PUBLICATIONS

Goes et al., "Effect of Recombinant Human Insulin-Like Growth Factor-1 on the Inflammatory Response to Acute Renal Injury," J Am Soc Nephrol, May 1996;7(5):710-720.
Grankvist et al., "Evaluation of five glycoprotein tumour markers (CEA, CA-50, CA-19-9, CA-125, CA-15-3) for the prognosis of renal-cell carcinoma," Int J Cancer, Apr. 22, 1997;74(2):233-236.
Grigoryev et al., "The Local and Systemic Inflammatory Transcriptome after Acute Kidney Injury," J Am Soc Nephrol, Jan. 2008 (Epub);19(3):547-558.
Gonads et al., "Serum Levels of Total Acid Phosphatase, Prostatic Acid Phosphatase, Total and Free Prostate-Specific Antigen in Patients Within Chronic Hemodialysis Program," Braz J Urol, Mar.-Apr. 2001;27(2):133-135.
Gupta et al., "Role of Protein C in Renal Dysfunction after Polymicrobial Sepsis," J Am Soc Nephrol, Mar. 18, 2007; (3):860-867.
Haase et al., "A comparison of the RIFLE and Acute Kidney Injury Network classifications for cardiac surgery-associated acute kidney injury: A prospective cohort study," J Thorac Cardiovasc Surg, Dec. 2009;138(6):1370-1376.
Han, "Biomarkers for Early Detection of Acute Kidney Injury," Nephrology Rounds Apr. 2008;6(4):6 pp.
Han et al, "Urinary biomarkers in the early diagnosis of acute kidney injury," Kidney Int, Dec. 2007 (pub online);73(7):863-869.
Han et al., "Upregulation of hyaluronan and its binding receptors in an experimental model of chronic cyclosporine nephropathy," Nephrology (Carlton), Mar. 2010;15(2):216-224.
Harpur et al., "Biological Qualification of Biomarkers of Chemical-Induced Renal Toxicity in Two Strains of Male Rat," Toxicol Sci, May 2011 (advance access pub);122(2):235-252.
Harris et al., "Growth Factors and Cytokines in Acute Renal Failure," Adv Ren Replace Ther, Apr. 1997;4(2) Suppl 1:43-53.
Hatta et al., Cytokine Array Comparisons of Plasma from Cycling Fertile Women on Cycle Day 5 and Ovulation. Am J Reprod Immunol. Sep. 2009;62(3):158-164.
He et al., "Interleukin-18 binding protein transgenic mice are protected against ischemic acute kidney injury," Am J Physiol Renal Physiol, Aug. 2008 (Epub);295(5):F1414-F1421.
Heinemann et al., "Association of Elevated Pretransplant sCD30 Levels with Graft Loss in 206 Patients Treated With Modern Immunosuppressive Therapies After Renal Transplantation," Transplantation, 2007, 83:706-711.
Herget-Rosenthal et al., "Early detection of acute renal failure by serum cystatin C," Kidney Int, Sep. 2004;66 (3):1115-1122.
Hidaka et al., "Urinary clusterin levels in the rat correlate with the severity of tubular damage and may help to differentiate between glomerular and tubular injuries," Cell Tissue Res, Oct. 2002 (Epub);310(3):289-296.
Hirai et al., "Plasma endothelin-1(ET-1) is a useful marker for renal dysfunction," Atheroscler Suppl, Jun. 19, 2006;7(3):60[Mo-P1:65].
Hirschberg et al., "Factors Predicting Poor Outcome In Patients with Acute Renal Failure (ARF)," J Am Soc Nephrol, Sep. 1, 1996;7(9):1374 [A0644].
Hoste et al., "RIFLE criteria for acute kidney injury are associated with hospital mortality in critically ill patients: a cohort analysis," Crit Care, May 2006;10(3):R73 (10 pp).
Hugo and Daniel, "Thrombospondin in Renal Disease," Nephron Exp Nephrol, 2009;111(3):e61-e66.
Hugo et al., "Thrombospondin 1 precedes and predicts the development of tubulointerstitial fibrosis in glomerular disease in the rat," Kidney Int, Feb. 1998;53(2):302-311.
Iglesias et al., "Thyroid Dysfunction and Kidney Disease," Revised version, Eur J Endocrinol, Dec. 18, 2008:32 pages retrieved from URL:///www.eje.org/content!early/2008/12/18/EJE-08-0837.full.pdf.
Jang and Rabb, "The innate immune response in ischemic acute kidney injury," Clin Immunol, Oct. 2008 (Epub);130(1):41-50.
Jang et al., "B Cells Limit Repair after Ischemic Acute Kidney Injury," J Am Soc Nephrol, Mar. 2010 (Epub);21(4):654-665.

Jehle et al., "Insulin-like growth factor system components in hyperparathyroidism and renal osteodystrophy," Kidney Int, 2000, 57:423-436.
Jonsson, "The role of fibroblast growth factor 23 in renal disease," Nephrol Dial Transplant, Mar. 2005;20(3):479-482.
Julian et al., "Sources of Urinary Proteins and their Analysis by Urinary Proteomics for the Detection of Biomarkers of Disease," Proteomics Clin Appl, Aug. 2009;3(9):1029-1043.
Jung et al., "Diagnostic significance of urinary enzymes in detecting acute rejection crises in renal transplant recipients depending on expression of results illustrated through the example of alanine aminopeptidase," Clin Biochem, Aug. 1985;18(4):257-260.
Kadiroglu et al., "The Evaluation of Effects of Demographic Features, Biochemical Parameters, and Cytokines on Clinical Outcomes in Patients with Acute Renal Failure," Ren Fail, 2007;29(4):503-508.
Kalousova et al., "Soluble Receptor for Advanced Glycation End Products in Patients With Decreased Renal Function," Am J Kidney Dis, Mar. 2006;47(3):406-411.
Kamata et al., "Up-regulation of glomerular extracellular matrix and transforming growth factor-beta expression in RF/J mice," Kidney Int, Mar. 1999;55(3):864-876.
Kasahara et al., "Clinical Significance of Serum Oxidized Low-Density Lipoprotein/beta2-Giycoprotein I Complexes in Patients with Chronic Renal Diseases," Nephron Clin Pract, 2004;98(1):c15-c24.
Kehoe et al., "Elevated Plasma Renin Activity Associated with Renal Dysfunction," Nephron 1986;44:51-57 (abstract only).
Kellum, "Acute kidney injury," Crit Care Med, 2008;36(4) Supp;:S141-S145.
Kellum et al., "Definition and Classification of Acute Kidney Injury," Nephron Clin Pract, Sep. 2008;109(4):c182-c187.
Keyes and Bagshaw, "Early diagnosis of acute kidney injury in critically ill patients," Expert Rev Mol Diagn, Jul. 2008;8(4):455-464.
Khanna et al., "Expression of TGF-beta and fibrogenic genes in transplant recipients with tacrolimus and cyclosporine nephrotoxicity," Kidney Int, Dec. 2002;62(6):2257-2263.
Kharasch et al., "Gene Expression Profiling of Nephrotoxicity from the Sevoflurane Degradation Product Fluoromethyl-2,2-difluoro-1-(trifluoromethyl)vinyl Ether ("Compound A") in Rats," Toxicol Sci, Oct. 2005 (advance access pub);90(2):419-431.
Kiley and Chevalier, "Urinary biomarkers: The future looks promising," Kidney Int, Jul. 2009;76(2):133-134.
Kiliś-Pstrusińska et al., [Levels of selected soluble adhesion molecules in blood serum of children with chronic glomerulonephritis,] Pol Merkur Lekarski, Apr. 2001;10(58):247-249.
Kilis-Pstrusinska et al., "Serum levels of soluble adhesion molecules in children with glomerulonephritis (GN)," Nephrol Dialysis Transplant, Jun. 2001;16(6):A62.
Kimmel et al., "Immunologic function and survival in hemodialysis patients," Kidney Int, Jul. 1998;54(1):236-244.
Kinsey et al., "Inflammation in Acute Kidney Injury," Nephron Exp Nephrol, Sep. 2008 (Epub);109(4):e102-e107.
Koo et al., "Cadaver versus living donor kidneys: Impact of donor factors on antigen induction before transplantation," Kidney Int, Oct. 1999;56(4):1551-1559.
Kos et al., "Cathepsins B,H and L and Their Inhibitors Stefin A and Cystatin C in Sera of Melanoma Patients," Clin Cancer Res, Oct. 1997;3(10):1815-1822.
Landray et al., "Inflammation, Endothelial Dysfunction, and Platelet Activation in Patients With Chronic Kidney Disease: The Chronic Renal Impairment in Birmingham (CRIB) Study," Am J Kidney Dis, Feb. 2004;43(2):244-253.
Lang et al., "Heat Shock Protein 60 Is Released in Immune-Mediated Glomerulonephritis and Aggravates Disease: In Vivo Evidence for an Immunologic Danger Signal," J Am Soc Nephrol, Dec. 2004 (Epub);16(2):383-391.
Lapsley et al., "Beta2-glycoprotein-1 (apolipoprotein H) excretion in chronic renal tubular disorders: Comparison with other protein markers of tubular malfunction," J Clin Pathol, Oct. 1991;44(10):812-816.

(56) References Cited

OTHER PUBLICATIONS

Larsson et al., "Circulating concentration of FGF-23 increases as renal function declines in patients with chronic kidney disease, but does not change in response to variation in Phosphate intake in healthy volunteers," Kidney Int, Dec. 2003;64(6):2272-2279.

Li et al., "Predictive value of RIFLE classification on prognosis of critically ill patients with acute kidney injury treated with continuous renal replacement therapy," Chin Med J (Engl), May 5, 2009;122(9):1020-1025.

Liu et al., "Predictive and pathogenetic value of plasma biomarkers for acute kidney injury in patients with acute lung injury," Crit Care Med, Dec. 2007;35(12):2755-2761.

Liu et al., "Serum Interleukin-6 and interleukin-8 are early biomarkers of acute kidney injury and predict prolonged mechanical ventilation in children undergoing cardiac surgery: a case-control study," Critical Care Jul. 2009 (Epub);13(4):R104 (9 pp).

Lopes-Virella et al., "Urinary high density lipoprotein in minimal change glomerular disease and chronic glomerulopathies," Clin Chim Acta, May 16, 1979;94(1):73-81.

Lu et al., "Increased Macrophage Infiltration and Fractalkine Expression in Cisplatin-Induced Acute Renal Failure in Mice," J Pharmacol Exp Ther, Oct. 2007 (Epub);324(1):111-117.

Maddens et al., "Chitinase-like Proteins are Candidate Biomarkers for Sepsis-induced Acute Kidney Injury," Mol Cell Proteomics, Jan. 10, 2012;11(6):1-13.

Malm et al., "Changes in the plasma levels of vitamin K-dependent proteins C and S and of C4b-binding protein during pregnancy and oral contraception," Br J Haematol, Apr. 1988;68(4):437-443.

Malyszko et al., "Visfatin and apelin, new adipocytokines, and their relation to endothelial function in patients with chronic renal failure," Adv Med Sci, 2008;53(1):32-36.

Mast et al., "Clinical utility of the soluble transferrin receptor and comparison with serum ferritin in several populations," Clin Chem, Jan. 1998;44(1):45-51.

Matousovic et al., "IgA-containing immune complexes in the urine of IgA nephropathy patients," Nephrol Dial Transplant, Jun. 2006 (Epub);21(9):2478-2484.

Matsuda et al., "Beta 2-Glycoprotein I-Dependent and -Independent Anticardiolipin Antibody in Patients with End-Stage Renal Disease," Thromb Res, Oct. 15, 1993;72(2):109-117.

Matsuzaka et al., "Relationship between vitamin K dependent coagulation factors and anticoagulants (protein C and protein S) in neonatal vitamin K deficiency," Arch Dis Child, Mar. 1993;68:297-302.

Mattes, "Experience With a Biomarker Consortium," CPath Predictive Safety Training Consortium, Critical Path Institute:48 pp.

Melnikov et al., "Impaired IL-18 processing protects caspase-1-deficient mice from ischemic acute renal failure," J Clin Invest, May 2001;107(9):1145-1152.

Mezzano et al., "Endothelial Cell Markers in Chronic Uremia: Relationship with Hemostatic Defects and Severity of Renal Failure," Thromb Res, Dec. 15, 1997;88(6):465-472.

Milford et al., "Prognostic Markers in Diarrhoea-Associated Haemolytic-Uraemic Syndrome: Initial Neutrophil Count, Human Neutrophil Elastase and Von Willebrand Factor Antigen," Nephrol Dial Transplant, 1991;6(4):232-237.

Mills et al., "Implications of lowering threshold of plasma troponin concentration in diagnosis of myocardial infarction: cohort study," BMJ Mar. 2012;344:e1533 doi: 10.1136/bmj.e1533.

Mishra et al., "Neutrophil gelatinase-associated lipocalin (NGAL) as a biomarker for acute renal injury after cardiac surgery," Lancet, Apr. 2-8, 2005;365(9466):1231-1238.

Montagna et al., "Impairment of cellular redox status and membrane protein activities in kidneys from rats with ischemic acute renal failure," Biochim Biophys Acta, Aug. 14, 1998;1407(2):99-108.

Musial et al., "The Heat Shock Protein Profile in Children with Chronic Kidney Disease," Pent Dial Int, Jan. 2010 (Epub);30(2):227-232.

Musial et al., "Soluble adhesion molecules in chronic renal failure (CRF) children treated conservatively," Nephrol Dialysis Transplant, 2002;17(Abstracts Suppl 1):232.

Nafar et al., "Pre-transplant and post-transplant soluble CD30 for prediction and diagnosis of acute kidney allograft rejection," Int Urol Nephrol, Dec. 2008 (Epub), 41(3):687-693 (abstract only).

Nambi et al., "Down regulation of kidney neutral endopeptidase mRNA, protein and activity during acute renal failure: possible mechanism for ischemia-induced acute renal failure in rats?," Mol Cell Biochem, Jul. 1999;197(1-2):53-59.

Neziri et al., "Cloning and molecular characterization of Dashurin encoded by C20ort116, a PCI-domain containing protein," Biochim Biophys Acta, Dec. 2009 (Epub);1800(4):430-438.

Nguyen et al., "Heparin-Binding EGF-Like Growth Factor Is Up-Regulated in the Obstructed Kidney in a Cell- and Region-Specific Manner and Acts to Inhibit Apoptosis," Am J Pathol, Mar. 2000;156(3):889-898.

Nishiyama et al., "Up-Regulation of Galectin-3 in Acute Renal Failure of the Rat," Am J Pathol, Sep. 2000;157(3):815-823.

Norman et al., "Progressive Renal Disease: Fibroblasts, Extracellular Matrix, and Integrins," Exp Nephrol, Mar.-Apr. 1999;7(2):167-177.

Obuchowski et al., "ROC curves in clinical chemistry: uses, misuses, and possible solutions," Clin Chem, May 2004 (Epub);50(7):1118-25.

Ohno et al., "Prognostic significance of tenascin-C expression in clear cell renal cell carcinoma," Oncol Rep, Sep. 2008;20(3):511-516.

Ozer et al., "A panel of urinary biomarkers to monitor reversibility of renal injury and a serum marker with improved potential to assess renal function," Nat Biotechnol, May 2010;28(5):486-494.

Parikh and Devarajan, "New biomarkers of acute kidney injury," Crit Care Med, Apr. 2008;36(4 Suppl):S159-5165.

Parikh et al., "Urinary IL-18 is an early predictive biomarker of acute kidney injury after cardiac surgery," Kidney Int, May 2006 (Epub);70(1):199-203.

Perco et al., "Protein biomarkers associated with acute renal failure and chronic kidney disease," Eur J Clin Invest, Nov. 2006;36(11):753-763.

Picard et al., "Origin of renal myofibroblasts in the model of unilateral ureter obstruction in the rat," Histochem Cell Biol, May 2008 (Epub);130(1):141-155.

Powell et al., "Characterization of Insulin-Like Growth Factor Binding Protein-3 in Chronic Renal Failure Serum," Pediatr Res, Feb. 1993;33(2):136-143.

Price, "Abrupt Changes In Prostate-Specific Antigen Concentration in Acute Renal Failure," Clin Chem, Jan. 1993;39(1):161-162.

Prozialeck and Edwards, "Cell Adhesion Molecules in Chemically-Induced Renal Injury," Pharmacol Ther, Jan. 2007 (Epub);114(1):74-93.

Radford, Jr. et al., "Predicting renal outcome in IgA nephropathy," J Am Soc Nephrol, Feb. 1997;8(2):199-207.

Rajakariar et al., "High Pre-Transplant Soluble CD30 levels are Predictive of the Grade of Rejection," Am J Transplant, 2005, 5:1922-1925.

Rajashekar et al., "Systemic diseases with renal manifestations," Prim Care, Jun. 2008;35(2):297-328, abstract retrieved from URL:www.ncbi.nlm.nih.gov/pubmed/18486717.

Ramesh and Reeves, "TNF-a mediates chemokine and cytokine expression and renal injury in cisplatin nephrotoxicity," J Clin Invest, Sep. 2002;110(6):835-842.

Ramesh et al., "Endotoxin and cisplatin synergistically induce renal dysfunction and cytokine production in mice," Am J Physiol Renal Physiol, May 2007 (Epub);293(1):F325-F332.

Ramirez et al., "Prospective Study on Autoantibodies Against Apolipoprotein H (B2GPI) in Several Clinical Parameters From Patients With Terminal Renal Failure and Functioning Renal Transplants," Transplantation Proceedings, Jul.-Aug. 2009;41(6):2370-2372.

Ricci et al., "The RIFLE criteria and mortality in acute kidney injury: A systematic review," Kidney Int, Dec. 2007 (Epub);73(5):538-546.

(56) References Cited

OTHER PUBLICATIONS

Ridker, "C-Reactive Protein: A Simple Test to Help Predict Risk of Heart Attack and Stroke," Circulation, Sep. 2003;108:e81-e85.
Ridker, "Clinical Application of C-Reactive Protein for Cardiovascular Disease Detection and Prevention," Circulation, Jan. 2003;107(3):363-369.
Rini et al., "Renal cell carcinoma," Lancet, Mar. 28, 2009;373(9669):1119-1132.
Rosenkranz et al., "P-selectin deficiency exacerbates experimental glomerulonephritis: a protective role for endothelial P-selectin in inflammation," J Clin Invest, Mar. 1999;103(5):649-659.
Rouschop et al., "Pre-transplant plasma and cellular levels of CD44 correlate with acute renal allograft rejection," Nephrol Dial Transplant, Oct. 2005;20(10):2248-2254.
Rouschop et al., "Renal expression of CD44 correlates with acute renal allograft rejection," Kidney Int, Jul. 2006 (Epub);70(6):1127-1134.
Schaefer et al., "Urinary excretion of cathepsin B and cystatins as parameters of tubular damage," Kidney Int Suppl, Nov. 1994;47:S64-S67.
Schena et al., "EGF and MCP-1 Urinary Excretion Is a Suitable Prognostic Marker in Iga Nephropathy," J Am Soc of Nephrology; Meeting of the American Society of Nephrology, Sep. 1, 2002;13(Program and Abstracts Issue):458A.
Schiffer et al., "Activated Renal Macrophages Are Markers of Disease Onset and Disease Remission in Lupus Nephritis," J Immunol, Feb. 1, 2008;180(3):1938-1947.
Schmaldienst et al., "Angiogenin: a novel inhibitor of neutrophil-lactoferrin release during extracorporeal circulation," Kidney Blood Press Res, 2003;26(2):107-112.
Schmidt et al., "Sexual hormone abnormalities in male patients with renal failure," Nephrol Dial Transplant, Mar. 2002;17(3):368-371.
Schulz et al., "Endothelin-1 as an early prognostic marker in acute renal failure (ARF) and sepsis," Kidney Blood Press Res, 2000;23(3-5):341-342.
Segawa et al., "In situ expression and soluble form of P-selectin in human glomerulonephritis," Kidney Int, Oct. 1997;52(4):1054-1063.
Segerer et al., "Chemokines, Chemokine Receptors, and Renal Disease: From Basic Science to Pathophysiologic and Therapeutic Studies," J Am Soc Nephrol, Jan. 2000;11(1):152-176.
Senatorski et al., "Urine activity of cathepsin B, collagenase and urine excretion of TGF-beta1 and fibronectin in membranous glomerulonephritis," Res Exp Med (Berl), Dec. 1998;198(4):199-206.
Severini and Aliberti, "Diagnostic significance of urinary enzymes: Development of a high performance liquid chromatographic method for the measurement of urinary lysozyme," Clin Chim Acta, Feb. 27, 1987;163(1):97-103.
Sharma et al., "Two-dimensional fluorescence difference gel electrophoresis analysis of the urine proteome in human diabetic nephropathy," Proteomics, Jul. 2005;5(10):2648-2655.
Shlipak et al., "Elevations of Inflammatory and Procoagulant Biomarkers in Elderly Persons With Renal Insufficiency," Circulation, Jan. 2003;107(1):87-92.
Shoji et al., "Plasma angiopoietin-like protein 3 (ANGPTL3) concentration is associated with uremic dyslipidemia," Atherosclerosis, May 2009 (Epub);207(2):579-584.
Simmons et al., "Plasma cytokine levels predict mortality in patients with acute renal failure," Kidney Int, Apr. 2004;65 (4):1357-1365.
Song et al., "Expression of TRAIL, DR4, and DR5 in kidney and serum from patients receiving renal transplantation," Transplant Proc, Jun. 2004;36(5):1340-1343.
Stafford-Smith et al., "Acute Kidney Injury and Chronic Kidney Disease After Cardiac Surgery," Adv Chronic Kidney Dis, Jul. 2008;15(3):257-277.
Staško et al., "Soluble P-Selectin During a Single Hemodialysis Session in Patients With Chronic Renal Failure and Erythropoietin Treatment," Clin Appl Thromb Hemost, Oct. 2007;13(4):410-415.
Pelzl et al., "Evaluation of posttransplantation soluble CD30 for diagnosis of acute renal allograft rejection," Transplantation, Feb. 15, 2003;75(3):421-423 (abstract only).
Stenvinkel et al., "High Serum Hyaluronan Indicates Poor Survival in Renal Replacement Therapy," Am J Kidney Dis, Dec. 1999;34(6):1083-1088.
Stuard et al., Soluble adhesion molecules in chronic renal failure patients, Nephrol Dialysis Transplant, 1997;12(9):A100.
Sun et al., "A Survey on the Relationship between the Epidermal Growth Factor and Renal Function," Int J Transpl Hemopurific, Dec. 31, 2006;4(1):41-44 (abstract English translation).
Supavekin et al., "Differential gene expression following early renal ischemia/repertusion," Kidney Int, May 2003;63 (5):1714-1724.
Sutton, "Alteration of microvascular permeability in acute kidney injury," Microvasc Res, Jan. 2009;77(1):4-7.
Sutton et al., "Injury of the renal microvascular endothelium alters barrier function after ischemia," Am J Physiol Renal Physiol, Apr. 2003 (Epub);285(2):F191-F198.
Sutton et al., "Microvascular endothelial injury and dysfunction during ischemic acute renal failure," Kidney Int, Nov. 2002;62(5):1539-1549.
Sykes et al., "Analytical relationships among Biosite, Bayer, and Roche methods for BNP and NT-proBNP," Am J Clin Pathol, Apr. 2005;123(4):584-590.
Symon et al., "The endogenous insulin-like growth factor system in radiocontrast nephropathy," Am J Physiol Renal Physiol, Mar. 1998;274(3 Pt 2):F490-497.
Takada et al., "The Cytokine-adhesion Molecule Cascade in lschemia/Reperfusion Injury of the Rat Kidney Inhibition by a Soluble P-selectin Ligand," J Clin Invest, Jun. 1997;99(11):2682-2690.
Tan et al., "The level of urinary secretory immunoglobulin A (sIgA) of patients with IgA nephropathy is elevated and associated with pathological phenotypes," Clin Exp Immunol, Jan. 2009 (Epub);156(1):111-116.
Tao et al., "Expression of 60-kDa and Inducible 70-kDa Stress Proteins in Gentamicin-Induced Acute Renal Failure," Clin Exp Nephrol, Jul. 1997;1:254-260.
Tary-Lehmann et al., "Enzyme-Linked Immunosorbent Assay Spot Detection of Interferon-Gamma and Interleukin 5-Producing Cells as a Predictive Marker for Renal Allograft Failure," Transplantation, Jul. 27, 1998;66(2):219-224.
Taulan et al., "Comprehensive analysis of the renal transcriptional response to acute uranyl nitrate exposure," BMC Genomics Jan. 11, 2006;7(2), 14 pp.
Teppo et al., "Soluble Intercellular Adhesion Molecule-1 (Sicam-1) after Kidney Transplantation: The Origin and Role of Urinary Sicam-1?," Transplantation, Apr. 27, 2001;71(8):1113-1119.
Thaker et al., "Identification of thrombospondin 1 (TSP-1) as a novel mediator of cell injury in kidney ischemia," J Clin Invest, Nov. 2005 (Epub);115(12):3451-3458.
Thorburn et al., "CXC and CC chemokines induced in human renal epithelial cells by inflammatory cytokines," APMIS, Jul. 2009;117(7):477-487.
Timoshanko et al., "Interleukin-12 from Intrinsic Cells Is an Effector of Renal Injury in Crescentic Glomerulonephritis," J Am Soc Nephrol, Mar. 2001;12(3):464-471.
Torres et al., "The ratio of epidermal growth factor to monocyte chemotactic peptide-1 in the urine predicts renal prognosis in IgA nephropathy," Kidney Int, Oct. 2007 (Epub);73(3):327-333.
Tzitzikos et al., "Measurement of Tumor Markers in Chronic Hemodialysis Patients," Saudi J Kidney Dis Transpl, Jan. 2010;21(1):50-53.
Ulinski et al., "Serum insulin-like growth factor binding protein (IGFBP)-4 and IGFBP-5 in children with chronic renal failure: relationship to growth and glomerular filtration rate," Pediatr Nephrol, 2000, 14:589-597.
Vaidya and Bonventre, "Mechanistic biomarkers for cytotoxic acute kidney injury," Expert Opin Drug Metab Toxicol, Oct. 2006;2(5):697-713.
Vaidya et al., "Biomarkers of Acute Kidney Injury," Annu Rev Pharmacol Toxicol, Oct. 2007 (pub online);48:463-493.

(56) References Cited

OTHER PUBLICATIONS

Vanhoutte et al., "Biomarker discovery with SELDI-TOF MS in human urine associated with early renal injury: evaluation with computational analytical tools," Nephrol Dial Transplant, Jul. 2007 (Epub);22(10):2932-2943.
Villanueva et al., "Ischemic acute renal failure induces the expression of a wide range of nephrogenic proteins," Am J Physiol Regul Integr Comp Physiol, Nov. 2005 (Epub);290(4):R861-R870.
Vonderscher, "Biomarker of Drug Induced Kidney Injury Qualification for Regulatory Decision Making (CRADA)," IOM/FDA, Silver Spring, MD, Apr. 2007;23:31 pp.
Voshol et al., "Evaluation of Biomarker Discovery Approaches to Detect Protein Biomarkers of Acute Renal Allograft Rejection," J Proteome Res, Jul.-Aug. 2005;4(4):1192-1199.
Wagner et al., "Evaluation of IGF system component levels and mitogenic activity of uremic serum on normal human osteoblasts," Nephron, Feb. 2000, 84(2):158-166.
Waikar et al., "Diagnosis, Epidemiology and Outcomes of Acute Kidney Injury," Clin J Am Soc Nephrol, Mar. 2008 (Epub);3 (3):844-861.
Wan et al., "The pathogenesis of septic acute renal failure," Curr Opin Crit Care, Dec. 2003;9(6):496-502.
Wang et al., "Netrin-1 and kidney injury. I. Netrin-1 protects against ischemia-repertusion injury of the kidney," Am J Physiol Renal Physiol, Jan. 2008 (Epub);294(4):F739-F747.
Wang et al., "Validation of putative genomic biomarkers of nephrotoxicity in rats," Toxicology, Jan. 2008 (Epub);246(2-3):91-100.
Weinzimer et al., "Elevated Urinary Insulin-Like Growth Factor Binding Protein-3 Predicts Renal Outcome in Fetuses with Lower Urinary Tract Obstruction," Am J Obst Gyn, Jan. 2001;184(1):S132;0433.
Winchester et al., "Sorbents in Acute Renal Failure and End-Stage Renal Disease: Middle Molecule and Cytokine Removal," Blood Purif, 2004;22(1):73-77.
Xiaofang et al., "Serum tumour markers in patients with chronic kidney disease," Scand J Clin Lab Invest, 2007;67(6):661-667.
Yang et al., "Frequency of anti-bactericidal/permeability-increasing protein (BPI) and anti-azurocidin in patients with renal disease," Clin Exp Immunol, Jul. 1996;105(1):125-131.
Yu et al., "Urinary biomarkers trefoil factor 3 and albumin enable early detection of kidney tubular injury," Nat Biotechnol, May 2010;128(5):470-477.
Yuen et al., "Ischemic and Nephrotoxic Acute Renal Failure are Distinguished by their Broad Transcriptomic Responses," Physiol Genomics, Feb. 2006 (Epub);25(3):375-386.
Zaffanello et al., "Early diagnosis of acute kidney injury with urinary biomarkers in the newborn," J Matern Fetal Neonatal Med, Oct. 2009;22 Suppl 3:62-66.
Zager et al., "Proximal tubular cytochrome c efflux: Determinant, and potential marker, of mitochondria! Injury," Kidney Int, Jun. 2004;65(6):2123-2134.
Zhang et al., "The level of serum secretory IgA of patients with IgA nephropathy is elevated and associated with pathological phenotypes," Nephrol Dial Transplant, Oct. 2007 (Epub);23(1):207-212.
Zheng et al., "Antiphospholipid antibody profiles in lupus nephritis with glomerular microthrombosis: a prospective study of 124 cases," Arthritis Res Ther, Jun. 2009;11(3):R93;1-9.
Zhu et al., "Expression of Urinary Epidermal Growth Factor and Renal Function," J Clin Urol, Dec. 31, 1998;13(8):374-379 (abstract English translation).
Office Action dated Sep. 19, 2013 issued in Australian application No. 2011269847.
Office Action dated Oct. 21, 2016 issued in Australian application No. 2015203382.
Office Action dated Apr. 20, 2017 issued in Canadian application No. 2,803,498.
Office Action dated May 29, 2013 issued in Chinese application No. 200980140694.6—includes English translation.
Office Action dated Jul. 1, 2013 issued in Chinese application No. 200980149555.X—includes English translation.
Office Action dated Jul. 1, 2013 issued in Chinese application No. 200980149636.X—includes English translation.
Office Action dated Dec. 17, 2012 issued in Chinese application No. 20980154224.5.
Office Action dated Jun. 25, 2013 issued in Chinese application No. 201080014932.1—includes English translation.
Office Action and Search Report dated Dec. 17, 2013 issued in Chinese application No. 2011800388045—includes English translation.
Office Action and Search Report dated May 16, 2013 issued in Chinese application No. 200980140805.3—includes English translation.
Office Action and Search Report dated May 22, 2016 issued in Chinese application No. 2015104280932—includes Englishg translation.
Search Report dated Jul. 8, 2013 issued in Chinese application No. 201080057014.7—includes English translation.
Search Report dated Apr. 15, 2013 issued in Chinese application No. 200980140694.6—includes English translation.
Search Report dated May 23, 2013 issued in Chinese application No. 200980149555.X—includes English translation.
Search Report dated Jun. 17, 2013 issued in Chinese application No. 200980149636.X—includes English translation.
Search Report dated Nov. 23, 2012 issued in Chinese application No. 200980154224.5—includes English translation.
Search Report dated Jun. 9, 2013 issued in Chinese application No. 201080014932.1—includes English translation.
Extended European Search Report and Written Opinion dated Jul. 16, 2013 issued in European application No. 10812639.
Extended European Search Report and Opinion dated Apr. 15, 2013 issued in European application No. 10817878.
Extended European Search Report and Written Opinion dated May 24, 2013 issued in European application No. 10829191.
Extended European Search Report and Opinion dated May 21, 2013 issued in European application No. 10829198.
Extended European Search Report and Written Opinion dated Dec. 3, 2012 issued in European application No. 10807254.7 (PCT/US2010/044772).
Extended European Search Report and Written Opinion dated Dec. 3, 2012 issued in European application No. 10807232.3 (PCT/US2010/044708).
Extended European Search Report and Opinion dated Oct. 24, 2011 issued in European application No. 09810695.8 (PCT/US2009/055449).
Extended European Search Report and Written Opinion dated Feb. 22, 2012 issued in European application No. 09810705.5 (PCT/US2009/055460).
Extended European Search Report and Opinion dated Jun. 13, 2013 issued in European application No. 11740468.
Extended European Search Report and Opinion dated Jun. 18, 2013 issued in European application No. 11740470.
Extended European Search Report and Opinion dated Aug. 16, 2013 issued in European application No. 11748210.
Extended European Search Report and Written Opinion dated Aug. 13, 2013 issued in European application No. 11751238.
Extended European Search Report and Opinion dated Jul. 9, 2012 issued in European application No. 09822669.9 (PCT/US2009/061561).
Extended European Search Report and Opinion dated Aug. 23, 2012 issued in European application No. 09822670.7 (PCT/US2009/061562).
Extended European Search Report dated Nov. 6, 2013 issued in European application No. 11798515.
Extended European Search Report dated Nov. 4, 2013 issued in European application No. 11798516.
Extended European Search Report dated May 22, 2015 issued in European application No. 15151607.
Extended European Search Report dated Nov. 13, 2013 issued in European application No. 11798514.3.
Extended European Search Report and Written Opinion dated Mar. 22, 2018 issued in EP 18150690.

(56) References Cited

OTHER PUBLICATIONS

Extended European Search Report and Opinion dated Feb. 23, 2012 issued in European application No. 09828325.2 (PCT/US2009/065419).
Extended European Search Report and Opinion dated Jun. 3, 2013 issued in European application No. 10838357.
Extended European Search Report and Written Opinion dated Jul. 9, 2012 issued in European application No. 10739150.0 (PCT/US2010/023292).
Extended European Search Report and Written Opinion dated Jul. 27, 2012 in European application No. 10739152.6 (PCT/US2010/023294).
Extended European Search Report and Written Opinion dated Aug. 23, 2012 issued in European application No. 10739155.9 (PCT/US2010/023297).
Extended European Search Report and Opinion dated Jun. 8, 2012 issued in European application No. 09825600.1 (PCT/US2009/063906).
Extended European Search Report and Opinion dated Jun. 13, 2013 issued in European application No. 11740469.
Extended European Search Report and Opinion dated Jun. 6, 2013 issued in EP 10818036.
Office Action dated Dec. 16, 2019 issued in European application No. 18150690.8.
Office Action dated Jul. 18, 2013 issued in European application No. 201080057014.7—includes English translation.
Office Action dated Dec. 10, 2014 issued in European application No. 11798514.3.
Office Action dated Sep. 29, 2015 issued in European application No. 11798514.3.
Office Action dated Aug. 19, 2016 issued in European application No. 11798514.3.
International Preliminary Report on Patentability dated Mar. 29, 2011 issued in PCT/US2010/049234.
International Preliminary Report on Patentability dated May 24, 2013 issued in PCT/US2011/055055.
International Preliminary Report on Patentability dated May 18, 2012 issued in PCT/US2010/055730.
International Preliminary Report on Patentability dated Mar. 10, 2011 issued in PCT/US2009/055449.
International Preliminary Report on Patentability dated Mar. 10, 2011 issued in PCT/US2009/055460.
International Preliminary Report on Patentability dated Aug. 16, 2012 issued in PCT/US2011/023830.
International Preliminary Report on Patentability dated Aug. 16, 2012 issued in PCT/US2011/023831.
International Preliminary Report on Patentability dated Aug. 16, 2012 issued in PCT/US2011/023832.
International Preliminary Report on Patentability dated Sep. 7, 2012 issued in PCT/US2011/026384.
International Preliminary Report on Patentability dated Apr. 5, 2012 issued in PCT/US2010/049695.
International Preliminary Report on Patentability dated May 5, 2011 issued in PCT/US2009/061561.
International Preliminary Report on Patentability dated May 5, 2011 issued in PCT/US2009/061562.
International Preliminary Report on Patentability dated Jun. 3, 2011 issued in PCT/US2009/065419.
International Preliminary Report on Patentability dated Jul. 5, 2012 issued in PCT/US2010/061377.
International Preliminary Report on Patentability dated Aug. 18, 2011 issued in PCT/US2010/023292.
International Preliminary Report on Patentability dated Aug. 18, 2011 issued in PCT/US2010/023294.
International Preliminary Report on Patentability dated Oct. 21, 2011 issued in PCT/US2010/023297.
International Preliminary Report on Patentability dated May 10, 2011 issued in PCT/US2009/063906.
International Search Report and Written Opinion dated Nov. 25, 2011 issued in PCT/US2011/001125.
International Search Report and Written Opinion dated Nov. 25, 2011 issued in PCT/US2011/001128.
International Search Report and Written Opinion dated Nov. 18, 2010 issued in PCT/US2010/046910.
International Search Report and Written Opinion dated Dec. 3, 2010 issued in PCT/US2010/049234.
International Search Report and Written Opinion dated Jan. 18, 2012 issued in PCT/US2011/053015.
International Search Report and Written Opinion dated Feb. 24, 2012 issued in PCT/US2011/055055.
International Search Report and Written Opinion dated Jan. 19, 2011 issued in PCT/US2010/055721.
International Search Report and Written Opinion dated Feb. 8, 2011 issued in PCT/US2010/055730.
International Search Report and Written Opinion dated May 10, 2012 issued in PCT/US2012/020571.
International Search Report and Written Opinion dated Oct. 28, 2010 issued in PCT/US2010/044772.
International Search Report and Written Opinion dated Oct. 8, 2010 issued in PCT/US2010/044708.
International Search Report and Written Opinion dated Dec. 10, 2009 issued in PCT/US2009/055449.
International Search Report and Written Opinion dated Dec. 31, 2009 issued in PCT/US2009/055460.
International Search Report and Written Opinion dated Apr. 27, 2011 issued in PCT/US2011/023830.
International Search Report and Written Opinion dated Apr. 27, 2011 issued in PCT/US2011/023831.
International Search Report and Written Opinion dated Apr. 29, 2011 issued in PCT/US2011/023832.
International Search Report and Written Opinion dated May 17, 2011 issued in PCT/US2011/026384.
International Search Report and Written Opinion dated Jun. 3, 2011 issued in PCT/US2011/026759.
International Search Report and Written Opinion dated Jan. 20, 2010 issued in PCT/US2009/061561.
International Search Report and Written Opinion dated Apr. 13, 2010 issued in PCT/US2009/061562.
International Search Report and Written Opinion dated Sep. 7, 2012 issued in PCT/US2012/043279.
International Search Report and Written Opinion dated Dec. 15, 2011 issued in PCT/US2011/001126.
International Search Report and Written Opinion dated Nov. 25, 2011 issued in PCT/US2011/001127.
International Search Report and Written Opinion dated Sep. 21, 2012 issued in PCT/US2012/045583.
International Search Report and Written Opinion dated Mar. 30, 2010 issued in PCT/US2009/065419.
International Search Report and Written Opinion dated Mar. 8, 2011 issued in PCT/US2010/061377.
International Search Report and Written Opinion dated Apr. 30, 2010 issued in PCT/US2010/023292.
International Search Report and Written Opinion dated Apr. 22, 2010 issued in PCT/US2010/023294.
International Search Report and Written Opinion dated Jun. 3, 2010 issued in PCT/US2010/023297.
International Search Report and Written Opinion dated Jun. 20, 2012 issued in PCT/US2012/020572.
International Search Report and Written Opinion dated May 2, 2012 issued in PCT/US2012/022926.
International Search Report and Written Opinion dated Jan. 15, 2010 issued in PCT/US2009/063906.
International Search Report and Written Opinion dated Jun. 18, 2013 issued in PCT/US2013/028005.
International Search Report and Written Opinion dated Mar. 15, 2013 issued in PCT/US2012/066152.
International Search Report and Written Opinion dated May 15, 2013 issued in PCT/US2013/023479.
International Search Report and Written Opinion dated Dec. 3, 2010 issued in PCT/US2010/049695.
Office Action dated Nov. 2, 2015 issued in Japanese application No. 2013-516566—includes English translation.

(56) References Cited

OTHER PUBLICATIONS

Office Action dated Jan. 24, 2017 issued in Japanese application No. 2016-040339—includes English translation.
Non-final Office Action dated Feb. 5, 2013 issued in Japanese application No. 2011-525262—includes English translation.
Office Action and Search Report dated Jan. 20, 2014 issued in Japanese application No. 2013-516566—includes English translation.
Office Action dated Nov. 20, 2015 issued in Mexican application No. MX/a/2013/000220—includes English translation.
Office Action dated Dec. 7, 2017 issued in Mexican application No. MX/a/2016/002060—includes English translation, summary only.
Office Action dated Jun. 14, 2013 issued in New Zealand application No. 605561.
Office Action dated Dec. 18, 2014 issued in New Zealand application No. 703055.
Office Action dated Jun. 21, 2016 issued in New Zealand application No. 720843.
Non-final Office Action dated Aug. 27, 2013 issued in U.S. Appl. No. 13/125,360.
Non-final Office Action dated Nov. 16, 2012 issued in U.S. Appl. No. 13/389,351.
Non-final Office Action dated Apr. 18, 2013 issued in U.S. Appl. No. 13/389,363.
Non-final Office Action dated Jan. 2, 2013 issued in U.S. Appl. No. 13/061,413.
Final Office Action dated Aug. 23, 2013 issued in U.S. Appl. No. 13/061,413.
Non-final Office Action dated Jun. 20, 2013 issued in U.S. Appl. No. 13/577,242.
Non-final Office Action dated Jan. 24, 2013 ssued in U.S. Appl. No. 13/125,360.
Non-final Office Action dated Mar. 5, 2013 issued in U.S. Appl. No. 13/125,454.
Non-final Office Action dated Dec. 18, 2012 issued in U.S. Appl. No. 13/164,768.
Non-final Office Action dated Jul. 2, 2018 issued in U.S. Appl. No. 15/604,573.
Non-final Office Action dated Apr. 27, 2015 issued in U.S. Appl. No. 13/806,759.
Non-final Office Action dated Nov. 27, 2012 issued in U.S. Appl. No. 13/130,474.
Restriction Requirement dated Jul. 1, 2013 issued in U.S. Appl. No. 13/517,244.
Non-final Office Action dated May 1, 2013 issued in U.S. Appl. No. 13/148,030.
Response to Non-final Office Action filed on Jul. 2, 2013 in U.S. Appl. No. 13/061,413.
Final Office Action dated Oct. 11, 2012 issued in U.S. Appl. No. 13/061,446.
Final Office Action dated Jun. 7, 2013 issued in U.S. Appl. No. 13/061,446.
Non-final Office Action dated Feb. 14, 2013 issued in U.S. Appl. No. 13/577,243.
Non-final Office Action dated Feb. 1, 2013 issued in U.S. Appl. No. 13/508,363.
Restriction Requirement dated Sep. 5, 2012 issued in U.S. Appl. No. 13/061,413.
Restriction Requirement dated Mar. 20, 2013 issued in U.S. Appl. No. 13/148,031.
Response to Restriction Requirement filed on Oct. 16, 2012 in U.S. Appl. No. 13/061,413.

* cited by examiner

```
                              SEQUENCE LISTING

<160> NUMBER OF SEQ ID NOS: 35

<210> SEQ ID NO 1
    <211> LENGTH: 99
    <212> TYPE: PRT
    <213> ORGANISM: Homo sapiens

<400> SEQUENCE: 1

Met Lys Ala Ser Ala Ala Leu Leu Cys Leu Leu Leu Thr Ala Ala Ala
    1               5                   10                  15

Phe Ser Pro Gln Gly Leu Ala Gln Pro Val Gly Ile Asn Thr Ser Thr
                    20                  25                  30

Thr Cys Cys Tyr Arg Phe Ile Asn Lys Lys Ile Pro Lys Gln Arg Leu
                35                  40                  45

Glu Ser Tyr Arg Arg Thr Thr Ser Ser His Cys Pro Arg Glu Ala Val
            50                  55                  60

Ile Phe Lys Thr Lys Leu Asp Lys Glu Ile Cys Ala Asp Pro Thr Gln
    65                  70                  75                  80

Lys Trp Val Gln Asp Phe Met Lys His Leu Asp Lys Lys Thr Gln Thr
                    85                  90                  95

Pro Lys Leu

<210> SEQ ID NO 2
    <211> LENGTH: 94
    <212> TYPE: PRT
    <213> ORGANISM: Homo sapiens

<400> SEQUENCE: 2

Met Met Gly Leu Ser Leu Ala Ser Ala Val Leu Leu Ala Ser Leu Leu
    1               5                   10                  15

Ser Leu His Leu Gly Thr Ala Thr Arg Gly Ser Asp Ile Ser Lys Thr
                    20                  25                  30

Cys Cys Phe Gln Tyr Ser His Lys Pro Leu Pro Trp Thr Trp Val Arg
                35                  40                  45

Ser Tyr Glu Phe Thr Ser Asn Ser Cys Ser Gln Arg Ala Val Ile Phe
            50                  55                  60

Thr Thr Lys Arg Gly Lys Lys Val Cys Thr His Pro Arg Lys Lys Trp
    65                  70                  75                  80

Val Gln Lys Tyr Ile Ser Leu Leu Lys Thr Pro Lys Gln Leu
                    85                  90
```

<210> SEQ ID NO 3
<211> LENGTH: 1744
<212> TYPE: PRT
<213> ORGANISM: Homo sapiens

<400> SEQUENCE: 3

```
Met Arg Leu Leu Trp Gly Leu Ile Trp Ala Ser Ser Phe Phe Thr Leu
1               5                   10                  15

Ser Leu Gln Lys Pro Arg Leu Leu Phe Ser Pro Ser Val Val His
            20                  25                  30

Leu Gly Val Pro Leu Ser Val Gly Val Gln Leu Gln Asp Val Pro Arg
        35                  40                  45

Gly Gln Val Val Lys Gly Ser Val Phe Leu Arg Asn Pro Ser Arg Asn
    50                  55                  60

Asn Val Pro Cys Ser Pro Lys Val Asp Phe Thr Leu Ser Ser Glu Arg
65                  70                  75                  80

Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
    130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
    210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
        275                 280                 285

Glu Asp Gly Lys Lys Thr Phe Phe Arg Gly Leu Glu Ser Gln Thr Lys
    290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ala Ile Ile Glu Ser Pro Gly Gly Glu Met
            340                 345                 350

Glu Glu Ala Glu Leu Thr Ser Trp Tyr Phe Val Ser Ser Pro Phe Ser
        355                 360                 365

Leu Asp Leu Ser Lys Thr Lys Arg His Leu Val Pro Gly Ala Pro Phe
    370                 375                 380
```

```
Leu Leu Gln Ala Leu Val Arg Glu Met Ser Gly Ser Pro Ala Ser Gly
385                 390                 395                 400

Ile Pro Val Lys Val Ser Ala Thr Val Ser Ser Pro Gly Ser Val Pro
            405                 410                 415

Glu Val Gln Asp Ile Gln Gln Asn Thr Asp Gly Ser Gly Gln Val Ser
                420                 425                 430

Ile Pro Ile Ile Ile Pro Gln Thr Ile Ser Glu Leu Gln Leu Ser Val
            435                 440                 445

Ser Ala Gly Ser Pro His Pro Ala Ile Ala Arg Leu Thr Val Ala Ala
        450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
                485                 490                 495

Gly Ser Gly Ala Thr Phe Ser His Tyr Tyr Met Ile Leu Ser Arg
            500                 505                 510

Gly Gln Ile Val Phe Met Asn Arg Glu Pro Lys Arg Thr Leu Thr Ser
        515                 520                 525

Val Ser Val Phe Val Asp His His Leu Ala Pro Ser Phe Tyr Phe Val
530                 535                 540

Ala Phe Tyr Tyr His Gly Asp His Pro Val Ala Asn Ser Leu Arg Val
545                 550                 555                 560

Asp Val Gln Ala Gly Ala Cys Glu Gly Lys Leu Glu Leu Ser Val Asp
                565                 570                 575

Gly Ala Lys Gln Tyr Arg Asn Gly Glu Ser Val Lys Leu His Leu Glu
            580                 585                 590

Thr Asp Ser Leu Ala Leu Val Ala Leu Gly Ala Leu Asp Thr Ala Leu
        595                 600                 605

Tyr Ala Ala Gly Ser Lys Ser His Lys Pro Leu Asn Met Gly Lys Val
610                 615                 620

Phe Glu Ala Met Asn Ser Tyr Asp Leu Gly Cys Gly Pro Gly Gly Gly
625                 630                 635                 640

Asp Ser Ala Leu Gln Val Phe Gln Ala Ala Gly Leu Ala Phe Ser Asp
                645                 650                 655

Gly Asp Gln Trp Thr Leu Ser Arg Lys Arg Leu Ser Cys Pro Lys Glu
            660                 665                 670

Lys Thr Thr Arg Lys Lys Arg Asn Val Asn Phe Gln Lys Ala Ile Asn
        675                 680                 685

Glu Lys Leu Gly Gln Tyr Ala Ser Pro Thr Ala Lys Arg Cys Cys Gln
690                 695                 700

Asp Gly Val Thr Arg Leu Pro Met Met Arg Ser Cys Glu Gln Arg Ala
705                 710                 715                 720

Ala Arg Val Gln Gln Pro Asp Cys Arg Glu Pro Phe Leu Ser Cys Cys
                725                 730                 735

Gln Phe Ala Glu Ser Leu Arg Lys Lys Ser Arg Asp Lys Gly Gln Ala
            740                 745                 750

Gly Leu Gln Arg Ala Leu Glu Ile Leu Gln Glu Asp Leu Ile Asp
        755                 760                 765

Glu Asp Asp Ile Pro Val Arg Ser Phe Phe Pro Glu Asn Trp Leu Trp
770                 775                 780

Arg Val Glu Thr Val Asp Arg Phe Gln Ile Leu Thr Leu Trp Leu Pro
785                 790                 795                 800

Asp Ser Leu Thr Thr Trp Glu Ile His Gly Leu Ser Leu Ser Lys Thr
```

```
                805                 810                 815
Lys Gly Leu Cys Val Ala Thr Pro Val Gln Leu Arg Val Phe Arg Glu
                820                 825                 830

Phe His Leu His Leu Arg Leu Pro Met Ser Val Arg Arg Phe Glu Gln
                835                 840                 845

Leu Glu Leu Arg Pro Val Leu Tyr Asn Tyr Leu Asp Lys Asn Leu Thr
    850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
                885                 890                 895

Val Ala Phe Ser Val Val Pro Thr Ala Ala Ala Val Ser Leu Lys
                900                 905                 910

Val Val Ala Arg Gly Ser Phe Glu Phe Pro Val Gly Asp Ala Val Ser
                915                 920                 925

Lys Val Leu Gln Ile Glu Lys Glu Gly Ala Ile His Arg Glu Glu Leu
    930                 935                 940

Val Tyr Glu Leu Asn Pro Leu Asp His Arg Gly Arg Thr Leu Glu Ile
945                 950                 955                 960

Pro Gly Asn Ser Asp Pro Asn Met Ile Pro Asp Gly Asp Phe Asn Ser
                965                 970                 975

Tyr Val Arg Val Thr Ala Ser Asp Pro Leu Asp Thr Leu Gly Ser Glu
                980                 985                 990

Gly Ala Leu Ser Pro Gly Gly Val Ala Ser Leu Leu Arg Leu Pro Arg
                995                 1000                1005

Gly Cys Gly Glu Gln Thr Met Ile Tyr Leu Ala Pro Thr Leu Ala
    1010                1015                1020

Ala Ser Arg Tyr Leu Asp Lys Thr Glu Gln Trp Ser Thr Leu Pro
    1025                1030                1035

Pro Glu Thr Lys Asp His Ala Val Asp Leu Ile Gln Lys Gly Tyr
    1040                1045                1050

Met Arg Ile Gln Gln Phe Arg Lys Ala Asp Gly Ser Tyr Ala Ala
    1055                1060                1065

Trp Leu Ser Arg Asp Ser Ser Thr Trp Leu Thr Ala Phe Val Leu
    1070                1075                1080

Lys Val Leu Ser Leu Ala Gln Glu Gln Val Gly Gly Ser Pro Glu
    1085                1090                1095

Lys Leu Gln Glu Thr Ser Asn Trp Leu Leu Ser Gln Gln Gln Ala
    1100                1105                1110

Asp Gly Ser Phe Gln Asp Leu Ser Pro Val Ile His Arg Ser Met
    1115                1120                1125

Gln Gly Gly Leu Val Gly Asn Asp Glu Thr Val Ala Leu Thr Ala
    1130                1135                1140

Phe Val Thr Ile Ala Leu His His Gly Leu Ala Val Phe Gln Asp
    1145                1150                1155

Glu Gly Ala Glu Pro Leu Lys Gln Arg Val Glu Ala Ser Ile Ser
    1160                1165                1170

Lys Ala Asn Ser Phe Leu Gly Glu Lys Ala Ser Ala Gly Leu Leu
    1175                1180                1185

Gly Ala His Ala Ala Ala Ile Thr Ala Tyr Ala Leu Ser Leu Thr
    1190                1195                1200

Lys Ala Pro Val Asp Leu Leu Gly Val Ala His Asn Asn Leu Met
    1205                1210                1215
```

```
Ala Met Ala Gln Glu Thr Gly Asp Asn Leu Tyr Trp Gly Ser Val
    1220                1225                1230

Thr Gly Ser Gln Ser Asn Ala Val Ser Pro Thr Pro Ala Pro Arg
    1235                1240                1245

Asn Pro Ser Asp Pro Met Pro Gln Ala Pro Ala Leu Trp Ile Glu
    1250                1255                1260

Thr Thr Ala Tyr Ala Leu Leu His Leu Leu His Glu Gly Lys
    1265                1270                1275

Ala Glu Met Ala Asp Gln Ala Ser Ala Trp Leu Thr Arg Gln Gly
    1280                1285                1290

Ser Phe Gln Gly Gly Phe Arg Ser Thr Gln Asp Thr Val Ile Ala
    1295                1300                1305

Leu Asp Ala Leu Ser Ala Tyr Trp Ile Ala Ser His Thr Thr Glu
    1310                1315                1320

Glu Arg Gly Leu Asn Val Thr Leu Ser Ser Thr Gly Arg Asn Gly
    1325                1330                1335

Phe Lys Ser His Ala Leu Gln Leu Asn Asn Arg Gln Ile Arg Gly
    1340                1345                1350

Leu Glu Glu Glu Leu Gln Phe Ser Leu Gly Ser Lys Ile Asn Val
    1355                1360                1365

Lys Val Gly Gly Asn Ser Lys Gly Thr Leu Lys Val Leu Arg Thr
    1370                1375                1380

Tyr Asn Val Leu Asp Met Lys Asn Thr Thr Cys Gln Asp Leu Gln
    1385                1390                1395

Ile Glu Val Thr Val Lys Gly His Val Glu Tyr Thr Met Glu Ala
    1400                1405                1410

Asn Glu Asp Tyr Glu Asp Tyr Glu Tyr Asp Glu Leu Pro Ala Lys
    1415                1420                1425

Asp Asp Pro Asp Ala Pro Leu Gln Pro Val Thr Pro Leu Gln Leu
    1430                1435                1440

Phe Glu Gly Arg Arg Asn Arg Arg Arg Arg Glu Ala Pro Lys Val
    1445                1450                1455

Val Glu Glu Gln Glu Ser Arg Val His Tyr Thr Val Cys Ile Trp
    1460                1465                1470

Arg Asn Gly Lys Val Gly Leu Ser Gly Met Ala Ile Ala Asp Val
    1475                1480                1485

Thr Leu Leu Ser Gly Phe His Ala Leu Arg Ala Asp Leu Glu Lys
    1490                1495                1500

Leu Thr Ser Leu Ser Asp Arg Tyr Val Ser His Phe Glu Thr Glu
    1505                1510                1515

Gly Pro His Val Leu Leu Tyr Phe Asp Ser Val Pro Thr Ser Arg
    1520                1525                1530

Glu Cys Val Gly Phe Glu Ala Val Gln Glu Val Pro Val Gly Leu
    1535                1540                1545

Val Gln Pro Ala Ser Ala Thr Leu Tyr Asp Tyr Tyr Asn Pro Glu
    1550                1555                1560

Arg Arg Cys Ser Val Phe Tyr Gly Ala Pro Ser Lys Ser Arg Leu
    1565                1570                1575

Leu Ala Thr Leu Cys Ser Ala Glu Val Cys Gln Cys Ala Glu Gly
    1580                1585                1590

Lys Cys Pro Arg Gln Arg Arg Ala Leu Glu Arg Gly Leu Gln Asp
    1595                1600                1605
```

```
Glu Asp Gly Tyr Arg Met Lys Phe Ala Cys Tyr Tyr Pro Arg Val
1610                1615                1620

Glu Tyr Gly Phe Gln Val Lys Val Leu Arg Glu Asp Ser Arg Ala
    1625                1630                1635

Ala Phe Arg Leu Phe Glu Thr Lys Ile Thr Gln Val Leu His Phe
    1640                1645                1650

Thr Lys Asp Val Lys Ala Ala Ala Asn Gln Met Arg Asn Phe Leu
    1655                1660                1665

Val Arg Ala Ser Cys Arg Leu Arg Leu Glu Pro Gly Lys Glu Tyr
    1670                1675                1680

Leu Ile Met Gly Leu Asp Gly Ala Thr Tyr Asp Leu Glu Gly His
    1685                1690                1695

Pro Gln Tyr Leu Leu Asp Ser Asn Ser Trp Ile Glu Glu Met Pro
    1700                1705                1710

Ser Glu Arg Leu Cys Arg Ser Thr Arg Gln Arg Ala Ala Cys Ala
    1715                1720                1725

Gln Leu Asn Asp Phe Leu Gln Glu Tyr Gly Thr Gln Gly Cys Gln
    1730                1735                1740

Val

<210> SEQ ID NO 4
<211> LENGTH: 267
<212> TYPE: PRT
<213> ORGANISM: Homo sapiens

<400> SEQUENCE: 4

Met Pro Arg Ser Cys Cys Ser Arg Ser Gly Ala Leu Leu Leu Ala Leu
1               5                   10                  15

Leu Leu Gln Ala Ser Met Glu Val Arg Gly Trp Cys Leu Glu Ser Ser
                20                  25                  30

Gln Cys Gln Asp Leu Thr Thr Glu Ser Asn Leu Leu Glu Cys Ile Arg
            35                  40                  45

Ala Cys Lys Pro Asp Leu Ser Ala Glu Thr Pro Met Phe Pro Gly Asn
        50                  55                  60

Gly Asp Glu Gln Pro Leu Thr Glu Asn Pro Arg Lys Tyr Val Met Gly
65                  70                  75                  80

His Phe Arg Trp Asp Arg Phe Gly Arg Arg Asn Ser Ser Ser Ser Gly
                85                  90                  95

Ser Ser Gly Ala Gly Gln Lys Arg Glu Asp Val Ser Ala Gly Glu Asp
            100                 105                 110

Cys Gly Pro Leu Pro Glu Gly Gly Pro Glu Pro Arg Ser Asp Gly Ala
        115                 120                 125

Lys Pro Gly Pro Arg Glu Gly Lys Arg Ser Tyr Ser Met Glu His Phe
    130                 135                 140

Arg Trp Gly Lys Pro Val Gly Lys Lys Arg Arg Pro Val Lys Val Tyr
145                 150                 155                 160

Pro Asn Gly Ala Glu Asp Glu Ser Ala Glu Ala Phe Pro Leu Glu Phe
                165                 170                 175

Lys Arg Glu Leu Thr Gly Gln Arg Leu Arg Glu Gly Asp Gly Pro Asp
            180                 185                 190

Gly Pro Ala Asp Asp Gly Ala Gly Ala Gln Ala Asp Leu Glu His Ser
        195                 200                 205

Leu Leu Val Ala Ala Glu Lys Lys Asp Glu Gly Pro Tyr Arg Met Glu
    210                 215                 220
```

His Phe Arg Trp Gly Ser Pro Pro Lys Asp Lys Arg Tyr Gly Gly Phe
225                 230                 235                 240

Met Thr Ser Glu Lys Ser Gln Thr Pro Leu Val Thr Leu Phe Lys Asn
                245                 250                 255

Ala Ile Ile Lys Asn Ala Tyr Lys Lys Gly Glu
            260                 265

<210> SEQ ID NO 5
<211> LENGTH: 188
<212> TYPE: PRT
<213> ORGANISM: Homo sapiens

<400> SEQUENCE: 5

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Lys Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 6
<211> LENGTH: 825
<212> TYPE: PRT
<213> ORGANISM: Homo sapiens

<400> SEQUENCE: 6

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

```
Asp Asn Tyr Thr Leu Asp Leu Trp Ala Gly Gln Gln Leu Leu Trp Lys
                100                 105                 110

Gly Ser Phe Lys Pro Ser Glu His Val Lys Pro Arg Ala Pro Gly Asn
            115                 120                 125

Leu Thr Val His Thr Asn Val Ser Asp Thr Leu Leu Leu Thr Trp Ser
        130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Cys Tyr
        195                 200                 205

Asn Thr Thr Trp Ser Glu Trp Ser Pro Ser Thr Lys Trp His Asn Ser
        210                 215                 220

Tyr Arg Glu Pro Phe Glu Gln His Leu Leu Gly Val Ser Val Ser
225                 230                 235                 240

Cys Ile Val Ile Leu Ala Val Cys Leu Leu Cys Tyr Val Ser Ile Thr
                245                 250                 255

Lys Ile Lys Lys Glu Trp Trp Asp Gln Ile Pro Asn Pro Ala Arg Ser
            260                 265                 270

Arg Leu Val Ala Ile Ile Gln Asp Ala Gln Gly Ser Gln Trp Glu
            275                 280                 285

Lys Arg Ser Arg Gly Gln Glu Pro Ala Lys Cys Pro His Trp Lys Asn
290                 295                 300

Cys Leu Thr Lys Leu Leu Pro Cys Phe Leu Glu His Asn Met Lys Arg
305                 310                 315                 320

Asp Glu Asp Pro His Lys Ala Ala Lys Glu Met Pro Phe Gln Gly Ser
                325                 330                 335

Gly Lys Ser Ala Trp Cys Pro Val Glu Ile Ser Lys Thr Val Leu Trp
            340                 345                 350

Pro Glu Ser Ile Ser Val Val Arg Cys Val Glu Leu Phe Glu Ala Pro
            355                 360                 365

Val Glu Cys Glu Glu Glu Glu Val Glu Glu Glu Lys Gly Ser Phe
370                 375                 380

Cys Ala Ser Pro Glu Ser Ser Arg Asp Asp Phe Gln Glu Gly Arg Glu
385                 390                 395                 400

Gly Ile Val Ala Arg Leu Thr Glu Ser Leu Phe Leu Asp Leu Leu Gly
                405                 410                 415

Glu Glu Asn Gly Gly Phe Cys Gln Gln Asp Met Gly Glu Ser Cys Leu
            420                 425                 430

Leu Pro Pro Ser Gly Ser Thr Ser Ala His Met Pro Trp Asp Glu Phe
        435                 440                 445

Pro Ser Ala Gly Pro Lys Glu Ala Pro Pro Trp Gly Lys Glu Gln Pro
450                 455                 460

Leu His Leu Glu Pro Ser Pro Pro Ala Ser Pro Thr Gln Ser Pro Asp
465                 470                 475                 480

Asn Leu Thr Cys Thr Glu Thr Pro Leu Val Ile Ala Gly Asn Pro Ala
                485                 490                 495

Tyr Arg Ser Phe Ser Asn Ser Leu Ser Gln Ser Pro Cys Pro Arg Glu
            500                 505                 510

Leu Gly Pro Asp Pro Leu Leu Ala Arg His Leu Glu Glu Val Glu Pro
```

```
            515                 520                 525
Glu Met Pro Cys Val Pro Gln Leu Ser Glu Pro Thr Thr Val Pro Gln
        530                 535                 540

Pro Glu Pro Glu Thr Trp Glu Gln Ile Leu Arg Arg Asn Val Leu Gln
545                 550                 555                 560

His Gly Ala Ala Ala Pro Val Ser Ala Pro Thr Ser Gly Tyr Gln
                565                 570                 575

Glu Phe Val His Ala Val Glu Gln Gly Gly Thr Gln Ala Ser Ala Val
                580                 585                 590

Val Gly Leu Gly Pro Pro Gly Glu Ala Gly Tyr Lys Ala Phe Ser Ser
                595                 600                 605

Leu Leu Ala Ser Ser Ala Val Ser Pro Glu Lys Cys Gly Phe Gly Ala
        610                 615                 620

Ser Ser Gly Glu Glu Gly Tyr Lys Pro Phe Gln Asp Leu Ile Pro Gly
625                 630                 635                 640

Cys Pro Gly Asp Pro Ala Pro Val Pro Val Pro Leu Phe Thr Phe Gly
                645                 650                 655

Leu Asp Arg Glu Pro Pro Arg Ser Pro Gln Ser Ser His Leu Pro Ser
                660                 665                 670

Ser Ser Pro Glu His Leu Gly Leu Glu Pro Gly Glu Lys Val Glu Asp
                675                 680                 685

Met Pro Lys Pro Pro Leu Pro Gln Glu Gln Ala Thr Asp Pro Leu Val
        690                 695                 700

Asp Ser Leu Gly Ser Gly Ile Val Tyr Ser Ala Leu Thr Cys His Leu
705                 710                 715                 720

Cys Gly His Leu Lys Gln Cys His Gly Gln Glu Asp Gly Gly Gln Thr
                725                 730                 735

Pro Val Met Ala Ser Pro Cys Cys Gly Cys Cys Cys Gly Asp Arg Ser
                740                 745                 750

Ser Pro Pro Thr Thr Pro Leu Arg Ala Pro Asp Pro Ser Pro Gly Gly
                755                 760                 765

Val Pro Leu Glu Ala Ser Leu Cys Pro Ala Ser Leu Ala Pro Ser Gly
        770                 775                 780

Ile Ser Glu Lys Ser Lys Ser Ser Ser Phe His Pro Ala Pro Gly
785                 790                 795                 800

Asn Ala Gln Ser Ser Ser Gln Thr Pro Lys Ile Val Asn Phe Val Ser
                805                 810                 815

Val Gly Pro Thr Tyr Met Arg Val Ser
                820                 825

<210> SEQ ID NO 7
<211> LENGTH: 258
<212> TYPE: PRT
<213> ORGANISM: Homo sapiens

<400> SEQUENCE: 7

Met Leu Pro Leu Cys Leu Val Ala Ala Leu Leu Ala Ala Gly Pro
1               5                   10                  15

Gly Pro Ser Leu Gly Asp Glu Ala Ile His Cys Pro Pro Cys Ser Glu
                20                  25                  30

Glu Lys Leu Ala Arg Cys Arg Pro Pro Val Gly Cys Glu Glu Leu Val
            35                  40                  45

Arg Glu Pro Gly Cys Gly Cys Cys Ala Thr Cys Ala Leu Gly Leu Gly
        50                  55                  60
```

```
Met Pro Cys Gly Val Tyr Thr Pro Arg Cys Gly Ser Gly Leu Arg Cys
 65                  70                  75                  80

Tyr Pro Pro Arg Gly Val Glu Lys Pro Leu His Thr Leu Met His Gly
                 85                  90                  95

Gln Gly Val Cys Met Glu Leu Ala Glu Ile Glu Ala Ile Gln Glu Ser
            100                 105                 110

Leu Gln Pro Ser Asp Lys Asp Glu Gly Asp His Pro Asn Asn Ser Phe
        115                 120                 125

Ser Pro Cys Ser Ala His Asp Arg Arg Cys Leu Gln Lys His Phe Ala
    130                 135                 140

Lys Ile Arg Asp Arg Ser Thr Ser Gly Gly Lys Met Lys Val Asn Gly
145                 150                 155                 160

Ala Pro Arg Glu Asp Ala Arg Pro Val Pro Gln Gly Ser Cys Gln Ser
                165                 170                 175

Glu Leu His Arg Ala Leu Glu Arg Leu Ala Ala Ser Gln Ser Arg Thr
            180                 185                 190

His Glu Asp Leu Tyr Ile Ile Pro Ile Pro Asn Cys Asp Arg Asn Gly
        195                 200                 205

Asn Phe His Pro Lys Gln Cys His Pro Ala Leu Asp Gly Gln Arg Gly
    210                 215                 220

Lys Cys Trp Cys Val Asp Arg Lys Thr Gly Val Lys Leu Pro Gly Gly
225                 230                 235                 240

Leu Glu Pro Lys Gly Glu Leu Asp Cys His Gln Leu Ala Asp Ser Phe
                245                 250                 255

Arg Glu

<210> SEQ ID NO 8
<211> LENGTH: 272
<212> TYPE: PRT
<213> ORGANISM: Homo sapiens

<400> SEQUENCE: 8

Met Val Leu Leu Thr Ala Val Leu Leu Leu Ala Ala Tyr Ala Gly
 1               5                  10                  15

Pro Ala Gln Ser Leu Gly Ser Phe Val His Cys Glu Pro Cys Asp Glu
                 20                  25                  30

Lys Ala Leu Ser Met Cys Pro Pro Ser Pro Leu Gly Cys Glu Leu Val
             35                  40                  45

Lys Glu Pro Gly Cys Gly Cys Cys Met Thr Cys Ala Leu Ala Glu Gly
         50                  55                  60

Gln Ser Cys Gly Val Tyr Thr Glu Arg Cys Ala Gln Gly Leu Arg Cys
 65                  70                  75                  80

Leu Pro Arg Gln Asp Glu Glu Lys Pro Leu His Ala Leu Leu His Gly
                 85                  90                  95

Arg Gly Val Cys Leu Asn Glu Lys Ser Tyr Arg Glu Gln Val Lys Ile
            100                 105                 110

Glu Arg Asp Ser Arg Glu His Glu Glu Pro Thr Thr Ser Glu Met Ala
        115                 120                 125

Glu Glu Thr Tyr Ser Pro Lys Ile Phe Arg Pro Lys His Thr Arg Ile
    130                 135                 140

Ser Glu Leu Lys Ala Glu Ala Val Lys Lys Asp Arg Arg Lys Lys Leu
145                 150                 155                 160

Thr Gln Ser Lys Phe Val Gly Gly Ala Glu Asn Thr Ala His Pro Arg
                165                 170                 175
```

Ile Ile Ser Ala Pro Glu Met Arg Gln Ser Glu Gln Gly Pro Cys
            180                 185                 190

Arg Arg His Met Glu Ala Ser Leu Gln Glu Leu Lys Ala Ser Pro Arg
        195                 200                 205

Met Val Pro Arg Ala Val Tyr Leu Pro Asn Cys Asp Arg Lys Gly Phe
    210                 215                 220

Tyr Lys Arg Lys Gln Cys Lys Pro Ser Arg Gly Arg Lys Arg Gly Ile
225                 230                 235                 240

Cys Trp Cys Val Asp Lys Tyr Gly Met Lys Leu Pro Gly Met Glu Tyr
                245                 250                 255

Val Asp Gly Asp Phe Gln Cys His Thr Phe Asp Ser Ser Asn Val Glu
            260                 265                 270

<210> SEQ ID NO 9
<211> LENGTH: 189
<212> TYPE: PRT
<213> ORGANISM: Homo sapiens

<400> SEQUENCE: 9

Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 10
<211> LENGTH: 200
<212> TYPE: PRT
<213> ORGANISM: Homo sapiens

<400> SEQUENCE: 10

Met Lys Leu Asp Met Thr Gly Asp Cys Thr Pro Val Leu Val Leu Met
1               5                   10                  15

Ala Ala Val Leu Thr Val Thr Gly Ala Val Pro Val Ala Arg Leu His
            20                  25                  30

Gly Ala Leu Pro Asp Ala Arg Gly Cys His Ile Ala Gln Phe Lys Ser
        35                  40                  45

```
Leu Ser Pro Gln Glu Leu Gln Ala Phe Lys Arg Ala Lys Asp Ala Leu
        50                  55                  60

Glu Glu Ser Leu Leu Lys Asp Cys Arg Cys His Ser Arg Leu Phe
65                  70                  75                  80

Pro Arg Thr Trp Asp Leu Arg Gln Leu Gln Val Arg Glu Arg Pro Met
                    85                  90                  95

Ala Leu Glu Ala Glu Leu Ala Leu Thr Leu Lys Val Leu Glu Ala Thr
                100                 105                 110

Ala Asp Thr Asp Pro Ala Leu Val Asp Val Leu Asp Gln Pro Leu His
                115                 120                 125

Thr Leu His His Ile Leu Ser Gln Phe Arg Ala Cys Ile Gln Pro Gln
130                 135                 140

Pro Thr Ala Gly Pro Arg Thr Arg Gly Arg Leu His His Trp Leu Tyr
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Asp Leu Asn Cys
                180                 185                 190

Val Ala Ser Gly Asp Leu Cys Val
                195                 200

<210> SEQ ID NO 11
<211> LENGTH: 270
<212> TYPE: PRT
<213> ORGANISM: Homo sapiens

<400> SEQUENCE: 11

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
                20                  25                  30

Gln Gln Lys Ala Lys Glu Val Cys Pro Met Tyr Phe Met Lys Leu Arg
            35                  40                  45

Ser Gly Leu Met Ile Lys Lys Glu Ala Cys Tyr Phe Arg Arg Glu Thr
50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
                100                 105                 110

Ile Thr Gly Ile Ser Pro Ile Thr Glu Tyr Leu Ala Ser Leu Ser Thr
                115                 120                 125

Tyr Asn Asp Gln Ser Ile Thr Phe Ala Leu Glu Asp Glu Ser Tyr Glu
130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
                180                 185                 190

Trp Leu His Ala Asn Asn Lys Glu His Ser Val Glu Leu His Lys Cys
            195                 200                 205

Glu Lys Pro Leu Pro Asp Gln Ala Phe Phe Val Leu His Asn Met His
210                 215                 220
```

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
            245                 250                 255

Asn Leu Cys Thr Glu Asn Ile Leu Phe Lys Leu Ser Glu Thr
        260                 265                 270

<210> SEQ ID NO 12
<211> LENGTH: 141
<212> TYPE: PRT
<213> ORGANISM: Homo sapiens

<400> SEQUENCE: 12

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
        35                  40                  45

Val Asn Thr Thr Ile Cys Ala Gly Tyr Cys Pro Thr Met Met Arg Val
50                  55                  60

Leu Gln Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
            100                 105                 110

Cys Arg Arg Ser Thr Ser Asp Cys Gly Gly Pro Lys Asp His Pro Leu
        115                 120                 125

Thr Cys Asp His Pro Gln Leu Ser Gly Leu Leu Phe Leu
        130                 135                 140

<210> SEQ ID NO 13
<211> LENGTH: 469
<212> TYPE: PRT
<213> ORGANISM: Homo sapiens

<400> SEQUENCE: 13

Met His Ser Phe Pro Pro Leu Leu Leu Leu Phe Trp Gly Val Val
1               5                   10                  15

Ser His Ser Phe Pro Ala Thr Leu Glu Thr Gln Glu Gln Asp Val Asp
            20                  25                  30

Leu Val Gln Lys Tyr Leu Glu Lys Tyr Tyr Asn Leu Lys Asn Asp Gly
        35                  40                  45

Arg Gln Val Glu Lys Arg Arg Asn Ser Gly Pro Val Val Glu Lys Leu
50                  55                  60

Lys Gln Met Gln Glu Phe Phe Gly Leu Lys Val Thr Gly Lys Pro Asp
65                  70                  75                  80

Ala Glu Thr Leu Lys Val Met Lys Gln Pro Arg Cys Gly Val Pro Asp
                85                  90                  95

Val Ala Gln Phe Val Leu Thr Glu Gly Asn Pro Arg Trp Glu Gln Thr
            100                 105                 110

His Leu Thr Tyr Arg Ile Glu Asn Tyr Thr Pro Asp Leu Pro Arg Ala
        115                 120                 125

Asp Val Asp His Ala Ile Glu Lys Ala Phe Gln Leu Trp Ser Asn Val
        130                 135                 140

Thr Pro Leu Thr Phe Thr Lys Val Ser Glu Gly Gln Ala Asp Ile Met
145                 150                 155                 160

Ile Ser Phe Val Arg Gly Asp His Arg Asp Asn Ser Pro Phe Asp Gly
                165                 170                 175

```
Pro Gly Gly Asn Leu Ala His Ala Phe Gln Pro Gly Pro Gly Ile Gly
                180                 185                 190

Gly Asp Ala His Phe Asp Glu Asp Arg Trp Thr Asn Asn Phe Arg
            195                 200                 205

Glu Tyr Asn Leu His Arg Val Ala Ala His Glu Leu Gly His Ser Leu
        210                 215                 220

Gly Leu Ser His Ser Thr Asp Ile Gly Ala Leu Met Tyr Pro Ser Tyr
225                 230                 235                 240

Thr Phe Ser Gly Asp Val Gln Leu Ala Gln Asp Ile Asp Gly Ile
                245                 250                 255

Gln Ala Ile Tyr Gly Arg Ser Gln Asn Pro Val Gln Pro Ile Gly Pro
            260                 265                 270

Gln Thr Pro Lys Ala Cys Asp Ser Lys Leu Thr Phe Asp Ala Ile Thr
        275                 280                 285

Thr Ile Arg Gly Glu Val Met Phe Phe Lys Asp Arg Phe Tyr Met Arg
        290                 295                 300

Thr Asn Pro Phe Tyr Pro Glu Val Glu Leu Asn Phe Ile Ser Val Phe
305                 310                 315                 320

Trp Pro Gln Leu Pro Asn Gly Leu Glu Ala Ala Tyr Glu Phe Ala Asp
                325                 330                 335

Arg Asp Glu Val Arg Phe Phe Lys Gly Asn Lys Tyr Trp Ala Val Gln
            340                 345                 350

Gly Gln Asn Val Leu His Gly Tyr Pro Lys Asp Ile Tyr Ser Ser Phe
        355                 360                 365

Gly Phe Pro Arg Thr Val Lys His Ile Asp Ala Ala Leu Ser Glu Glu
        370                 375                 380

Asn Thr Gly Lys Thr Tyr Phe Phe Val Ala Asn Lys Tyr Trp Arg Tyr
385                 390                 395                 400

Asp Glu Tyr Lys Arg Ser Met Asp Pro Gly Tyr Pro Lys Met Ile Ala
                405                 410                 415

His Asp Phe Pro Gly Ile Gly His Lys Val Asp Ala Val Phe Met Lys
            420                 425                 430

Asp Gly Phe Phe Tyr Phe Phe His Gly Thr Arg Gln Tyr Lys Phe Asp
        435                 440                 445

Pro Lys Thr Lys Arg Ile Leu Thr Leu Gln Lys Ala Asn Ser Trp Phe
450                 455                 460

Asn Cys Arg Lys Asn
465

<210> SEQ ID NO 14
<211> LENGTH: 858
<212> TYPE: PRT
<213> ORGANISM: Homo sapiens

<400> SEQUENCE: 14

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
                20                  25                  30

Val Gly Glu Ser Lys Phe Phe Leu Cys Gln Val Ala Gly Asp Ala Lys
            35                  40                  45

Asp Lys Asp Ile Ser Trp Phe Ser Pro Asn Gly Glu Lys Leu Thr Pro
        50                  55                  60

Asn Gln Gln Arg Ile Ser Val Val Trp Asn Asp Asp Ser Ser Ser Thr
65                  70                  75                  80
```

```
Leu Thr Ile Tyr Asn Ala Asn Ile Asp Asp Ala Gly Ile Tyr Lys Cys
                 85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
    210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
    290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350

Lys Ala Ser Trp Thr Arg Pro Glu Lys Gln Glu Thr Leu Asp Gly His
        355                 360                 365

Met Val Val Arg Ser His Ala Arg Val Ser Ser Leu Thr Leu Lys Ser
    370                 375                 380

Ile Gln Tyr Thr Asp Ala Gly Glu Tyr Ile Cys Thr Ala Ser Asn Thr
385                 390                 395                 400

Ile Gly Gln Asp Ser Gln Ser Met Tyr Leu Glu Val Gln Tyr Ala Pro
                405                 410                 415

Lys Leu Gln Gly Pro Val Ala Val Tyr Thr Trp Glu Gly Asn Gln Val
            420                 425                 430

Asn Ile Thr Cys Glu Val Phe Ala Tyr Pro Ser Ala Thr Ile Ser Trp
        435                 440                 445

Phe Arg Asp Gly Gln Leu Leu Pro Ser Ser Asn Tyr Ser Asn Ile Lys
    450                 455                 460

Ile Tyr Asn Thr Pro Ser Ala Ser Tyr Leu Glu Val Thr Pro Asp Ser
465                 470                 475                 480

Glu Asn Asp Phe Gly Asn Tyr Asn Cys Thr Ala Val Asn Arg Ile Gly
                485                 490                 495
```

-continued

Gln Glu Ser Leu Glu Phe Ile Leu Val Gln Ala Asp Thr Pro Ser Ser
                500                 505                 510

Pro Ser Ile Asp Gln Val Glu Pro Tyr Ser Ser Thr Ala Gln Val Gln
            515                 520                 525

Phe Asp Glu Pro Glu Ala Thr Gly Gly Val Pro Ile Leu Lys Tyr Lys
        530                 535                 540

Ala Glu Trp Arg Ala Val Gly Glu Glu Val Trp His Ser Lys Trp Tyr
545                 550                 555                 560

Asp Ala Lys Glu Ala Ser Met Glu Gly Ile Val Thr Ile Val Gly Leu
                565                 570                 575

Lys Pro Glu Thr Thr Tyr Ala Val Arg Leu Ala Ala Leu Asn Gly Lys
            580                 585                 590

Gly Leu Gly Glu Ile Ser Ala Ala Ser Glu Phe Lys Thr Gln Pro Val
        595                 600                 605

Gln Gly Glu Pro Ser Ala Pro Lys Leu Glu Gly Gln Met Gly Glu Asp
610                 615                 620

Gly Asn Ser Ile Lys Val Asn Leu Ile Lys Gln Asp Asp Gly Gly Ser
625                 630                 635                 640

Pro Ile Arg His Tyr Leu Val Arg Tyr Arg Ala Leu Ser Ser Glu Trp
                645                 650                 655

Lys Pro Glu Ile Arg Leu Pro Ser Gly Ser Asp His Val Met Leu Lys
            660                 665                 670

Ser Leu Asp Trp Asn Ala Glu Tyr Glu Val Tyr Val Val Ala Glu Asn
        675                 680                 685

Gln Gln Gly Lys Ser Lys Ala Ala His Phe Val Phe Arg Thr Ser Ala
        690                 695                 700

Gln Pro Thr Ala Ile Pro Ala Asn Gly Ser Pro Thr Ser Gly Leu Ser
705                 710                 715                 720

Thr Gly Ala Ile Val Gly Ile Leu Ile Val Ile Phe Val Leu Leu Leu
                725                 730                 735

Val Val Val Asp Ile Thr Cys Tyr Phe Leu Asn Lys Cys Gly Leu Phe
            740                 745                 750

Met Cys Ile Ala Val Asn Leu Cys Gly Lys Ala Gly Pro Gly Ala Lys
        755                 760                 765

Gly Lys Asp Met Glu Glu Gly Lys Ala Ala Phe Ser Lys Asp Glu Ser
        770                 775                 780

Lys Glu Pro Ile Val Glu Val Arg Thr Glu Glu Arg Thr Pro Asn
785                 790                 795                 800

His Asp Gly Gly Lys His Thr Glu Pro Asn Glu Thr Thr Pro Leu Thr
                805                 810                 815

Glu Pro Glu Lys Gly Pro Val Glu Ala Lys Pro Glu Cys Gln Glu Thr
            820                 825                 830

Glu Thr Lys Pro Ala Pro Ala Glu Val Lys Thr Val Pro Asn Asp Ala
        835                 840                 845

Thr Gln Thr Lys Glu Asn Glu Ser Lys Ala
        850                 855

<210> SEQ ID NO 15
<211> LENGTH: 36
<212> TYPE: PRT
<213> ORGANISM: Homo sapiens

<400> SEQUENCE: 15

His Ser Pro Pro Pro Ala Ser Ala Ser Ser Ser Thr Pro Val Pro
1               5                   10                  15

Leu Ser Pro Pro Asp Thr Thr Trp Pro Leu Pro Ala Leu Ala Thr Thr
            20                  25                  30

Glu Pro Ala Lys
        35

<210> SEQ ID NO 16
<211> LENGTH: 25
<212> TYPE: PRT
<213> ORGANISM: Homo sapiens

<400> SEQUENCE: 16

Asn Gly Ser Pro Thr Ser Gly Leu Ser Thr Gly Ala Ile Val Gly Ile
1               5                   10                  15

Leu Ile Val Ile Phe Val Leu Leu Leu
            20                  25

<210> SEQ ID NO 17
<211> LENGTH: 25
<212> TYPE: PRT
<213> ORGANISM: Homo sapiens

<400> SEQUENCE: 17

Thr Leu Gly Gly Asn Ser Ala Ser Tyr Thr Phe Val Ser Leu Leu Phe
1               5                   10                  15

Ser Ala Val Thr Leu Leu Leu Leu Cys
            20                  25

<210> SEQ ID NO 18
<211> LENGTH: 25
<212> TYPE: PRT
<213> ORGANISM: Homo sapiens

<400> SEQUENCE: 18

Asn Gly Ser Pro Thr Ser Gly Leu Ser Thr Gly Ala Ile Val Gly Ile
1               5                   10                  15

Leu Ile Val Ile Phe Val Leu Leu Leu
            20                  25

<210> SEQ ID NO 19
<211> LENGTH: 25
<212> TYPE: PRT
<213> ORGANISM: Homo sapiens

<400> SEQUENCE: 19

Thr Leu Gly Gly Asn Ser Ala Ser Tyr Thr Phe Val Ser Leu Leu Phe
1               5                   10                  15

Ser Ala Val Thr Leu Leu Leu Leu Cys
            20                  25

<210> SEQ ID NO 20
<211> LENGTH: 10
<212> TYPE: PRT
<213> ORGANISM: Homo sapiens

<400> SEQUENCE: 20

Trp Lys Pro Glu Ile Arg Leu Pro Ser Gly
1               5                   10

<210> SEQ ID NO 21
<211> LENGTH: 57
<212> TYPE: PRT
<213> ORGANISM: Homo sapiens

<400> SEQUENCE: 21

| His | Ser | Pro | Pro | Pro | Ala | Ser | Ala | Ser | Ser | Thr | Pro | Val | Pro |
| 1 | | | | 5 | | | | | 10 | | | | 15 |

| Leu | Ser | Pro | Pro | Asp | Thr | Thr | Trp | Pro | Leu | Pro | Ala | Leu | Ala | Thr | Thr |
| | | | 20 | | | | | 25 | | | | | 30 | | |

| Glu | Pro | Ala | Lys | Asn | Ile | Ala | Gln | Asn | His | Cys | Cys | Asn | Met | Phe | Gln |
| | | 35 | | | | | 40 | | | | | 45 | | | |

| Ala | Gly | Leu | His | Asn | Ala | Leu | Met | Lys |
| | 50 | | | | | 55 | | |

<210> SEQ ID NO 22
<211> LENGTH: 418
<212> TYPE: PRT
<213> ORGANISM: Homo sapiens

<400> SEQUENCE: 22

| Met | Gln | Ala | Leu | Val | Leu | Leu | Leu | Cys | Ile | Gly | Ala | Leu | Leu | Gly | His |
| 1 | | | | 5 | | | | | 10 | | | | | 15 | |

| Ser | Ser | Cys | Gln | Asn | Pro | Ala | Ser | Pro | Pro | Glu | Glu | Gly | Ser | Pro | Asp |
| | | | 20 | | | | | 25 | | | | | 30 | | |

| Pro | Asp | Ser | Thr | Gly | Ala | Leu | Val | Glu | Glu | Glu | Asp | Pro | Phe | Phe | Lys |
| | | 35 | | | | | 40 | | | | | 45 | | | |

| Val | Pro | Val | Asn | Lys | Leu | Ala | Ala | Ala | Val | Ser | Asn | Phe | Gly | Tyr | Asp |
| | 50 | | | | | 55 | | | | | 60 | | | | |

| Leu | Tyr | Arg | Val | Arg | Ser | Ser | Met | Ser | Pro | Thr | Thr | Asn | Val | Leu | Leu |
| 65 | | | | | 70 | | | | | 75 | | | | | 80 |

| Ser | Pro | Leu | Ser | Val | Ala | Thr | Ala | Leu | Ser | Ala | Leu | Ser | Leu | Gly | Ala |
| | | | | 85 | | | | | 90 | | | | | 95 | |

| Glu | Gln | Arg | Thr | Glu | Ser | Ile | Ile | His | Arg | Ala | Leu | Tyr | Tyr | Asp | Leu |
| | | | 100 | | | | | 105 | | | | | 110 | | |

| Ile | Ser | Ser | Pro | Asp | Ile | His | Gly | Thr | Tyr | Lys | Glu | Leu | Leu | Asp | Thr |
| | | 115 | | | | | 120 | | | | | 125 | | | |

| Val | Thr | Ala | Pro | Gln | Lys | Asn | Leu | Lys | Ser | Ala | Ser | Arg | Ile | Val | Phe |
| | 130 | | | | | 135 | | | | | 140 | | | | |

| Glu | Lys | Lys | Leu | Arg | Ile | Lys | Ser | Ser | Phe | Val | Ala | Pro | Leu | Glu | Lys |
| 145 | | | | | 150 | | | | | 155 | | | | | 160 |

| Ser | Tyr | Gly | Thr | Arg | Pro | Arg | Val | Leu | Thr | Gly | Asn | Pro | Arg | Leu | Asp |
| | | | | 165 | | | | | 170 | | | | | 175 | |

| Leu | Gln | Glu | Ile | Asn | Asn | Trp | Val | Gln | Ala | Gln | Met | Lys | Gly | Lys | Leu |
| | | | 180 | | | | | 185 | | | | | 190 | | |

| Ala | Arg | Ser | Thr | Lys | Glu | Ile | Pro | Asp | Glu | Ile | Ser | Ile | Leu | Leu | Leu |
| | | 195 | | | | | 200 | | | | | 205 | | | |

| Gly | Val | Ala | His | Phe | Lys | Gly | Gln | Trp | Val | Thr | Lys | Phe | Asp | Ser | Arg |
| | 210 | | | | | 215 | | | | | 220 | | | | |

| Lys | Thr | Ser | Leu | Glu | Asp | Phe | Tyr | Leu | Asp | Glu | Glu | Arg | Thr | Val | Arg |
| 225 | | | | | 230 | | | | | 235 | | | | | 240 |

| Val | Pro | Met | Met | Ser | Asp | Pro | Lys | Ala | Val | Leu | Arg | Tyr | Gly | Leu | Asp |
| | | | | 245 | | | | | 250 | | | | | 255 | |

| Ser | Asp | Leu | Ser | Cys | Lys | Ile | Ala | Gln | Leu | Pro | Leu | Thr | Gly | Ser | Met |
| | | | 260 | | | | | 265 | | | | | 270 | | |

| Ser | Ile | Ile | Phe | Phe | Leu | Pro | Leu | Lys | Val | Thr | Gln | Asn | Leu | Thr | Leu |
| | | 275 | | | | | 280 | | | | | 285 | | | |

| Ile | Glu | Glu | Ser | Leu | Thr | Ser | Glu | Phe | Ile | His | Asp | Ile | Asp | Arg | Glu |
| | 290 | | | | | 295 | | | | | 300 | | | | |

```
Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 23
<211> LENGTH: 211
<212> TYPE: PRT
<213> ORGANISM: Homo sapiens

<400> SEQUENCE: 23

Met Arg Thr Leu Ala Cys Leu Leu Leu Leu Gly Cys Gly Tyr Leu Ala
1               5                   10                  15

His Val Leu Ala Glu Glu Ala Glu Ile Pro Arg Glu Val Ile Glu Arg
                20                  25                  30

Leu Ala Arg Ser Gln Ile His Ser Ile Arg Asp Leu Gln Arg Leu Leu
            35                  40                  45

Glu Ile Asp Ser Val Gly Ser Glu Asp Ser Leu Asp Thr Ser Leu Arg
        50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
                100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
        130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Gly Arg Pro Arg Glu Ser Gly Lys Lys Arg Lys Arg Lys Arg Leu
        195                 200                 205

Lys Pro Thr
    210

<210> SEQ ID NO 24
<211> LENGTH: 1356
<212> TYPE: PRT
<213> ORGANISM: Homo sapiens
```

<400> SEQUENCE: 24

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val

```
                    405                 410                 415
Val Tyr Val Pro Pro Gln Ile Gly Glu Lys Ser Leu Ile Ser Pro Val
                420                 425                 430

Asp Ser Tyr Gln Tyr Gly Thr Thr Gln Thr Leu Thr Cys Thr Val Tyr
            435                 440                 445

Ala Ile Pro Pro His His Ile His Trp Tyr Trp Gln Leu Glu Glu
450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
            515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
    690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Leu
        755                 760                 765

Val Gly Thr Ala Val Ile Ala Met Phe Phe Trp Leu Leu Leu Val Ile
    770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830
```

Arg Leu Lys Leu Gly Lys Pro Leu Gly Arg Gly Ala Phe Gly Gln Val
        835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
                900                 905                 910

Met Val Ile Val Glu Phe Cys Lys Phe Gly Asn Leu Ser Thr Tyr Leu
                915                 920                 925

Arg Ser Lys Arg Asn Glu Phe Val Pro Tyr Lys Thr Lys Gly Ala Arg
930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Glu Ala Pro
                980                 985                 990

Glu Asp Leu Tyr Lys Asp Phe Leu Thr Leu Glu His Leu Ile Cys Tyr
                995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

```
Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 25
<211> LENGTH: 1298
<212> TYPE: PRT
<213> ORGANISM: Homo sapiens

<400> SEQUENCE: 25

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
                20                  25                  30

Asn Ile Thr Glu Glu Ser His Val Ile Asp Thr Gly Asp Ser Leu Ser
                35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
                100                 105                 110

Tyr Lys Tyr Ile Lys Ala Arg Ile Glu Gly Thr Thr Ala Ala Ser Ser
            115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
                180                 185                 190

Val Ser Thr Pro Leu Leu His Asp Ala Leu Tyr Leu Gln Cys Glu Thr
            195                 200                 205

Thr Trp Gly Asp Gln Asp Phe Leu Ser Asn Pro Phe Leu Val His Ile
    210                 215                 220

Thr Gly Asn Glu Leu Tyr Asp Ile Gln Leu Leu Pro Arg Lys Ser Leu
225                 230                 235                 240
```

```
Glu Leu Leu Val Gly Glu Lys Leu Val Leu Asn Cys Thr Val Trp Ala
                245                 250                 255
Glu Phe Asn Ser Gly Val Thr Phe Asp Trp Asp Tyr Pro Gly Lys Gln
            260                 265                 270
Ala Glu Arg Gly Lys Trp Val Pro Glu Arg Arg Ser Gln Gln Thr His
        275                 280                 285
Thr Glu Leu Ser Ser Ile Leu Thr Ile His Asn Val Ser Gln His Asp
290                 295                 300
Leu Gly Ser Tyr Val Cys Lys Ala Asn Asn Gly Ile Gln Arg Phe Arg
305                 310                 315                 320
Glu Ser Thr Glu Val Ile Val His Glu Asn Pro Phe Ile Ser Val Glu
                325                 330                 335
Trp Leu Lys Gly Pro Ile Leu Glu Ala Thr Ala Gly Asp Glu Leu Val
            340                 345                 350
Lys Leu Pro Val Lys Leu Ala Ala Tyr Pro Pro Pro Glu Phe Gln Trp
        355                 360                 365
Tyr Lys Asp Gly Lys Ala Leu Ser Gly Arg His Ser Pro His Ala Leu
        370                 375                 380
Val Leu Lys Glu Val Thr Glu Ala Ser Thr Gly Thr Tyr Thr Leu Ala
385                 390                 395                 400
Leu Trp Asn Ser Ala Ala Gly Leu Arg Arg Asn Ile Ser Leu Glu Leu
                405                 410                 415
Val Val Asn Val Pro Pro Gln Ile His Glu Lys Glu Ala Ser Ser Pro
            420                 425                 430
Ser Ile Tyr Ser Arg His Ser Arg Gln Ala Leu Thr Cys Thr Ala Tyr
        435                 440                 445
Gly Val Pro Leu Pro Leu Ser Ile Gln Trp His Trp Arg Pro Trp Thr
        450                 455                 460
Pro Cys Lys Met Phe Ala Gln Arg Ser Leu Arg Arg Arg Gln Gln Gln
465                 470                 475                 480
Asp Leu Met Pro Gln Cys Arg Asp Trp Arg Ala Val Thr Thr Gln Asp
                485                 490                 495
Ala Val Asn Pro Ile Glu Ser Leu Asp Thr Trp Thr Glu Phe Val Glu
            500                 505                 510
Gly Lys Asn Lys Thr Val Ser Lys Leu Val Ile Gln Asn Ala Asn Val
        515                 520                 525
Ser Ala Met Tyr Lys Cys Val Val Ser Asn Lys Val Gly Gln Asp Glu
530                 535                 540
Arg Leu Ile Tyr Phe Tyr Val Thr Thr Ile Pro Asp Gly Phe Thr Ile
545                 550                 555                 560
Glu Ser Lys Pro Ser Glu Glu Leu Leu Glu Gly Gln Pro Val Leu Leu
                565                 570                 575
Ser Cys Gln Ala Asp Ser Tyr Lys Tyr Glu His Leu Arg Trp Tyr Arg
            580                 585                 590
Leu Asn Leu Ser Thr Leu His Asp Ala His Gly Asn Pro Leu Leu Leu
        595                 600                 605
Asp Cys Lys Asn Val His Leu Phe Ala Thr Pro Leu Ala Ala Ser Leu
        610                 615                 620
Glu Glu Val Ala Pro Gly Ala Arg His Ala Thr Leu Ser Leu Ser Ile
625                 630                 635                 640
Pro Arg Val Ala Pro Glu His Glu Gly His Tyr Val Cys Glu Val Gln
                645                 650                 655
```

```
Asp Arg Arg Ser His Asp Lys His Cys His Lys Lys Tyr Leu Ser Val
            660                 665                 670

Gln Ala Leu Glu Ala Pro Arg Leu Thr Gln Asn Leu Thr Asp Leu Leu
            675                 680                 685

Val Asn Val Ser Asp Ser Leu Glu Met Gln Cys Leu Val Ala Gly Ala
        690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
                725                 730                 735

Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
        755                 760                 765

Glu Asp Lys Gly Ser Met Glu Ile Val Ile Leu Val Gly Thr Gly Val
    770                 775                 780

Ile Ala Val Phe Phe Trp Val Leu Leu Leu Ile Phe Cys Asn Met
785                 790                 795                 800

Arg Arg Pro Ala His Ala Asp Ile Lys Thr Gly Tyr Leu Ser Ile Ile
            805                 810                 815

Met Asp Pro Gly Glu Val Pro Leu Glu Glu Gln Cys Glu Tyr Leu Ser
        820                 825                 830

Tyr Asp Ala Ser Gln Trp Glu Phe Pro Arg Glu Arg Leu His Leu Gly
            835                 840                 845

Arg Val Leu Gly Tyr Gly Ala Phe Gly Lys Val Val Glu Ala Ser Ala
850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
            885                 890                 895

Leu Lys Ile Leu Ile His Ile Gly Asn His Leu Asn Val Val Asn Leu
        900                 905                 910

Leu Gly Ala Cys Thr Lys Pro Gln Gly Pro Leu Met Val Ile Val Glu
    915                 920                 925

Phe Cys Lys Tyr Gly Asn Leu Ser Asn Phe Leu Arg Ala Lys Arg Asp
930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Arg Pro Gly Ser
            965                 970                 975

Ser Asp Arg Val Leu Phe Ala Arg Phe Ser Lys Thr Glu Gly Gly Ala
        980                 985                 990

Arg Arg Ala Ser Pro Asp Gln Glu  Ala Glu Asp Leu Trp Leu Ser Pro
    995                 1000                1005

Leu Thr Met Glu Asp Leu Val Cys Tyr Ser Phe Gln Val Ala Arg
    1010                1015                1020

Gly Met Glu Phe Leu Ala Ser Arg Lys Cys Ile His Arg Asp Leu
    1025                1030                1035

Ala Ala Arg Asn Ile Leu Leu Ser Glu Ser Asp Val Val Lys Ile
    1040                1045                1050

Cys Asp Phe Gly Leu Ala Arg Asp Ile Tyr Lys Asp Pro Asp Tyr
    1055                1060                1065

Val Arg Lys Gly Ser Ala Arg Leu Pro Leu Lys Trp Met Ala Pro
```

```
                    1070                1075                1080
Glu Ser Ile Phe Asp Lys Val Tyr Thr Thr Gln Ser Asp Val Trp
    1085                1090                1095

Ser Phe Gly Val Leu Leu Trp Glu Ile Phe Ser Leu Gly Ala Ser
    1100                1105                1110

Pro Tyr Pro Gly Val Gln Ile Asn Glu Glu Phe Cys Gln Arg Leu
    1115                1120                1125

Arg Asp Gly Thr Arg Met Arg Ala Pro Glu Leu Ala Thr Pro Ala
    1130                1135                1140

Ile Arg Arg Ile Met Leu Asn Cys Trp Ser Gly Asp Pro Lys Ala
    1145                1150                1155

Arg Pro Ala Phe Ser Glu Leu Val Glu Ile Leu Gly Asp Leu Leu
    1160                1165                1170

Gln Gly Arg Gly Leu Gln Glu Glu Glu Glu Val Cys Met Ala Pro
    1175                1180                1185

Arg Ser Ser Gln Ser Ser Glu Glu Gly Ser Phe Ser Gln Val Ser
    1190                1195                1200

Thr Met Ala Leu His Ile Ala Gln Ala Asp Ala Glu Asp Ser Pro
    1205                1210                1215

Pro Ser Leu Gln Arg His Ser Leu Ala Ala Arg Tyr Tyr Asn Trp
    1220                1225                1230

Val Ser Phe Pro Gly Cys Leu Ala Arg Gly Ala Glu Thr Arg Gly
    1235                1240                1245

Ser Ser Arg Met Lys Thr Phe Glu Glu Phe Pro Met Thr Pro Thr
    1250                1255                1260

Thr Tyr Lys Gly Ser Val Asp Asn Gln Thr Asp Ser Gly Met Val
    1265                1270                1275

Leu Ala Ser Glu Glu Phe Glu Gln Ile Glu Ser Arg His Arg Gln
    1280                1285                1290

Glu Ser Gly Phe Arg
    1295

<210> SEQ ID NO 26
<211> LENGTH: 595
<212> TYPE: PRT
<213> ORGANISM: Homo sapiens

<400> SEQUENCE: 26

Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
                20                  25                  30

Pro Ser His Tyr Tyr Asp Lys Ala Val Arg Arg Cys Cys Tyr Arg Cys
            35                  40                  45

Pro Met Gly Leu Phe Pro Thr Gln Gln Cys Pro Gln Arg Pro Thr Asp
        50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe His
        115                 120                 125
```

-continued

Ser Val Cys Pro Ala Gly Met Ile Val Lys Phe Pro Gly Thr Ala Gln
130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Cys Ala Arg Cys Val Pro Tyr Pro
    290                 295                 300

Ile Cys Ala Ala Glu Thr Val Thr Lys Pro Gln Asp Met Ala Glu Lys
305                 310                 315                 320

Asp Thr Thr Phe Glu Ala Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
        355                 360                 365

Ser Ala Pro Val Ala Leu Ser Ser Thr Gly Lys Pro Val Leu Asp Ala
370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
        515                 520                 525

Thr Val Lys Ala Glu Leu Pro Glu Gly Arg Gly Leu Ala Gly Pro Ala
530                 535                 540

Glu Pro Glu Leu Glu Glu Glu Leu Glu Ala Asp His Thr Pro His Tyr

```
                545                 550                 555                 560
Pro Glu Gln Glu Thr Glu Pro Leu Gly Ser Cys Ser Asp Val Met
                565                 570                 575

Leu Ser Val Glu Glu Glu Gly Lys Glu Asp Pro Leu Pro Thr Ala Ala
                580                 585                 590

Ser Gly Lys
        595

<210> SEQ ID NO 27
<211> LENGTH: 609
<212> TYPE: PRT
<213> ORGANISM: Homo sapiens

<400> SEQUENCE: 27

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
                20                  25                  30

Asp Ser Tyr Gln Cys Thr Ala Glu Ile Ser Leu Ala Asp Leu Ala Thr
            35                  40                  45

Ile Phe Phe Ala Gln Phe Val Gln Glu Ala Thr Tyr Lys Glu Val Ser
50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
                100                 105                 110

Cys Cys Ser Gln Ser Glu Glu Gly Arg His Asn Cys Phe Leu Ala His
            115                 120                 125

Lys Lys Pro Thr Pro Ala Ser Ile Pro Leu Phe Gln Val Pro Glu Pro
130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
            195                 200                 205

Val Thr Lys Glu Leu Arg Glu Ser Ser Leu Leu Asn Gln His Ala Cys
210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
                260                 265                 270

Asp Val Leu Asp Cys Leu Gln Asp Gly Glu Lys Ile Met Ser Tyr Ile
            275                 280                 285

Cys Ser Gln Gln Asp Thr Leu Ser Asn Lys Ile Thr Glu Cys Cys Lys
            290                 295                 300

Leu Thr Thr Leu Glu Arg Gly Gln Cys Ile Ile His Ala Glu Asn Asp
305                 310                 315                 320
```

```
Glu Lys Pro Glu Gly Leu Ser Pro Asn Leu Asn Arg Phe Leu Gly Asp
            325                 330                 335

Arg Asp Phe Asn Gln Phe Ser Ser Gly Glu Lys Asn Ile Phe Leu Ala
        340                 345                 350

Ser Phe Val His Glu Tyr Ser Arg Arg His Pro Gln Leu Ala Val Ser
        355                 360                 365

Val Ile Leu Arg Val Ala Lys Gly Tyr Gln Glu Leu Leu Glu Lys Cys
370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
        435                 440                 445

Ala Ile Thr Arg Lys Met Ala Ala Thr Ala Ala Thr Cys Cys Gln Leu
    450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
                485                 490                 495

Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
        515                 520                 525

Asp Lys Phe Ile Phe His Lys Asp Leu Cys Gln Ala Gln Gly Val Ala
        530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
                565                 570                 575

Gly Leu Leu Glu Lys Cys Cys Gln Gly Gln Glu Gln Glu Val Cys Phe
            580                 585                 590

Ala Glu Glu Gly Gln Lys Leu Ile Ser Lys Thr Arg Ala Ala Leu Gly
        595                 600                 605

Val

<210> SEQ ID NO 28
<211> LENGTH: 415
<212> TYPE: PRT
<213> ORGANISM: Homo sapiens

<400> SEQUENCE: 28

Met Ser Pro Phe Leu Tyr Leu Val Leu Leu Val Leu Gly Leu His Ala
1               5                   10                  15

Thr Ile His Cys Ala Ser Pro Glu Gly Lys Val Thr Ala Cys His Ser
            20                  25                  30

Ser Gln Pro Asn Ala Thr Leu Tyr Lys Met Ser Ser Ile Asn Ala Asp
        35                  40                  45

Phe Ala Phe Asn Leu Tyr Arg Arg Phe Thr Val Glu Thr Pro Asp Lys
    50                  55                  60

Asn Ile Phe Phe Ser Pro Val Ser Ile Ser Ala Ala Leu Val Met Leu
65                  70                  75                  80
```

```
Ser Phe Gly Ala Cys Cys Ser Thr Gln Thr Glu Ile Val Glu Thr Leu
                85                  90                  95

Gly Phe Asn Leu Thr Asp Thr Pro Met Val Glu Ile Gln His Gly Phe
            100                 105                 110

Gln His Leu Ile Cys Ser Leu Asn Phe Pro Lys Lys Glu Leu Glu Leu
        115                 120                 125

Gln Ile Gly Asn Ala Leu Phe Ile Gly Lys His Leu Lys Pro Leu Ala
    130                 135                 140

Lys Phe Leu Asn Asp Val Lys Thr Leu Tyr Glu Thr Glu Val Phe Ser
145                 150                 155                 160

Thr Asp Phe Ser Asn Ile Ser Ala Ala Lys Gln Glu Ile Asn Ser His
                165                 170                 175

Val Glu Met Gln Thr Lys Gly Lys Val Val Gly Leu Ile Gln Asp Leu
            180                 185                 190

Lys Pro Asn Thr Ile Met Val Leu Val Asn Tyr Ile His Phe Lys Ala
        195                 200                 205

Gln Trp Ala Asn Pro Phe Asp Pro Ser Lys Thr Glu Asp Ser Ser Ser
    210                 215                 220

Phe Leu Ile Asp Lys Thr Thr Thr Val Gln Val Pro Met Met His Gln
225                 230                 235                 240

Met Glu Gln Tyr Tyr His Leu Val Asp Met Glu Leu Asn Cys Thr Val
                245                 250                 255

Leu Gln Met Asp Tyr Ser Lys Asn Ala Leu Ala Leu Phe Val Leu Pro
            260                 265                 270

Lys Glu Gly Gln Met Glu Ser Val Glu Ala Ala Met Ser Ser Lys Thr
        275                 280                 285

Leu Lys Lys Trp Asn Arg Leu Leu Gln Lys Gly Trp Val Asp Leu Phe
    290                 295                 300

Val Pro Lys Phe Ser Ile Ser Ala Thr Tyr Asp Leu Gly Ala Thr Leu
305                 310                 315                 320

Leu Lys Met Gly Ile Gln His Ala Tyr Ser Glu Asn Ala Asp Phe Ser
                325                 330                 335

Gly Leu Thr Glu Asp Asn Gly Leu Lys Leu Ser Asn Ala Ala His Lys
            340                 345                 350

Ala Val Leu His Ile Gly Glu Lys Gly Thr Glu Ala Ala Ala Val Pro
        355                 360                 365

Glu Val Glu Leu Ser Asp Gln Pro Glu Asn Thr Phe Leu His Pro Ile
    370                 375                 380

Ile Gln Ile Asp Arg Ser Phe Met Leu Leu Ile Leu Glu Arg Ser Thr
385                 390                 395                 400

Arg Ser Ile Leu Phe Leu Gly Lys Val Val Asn Pro Thr Glu Ala
                405                 410                 415

<210> SEQ ID NO 29
<211> LENGTH: 261
<212> TYPE: PRT
<213> ORGANISM: Homo sapiens

<400> SEQUENCE: 29

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45
```

```
Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
                100                 105                 110

Pro Gly Asp Asp Ser Ser His Asp Leu Met Leu Arg Leu Ser Glu
                115                 120                 125

Pro Ala Glu Leu Thr Asp Ala Val Lys Val Met Asp Leu Pro Thr Gln
            130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
                180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
                260

<210> SEQ ID NO 30
<211> LENGTH: 4548
<212> TYPE: PRT
<213> ORGANISM: Homo sapiens

<400> SEQUENCE: 30

Met Glu His Lys Glu Val Val Leu Leu Leu Leu Phe Leu Lys Ser
1               5                   10                  15

Ala Ala Pro Glu Gln Ser His Val Val Gln Asp Cys Tyr His Gly Asp
                20                  25                  30

Gly Gln Ser Tyr Arg Gly Thr Tyr Ser Thr Val Thr Gly Arg Thr
            35                  40                  45

Cys Gln Ala Trp Ser Ser Met Thr Pro His Gln His Asn Arg Thr Thr
    50                  55                  60

Glu Asn Tyr Pro Asn Ala Gly Leu Ile Met Asn Tyr Cys Arg Asn Pro
65                  70                  75                  80

Asp Ala Val Ala Ala Pro Tyr Cys Tyr Thr Arg Asp Pro Gly Val Arg
                85                  90                  95

Trp Glu Tyr Cys Asn Leu Thr Gln Cys Ser Asp Ala Glu Gly Thr Ala
                100                 105                 110

Val Ala Pro Pro Thr Val Thr Pro Val Pro Ser Leu Glu Ala Pro Ser
                115                 120                 125

Glu Gln Ala Pro Thr Glu Gln Arg Pro Gly Val Gln Glu Cys Tyr His
            130                 135                 140

Gly Asn Gly Gln Ser Tyr Arg Gly Thr Tyr Ser Thr Thr Val Thr Gly
```

-continued

```
            145                 150                 155                 160
Arg Thr Cys Gln Ala Trp Ser Ser Met Thr Pro His Ser His Ser Arg
                165                 170                 175
Thr Pro Glu Tyr Tyr Pro Asn Ala Gly Leu Ile Met Asn Tyr Cys Arg
            180                 185                 190
Asn Pro Asp Ala Val Ala Ala Pro Tyr Cys Tyr Thr Arg Asp Pro Gly
            195                 200                 205
Val Arg Trp Glu Tyr Cys Asn Leu Thr Gln Cys Ser Asp Ala Glu Gly
        210                 215                 220
Thr Ala Val Ala Pro Pro Thr Val Thr Pro Val Pro Ser Leu Glu Ala
225                 230                 235                 240
Pro Ser Glu Gln Ala Pro Thr Glu Gln Arg Pro Gly Val Gln Glu Cys
                245                 250                 255
Tyr His Gly Asn Gly Gln Ser Tyr Arg Gly Thr Tyr Ser Thr Thr Val
                260                 265                 270
Thr Gly Arg Thr Cys Gln Ala Trp Ser Ser Met Thr Pro His Ser His
            275                 280                 285
Ser Arg Thr Pro Glu Tyr Tyr Pro Asn Ala Gly Leu Ile Met Asn Tyr
            290                 295                 300
Cys Arg Asn Pro Asp Ala Val Ala Ala Pro Tyr Cys Tyr Thr Arg Asp
305                 310                 315                 320
Pro Gly Val Arg Trp Glu Tyr Cys Asn Leu Thr Gln Cys Ser Asp Ala
                325                 330                 335
Glu Gly Thr Ala Val Ala Pro Pro Thr Val Thr Pro Val Pro Ser Leu
            340                 345                 350
Glu Ala Pro Ser Glu Gln Ala Pro Thr Glu Gln Arg Pro Gly Val Gln
            355                 360                 365
Glu Cys Tyr His Gly Asn Gly Gln Ser Tyr Arg Gly Thr Tyr Ser Thr
        370                 375                 380
Thr Val Thr Gly Arg Thr Cys Gln Ala Trp Ser Ser Met Thr Pro His
385                 390                 395                 400
Ser His Ser Arg Thr Pro Glu Tyr Tyr Pro Asn Ala Gly Leu Ile Met
                405                 410                 415
Asn Tyr Cys Arg Asn Pro Asp Ala Val Ala Ala Pro Tyr Cys Tyr Thr
                420                 425                 430
Arg Asp Pro Gly Val Arg Trp Glu Tyr Cys Asn Leu Thr Gln Cys Ser
            435                 440                 445
Asp Ala Glu Gly Thr Ala Val Ala Pro Pro Thr Val Thr Pro Val Pro
450                 455                 460
Ser Leu Glu Ala Pro Ser Glu Gln Ala Pro Thr Glu Gln Arg Pro Gly
465                 470                 475                 480
Val Gln Glu Cys Tyr His Gly Asn Gly Gln Ser Tyr Arg Gly Thr Tyr
                485                 490                 495
Ser Thr Thr Val Thr Gly Arg Thr Cys Gln Ala Trp Ser Ser Met Thr
            500                 505                 510
Pro His Ser His Ser Arg Thr Pro Glu Tyr Tyr Pro Asn Ala Gly Leu
            515                 520                 525
Ile Met Asn Tyr Cys Arg Asn Pro Asp Ala Val Ala Ala Pro Tyr Cys
        530                 535                 540
Tyr Thr Arg Asp Pro Gly Val Arg Trp Glu Tyr Cys Asn Leu Thr Gln
545                 550                 555                 560
Cys Ser Asp Ala Glu Gly Thr Ala Val Ala Pro Pro Thr Val Thr Pro
                565                 570                 575
```

-continued

```
Val Pro Ser Leu Glu Ala Pro Ser Glu Gln Ala Pro Thr Glu Gln Arg
            580                 585                 590

Pro Gly Val Gln Glu Cys Tyr His Gly Asn Gly Gln Ser Tyr Arg Gly
            595                 600                 605

Thr Tyr Ser Thr Thr Val Thr Gly Arg Thr Cys Gln Ala Trp Ser Ser
            610                 615                 620

Met Thr Pro His Ser His Ser Arg Thr Pro Glu Tyr Tyr Pro Asn Ala
625                 630                 635                 640

Gly Leu Ile Met Asn Tyr Cys Arg Asn Pro Asp Ala Val Ala Ala Pro
                    645                 650                 655

Tyr Cys Tyr Thr Arg Asp Pro Gly Val Arg Trp Glu Tyr Cys Asn Leu
            660                 665                 670

Thr Gln Cys Ser Asp Ala Glu Gly Thr Ala Val Ala Pro Pro Thr Val
            675                 680                 685

Thr Pro Val Pro Ser Leu Glu Ala Pro Ser Glu Gln Ala Pro Thr Glu
            690                 695                 700

Gln Arg Pro Gly Val Gln Glu Cys Tyr His Gly Asn Gly Gln Ser Tyr
705                 710                 715                 720

Arg Gly Thr Tyr Ser Thr Thr Val Thr Gly Arg Thr Cys Gln Ala Trp
                    725                 730                 735

Ser Ser Met Thr Pro His Ser His Ser Arg Thr Pro Glu Tyr Tyr Pro
            740                 745                 750

Asn Ala Gly Leu Ile Met Asn Tyr Cys Arg Asn Pro Asp Ala Val Ala
            755                 760                 765

Ala Pro Tyr Cys Tyr Thr Arg Asp Pro Gly Val Arg Trp Glu Tyr Cys
            770                 775                 780

Asn Leu Thr Gln Cys Ser Asp Ala Glu Gly Thr Ala Val Ala Pro Pro
785                 790                 795                 800

Thr Val Thr Pro Val Pro Ser Leu Glu Ala Pro Ser Glu Gln Ala Pro
                    805                 810                 815

Thr Glu Gln Arg Pro Gly Val Gln Glu Cys Tyr His Gly Asn Gly Gln
            820                 825                 830

Ser Tyr Arg Gly Thr Tyr Ser Thr Thr Val Thr Gly Arg Thr Cys Gln
            835                 840                 845

Ala Trp Ser Ser Met Thr Pro His Ser His Ser Arg Thr Pro Glu Tyr
            850                 855                 860

Tyr Pro Asn Ala Gly Leu Ile Met Asn Tyr Cys Arg Asn Pro Asp Ala
865                 870                 875                 880

Val Ala Ala Pro Tyr Cys Tyr Thr Arg Asp Pro Gly Val Arg Trp Glu
                    885                 890                 895

Tyr Cys Asn Leu Thr Gln Cys Ser Asp Ala Glu Gly Thr Ala Val Ala
            900                 905                 910

Pro Pro Thr Val Thr Pro Val Pro Ser Leu Glu Ala Pro Ser Glu Gln
            915                 920                 925

Ala Pro Thr Glu Gln Arg Pro Gly Val Gln Glu Cys Tyr His Gly Asn
            930                 935                 940

Gly Gln Ser Tyr Arg Gly Thr Tyr Ser Thr Thr Val Thr Gly Arg Thr
945                 950                 955                 960

Cys Gln Ala Trp Ser Ser Met Thr Pro His Ser His Ser Arg Thr Pro
                    965                 970                 975

Glu Tyr Tyr Pro Asn Ala Gly Leu Ile Met Asn Tyr Cys Arg Asn Pro
            980                 985                 990
```

```
Asp Ala Val Ala Ala Pro Tyr Cys Tyr Thr Arg Asp Pro Gly Val Arg
            995                 1000                1005

Trp Glu Tyr Cys Asn Leu Thr Gln Cys Ser Asp Ala Glu Gly Thr
    1010                1015                1020

Ala Val Ala Pro Pro Thr Val Thr Pro Val Pro Ser Leu Glu Ala
    1025                1030                1035

Pro Ser Glu Gln Ala Pro Thr Glu Gln Arg Pro Gly Val Gln Glu
    1040                1045                1050

Cys Tyr His Gly Asn Gly Gln Ser Tyr Arg Gly Thr Tyr Ser Thr
    1055                1060                1065

Thr Val Thr Gly Arg Thr Cys Gln Ala Trp Ser Ser Met Thr Pro
    1070                1075                1080

His Ser His Ser Arg Thr Pro Glu Tyr Tyr Pro Asn Ala Gly Leu
    1085                1090                1095

Ile Met Asn Tyr Cys Arg Asn Pro Asp Ala Val Ala Ala Pro Tyr
    1100                1105                1110

Cys Tyr Thr Arg Asp Pro Gly Val Arg Trp Glu Tyr Cys Asn Leu
    1115                1120                1125

Thr Gln Cys Ser Asp Ala Glu Gly Thr Ala Val Ala Pro Pro Thr
    1130                1135                1140

Val Thr Pro Val Pro Ser Leu Glu Ala Pro Ser Glu Gln Ala Pro
    1145                1150                1155

Thr Glu Gln Arg Pro Gly Val Gln Glu Cys Tyr His Gly Asn Gly
    1160                1165                1170

Gln Ser Tyr Arg Gly Thr Tyr Ser Thr Thr Val Thr Gly Arg Thr
    1175                1180                1185

Cys Gln Ala Trp Ser Ser Met Thr Pro His Ser His Ser Arg Thr
    1190                1195                1200

Pro Glu Tyr Tyr Pro Asn Ala Gly Leu Ile Met Asn Tyr Cys Arg
    1205                1210                1215

Asn Pro Asp Ala Val Ala Ala Pro Tyr Cys Tyr Thr Arg Asp Pro
    1220                1225                1230

Gly Val Arg Trp Glu Tyr Cys Asn Leu Thr Gln Cys Ser Asp Ala
    1235                1240                1245

Glu Gly Thr Ala Val Ala Pro Pro Thr Val Thr Pro Val Pro Ser
    1250                1255                1260

Leu Glu Ala Pro Ser Glu Gln Ala Pro Thr Glu Gln Arg Pro Gly
    1265                1270                1275

Val Gln Glu Cys Tyr His Gly Asn Gly Gln Ser Tyr Arg Gly Thr
    1280                1285                1290

Tyr Ser Thr Thr Val Thr Gly Arg Thr Cys Gln Ala Trp Ser Ser
    1295                1300                1305

Met Thr Pro His Ser His Ser Arg Thr Pro Glu Tyr Tyr Pro Asn
    1310                1315                1320

Ala Gly Leu Ile Met Asn Tyr Cys Arg Asn Pro Asp Ala Val Ala
    1325                1330                1335

Ala Pro Tyr Cys Tyr Thr Arg Asp Pro Gly Val Arg Trp Glu Tyr
    1340                1345                1350

Cys Asn Leu Thr Gln Cys Ser Asp Ala Glu Gly Thr Ala Val Ala
    1355                1360                1365

Pro Pro Thr Val Thr Pro Val Pro Ser Leu Glu Ala Pro Ser Glu
    1370                1375                1380

Gln Ala Pro Thr Glu Gln Arg Pro Gly Val Gln Glu Cys Tyr His
```

-continued

```
              1385                1390                1395
Gly Asn Gly Gln Ser Tyr Arg Gly Thr Tyr Ser Thr Thr Val Thr
    1400                1405                1410

Gly Arg Thr Cys Gln Ala Trp Ser Ser Met Thr Pro His Ser His
    1415                1420                1425

Ser Arg Thr Pro Glu Tyr Tyr Pro Asn Ala Gly Leu Ile Met Asn
    1430                1435                1440

Tyr Cys Arg Asn Pro Asp Ala Val Ala Pro Tyr Cys Tyr Thr
    1445                1450                1455

Arg Asp Pro Gly Val Arg Trp Glu Tyr Cys Asn Leu Thr Gln Cys
    1460                1465                1470

Ser Asp Ala Glu Gly Thr Ala Val Ala Pro Pro Thr Val Thr Pro
    1475                1480                1485

Val Pro Ser Leu Glu Ala Pro Ser Glu Gln Ala Pro Thr Glu Gln
    1490                1495                1500

Arg Pro Gly Val Gln Glu Cys Tyr His Gly Asn Gly Gln Ser Tyr
    1505                1510                1515

Arg Gly Thr Tyr Ser Thr Thr Val Thr Gly Arg Thr Cys Gln Ala
    1520                1525                1530

Trp Ser Ser Met Thr Pro His Ser His Ser Arg Thr Pro Glu Tyr
    1535                1540                1545

Tyr Pro Asn Ala Gly Leu Ile Met Asn Tyr Cys Arg Asn Pro Asp
    1550                1555                1560

Ala Val Ala Ala Pro Tyr Cys Tyr Thr Arg Asp Pro Gly Val Arg
    1565                1570                1575

Trp Glu Tyr Cys Asn Leu Thr Gln Cys Ser Asp Ala Glu Gly Thr
    1580                1585                1590

Ala Val Ala Pro Pro Thr Val Thr Pro Val Pro Ser Leu Glu Ala
    1595                1600                1605

Pro Ser Glu Gln Ala Pro Thr Glu Gln Arg Pro Gly Val Gln Glu
    1610                1615                1620

Cys Tyr His Gly Asn Gly Gln Ser Tyr Arg Gly Thr Tyr Ser Thr
    1625                1630                1635

Thr Val Thr Gly Arg Thr Cys Gln Ala Trp Ser Ser Met Thr Pro
    1640                1645                1650

His Ser His Ser Arg Thr Pro Glu Tyr Tyr Pro Asn Ala Gly Leu
    1655                1660                1665

Ile Met Asn Tyr Cys Arg Asn Pro Asp Ala Val Ala Ala Pro Tyr
    1670                1675                1680

Cys Tyr Thr Arg Asp Pro Gly Val Arg Trp Glu Tyr Cys Asn Leu
    1685                1690                1695

Thr Gln Cys Ser Asp Ala Glu Gly Thr Ala Val Ala Pro Pro Thr
    1700                1705                1710

Val Thr Pro Val Pro Ser Leu Glu Ala Pro Ser Glu Gln Ala Pro
    1715                1720                1725

Thr Glu Gln Arg Pro Gly Val Gln Glu Cys Tyr His Gly Asn Gly
    1730                1735                1740

Gln Ser Tyr Arg Gly Thr Tyr Ser Thr Thr Val Thr Gly Arg Thr
    1745                1750                1755

Cys Gln Ala Trp Ser Ser Met Thr Pro His Ser His Ser Arg Thr
    1760                1765                1770

Pro Glu Tyr Tyr Pro Asn Ala Gly Leu Ile Met Asn Tyr Cys Arg
    1775                1780                1785
```

```
Asn Pro Asp Ala Val Ala Ala Pro Tyr Cys Tyr Thr Arg Asp Pro
    1790                1795                1800

Gly Val Arg Trp Glu Tyr Cys Asn Leu Thr Gln Cys Ser Asp Ala
    1805                1810                1815

Glu Gly Thr Ala Val Ala Pro Pro Thr Val Thr Pro Val Pro Ser
    1820                1825                1830

Leu Glu Ala Pro Ser Glu Gln Ala Pro Thr Glu Gln Arg Pro Gly
    1835                1840                1845

Val Gln Glu Cys Tyr His Gly Asn Gly Gln Ser Tyr Arg Gly Thr
    1850                1855                1860

Tyr Ser Thr Thr Val Thr Gly Arg Thr Cys Gln Ala Trp Ser Ser
    1865                1870                1875

Met Thr Pro His Ser His Ser Arg Thr Pro Glu Tyr Tyr Pro Asn
    1880                1885                1890

Ala Gly Leu Ile Met Asn Tyr Cys Arg Asn Pro Asp Ala Val Ala
    1895                1900                1905

Ala Pro Tyr Cys Tyr Thr Arg Asp Pro Gly Val Arg Trp Glu Tyr
    1910                1915                1920

Cys Asn Leu Thr Gln Cys Ser Asp Ala Glu Gly Thr Ala Val Ala
    1925                1930                1935

Pro Pro Thr Val Thr Pro Val Pro Ser Leu Glu Ala Pro Ser Glu
    1940                1945                1950

Gln Ala Pro Thr Glu Gln Arg Pro Gly Val Gln Glu Cys Tyr His
    1955                1960                1965

Gly Asn Gly Gln Ser Tyr Arg Gly Thr Tyr Ser Thr Thr Val Thr
    1970                1975                1980

Gly Arg Thr Cys Gln Ala Trp Ser Ser Met Thr Pro His Ser His
    1985                1990                1995

Ser Arg Thr Pro Glu Tyr Tyr Pro Asn Ala Gly Leu Ile Met Asn
    2000                2005                2010

Tyr Cys Arg Asn Pro Asp Ala Val Ala Ala Pro Tyr Cys Tyr Thr
    2015                2020                2025

Arg Asp Pro Gly Val Arg Trp Glu Tyr Cys Asn Leu Thr Gln Cys
    2030                2035                2040

Ser Asp Ala Glu Gly Thr Ala Val Ala Pro Pro Thr Val Thr Pro
    2045                2050                2055

Val Pro Ser Leu Glu Ala Pro Ser Glu Gln Ala Pro Thr Glu Gln
    2060                2065                2070

Arg Pro Gly Val Gln Glu Cys Tyr His Gly Asn Gly Gln Ser Tyr
    2075                2080                2085

Arg Gly Thr Tyr Ser Thr Thr Val Thr Gly Arg Thr Cys Gln Ala
    2090                2095                2100

Trp Ser Ser Met Thr Pro His Ser His Ser Arg Thr Pro Glu Tyr
    2105                2110                2115

Tyr Pro Asn Ala Gly Leu Ile Met Asn Tyr Cys Arg Asn Pro Asp
    2120                2125                2130

Ala Val Ala Ala Pro Tyr Cys Tyr Thr Arg Asp Pro Gly Val Arg
    2135                2140                2145

Trp Glu Tyr Cys Asn Leu Thr Gln Cys Ser Asp Ala Glu Gly Thr
    2150                2155                2160

Ala Val Ala Pro Pro Thr Val Thr Pro Val Pro Ser Leu Glu Ala
    2165                2170                2175
```

```
Pro Ser Glu Gln Ala Pro Thr Glu Gln Arg Pro Gly Val Gln Glu
    2180                2185                2190

Cys Tyr His Gly Asn Gly Gln Ser Tyr Arg Gly Thr Tyr Ser Thr
    2195                2200                2205

Thr Val Thr Gly Arg Thr Cys Gln Ala Trp Ser Ser Met Thr Pro
    2210                2215                2220

His Ser His Ser Arg Thr Pro Glu Tyr Tyr Pro Asn Ala Gly Leu
    2225                2230                2235

Ile Met Asn Tyr Cys Arg Asn Pro Asp Ala Val Ala Ala Pro Tyr
    2240                2245                2250

Cys Tyr Thr Arg Asp Pro Gly Val Arg Trp Glu Tyr Cys Asn Leu
    2255                2260                2265

Thr Gln Cys Ser Asp Ala Glu Gly Thr Ala Val Ala Pro Pro Thr
    2270                2275                2280

Val Thr Pro Val Pro Ser Leu Glu Ala Pro Ser Glu Gln Ala Pro
    2285                2290                2295

Thr Glu Gln Arg Pro Gly Val Gln Glu Cys Tyr His Gly Asn Gly
    2300                2305                2310

Gln Ser Tyr Arg Gly Thr Tyr Ser Thr Thr Val Thr Gly Arg Thr
    2315                2320                2325

Cys Gln Ala Trp Ser Ser Met Thr Pro His Ser His Ser Arg Thr
    2330                2335                2340

Pro Glu Tyr Tyr Pro Asn Ala Gly Leu Ile Met Asn Tyr Cys Arg
    2345                2350                2355

Asn Pro Asp Ala Val Ala Ala Pro Tyr Cys Tyr Thr Arg Asp Pro
    2360                2365                2370

Gly Val Arg Trp Glu Tyr Cys Asn Leu Thr Gln Cys Ser Asp Ala
    2375                2380                2385

Glu Gly Thr Ala Val Ala Pro Pro Thr Val Thr Pro Val Pro Ser
    2390                2395                2400

Leu Glu Ala Pro Ser Glu Gln Ala Pro Thr Glu Gln Arg Pro Gly
    2405                2410                2415

Val Gln Glu Cys Tyr His Gly Asn Gly Gln Ser Tyr Arg Gly Thr
    2420                2425                2430

Tyr Ser Thr Thr Val Thr Gly Arg Thr Cys Gln Ala Trp Ser Ser
    2435                2440                2445

Met Thr Pro His Ser His Ser Arg Thr Pro Glu Tyr Tyr Pro Asn
    2450                2455                2460

Ala Gly Leu Ile Met Asn Tyr Cys Arg Asn Pro Asp Ala Val Ala
    2465                2470                2475

Ala Pro Tyr Cys Tyr Thr Arg Asp Pro Gly Val Arg Trp Glu Tyr
    2480                2485                2490

Cys Asn Leu Thr Gln Cys Ser Asp Ala Glu Gly Thr Ala Val Ala
    2495                2500                2505

Pro Pro Thr Val Thr Pro Val Pro Ser Leu Glu Ala Pro Ser Glu
    2510                2515                2520

Gln Ala Pro Thr Glu Gln Arg Pro Gly Val Gln Glu Cys Tyr His
    2525                2530                2535

Gly Asn Gly Gln Ser Tyr Arg Gly Thr Tyr Ser Thr Thr Val Thr
    2540                2545                2550

Gly Arg Thr Cys Gln Ala Trp Ser Ser Met Thr Pro His Ser His
    2555                2560                2565

Ser Arg Thr Pro Glu Tyr Tyr Pro Asn Ala Gly Leu Ile Met Asn
```

2570                2575                2580
Tyr Cys Arg Asn Pro Asp Ala Val Ala Pro Tyr Cys Tyr Thr
    2585            2590                2595

Arg Asp Pro Gly Val Arg Trp Glu Tyr Cys Asn Leu Thr Gln Cys
    2600            2605                2610

Ser Asp Ala Glu Gly Thr Ala Val Ala Pro Pro Thr Val Thr Pro
    2615            2620                2625

Val Pro Ser Leu Glu Ala Pro Ser Glu Gln Ala Pro Thr Glu Gln
    2630            2635                2640

Arg Pro Gly Val Gln Glu Cys Tyr His Gly Asn Gly Gln Ser Tyr
    2645            2650                2655

Arg Gly Thr Tyr Ser Thr Thr Val Thr Gly Arg Thr Cys Gln Ala
    2660            2665                2670

Trp Ser Ser Met Thr Pro His Ser His Ser Arg Thr Pro Glu Tyr
    2675            2680                2685

Tyr Pro Asn Ala Gly Leu Ile Met Asn Tyr Cys Arg Asn Pro Asp
    2690            2695                2700

Ala Val Ala Ala Pro Tyr Cys Tyr Thr Arg Asp Pro Gly Val Arg
    2705            2710                2715

Trp Glu Tyr Cys Asn Leu Thr Gln Cys Ser Asp Ala Glu Gly Thr
    2720            2725                2730

Ala Val Ala Pro Pro Thr Val Thr Pro Val Pro Ser Leu Glu Ala
    2735            2740                2745

Pro Ser Glu Gln Ala Pro Thr Glu Gln Arg Pro Gly Val Gln Glu
    2750            2755                2760

Cys Tyr His Gly Asn Gly Gln Ser Tyr Arg Gly Thr Tyr Ser Thr
    2765            2770                2775

Thr Val Thr Gly Arg Thr Cys Gln Ala Trp Ser Ser Met Thr Pro
    2780            2785                2790

His Ser His Ser Arg Thr Pro Glu Tyr Tyr Pro Asn Ala Gly Leu
    2795            2800                2805

Ile Met Asn Tyr Cys Arg Asn Pro Asp Ala Val Ala Ala Pro Tyr
    2810            2815                2820

Cys Tyr Thr Arg Asp Pro Gly Val Arg Trp Glu Tyr Cys Asn Leu
    2825            2830                2835

Thr Gln Cys Ser Asp Ala Glu Gly Thr Ala Val Ala Pro Pro Thr
    2840            2845                2850

Val Thr Pro Val Pro Ser Leu Glu Ala Pro Ser Glu Gln Ala Pro
    2855            2860                2865

Thr Glu Gln Arg Pro Gly Val Gln Glu Cys Tyr His Gly Asn Gly
    2870            2875                2880

Gln Ser Tyr Arg Gly Thr Tyr Ser Thr Thr Val Thr Gly Arg Thr
    2885            2890                2895

Cys Gln Ala Trp Ser Ser Met Thr Pro His Ser His Ser Arg Thr
    2900            2905                2910

Pro Glu Tyr Tyr Pro Asn Ala Gly Leu Ile Met Asn Tyr Cys Arg
    2915            2920                2925

Asn Pro Asp Ala Val Ala Ala Pro Tyr Cys Tyr Thr Arg Asp Pro
    2930            2935                2940

Gly Val Arg Trp Glu Tyr Cys Asn Leu Thr Gln Cys Ser Asp Ala
    2945            2950                2955

Glu Gly Thr Ala Val Ala Pro Pro Thr Val Thr Pro Val Pro Ser
    2960            2965                2970

-continued

```
Leu Glu Ala Pro Ser Glu Gln Ala Pro Thr Glu Gln Arg Pro Gly
    2975            2980            2985

Val Gln Glu Cys Tyr His Gly Asn Gly Gln Ser Tyr Arg Gly Thr
    2990            2995            3000

Tyr Ser Thr Thr Val Thr Gly Arg Thr Cys Gln Ala Trp Ser Ser
    3005            3010            3015

Met Thr Pro His Ser His Ser Arg Thr Pro Glu Tyr Tyr Pro Asn
    3020            3025            3030

Ala Gly Leu Ile Met Asn Tyr Cys Arg Asn Pro Asp Ala Val Ala
    3035            3040            3045

Ala Pro Tyr Cys Tyr Thr Arg Asp Pro Gly Val Arg Trp Glu Tyr
    3050            3055            3060

Cys Asn Leu Thr Gln Cys Ser Asp Ala Glu Gly Thr Ala Val Ala
    3065            3070            3075

Pro Pro Thr Val Thr Pro Val Pro Ser Leu Glu Ala Pro Ser Glu
    3080            3085            3090

Gln Ala Pro Thr Glu Gln Arg Pro Gly Val Gln Glu Cys Tyr His
    3095            3100            3105

Gly Asn Gly Gln Ser Tyr Arg Gly Thr Tyr Ser Thr Thr Val Thr
    3110            3115            3120

Gly Arg Thr Cys Gln Ala Trp Ser Ser Met Thr Pro His Ser His
    3125            3130            3135

Ser Arg Thr Pro Glu Tyr Tyr Pro Asn Ala Gly Leu Ile Met Asn
    3140            3145            3150

Tyr Cys Arg Asn Pro Asp Ala Val Ala Ala Pro Tyr Cys Tyr Thr
    3155            3160            3165

Arg Asp Pro Gly Val Arg Trp Glu Tyr Cys Asn Leu Thr Gln Cys
    3170            3175            3180

Ser Asp Ala Glu Gly Thr Ala Val Ala Pro Pro Thr Val Thr Pro
    3185            3190            3195

Val Pro Ser Leu Glu Ala Pro Ser Glu Gln Ala Pro Thr Glu Gln
    3200            3205            3210

Arg Pro Gly Val Gln Glu Cys Tyr His Gly Asn Gly Gln Ser Tyr
    3215            3220            3225

Arg Gly Thr Tyr Ser Thr Thr Val Thr Gly Arg Thr Cys Gln Ala
    3230            3235            3240

Trp Ser Ser Met Thr Pro His Ser His Ser Arg Thr Pro Glu Tyr
    3245            3250            3255

Tyr Pro Asn Ala Gly Leu Ile Met Asn Tyr Cys Arg Asn Pro Asp
    3260            3265            3270

Ala Val Ala Ala Pro Tyr Cys Tyr Thr Arg Asp Pro Gly Val Arg
    3275            3280            3285

Trp Glu Tyr Cys Asn Leu Thr Gln Cys Ser Asp Ala Glu Gly Thr
    3290            3295            3300

Ala Val Ala Pro Pro Thr Val Thr Pro Val Pro Ser Leu Glu Ala
    3305            3310            3315

Pro Ser Glu Gln Ala Pro Thr Glu Gln Arg Pro Gly Val Gln Glu
    3320            3325            3330

Cys Tyr His Gly Asn Gly Gln Ser Tyr Arg Gly Thr Tyr Ser Thr
    3335            3340            3345

Thr Val Thr Gly Arg Thr Cys Gln Ala Trp Ser Ser Met Thr Pro
    3350            3355            3360
```

-continued

His Ser His Ser Arg Thr Pro Glu Tyr Tyr Pro Asn Ala Gly Leu
3365                  3370              3375

Ile Met Asn Tyr Cys Arg Asn Pro Asp Pro Val Ala Ala Pro Tyr
3380              3385              3390

Cys Tyr Thr Arg Asp Pro Ser Val Arg Trp Glu Tyr Cys Asn Leu
3395              3400              3405

Thr Gln Cys Ser Asp Ala Glu Gly Thr Ala Val Ala Pro Pro Thr
3410              3415              3420

Ile Thr Pro Ile Pro Ser Leu Glu Ala Pro Ser Glu Gln Ala Pro
3425              3430              3435

Thr Glu Gln Arg Pro Gly Val Gln Glu Cys Tyr His Gly Asn Gly
3440              3445              3450

Gln Ser Tyr Gln Gly Thr Tyr Phe Ile Thr Val Thr Gly Arg Thr
3455              3460              3465

Cys Gln Ala Trp Ser Ser Met Thr Pro His Ser His Ser Arg Thr
3470              3475              3480

Pro Ala Tyr Tyr Pro Asn Ala Gly Leu Ile Lys Asn Tyr Cys Arg
3485              3490              3495

Asn Pro Asp Pro Val Ala Ala Pro Trp Cys Tyr Thr Thr Asp Pro
3500              3505              3510

Ser Val Arg Trp Glu Tyr Cys Asn Leu Thr Arg Cys Ser Asp Ala
3515              3520              3525

Glu Trp Thr Ala Phe Val Pro Pro Asn Val Ile Leu Ala Pro Ser
3530              3535              3540

Leu Glu Ala Phe Phe Glu Gln Ala Leu Thr Glu Glu Thr Pro Gly
3545              3550              3555

Val Gln Asp Cys Tyr Tyr His Tyr Gly Gln Ser Tyr Arg Gly Thr
3560              3565              3570

Tyr Ser Thr Thr Val Thr Gly Arg Thr Cys Gln Ala Trp Ser Ser
3575              3580              3585

Met Thr Pro His Gln His Ser Arg Thr Pro Glu Asn Tyr Pro Asn
3590              3595              3600

Ala Gly Leu Thr Arg Asn Tyr Cys Arg Asn Pro Asp Ala Glu Ile
3605              3610              3615

Arg Pro Trp Cys Tyr Thr Met Asp Pro Ser Val Arg Trp Glu Tyr
3620              3625              3630

Cys Asn Leu Thr Gln Cys Leu Val Thr Glu Ser Ser Val Leu Ala
3635              3640              3645

Thr Leu Thr Val Val Pro Asp Pro Ser Thr Glu Ala Ser Ser Glu
3650              3655              3660

Glu Ala Pro Thr Glu Gln Ser Pro Gly Val Gln Asp Cys Tyr His
3665              3670              3675

Gly Asp Gly Gln Ser Tyr Arg Gly Ser Phe Ser Thr Thr Val Thr
3680              3685              3690

Gly Arg Thr Cys Gln Ser Trp Ser Ser Met Thr Pro His Trp His
3695              3700              3705

Gln Arg Thr Thr Glu Tyr Tyr Pro Asn Gly Gly Leu Thr Arg Asn
3710              3715              3720

Tyr Cys Arg Asn Pro Asp Ala Glu Ile Ser Pro Trp Cys Tyr Thr
3725              3730              3735

Met Asp Pro Asn Val Arg Trp Glu Tyr Cys Asn Leu Thr Gln Cys
3740              3745              3750

Pro Val Thr Glu Ser Ser Val Leu Ala Thr Ser Thr Ala Val Ser

-continued

```
            3755                3760                3765

Glu Gln Ala Pro Thr Glu Gln Ser Pro Thr Val Gln Asp Cys Tyr
    3770                3775                3780

His Gly Asp Gly Gln Ser Tyr Arg Gly Ser Phe Ser Thr Thr Val
    3785                3790                3795

Thr Gly Arg Thr Cys Gln Ser Trp Ser Ser Met Thr Pro His Trp
    3800                3805                3810

His Gln Arg Thr Thr Glu Tyr Tyr Pro Asn Gly Gly Leu Thr Arg
    3815                3820                3825

Asn Tyr Cys Arg Asn Pro Asp Ala Glu Ile Arg Pro Trp Cys Tyr
    3830                3835                3840

Thr Met Asp Pro Ser Val Arg Trp Glu Tyr Cys Asn Leu Thr Gln
    3845                3850                3855

Cys Pro Val Met Glu Ser Thr Leu Leu Thr Thr Pro Thr Val Val
    3860                3865                3870

Pro Val Pro Ser Thr Glu Leu Pro Ser Glu Glu Ala Pro Thr Glu
    3875                3880                3885

Asn Ser Thr Gly Val Gln Asp Cys Tyr Arg Gly Asp Gly Gln Ser
    3890                3895                3900

Tyr Arg Gly Thr Leu Ser Thr Thr Ile Thr Gly Arg Thr Cys Gln
    3905                3910                3915

Ser Trp Ser Ser Met Thr Pro His Trp His Arg Arg Ile Pro Leu
    3920                3925                3930

Tyr Tyr Pro Asn Ala Gly Leu Thr Arg Asn Tyr Cys Arg Asn Pro
    3935                3940                3945

Asp Ala Glu Ile Arg Pro Trp Cys Tyr Thr Met Asp Pro Ser Val
    3950                3955                3960

Arg Trp Glu Tyr Cys Asn Leu Thr Arg Cys Pro Val Thr Glu Ser
    3965                3970                3975

Ser Val Leu Thr Thr Pro Thr Val Ala Pro Val Pro Ser Thr Glu
    3980                3985                3990

Ala Pro Ser Glu Gln Ala Pro Pro Glu Lys Ser Pro Val Val Gln
    3995                4000                4005

Asp Cys Tyr His Gly Asp Gly Arg Ser Tyr Arg Gly Ile Ser Ser
    4010                4015                4020

Thr Thr Val Thr Gly Arg Thr Cys Gln Ser Trp Ser Ser Met Ile
    4025                4030                4035

Pro His Trp His Gln Arg Thr Pro Glu Asn Tyr Pro Asn Ala Gly
    4040                4045                4050

Leu Thr Glu Asn Tyr Cys Arg Asn Pro Asp Ser Gly Lys Gln Pro
    4055                4060                4065

Trp Cys Tyr Thr Thr Asp Pro Cys Val Arg Trp Glu Tyr Cys Asn
    4070                4075                4080

Leu Thr Gln Cys Ser Glu Thr Glu Ser Gly Val Leu Glu Thr Pro
    4085                4090                4095

Thr Val Val Pro Val Pro Ser Met Glu Ala His Ser Glu Ala Ala
    4100                4105                4110

Pro Thr Glu Gln Thr Pro Val Val Arg Gln Cys Tyr His Gly Asn
    4115                4120                4125

Gly Gln Ser Tyr Arg Gly Thr Phe Ser Thr Thr Val Thr Gly Arg
    4130                4135                4140

Thr Cys Gln Ser Trp Ser Ser Met Thr Pro His Arg His Gln Arg
    4145                4150                4155
```

```
Thr Pro Glu Asn Tyr Pro Asn Asp Gly Leu Thr Met Asn Tyr Cys
    4160            4165                4170
Arg Asn Pro Asp Ala Asp Thr Gly Pro Trp Cys Phe Thr Met Asp
    4175            4180                4185
Pro Ser Ile Arg Trp Glu Tyr Cys Asn Leu Thr Arg Cys Ser Asp
    4190            4195                4200
Thr Glu Gly Thr Val Val Ala Pro Pro Thr Val Ile Gln Val Pro
    4205            4210                4215
Ser Leu Gly Pro Pro Ser Glu Gln Asp Cys Met Phe Gly Asn Gly
    4220            4225                4230
Lys Gly Tyr Arg Gly Lys Lys Ala Thr Thr Val Thr Gly Thr Pro
    4235            4240                4245
Cys Gln Glu Trp Ala Ala Gln Glu Pro His Arg His Ser Thr Phe
    4250            4255                4260
Ile Pro Gly Thr Asn Lys Trp Ala Gly Leu Glu Lys Asn Tyr Cys
    4265            4270                4275
Arg Asn Pro Asp Gly Asp Ile Asn Gly Pro Trp Cys Tyr Thr Met
    4280            4285                4290
Asn Pro Arg Lys Leu Phe Asp Tyr Cys Asp Ile Pro Leu Cys Ala
    4295            4300                4305
Ser Ser Ser Phe Asp Cys Gly Lys Pro Gln Val Glu Pro Lys Lys
    4310            4315                4320
Cys Pro Gly Ser Ile Val Gly Gly Cys Val Ala His Pro His Ser
    4325            4330                4335
Trp Pro Trp Gln Val Ser Leu Arg Thr Arg Phe Gly Lys His Phe
    4340            4345                4350
Cys Gly Gly Thr Leu Ile Ser Pro Glu Trp Val Leu Thr Ala Ala
    4355            4360                4365
His Cys Leu Lys Lys Ser Ser Arg Pro Ser Ser Tyr Lys Val Ile
    4370            4375                4380
Leu Gly Ala His Gln Glu Val Asn Leu Glu Ser His Val Gln Glu
    4385            4390                4395
Ile Glu Val Ser Arg Leu Phe Leu Glu Pro Thr Gln Ala Asp Ile
    4400            4405                4410
Ala Leu Leu Lys Leu Ser Arg Pro Ala Val Ile Thr Asp Lys Val
    4415            4420                4425
Met Pro Ala Cys Leu Pro Ser Pro Asp Tyr Met Val Thr Ala Arg
    4430            4435                4440
Thr Glu Cys Tyr Ile Thr Gly Trp Gly Glu Thr Gln Gly Thr Phe
    4445            4450                4455
Gly Thr Gly Leu Leu Lys Glu Ala Gln Leu Leu Val Ile Glu Asn
    4460            4465                4470
Glu Val Cys Asn His Tyr Lys Tyr Ile Cys Ala Glu His Leu Ala
    4475            4480                4485
Arg Gly Thr Asp Ser Cys Gln Gly Asp Ser Gly Gly Pro Leu Val
    4490            4495                4500
Cys Phe Glu Lys Asp Lys Tyr Ile Leu Gln Gly Val Thr Ser Trp
    4505            4510                4515
Gly Leu Gly Cys Ala Arg Pro Asn Lys Pro Gly Val Tyr Ala Arg
    4520            4525                4530
Val Ser Arg Phe Val Thr Trp Ile Glu Gly Met Met Arg Asn Asn
    4535            4540                4545
```

<210> SEQ ID NO 31
<211> LENGTH: 317
<212> TYPE: PRT
<213> ORGANISM: Homo sapiens

<400> SEQUENCE: 31

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315

<210> SEQ ID NO 32
<211> LENGTH: 138
<212> TYPE: PRT
<213> ORGANISM: Homo sapiens

<400> SEQUENCE: 32

Met Thr Ala Leu Phe Leu Met Ser Met Leu Phe Gly Leu Ala Cys Gly
1               5                   10                  15

```
Gln Ala Met Ser Phe Cys Ile Pro Thr Glu Tyr Thr Met His Ile Glu
            20                  25                  30

Arg Arg Glu Cys Ala Tyr Cys Leu Thr Ile Asn Thr Thr Ile Cys Ala
        35                  40                  45

Gly Tyr Cys Met Thr Arg Asp Ile Asn Gly Lys Leu Phe Leu Pro Lys
    50                  55                  60

Tyr Ala Leu Ser Gln Asp Val Cys Thr Tyr Arg Asp Phe Ile Tyr Arg
65                  70                  75                  80

Thr Val Glu Ile Pro Gly Cys Pro Leu His Val Ala Pro Tyr Phe Ser
                85                  90                  95

Tyr Pro Val Ala Leu Ser Cys Lys Cys Gly Lys Cys Asn Thr Asp Tyr
            100                 105                 110

Ser Asp Cys Ile His Glu Ala Ile Lys Thr Asn Tyr Cys Thr Lys Pro
        115                 120                 125

Gln Lys Ser Tyr Leu Val Gly Phe Ser Val
    130                 135
```

<210> SEQ ID NO 33
<211> LENGTH: 241
<212> TYPE: PRT
<213> ORGANISM: Homo sapiens

<400> SEQUENCE: 33

```
Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala
```

```
<210> SEQ ID NO 34
<211> LENGTH: 155
<212> TYPE: PRT
<213> ORGANISM: Homo sapiens

<400> SEQUENCE: 34

Met Glu Arg Ile Val Ile Cys Leu Met Val Ile Phe Leu Gly Thr Leu
1               5                   10                  15

Val His Lys Ser Ser Ser Gln Gly Gln Asp Arg His Met Ile Arg Met
            20                  25                  30

Arg Gln Leu Ile Asp Ile Val Asp Gln Leu Lys Asn Tyr Val Asn Asp
            35                  40                  45

Leu Val Pro Glu Phe Leu Pro Ala Pro Glu Asp Val Glu Thr Asn Cys
    50                  55                  60

Glu Trp Ser Ala Phe Ser Cys Phe Gln Lys Ala Gln Leu Lys Ser Ala
65                  70                  75                  80

Asn Thr Gly Asn Asn Glu Arg Ile Ile Asn Val Ser Ile Lys Lys Leu
                85                  90                  95

Lys Arg Lys Pro Pro Ser Thr Asn Ala Gly Arg Arg Gln Lys His Arg
                100                 105                 110

Leu Thr Cys Pro Ser Cys Asp Ser Tyr Glu Lys Lys Pro Pro Lys Glu
            115                 120                 125

Phe Leu Glu Arg Phe Lys Ser Leu Leu Gln Lys Met Ile His Gln His
        130                 135                 140

Leu Ser Ser Arg Thr His Gly Ser Glu Asp Ser
145                 150                 155

<210> SEQ ID NO 35
<211> LENGTH: 10
<212> TYPE: PRT
<213> ORGANISM: Homo sapiens

<400> SEQUENCE: 35

Gln Gly Glu Pro Ser Ala Pro Lys Leu Glu
1               5                   10
```

METHODS AND COMPOSITIONS FOR DIAGNOSIS AND PROGNOSIS OF RENAL INJURY AND RENAL FAILURE

CROSS-REFERENCE TO RELATED APPLICATIONS

The present invention is a continuation of U.S. application Ser. No. 13/806,761, filed under 35 U.S.C. § 371 as the U.S. national phase of International Application No. PCT/US2011/001125, filed Jun. 23, 2011, which designated the U.S. and claims priority to U.S. Provisional Patent Application No. 61/357,965 filed Jun. 23, 2010; U.S. Provisional Patent Application No. 61/357,956 filed Jun. 23, 2010; U.S. Provisional Patent Application No. 61/357,966 filed Jun. 23, 2010; U.S. Provisional Patent Application No. 61/364,305 filed Jul. 14, 2010; and U.S. Provisional Patent Application No. 61/364,296 filed Jul. 14, 2010, each of which is hereby incorporated in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on May 22, 2017, is named AST_1940_CT_SeqListing.txt and is 144 kilobytes in size.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, $17^{th}$ Ed., McGraw Hill, N.Y., pages 1741-1830, which are hereby incorporated by reference in their entirety. Renal disease and/or injury may be acute or chronic. Acute and chronic kidney disease are described as follows (from Current Medical Diagnosis & Treatment 2008, $47^{th}$ Ed, McGraw Hill, N.Y., pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, $17^{th}$ ed., Chapter 222, and which is hereby incorporated by reference in their entirety:

| Type | Risk Factors |
| --- | --- |
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |

-continued

| Type | Risk Factors |
| --- | --- |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, Curr Opin Nephrol Hypertens 14:265-270, 2005 and Chertow et al, J Am Soc Nephrol 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, J Am Soc Nephrol 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., *Crit Care.* 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production<0.5 ml/kg/hr for 12 h;

"Failure": serum creatinine increased 3.0 fold from baseline OR creatinine >355 μmol/l (with a rise of >44) or urine output below 0.3 ml/kg/hr for 24 h or anuria for at least 12 hours;

And included two clinical outcomes:

"Loss": persistent need for renal replacement therapy for more than four weeks.

"ESRD": end stage renal disease—the need for dialysis for more than 3 months.

These criteria are called the RIFLE criteria, which provide a useful clinical tool to classify renal status. As discussed in Kellum, *Crit. Care Med.* 36: S141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 μmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine ≥354 μmol/L accompanied by an acute increase of at least 44 μmol/L OR urine output less than 0.3 mL/kg per hour for 24 hours or anuria for 12 hours.

The CIN Consensus Working Panel (McCollough et al, Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a subject. As described herein, measurement of one or more biomarkers selected from the group consisting of Tumor necrosis factor receptor superfamily member 8, Alpha-Fetoprotein, Thyroxine-binding globulin, Prostate-specific antigen (free form), Apolipoprotein A, Apolipoprotein E, Thyrotropin subunit beta, Platelet-derived growth factor B/B dimer, C-C motif chemokine 7, C-C motif chemokine 26, Complement C4-B, Corticotropin, Interferon alpha-2, Interleukin-4 receptor alpha chain, Insulin-like growth factor-binding protein 4, Insulin-like growth factor-binding protein 5, Interleukin 21, Interleukin 23 alpha subunit, Interleukin-28A, Interleukin-33, Lutropin subunit beta, Matrix Metalloproteinase-1, Neural cell adhesion molecule 1, Pigment epithelium-derived factor, Vascular endothelial growth factor receptor 2, Vascular endothelial growth factor receptor 3, and IgG4 (each referred to herein as a "kidney injury marker") can be used for diagnosis, prognosis, risk stratification, staging, monitoring, categorizing and determination of further diagnosis and treatment regimens in subjects suffering or at risk of suffering from an injury to renal function, reduced renal function, and/or acute renal failure (also called acute kidney injury).

The kidney injury markers of the present invention may be used, individually or in panels comprising a plurality of kidney injury markers, for risk stratification (that is, to identify subjects at risk for a future injury to renal function, for future progression to reduced renal function, for future progression to ARF, for future improvement in renal function, etc.); for diagnosis of existing disease (that is, to identify subjects who have suffered an injury to renal function, who have progressed to reduced renal function, who have progressed to ARF, etc.); for monitoring for deterioration or improvement of renal function; and for predicting a future medical outcome, such as improved or worsening renal function, a decreased or increased mortality risk, a decreased or increased risk that a subject will require renal replacement therapy (i.e., hemodialysis, peritoneal dialysis, hemofiltration, and/or renal transplantation, a decreased or increased risk that a subject will recover from an injury to renal function, a decreased or increased risk that a subject will recover from ARF, a decreased or increased risk that a subject will progress to end stage renal disease, a decreased or increased risk that a subject will progress to chronic renal failure, a decreased or increased risk that a subject will suffer rejection of a transplanted kidney, etc.

In a first aspect, the present invention relates to methods for evaluating renal status in a subject. These methods comprise performing an assay method that is configured to detect one or more biomarkers selected from the group consisting of Tumor necrosis factor receptor superfamily member 8, Alpha-Fetoprotein, Thyroxine-binding globulin, Prostate-specific antigen (free form), Apolipoprotein A, Apolipoprotein E, Thyrotropin subunit beta, Platelet-derived growth factor B/B dimer, C-C motif chemokine 7, C-C motif chemokine 26, Complement C4-B, Corticotropin, Interferon alpha-2, Interleukin-4 receptor alpha chain, Insulin-like growth factor-binding protein 4, Insulin-like growth factor-binding protein 5, Interleukin 21, Interleukin 23 alpha subunit, Interleukin-28A, Interleukin-33, Lutropin subunit beta, Matrix Metalloproteinase-1, Neural cell adhesion molecule 1, Pigment epithelium-derived factor, Vascular endothelial growth factor receptor 2, Vascular endothelial growth factor receptor 3, and IgG4 complex is/are then correlated to the renal status of the subject. This correlation to renal status may include correlating the assay result(s) to one or more of risk stratification, diagnosis, prognosis, staging, classifying and monitoring of the subject as described herein. Thus, the present invention utilizes one or more kidney injury markers of the present invention for the evaluation of renal injury.

In certain embodiments, the methods for evaluating renal status described herein are methods for risk stratification of the subject; that is, assigning a likelihood of one or more future changes in renal status to the subject. In these embodiments, the assay result(s) is/are correlated to one or more such future changes. The following are preferred risk stratification embodiments.

In preferred risk stratification embodiments, these methods comprise determining a subject's risk for a future injury to renal function, and the assay result(s) is/are correlated to a likelihood of such a future injury to renal function. For example, the measured concentration(s) may each be compared to a threshold value. For a "positive going" kidney injury marker, an increased likelihood of suffering a future injury to renal function is assigned to the subject when the measured concentration is above the threshold, relative to a likelihood assigned when the measured concentration is below the threshold. For a "negative going" kidney injury marker, an increased likelihood of suffering a future injury to renal function is assigned to the subject when the measured concentration is below the threshold, relative to a likelihood assigned when the measured concentration is above the threshold.

In other preferred risk stratification embodiments, these methods comprise determining a subject's risk for future reduced renal function, and the assay result(s) is/are correlated to a likelihood of such reduced renal function. For example, the measured concentrations may each be compared to a threshold value. For a "positive going" kidney injury marker, an increased likelihood of suffering a future reduced renal function is assigned to the subject when the measured concentration is above the threshold, relative to a likelihood assigned when the measured concentration is below the threshold. For a "negative going" kidney injury marker, an increased likelihood of future reduced renal function is assigned to the subject when the measured concentration is below the threshold, relative to a likelihood assigned when the measured concentration is above the threshold.

In still other preferred risk stratification embodiments, these methods comprise determining a subject's likelihood for a future improvement in renal function, and the assay result(s) is/are correlated to a likelihood of such a future improvement in renal function. For example, the measured concentration(s) may each be compared to a threshold value. For a "positive going" kidney injury marker, an increased likelihood of a future improvement in renal function is assigned to the subject when the measured concentration is below the threshold, relative to a likelihood assigned when the measured concentration is above the threshold. For a "negative going" kidney injury marker, an increased likelihood of a future improvement in renal function is assigned to the subject when the measured concentration is above the threshold, relative to a likelihood assigned when the measured concentration is below the threshold.

In yet other preferred risk stratification embodiments, these methods comprise determining a subject's risk for progression to ARF, and the result(s) is/are correlated to a likelihood of such progression to ARF. For example, the measured concentration(s) may each be compared to a threshold value. For a "positive going" kidney injury marker, an increased likelihood of progression to ARF is assigned to the subject when the measured concentration is above the threshold, relative to a likelihood assigned when the measured concentration is below the threshold. For a "negative going" kidney injury marker, an increased likelihood of progression to ARF is assigned to the subject when the measured concentration is below the threshold, relative to a likelihood assigned when the measured concentration is above the threshold.

And in other preferred risk stratification embodiments, these methods comprise determining a subject's outcome risk, and the assay result(s) is/are correlated to a likelihood of the occurrence of a clinical outcome related to a renal injury suffered by the subject. For example, the measured concentration(s) may each be compared to a threshold value. For a "positive going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is above the threshold, relative to a likelihood assigned when the measured concentration is below the threshold. For a "negative going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is below the threshold, relative to a likelihood assigned when the measured concentration is above the threshold.

In such risk stratification embodiments, preferably the likelihood or risk assigned is that an event of interest is more or less likely to occur within 180 days of the time at which the body fluid sample is obtained from the subject. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the subject is equivalent to diagnosis of a current condition.

In preferred risk stratification embodiments, the subject is selected for risk stratification based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin are all preferred subjects for monitoring risks according to the methods described herein. This list is not meant to be limiting. By "pre-existence" in this context is meant that the risk factor exists at the time the body fluid sample is obtained from the subject. In particularly preferred embodiments, a subject is chosen for risk stratification based on an existing diagnosis of injury to renal function, reduced renal function, or ARF.

In other embodiments, the methods for evaluating renal status described herein are methods for diagnosing a renal injury in the subject; that is, assessing whether or not a subject has suffered from an injury to renal function, reduced renal function, or ARF. In these embodiments, the assay result(s), for example measured concentration(s) of one or more biomarkers selected from the group consisting of Tumor necrosis factor receptor superfamily member 8, Alpha-Fetoprotein, Thyroxine-binding globulin, Prostate-specific antigen (free form), Apolipoprotein A, Apolipoprotein E, Thyrotropin subunit beta, Platelet-derived growth factor B/B dimer, C-C motif chemokine 7, C-C motif chemokine 26, Complement C4-B, Corticotropin, Interferon alpha-2, Interleukin-4 receptor alpha chain, Insulin-like growth factor-binding protein 4, Insulin-like growth factor-binding protein 5, Interleukin 21, Interleukin 23 alpha subunit, Interleukin-28A, Interleukin-33, Lutropin subunit beta, Matrix Metalloproteinase-1, Neural cell adhesion molecule 1, Pigment epithelium-derived factor, Vascular endothelial growth factor receptor 2, Vascular endothelial growth factor receptor 3, and IgG4 is/are correlated to the occurrence or nonoccurrence of a change in renal status. The following are preferred diagnostic embodiments.

In preferred diagnostic embodiments, these methods comprise diagnosing the occurrence or nonoccurrence of an injury to renal function, and the assay result(s) is/are correlated to the occurrence or nonoccurrence of such an injury. For example, each of the measured concentration(s) may be compared to a threshold value. For a positive going marker, an increased likelihood of the occurrence of an injury to renal function is assigned to the subject when the measured concentration is above the threshold (relative to the likelihood assigned when the measured concentration is below the threshold); alternatively, when the measured concentration is below the threshold, an increased likelihood of the nonoccurrence of an injury to renal function may be assigned to the subject (relative to the likelihood assigned when the measured concentration is above the threshold). For a negative going marker, an increased likelihood of the occurrence of an injury to renal function is assigned to the subject when the measured concentration is below the threshold (relative to the likelihood assigned when the measured concentration is above the threshold); alternatively, when the measured concentration is above the threshold, an increased likelihood of the nonoccurrence of an injury to renal function may be assigned to the subject (relative to the likelihood assigned when the measured concentration is below the threshold).

In other preferred diagnostic embodiments, these methods comprise diagnosing the occurrence or nonoccurrence of reduced renal function, and the assay result(s) is/are correlated to the occurrence or nonoccurrence of an injury causing reduced renal function. For example, each of the measured concentration(s) may be compared to a threshold value. For a positive going marker, an increased likelihood of the occurrence of an injury causing reduced renal function is assigned to the subject when the measured concentration is above the threshold (relative to the likelihood assigned when the measured concentration is below the threshold); alternatively, when the measured concentration is below the threshold, an increased likelihood of the nonoccurrence of an injury causing reduced renal function may be assigned to the subject (relative to the likelihood assigned when the measured concentration is above the threshold). For a negative going marker, an increased likelihood of the occurrence of an injury causing reduced renal function is assigned to the subject when the measured concentration is below the threshold (relative to the likelihood assigned when the measured concentration is above the threshold); alternatively, when the measured concentration is above the threshold, an increased likelihood of the nonoccurrence of an injury causing reduced renal function may be assigned to the subject (relative to the likelihood assigned when the measured concentration is below the threshold).

In yet other preferred diagnostic embodiments, these methods comprise diagnosing the occurrence or nonoccurrence of ARF, and the assay result(s) is/are correlated to the occurrence or nonoccurrence of an injury causing ARF. For example, each of the measured concentration(s) may be compared to a threshold value. For a positive going marker, an increased likelihood of the occurrence of ARF is assigned to the subject when the measured concentration is above the threshold (relative to the likelihood assigned when the measured concentration is below the threshold); alternatively, when the measured concentration is below the threshold, an increased likelihood of the nonoccurrence of ARF may be assigned to the subject (relative to the likelihood assigned when the measured concentration is above the threshold). For a negative going marker, an increased likelihood of the occurrence of ARF is assigned to the subject when the measured concentration is below the threshold (relative to the likelihood assigned when the measured concentration is above the threshold); alternatively, when the measured concentration is above the threshold, an increased likelihood of the nonoccurrence of ARF may be assigned to the subject (relative to the likelihood assigned when the measured concentration is below the threshold).

In still other preferred diagnostic embodiments, these methods comprise diagnosing a subject as being in need of renal replacement therapy, and the assay result(s) is/are correlated to a need for renal replacement therapy. For example, each of the measured concentration(s) may be compared to a threshold value. For a positive going marker, an increased likelihood of the occurrence of an injury creating a need for renal replacement therapy is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal replacement therapy may be assigned to the subject (relative to the likelihood assigned when the measured concentration is above the threshold). For a negative going marker, an increased likelihood of the occurrence of an injury creating a need for renal replacement therapy is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal replacement therapy may be assigned to the subject (relative to the likelihood assigned when the measured concentration is below the threshold).

In still other preferred diagnostic embodiments, these methods comprise diagnosing a subject as being in need of renal transplantation, and the assay result(s0 is/are correlated to a need for renal transplantation. For example, each of the measured concentration(s) may be compared to a threshold value. For a positive going marker, an increased likelihood of the occurrence of an injury creating a need for renal transplantation is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal transplantation may be assigned to the subject (relative to the likelihood assigned when the measured concentration is above the threshold). For a negative going marker, an increased likelihood of the occurrence of an injury creating a need for renal transplantation is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal transplantation may be assigned to the subject (relative to the likelihood assigned when the measured concentration is below the threshold).

In still other embodiments, the methods for evaluating renal status described herein are methods for monitoring a renal injury in the subject; that is, assessing whether or not renal function is improving or worsening in a subject who has suffered from an injury to renal function, reduced renal function, or ARF. In these embodiments, the assay result(s), for example measured concentration(s) of one or more biomarkers selected from the group consisting of Tumor necrosis factor receptor superfamily member 8, Alpha-Fetoprotein, Thyroxine-binding globulin, Prostate-specific antigen (free form), Apolipoprotein A, Apolipoprotein E, Thyrotropin subunit beta, Platelet-derived growth factor B/B dimer, C-C motif chemokine 7, C-C motif chemokine 26, Complement C4-B, Corticotropin, Interferon alpha-2, Interleukin-4 receptor alpha chain, Insulin-like growth factor-binding protein 4, Insulin-like growth factor-binding protein 5, Interleukin 21, Interleukin 23 alpha subunit, Interleukin-28A, Interleukin-33, Lutropin subunit beta, Matrix Metalloproteinase-1, Neural cell adhesion molecule 1, Pigment epithelium-derived factor, Vascular endothelial growth factor receptor 2, Vascular endothelial growth factor receptor 3, and IgG4 is/are correlated to the occurrence or nonoccurrence of a change in renal status. The following are preferred monitoring embodiments.

In preferred monitoring embodiments, these methods comprise monitoring renal status in a subject suffering from an injury to renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other preferred monitoring embodiments, these methods comprise monitoring renal status in a subject suffering from reduced renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject suffering from acute renal failure, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other additional preferred monitoring embodiments, these methods comprise monitoring renal status in a subject at risk of an injury to renal function due to the pre-existence of one or more known risk factors for prerenal, intrinsic renal, or postrenal ARF, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In still other embodiments, the methods for evaluating renal status described herein are methods for classifying a renal injury in the subject; that is, determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage. In these embodiments, the assay result(s), for example measured concentration(s) of one or more biomarkers selected from the group consisting of Tumor necrosis factor receptor superfamily member 8, Alpha-Fetoprotein, Thyroxine-binding globulin, Prostate-specific antigen (free form), Apolipoprotein A, Apolipoprotein E, Thyrotropin subunit beta, Platelet-derived growth factor B/B dimer, C-C motif chemokine 7, C-C motif chemokine 26, Complement C4-B, Corticotropin, Interferon alpha-2, Interleukin-4 receptor alpha chain, Insulin-like growth factor-binding protein 4, Insulin-like growth factor-binding protein 5, Interleukin 21, Interleukin 23 alpha subunit, Interleukin-28A, Interleukin-33, Lutropin subunit beta, Matrix Metalloproteinase-1, Neural cell adhesion molecule 1, Pigment epithelium-derived factor, Vascular endothelial growth factor receptor 2, Vascular endothelial growth factor receptor 3, and IgG4 is/are correlated to a particular class and/or subclass. The following are preferred classification embodiments.

In preferred classification embodiments, these methods comprise determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage, and the assay result(s) is/are correlated to the injury classification for the subject. For example, the measured concentration may be compared to a threshold value, and when the measured concentration is above the threshold, a particular classification is assigned; alternatively, when the measured concentration is below the threshold, a different classification may be assigned to the subject.

A variety of methods may be used by the skilled artisan to arrive at a desired threshold value for use in these methods. For example, the threshold value may be determined from a population of normal subjects by selecting a concentration representing the 75th, 85th, 90th, 95th, or 99th percentile of a kidney injury marker measured in such normal subjects. Alternatively, the threshold value may be determined from a "diseased" population of subjects, e.g., those suffering from an injury or having a predisposition for an injury (e.g., progression to ARF or some other clinical outcome such as death, dialysis, renal transplantation, etc.), by selecting a concentration representing the 75th, 85th, 90th, 95th, or 99th percentile of a kidney injury marker measured in such subjects. In another alternative, the threshold value may be determined from a prior measurement of a kidney injury marker in the same subject; that is, a temporal change in the level of a kidney injury marker in the subject may be used to assign risk to the subject.

The foregoing discussion is not meant to imply, however, that the kidney injury markers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that the kidney injury marker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the subject selected from the group consisting of demographic information (e.g., weight, sex, age, race), medical history (e.g., family history, type of surgery, preexisting disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score, risk scores of Thakar et al. (J. Am. Soc. Nephrol. 16: 162-68, 2005), Mehran et al. (J. Am. Coll. Cardiol. 44: 1393-99, 2004), Wijeysundera et al. (JAMA 297: 1801-9, 2007), Goldstein and Chawla (Clin. J. Am. Soc. Nephrol. 5: 943-49, 2010), or Chawla et al. (Kidney Intl. 68: 2274-80, 2005)), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

DETAILED DESCRIPTION OF THE INVENTION

The present invention relates to methods and compositions for diagnosis, differential diagnosis, risk stratification, monitoring, classifying and determination of treatment regimens in subjects suffering or at risk of suffering from injury to renal function, reduced renal function and/or acute renal failure through measurement of one or more kidney injury markers. In various embodiments, a measured concentration of one or more biomarkers selected from the group consisting of Tumor necrosis factor receptor superfamily member 8, Alpha-Fetoprotein, Thyroxine-binding globulin, Prostate-specific antigen (free form), Apolipoprotein A, Apolipoprotein E, Thyrotropin subunit beta, Platelet-derived growth factor B/B dimer, C-C motif chemokine 7, C-C motif chemokine 26, Complement C4-B, Corticotropin, Interferon alpha-2, Interleukin-4 receptor alpha chain, Insulin-like growth factor-binding protein 4, Insulin-like growth factor-binding protein 5, Interleukin 21, Interleukin 23 alpha subunit, Interleukin-28A, Interleukin-33, Lutropin subunit beta, Matrix Metalloproteinase-1, Neural cell adhesion molecule 1, Pigment epithelium-derived factor, Vascular endothelial growth factor receptor 2, Vascular endothelial growth factor receptor 3, and IgG4 or one or more markers related thereto, are correlated to the renal status of the subject.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL (≥8.8 µmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl (≥26.4 µmol/l), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

As used herein, the term "C-C motif chemokine 7" refers to one or more polypeptides present in a biological sample that are derived from the C-C motif chemokine 7 precursor (Swiss-Prot P80098 (SEQ ID NO: 1)).

```
         10         20         30         40
MKASAALLCL LLTAAAFSPQ GLAQPVGINT STTCCYRFIN 50         60         70         80
KKIPKQRLES YRRTTSSHCP REAVIFKTKL DKEICADPTQ

90
KWVQDFMKHL DKKTQTPKL
```

The following domains have been identified in C-C motif chemokine 7:

| Residues | Length | Domain ID |
|---|---|---|
| 1-23 | 23 | Signal peptide |
| 24-99 | 76 | C-C motif chemokine 7 |

As used herein, the term "C-C motif chemokine 26" refers to one or more polypeptides present in a biological sample that are derived from the C-C motif chemokine 26 precursor (Swiss-Prot Q9Y258 (SEQ ID NO: 2)).

```
         10         20         30         40
MMGLSLASAV LLASLLSLHL GTATRGSDIS KTCCFQYSHK 50         60         70         80
PLPWTWVRSY EFTSNSCSQR AVIFTTKRGK KVCTHPRKKW

90
VQKYISLLKT PKQL
```

The following domains have been identified in C-C motif chemokine 26:

| Residues | Length | Domain ID |
|---|---|---|
| 1-23 | 23 | Signal peptide |
| 24-94 | 71 | C-C motif chemokine 26 |

As used herein, the term "Complement C4-B" refers to one or more polypeptides present in a biological sample that are derived from Complement C4-B precursor (Swiss-Prot POCOL5 (SEQ ID NO: 3)).

```
         10         20         30         40
MRLLWGLIWA SSFFTLSLQK PRLLLFSPSV VHLGVPLSVG 50         60         70         80
VQLQDVPRGQ VVKGSVFLRN PSRNNVPCSP KVDFTLSSER 90        100        110        120
DFALLSLQVP LKDAKSCGLH QLLRGPEVQL VAHSPWLKDS 130        140        150        160
LSRTTNIQGI NLLFSSRRGH LFLQTDQPIY NPGQRVRYRV 170        180        190        200
FALDQKMRPS TDTITVMVEN SHGLRVRKKE VYMPSSIFQD 210        220        230        240
DFVIPDISEP GTWKISARFS DGLESNSSTQ FEVKKYVLPN 250        260        270        280
FEVKITPGKP YILTVPGHLD EMQLDIQARY IYGKPVQGVA 290        300        310        320
YVRFGLLDED GKKTFFRGLE SQTKLVNGQS HISLSKAEFQ 330        340        350        360
DALEKLNMGI TDLQGLRLYV AAAIIESPGG EMEEAELTSW
```

```
            370        380        390        400
YFVSSPFSLD LSKTKRHLVP GAPFLLQALV REMSGSPASG 410        420        430        440
IPVKVSATVS SPGSVPEVQD IQQNTDGSGQ VSIPIIIPQT 450        460        470        480
ISELQLSVSA GSPHPAIARL TVAAPPSGGP GFLSIERPDS 490        500        510        520
RPPRVGDTLN LNLRAVGSGA TFSHYYYMIL SRGQIVFMNR 530        540        550        560
EPKRTLTSVS VFVDHHLAPS FYFVAFYYHG DHPVANSLRV 570        580        590        600
DVQAGACEGK LELSVDGAKQ YRNGESVKLH LETDSLALVA 610        620        630        640
LGALDTALYA AGSKSHKPLN MGKVFEAMNS YDLGCGPGGG 650        660        670        680
DSALQVFQAA GLAFSDGDQW TLSRKRLSCP KEKTTRKKRN 690        700        710        720
VNFQKAINEK LGQYASPTAK RCCQDGVTRL PMMRSCEQRA 730        740        750        760
ARVQQPDCRE PFLSCCQFAE SLRKKSRDKG QAGLQRALEI 770        780        790        800
LQEEDLIDED DIPVRSFFPE NWLWRVETVD RFQILTLWLP 810        820        830        840
DSLTTWEIHG LSLSKTKGLC VATPVQLRVF REFHLHLRLP 850        860        870        880
MSVRRFEQLE LRPVLYNYLD KNLTVSVHVS PVEGLCLAGG 890        900        910        920
GGLAQQVLVP AGSARPVAFS VVPTAAAAVS LKVVARGSFE 930        940        950        960
FPVGDAVSKV LQIEKEGAIH REELVYELNP LDHRGRTLEI 970        980        990       1000
PGNSDPNMIP DGDFNSYVRV TASDPLDTLG SEGALSPGGV 1010       1020       1030       1040
ASLLRLPRGC GEQTMIYLAP TLAASRYLDK TEQWSTLPPE 1050       1060       1070       1080
TKDHAVDLIQ KGYMRIQQFR KADGSYAAWL SRDSSTWLTA 1090       1100       1110       1120
FVLKVLSLAQ EQVGGSPEKL QETSNWLLSQ QQADGSFQDL 1130       1140       1150       1160
SPVIHRSMQG GLVGNDETVA LTAFVTIALH HGLAVFQDEG 1170       1180       1190       1200
AEPLKQRVEA SISKANSFLG EKASAGLLGA HAAAITAYAL 1210       1220       1230       1240
SLTKAPVDLL GVAHNNLMAM AQETGDNLYW GSVTGSQSNA 1250       1260       1270       1280
VSPTPAPRNP SDPMPQAPAL WIETTAYALL HLLLHEGKAE 1290       1300       1310       1320
MADQASAWLT RQGSFQGGFR STQDTVIALD ALSAYWIASH 1330       1340       1350       1360
TTEERGLNVT LSSTGRNGFK SHALQLNNRQ IRGLEEELQF 1370       1380       1390       1400
SLGSKINVKV GGNSKGTLKV LRTYNVLDMK NTTCQDLQIE 1410       1420       1430       1440
VTVKGHVEYT MEANEDYEDY EYDELPAKDD PDAPLQPVTP 1450       1460       1470       1480
LQLFEGRRNR RRREAPKVVE EQESRVHYTV CIWRNGKVGL 1490       1500       1510       1520
SGMAIADVTL LSGFHALRAD LEKLTSLSDR YVSHFETEGP 1530       1540       1550       1560
HVLLYFDSVP TSRECVGFEA VQEVPVGLVQ PASATLYDYY 1570       1580       1590       1600
NPERRCSVFY GAPSKSRLLA TLCSAEVCQC AEGKCPRQRR 1610       1620       1630       1640
ALERGLQDED GYRMKFACYY PRVEYGFQVK VLREDSRAAF 1650       1660       1670       1680
RLFETKITQV LHFTKDVKAA ANQMRNFLVR ASCRLRLEPG 1690       1700       1710       1720
KEYLIMGLDG ATYDLEGHPQ YLLDSNSWIE EMPSERLCRS 1730       1740
TRQRAACAQL NDFLQEYGTQ GCQV
```

The following domains have been identified in Complement C4-B:

| Residues | Length | Domain ID |
| --- | --- | --- |
| 1-19 | 19 | Signal peptide |
| 20-675 | 656 | Complement C4-B beta chain |
| 676-679 | 4 | Propeptide |
| 680-1446 | 767 | Complement C4-B alpha chain |
| 680-756 | 77 | Complement C4-a anaphylatoxin |
| 757-1446 | 690 | Complement C4b-B |
| 957-1336 | 380 | Complement C4d-B |
| 1447-1453 | 7 | propeptide |
| 1454-1744 | 291 | Complement C4-B gamma chain |

As used herein, the term "Corticotropin" refers to one or more polypeptides present in a biological sample that are derived from pro-opiomelanocortin precursor (Swiss-Prot P01189 (SEQ ID NO: 4)) containing one or more epitopes of corticotropin.

```
            10         20         30         40
MPRSCCSRSG ALLLALLLQA SMEVRGWCLE SSQCQDLTTE 50         60         70         80
SNLLECIRAC KPDLSAETPM FPGNGDEQPL TENPRKYVMG 90        100        110        120
HFRWDRFGRR NSSSSGSSGA GQKREDVSAG EDCGPLPEGG 130        140        150        160
PEPRSDGAKP GPREGKRSYS MEHFRWGKPV GKKRRPVKVY 170        180        190        200
PNGAEDESAE AFPLEFKREL TGQRLREGDG PDGPADDGAG 210        220        230        240
AQADLEHSLL VAAEKKDEGP YRMEHFRWGS PPKDKRYGGF 250        260
MTSEKSQTPL VTLFKNAIIK NAYKKGE
```

The following domains have been identified in pro-opiomelanocortin:

| Residues | Length | Domain ID |
| --- | --- | --- |
| 1-26 | 26 | Signal peptide |
| 27-102 | 76 | NPP |
| 77-87 | 11 | Melanotropin gamma |

| Residues | Length | Domain ID |
|---|---|---|
| 105-134 | 30 | peptide |
| 138-176 | 39 | Corticotropin |
| 138-150 | 13 | Melanotropin alpha |
| 156-176 | 21 | Corticotropin-like intermediary peptide |
| 179-267 | 89 | Lipotropin beta |
| 179-234 | 56 | Lipotropin gamma |
| 217-234 | 18 | Melanotropin beta |
| 237-267 | 31 | beta endorphin |
| 237-241 | 5 | met enkephalin |

As used herein, the term "Interferon alpha-2" refers to one or more polypeptides present in a biological sample that are derived from the Interferon alpha-2 precursor (Swiss-Prot P01563 (SEQ ID NO: 5)).

```
             10         20         30         40
     MALTFALLVA LLVLSCKSSC SVGCDLPQTH SLGSRRTLML 50         60         70         80
     LAQMRKISLF SCLKDRHDFG FPQEEFGNQF QKAETIPVLH 90        100        110        120
     EMIQQIFNLF STKDSSAAWD ETLLDKFYTE LYQQLNDLEA 130        140        150        160
     CVIQGVGVTE TPLMKEDSIL AVRKYFQRIT LYLKEKKYSP 170        180
     CAWEVVRAEI MRSFSLSTNL QESLRSKE
```

The following domains have been identified in Interferon alpha-2:

| Residues | Length | Domain ID |
|---|---|---|
| 1-23 | 23 | Signal peptide |
| 24-188 | 209 | Interferon alpha-2 |

As used herein, the term "Interleukin-4 receptor subunit alpha" refers to one or more polypeptides present in a biological sample that are derived from the Interleukin-4 receptor subunit alpha precursor (Swiss-Prot P24394 (SEQ ID NO: 6):

```
             10         20         30         40
     MGWLCSGLLF PVSCLVLLQV ASSGNMKVLQ EPTCVSDYMS 50         60         70         80
     ISTCEWKMNG PTNCSTELRL LYQLVFLLSE AHTCIPENNG 90        100        110        120
     GAGCVCHLLM DDVVSADNYT LDLWAGQQLL WKGSFKPSEH 130        140        150        160
     VKPRAPGNLT VHTNVSDTLL LTWSNPYPPD NYLYNHLTYA 170        180        190        200
     VNIWSENDPA DFRIYNVTYL EPSLRIAAST LKSGISYRAR 210        220        230        240
     VRAWAQCYNT TWSEWSPSTK WHNSYREPFE QHLLLGVSVS 250        260        270        280
     CIVILAVCLL CYVSITKIKK EWWDQIPNPA RSRLVAIIIQ 290        300        310        320
     DAQGSQWEKR SRGQEPAKCP HWKNCLTKLL PCFLEHNMKR 330        340        350        360
     DEDPHKAAKE MPFQGSGKSA WCPVEISKTV LWPESISVVR 370        380        390        400
     CVELFEAPVE CEEEEEVEEE KGSFCASPES SRDDFQEGRE 410        420        430        440
     GIVARLTESL FLDLLGEENG GFCQQDMGES CLLPPSGSTS 450        460        470        480
     AHMPWDEFPS AGPKEAPPWG KEQPLHLEPS PPASPTQSPD 490        500        510        520
     NLTCTETPLV IAGNPAYRSF SNSLSQSPCP RELGPDPLLA 530        540        550        560
     RHLEEVEPEM PCVPQLSEPT TVPQPEPETW EQILRRNVLQ 570        580        590        600
     HGAAAAPVSA PTSGYQEFVH AVEQGGTQAS AVVGLGPPGE 610        620        630        640
     AGYKAFSSLL ASSAVSPEKC GFGASSGEEG YKPFQDLIPG 650        660        670        680
     CPGDPAPVPV PLFTFGLDRE PPRSPQSSHL PSSSPEHLGL 690        700        710        720
     EPGEKVEDMP KPPLPQEQAT DPLVDSLGSG IVYSALTCHL 730        740        750        760
     CGHLKQCHGQ EDGGQTPVMA SPCCGCCCGD RSSPPTTPLR 770        780        790        800
     APDPSPGGVP LEASLCPASL APSGISEKSK SSSSFHPAPG 810        820
     NAQSSSQTPK IVNFVSVGPT YMRVS
```

Interleukin-4 receptor subunit alpha is a single-pass type I membrane protein having a large extracellular domain, some or all of which is present in soluble forms of Interleukin-4 receptor subunit alpha generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Interleukin-4 receptor subunit alpha:

| Residues | Length | Domain ID |
|---|---|---|
| 1-25 | 25 | Signal peptide |
| 26-825 | 800 | Interleukin-4 receptor subunit alpha |
| 26-232 | 319 | Extracellular domain |
| 233-256 | 20 | Transmembrane domain |
| 257-825 | 213 | Cytoplasmic domain |
| 228-825 | | Missing in soluble isoform 2 |
| 225-227 | | YRE → NIC in soluble isoform 2 |

As used herein, the term "Insulin-like growth factor-binding protein 4" refers to one or more polypeptides present in a biological sample that are derived from the Insulin-like growth factor-binding protein 4 precursor (Swiss-Prot P22692 (SEQ ID NO: 7)).

```
             10         20         30         40
     MLPLCLVAAL LLAAGPGPSL GDEAIHCPPC SEEKLARCRP 50         60         70         80
     PVGCEELVRE PGCGCCATCA LGLGMPCGVY TPRCGSGLRC 90        100        110        120
```

```
              YPPRGVEKPL HTLMHGQGVC MELAEIEAIQ ESLQPSDKDE
         130        140        150        160
      GDHPNNSFSP CSAHDRRCLQ KHFAKIRDRS TSGGKMKVNG
         170        180        190        200
      APREDARPVP QGSCQSELHR ALERLAASQS RTHEDLYIIP
         210        220        230        240
      IPNCDRNGNF HPKQCHPALD GQRGKCWCVD RKTGVKLPGG
         250
      LEPKGELDCH QLADSFRE
```

The following domains have been identified in Insulin-like growth factor-binding protein 4:

| Residues | Length | Domain ID |
|---|---|---|
| 1-21 | 21 | Signal peptide |
| 22-258 | 237 | Insulin-like growth factor-binding protein 4 |

As used herein, the term "Insulin-like growth factor-binding protein 5" refers to one or more polypeptides present in a biological sample that are derived from the Insulin-like growth factor-binding protein 5 precursor (Swiss-Prot P24593 (SEQ ID NO: 8)).

```
          10         20         30         40
      MVLLTAVLLL LAAYAGPAQS LGSFVHCEPC DEKALSMCPP
          50         60         70         80
      SPLGCELVKE PGCGCCMTCA LAEGQSCGVY TERCAQGLRC
          90        100        110        120
      LPRQDEEKPL HALLHGRGVC LNEKSYREQV KIERDSREHE
         130        140        150        160
      EPTTSEMAEE TYSPKIFRPK HTRISELKAE AVKKDRRKKL
         170        180        190        200
      TQSKFVGGAE NTAHPRIISA PEMRQESEQG PCRRHMEASL
         210        220        230        240
      QELKASPRMV PRAVYLPNCD RKGFYKRKQC KPSRGRKRGI
         250        260        270
      CWCVDKYGMK LPGMEYVDGD FQCHTFDSSN VE
```

The following domains have been identified in Insulin-like growth factor-binding protein 5:

| Residues | Length | Domain ID |
|---|---|---|
| 1-20 | 20 | Signal peptide |
| 21-272 | 252 | Insulin-like growth factor-binding protein 5 |

As used herein, the term "Interleukin-21" refers to one or more polypeptides present in a biological sample that are derived from the Interleukin-21 precursor (Swiss-Prot Q9HBE4 (SEQ ID NO: 8)).

```
          10         20         30         40
      MERIVICLMV IFLGTLVHKS SSQGQDRHMI RMRQLIDIVD
          50         60         70         80
      QLKNYVNDLV PEFLPAPEDV ETNCEWSAFS CFQKAQLKSA
          90        100        110        120
      NTGNNERIIN VSIKKLKRKP PSTNAGRRQK HRLTCPSCDS
         130        140        150
      YEKKPPKEFL ERFKSLLQKM IHQHLSSRTH GSEDS
```

The following domains have been identified in Interleukin-21:

| Residues | Length | Domain ID |
|---|---|---|
| 1-22 | 22 | Signal peptide |
| 23-155 | 133 | Interleukin-21 |

As used herein, the term "Interleukin-23 subunit alpha" refers to one or more polypeptides present in a biological sample that are derived from the Interleukin-23 subunit alpha precursor (Swiss-Prot Q9NPF7 (SEQ ID NO: 9)).

```
          10         20         30         40
      MLGSRAVMLL LLLPWTAQGR AVPGGSSPAW TQCQQLSQKL
          50         60         70         80
      CTLAWSAHPL VGHMDLREEG DEETTNDVPH IQCGDGCDPQ
          90        100        110        120
      GLRDNSQFCL QRIHQGLIFY EKLLGSDIFT GEPSLLPDSP
         130        140        150        160
      VGQLHASLLG LSQLLQPEGH HWETQQIPSL SPSQPWQRLL
         170        180
      LRFKILRSLQ AFVAVAARVF AHGAATLSP
```

The following domains have been identified in Interleukin-23 subunit alpha:

| Residues | Length | Domain ID |
|---|---|---|
| 1-19 | 19 | Signal peptide |
| 20-189 | 170 | Interleukin-23 subunit alpha |

As used herein, the term "Interleukin-28A" refers to one or more polypeptides present in a biological sample that are derived from the Interleukin-28A precursor (Swiss-Prot Q8IZJ0 (SEQ ID NO: 10)).

```
          10         20         30         40
      MKLDMTGDCT PVLVLMAAVL TVTGAVPVAR LHGALPDARG
          50         60         70         80
      CHIAQFKSLS PQELQAFKRA KDALEESLLL KDCRCHSRLF
          90        100        110        120
      PRTWDLRQLQ VRERPMALEA ELALTLKVLE ATADTDPALV
         130        140        150        160
      DVLDQPLHTL HHILSQFRAC IQPQPTAGPR TRGRLHHWLY
         170        180        190        200
      RLQEAPKKES PGCLEASVTF NLFRLLTRDL NCVASGDLCV
```

The following domains have been identified in Interleukin-28A:

| Residues | Length | Domain ID |
|---|---|---|
| 1-25 | 25 | Signal peptide |
| 26-200 | 175 | Interleukin-28A |

As used herein, the term "Interleukin-33" refers to one or more polypeptides present in a biological sample that are derived from the Interleukin-33 precursor (Swiss-Prot O95760 (SEQ ID NO: 11)).

```
          10         20         30         40
  MKPKMKYSTN KISTAKWKNT ASKALCFKLG KSQQKAKEVC 50         60         70         80
  PMYFMKLRSG LMIKKEACYF RRETTKRPSL KTGRKHKRHL 90        100        110        120
  VLAACQQQST VECFAFGISG VQKYTRALHD SSITGISPIT 130        140        150        160
  EYLASLSTYN DQSITFALED ESYEIYVEDL KKDEKKDKVL 170        180        190        200
  LSYYESQHPS NESGDGVDGK MLMVTLSPTK DFWLHANNKE 210        220        230        240
  HSVELHKCEK PLPDQAFFVL HNMHSNCVSF ECKTDPGVFI 250        260        270
  GVKDNHLALI KVDSSENLCT ENILFKLSET
```

The following domains have been identified in Interleukin-33:

| Residues | Length | Domain ID |
|---|---|---|
| 1-270 | 270 | Interleukin-33 |

As used herein, the term "Lutropin subunit beta" refers to one or more polypeptides present in a biological sample that are derived from the Lutropin subunit beta precursor (Swiss-Prot P01229 (SEQ ID NO: 12)).

```
          10         20         30         40
  MEMLQGLLLL LLLSMGGAWA SREPLRPWCH PINAILAVEK 50         60         70         80
  EGCPVCITVN TTICAGYCPT MMRVLQAVLP PLPQVVCTYR 90        100        110        120
  DVRFESIRLP GCPRGVDPVV SFPVALSCRC GPCRRSTSDC 130        140
  GGPKDHPLTC DHPQLSGLLF L
```

The following domains have been identified in Lutropin subunit beta:

| Residues | Length | Domain ID |
|---|---|---|
| 1-20 | 20 | Signal peptide |
| 21-141 | 121 | Lutropin subunit beta |

As used herein, the term "Interstitial collagenase" (also known as MMP-1 and matrix metalloproteinase 1) refers to one or more polypeptides present in a biological sample that are derived from the Interstitial collagenase precursor (Swiss-Prot P03956 (SEQ ID NO: 13)).

```
          10         20         30         40
  MHSFPPLLLL LFWGVVSHSF PATLETQEQD VDLVQKYLEK 50         60         70         80
  YYNLKNDGRQ VEKRRNSGPV VEKLKQMQEF FGLKVTGKPD 90        100        110        120
  AETLKVMKQP RCGVPDVAQF VLTEGNPRWE QTHLTYRIEN 130        140        150        160
  YTPDLPRADV DHAIEKAFQL WSNVTPLTFT KVSEGQADIM 170        180        190        200
  ISFVRGDHRD NSPFDGPGGN LAHAFQPGPG IGGDAHFDED 210        220        230        240
  ERWTNNFREY NLHRVAAHEL GHSLGLSHST DIGALMYPSY 250        260        270        280
  TFSGDVQLAQ DDIDGIQAIY GRSQNPVQPI GPQTPKACDS 290        300        310        320
  KLTFDAITTI RGEVMFFKDR FYMRTNPFYP EVELNFISVF 330        340        350        360
  WPQLPNGLEA AYEFADRDEV RFFKGNKYWA VQGQNVLHGY 370        380        390        400
  PKDIYSSFGF PRTVKHIDAA LSEENTGKTY FFVANKYWRY 410        420        430        440
  DEYKRSMDPG YPKMIAHDFP GIGHKVDAVF MKDGFFYFFH 450        460
  GTRQYKFDPK TKRILTLQKA NSWFNCRKN
```

The following domains have been identified in Interstitial collagenase:

| Residues | Length | Domain ID |
|---|---|---|
| 1-19 | 19 | Signal peptide |
| 20-99 | 80 | Activation peptide |
| 100-469 | 370 | Interstitial collagenase |
| 100-269 | 170 | 22 kDa Interstitial collagenase |
| 270-469 | 200 | 27 kDa Interstitial collagenase |

As used herein, the term "Neural cell adhesion molecule 1" refers to one or more polypeptides present in a biological sample that are derived from the Neural cell adhesion molecule 1 precursor (Swiss-Prot P13591 (SEQ ID NO: 14)):

```
          10         20         30         40
  MLQTKDLIWT LFFLGTAVSL QVDIVPSQGE ISVGESKFFL 50         60         70         80
  CQVAGDAKDK DISWFSPNGE KLTPNQQRIS VVWNDDSSST 90        100        110        120
  LTIYNANIDD AGIYKCVVTG EDGSESEATV NVKIFQKLMF 130        140        150        160
  KNAPTPQEFR EGEDAVIVCD VVSSLPPTII WKHKGRDVIL 170        180        190        200
  KKDVRFIVLS NNYLQIRGIK KTDEGTYRCE GRILARGEIN 210        220        230        240
  FKDIQVIVNV PPTIQARQNI VNATANLGQS VTLVCDAEGF 250        260        270        280
  PEPTMSWTKD GEQIEQEEDD EKYIFSDDSS QLTIKKVDKN 290        300        310        320
  DEAEYICIAE NKAGEQDATI HLKVFAKPKI TYVENQTAME 330        340        350        360
  LEEQVTLTCE ASGDPIPSIT WRTSTRNISS EEKASWTRPE 370        380        390        400
  KQETLDGHMV VRSHARVSSL TLKSIQYTDA GEYICTASNT
```

```
              410        420        430        440
    IGQDSQSMYL EVQYAPKLQG PVAVYTWEGN QVNITCEVFA 450        460        470        480
    YPSATISWFR DGQLLPSSNY SNIKIYNTPS ASYLEVTPDS 490        500        510        520
    ENDFGNYNCT AVNRIGQESL EFILVQADTP SSPSIDQVEP 530        540        550        560
    YSSTAQVQFD EPEATGGVPI LKYKAEWRAV GEEVWHSKWY 570        580        590        600
    DAKEASMEGI VTIVGLKPET TYAVRLAALN GKGLGEISAA 610        620        630        640
    SEFKTQPVQG EPSAPKLEGQ MGEDGNSIKV NLIKQDDGGS 650        660        670        680
    PIRHYLVRYR ALSSEWKPEI RLPSGSDHVM LKSLDWNAEY 690        700        710        720
    EVYVVAENQQ GKSKAAHFVF RTSAQPTAIP ANGSPTSGLS 730        740        750        760
    TGAIVGILIV IFVLLLVVVD ITCYFLNKCG LFMCIAVNLC 770        780        790        800
    GKAGPGAKGK DMEEGKAAFS KDESKEPIVE VRTEEERTPN 810        820        830        840
    HDGGKHTEPN ETTPLTEPEK GPVEAKPECQ ETETKPAPAE

850
    VKTVPNDATQ TKENESKA
```

Neural cell adhesion molecule 1 is a single-pass type I membrane protein having a large extracellular domain, some or all of which is present in soluble forms of Neural cell adhesion molecule 1 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Neural cell adhesion molecule 1:

| Residues | Length | Domain ID |
|---|---|---|
| 1-19 | 19 | Signal peptide |
| 20-858 | 839 | Neural cell adhesion molecule 1 |
| 20-718 | 699 | Extracellular domain |
| 719-739 | 21 | Transmembrane domain |
| 740-858 | 119 | Cytoplasmic domain |
| 354-363 | | Missing in isoform 2 |
| 354-363 | | Missing in isoform 3 |
| 609 | | Q → HSPPPPASASSSTPVPLSPPD TTWPLP ALATTEPAK (SEQ ID NO: 15) in isoform 3 |
| 712-736 | | NGSPTSGLSTGAIVGILIVIFVLLL (SEQ ID NO: 16) → TLGGNSASYTFVSLLFSAVTLLLLC (SEQ ID NO: 17) in isoform 3 |
| 737-858 | | Missing in isoform 3 |
| 354-363 | | Missing in isoform 4 |
| 712-736 | | NGSPTSGLSTGAIVGILIVIFVLLL (SEQ ID NO: 18) → TLGGNSASYTFVSLLFSAVTLLLLC ((SEQ ID NO: 19) in isoform 4 |
| 737-858 | | Missing in isoform 4 |
| 609-665 | | QGEPSAPKLE...WKPEIRLPSG (SEQ ID NO: 20) → HSPPPPASASSSTPVPLSPPDTTWPL PALATTEPAKNIAQNHCCNMFQAGLHNALMK (SEQ ID NO: 21) in isoform 5 |
| 364 | | T → V in isoform 6 |
| 365-858 | | Missing in isoform 6 |

As used herein, the term "Pigment epithelium-derived factor" refers to one or more polypeptides present in a biological sample that are derived from the Pigment epithelium-derived factor precursor (Swiss-Prot P36955 (SEQ ID NO: 22)).

```
              10         20         30         40
    MQALVLLLCI GALLGHSSCQ NPASPPEEGS PDPDSTGALV 50         60         70         80
    EEEDPFFKVP VNKLAAAVSN FGYDLYRVRS SMSPTTNVLL 90        100        110        120
    SPLSVATALS ALSLGAEQRT ESIIHRALYY DLISSPDIHG 130        140        150        160
    TYKELLDTVT APQKNLKSAS RIVFEKKLRI KSSFVAPLEK 170        180        190        200
    SYGTRPRVLT GNPRLDLQEI NNWVQAQMKG KLARSTKEIP 210        220        230        240
    DEISILLLGV AHFKGQWVTK FDSRKTSLED FYLDEERTVR 250        260        270        280
    VPMMSDPKAV LRYGLDSDLS CKIAQLPLTG SMSIIFFLPL 290        300        310        320
    KVTQNLTLIE ESLTSEFIHD IDRELKTVQA VLTVPKLKLS 330        340        350        360
    YEGEVTKSLQ EMKLQSLFDS PDFSKITGKP IKLTQVEHRA 370        380        390        400
    GFEWNEDGAG TTPSPGLQPA HLTFPLDYHL NQPFIFVLRD

410
    TDTGALLFIG KILDPRGP
```

The following domains have been identified in Pigment epithelium-derived factor:

| Residues | Length | Domain ID |
|---|---|---|
| 1-19 | 19 | Signal peptide |
| 20-418 | 399 | Pigment epithelium-derived factor |

As used herein, the term "Platelet-derived growth factor subunit A" refers to one or more polypeptides present in a biological sample that are derived from the Platelet-derived growth factor subunit A precursor (Swiss-Prot P04085 (SEQ ID NO: 23)).

```
         10         20         30         40
MRTLACLLLL GCGYLAHVLA EEAEIPREVI ERLARSQIHS 50         60         70         80
IRDLQRLLEI DSVGSEDSLD TSLRAHGVHA TKHVPEKRPL 90        100        110        120
PIRRKRSIEE AVPAVCKTRT VIYEIPRSQV DPTSANFLIW 130        140        150        160
PPCVEVKRCT GCCNTSSVKC QPSRVHHRSV KVAKVEYVRK 170        180        190        200
KPKLKEVQVR LEEHLECACA TTSLNPDYRE EDTGRPRESG

210
KKRKRKRLKP T
```

The following domains have been identified in Platelet-derived growth factor subunit A:

| Residues | Length | Domain ID |
|---|---|---|
| 1-20 | 20 | Signal peptide |
| 21-86 | 66 | Propeptide |
| 87-211 | 125 | Platelet-derived growth factor subunit A |

As used herein, the term "Vascular endothelial growth factor receptor 2" refers to one or more polypeptides present in a biological sample that are derived from the Vascular endothelial growth factor receptor 2 precursor (Swiss-Prot P35968 (SEQ ID NO: 24):

```
         10         20         30         40
MQSKVLLAVA LWLCVETRAA SVGLPSVSLD LPRLSIQKDI 50         60         70         80
LTIKANTTLQ ITCRGQRDLD WLWPNNQSGS EQRVEVTECS 90        100        110        120
DGLFCKTLTI PKVIGNDTGA YKCFYRETDL ASVIYVYVQD 130        140        150        160
YRSPFIASVS DQHGVVYITE NKNKTVVIPC LGSISNLNVS 170        180        190        200
LCARYPEKRF VPDGNRISWD SKKGFTIPSY MISYAGMVFC 210        220        230        240
EAKINDESYQ SIMYIVVVVG YRIYDVVLSP SHGIELSVGE 250        260        270        280
KLVLNCTART ELNVGIDFNW EYPSSKHQHK KLVNRDLKTQ 290        300        310        320
SGSEMKKFLS TLTIDGVTRS DQGLYTCAAS SGLMTKKNST 330        340        350        360
FVRVHEKPFV AFGSGMESLV EATVGERVRI PAKYLGYPPP 370        380        390        400
EIKWYKNGIP LESNHTIKAG HVLTIMEVSE RDTGNYTVIL 410        420        430        440
TNPISKEKQS HVVSLVVYVP PQIGEKSLIS PVDSYQYGTT 450        460        470        480
QTLTCTVYAI PPPHHIHWYW QLEEECANEP SQAVSVTNPY 490        500        510        520
PCEEWRSVED FQGGNKIEVN KNQFALIEGK NKTVSTLVIQ 530        540        550        560
AANVSALYKC EAVNKVGRGE RVISFHVTRG PEITLQPDMQ 570        580        590        600
PTEQESVSLW CTADRSTFEN LTWYKLGPQP LPIHVGELPT 610        620        630        640
PVCKNLDTLW KLNATMFSNS TNDILIMELK NASLQDQGDY 650        660        670        680
VCLAQDRKTK KRHCVVRQLT VLERVAPTIT GNLENQTTSI 690        700        710        720
GESIEVSCTA SGNPPPQIMW FKDNETLVED SGIVLKDGNR 730        740        750        760
NLTIRRVRKE DEGLYTCQAC SVLGCAKVEA FFIIEGAQEK 770        780        790        800
TNLEIIILVG TAVIAMFFWL LLVIILRTVK RANGGELKTG 810        820        830        840
YLSIVMDPDE LPLDEHCERL PYDASKWEFP RDRLKLGKPL 850        860        870        880
GRGAFGQVIE ADAFGIDKTA TCRTVAVKML KEGATHSEHR 890        900        910        920
ALMSELKILI HIGHHLNVVN LLGACTKPGG PLMVIVEFCK 930        940        950        960
FGNLSTYLRS KRNEFVPYKT KGARFRQGKD YVGAIPVDLK 970        980        990       1000
RRLDSITSSQ SSASSGFVEE KSLSDVEEEE APEDLYKDFL 1010       1020       1030       1040
TLEHLICYSF QVAKGMEFLA SRKCIHRDLA ARNILLSEKN 1050       1060       1070       1080
VVKICDFGLA RDIYKDPDYV RKGDARLPLK WMAPETIFDR 1090       1100       1110       1120
VYTIQSDVWS FGVLLWEIFS LGASPYPGVK IDEEFCRRLK 1130       1140       1150       1160
EGTRMRAPDY TTPEMYQTML DCWHGEPSQR PTFSELVEHL 1170       1180       1190       1200
GNLLQANAQQ DGKDYIVLPI SETLSMEEDS GLSLPTSPVS 1210       1220       1230       1240
CMEEEEVCDP KFHYDNTAGI SQYLQNSKRK SRPVSVKTFE 1250       1260       1270       1280
DIPLEEPEVK VIPDDNQTDS GMVLASEELK TLEDRTKLSP 1290       1300       1310       1320
SFGGMVPSKS RESVASEGSN QTSGYQSGYH SDDTDTTVYS 1330       1340       1350
SEEAELLKLI EIGVQTGSTA QILQPDSGTT LSSPPV
```

Vascular endothelial growth factor receptor 2 is a single-pass type I membrane protein having a large extracellular domain, some or all of which is present in soluble forms of Vascular endothelial growth factor receptor 2 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Vascular endothelial growth factor receptor 2:

| Residues | Length | Domain ID |
|---|---|---|
| 1-19 | 19 | Signal peptide |
| 20-1356 | 1337 | Vascular endothelial growth factor receptor 2 |

| Residues | Length | Domain ID |
|---|---|---|
| 20-764 | 745 | Extracellular domain |
| 765-789 | 25 | Transmembrane domain |
| 790-1356 | 567 | Cytoplasmic domain |

As used herein, the term "Vascular endothelial growth factor receptor 3" refers to one or more polypeptides present in a biological sample that are derived from the Vascular endothelial growth factor receptor 3 precursor (Swiss-Prot P35916 (SEQ ID NO: 25):

```
           10         20         30         40
   MQRGAALCLR LWLCLGLLDG LVSGYSMTPP TLNITEESHV
           50         60         70         80
   IDTGDSLSIS CRGQHPLEWA WPGAQEAPAT GDKDSEDTGV
           90        100        110        120
   VRDCEGTDAR PYCKVLLLHE VHANDTGSYV CYYKYIKARI
          130        140        150        160
   EGTTAASSYV FVRDFEQPFI NKPDTLLVNR KDAMWVPCLV
          170        180        190        200
   SIPGLNVTLR SQSSVLWPDG QEVVWDDRRG MLVSTPLLHD
          210        220        230        240
   ALYLQCETTW GDQDFLSNPF LVHITGNELY DIQLLPRKSL
          250        260        270        280
   ELLVGEKLVL NCTVWAEFNS GVTFDWDYPG KQAERGKWVP
          290        300        310        320
   ERRSQQTHTE LSSILTIHNV SQHDLGSYVC KANNGIQRFR
          330        340        350        360
   ESTEVIVHEN PFISVEWLKG PILEATAGDE LVKLPVKLAA
          370        380        390        400
   YPPPEFQWYK DGKALSGRHS PHALVLKEVT EASTGTYTLA
          410        420        430        440
   LWNSAAGLRR NISLELVVNV PPQIHEKEAS SPSIYSRHSR
          450        460        470        480
   QALTCTAYGV PLPLSIQWHW RPWTPCKMFA QRSLRRRQQQ
          490        500        510        520
   DLMPQCRDWR AVTTQDAVNP IESLDTWTEF VEGKNKTVSK
          530        540        550        560
   LVIQNANVSA MYKCVVSNKV GQDERLIYFY VTTIPDGFTI
          570        580        590        600
   ESKPSEELLE GQPVLLSCQA DSYKYEHLRW YRLNLSTLHD
          610        620        630        640
   AHGNPLLLDC KNVHLFATPL AASLEEVAPG ARHATLSLSI
          650        660        670        680
   PRVAPEHEGH YVCEVQDRRS HDKHCHKKYL SVQALEAPRL
          690        700        710        720
   TQNLTDLLVN VSDSLEMQCL VAGAHAPSIV WYKDERLLEE
          730        740        750        760
   KSGVDLADSN QKLSIQRVRE EDAGRYLCSV CNAKGCVNSS
          770        780        790        800
   ASVAVEGSED KGSMEIVILV GTGVIAVFFW VLLLLIFCNM
          810        820        830        840
   RRPAHADIKT GYLSIIMDPG EVPLEEQCEY LSYDASQWEF
          850        860        870        880
   PRERLHLGRV LGYGAFGKVV EASAFGIHKG SSCDTVAVKM
          890        900        910        920
   LKEGATASEH RALMSELKIL IHIGNHLNVV NLLGACTKPQ
          930        940        950        960
   GPLMVIVEFC KYGNLSNFLR AKRDAFSPCA EKSPEQRGRF
          970        980        990       1000
   RAMVELARLD RRRPGSSDRV LFARFSKTEG GARRASPDQE
         1010       1020       1030       1040
   AEDLWLSPLT MEDLVCYSFQ VARGMEFLAS RKCIHRDLAA
         1050       1060       1070       1080
   RNILLSESDV VKICDFGLAR DIYKDPDYVR KGSARLPLKW
         1090       1100       1110       1120
   MAPESIFDKV YTTQSDVWSF GVLLWEIFSL GASPYPGVQI
         1130       1140       1150       1160
   NEEFCQRLRD GTRMRAPELA TPAIRRIMLN CWSGDPKARP
         1170       1180       1190       1200
   AFSELVEILG DLLQGRGLQE EEEVCMAPRS SQSSEEGSFS
         1210       1220       1230       1240
   QVSTMALHIA QADAEDSPPS LQRHSLAARY YNWVSFPGCL
         1250       1260       1270       1280
   ARGAETRGSS RMKTFEEFPM TPTTYKGSVD NQTDSGMVLA
         1290
   SEEFEQIESR HRQESGFR
```

Vascular endothelial growth factor receptor 3 is a single-pass type I membrane protein having a large extracellular domain, some or all of which is present in soluble forms of Vascular endothelial growth factor receptor 3 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Vascular endothelial growth factor receptor 3:

| Residues | Length | Domain ID |
|---|---|---|
| 1-24 | 24 | Signal peptide |
| 25-1298 | 1274 | Vascular endothelial growth factor receptor 3 |
| 25-775 | 751 | Extracellular domain |
| 776-797 | 25 | Transmembrane domain |
| 798-1298 | 501 | Cytoplasmic domain |

As used herein, the term "Tumor necrosis factor receptor superfamily member 8" refers to one or more polypeptides present in a biological sample that are derived from the Tumor necrosis factor receptor superfamily member 8 precursor (Swiss-Prot P28908 (SEQ ID NO: 26)):

```
           10         20         30         40
   MRVLLAALGL LFLGALRAFP QDRPFEDTCH GNPSHYYDKA
           50         60         70         80
   VRRCCYRCPM GLFPTQQCPQ RPTDCRKQCE PDYYLDEADR
           90        100        110        120
   CTACVTCSRD DLVEKTPCAW NSSRVCECRP GMFCSTSAVN
          130        140        150        160
   SCARCFFHSV CPAGMIVKFP GTAQKNTVCE PASPGVSPAC
```

```
         170        180        190        200
ASPENCKEPS SGTIPQAKPT PVSPATSSAS TMPVRGGTRL 210        220        230        240
AQEAASKLTR APDSPSSVGR PSSDPGLSPT QPCPEGSGDC 250        260        270        280
RKQCEPDYYL DEAGRCTACV SCSRDDLVEK TPCAWNSSRT 290        300        310        320
CECRPGMICA TSATNSCARC VPYPICAAET VTKPQDMAEK 330        340        350        360
DTTFEAPPLG TQPDCNPTPE NGEAPASTSP TQSLLVDSQA 370        380        390        400
SKTLPIPTSA PVALSSTGKP VLDAGPVLFW VILVLVVVVG 410        420        430        440
SSAFLLCHRR ACRKRIRQKL HLCYPVQTSQ PKLELVDSRP 450        460        470        480
RRSSTQLRSG ASVTEPVAEE RGLMSQPLME TCHSVGAAYL 490        500        510        520
ESLPLQDASP AGGPSSPRDL PEPRVSTEHT NNKIEKIYIM 530        540        550        560
KADTVIVGTV KAELPEGRGL AGPAEPELEE ELEADHTPHY 570        580        590
PEQETEPPLG SCSDVMLSVE EEGKEDPLPT AASGK
```

Tumor necrosis factor receptor superfamily member 8 is a single-pass type I membrane protein having a large extracellular domain, some or all of which is present in soluble forms of Tumor necrosis factor receptor superfamily member 8 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Tumor necrosis factor receptor superfamily member 8:

| Residues | Length | Domain ID |
|---|---|---|
| 1-18 | 18 | Signal peptide |
| 19-595 | 577 | Tumor necrosis factor receptor superfamily member 8 |
| 19-379 | 361 | Extracellular domain |
| 380-407 | 28 | Transmembrane domain |
| 1-463 | 463 | Missing in short isoform |

As used herein, the term "Alpha-fetoprotein" refers to one or more polypeptides present in a biological sample that are derived from the Alpha-fetoprotein precursor (Swiss-Prot P02771 (SEQ ID NO: 27)):

```
         10         20         30         40
MKWVESIFLI FLLNFTESRT LHRNEYGIAS ILDSYQCTAE 50         60         70         80
ISLADLATIF FAQFVQEATY KEVSKMVKDA LTAIEKPTGD 90        100        110        120
EQSSGCLENQ LPAFLEELCH EKEILEKYGH SDCCSQSEEG 130        140        150        160
RHNCFLAHKK PTPASIPLFQ VPEPVTSCEA YEEDRETFMN 170        180        190        200
KFIYEIARRH PFLYAPTILL WAARYDKIIP SCCKAENAVE 210        220        230        240
CFQTKAATVT KELRESSLLN QHACAVMKNF GTRTFQAITV 250        260        270        280
TKLSQKFTKV NFTEIQKLVL DVAHVHEHCC RGDVLDCLQD 290        300        310        320
GEKIMSYICS QQDTLSNKIT ECCKLTTLER GQCIIHAEND 330        340        350        360
EKPEGLSPNL NRFLGDRDFN QFSSGEKNIF LASFVHEYSR 370        380        390        400
RHPQLAVSVI LRVAKGYQEL LEKCFQTENP LECQDKGEEE 410        420        430        440
LQKYIQESQA LAKRSCGLFQ KLGEYYLQNA FLVAYTKKAP 450        460        470        480
QLTSSELMAI TRKMAATAAT CCQLSEDKLL ACGEGAADII 490        500        510        520
IGHLCIRHEM TPVNPGVGQC CTSSYANRRP CFSSLVVDET 530        540        550        560
YVPPAFSDDK FIFHKDLCQA QGVALQTMKQ EFLINLVKQK 570        580        590        600
PQITEEQLEA VIADFSGLLE KCCQGQEQEV CFAEEGQKLI

SKTRAALGV
```

The following domains have been identified in Alpha-fetoprotein:

| Residues | Length | Domain ID |
|---|---|---|
| 1-18 | 18 | Signal peptide |
| 19-609 | 591 | Alpha-fetoprotein |

As used herein, the term "Thyroxine-binding globulin" refers to one or more polypeptides present in a biological sample that are derived from the Thyroxine-binding globulin precursor (Swiss-Prot P05543 (SEQ ID NO: 28)).

```
         10         20         30         40
MSPFLYLVLL VLGLHATIHC ASPEGKVTAC HSSQPNATLY 50         60         70         80
KMSSINADFA FNLYRRFTVE TPDKNIFFSP VSISAALVML 90        100        110        120
SFGACCSTQT EIVETLGFNL TDTPMVEIQH GFQHLICSLN 130        140        150        160
FPKKELELQI GNALFIGKHL KPLAKFLNDV KTLYETEVFS 170        180        190        200
TDFSNISAAK QEINSHVEMQ TKGKVVGLIQ DLKPNTIMVL 210        220        230        240
VNYIHFKAQW ANPFDPSKTE DSSSFLIDKT TTVQVPMMHQ 250        260        270        280
MEQYYHLVDM ELNCTVLQMD YSKNALALFV LPKEGQMESV 290        300        310        320
EAAMSSKTLK KWNRLLQKGW VDLFVPKFSI SATYDLGATL 330        340        350        360
LKMGIQHAYS ENADFSGLTE DNGLKLSNAA HKAVLHIGEK
```

```
                       370        380        390        400
              GTEAAAVPEV ELSDQPENTF LHPIIQIDRS FMLLILERST

410
              RSILFLGKVV NPTEA
```

The following domains have been identified in Thyroxine-binding globulin:

| Residues | Length | Domain ID |
|---|---|---|
| 1-20 | 20 | Signal peptide |
| 21-415 | 395 | Thyroxine-binding globulin |

As used herein, the term "Prostate-specific antigen" refers to one or more polypeptides present in a biological sample that are derived from the Prostate-specific antigen precursor (Swiss-Prot P07288 (SEQ ID NO: 29)).

```
                        10         20         30         40
              MWVPVVFLTL SVTWIGAAPL ILSRIVGGWE CEKHSQPWQV 50         60         70         80
              LVASRGRAVC GGVLVHPQWV LTAAHCIRNK SVILLGRHSL 90        100        110        120
              FHPEDTGQVF QVSHSFPHPL YDMSLLKNRF LRPGDDSSHD 130        140        150        160
              LMLLRLSEPA ELTDAVKVMD LPTQEPALGT TCYASGWGSI 170        180        190        200
              EPEEFLTPKK LQCVDLHVIS NDVCAQVHPQ KVTKFMLCAG 210        220        230        240
              RWTGGKSTCS GDSGGPLVCN GVLQGITSWG SEPCALPERP 250        260
              SLYTKVVHYR KWIKDTIVAN P
```

The following domains have been identified in Prostate-specific antigen:

| Residues | Length | Domain ID |
|---|---|---|
| 1-17 | 17 | Signal peptide |
| 18-24 | 7 | Activation peptide |
| 25-261 | 237 | Prostate-specific antigen |

As used herein, the terms "Apolipoprotein(a)" and "Apolipoprotein A" refer to one or more polypeptides present in a biological sample that are derived from the Apolipoprotein (a) precursor (Swiss-Prot P08519 (SEQ ID NO: 30)).

```
                        10         20         30         40
              MEHKEVVLLL LLFLKSAAPE QSHVVQDCYH GDGQSYRGTY 50         60         70         80
              STTVTGRTCQ AWSSMTPHQH NRTTENYPNA GLIMNYCRNP 90        100        110        120
              DAVAAPYCYT RDPGVRWEYC NLTQCSDAEG TAVAPPTVTP 130        140        150        160
              VPSLEAPSEQ APTEQRPGVQ ECYHGNGQSY RGTYSTTVTG 170        180        190        200
              RTCQAWSSMT PHSHSRTPEY YPNAGLIMNY CRNPDAVAAP 210        220        230        240
              YCYTRDPGVR WEYCNLTQCS DAEGTAVAPP TVTPVPSLEA 250        260        270        280
              PSEQAPTEQR PGVQECYHGN GQSYRGTYST TVTGRTCQAW 290        300        310        320
              SSMTPHSHSR TPEYYPNAGL IMNYCRNPDA VAAPYCYTRD 330        340        350        360
              PGVRWEYCNL TQCSDAEGTA VAPPTVTPVP SLEAPSEQAP 370        380        390        400
              TEQRPGVQEC YHGNGQSYRG TYSTTVTGRT CQAWSSMTPH 410        420        430        440
              SHSRTPEYYP NAGLIMNYCR NPDAVAAPYC YTRDPGVRWE 450        460        470        480
              YCNLTQCSDA EGTAVAPPTV TPVPSLEAPS EQAPTEQRPG 490        500        510        520
              VQECYHGNGQ SYRGTYSTTV TGRTCQAWSS MTPHSHSRTP 530        540        550        560
              EYYPNAGLIM NYCRNPDAVA APYCYTRDPG VRWEYCNLTQ 570        580        590        600
              CSDAEGTAVA PPTVTPVPSL EAPSEQAPTE QRPGVQECYH 610        620        630        640
              GNGQSYRGTY STTVTGRTCQ AWSSMTPHSH SRTPEYYPNA 650        660        670        680
              GLIMNYCRNP DAVAAPYCYT RDPGVRWEYC NLTQCSDAEG 690        700        710        720
              TAVAPPTVTP VPSLEAPSEQ APTEQRPGVQ ECYHGNGQSY 730        740        750        760
              RGTYSTTVTG RTCQAWSSMT PHSHSRTPEY YPNAGLIMNY 770        780        790        800
              CRNPDAVAAP YCYTRDPGVR WEYCNLTQCS DAEGTAVAPP 810        820        830        840
              TVTPVPSLEA PSEQAPTEQR PGVQECYHGN GQSYRGTYST 850        860        870        880
              TVTGRTCQAW SSMTPHSHSR TPEYYPNAGL IMNYCRNPDA 890        900        910        920
              VAAPYCYTRD PGVRWEYCNL TQCSDAEGTA VAPPTVTPVP 930        940        950        960
              SLEAPSEQAP TEQRPGVQEC YHGNGQSYRG TYSTTVTGRT 970        980        990       1000
              CQAWSSMTPH SHSRTPEYYP NAGLIMNYCR NPDAVAAPYC 1010       1020       1030       1040
              YTRDPGVRWE YCNLTQCSDA EGTAVAPPTV TPVPSLEAPS 1050       1060       1070       1080
              EQAPTEQRPG VQECYHGNGQ SYRGTYSTTV TGRTCQAWSS 1090       1100       1110       1120
              MTPHSHSRTP EYYPNAGLIM NYCRNPDAVA APYCYTRDPG 1130       1140       1150       1160
              VRWEYCNLTQ CSDAEGTAVA PPTVTPVPSL EAPSEQAPTE 1170       1180       1190       1200
              QRPGVQECYH GNGQSYRGTY STTVTGRTCQ AWSSMTPHSH 1210       1220       1230       1240
              SRTPEYYPNA GLIMNYCRNP DAVAAPYCYT RDPGVRWEYC 1250       1260       1270       1280
              NLTQCSDAEG TAVAPPTVTP VPSLEAPSEQ APTEQRPGVQ 1290       1300       1310       1320
              ECYHGNGQSY RGTYSTTVTG RTCQAWSSMT PHSHSRTPEY
```

-continued

```
      1330       1340       1350       1360
YPNAGLIMNY CRNPDAVAAP YCYTRDPGVR WEYCNLTQCS 1370       1380       1390       1400
DAEGTAVAPP TVTPVPSLEA PSEQAPTEQR PGVQECYHGN 1410       1420       1430       1440
GQSYRGTYST TVTGRTCQAW SSMTPHSHSR TPEYYPNAGL 1450       1460       1470       1480
IMNYCRNPDA VAAPYCYTRD PGVRWEYCNL TQCSDAEGTA 1490       1500       1510       1520
VAPPTVTPVP SLEAPSEQAP TEQRPGVQEC YHGNGQSYRG 1530       1540       1550       1560
TYSTTVTGRT CQAWSSMTPH SHSRTPEYYP NAGLIMNYCR 1570       1580       1590       1600
NPDAVAAPYC YTRDPGVRWE YCNLTQCSDA EGTAVAPPTV 1610       1620       1630       1640
TPVPSLEAPS EQAPTEQRPG VQECYHGNGQ SYRGTYSTTV 1650       1660       1670       1680
TGRTCQAWSS MTPHSHSRTP EYYPNAGLIM NYCRNPDAVA 1690       1700       1710       1720
APYCYTRDPG VRWEYCNLTQ CSDAEGTAVA PPTVTPVPSL 1730       1740       1750       1760
EAPSEQAPTE QRPGVQECYH GNGQSYRGTY STTVTGRTCQ 1770       1780       1790       1800
AWSSMTPHSH SRTPEYYPNA GLIMNYCRNP DAVAAPYCYT 1810       1820       1830       1840
RDPGVRWEYC NLTQCSDAEG TAVAPPTVTP VPSLEAPSEQ 1850       1860       1870       1880
APTEQRPGVQ ECYHGNGQSY RGTYSTTVTG RTCQAWSSMT 1890       1900       1910       1920
PHSHSRTPEY YPNAGLIMNY CRNPDAVAAP YCYTRDPGVR 1930       1940       1950       1960
WEYCNLTQCS DAEGTAVAPP TVTPVPSLEA PSEQAPTEQR 1970       1980       1990       2000
PGVQECYHGN GQSYRGTYST TVTGRTCQAW SSMTPHSHSR 2010       2020       2030       2040
TPEYYPNAGL IMNYCRNPDA VAAPYCYTRD PGVRWEYCNL 2050       2060       2070       2080
TQCSDAEGTA VAPPTVTPVP SLEAPSEQAP TEQRPGVQEC 2090       2100       2110       2120
YHGNGQSYRG TYSTTVTGRT CQAWSSMTPH SHSRTPEYYP 2130       2140       2150       2160
NAGLIMNYCR NPDAVAAPYC YTRDPGVRWE YCNLTQCSDA 2170       2180       2190       2200
EGTAVAPPTV TPVPSLEAPS EQAPTEQRPG VQECYHGNGQ 2210       2220       2230       2240
SYRGTYSTTV TGRTCQAWSS MTPHSHSRTP EYYPNAGLIM 2250       2260       2270       2280
NYCRNPDAVA APYCYTRDPG VRWEYCNLTQ CSDAEGTAVA 2290       2300       2310       2320
PPTVTPVPSL EAPSEQAPTE QRPGVQECYH GNGQSYRGTY 2330       2340       2350       2360
STTVTGRTCQ AWSSMTPHSH SRTPEYYPNA GLIMNYCRNP 2370       2380       2390       2400
DAVAAPYCYT RDPGVRWEYC NLTQCSDAEG TAVAPPTVTP 2410       2420       2430       2440
VPSLEAPSEQ APTEQRPGVQ ECYHGNGQSY RGTYSTTVTG 2450       2460       2470       2480
RTCQAWSSMT PHSHSRTPEY YPNAGLIMNY CRNPDAVAAP 2490       2500       2510       2520
YCYTRDPGVR WEYCNLTQCS DAEGTAVAPP TVTPVPSLEA 2530       2540       2550       2560
PSEQAPTEQR PGVQECYHGN GQSYRGTYST TVTGRTCQAW 2570       2580       2590       2600
SSMTPHSHSR TPEYYPNAGL IMNYCRNPDA VAAPYCYTRD 2610       2620       2630       2640
PGVRWEYCNL TQCSDAEGTA VAPPTVTPVP SLEAPSEQAP 2650       2660       2670       2680
TEQRPGVQEC YHGNGQSYRG TYSTTVTGRT CQAWSSMTPH 2690       2700       2710       2720
SHSRTPEYYP NAGLIMNYCR NPDAVAAPYC YTRDPGVRWE 2730       2740       2750       2760
YCNLTQCSDA EGTAVAPPTV TPVPSLEAPS EQAPTEQRPG 2770       2780       2790       2800
VQECYHGNGQ SYRGTYSTTV TGRTCQAWSS MTPHSHSRTP 2810       2820       2830       2840
EYYPNAGLIM NYCRNPDAVA APYCYTRDPG VRWEYCNLTQ 2850       2860       2870       2880
CSDAEGTAVA PPTVTPVPSL EAPSEQAPTE QRPGVQECYH 2890       2900       2910       2920
GNGQSYRGTY STTVTGRTCQ AWSSMTPHSH SRTPEYYPNA 2930       2940       2950       2960
GLIMNYCRNP DAVAAPYCYT RDPGVRWEYC NLTQCSDAEG 2970       2980       2990       3000
TAVAPPTVTP VPSLEAPSEQ APTEQRPGVQ ECYHGNGQSY 3010       3020       3030       3040
RGTYSTTVTG RTCQAWSSMT PHSHSRTPEY YPNAGLIMNY 3050       3060       3070       3080
CRNPDAVAAP YCYTRDPGVR WEYCNLTQCS DAEGTAVAPP 3090       3100       3110       3120
TVTPVPSLEA PSEQAPTEQR PGVQECYHGN GQSYRGTYST 3130       3140       3150       3160
TVTGRTCQAW SSMTPHSHSR TPEYYPNAGL IMNYCRNPDA 3170       3180       3190       3200
VAAPYCYTRD PGVRWEYCNL TQCSDAEGTA VAPPTVTPVP 3210       3220       3230       3240
SLEAPSEQAP TEQRPGVQEC YHGNGQSYRG TYSTTVTGRT 3250       3260       3270       3280
CQAWSSMTPH SHSRTPEYYP NAGLIMNYCR NPDAVAAPYC 3290       3300       3310       3320
YTRDPGVRWE YCNLTQCSDA EGTAVAPPTV TPVPSLEAPS 3330       3340       3350       3360
EQAPTEQRPG VQECYHGNGQ SYRGTYSTTV TGRTCQAWSS 3370       3380       3390       3400
MTPHSHSRTP EYYPNAGLIM NYCRNPDPVA APYCYTRDPS 3410       3420       3430       3440
VRWEYCNLTQ CSDAEGTAVA PPTITPIPSL EAPSEQAPTE 3450       3460       3470       3480
QRPGVQECYH GNGQSYQGTY FITVTGRTCQ AWSSMTPHSH
```

```
            3490       3500       3510       3520
      SRTPAYYPNA GLIKNYCRNP DPVAAPWCYT TDPSVRWEYC 3530       3540       3550       3560
      NLTRCSDAEW TAFVPPNVIL APSLEAFFEQ ALTEETPGVQ 3570       3580       3590       3600
      DCYYHYGQSY RGTYSTTVTG RTCQAWSSMT PHQHSRTPEN 3610       3620       3630       3640
      YPNAGLTRNY CRNPDAEIRP WCYTMDPSVR WEYCNLTQCL 3650       3660       3670       3680
      VTESSVLATL TVVPDPSTEA SSEEAPTEQS PGVQDCYHGD 3690       3700       3710       3720
      GQSYRGSFST TVTGRTCQSW SSMTPHWHQR TTEYYPNGGL 3730       3740       3750       3760
      TRNYCRNPDA EISPWCYTMD PNVRWEYCNL TQCPVTESSV 3770       3780       3790       3800
      LATSTAVSEQ APTEQSPTVQ DCYHGDGQSY RGSFSTTVTG 3810       3820       3830       3840
      RTCQSWSSMT PHWHQRTTEY YPNGGLTRNY CRNPDAEIRP 3850       3860       3870       3880
      WCYTMDPSVR WEYCNLTQCP VMESTLLTTP TVVPVPSTEL 3890       3900       3910       3920
      PSEEAPTENS TGVQDCYRGD GQSYRGTLST TITGRTCQSW 3930       3940       3950       3960
      SSMTPHWHRR IPLYYPNAGL TRNYCRNPDA EIRPWCYTMD 3970       3980       3990       4000
      PSVRWEYCNL TRCPVTESSV LTTPTVAPVP STEAPSEQAP 4010       4020       4030       4040
      PEKSPVVQDC YHGDGRSYRG ISSTTVTGRT CQSWSSMIPH 4050       4060       4070       4080
      WHQRTPENYP NAGLTENYCR NPDSGKQPWC YTTDPCVRWE 4090       4100       4110       4120
      YCNLTQCSET ESGVLETPTV VPVPSMEAHS EAAPTEQTPV 4130       4140       4150       4160
      VRQCYHGNGQ SYRGTFSTTV TGRTCQSWSS MTPHRHQRTP 4170       4180       4190       4200
      ENYPNDGLTM NYCRNPDADT GPWCFTMDPS IRWEYCNLTR 4210       4220       4230       4240
      CSDTEGTVVA PPTVIQVPSL GPPSEQDCMF GNGKGYRGKK 4250       4260       4270       4280
      ATTVTGTPCQ EWAAQEPHRH STFIPGTNKW AGLEKNYCRN 4290       4300       4310       4320
      PDGDINGPWC YTMNPRKLFD YCDIPLCASS SFDCGKPQVE 4330       4340       4350       4360
      PKKCPGSIVG GCVAHPHSWP WQVSLRTRFG KHFCGGTLIS 4370       4380       4390       4400
      PEWVLTAAHC LKKSSRPSSY KVILGAHQEV NLESHVQEIE 4410       4420       4430       4440
      VSRLFLEPTQ ADIALLKLSR PAVITDKVMP ACLPSPDYMV 4450       4460       4470       4480
      TARTECYITG WGETQGTFGT GLLKEAQLLV IENEVCNHYK 4490       4500       4510       4520
      YICAEHLARG TDSCQGDSGG PLVCFEKDKY ILQGVTSWGL 4530       4540
      GCARPNKPGV YARVSRFVTW IEGMMRNN
```

The following domains have been identified in Apolipoprotein(a):

| Residues | Length | Domain ID |
| --- | --- | --- |
| 1-19 | 19 | Signal peptide |
| 20-4548 | 4529 | Apolipoprotein(a) |

As used herein, the term "Apolipoprotein E" refers to one or more polypeptides present in a biological sample that are derived from the Apolipoprotein E precursor (Swiss-Prot P02649 (SEQ ID NO: 31)).

```
               10         20         30         40
       MKVLWAALLV TFLAGCQAKV EQAVETEPEP ELRQQTEWQS 50         60         70         80
       GQRWELALGR FWDYLRWVQT LSEQVQEELL SSQVTQELRA 90        100        110        120
       LMDETMKELK AYKSELEEQL TPVAEETRAR LSKELQAAQA 130        140        150        160
       RLGADMEDVC GRLVQYRGEV QAMLGQSTEE LRVRLASHLR 170        180        190        200
       KLRKRLLRDA DDLQKRLAVY QAGAREGAER GLSAIRERLG 210        220        230        240
       PLVEQGRVRA ATVGSLAGQP LQERAQAWGE RLRARMEEMG 250        260        270        280
       SRTRDRLDEV KEQVAEVRAK LEEQAQQIRL QAEAFQARLK 290        300        310
       SWFEPLVEDM QRQWAGLVEK VQAAVGTSAA PVPSDNH
```

The following domains have been identified in Apolipoprotein E:

| Residues | Length | Domain ID |
| --- | --- | --- |
| 1-18 | 18 | Signal peptide |
| 19-317 | 299 | Apolipoprotein E |

As used herein, the term "Thyrotropin subunit beta" refers to one or more polypeptides present in a biological sample that are derived from the Thyrotropin subunit betaprecursor (Swiss-Prot P01222 (SEQ ID NO: 32)).

```
               10         20         30         40
       MTALFLMSML FGLACGQAMS FCIPTEYTMH IERRECAYCL 50         60         70         80
       TINTTICAGY CMTRDINGKL FLPKYALSQD VCTYRDFIYR 90        100        110        120
       TVEIPGCPLH VAPYFSYPVA LSCKCGKCNT DYSDCIHEAI

130
       KTNYCTKPQK SYLVGFSV
```

The following domains have been identified in Thyrotropin subunit beta:

| Residues | Length | Domain ID |
|---|---|---|
| 1-20 | 20 | Signal peptide |
| 21-132 | 112 | Thyrotropin subunit beta |
| 133-138 | 6 | Propeptide |

As used herein, the term "Platelet-derived Growth Factor B/B dimer" refers to one or more polypeptides present in a biological sample that are derived from the Platelet-derived Growth Factor V precursor and that form a homodimer (Swiss-Prot P01127 (SEQ ID NO: 33)).

```
          10         20         30         40
   MNRCWALFLS LCCYLRLVSA EGDPIPEELY EMLSDHSIRS 50         60         70         80
   FDDLQRLLHG DPGEEDGAEL DLNMTRSHSG GELESLARGR 90        100        110        120
   RSLGSLTIAE PAMIAECKTR TEVFEISRRL IDRTNANFLV 130        140        150        160
   WPPCVEVQRC SGCCNNRNVQ CRPTQVQLRP VQVRKIEIVR 170        180        190        200
   KKPIFKKATV TLEDHLACKC ETVAAARPVT RSPGGSQEQR 210        220        230        240
   AKTPQTRVTI RTVRVRRPPK GKHRKFKHTH DKTALKETLG

A
```

The following domains have been identified in Platelet-derived Growth Factor B:

| Residues | Length | Domain ID |
|---|---|---|
| 1-20 | 20 | Signal peptide |
| 21-81 | 61 | Propeptide |
| 82-190 | 109 | Platelet-derived Growth Factor B |
| 191-241 | 51 | Propeptide |

As used herein, the term "IgG4" refers to subclass 4 of the glycoprotein immunoglobulin G (IgG), a major effector molecule of the humoral immune response in man. Antibodies of the IgG class express their predominant activity during a secondary antibody response. The basic immunoglobulin G molecule has a four-chain structure, comprising two identical heavy (H) chains and two identical light (L) chains, linked together by inter-chain disulfide bonds. Each heavy chain is encoded by 4 distinct types of gene segments, designated $V_H$ (variable), D (diversity), $J_H$ (joining) and $C_H$ (constant). The variable region of the heavy chain is encoded by the $V_H$, D and $J_H$ segments. The light chains are encoded by the 3 gene segments, $V_L$, $J_L$ and $C_L$. The variable region of the light chains is encoded by the $V_L$ and $J_L$ segments.

The length and flexibility of the hinge region varies among the IgG subclasses. The hinge region of IgG1 encompasses amino acids 216-231 and since it is freely flexible, the Fab fragments can rotate about their axes of symmetry and move within a sphere centered at the first of two inter-heavy chain disulfide bridges (23). IgG2 has a shorter hinge than IgG1, with 12 amino acid residues and four disulfide bridges. The hinge region of IgG2 lacks a glycine residue, it is relatively short and contains a rigid poly-proline double helix, stabilised by extra inter-heavy chain disulfide bridges. These properties restrict the flexibility of the IgG2 molecule (24). IgG3 differs from the other subclasses by its unique extended hinge region (about four times as long as the IgG1 hinge), containing 62 amino acids (including 21 prolines and 11 cysteines), forming an inflexible poly-proline double helix (25,26). In IgG3 the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2.

The four IgG subclasses also differ with respect to the number of inter-heavy chain disulfide bonds in the hinge region (26). The structural differences between the IgG subclasses are also reflected in their susceptibility to proteolytic enzymes. IgG3 is very susceptible to cleavage by these enzymes, whereas IgG2 is relatively resistant. IgG1 and IgG4 exhibit an intermediary sensitivity, depending upon the enzyme used. Since these proteolytic enzymes all cleave IgG molecules near or within the hinge region, it is likely that the high sensitivity of IgG3 to enzyme digestion is related to its accessible hinge. Another structural difference between the human IgG subclasses is the linkage of the heavy and light chain by a disulfide bond. This bond links the carboxy-terminal of the light chain with the cysteine residue at position 220 (in IgG) or at position 131 (in IgG2, IgG3 and IgG4) of the CH1 sequence of the heavy chain.

As a consequence of the structural differences, the four IgG subclasses may be distinguished from one another, for example using antibodies that are specific for differences between the isoforms. In the present application, a level of IgG1 is determined using an assay which distinguishes this subclass, relative to the other subclasses.

As used herein, the term "relating a signal to the presence or amount" of an analyte reflects the following understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quatitation). This list is not meant to be limiting.

The term "positive going" marker as that term is used herein refer to a marker that is determined to be elevated in subjects suffering from a disease or condition, relative to subjects not suffering from that disease or condition. The term "negative going" marker as that term is used herein refer to a marker that is determined to be reduced in subjects suffering from a disease or condition, relative to subjects not suffering from that disease or condition.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather use test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and *The Immunoassay Handbook*, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGel™ resins (Rapp Polymere GmbH), AgroGel™ resins (I.L.S.A. Industria Lavorazione Sottoprodotti Animali S.P.A.), polyethylene glycol and acrylamide PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ M$^{-1}$, and preferably between about $10^8$ M$^{-1}$ to about $10^9$ M$^{-1}$, about $10^9$ M$^{-1}$ to about $10^{10}$ M$^{-1}$, or about $10^{10}$ M$^{-1}$ to about $10^{12}$ M$^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c = K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

While the present application describes antibody-based binding assays in detail, alternatives to antibodies as binding species in assays are well known in the art. These include receptors for a particular target, aptamers, etc. Aptamers are oligonucleic acid or peptide molecules that bind to a specific target molecule. Aptamers are usually created by selecting them from a large random sequence pool, but natural aptamers also exist. High-affinity aptamers containing modified nucleotides conferring improved characteristics on the ligand, such as improved in vivo stability or improved delivery characteristics. Examples of such modifications include chemical substitutions at the ribose and/or phosphate and/or base positions, and may include amino acid side chain functionalities.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same patient, where a prior "baseline" result is used to monitor for temporal changes in a biomarker level.

Population studies may also be used to select a decision threshold. Reciever Operating Characteristic ("ROC") arose from the field of signal dectection therory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1-specificity, the ROC graph is sometimes called the sensitivity vs (1-specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Additional clinical indicia may be combined with the kidney injury marker assay result(s) of the present invention. These include other biomarkers related to renal status. Examples include the following, which recite the common biomarker name, followed by the Swiss-Prot entry number for that biomarker or its parent: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase (Renin, P00797); Annexin A2 (P07355); Beta-glucuronidase (P08236); B-2-microglobulin (P61679); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase (Q16790); Casein Kinase 2 (P68400); Ceruloplasmin (P00450); Clusterin (P10909); Complement C3 (P01024); Cysteine-rich protein (CYR61, O00622); Cytochrome C (P99999); Epidermal growth factor (EGF, P01133); Endothelin-1 (P05305); Exosomal Fetuin-A (P02765); Fatty acid-binding protein, heart (FABP3, P05413); Fatty acid-binding protein, liver (P07148); Ferritin (light chain, P02793; heavy chain P02794); Fructose-1,6-biphosphatase (P09467); GRO-alpha (CXCL1, (P09341); Growth Hormone (P01241); Hepatocyte growth factor (P14210); Insulin-like growth factor I (P01343); Immunoglobulin G; Immunoglobulin Light Chains (Kappa and Lambda); Interferon gamma (P01308); Lysozyme (P61626); Interleukin-1alpha (P01583); Interleukin-2 (P60568); Interleukin-4 (P60568); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (O95631); Neutral endopeptidase (P08473); Osteopontin (P10451); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform (NHE3, P48764); Spermidine/spermine N1-acetyltransferase (P21673); TGF-Beta1 (P01137); Transferrin (P02787); Trefoil factor 3 (TFF3, Q07654); Toll-Like protein 4 (O00206); Total protein; Tubulointerstitial nephritis antigen (Q9UJW2); Uromodulin (Tamm-Horsfall protein, P07911).

For purposes of risk stratification, Adiponectin (Q15848); Alkaline phosphatase (P05186); Aminopeptidase N (P15144); CalbindinD28k (P05937); Cystatin C (P01034); δ subunit of F1FO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itm1, P46977); Interleukin-6 (P05231); Interleukin-8 (P10145); Interleukin-18 (Q14116); IP-10 (10 kDa interferon-gamma-induced protein, P02778); IRPR (IFRD1, O00458); Isovaleryl-CoA dehydrogenase (IVD, P26440); I-TAC/CXCL11 (O14625); Keratin 19 (P08727); Kim-1 (Hepatitis A virus cellular receptor 1, O43656); L-arginine:glycine amidinotransferase (P50440); Leptin (P41159); Lipocalin2 (NGAL, P80188); MCP-1 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, O15244); Osteoprotegerin (O14788); P8 protein (O60356); Plasminogen activator inhibitor 1 (PAI-1, P05121); ProANP (1-98) (P01160); Protein phosphatase 1-beta (PPI-beta, P62140); Rab GDI-beta (P50395); Renal kallikrein (Q86U61); RT1.B-1 (alpha) chain of the integral membrane protein (Q5Y7A8); Soluble tumor necrosis factor receptor superfamily member 1A (sTNFR-I, P19438); Soluble tumor necrosis factor receptor superfamily member 1B (sTNFR-II, P20333); Tissue inhibitor of metalloproteinases 3 (TIMP-3, P35625); uPAR (Q03405) may be combined with the kidney injury marker assay result(s) of the present invention.

Other clinical indicia which may be combined with the kidney injury marker assay result(s) of the present invention includes demographic information (e.g., weight, sex, age, race), medical history (e.g., family history, type of surgery, pre-existing disease such as aneurysm, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined with the kidney injury marker assay result(s) are described hereinafter and in Harrison's Principles of Internal Medicine, 17$^{th}$ Ed., McGraw Hill, N.Y., pages 1741-1830, and Current Medical Diagnosis & Treatment 2008, 47$^{th}$ Ed, McGraw Hill, N.Y., pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m$^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr}$xV) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr\text{-}corrected} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., Nephrol. Dial. Transplant. 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N.J., 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1: Contrast-Induced Nephropathy Sample Collection

The objective of this sample collection study is to collect samples of plasma and urine and clinical data from patients before and after receiving intravascular contrast media. Approximately 250 adults undergoing radiographic/angiographic procedures involving intravascular administration of iodinated contrast media are enrolled. To be enrolled in the study, each patient must meet all of the following inclusion criteria and none of the following exclusion criteria:

Inclusion Criteria
males and females 18 years of age or older;
undergoing a radiographic/angiographic procedure (such as a CT scan or coronary intervention) involving the intravascular administration of contrast media;
expected to be hospitalized for at least 48 hours after contrast administration.
able and willing to provide written informed consent for study participation and to comply with all study procedures.

Exclusion Criteria
renal transplant recipients;
acutely worsening renal function prior to the contrast procedure;
already receiving dialysis (either acute or chronic) or in imminent need of dialysis at enrollment;
expected to undergo a major surgical procedure (such as involving cardiopulmonary bypass) or an additional imaging procedure with contrast media with significant risk for further renal insult within the 48 hrs following contrast administration;
participation in an interventional clinical study with an experimental therapy within the previous 30 days;
known infection with human immunodeficiency virus (HIV) or a hepatitis virus.

Immediately prior to the first contrast administration (and after any pre-procedure hydration), an EDTA anti-coagulated blood sample (10 mL) and a urine sample (10 mL) are collected from each patient. Blood and urine samples are then collected at 4 (±0.5), 8 (±1), 24 (±2) 48 (±2), and 72 (±2) hrs following the last administration of contrast media during the index contrast procedure. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Serum creatinine is assessed at the site immediately prior to the first contrast administration (after any pre-procedure hydration) and at 4 (±0.5), 8 (±1), 24 (±2) and 48 (±2)), and 72 (±2) hours following the last administration of contrast (ideally at the same time as the study samples are obtained). In addition, each patient's status is evaluated through day 30 with regard to additional serum and urine creatinine measurements, a need for dialysis, hospitalization status, and adverse clinical outcomes (including mortality).

Prior to contrast administration, each patient is assigned a risk based on the following assessment: systolic blood pressure<80 mm Hg=5 points; intra-arterial balloon pump=5 points; congestive heart failure (Class III-IV or history of pulmonary edema)=5 points; age >75 yrs=4 points; hematocrit level <39% for men, <35% for women=3 points; diabetes=3 points; contrast media volume=1 point for each 100 mL; serum creatinine level >1.5 g/dL=4 points OR estimated GFR 40-60 mL/min/1.73 m$^2$=2 points, 20-40 mL/min/1.73 m$^2$=4 points, <20 mL/min/1.73 m$^2$=6 points. The risks assigned are as follows: risk for CIN and dialysis: 5 or less total points=risk of CIN—7.5%, risk of dialysis—0.04%; 6-10 total points=risk of CIN—14%, risk of dialysis 0.12%; 11-16 total points=risk of CIN—26.1%, risk of dialysis–1.09%; >16 total points=risk of CIN—57.3%, risk of dialysis—12.8%.

Example 2: Cardiac Surgery Sample Collection

The objective of this sample collection study is to collect samples of plasma and urine and clinical data from patients before and after undergoing cardiovascular surgery, a procedure known to be potentially damaging to kidney function. Approximately 900 adults undergoing such surgery are enrolled. To be enrolled in the study, each patient must meet all of the following inclusion criteria and none of the following exclusion criteria:

Inclusion Criteria
males and females 18 years of age or older;
undergoing cardiovascular surgery;
Toronto/Ottawa Predictive Risk Index for Renal Replacement risk score of at least 2 (Wijeysundera et al., *JAMA* 297: 1801-9, 2007); and
able and willing to provide written informed consent for study participation and to comply with all study procedures.

Exclusion Criteria
known pregnancy;
previous renal transplantation;
acutely worsening renal function prior to enrollment (e.g., any category of PRIFLE criteria);
already receiving dialysis (either acute or chronic) or in imminent need of dialysis at enrollment;
currently enrolled in another clinical study or expected to be enrolled in another clinical study within 7 days of cardiac surgery that involves drug infusion or a therapeutic intervention for AKI;
known infection with human immunodeficiency virus (HIV) or a hepatitis virus.

Within 3 hours prior to the first incision (and after any pre-procedure hydration), an EDTA anti-coagulated blood sample (10 mL), whole blood (3 mL), and a urine sample (35 mL) are collected from each patient. Blood and urine samples are then collected at 3 (±0.5), 6 (±0.5), 12 (±1), 24 (±2) and 48 (±2) hrs following the procedure and then daily on days 3 through 7 if the subject remains in the hospital. Blood is collected via direct venipuncture or via other available venous access, such as an existing femoral sheath, central venous line, peripheral intravenous line or hep-lock. These study blood samples are frozen and shipped to Astute Medical, Inc., San Diego, Calif. The study urine samples are frozen and shipped to Astute Medical, Inc.

Example 3: Acutely Ill Subject Sample Collection

The objective of this study is to collect samples from acutely ill patients. Approximately 1900 adults expected to be in the ICU for at least 48 hours will be enrolled. To be enrolled in the study, each patient must meet all of the following inclusion criteria and none of the following exclusion criteria:

Inclusion Criteria
males and females 18 years of age or older;
Study population 1: approximately 300 patients that have at least one of:
shock (SBP<90 mmHg and/or need for vasopressor support to maintain MAP>60 mmHg and/or documented drop in SBP of at least 40 mmHg); and
sepsis;
Study population 2: approximately 300 patients that have at least one of:
IV antibiotics ordered in computerized physician order entry (CPOE) within 24 hours of enrollment;
contrast media exposure within 24 hours of enrollment;
increased Intra-Abdominal Pressure with acute decompensated heart failure; and
severe trauma as the primary reason for ICU admission and likely to be hospitalized in the ICU for 48 hours after enrollment;
Study population 3: approximately 300 patients expected to be hospitalized through acute care setting (ICU or ED) with a known risk factor for acute renal injury (e.g. sepsis, hypotension/shock (Shock=systolic BP<90 mmHg and/or the need for vasopressor support to maintain a MAP>60 mmHg and/or a documented drop in SBP>40 mmHg), major trauma, hemorrhage, or major surgery); and/or expected to be hospitalized to the ICU for at least 24 hours after enrollment;
Study population 4: approximately 1000 patients that are 21 years of age or older, within 24 hours of being admitted into the ICU, expected to have an indwelling urinary catheter for at least 48 hours after enrollment, and have at least one of the following acute conditions within 24 hours prior to enrollment:
(i) respiratory SOFA score of ≥2 (PaO2/FiO2<300), (ii) cardiovascular SOFA score of ≥1 (MAP<70 mm Hg and/or any vasopressor required).

Exclusion Criteria
known pregnancy;
institutionalized individuals;
previous renal transplantation;
known acutely worsening renal function prior to enrollment (e.g., any category of RIFLE criteria);
received dialysis (either acute or chronic) within 5 days prior to enrollment or in imminent need of dialysis at the time of enrollment;
known infection with human immunodeficiency virus (HIV) or a hepatitis virus; meets any of the following:
(i) active bleeding with an anticipated need for >4 units PRBC in a day;
(ii) hemoglobin <7 g/dL;
(iii) any other condition that in the physician's opinion would contraindicate drawing serial blood samples for clinical study purposes;
meets only the SBP<90 mmHg inclusion criterion set forth above, and does not have shock in the attending physician's or principal investigator's opinion;

After obtaining informed consent, an EDTA anti-coagulated blood sample (10 mL) and a urine sample (25-50 mL) are collected from each patient. Blood and urine samples are then collected at 4 (±0.5) and 8 (±1) hours after contrast administration (if applicable); at 12 (±1), 24 (±2), 36 (±2), 48 (±2), 60 (±2), 72 (±2), and 84 (±2) hours after enrollment, and thereafter daily up to day 7 to day 14 while the subject is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Example 4: Immunoassay Format

Analytes are measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards. In the case of kidney injury markers that are membrane proteins, assays are directed to soluble forms thereof as described above.

Commercially-available reagents were sourced from the following vendors:

| Analyte | Assay Source | Catalog number |
| --- | --- | --- |
| Platelet-derived growth factor (AB/BB) | Millipore | Cat. #HNDG3-36K |
| Platelet-derived growth factor subunit A (AA-dimer) | Millipore | Cat. #HNDG3-36K |
| Immunoglobulin G, subclass 4 | Millipore | Cat. # HGAM-301 |
| Interleukin-4 receptor alpha chain | Millipore | Cat. #HSCR-32K |
| Alpha-Fetoprotein | EMD Chemicals | Cat. #BPHCP001-6 |
| Apolipoprotein E | EMD Chemicals | Cat. #BPHCVD01-7 |
| Apolipoprotein(a) | EMD Chemicals | Cat. #BPHCVD05-8 |
| C-C motif chemokine 26 | Millipore | Cat. #MPXHCYP2-62K |
| C-C motif chemokine 7 | Millipore | Cat. #MPXHCYTO-60K |
| Complement C4-B | Millipore | Cat. #HNDG2-36K |
| Corticotropin | Millipore | Cat. #HPT-66K |
| Insulin-like growth factor-binding protein 4 | Millipore | Cat. #HIGFBP-53K |

-continued

| Analyte | Assay Source | Catalog number |
| --- | --- | --- |
| Insulin-like growth factor-binding protein 5 | Millipore | Cat. #HIGFBP-53K |
| Interferon alpha-2 | Millipore | Cat. #MPXHCYTO-60K |
| Interleukin 23, alpha subunit | Millipore | Cat. #MPXHCYP2-62K |
| Interleukin-21 | Millipore | Cat. #MPXHCYP2-62K |
| Interleukin-28A (interferon, lambda 2) | Millipore | Cat. #MPXHCYP2-62K |
| Interleukin-33 (IL-33) | Millipore | Cat. #MPXHCYP2-62K |
| Lutropin subunit beta | Millipore | Cat #HBDP-33K |
| Matrix Metalloproteinase-1 | R & D Systems | Cat. #LMP000 |
| Neural cell adhesion molecule 1 | Millipore | Cat. #HNDG3-36K |
| Pigment epithelium-derived factor | Millipore | Cat. #HNDG2-36K |
| Platelet-derived growth factor (BB-dimer) | Bio-Rad | Cat. #171-A4011M |
| Prostate-specific antigen, free | Millipore | Cat #HCCBP1MAG-58K |
| Thyrotropin subunit beta | Millipore | Cat #HPT-66K |
| Thyroxine-binding globulin | Rules-Based Medicine | No catalog number |
| Tumor necrosis factor receptor superfamily member 8 | Millipore | Cat. #HSCR-32K |
| Vascular endothelial growth factor receptor 2 | Millipore | Cat. #HSCR-32K |
| Vascular endothelial growth factor receptor 3 | Millipore | Cat. #HSCR-32K |

Units for the concentrations reported in the following data tables are as follows: Tumor necrosis factor receptor superfamily member 8—pg/mL, Alpha-Fetoprotein—ng/mL, Thyroxine-binding globulin—µg/mL, Prostate-specific antigen (free form)—ng/mL, Apolipoprotein A—ng/mL, Apolipoprotein E—ng/mL, Thyrotropin subunit beta—µg/mL, Platelet-derived growth factor B/B dimer—pg/mL, C-C motif chemokine 7—pg/mL, C-C motif chemokine 26—pg/mL, Complement C4-B—ng/mL, Corticotropin—ng/mL, Interferon alpha-2—pg/mL, Interleukin-4 receptor alpha chain—pg/mL, Insulin-like growth factor-binding protein 4—ng/mL, Insulin-like growth factor-binding protein 5—ng/mL, Interleukin 21—pg/mL, Interleukin 23 alpha subunit—pg/mL, Interleukin-28A—pg/mL, Interleukin-33—pg/mL, Lutropin subunit beta—mIU/mL, Matrix Metalloproteinase-1—pg/mL, Neural cell adhesion molecule 1—pg/mL, Pigment epithelium-derived factor—ng/mL, Vascular Vascular endothelial growth factor receptor 2—pg/mL, Vascular endothelial growth factor receptor 3—pg/mL, IgG4—ng/mL.

Example 5: Apparently Healthy Donor and Chronic Disease Patient Samples

Human urine samples from donors with no known chronic or acute disease ("Apparently Healthy Donors") were purchased from two vendors (Golden West Biologicals, Inc., 27625 Commerce Center Dr., Temecula, Calif. 92590 and Virginia Medical Research, Inc., 915 First Colonial Rd., Virginia Beach, Va. 23454). The urine samples were shipped and stored frozen at less than −20° C. The vendors supplied demographic information for the individual donors including gender, race (Black/White), smoking status and age.

Human urine samples from donors with various chronic diseases ("Chronic Disease Patients") including congestive heart failure, coronary artery disease, chronic kidney disease, chronic obstructive pulmonary disease, diabetes mellitus and hypertension were purchased from Virginia Medical Research, Inc., 915 First Colonial Rd., Virginia Beach, Va. 23454. The urine samples were shipped and stored frozen at less than −20 degrees centigrade. The vendor provided a case report form for each individual donor with age, gender, race (Black/White), smoking status and alcohol use, height, weight, chronic disease(s) diagnosis, current medications and previous surgeries.

Example 6: Use of Kidney Injury Markers for Evaluating Renal Status in Patients

Patients from the intensive care unit (ICU) were enrolled in the following study. Each patient was classified by kidney status as non-injury (0), risk of injury (R), injury (I), and failure (F) according to the maximum stage reached within 7 days of enrollment as determined by the RIFLE criteria. EDTA anti-coagulated blood samples (10 mL) and a urine samples (25-30 mL) were collected from each patient at enrollment, 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Markers were each measured by standard immunoassay methods using commercially available assay reagents in the urine samples and the plasma component of the blood samples collected.

Two cohorts were defined to represent a "diseased" and a "normal" population. While these terms are used for convenience, "diseased" and "normal" simply represent two cohorts for comparison (say RIFLE 0 vs RIFLE R, I and F; RIFLE 0 vs RIFLE R; RIFLE 0 and R vs RIFLE I and F; etc.). The time "prior max stage" represents the time at which a sample is collected, relative to the time a particular patient reaches the lowest disease stage as defined for that cohort, binned into three groups which are +/−12 hours. For example, "24 hr prior" which uses 0 vs R, I, F as the two cohorts would mean 24 hr (+/−12 hours) prior to reaching stage R (or I if no sample at R, or F if no sample at R or I).

A receiver operating characteristic (ROC) curve was generated for each biomarker measured and the area under each ROC curve (AUC) is determined. Patients in Cohort 2 were also separated according to the reason for adjudication to cohort 2 as being based on serum creatinine measurements (sCr), being based on urine output (UO), or being based on either serum creatinine measurements or urine output. Using the same example discussed above (0 vs R, I, F), for those patients adjudicated to stage R, I, or F on the basis of serum creatinine measurements alone, the stage 0 cohort may include patients adjudicated to stage R, I, or F on the basis of urine output; for those patients adjudicated to stage R, I, or F on the basis of urine output alone, the stage 0 cohort may include patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, in the data for patients adjudicated on the basis of serum creatinine measurements or urine output, the adjudication method which yielded the most severe RIFLE stage is used.

The ability to distinguish cohort 1 from Cohort 2 was determined using ROC analysis. SE is the standard error of the AUC, n is the number of sample or individual patients ("pts," as indicated). Standard errors are calculated as described in Hanley, J. A., and McNeil, B. J., The meaning and use of the area under a receiver operating characteristic (ROC) curve. Radiology (1982) 143: 29-36; p values are calculated with a two-tailed Z-test. An AUC<0.5 is indicative of a negative going marker for the comparison, and an AUC>0.5 is indicative of a positive going marker for the comparison.

Various threshold (or "cutoff") concentrations were selected, and the associated sensitivity and specificity for distinguishing cohort 1 from cohort 2 are determined. OR is the odds ratio calculated for the particular cutoff concentration, and 95% CI is the confidence interval for the odds ratio.

FIG. 1: Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | Complement C4-B | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 14.6 | 18.7 | 14.6 | 18.9 | 14.6 | 22.3 |
| Average | 52.6 | 70.9 | 52.6 | 51.2 | 52.6 | 47.9 |
| Stdev | 134 | 196 | 134 | 98.2 | 134 | 92.5 |
| p (t-test) | | 0.23 | | 0.91 | | 0.81 |
| Min | 0.00607 | 0.383 | 0.00607 | 0.211 | 0.00607 | 0.448 |
| Max | 1950 | 2000 | 1950 | 625 | 1950 | 562 |
| n (Samp) | 463 | 119 | 463 | 128 | 463 | 47 |
| n (Patient) | 223 | 119 | 223 | 128 | 223 | 47 |
| sCr only | | | | | | |
| Median | 17.3 | 14.0 | 17.3 | 22.3 | 17.3 | 21.1 |
| Average | 59.1 | 23.1 | 59.1 | 43.1 | 59.1 | 48.7 |
| Stdev | 139 | 29.6 | 139 | 84.8 | 139 | 65.3 |
| p (t-test) | | 0.10 | | 0.44 | | 0.70 |
| Min | 0.00607 | 0.754 | 0.00607 | 0.211 | 0.00607 | 0.448 |
| Max | 2000 | 130 | 2000 | 556 | 2000 | 252 |
| n (Samp) | 1015 | 40 | 1015 | 46 | 1015 | 26 |
| n (Patient) | 374 | 40 | 374 | 46 | 374 | 26 |
| UO only | | | | | | |
| Median | 17.7 | 27.6 | 17.7 | 19.8 | 17.7 | 23.2 |
| Average | 53.8 | 80.7 | 53.8 | 53.9 | 53.8 | 44.1 |
| Stdev | 128 | 206 | 128 | 95.8 | 128 | 89.5 |
| p (t-test) | | 0.090 | | 0.99 | | 0.62 |
| Min | 0.00329 | 0.383 | 0.00329 | 0.259 | 0.00329 | 0.544 |
| Max | 1950 | 2000 | 1950 | 625 | 1950 | 562 |
| n (Samp) | 436 | 107 | 436 | 117 | 436 | 44 |
| n (Patient) | 173 | 107 | 173 | 117 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.56 | 0.44 | 0.56 | 0.52 | 0.51 | 0.50 | 0.55 | 0.52 | 0.51 |
| SE | 0.030 | 0.048 | 0.032 | 0.029 | 0.044 | 0.030 | 0.045 | 0.058 | 0.046 |
| p | 0.041 | 0.23 | 0.042 | 0.51 | 0.77 | 0.89 | 0.25 | 0.69 | 0.81 |
| nCohort 1 | 463 | 1015 | 436 | 463 | 1015 | 436 | 463 | 1015 | 436 |
| nCohort 2 | 119 | 40 | 107 | 128 | 46 | 117 | 47 | 26 | 44 |
| Cutoff 1 | 8.26 | 4.22 | 10.2 | 4.60 | 5.88 | 5.01 | 10.5 | 6.04 | 6.59 |
| Sens 1 | 71% | 70% | 70% | 70% | 72% | 70% | 70% | 73% | 70% |
| Spec 1 | 40% | 26% | 39% | 30% | 31% | 26% | 45% | 31% | 30% |
| Cutoff 2 | 3.27 | 2.69 | 4.12 | 1.77 | 4.60 | 2.22 | 4.27 | 2.22 | 3.99 |
| Sens 2 | 81% | 80% | 80% | 80% | 80% | 80% | 81% | 81% | 82% |
| Spec 2 | 23% | 19% | 21% | 15% | 28% | 13% | 28% | 17% | 21% |
| Cutoff 3 | 1.35 | 1.88 | 1.30 | 0.895 | 1.66 | 1.09 | 3.00 | 0.995 | 2.76 |
| Sens 3 | 91% | 90% | 91% | 91% | 91% | 91% | 91% | 92% | 91% |
| Spec 3 | 12% | 15% | 9% | 8% | 14% | 7% | 22% | 9% | 15% |
| Cutoff 4 | 36.1 | 41.3 | 40.6 | 36.1 | 41.3 | 40.6 | 36.1 | 41.3 | 40.6 |
| Sens 4 | 42% | 18% | 44% | 34% | 33% | 35% | 26% | 31% | 27% |
| Spec 4 | 70% | 70% | 70% | 70% | 70% | 70% | 70% | 70% | 70% |
| Cutoff 5 | 60.0 | 68.7 | 60.5 | 60.0 | 68.7 | 60.5 | 60.0 | 68.7 | 60.5 |
| Sens 5 | 28% | 8% | 34% | 23% | 13% | 26% | 21% | 23% | 18% |
| Spec 5 | 80% | 80% | 80% | 80% | 80% | 80% | 80% | 80% | 80% |
| Cutoff 6 | 133 | 144 | 133 | 133 | 144 | 133 | 133 | 144 | 133 |

-continued

| | | | | | | | | | |
|---|---|---|---|---|---|---|---|---|---|
| Sens 6 | 12% | 0% | 16% | 9% | 4% | 10% | 6% | 12% | 5% |
| Spec 6 | 90% | 90% | 90% | 90% | 90% | 90% | 90% | 90% | 90% |
| OR Quart 2 | 0.99 | 4.1 | 0.90 | 0.77 | 1.3 | 0.58 | 1.6 | 0.83 | 0.71 |
| p Value | 0.98 | 0.029 | 0.73 | 0.36 | 0.51 | 0.074 | 0.34 | 0.76 | 0.47 |
| 95% CI of | 0.54 | 1.2 | 0.48 | 0.43 | 0.56 | 0.32 | 0.60 | 0.25 | 0.27 |
| OR Quart 2 | 1.8 | 15 | 1.7 | 1.4 | 3.3 | 1.1 | 4.3 | 2.8 | 1.8 |
| OR Quart 3 | 1.1 | 4.9 | 0.85 | 1.0 | 1.8 | 0.68 | 2.8 | 1.2 | 1.4 |
| p Value | 0.65 | 0.014 | 0.61 | 0.91 | 0.16 | 0.19 | 0.025 | 0.78 | 0.41 |
| 95% CI of | 0.64 | 1.4 | 0.45 | 0.59 | 0.79 | 0.38 | 1.1 | 0.39 | 0.62 |
| OR Quart 3 | 2.1 | 17 | 1.6 | 1.8 | 4.2 | 1.2 | 7.0 | 3.5 | 3.2 |
| OR Quart 4 | 1.6 | 3.8 | 1.6 | 1.2 | 1.00 | 1.1 | 1.6 | 1.3 | 0.90 |
| p Value | 0.097 | 0.042 | 0.090 | 0.51 | 0.99 | 0.81 | 0.34 | 0.59 | 0.82 |
| 95% CI of | 0.92 | 1.0 | 0.92 | 0.70 | 0.39 | 0.62 | 0.60 | 0.46 | 0.37 |
| OR Quart 4 | 2.8 | 14 | 2.9 | 2.1 | 2.6 | 1.8 | 4.3 | 3.9 | 2.2 |

C-C motif chemokine 26

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.0320 | 0.0240 | 0.0320 | 0.0311 | 0.0320 | 0.0254 |
| Average | 0.0543 | 0.155 | 0.0543 | 0.391 | 0.0543 | 0.0836 |
| Stdev | 0.424 | 1.33 | 0.424 | 3.72 | 0.424 | 0.251 |
| p (t-test) | | 0.17 | | 0.057 | | 0.64 |
| Min | 0.00872 | 0.00872 | 0.00872 | 0.00872 | 0.00872 | 0.00872 |
| Max | 9.14 | 14.6 | 9.14 | 42.3 | 9.14 | 1.25 |
| n (Samp) | 463 | 120 | 463 | 130 | 463 | 46 |
| n (Patient) | 223 | 120 | 223 | 130 | 223 | 46 |
| sCr only | | | | | | |
| Median | 0.0368 | 0.0240 | 0.0368 | 0.0311 | 0.0368 | 0.0240 |
| Average | 0.243 | 0.0346 | 0.243 | 0.0675 | 0.243 | 0.0794 |
| Stdev | 2.46 | 0.0171 | 2.46 | 0.239 | 2.46 | 0.244 |
| p (t-test) | | 0.59 | | 0.63 | | 0.74 |
| Min | 0.00872 | 0.00872 | 0.00872 | 0.00872 | 0.00872 | 0.00872 |
| Max | 42.3 | 0.0633 | 42.3 | 1.65 | 42.3 | 1.25 |
| n (Samp) | 1019 | 40 | 1019 | 46 | 1019 | 25 |
| n (Patient) | 375 | 40 | 375 | 46 | 375 | 25 |
| UO only | | | | | | |
| Median | 0.0383 | 0.0276 | 0.0383 | 0.0247 | 0.0383 | 0.0240 |
| Average | 0.0390 | 0.387 | 0.0390 | 0.473 | 0.0390 | 0.0572 |
| Stdev | 0.0608 | 2.15 | 0.0608 | 3.94 | 0.0608 | 0.184 |
| p (t-test) | | 7.5E−4 | | 0.022 | | 0.15 |
| Min | 0.00872 | 0.00872 | 0.00872 | 0.00872 | 0.00872 | 0.00872 |
| Max | 1.25 | 14.6 | 1.25 | 42.3 | 1.25 | 1.25 |
| n (Samp) | 435 | 108 | 435 | 119 | 435 | 44 |
| n (Patient) | 173 | 108 | 173 | 119 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.49 | 0.50 | 0.47 | 0.47 | 0.46 | 0.43 | 0.47 | 0.45 | 0.40 |
| SE | 0.030 | 0.047 | 0.031 | 0.029 | 0.044 | 0.030 | 0.045 | 0.060 | 0.047 |
| p | 0.78 | 0.98 | 0.36 | 0.29 | 0.32 | 0.025 | 0.46 | 0.45 | 0.028 |
| nCohort 1 | 463 | 1019 | 435 | 463 | 1019 | 435 | 463 | 1019 | 435 |
| nCohort 2 | 120 | 40 | 108 | 130 | 46 | 119 | 46 | 25 | 44 |
| Cutoff 1 | 0.0195 | 0.0226 | 0.0195 | 0.0204 | 0.0232 | 0.0204 | 0.0218 | 0.0218 | 0.0204 |
| Sens 1 | 78% | 72% | 79% | 72% | 72% | 71% | 72% | 72% | 70% |
| Spec 1 | 19% | 26% | 16% | 23% | 31% | 21% | 29% | 26% | 21% |
| Cutoff 2 | 0.0192 | 0.0195 | 0.0192 | 0.0192 | 0.0195 | 0.0143 | 0.0195 | 0.0204 | 0.0173 |
| Sens 2 | 80% | 85% | 81% | 82% | 80% | 86% | 80% | 84% | 82% |
| Spec 2 | 13% | 16% | 11% | 13% | 16% | 7% | 19% | 21% | 11% |
| Cutoff 3 | 0.0143 | 0.0143 | 0.00872 | 0.00872 | 0.00872 | 0.00872 | 0.00872 | 0.00872 | 0.00872 |
| Sens 3 | 90% | 90% | 95% | 95% | 96% | 93% | 98% | 92% | 95% |
| Spec 3 | 9% | 8% | 4% | 6% | 4% | 4% | 6% | 4% | 4% |
| Cutoff 4 | 0.0443 | 0.0443 | 0.0486 | 0.0443 | 0.0443 | 0.0486 | 0.0443 | 0.0443 | 0.0486 |
| Sens 4 | 35% | 35% | 26% | 20% | 20% | 16% | 17% | 24% | 9% |
| Spec 4 | 74% | 73% | 75% | 74% | 73% | 75% | 74% | 73% | 75% |
| Cutoff 5 | 0.0504 | 0.0504 | 0.0504 | 0.0504 | 0.0504 | 0.0504 | 0.0504 | 0.0504 | 0.0504 |
| Sens 5 | 22% | 28% | 22% | 14% | 9% | 15% | 13% | 16% | 9% |
| Spec 5 | 84% | 83% | 81% | 84% | 83% | 81% | 84% | 83% | 81% |
| Cutoff 6 | 0.0526 | 0.0526 | 0.0526 | 0.0526 | 0.0526 | 0.0526 | 0.0526 | 0.0526 | 0.0526 |
| Sens 6 | 8% | 8% | 10% | 8% | 7% | 8% | 11% | 12% | 5% |

-continued

| | | | | | | | | | |
|---|---|---|---|---|---|---|---|---|---|
| Spec 6 | 92% | 90% | 91% | 92% | 90% | 91% | 92% | 90% | 91% |
| OR Quart 2 | 0.54 | 0.45 | 0.83 | 1.6 | 2.1 | 1.8 | 1.7 | 0.60 | 3.8 |
| p Value | 0.042 | 0.11 | 0.54 | 0.11 | 0.12 | 0.049 | 0.25 | 0.48 | 0.021 |
| 95% CI of | 0.30 | 0.17 | 0.45 | 0.90 | 0.82 | 1.0 | 0.68 | 0.14 | 1.2 |
| OR Quart 2 | 0.98 | 1.2 | 1.5 | 2.8 | 5.2 | 3.4 | 4.3 | 2.5 | 12 |
| OR Quart 3 | 0.60 | 0.76 | 0.74 | 1.2 | 2.1 | 1.4 | 1.9 | 2.3 | 3.2 |
| p Value | 0.084 | 0.52 | 0.35 | 0.53 | 0.12 | 0.34 | 0.18 | 0.14 | 0.048 |
| 95% CI of | 0.34 | 0.33 | 0.40 | 0.67 | 0.82 | 0.72 | 0.75 | 0.77 | 1.0 |
| OR Quart 3 | 1.1 | 1.8 | 1.4 | 2.2 | 5.2 | 2.5 | 4.6 | 6.6 | 10 |
| OR Quart 4 | 1.1 | 0.84 | 1.3 | 1.6 | 1.6 | 2.1 | 1.4 | 1.2 | 3.9 |
| p Value | 0.76 | 0.68 | 0.37 | 0.11 | 0.34 | 0.018 | 0.47 | 0.76 | 0.020 |
| 95% CI of | 0.64 | 0.37 | 0.74 | 0.90 | 0.61 | 1.1 | 0.55 | 0.36 | 1.2 |
| OR Quart 4 | 1.8 | 1.9 | 2.3 | 2.8 | 4.2 | 3.7 | 3.7 | 4.0 | 12 |

C-C motif chemokine 7

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.515 | 0.812 | 0.515 | 0.584 | 0.515 | 0.584 |
| Average | 1.72 | 3.44 | 1.72 | 3.13 | 1.72 | 1.59 |
| Stdev | 7.00 | 16.1 | 7.00 | 15.0 | 7.00 | 3.45 |
| p (t-test) | | 0.082 | | 0.13 | | 0.90 |
| Min | 0.146 | 0.146 | 0.146 | 0.146 | 0.146 | 0.146 |
| Max | 125 | 161 | 125 | 163 | 125 | 13.6 |
| n (Samp) | 462 | 120 | 462 | 130 | 462 | 47 |
| n (Patient) | 223 | 120 | 223 | 130 | 223 | 47 |
| sCr only | | | | | | |
| Median | 0.584 | 0.604 | 0.584 | 0.737 | 0.584 | 0.625 |
| Average | 2.20 | 2.18 | 2.20 | 3.16 | 2.20 | 2.44 |
| Stdev | 13.0 | 6.16 | 13.0 | 8.29 | 13.0 | 4.49 |
| p (t-test) | | 0.99 | | 0.62 | | 0.93 |
| Min | 0.146 | 0.146 | 0.146 | 0.146 | 0.146 | 0.146 |
| Max | 291 | 29.9 | 291 | 43.8 | 291 | 13.6 |
| n (Samp) | 1019 | 40 | 1019 | 46 | 1019 | 26 |
| n (Patient) | 375 | 40 | 375 | 46 | 375 | 26 |
| UO only | | | | | | |
| Median | 0.584 | 0.812 | 0.584 | 0.584 | 0.584 | 0.484 |
| Average | 1.83 | 5.88 | 1.83 | 4.24 | 1.83 | 1.66 |
| Stdev | 7.17 | 23.3 | 7.17 | 18.7 | 7.17 | 5.26 |
| p (t-test) | | 0.0021 | | 0.030 | | 0.88 |
| Min | 0.146 | 0.146 | 0.146 | 0.146 | 0.146 | 0.146 |
| Max | 125 | 166 | 125 | 163 | 125 | 33.0 |
| n (Samp) | 436 | 108 | 436 | 119 | 436 | 44 |
| n (Patient) | 173 | 108 | 173 | 119 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.60 | 0.50 | 0.60 | 0.56 | 0.59 | 0.51 | 0.51 | 0.53 | 0.46 |
| SE | 0.030 | 0.047 | 0.031 | 0.029 | 0.045 | 0.030 | 0.044 | 0.058 | 0.047 |
| p | 5.6E-4 | 0.99 | 9.7E-4 | 0.054 | 0.046 | 0.65 | 0.81 | 0.65 | 0.37 |
| nCohort 1 | 462 | 1019 | 436 | 462 | 1019 | 436 | 462 | 1019 | 436 |
| nCohort 2 | 120 | 40 | 108 | 130 | 46 | 119 | 47 | 26 | 44 |
| Cutoff 1 | 0.551 | 0.320 | 0.584 | 0.336 | 0.512 | 0.320 | 0.336 | 0.320 | 0.336 |
| Sens 1 | 70% | 78% | 71% | 72% | 74% | 76% | 77% | 73% | 73% |
| Spec 1 | 52% | 30% | 50% | 39% | 44% | 31% | 39% | 30% | 36% |
| Cutoff 2 | 0.320 | 0.319 | 0.483 | 0.319 | 0.336 | 0.319 | 0.282 | 0.319 | 0.319 |
| Sens 2 | 81% | 82% | 81% | 82% | 80% | 82% | 85% | 81% | 82% |
| Spec 2 | 35% | 26% | 44% | 29% | 34% | 27% | 18% | 26% | 23% |
| Cutoff 3 | 0.282 | 0.254 | 0.282 | 0.301 | 0.254 | 0.301 | 0.254 | 0.301 | 0.264 |
| Sens 3 | 92% | 92% | 93% | 91% | 93% | 91% | 91% | 92% | 91% |
| Spec 3 | 18% | 8% | 18% | 18% | 8% | 18% | 9% | 17% | 14% |
| Cutoff 4 | 0.816 | 1.04 | 1.04 | 0.816 | 1.04 | 1.04 | 0.816 | 1.04 | 1.04 |
| Sens 4 | 38% | 20% | 31% | 35% | 39% | 23% | 26% | 27% | 14% |
| Spec 4 | 71% | 72% | 72% | 71% | 72% | 72% | 71% | 72% | 72% |
| Cutoff 5 | 1.12 | 1.12 | 1.12 | 1.12 | 1.12 | 1.12 | 1.12 | 1.12 | 1.12 |
| Sens 5 | 27% | 20% | 31% | 22% | 33% | 20% | 17% | 23% | 14% |
| Spec 5 | 83% | 81% | 80% | 83% | 81% | 80% | 83% | 81% | 80% |
| Cutoff 6 | 1.59 | 1.59 | 1.59 | 1.59 | 1.59 | 1.59 | 1.59 | 1.59 | 1.59 |
| Sens 6 | 7% | 8% | 11% | 8% | 11% | 9% | 9% | 15% | 7% |
| Spec 6 | 94% | 94% | 94% | 94% | 94% | 94% | 94% | 94% | 94% |

-continued

| | | | | | | | | | |
|---|---|---|---|---|---|---|---|---|---|
| OR Quart 2 | 1.7 | 1.7 | 2.6 | 1.8 | 1.0 | 2.2 | 1.1 | 1.0 | 1.9 |
| p Value | 0.14 | 0.27 | 0.0087 | 0.057 | 1.0 | 0.010 | 0.82 | 1.0 | 0.21 |
| 95% CI of | 0.85 | 0.68 | 1.3 | 0.98 | 0.37 | 1.2 | 0.45 | 0.29 | 0.69 |
| OR Quart 2 | 3.3 | 4.1 | 5.2 | 3.2 | 2.7 | 3.9 | 2.7 | 3.5 | 5.4 |
| OR Quart 3 | 3.7 | 1.5 | 2.9 | 2.0 | 1.8 | 1.7 | 1.8 | 1.8 | 3.4 |
| p Value | 3.6E−5 | 0.37 | 0.0026 | 0.016 | 0.20 | 0.075 | 0.16 | 0.29 | 0.014 |
| 95% CI of | 2.0 | 0.61 | 1.5 | 1.1 | 0.74 | 0.95 | 0.79 | 0.60 | 1.3 |
| OR Quart 3 | 7.0 | 3.8 | 5.8 | 3.7 | 4.3 | 3.2 | 4.1 | 5.5 | 8.8 |
| OR Quart 4 | 2.4 | 0.88 | 3.2 | 1.7 | 2.1 | 1.3 | 0.88 | 1.4 | 1.5 |
| p Value | 0.0096 | 0.80 | 0.0011 | 0.077 | 0.10 | 0.44 | 0.80 | 0.57 | 0.43 |
| 95% CI of | 1.2 | 0.31 | 1.6 | 0.94 | 0.86 | 0.68 | 0.35 | 0.44 | 0.53 |
| OR Quart 4 | 4.5 | 2.4 | 6.3 | 3.1 | 4.9 | 2.4 | 2.3 | 4.5 | 4.5 |

Thyrotropin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.1000 | 0.118 | 0.1000 | 0.106 | 0.1000 | 0.124 |
| Average | 0.296 | 0.126 | 0.296 | 0.195 | 0.296 | 0.214 |
| Stdev | 1.96 | 0.0588 | 1.96 | 0.250 | 1.96 | 0.408 |
| p (t-test) | | 0.55 | | 0.71 | | 0.83 |
| Min | 0.0321 | 0.0383 | 0.0321 | 0.0574 | 0.0321 | 0.0189 |
| Max | 21.8 | 0.303 | 21.8 | 1.58 | 21.8 | 2.18 |
| n (Samp) | 122 | 47 | 122 | 51 | 122 | 26 |
| n (Patient) | 99 | 47 | 99 | 51 | 99 | 26 |
| sCr only | | | | | | |
| Median | 0.106 | 0.132 | 0.106 | 0.123 | 0.106 | 0.123 |
| Average | 0.232 | 0.129 | 0.232 | 0.152 | 0.232 | 0.130 |
| Stdev | 1.35 | 0.0472 | 1.35 | 0.0958 | 1.35 | 0.0635 |
| p (t-test) | | 0.78 | | 0.80 | | 0.79 |
| Min | 0.0321 | 0.0383 | 0.0321 | 0.0698 | 0.0321 | 0.0189 |
| Max | 21.8 | 0.198 | 21.8 | 0.430 | 21.8 | 0.248 |
| n (Samp) | 262 | 14 | 262 | 19 | 262 | 13 |
| n (Patient) | 160 | 14 | 160 | 19 | 160 | 13 |
| UO only | | | | | | |
| Median | 0.109 | 0.118 | 0.109 | 0.105 | 0.109 | 0.130 |
| Average | 0.322 | 0.126 | 0.322 | 0.202 | 0.322 | 0.234 |
| Stdev | 2.05 | 0.0582 | 2.05 | 0.257 | 2.05 | 0.431 |
| p (t-test) | | 0.53 | | 0.69 | | 0.84 |
| Min | 0.0230 | 0.0403 | 0.0230 | 0.0574 | 0.0230 | 0.0383 |
| Max | 21.8 | 0.303 | 21.8 | 1.58 | 21.8 | 2.18 |
| n (Samp) | 111 | 44 | 111 | 47 | 111 | 23 |
| n (Patient) | 86 | 44 | 86 | 47 | 86 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.56 | 0.56 | 0.52 | 0.60 | 0.59 | 0.57 | 0.58 | 0.55 | 0.59 |
| SE | 0.050 | 0.082 | 0.052 | 0.048 | 0.071 | 0.051 | 0.064 | 0.084 | 0.068 |
| p | 0.22 | 0.43 | 0.71 | 0.036 | 0.22 | 0.15 | 0.19 | 0.56 | 0.17 |
| nCohort 1 | 122 | 262 | 111 | 122 | 262 | 111 | 122 | 262 | 111 |
| nCohort 2 | 47 | 14 | 44 | 51 | 19 | 47 | 26 | 13 | 23 |
| Cutoff 1 | 0.0862 | 0.114 | 0.0862 | 0.0930 | 0.105 | 0.0930 | 0.0862 | 0.104 | 0.0950 |
| Sens 1 | 70% | 71% | 70% | 71% | 74% | 72% | 73% | 77% | 74% |
| Spec 1 | 41% | 55% | 36% | 45% | 50% | 41% | 41% | 49% | 42% |
| Cutoff 2 | 0.0698 | 0.0808 | 0.0780 | 0.0854 | 0.0918 | 0.0854 | 0.0666 | 0.0877 | 0.0666 |
| Sens 2 | 81% | 86% | 82% | 80% | 84% | 81% | 81% | 85% | 83% |
| Spec 2 | 28% | 31% | 32% | 40% | 41% | 35% | 25% | 37% | 19% |
| Cutoff 3 | 0.0617 | 0.0715 | 0.0627 | 0.0717 | 0.0717 | 0.0717 | 0.0509 | 0.0360 | 0.0608 |
| Sens 3 | 91% | 93% | 91% | 92% | 95% | 91% | 92% | 92% | 91% |
| Spec 3 | 21% | 23% | 18% | 29% | 23% | 24% | 11% | 2% | 17% |
| Cutoff 4 | 0.146 | 0.154 | 0.151 | 0.146 | 0.154 | 0.151 | 0.146 | 0.154 | 0.151 |
| Sens 4 | 32% | 43% | 27% | 33% | 32% | 34% | 38% | 31% | 48% |
| Spec 4 | 71% | 71% | 70% | 71% | 71% | 70% | 71% | 71% | 70% |
| Cutoff 5 | 0.161 | 0.186 | 0.170 | 0.161 | 0.186 | 0.170 | 0.161 | 0.186 | 0.170 |
| Sens 5 | 21% | 7% | 18% | 27% | 21% | 30% | 31% | 23% | 35% |
| Spec 5 | 80% | 80% | 80% | 80% | 80% | 80% | 80% | 80% | 80% |
| Cutoff 6 | 0.212 | 0.248 | 0.215 | 0.212 | 0.248 | 0.215 | 0.212 | 0.248 | 0.215 |
| Sens 6 | 6% | 0% | 7% | 22% | 11% | 23% | 15% | 0% | 17% |
| Spec 6 | 90% | 90% | 90% | 90% | 90% | 90% | 90% | 90% | 90% |
| OR Quart 2 | 1.2 | 1.0 | 1.7 | 2.8 | 2.6 | 5.0 | 0.46 | 1.5 | 0.97 |

-continued

| | | | | | | | | | |
|---|---|---|---|---|---|---|---|---|---|
| p Value | 0.79 | 1.0 | 0.33 | 0.052 | 0.26 | 0.0032 | 0.29 | 0.66 | 0.96 |
| 95% CI of | 0.40 | 0.14 | 0.59 | 0.99 | 0.49 | 1.7 | 0.10 | 0.24 | 0.25 |
| OR Quart 2 | 3.4 | 7.3 | 4.7 | 7.7 | 14 | 14 | 2.0 | 9.3 | 3.7 |
| OR Quart 3 | 2.9 | 2.6 | 2.1 | 2.5 | 4.4 | 1.4 | 1.4 | 2.6 | 0.56 |
| p Value | 0.035 | 0.26 | 0.15 | 0.084 | 0.068 | 0.56 | 0.55 | 0.27 | 0.46 |
| 95% CI of | 1.1 | 0.49 | 0.76 | 0.89 | 0.90 | 0.44 | 0.44 | 0.48 | 0.12 |
| OR Quart 3 | 7.7 | 14 | 5.8 | 7.0 | 21 | 4.6 | 4.6 | 14 | 2.6 |
| OR Quart 4 | 1.8 | 2.6 | 1.3 | 2.7 | 2.0 | 3.0 | 1.7 | 1.5 | 2.3 |
| p Value | 0.24 | 0.26 | 0.63 | 0.061 | 0.42 | 0.050 | 0.39 | 0.66 | 0.17 |
| 95% CI of | 0.67 | 0.49 | 0.45 | 0.96 | 0.36 | 1.00 | 0.52 | 0.24 | 0.70 |
| OR Quart 4 | 5.0 | 14 | 3.7 | 7.4 | 11 | 8.8 | 5.3 | 9.3 | 7.8 |

Vascular endothelial growth factor receptor 3

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 277 | 318 | 277 | 351 | 277 | 366 |
| Average | 300 | 374 | 300 | 365 | 300 | 374 |
| Stdev | 237 | 217 | 237 | 181 | 237 | 229 |
| p (t-test) | | 0.011 | | 0.018 | | 0.096 |
| Min | 1.37 | 1.37 | 1.37 | 1.37 | 1.37 | 1.37 |
| Max | 2070 | 1280 | 2070 | 901 | 2070 | 942 |
| n (Samp) | 217 | 90 | 217 | 94 | 217 | 32 |
| n (Patient) | 128 | 90 | 128 | 94 | 128 | 32 |
| sCr only | | | | | | |
| Median | 318 | 359 | 318 | 375 | 318 | 307 |
| Average | 339 | 387 | 339 | 398 | 339 | 372 |
| Stdev | 246 | 241 | 246 | 213 | 246 | 295 |
| p (t-test) | | 0.32 | | 0.19 | | 0.59 |
| Min | 1.37 | 2.36 | 1.37 | 3.28 | 1.37 | 1.37 |
| Max | 2750 | 901 | 2750 | 913 | 2750 | 942 |
| n (Samp) | 513 | 28 | 513 | 32 | 513 | 18 |
| n (Patient) | 240 | 28 | 240 | 32 | 240 | 18 |
| UO only | | | | | | |
| Median | 282 | 346 | 282 | 351 | 282 | 354 |
| Average | 310 | 378 | 310 | 356 | 310 | 375 |
| Stdev | 240 | 213 | 240 | 167 | 240 | 200 |
| p (t-test) | | 0.026 | | 0.11 | | 0.15 |
| Min | 1.37 | 1.37 | 1.37 | 1.37 | 1.37 | 2.01 |
| Max | 2070 | 1280 | 2070 | 901 | 2070 | 854 |
| n (Samp) | 227 | 80 | 227 | 84 | 227 | 31 |
| n (Patient) | 122 | 80 | 122 | 84 | 122 | 31 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.61 | 0.55 | 0.62 | 0.62 | 0.59 | 0.61 | 0.62 | 0.51 | 0.62 |
| SE | 0.036 | 0.057 | 0.038 | 0.036 | 0.054 | 0.037 | 0.056 | 0.070 | 0.057 |
| p | 0.0022 | 0.34 | 0.0022 | 7.9E-4 | 0.100 | 0.0038 | 0.039 | 0.91 | 0.034 |
| nCohort 1 | 217 | 513 | 227 | 217 | 513 | 227 | 217 | 513 | 227 |
| nCohort 2 | 90 | 28 | 80 | 94 | 32 | 84 | 32 | 18 | 31 |
| Cutoff 1 | 249 | 230 | 249 | 251 | 251 | 277 | 249 | 166 | 282 |
| Sens 1 | 71% | 71% | 74% | 71% | 72% | 71% | 72% | 72% | 71% |
| Spec 1 | 44% | 32% | 42% | 46% | 38% | 48% | 44% | 20% | 52% |
| Cutoff 2 | 208 | 179 | 208 | 208 | 208 | 219 | 166 | 130 | 247 |
| Sens 2 | 80% | 82% | 81% | 81% | 81% | 81% | 81% | 83% | 81% |
| Spec 2 | 37% | 24% | 36% | 37% | 28% | 38% | 29% | 14% | 41% |
| Cutoff 3 | 136 | 127 | 136 | 161 | 160 | 163 | 39.3 | 0 | 130 |
| Sens 3 | 90% | 93% | 90% | 90% | 91% | 90% | 91% | 100% | 90% |
| Spec 3 | 22% | 13% | 19% | 26% | 16% | 23% | 10% | 0% | 18% |
| Cutoff 4 | 386 | 414 | 386 | 386 | 414 | 386 | 386 | 414 | 386 |
| Sens 4 | 42% | 32% | 46% | 43% | 41% | 42% | 41% | 39% | 39% |
| Spec 4 | 71% | 70% | 71% | 71% | 70% | 71% | 71% | 70% | 71% |
| Cutoff 5 | 440 | 468 | 440 | 440 | 468 | 440 | 440 | 468 | 440 |
| Sens 5 | 33% | 32% | 38% | 30% | 34% | 26% | 38% | 33% | 35% |
| Spec 5 | 80% | 80% | 80% | 80% | 80% | 80% | 80% | 80% | 80% |
| Cutoff 6 | 496 | 572 | 509 | 496 | 572 | 509 | 496 | 572 | 509 |
| Sens 6 | 26% | 21% | 24% | 24% | 25% | 17% | 25% | 28% | 23% |
| Spec 6 | 90% | 90% | 90% | 90% | 90% | 90% | 90% | 90% | 90% |
| OR Quart 2 | 2.3 | 1.6 | 1.7 | 2.3 | 1.2 | 2.0 | 1.2 | 0.27 | 0.98 |
| p Value | 0.030 | 0.40 | 0.18 | 0.030 | 0.78 | 0.088 | 0.75 | 0.11 | 0.98 |

-continued

| | | | | | | | | | |
|---|---|---|---|---|---|---|---|---|---|
| 95% CI of | 1.1 | 0.52 | 0.78 | 1.1 | 0.38 | 0.90 | 0.35 | 0.056 | 0.27 |
| OR Quart 2 | 5.0 | 5.1 | 3.7 | 5.0 | 3.6 | 4.4 | 4.2 | 1.3 | 3.6 |
| OR Quart 3 | 1.9 | 1.2 | 1.4 | 2.8 | 1.2 | 2.6 | 1.9 | 0.27 | 1.9 |
| p Value | 0.094 | 0.76 | 0.44 | 0.0084 | 0.78 | 0.018 | 0.26 | 0.11 | 0.26 |
| 95% CI of | 0.89 | 0.36 | 0.61 | 1.3 | 0.38 | 1.2 | 0.61 | 0.056 | 0.61 |
| OR Quart 3 | 4.2 | 4.1 | 3.1 | 5.9 | 3.6 | 5.6 | 6.1 | 1.3 | 6.1 |
| OR Quart 4 | 3.1 | 1.8 | 3.1 | 2.8 | 2.1 | 2.7 | 2.7 | 0.99 | 2.7 |
| p Value | 0.0033 | 0.28 | 0.0033 | 0.0084 | 0.16 | 0.012 | 0.081 | 0.99 | 0.082 |
| 95% CI of | 1.5 | 0.60 | 1.5 | 1.3 | 0.76 | 1.2 | 0.88 | 0.34 | 0.88 |
| OR Quart 4 | 6.6 | 5.6 | 6.6 | 5.9 | 5.7 | 5.9 | 8.1 | 2.9 | 8.1 |

Interferon alpha-2

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.0967 | 0.0974 | 0.0967 | 0.0974 | 0.0967 | 5.72 |
| Average | 7.58 | 12.0 | 7.58 | 9.69 | 7.58 | 15.2 |
| Stdev | 17.4 | 24.3 | 17.4 | 19.9 | 17.4 | 18.2 |
| p (t-test) | | 0.023 | | 0.24 | | 0.0045 |
| Min | 0.0238 | 0.0348 | 0.0238 | 0.0238 | 0.0238 | 0.0369 |
| Max | 126 | 125 | 126 | 108 | 126 | 67.1 |
| n (Samp) | 462 | 120 | 462 | 130 | 462 | 47 |
| n (Patient) | 223 | 120 | 223 | 130 | 223 | 47 |
| sCr only | | | | | | |
| Median | 0.0967 | 0.0974 | 0.0967 | 0.0967 | 0.0967 | 0.113 |
| Average | 7.94 | 7.91 | 7.94 | 9.73 | 7.94 | 14.4 |
| Stdev | 18.2 | 16.7 | 18.2 | 19.4 | 18.2 | 19.7 |
| p (t-test) | | 0.99 | | 0.52 | | 0.075 |
| Min | 0.0238 | 0.0348 | 0.0238 | 0.0348 | 0.0238 | 0.0369 |
| Max | 126 | 60.4 | 126 | 77.3 | 126 | 67.1 |
| n (Samp) | 1019 | 40 | 1019 | 46 | 1019 | 26 |
| n (Patient) | 375 | 40 | 375 | 46 | 375 | 26 |
| UO only | | | | | | |
| Median | 0.0974 | 0.0974 | 0.0974 | 0.0974 | 0.0974 | 2.50 |
| Average | 7.12 | 13.5 | 7.12 | 8.00 | 7.12 | 10.7 |
| Stdev | 16.4 | 26.2 | 16.4 | 18.0 | 16.4 | 14.9 |
| p (t-test) | | 0.0015 | | 0.61 | | 0.16 |
| Min | 0.0238 | 0.0348 | 0.0238 | 0.0238 | 0.0238 | 0.0348 |
| Max | 126 | 125 | 126 | 108 | 126 | 57.3 |
| n (Samp) | 436 | 108 | 436 | 119 | 436 | 44 |
| n (Patient) | 173 | 108 | 173 | 119 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.55 | 0.50 | 0.56 | 0.52 | 0.53 | 0.51 | 0.65 | 0.61 | 0.59 |
| SE | 0.030 | 0.047 | 0.032 | 0.029 | 0.044 | 0.030 | 0.045 | 0.059 | 0.047 |
| p | 0.093 | 0.92 | 0.066 | 0.41 | 0.45 | 0.68 | 6.6E−4 | 0.061 | 0.044 |
| nCohort 1 | 462 | 1019 | 436 | 462 | 1019 | 436 | 462 | 1019 | 436 |
| nCohort 2 | 120 | 40 | 108 | 130 | 46 | 119 | 47 | 26 | 44 |
| Cutoff 1 | 0.0724 | 0.0656 | 0.0724 | 0.0709 | 0.0709 | 0.0709 | 0.0815 | 0.0724 | 0.0724 |
| Sens 1 | 73% | 75% | 74% | 70% | 72% | 71% | 70% | 77% | 70% |
| Spec 1 | 39% | 29% | 36% | 36% | 37% | 33% | 47% | 41% | 36% |
| Cutoff 2 | 0.0656 | 0.0398 | 0.0709 | 0.0435 | 0.0606 | 0.0435 | 0.0709 | 0.0672 | 0.0656 |
| Sens 2 | 83% | 80% | 81% | 81% | 80% | 81% | 81% | 81% | 82% |
| Spec 2 | 29% | 14% | 33% | 19% | 26% | 17% | 36% | 33% | 26% |
| Cutoff 3 | 0.0369 | 0.0348 | 0.0398 | 0.0369 | 0.0369 | 0.0348 | 0.0398 | 0.0398 | 0.0369 |
| Sens 3 | 90% | 92% | 91% | 90% | 93% | 92% | 91% | 92% | 95% |
| Spec 3 | 8% | 7% | 12% | 8% | 11% | 6% | 14% | 14% | 9% |
| Cutoff 4 | 0.311 | 0.311 | 0.311 | 0.311 | 0.311 | 0.311 | 0.311 | 0.311 | 0.311 |
| Sens 4 | 26% | 22% | 30% | 29% | 30% | 28% | 60% | 46% | 50% |
| Spec 4 | 71% | 73% | 72% | 71% | 73% | 72% | 71% | 73% | 72% |
| Cutoff 5 | 10.9 | 12.7 | 9.75 | 10.9 | 12.7 | 9.75 | 10.9 | 12.7 | 9.75 |
| Sens 5 | 24% | 20% | 28% | 25% | 24% | 23% | 47% | 42% | 36% |
| Spec 5 | 80% | 80% | 80% | 80% | 80% | 80% | 80% | 80% | 80% |
| Cutoff 6 | 28.7 | 30.2 | 27.4 | 28.7 | 30.2 | 27.4 | 28.7 | 30.2 | 27.4 |
| Sens 6 | 20% | 15% | 21% | 15% | 15% | 11% | 21% | 19% | 14% |
| Spec 6 | 90% | 90% | 90% | 90% | 90% | 90% | 90% | 90% | 90% |
| OR Quart 2 | 2.0 | 0.89 | 2.9 | 0.96 | 1.8 | 0.95 | 1.3 | 1.0 | 1.0 |
| p Value | 0.020 | 0.81 | 0.0015 | 0.89 | 0.16 | 0.86 | 0.61 | 1.0 | 1.0 |
| 95% CI of | 1.1 | 0.36 | 1.5 | 0.55 | 0.79 | 0.52 | 0.47 | 0.29 | 0.36 |

-continued

| | | | | | | | | | |
|---|---|---|---|---|---|---|---|---|---|
| OR Quart 2 | 3.7 | 2.2 | 5.6 | 1.7 | 4.2 | 1.7 | 3.6 | 3.5 | 2.8 |
| OR Quart 3 | 1.8 | 1.2 | 1.9 | 1.1 | 1.0 | 1.2 | 1.3 | 0.80 | 1.0 |
| p Value | 0.050 | 0.67 | 0.065 | 0.78 | 1.0 | 0.58 | 0.61 | 0.74 | 1.0 |
| 95% CI of | 1.00 | 0.51 | 0.96 | 0.62 | 0.39 | 0.66 | 0.47 | 0.21 | 0.36 |
| OR Quart 3 | 3.4 | 2.8 | 3.8 | 1.9 | 2.6 | 2.1 | 3.6 | 3.0 | 2.8 |
| OR Quart 4 | 1.7 | 0.89 | 2.4 | 1.2 | 1.3 | 1.2 | 3.6 | 2.5 | 2.8 |
| p Value | 0.097 | 0.81 | 0.011 | 0.49 | 0.51 | 0.58 | 0.0052 | 0.096 | 0.019 |
| 95% CI of | 0.91 | 0.36 | 1.2 | 0.70 | 0.56 | 0.66 | 1.5 | 0.85 | 1.2 |
| OR Quart 4 | 3.1 | 2.2 | 4.7 | 2.1 | 3.2 | 2.1 | 8.7 | 7.1 | 6.6 |

Insulin-like growth factor-binding protein 4

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.733 | 0.670 | 0.733 | 0.896 | 0.733 | 0.957 |
| Average | 1.33 | 1.05 | 1.33 | 2.36 | 1.33 | 4.27 |
| Stdev | 4.52 | 1.46 | 4.52 | 5.77 | 4.52 | 17.0 |
| p (t-test) | | 0.63 | | 0.17 | | 0.072 |
| Min | 0.0319 | 0.0319 | 0.0319 | 0.0319 | 0.0319 | 0.0558 |
| Max | 53.9 | 7.51 | 53.9 | 42.8 | 53.9 | 85.6 |
| n (Samp) | 155 | 61 | 155 | 60 | 155 | 25 |
| n (Patient) | 109 | 61 | 109 | 60 | 109 | 25 |
| sCr only | | | | | | |
| Median | 0.733 | 0.733 | 0.733 | 0.398 | 0.733 | 0.660 |
| Average | 1.92 | 1.67 | 1.92 | 1.63 | 1.92 | 0.908 |
| Stdev | 6.94 | 2.39 | 6.94 | 2.27 | 6.94 | 1.12 |
| p (t-test) | | 0.88 | | 0.84 | | 0.59 |
| Min | 0.0319 | 0.0319 | 0.0319 | 0.0558 | 0.0319 | 0.0319 |
| Max | 85.6 | 9.68 | 85.6 | 7.59 | 85.6 | 3.90 |
| n (Samp) | 338 | 20 | 338 | 23 | 338 | 14 |
| n (Patient) | 184 | 20 | 184 | 23 | 184 | 14 |
| UO only | | | | | | |
| Median | 0.733 | 0.733 | 0.733 | 0.923 | 0.733 | 0.957 |
| Average | 1.20 | 1.20 | 1.20 | 2.56 | 1.20 | 4.79 |
| Stdev | 4.49 | 1.52 | 4.49 | 6.01 | 4.49 | 17.6 |
| p (t-test) | | 1.00 | | 0.079 | | 0.034 |
| Min | 0.0319 | 0.0319 | 0.0319 | 0.0319 | 0.0319 | 0.0319 |
| Max | 53.9 | 7.51 | 53.9 | 42.8 | 53.9 | 85.6 |
| n (Samp) | 155 | 54 | 155 | 56 | 155 | 23 |
| n (Patient) | 99 | 54 | 99 | 56 | 99 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.47 | 0.51 | 0.55 | 0.55 | 0.51 | 0.61 | 0.55 | 0.48 | 0.63 |
| SE | 0.044 | 0.067 | 0.046 | 0.044 | 0.063 | 0.045 | 0.064 | 0.080 | 0.066 |
| p | 0.44 | 0.86 | 0.29 | 0.23 | 0.85 | 0.019 | 0.39 | 0.84 | 0.052 |
| nCohort 1 | 155 | 338 | 155 | 155 | 338 | 155 | 155 | 338 | 155 |
| nCohort 2 | 61 | 20 | 54 | 60 | 23 | 56 | 25 | 14 | 23 |
| Cutoff 1 | 0.184 | 0.141 | 0.141 | 0.141 | 0.0585 | 0.341 | 0.382 | 0.141 | 0.382 |
| Sens 1 | 72% | 70% | 76% | 72% | 78% | 71% | 72% | 71% | 74% |
| Spec 1 | 25% | 28% | 30% | 25% | 16% | 39% | 32% | 28% | 39% |
| Cutoff 2 | 0.0558 | 0.0558 | 0.0558 | 0.0558 | 0.0558 | 0.0558 | 0.0439 | 0.0439 | 0.0439 |
| Sens 2 | 90% | 80% | 91% | 82% | 83% | 82% | 100% | 93% | 96% |
| Spec 2 | 14% | 16% | 15% | 14% | 16% | 15% | 10% | 10% | 13% |
| Cutoff 3 | 0.0558 | 0 | 0.0558 | 0.0439 | 0.0439 | 0 | 0.0439 | 0.0439 | 0.0439 |
| Sens 3 | 90% | 100% | 91% | 92% | 100% | 100% | 100% | 93% | 96% |
| Spec 3 | 14% | 0% | 15% | 10% | 10% | 0% | 10% | 10% | 13% |
| Cutoff 4 | 0.923 | 0.957 | 0.923 | 0.923 | 0.957 | 0.923 | 0.923 | 0.957 | 0.923 |
| Sens 4 | 25% | 40% | 31% | 43% | 35% | 43% | 52% | 21% | 57% |
| Spec 4 | 72% | 76% | 74% | 72% | 76% | 74% | 72% | 76% | 74% |
| Cutoff 5 | 1.05 | 1.37 | 0.957 | 1.05 | 1.37 | 0.957 | 1.05 | 1.37 | 0.957 |
| Sens 5 | 21% | 35% | 30% | 37% | 30% | 36% | 20% | 14% | 30% |
| Spec 5 | 80% | 80% | 81% | 80% | 80% | 81% | 80% | 80% | 81% |
| Cutoff 6 | 2.07 | 3.12 | 1.88 | 2.07 | 3.12 | 1.88 | 2.07 | 3.12 | 1.88 |
| Sens 6 | 20% | 20% | 28% | 27% | 17% | 29% | 12% | 7% | 22% |
| Spec 6 | 91% | 90% | 90% | 91% | 90% | 90% | 91% | 90% | 90% |
| OR Quart 2 | 0.91 | 0.81 | 1.4 | 0.59 | 0.48 | 0.59 | 0.81 | 1.3 | 0.56 |
| p Value | 0.82 | 0.74 | 0.50 | 0.24 | 0.24 | 0.30 | 0.75 | 0.70 | 0.44 |
| 95% CI of | 0.38 | 0.24 | 0.56 | 0.24 | 0.14 | 0.22 | 0.23 | 0.29 | 0.12 |
| OR Quart 2 | 2.2 | 2.8 | 3.3 | 1.4 | 1.6 | 1.6 | 2.9 | 6.2 | 2.5 |

-continued

| | | | | | | | | | |
|---|---|---|---|---|---|---|---|---|---|
| OR Quart 3 | 1.4 | 0.16 | 0.79 | 0.59 | 0.35 | 1.4 | 1.4 | 1.0 | 1.7 |
| p Value | 0.40 | 0.090 | 0.63 | 0.24 | 0.13 | 0.41 | 0.56 | 1.0 | 0.37 |
| 95% CI of | 0.62 | 0.019 | 0.31 | 0.24 | 0.091 | 0.60 | 0.44 | 0.20 | 0.52 |
| OR Quart 3 | 3.3 | 1.3 | 2.0 | 1.4 | 1.4 | 3.4 | 4.4 | 5.1 | 5.8 |
| OR Quart 4 | 1.2 | 1.3 | 1.6 | 1.6 | 0.99 | 2.0 | 1.0 | 1.3 | 1.4 |
| p Value | 0.67 | 0.59 | 0.30 | 0.26 | 0.98 | 0.11 | 1.0 | 0.70 | 0.56 |
| 95% CI of | 0.52 | 0.45 | 0.66 | 0.71 | 0.35 | 0.86 | 0.30 | 0.29 | 0.42 |
| OR Quart 4 | 2.8 | 4.1 | 3.7 | 3.5 | 2.8 | 4.7 | 3.4 | 6.2 | 4.9 |

Insulin-like growth factor-binding protein 5

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.0407 | 0.0682 | 0.0407 | 0.0682 | 0.0407 | 0.397 |
| Average | 0.473 | 0.722 | 0.473 | 0.778 | 0.473 | 0.991 |
| Stdev | 1.04 | 1.54 | 1.04 | 1.57 | 1.04 | 1.96 |
| p (t-test) | | 0.17 | | 0.099 | | 0.048 |
| Min | 0.0116 | 0.0116 | 0.0116 | 0.0116 | 0.0116 | 0.0393 |
| Max | 5.79 | 8.53 | 5.79 | 8.07 | 5.79 | 9.43 |
| n (Samp) | 155 | 61 | 155 | 60 | 155 | 25 |
| n (Patient) | 109 | 61 | 109 | 60 | 109 | 25 |
| sCr only | | | | | | |
| Median | 0.0682 | 0.0682 | 0.0682 | 0.0682 | 0.0682 | 0.403 |
| Average | 0.598 | 1.28 | 0.598 | 0.648 | 0.598 | 1.32 |
| Stdev | 1.31 | 2.31 | 1.31 | 1.19 | 1.31 | 1.56 |
| p (t-test) | | 0.034 | | 0.86 | | 0.047 |
| Min | 0.0116 | 0.0116 | 0.0116 | 0.0210 | 0.0116 | 0.0116 |
| Max | 9.43 | 10.0 | 9.43 | 4.35 | 9.43 | 4.63 |
| n (Samp) | 338 | 20 | 338 | 23 | 338 | 14 |
| n (Patient) | 184 | 20 | 184 | 23 | 184 | 14 |
| UO only | | | | | | |
| Median | 0.0407 | 0.0682 | 0.0407 | 0.0400 | 0.0407 | 0.397 |
| Average | 0.402 | 0.853 | 0.402 | 0.737 | 0.402 | 0.930 |
| Stdev | 0.925 | 1.66 | 0.925 | 1.54 | 0.925 | 2.00 |
| p (t-test) | | 0.014 | | 0.056 | | 0.035 |
| Min | 0.0116 | 0.0116 | 0.0116 | 0.0116 | 0.0116 | 0.0116 |
| Max | 5.79 | 8.53 | 5.79 | 8.07 | 5.79 | 9.43 |
| n (Samp) | 156 | 54 | 156 | 56 | 156 | 23 |
| n (Patient) | 100 | 54 | 100 | 56 | 100 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.55 | 0.55 | 0.60 | 0.54 | 0.56 | 0.51 | 0.74 | 0.71 | 0.67 |
| SE | 0.044 | 0.068 | 0.046 | 0.044 | 0.064 | 0.045 | 0.060 | 0.079 | 0.065 |
| p | 0.22 | 0.45 | 0.027 | 0.37 | 0.35 | 0.74 | 7.0E−5 | 0.0068 | 0.010 |
| nCohort 1 | 155 | 338 | 156 | 155 | 338 | 156 | 155 | 338 | 156 |
| nCohort 2 | 61 | 20 | 54 | 60 | 23 | 56 | 25 | 14 | 23 |
| Cutoff 1 | 0.0358 | 0.0400 | 0.0400 | 0.0255 | 0.0358 | 0.0116 | 0.0682 | 0.0838 | 0.0400 |
| Sens 1 | 70% | 70% | 72% | 78% | 83% | 88% | 80% | 79% | 74% |
| Spec 1 | 38% | 37% | 40% | 26% | 33% | 13% | 64% | 60% | 40% |
| Cutoff 2 | 0.0255 | 0.0116 | 0.0262 | 0.0116 | 0.0358 | 0.0116 | 0.0682 | 0.0544 | 0.0358 |
| Sens 2 | 87% | 80% | 91% | 92% | 83% | 88% | 80% | 86% | 87% |
| Spec 2 | 26% | 10% | 26% | 9% | 33% | 13% | 64% | 46% | 38% |
| Cutoff 3 | 0.0116 | 0 | 0.0262 | 0.0116 | 0.0255 | 0 | 0.0358 | 0.0358 | 0.0116 |
| Sens 3 | 92% | 100% | 91% | 92% | 91% | 100% | 100% | 93% | 96% |
| Spec 3 | 9% | 0% | 26% | 9% | 21% | 0% | 38% | 33% | 13% |
| Cutoff 4 | 0.0994 | 0.397 | 0.0994 | 0.0994 | 0.397 | 0.0994 | 0.0994 | 0.397 | 0.0994 |
| Sens 4 | 31% | 45% | 37% | 37% | 22% | 38% | 68% | 50% | 61% |
| Spec 4 | 72% | 79% | 75% | 72% | 79% | 75% | 72% | 79% | 75% |
| Cutoff 5 | 0.397 | 0.465 | 0.397 | 0.397 | 0.465 | 0.397 | 0.397 | 0.465 | 0.397 |
| Sens 5 | 26% | 45% | 30% | 23% | 22% | 23% | 32% | 43% | 26% |
| Spec 5 | 82% | 80% | 85% | 82% | 80% | 85% | 82% | 80% | 85% |
| Cutoff 6 | 1.75 | 1.99 | 1.58 | 1.75 | 1.99 | 1.58 | 1.75 | 1.99 | 1.58 |
| Sens 6 | 13% | 15% | 19% | 17% | 13% | 14% | 16% | 36% | 17% |
| Spec 6 | 91% | 90% | 90% | 91% | 90% | 90% | 91% | 90% | 90% |
| OR Quart 2 | 2.2 | 0.99 | 2.0 | 1.2 | 2.8 | 0.62 | >4.4 | 1.0 | 1.3 |
| p Value | 0.082 | 0.99 | 0.17 | 0.70 | 0.13 | 0.28 | <0.19 | 1.0 | 0.72 |
| 95% CI of | 0.90 | 0.28 | 0.75 | 0.50 | 0.73 | 0.26 | >0.47 | 0.062 | 0.28 |
| OR Quart 2 | 5.4 | 3.5 | 5.2 | 2.8 | 11 | 1.5 | na | 16 | 6.3 |
| OR Quart 3 | 2.0 | 0.19 | 2.4 | 1.4 | 2.1 | 0.27 | >15 | 5.2 | 0.98 |

-continued

|  | | | | | | | | | |
|---|---|---|---|---|---|---|---|---|---|
| p Value | 0.12 | 0.13 | 0.067 | 0.42 | 0.31 | 0.013 | <0.012 | 0.13 | 0.98 |
| 95% CI of | 0.83 | 0.022 | 0.94 | 0.60 | 0.50 | 0.097 | >1.8 | 0.60 | 0.19 |
| OR Quart 3 | 4.9 | 1.7 | 6.4 | 3.3 | 8.6 | 0.75 | na | 46 | 5.1 |
| OR Quart 4 | 1.9 | 1.9 | 2.4 | 1.2 | 2.0 | 1.4 | >13 | 7.5 | 5.6 |
| p Value | 0.18 | 0.28 | 0.075 | 0.70 | 0.32 | 0.42 | <0.017 | 0.062 | 0.012 |
| 95% CI of | 0.75 | 0.60 | 0.92 | 0.50 | 0.50 | 0.63 | >1.6 | 0.91 | 1.5 |
| OR Quart 4 | 4.6 | 5.8 | 6.2 | 2.8 | 8.5 | 3.1 | na | 62 | 21 |

Immunoglogulin G4

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 163 | 269 | 163 | 282 | 163 | 167 |
| Average | 430 | 558 | 430 | 525 | 430 | 487 |
| Stdev | 667 | 726 | 667 | 697 | 667 | 702 |
| p (t-test) |  | 0.069 |  | 0.16 |  | 0.58 |
| Min | 0.619 | 1.73 | 0.619 | 2.63 | 0.619 | 4.92 |
| Max | 2400 | 2400 | 2400 | 2400 | 2400 | 2400 |
| n (Samp) | 461 | 119 | 461 | 126 | 461 | 47 |
| n (Patient) | 222 | 119 | 222 | 126 | 222 | 47 |
| sCr only | | | | | | |
| Median | 210 | 293 | 210 | 358 | 210 | 291 |
| Average | 479 | 521 | 479 | 589 | 479 | 542 |
| Stdev | 689 | 736 | 689 | 742 | 689 | 675 |
| p (t-test) |  | 0.71 |  | 0.29 |  | 0.65 |
| Min | 0.00642 | 28.3 | 0.00642 | 5.21 | 0.00642 | 8.44 |
| Max | 2400 | 2400 | 2400 | 2400 | 2400 | 2400 |
| n (Samp) | 1011 | 40 | 1011 | 46 | 1011 | 26 |
| n (Patient) | 373 | 40 | 373 | 46 | 373 | 26 |
| UO only | | | | | | |
| Median | 203 | 309 | 203 | 307 | 203 | 172 |
| Average | 482 | 603 | 482 | 552 | 482 | 497 |
| Stdev | 702 | 741 | 702 | 708 | 702 | 707 |
| p (t-test) |  | 0.12 |  | 0.35 |  | 0.89 |
| Min | 0.619 | 1.73 | 0.619 | 2.63 | 0.619 | 4.92 |
| Max | 2400 | 2400 | 2400 | 2400 | 2400 | 2400 |
| n (Samp) | 433 | 107 | 433 | 115 | 433 | 44 |
| n (Patient) | 171 | 107 | 171 | 115 | 171 | 44 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.60 | 0.56 | 0.58 | 0.58 | 0.56 | 0.56 | 0.53 | 0.55 | 0.50 |
| SE | 0.030 | 0.048 | 0.032 | 0.029 | 0.045 | 0.031 | 0.045 | 0.059 | 0.046 |
| p | 0.0012 | 0.25 | 0.0089 | 0.0055 | 0.20 | 0.040 | 0.49 | 0.37 | 0.94 |
| nCohort 1 | 461 | 1011 | 433 | 461 | 1011 | 433 | 461 | 1011 | 433 |
| nCohort 2 | 119 | 40 | 107 | 126 | 46 | 115 | 47 | 26 | 44 |
| Cutoff 1 | 146 | 146 | 181 | 113 | 107 | 129 | 80.8 | 120 | 78.5 |
| Sens 1 | 71% | 70% | 70% | 71% | 72% | 70% | 70% | 73% | 70% |
| Spec 1 | 47% | 40% | 49% | 42% | 33% | 38% | 34% | 36% | 30% |
| Cutoff 2 | 75.7 | 108 | 93.8 | 80.8 | 55.4 | 98.1 | 55.4 | 53.9 | 55.4 |
| Sens 2 | 81% | 80% | 80% | 80% | 80% | 80% | 81% | 81% | 82% |
| Spec 2 | 34% | 33% | 32% | 34% | 23% | 32% | 29% | 23% | 25% |
| Cutoff 3 | 28.9 | 48.3 | 27.6 | 21.5 | 27.6 | 21.3 | 20.5 | 11.3 | 26.1 |
| Sens 3 | 91% | 90% | 91% | 90% | 91% | 90% | 91% | 92% | 91% |
| Spec 3 | 15% | 21% | 12% | 12% | 14% | 9% | 11% | 7% | 11% |
| Cutoff 4 | 356 | 402 | 402 | 356 | 402 | 402 | 356 | 402 | 402 |
| Sens 4 | 34% | 22% | 38% | 41% | 46% | 37% | 30% | 42% | 30% |
| Spec 4 | 70% | 70% | 70% | 70% | 70% | 70% | 70% | 70% | 70% |
| Cutoff 5 | 523 | 597 | 587 | 523 | 597 | 587 | 523 | 597 | 587 |
| Sens 5 | 26% | 18% | 26% | 27% | 28% | 26% | 26% | 27% | 23% |
| Spec 5 | 80% | 80% | 80% | 80% | 80% | 80% | 80% | 80% | 80% |
| Cutoff 6 | 1470 | 1640 | 1910 | 1470 | 1640 | 1910 | 1470 | 1640 | 1910 |
| Sens 6 | 13% | 12% | 11% | 12% | 13% | 10% | 13% | 8% | 9% |
| Spec 6 | 90% | 90% | 90% | 90% | 90% | 90% | 90% | 90% | 90% |
| OR Quart 2 | 1.2 | 0.62 | 1.5 | 1.4 | 0.72 | 1.6 | 1.5 | 0.66 | 1.6 |
| p Value | 0.61 | 0.40 | 0.24 | 0.35 | 0.49 | 0.15 | 0.37 | 0.53 | 0.28 |
| 95% CI of | 0.61 | 0.20 | 0.77 | 0.72 | 0.28 | 0.84 | 0.62 | 0.18 | 0.68 |
| OR Quart 2 | 2.4 | 1.9 | 2.9 | 2.6 | 1.8 | 3.0 | 3.6 | 2.4 | 3.9 |
| OR Quart 3 | 3.3 | 2.3 | 2.4 | 2.4 | 0.91 | 2.1 | 1.4 | 1.0 | 1.1 |
| p Value | 1.2E-4 | 0.051 | 0.0064 | 0.0033 | 0.82 | 0.023 | 0.50 | 1.0 | 0.81 |

-continued

| | | | | | | | | | |
|---|---|---|---|---|---|---|---|---|---|
| 95% CI of OR Quart 3 | 1.8 6.0 | 1.00 5.5 | 1.3 4.6 | 1.3 4.4 | 0.38 2.2 | 1.1 3.8 | 0.56 3.4 | 0.32 3.1 | 0.44 2.9 |
| OR Quart 4 | 2.2 | 1.1 | 2.1 | 2.3 | 1.6 | 2.1 | 1.5 | 1.7 | 1.2 |
| p Value | 0.016 | 0.81 | 0.028 | 0.0070 | 0.25 | 0.023 | 0.37 | 0.32 | 0.65 |
| 95% CI of OR Quart 4 | 1.2 4.0 | 0.43 3.0 | 1.1 4.0 | 1.3 4.1 | 0.72 3.4 | 1.1 3.8 | 0.62 3.6 | 0.60 4.7 | 0.49 3.1 |

| | Interleukin-21 | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 9.57 | 4.21 | 9.57 | 4.50 | 9.57 | 5.09 |
| Average | 11.9 | 7.35 | 11.9 | 8.30 | 11.9 | 8.54 |
| Stdev | 11.4 | 8.68 | 11.4 | 10.1 | 11.4 | 10.4 |
| p (t-test) | | 4.2E−5 | | 9.9E−4 | | 0.049 |
| Min | 0.00404 | 0.00411 | 0.00404 | 0.0122 | 0.00404 | 0.0210 |
| Max | 87.9 | 56.2 | 87.9 | 59.4 | 87.9 | 49.5 |
| n (Samp) | 463 | 120 | 463 | 130 | 463 | 47 |
| n (Patient) | 223 | 120 | 223 | 130 | 223 | 47 |
| sCr only | | | | | | |
| Median | 7.83 | 7.12 | 7.83 | 5.28 | 7.83 | 3.77 |
| Average | 10.7 | 10.9 | 10.7 | 8.66 | 10.7 | 5.91 |
| Stdev | 11.1 | 12.0 | 11.1 | 8.54 | 11.1 | 6.18 |
| p (t-test) | | 0.89 | | 0.23 | | 0.030 |
| Min | 0.00404 | 0.0177 | 0.00404 | 0.0122 | 0.00404 | 0.0210 |
| Max | 87.9 | 56.2 | 87.9 | 41.5 | 87.9 | 20.6 |
| n (Samp) | 1019 | 40 | 1019 | 46 | 1019 | 26 |
| n (Patient) | 375 | 40 | 375 | 46 | 375 | 26 |
| UO only | | | | | | |
| Median | 9.33 | 3.57 | 9.33 | 4.53 | 9.33 | 5.20 |
| Average | 11.6 | 6.81 | 11.6 | 8.06 | 11.6 | 8.62 |
| Stdev | 11.1 | 7.25 | 11.1 | 9.91 | 11.1 | 10.6 |
| p (t-test) | | 2.0E−5 | | 0.0016 | | 0.085 |
| Min | 0.00404 | 0.00404 | 0.00404 | 0.0122 | 0.00404 | 0.0177 |
| Max | 87.9 | 30.5 | 87.9 | 59.4 | 87.9 | 49.5 |
| n (Samp) | 435 | 108 | 435 | 119 | 435 | 44 |
| n (Patient) | 173 | 108 | 173 | 119 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.36 | 0.50 | 0.36 | 0.38 | 0.47 | 0.39 | 0.38 | 0.37 | 0.39 |
| SE | 0.030 | 0.047 | 0.031 | 0.029 | 0.044 | 0.030 | 0.045 | 0.059 | 0.047 |
| p | 2.4E−6 | 0.95 | 5.5E−6 | 6.4E−5 | 0.47 | 1.4E−4 | 0.010 | 0.027 | 0.024 |
| nCohort 1 | 463 | 1019 | 435 | 463 | 1019 | 435 | 463 | 1019 | 435 |
| nCohort 2 | 120 | 40 | 108 | 130 | 46 | 119 | 47 | 26 | 44 |
| Cutoff 1 | 1.82 | 3.10 | 1.62 | 1.99 | 3.10 | 1.76 | 1.29 | 0.728 | 1.57 |
| Sens 1 | 71% | 70% | 70% | 70% | 72% | 71% | 70% | 73% | 70% |
| Spec 1 | 17% | 32% | 17% | 18% | 32% | 17% | 13% | 14% | 17% |
| Cutoff 2 | 1.05 | 2.19 | 1.03 | 1.37 | 2.16 | 1.13 | 0.689 | 0.418 | 0.362 |
| Sens 2 | 80% | 80% | 81% | 80% | 80% | 81% | 81% | 81% | 82% |
| Spec 2 | 11% | 24% | 13% | 13% | 24% | 13% | 9% | 12% | 9% |
| Cutoff 3 | 0.0528 | 0.313 | 0.0528 | 0.296 | 0.968 | 0.227 | 0.136 | 0.0350 | 0.136 |
| Sens 3 | 90% | 90% | 91% | 90% | 91% | 91% | 91% | 92% | 91% |
| Spec 3 | 4% | 11% | 6% | 7% | 15% | 9% | 6% | 5% | 8% |
| Cutoff 4 | 15.8 | 13.5 | 14.9 | 15.8 | 13.5 | 14.9 | 15.8 | 13.5 | 14.9 |
| Sens 4 | 12% | 28% | 13% | 14% | 26% | 14% | 17% | 15% | 18% |
| Spec 4 | 70% | 70% | 70% | 70% | 70% | 70% | 70% | 70% | 70% |
| Cutoff 5 | 19.2 | 17.9 | 19.2 | 19.2 | 17.9 | 19.2 | 19.2 | 17.9 | 19.2 |
| Sens 5 | 11% | 22% | 9% | 10% | 17% | 9% | 13% | 4% | 14% |
| Spec 5 | 80% | 80% | 80% | 80% | 80% | 80% | 80% | 80% | 80% |
| Cutoff 6 | 26.2 | 25.1 | 25.4 | 26.2 | 25.1 | 25.4 | 26.2 | 25.1 | 25.4 |
| Sens 6 | 3% | 12% | 2% | 5% | 4% | 5% | 6% | 0% | 7% |
| Spec 6 | 90% | 90% | 90% | 90% | 90% | 90% | 90% | 90% | 90% |
| OR Quart 2 | 1.8 | 0.79 | 2.1 | 1.6 | 0.72 | 2.0 | 1.5 | 3.1 | 0.87 |
| p Value | 0.12 | 0.63 | 0.050 | 0.14 | 0.49 | 0.044 | 0.44 | 0.17 | 0.79 |
| 95% CI of OR Quart 2 | 0.87 3.6 | 0.31 2.0 | 1.0 4.4 | 0.85 3.1 | 0.29 1.8 | 1.0 4.0 | 0.54 4.0 | 0.61 15 | 0.30 2.5 |
| OR Quart 3 | 3.2 | 1.3 | 2.9 | 2.7 | 1.6 | 2.6 | 1.8 | 3.1 | 1.6 |
| p Value | 6.1E−4 | 0.52 | 0.0034 | 0.0015 | 0.24 | 0.0052 | 0.24 | 0.17 | 0.35 |
| 95% CI of | 1.6 | 0.57 | 1.4 | 1.5 | 0.73 | 1.3 | 0.68 | 0.61 | 0.61 |

-continued

| | | | | | | | | | |
|---|---|---|---|---|---|---|---|---|---|
| OR Quart 3 | 6.2 | 3.1 | 6.0 | 5.0 | 3.5 | 5.0 | 4.7 | 15 | 4.0 |
| OR Quart 4 | 4.4 | 0.90 | 4.8 | 3.2 | 0.91 | 3.9 | 2.9 | 6.3 | 2.3 |
| p Value | 9.1E−6 | 0.82 | 8.8E−6 | 1.8E−4 | 0.83 | 3.9E−5 | 0.024 | 0.017 | 0.060 |
| 95% CI of | 2.3 | 0.36 | 2.4 | 1.7 | 0.38 | 2.0 | 1.1 | 1.4 | 0.97 |
| OR Quart 4 | 8.4 | 2.3 | 9.7 | 5.8 | 2.2 | 7.4 | 7.1 | 28 | 5.6 |

Interleukin-23

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 392 | 156 | 392 | 186 | 392 | 127 |
| Average | 625 | 311 | 625 | 330 | 625 | 376 |
| Stdev | 802 | 435 | 802 | 412 | 802 | 537 |
| p (t-test) | | 4.1E−5 | | 5.8E−5 | | 0.038 |
| Min | 0.491 | 0.564 | 0.491 | 0.491 | 0.491 | 0.552 |
| Max | 8520 | 2340 | 8520 | 1760 | 8520 | 2000 |
| n (Samp) | 463 | 120 | 463 | 130 | 463 | 47 |
| n (Patient) | 223 | 120 | 223 | 130 | 223 | 47 |
| sCr only | | | | | | |
| Median | 272 | 185 | 272 | 167 | 272 | 145 |
| Average | 518 | 343 | 518 | 307 | 518 | 333 |
| Stdev | 706 | 468 | 706 | 375 | 706 | 454 |
| p (t-test) | | 0.12 | | 0.044 | | 0.18 |
| Min | 0.491 | 0.785 | 0.491 | 0.552 | 0.491 | 0.491 |
| Max | 8520 | 2000 | 8520 | 1370 | 8520 | 1820 |
| n (Samp) | 1019 | 40 | 1019 | 46 | 1019 | 26 |
| n (Patient) | 375 | 40 | 375 | 46 | 375 | 26 |
| UO only | | | | | | |
| Median | 385 | 138 | 385 | 150 | 385 | 135 |
| Average | 634 | 287 | 634 | 314 | 634 | 358 |
| Stdev | 804 | 401 | 804 | 419 | 804 | 500 |
| p (t-test) | | 1.6E−5 | | 3.3E−5 | | 0.026 |
| Min | 0.491 | 0.564 | 0.491 | 0.491 | 0.491 | 0.552 |
| Max | 8520 | 2340 | 8520 | 1760 | 8520 | 2000 |
| n (Samp) | 435 | 108 | 435 | 119 | 435 | 44 |
| n (Patient) | 173 | 108 | 173 | 119 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.38 | 0.47 | 0.35 | 0.39 | 0.43 | 0.36 | 0.39 | 0.43 | 0.37 |
| SE | 0.030 | 0.047 | 0.031 | 0.029 | 0.045 | 0.030 | 0.045 | 0.059 | 0.047 |
| p | 9.5E−5 | 0.50 | 2.2E−6 | 1.3E−4 | 0.14 | 6.6E−6 | 0.013 | 0.21 | 0.0044 |
| nCohort 1 | 463 | 1019 | 435 | 463 | 1019 | 435 | 463 | 1019 | 435 |
| nCohort 2 | 120 | 40 | 108 | 130 | 46 | 119 | 47 | 26 | 44 |
| Cutoff 1 | 38.3 | 66.6 | 1.31 | 3.48 | 1.41 | 3.02 | 1.41 | 1.41 | 1.11 |
| Sens 1 | 70% | 70% | 72% | 70% | 74% | 71% | 72% | 73% | 70% |
| Spec 1 | 25% | 32% | 19% | 21% | 25% | 20% | 20% | 25% | 17% |
| Cutoff 2 | 1.09 | 21.4 | 1.05 | 1.05 | 1.08 | 1.01 | 0.754 | 1.01 | 0.723 |
| Sens 2 | 81% | 80% | 81% | 81% | 83% | 81% | 85% | 81% | 82% |
| Spec 2 | 17% | 28% | 14% | 15% | 20% | 12% | 9% | 18% | 7% |
| Cutoff 3 | 0.844 | 1.09 | 0.723 | 0.723 | 0.754 | 0.720 | 0.720 | 0.682 | 0.643 |
| Sens 3 | 91% | 90% | 92% | 90% | 93% | 92% | 91% | 92% | 91% |
| Spec 3 | 11% | 21% | 7% | 9% | 11% | 7% | 8% | 6% | 3% |
| Cutoff 4 | 735 | 608 | 756 | 735 | 608 | 756 | 735 | 608 | 756 |
| Sens 4 | 11% | 20% | 9% | 14% | 17% | 13% | 19% | 23% | 16% |
| Spec 4 | 70% | 70% | 70% | 70% | 70% | 70% | 70% | 70% | 70% |
| Cutoff 5 | 1120 | 894 | 1020 | 1120 | 894 | 1020 | 1120 | 894 | 1020 |
| Sens 5 | 6% | 10% | 6% | 5% | 11% | 9% | 11% | 8% | 9% |
| Spec 5 | 80% | 80% | 80% | 80% | 80% | 80% | 80% | 80% | 80% |
| Cutoff 6 | 1580 | 1400 | 1630 | 1580 | 1400 | 1630 | 1580 | 1400 | 1630 |
| Sens 6 | 2% | 5% | 1% | 2% | 0% | 3% | 6% | 4% | 5% |
| Spec 6 | 90% | 90% | 90% | 90% | 90% | 90% | 90% | 90% | 90% |
| OR Quart 2 | 2.2 | 2.0 | 2.3 | 1.8 | 1.8 | 1.5 | 1.4 | 0.66 | 2.3 |
| p Value | 0.036 | 0.20 | 0.040 | 0.079 | 0.25 | 0.28 | 0.47 | 0.53 | 0.10 |
| 95% CI of | 1.1 | 0.69 | 1.0 | 0.94 | 0.68 | 0.73 | 0.55 | 0.19 | 0.85 |
| OR Quart 2 | 4.6 | 6.0 | 5.1 | 3.4 | 4.5 | 3.0 | 3.7 | 2.4 | 6.3 |
| OR Quart 3 | 5.6 | 4.0 | 5.1 | 2.8 | 2.2 | 3.7 | 1.3 | 1.5 | 1.0 |
| p Value | 6.9E−7 | 0.0065 | 1.9E−5 | 9.9E−4 | 0.087 | 7.0E−5 | 0.63 | 0.43 | 1.0 |
| 95% CI of | 2.8 | 1.5 | 2.4 | 1.5 | 0.89 | 1.9 | 0.48 | 0.53 | 0.31 |
| OR Quart 3 | 11 | 11 | 11 | 5.1 | 5.5 | 7.1 | 3.3 | 4.3 | 3.2 |

-continued

| | | | | | | | | | |
|---|---|---|---|---|---|---|---|---|---|
| OR Quart 4 | 3.6 | 1.2 | 4.9 | 2.9 | 1.8 | 3.4 | 2.5 | 1.2 | 3.6 |
| p Value | 4.0E−4 | 0.76 | 2.7E−5 | 6.5E−4 | 0.25 | 2.4E−4 | 0.042 | 0.77 | 0.0085 |
| 95% CI of | 1.8 | 0.36 | 2.3 | 1.6 | 0.68 | 1.8 | 1.0 | 0.39 | 1.4 |
| OR Quart 4 | 7.2 | 4.0 | 10 | 5.3 | 4.5 | 6.5 | 5.9 | 3.5 | 9.4 |

Interleukin-28A

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 20.8 | 11.8 | 20.8 | 10.4 | 20.8 | 12.4 |
| Average | 36.5 | 24.4 | 36.5 | 24.9 | 36.5 | 26.3 |
| Stdev | 43.7 | 31.6 | 43.7 | 34.6 | 43.7 | 39.8 |
| p (t-test) | | 0.0048 | | 0.0055 | | 0.12 |
| Min | 0.0254 | 0.0254 | 0.0254 | 0.0254 | 0.0254 | 0.0254 |
| Max | 228 | 168 | 228 | 172 | 228 | 186 |
| n (Samp) | 463 | 120 | 463 | 130 | 463 | 47 |
| n (Patient) | 223 | 120 | 223 | 130 | 223 | 47 |
| sCr only | | | | | | |
| Median | 16.1 | 10.1 | 16.1 | 10.4 | 16.1 | 7.94 |
| Average | 33.0 | 26.8 | 33.0 | 21.8 | 33.0 | 20.9 |
| Stdev | 41.3 | 37.0 | 41.3 | 30.9 | 41.3 | 29.6 |
| p (t-test) | | 0.35 | | 0.071 | | 0.14 |
| Min | 0.0254 | 0.0777 | 0.0254 | 0.0254 | 0.0254 | 0.0495 |
| Max | 235 | 168 | 235 | 131 | 235 | 89.5 |
| n (Samp) | 1019 | 40 | 1019 | 46 | 1019 | 26 |
| n (Patient) | 375 | 40 | 375 | 46 | 375 | 26 |
| UO only | | | | | | |
| Median | 23.1 | 11.8 | 23.1 | 12.0 | 23.1 | 12.3 |
| Average | 37.9 | 24.0 | 37.9 | 25.3 | 37.9 | 25.9 |
| Stdev | 44.6 | 29.8 | 44.6 | 34.5 | 44.6 | 40.1 |
| p (t-test) | | 0.0022 | | 0.0046 | | 0.089 |
| Min | 0.0254 | 0.0254 | 0.0254 | 0.0254 | 0.0254 | 0.0254 |
| Max | 228 | 127 | 228 | 172 | 228 | 186 |
| n (Samp) | 435 | 108 | 435 | 119 | 435 | 44 |
| n (Patient) | 173 | 108 | 173 | 119 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.45 | 0.49 | 0.43 | 0.44 | 0.45 | 0.43 | 0.43 | 0.42 | 0.42 |
| SE | 0.030 | 0.047 | 0.032 | 0.029 | 0.045 | 0.030 | 0.045 | 0.059 | 0.047 |
| p | 0.074 | 0.87 | 0.025 | 0.036 | 0.28 | 0.018 | 0.10 | 0.18 | 0.087 |
| nCohort 1 | 463 | 1019 | 435 | 463 | 1019 | 435 | 463 | 1019 | 435 |
| nCohort 2 | 120 | 40 | 108 | 130 | 46 | 119 | 47 | 26 | 44 |
| Cutoff 1 | 0.246 | 0.246 | 0.243 | 0.198 | 0.216 | 0.198 | 0.189 | 0.176 | 0.198 |
| Sens 1 | 72% | 70% | 73% | 72% | 72% | 71% | 70% | 73% | 70% |
| Spec 1 | 29% | 32% | 25% | 25% | 30% | 23% | 24% | 23% | 23% |
| Cutoff 2 | 0.182 | 0.194 | 0.176 | 0.176 | 0.184 | 0.155 | 0.134 | 0.0996 | 0.142 |
| Sens 2 | 81% | 80% | 82% | 80% | 80% | 81% | 81% | 81% | 82% |
| Spec 2 | 22% | 26% | 19% | 21% | 24% | 19% | 18% | 17% | 17% |
| Cutoff 3 | 0.0996 | 0.149 | 0.0775 | 0.0854 | 0.0854 | 0.0854 | 0.0775 | 0.0775 | 0.0784 |
| Sens 3 | 91% | 95% | 91% | 93% | 93% | 91% | 91% | 92% | 93% |
| Spec 3 | 16% | 20% | 7% | 12% | 12% | 11% | 7% | 6% | 10% |
| Cutoff 4 | 51.6 | 45.8 | 53.1 | 51.6 | 45.8 | 53.1 | 51.6 | 45.8 | 53.1 |
| Sens 4 | 18% | 20% | 16% | 17% | 17% | 16% | 17% | 15% | 16% |
| Spec 4 | 70% | 70% | 70% | 70% | 70% | 70% | 70% | 70% | 70% |
| Cutoff 5 | 68.1 | 62.2 | 68.3 | 68.1 | 62.2 | 68.3 | 68.1 | 62.2 | 68.3 |
| Sens 5 | 11% | 15% | 10% | 11% | 9% | 11% | 15% | 15% | 14% |
| Spec 5 | 80% | 80% | 80% | 80% | 80% | 80% | 80% | 80% | 80% |
| Cutoff 6 | 98.2 | 90.1 | 96.2 | 98.2 | 90.1 | 96.2 | 98.2 | 90.1 | 96.2 |
| Sens 6 | 3% | 8% | 4% | 5% | 7% | 5% | 4% | 0% | 7% |
| Spec 6 | 90% | 90% | 90% | 90% | 90% | 90% | 90% | 90% | 90% |
| OR Quart 2 | 1.6 | 1.6 | 1.9 | 1.7 | 2.7 | 2.1 | 1.6 | 1.5 | 1.2 |
| p Value | 0.12 | 0.34 | 0.070 | 0.092 | 0.063 | 0.026 | 0.32 | 0.52 | 0.79 |
| 95% CI of | 0.88 | 0.61 | 0.95 | 0.92 | 0.95 | 1.1 | 0.61 | 0.42 | 0.40 |
| OR Quart 2 | 3.0 | 4.2 | 3.6 | 3.1 | 7.7 | 4.0 | 4.4 | 5.4 | 3.3 |
| OR Quart 3 | 2.6 | 2.1 | 2.8 | 2.6 | 3.6 | 2.5 | 2.0 | 1.5 | 2.1 |
| p Value | 0.0013 | 0.13 | 0.0017 | 0.0014 | 0.014 | 0.0044 | 0.17 | 0.52 | 0.12 |
| 95% CI of | 1.5 | 0.82 | 1.5 | 1.4 | 1.3 | 1.3 | 0.75 | 0.42 | 0.83 |
| OR Quart 3 | 4.7 | 5.2 | 5.3 | 4.6 | 9.8 | 4.7 | 5.1 | 5.4 | 5.5 |
| OR Quart 4 | 1.4 | 1.2 | 2.0 | 1.7 | 2.3 | 2.4 | 2.5 | 2.6 | 2.3 |

-continued

| | | | | | | | | | |
|---|---|---|---|---|---|---|---|---|---|
| p Value | 0.26 | 0.79 | 0.048 | 0.069 | 0.14 | 0.0060 | 0.053 | 0.11 | 0.077 |
| 95% CI of | 0.77 | 0.41 | 1.0 | 0.96 | 0.77 | 1.3 | 0.99 | 0.80 | 0.91 |
| OR Quart 4 | 2.7 | 3.2 | 3.8 | 3.2 | 6.6 | 4.6 | 6.3 | 8.3 | 5.9 |

Interleukin-33

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 51.7 | 28.7 | 51.7 | 30.6 | 51.7 | 28.5 |
| Average | 66.3 | 36.4 | 66.3 | 41.3 | 66.3 | 35.3 |
| Stdev | 72.8 | 34.8 | 72.8 | 37.4 | 72.8 | 38.8 |
| p (t-test) | | 1.4E−5 | | 1.7E−4 | | 0.0041 |
| Min | 0.0232 | 0.0372 | 0.0232 | 0.0232 | 0.0232 | 0.0232 |
| Max | 958 | 148 | 958 | 162 | 958 | 155 |
| n (Samp) | 463 | 120 | 463 | 130 | 463 | 47 |
| n (Patient) | 223 | 120 | 223 | 130 | 223 | 47 |
| sCr only | | | | | | |
| Median | 42.7 | 32.7 | 42.7 | 31.8 | 42.7 | 18.8 |
| Average | 58.1 | 38.1 | 58.1 | 38.9 | 58.1 | 33.3 |
| Stdev | 62.9 | 30.5 | 62.9 | 34.0 | 62.9 | 33.5 |
| p (t-test) | | 0.046 | | 0.040 | | 0.046 |
| Min | 0.0232 | 0.0743 | 0.0232 | 0.0232 | 0.0232 | 0.0591 |
| Max | 958 | 138 | 958 | 133 | 958 | 122 |
| n (Samp) | 1019 | 40 | 1019 | 46 | 1019 | 26 |
| n (Patient) | 375 | 40 | 375 | 46 | 375 | 26 |
| UO only | | | | | | |
| Median | 50.4 | 23.2 | 50.4 | 28.8 | 50.4 | 33.1 |
| Average | 67.0 | 35.9 | 67.0 | 39.9 | 67.0 | 35.2 |
| Stdev | 74.1 | 38.6 | 74.1 | 38.5 | 74.1 | 37.5 |
| p (t-test) | | 2.9E−5 | | 1.3E−4 | | 0.0051 |
| Min | 0.0232 | 0.0372 | 0.0232 | 0.0232 | 0.0232 | 0.0232 |
| Max | 958 | 203 | 958 | 162 | 958 | 155 |
| n (Samp) | 435 | 108 | 435 | 119 | 435 | 44 |
| n (Patient) | 173 | 108 | 173 | 119 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.36 | 0.43 | 0.35 | 0.39 | 0.42 | 0.38 | 0.35 | 0.38 | 0.35 |
| SE | 0.030 | 0.048 | 0.031 | 0.029 | 0.045 | 0.030 | 0.045 | 0.059 | 0.047 |
| p | 4.7E−6 | 0.13 | 8.1E−7 | 2.2E−4 | 0.087 | 4.4E−5 | 7.1E−4 | 0.044 | 9.5E−4 |
| nCohort 1 | 463 | 1019 | 435 | 463 | 1019 | 435 | 463 | 1019 | 435 |
| nCohort 2 | 120 | 40 | 108 | 130 | 46 | 119 | 47 | 26 | 44 |
| Cutoff 1 | 12.9 | 16.3 | 9.92 | 16.8 | 17.0 | 15.3 | 4.46 | 6.25 | 6.20 |
| Sens 1 | 70% | 70% | 71% | 70% | 74% | 71% | 70% | 73% | 70% |
| Spec 1 | 21% | 27% | 18% | 24% | 28% | 21% | 14% | 18% | 15% |
| Cutoff 2 | 7.93 | 12.1 | 2.92 | 10.7 | 6.57 | 6.58 | 0.172 | 2.84 | 0.172 |
| Sens 2 | 80% | 80% | 81% | 80% | 80% | 81% | 81% | 81% | 82% |
| Spec 2 | 17% | 23% | 14% | 20% | 18% | 16% | 13% | 14% | 12% |
| Cutoff 3 | 0.0837 | 7.09 | 0.0731 | 0.0768 | 0.0768 | 0.0749 | 0.0591 | 0.0631 | 0.0686 |
| Sens 3 | 90% | 90% | 91% | 90% | 91% | 92% | 91% | 96% | 91% |
| Spec 3 | 11% | 19% | 6% | 9% | 10% | 8% | 5% | 6% | 5% |
| Cutoff 4 | 84.4 | 74.8 | 85.3 | 84.4 | 74.8 | 85.3 | 84.4 | 74.8 | 85.3 |
| Sens 4 | 10% | 15% | 11% | 14% | 20% | 12% | 11% | 12% | 9% |
| Spec 4 | 70% | 70% | 70% | 70% | 70% | 70% | 70% | 70% | 70% |
| Cutoff 5 | 109 | 96.1 | 109 | 109 | 96.1 | 109 | 109 | 96.1 | 109 |
| Sens 5 | 4% | 2% | 5% | 8% | 7% | 9% | 6% | 8% | 7% |
| Spec 5 | 80% | 80% | 80% | 80% | 80% | 80% | 80% | 80% | 80% |
| Cutoff 6 | 145 | 130 | 148 | 145 | 130 | 148 | 145 | 130 | 148 |
| Sens 6 | 1% | 2% | 1% | 1% | 2% | 1% | 2% | 0% | 2% |
| Spec 6 | 90% | 90% | 90% | 90% | 90% | 90% | 90% | 90% | 90% |
| OR Quart 2 | 2.5 | 4.1 | 2.3 | 1.7 | 1.1 | 2.0 | 1.7 | 2.4 | 1.5 |
| p Value | 0.012 | 0.029 | 0.031 | 0.11 | 0.80 | 0.057 | 0.39 | 0.21 | 0.52 |
| 95% CI of | 1.2 | 1.2 | 1.1 | 0.89 | 0.43 | 0.98 | 0.53 | 0.61 | 0.42 |
| OR Quart 2 | 5.2 | 15 | 5.0 | 3.2 | 3.0 | 4.0 | 5.2 | 9.3 | 5.6 |
| OR Quart 3 | 3.9 | 4.9 | 3.2 | 3.2 | 2.2 | 3.6 | 2.8 | 2.4 | 4.1 |
| p Value | 1.2E−4 | 0.014 | 0.0019 | 1.8E−4 | 0.070 | 1.5E−4 | 0.059 | 0.21 | 0.014 |
| 95% CI of | 2.0 | 1.4 | 1.5 | 1.7 | 0.94 | 1.9 | 0.96 | 0.61 | 1.3 |
| OR Quart 3 | 7.9 | 17 | 6.7 | 5.8 | 5.2 | 7.0 | 8.0 | 9.3 | 13 |
| OR Quart 4 | 4.7 | 3.8 | 5.5 | 2.6 | 1.5 | 3.6 | 4.9 | 3.1 | 5.5 |
| p Value | 1.1E−5 | 0.042 | 2.9E−6 | 0.0022 | 0.36 | 1.3E−4 | 0.0021 | 0.094 | 0.0026 |

-continued

| | | | | | | | | | |
|---|---|---|---|---|---|---|---|---|---|
| 95% CI of | 2.4 | 1.0 | 2.7 | 1.4 | 0.61 | 1.9 | 1.8 | 0.83 | 1.8 |
| OR Quart 4 | 9.4 | 14 | 11 | 4.8 | 3.8 | 7.1 | 13 | 12 | 17 |

Vascular endothelial growth factor receptor 2

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 393 | 825 | 393 | 599 | 393 | 370 |
| Average | 584 | 1020 | 584 | 794 | 584 | 576 |
| Stdev | 622 | 838 | 622 | 701 | 622 | 601 |
| p (t-test) | | 1.3E-6 | | 0.0092 | | 0.95 |
| Min | 0.218 | 0.218 | 0.218 | 0.386 | 0.218 | 1.13 |
| Max | 4170 | 3930 | 4170 | 4210 | 4170 | 2260 |
| n (Samp) | 212 | 87 | 212 | 93 | 212 | 31 |
| n (Patient) | 124 | 87 | 124 | 93 | 124 | 31 |
| sCr only | | | | | | |
| Median | 647 | 617 | 647 | 587 | 647 | 448 |
| Average | 807 | 876 | 807 | 747 | 807 | 884 |
| Stdev | 796 | 985 | 796 | 809 | 796 | 970 |
| p (t-test) | | 0.66 | | 0.68 | | 0.69 |
| Min | 0.218 | 0.218 | 0.218 | 0.386 | 0.218 | 1.13 |
| Max | 5940 | 3930 | 5940 | 4210 | 5940 | 2720 |
| n (Samp) | 504 | 28 | 504 | 32 | 504 | 18 |
| n (Patient) | 236 | 28 | 236 | 32 | 236 | 18 |
| UO only | | | | | | |
| Median | 407 | 916 | 407 | 665 | 407 | 455 |
| Average | 612 | 1160 | 612 | 897 | 612 | 639 |
| Stdev | 669 | 1080 | 669 | 987 | 669 | 684 |
| p (t-test) | | 3.3E-7 | | 0.0042 | | 0.84 |
| Min | 0.218 | 0.218 | 0.218 | 0.616 | 0.218 | 0.218 |
| Max | 4210 | 7140 | 4210 | 7060 | 4210 | 2820 |
| n (Samp) | 224 | 77 | 224 | 83 | 224 | 30 |
| n (Patient) | 120 | 77 | 120 | 83 | 120 | 30 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.67 | 0.49 | 0.70 | 0.61 | 0.48 | 0.62 | 0.50 | 0.48 | 0.51 |
| SE | 0.036 | 0.056 | 0.037 | 0.036 | 0.053 | 0.037 | 0.056 | 0.070 | 0.057 |
| p | 2.3E-6 | 0.89 | 6.1E-8 | 0.0018 | 0.65 | 0.0018 | 0.99 | 0.78 | 0.83 |
| nCohort 1 | 212 | 504 | 224 | 212 | 504 | 224 | 212 | 504 | 224 |
| nCohort 2 | 87 | 28 | 77 | 93 | 32 | 83 | 31 | 18 | 30 |
| Cutoff 1 | 524 | 291 | 606 | 346 | 288 | 346 | 140 | 92.0 | 196 |
| Sens 1 | 70% | 71% | 70% | 71% | 72% | 72% | 71% | 72% | 73% |
| Spec 1 | 58% | 30% | 62% | 46% | 30% | 46% | 27% | 15% | 31% |
| Cutoff 2 | 252 | 54.3 | 495 | 262 | 182 | 234 | 11.6 | 22.6 | 7.42 |
| Sens 2 | 80% | 82% | 81% | 81% | 81% | 81% | 81% | 83% | 80% |
| Spec 2 | 39% | 14% | 57% | 39% | 22% | 35% | 14% | 11% | 12% |
| Cutoff 3 | 27.3 | 1.40 | 140 | 113 | 64.5 | 119 | 1.40 | 1.48 | 1.40 |
| Sens 3 | 91% | 93% | 91% | 90% | 91% | 90% | 94% | 94% | 93% |
| Spec 3 | 16% | 8% | 25% | 25% | 14% | 23% | 12% | 8% | 10% |
| Cutoff 4 | 708 | 1010 | 710 | 708 | 1010 | 710 | 708 | 1010 | 710 |
| Sens 4 | 61% | 29% | 66% | 43% | 28% | 47% | 35% | 39% | 37% |
| Spec 4 | 70% | 70% | 70% | 70% | 70% | 70% | 70% | 70% | 70% |
| Cutoff 5 | 975 | 1360 | 1070 | 975 | 1360 | 1070 | 975 | 1360 | 1070 |
| Sens 5 | 43% | 18% | 42% | 34% | 12% | 30% | 19% | 28% | 17% |
| Spec 5 | 80% | 80% | 80% | 80% | 80% | 80% | 80% | 80% | 80% |
| Cutoff 6 | 1410 | 1740 | 1450 | 1410 | 1740 | 1450 | 1410 | 1740 | 1450 |
| Sens 6 | 29% | 14% | 32% | 15% | 6% | 16% | 10% | 22% | 10% |
| Spec 6 | 90% | 90% | 90% | 90% | 90% | 90% | 90% | 90% | 90% |
| OR Quart 2 | 0.68 | 1.4 | 0.89 | 1.8 | 1.6 | 1.6 | 0.63 | 0 | 0.58 |
| p Value | 0.37 | 0.58 | 0.81 | 0.13 | 0.40 | 0.25 | 0.41 | na | 0.37 |
| 95% CI of | 0.29 | 0.46 | 0.34 | 0.84 | 0.52 | 0.72 | 0.21 | na | 0.18 |
| OR Quart 2 | 1.6 | 4.0 | 2.3 | 3.9 | 5.1 | 3.5 | 1.9 | na | 1.9 |
| OR Quart 3 | 2.1 | 1.0 | 3.4 | 2.2 | 2.5 | 1.9 | 0.75 | 0.56 | 1.3 |
| p Value | 0.051 | 1.0 | 0.0030 | 0.043 | 0.089 | 0.094 | 0.59 | 0.36 | 0.61 |
| 95% CI of | 1.00 | 0.31 | 1.5 | 1.0 | 0.87 | 0.89 | 0.26 | 0.16 | 0.48 |
| OR Quart 3 | 4.4 | 3.2 | 7.8 | 4.6 | 7.4 | 4.2 | 2.2 | 2.0 | 3.5 |
| OR Quart 4 | 3.4 | 1.4 | 4.7 | 3.1 | 1.4 | 2.9 | 1.0 | 1.0 | 0.84 |

|  |  |  |  |  |  |  |  |  |  |
|---|---|---|---|---|---|---|---|---|---|
| p Value | 8.5E-4 | 0.58 | 1.6E-4 | 0.0023 | 0.56 | 0.0052 | 0.97 | 0.99 | 0.76 |
| 95% CI of | 1.7 | 0.46 | 2.1 | 1.5 | 0.44 | 1.4 | 0.37 | 0.34 | 0.29 |
| OR Quart 4 | 7.1 | 4.0 | 11 | 6.6 | 4.6 | 6.2 | 2.8 | 3.0 | 2.5 |

Prostate-specific antigen

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 0.0131 | 0.0123 | 0.0131 | 0.126 | nd | nd |
| Average | 4.19 | 4.25 | 4.19 | 7.92 | nd | nd |
| Stdev | 7.89 | 8.36 | 7.89 | 9.60 | nd | nd |
| p (t-test) | | 0.98 | | 0.10 | nd | nd |
| Min | 0.00354 | 0.00392 | 0.00354 | 0.00462 | nd | nd |
| Max | 20.0 | 20.0 | 20.0 | 20.0 | nd | nd |
| n (Samp) | 52 | 19 | 52 | 19 | nd | nd |
| n (Patient) | 41 | 19 | 41 | 19 | nd | nd |
| UO only | | | | | | |
| Median | 0.0140 | 0.0349 | 0.0140 | 0.0849 | nd | nd |
| Average | 3.70 | 4.05 | 3.70 | 6.79 | nd | nd |
| Stdev | 7.37 | 8.26 | 7.37 | 9.06 | nd | nd |
| p (t-test) | | 0.88 | | 0.15 | nd | nd |
| Min | 0.00354 | 0.00392 | 0.00354 | 0.00462 | nd | nd |
| Max | 20.0 | 20.0 | 20.0 | 20.0 | nd | nd |
| n (Samp) | 44 | 15 | 44 | 20 | nd | nd |
| n (Patient) | 34 | 15 | 34 | 20 | nd | nd |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.55 | nd | 0.53 | 0.65 | nd | 0.63 | nd | nd | nd |
| SE | 0.079 | nd | 0.088 | 0.077 | nd | 0.078 | nd | nd | nd |
| p | 0.54 | nd | 0.71 | 0.046 | nd | 0.11 | nd | nd | nd |
| nCohort 1 | 52 | nd | 44 | 52 | nd | 44 | nd | nd | nd |
| nCohort 2 | 19 | nd | 15 | 19 | nd | 20 | nd | nd | nd |
| Cutoff 1 | 0.0105 | nd | 0.00959 | 0.0127 | nd | 0.0135 | nd | nd | nd |
| Sens 1 | 74% | nd | 73% | 74% | nd | 70% | nd | nd | nd |
| Spec 1 | 44% | nd | 36% | 50% | nd | 50% | nd | nd | nd |
| Cutoff 2 | 0.00897 | nd | 0.00870 | 0.00938 | nd | 0.0127 | nd | nd | nd |
| Sens 2 | 84% | nd | 87% | 84% | nd | 80% | nd | nd | nd |
| Spec 2 | 33% | nd | 25% | 37% | nd | 45% | nd | nd | nd |
| Cutoff 3 | 0.00606 | nd | 0.00776 | 0.00776 | nd | 0.00781 | nd | nd | nd |
| Sens 3 | 95% | nd | 93% | 95% | nd | 90% | nd | nd | nd |
| Spec 3 | 8% | nd | 18% | 21% | nd | 18% | nd | nd | nd |
| Cutoff 4 | 0.105 | nd | 0.127 | 0.105 | nd | 0.127 | nd | nd | nd |
| Sens 4 | 26% | nd | 27% | 53% | nd | 45% | nd | nd | nd |
| Spec 4 | 71% | nd | 70% | 71% | nd | 70% | nd | nd | nd |
| Cutoff 5 | 11.9 | nd | 4.24 | 11.9 | nd | 4.24 | nd | nd | nd |
| Sens 5 | 21% | nd | 20% | 37% | nd | 40% | nd | nd | nd |
| Spec 5 | 81% | nd | 82% | 81% | nd | 82% | nd | nd | nd |
| Cutoff 6 | 20.0 | nd | 20.0 | 20.0 | nd | 20.0 | nd | nd | nd |
| Sens 6 | 0% | nd | 0% | 0% | nd | 0% | nd | nd | nd |
| Spec 6 | 100% | nd | 100% | 100% | nd | 100% | nd | nd | nd |
| OR Quart 2 | 3.0 | nd | 3.0 | 2.9 | nd | 2.0 | nd | nd | nd |
| p Value | 0.17 | nd | 0.24 | 0.25 | nd | 0.42 | nd | nd | nd |
| 95% CI of | 0.62 | nd | 0.48 | 0.48 | nd | 0.38 | nd | nd | nd |
| OR Quart 2 | 14 | nd | 19 | 17 | nd | 10 | nd | nd | nd |
| OR Quart 3 | 1.8 | nd | 3.0 | 2.9 | nd | 1.4 | nd | nd | nd |
| p Value | 0.48 | nd | 0.24 | 0.25 | nd | 0.67 | nd | nd | nd |
| 95% CI of | 0.36 | nd | 0.48 | 0.48 | nd | 0.27 | nd | nd | nd |
| OR Quart 3 | 9.1 | nd | 19 | 17 | nd | 7.8 | nd | nd | nd |
| OR Quart 4 | 1.3 | nd | 1.5 | 4.8 | nd | 4.3 | nd | nd | nd |
| p Value | 0.74 | nd | 0.69 | 0.081 | nd | 0.071 | nd | nd | nd |
| 95% CI of | 0.25 | nd | 0.21 | 0.83 | nd | 0.88 | nd | nd | nd |
| OR Quart 4 | 7.1 | nd | 11 | 28 | nd | 21 | nd | nd | nd |

-continued

| Lutropin subunit beta | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 19.2 | 16.5 | 19.2 | 25.6 | nd | nd |
| Average | 60.1 | 41.4 | 60.1 | 69.5 | nd | nd |
| Stdev | 101 | 64.5 | 101 | 92.5 | nd | nd |
| p (t-test) | | 0.20 | | 0.58 | nd | nd |
| Min | 0.0297 | 0.130 | 0.0297 | 0.0746 | nd | nd |
| Max | 400 | 277 | 400 | 325 | nd | nd |
| n (Samp) | 127 | 59 | 127 | 46 | nd | nd |
| n (Patient) | 68 | 59 | 68 | 46 | nd | nd |
| sCr only | | | | | | |
| Median | 21.0 | 5.20 | 21.0 | 23.1 | 21.0 | 9.45 |
| Average | 60.1 | 36.1 | 60.1 | 77.8 | 60.1 | 12.5 |
| Stdev | 92.4 | 55.8 | 92.4 | 91.5 | 92.4 | 13.5 |
| p (t-test) | | 0.29 | | 0.45 | | 0.21 |
| Min | 0.0297 | 0.211 | 0.0297 | 0.146 | 0.0297 | 0.505 |
| Max | 400 | 179 | 400 | 256 | 400 | 36.9 |
| n (Samp) | 267 | 17 | 267 | 16 | 267 | 6 |
| n (Patient) | 128 | 17 | 128 | 16 | 128 | 6 |
| UO only | | | | | | |
| Median | 19.4 | 21.0 | 19.4 | 23.6 | 19.4 | 16.2 |
| Average | 63.9 | 48.5 | 63.9 | 68.9 | 63.9 | 86.8 |
| Stdev | 99.3 | 74.9 | 99.3 | 100 | 99.3 | 119 |
| p (t-test) | | 0.31 | | 0.76 | | 0.51 |
| Min | 0.0297 | 0.130 | 0.0297 | 0.0746 | 0.0297 | 0.463 |
| Max | 400 | 325 | 400 | 393 | 400 | 332 |
| n (Samp) | 148 | 51 | 148 | 47 | 148 | 9 |
| n (Patient) | 72 | 51 | 72 | 47 | 72 | 9 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.48 | 0.39 | 0.51 | 0.57 | 0.54 | 0.55 | nd | 0.33 | 0.57 |
| SE | 0.046 | 0.075 | 0.047 | 0.050 | 0.076 | 0.049 | nd | 0.12 | 0.10 |
| p | 0.74 | 0.16 | 0.89 | 0.19 | 0.63 | 0.28 | nd | 0.17 | 0.51 |
| nCohort 1 | 127 | 267 | 148 | 127 | 267 | 148 | nd | 267 | 148 |
| nCohort 2 | 59 | 17 | 51 | 46 | 16 | 47 | nd | 6 | 9 |
| Cutoff 1 | 4.35 | 3.23 | 7.60 | 10.6 | 5.10 | 10.6 | nd | 3.00 | 11.6 |
| Sens 1 | 71% | 71% | 71% | 72% | 75% | 70% | nd | 83% | 78% |
| Spec 1 | 28% | 19% | 35% | 41% | 24% | 39% | nd | 18% | 40% |
| Cutoff 2 | 2.03 | 1.98 | 4.33 | 6.10 | 4.35 | 6.19 | nd | 3.00 | 6.57 |
| Sens 2 | 81% | 82% | 80% | 80% | 81% | 81% | nd | 83% | 89% |
| Spec 2 | 16% | 15% | 26% | 37% | 22% | 34% | nd | 18% | 34% |
| Cutoff 3 | 0.393 | 0.339 | 0.986 | 0.933 | 0.408 | 3.86 | nd | 0.448 | 0.422 |
| Sens 3 | 92% | 94% | 90% | 91% | 94% | 91% | nd | 100% | 100% |
| Spec 3 | 9% | 8% | 11% | 13% | 9% | 26% | nd | 10% | 9% |
| Cutoff 4 | 38.7 | 46.3 | 43.9 | 38.7 | 46.3 | 43.9 | nd | 46.3 | 43.9 |
| Sens 4 | 29% | 24% | 29% | 37% | 38% | 32% | nd | 0% | 33% |
| Spec 4 | 70% | 70% | 70% | 70% | 70% | 70% | nd | 70% | 70% |
| Cutoff 5 | 80.9 | 89.1 | 134 | 80.9 | 89.1 | 134 | nd | 89.1 | 134 |
| Sens 5 | 14% | 18% | 10% | 28% | 38% | 19% | nd | 0% | 33% |
| Spec 5 | 80% | 80% | 80% | 80% | 80% | 80% | nd | 80% | 80% |
| Cutoff 6 | 232 | 225 | 217 | 232 | 225 | 217 | nd | 225 | 217 |
| Sens 6 | 5% | 0% | 8% | 11% | 6% | 13% | nd | 0% | 22% |
| Spec 6 | 91% | 90% | 91% | 91% | 90% | 91% | nd | 90% | 91% |
| OR Quart 2 | 0.84 | 0.49 | 1.7 | 3.0 | 0.57 | 1.8 | nd | >1.0 | 4.3 |
| p Value | 0.70 | 0.41 | 0.27 | 0.046 | 0.46 | 0.24 | nd | <0.98 | 0.20 |
| 95% CI of | 0.35 | 0.086 | 0.67 | 1.0 | 0.13 | 0.67 | nd | >0.063 | 0.46 |
| OR Quart 2 | 2.0 | 2.7 | 4.2 | 8.7 | 2.5 | 4.9 | nd | na | 41 |
| OR Quart 3 | 1.2 | 0.74 | 1.7 | 2.4 | 0.38 | 2.0 | nd | >2.1 | 1.0 |
| p Value | 0.66 | 0.70 | 0.27 | 0.12 | 0.25 | 0.17 | nd | <0.55 | 1.0 |
| 95% CI of | 0.51 | 0.16 | 0.67 | 0.80 | 0.071 | 0.75 | nd | >0.19 | 0.060 |
| OR Quart 3 | 2.8 | 3.4 | 4.2 | 7.1 | 2.0 | 5.3 | nd | na | 17 |
| OR Quart 4 | 0.93 | 2.1 | 1.1 | 2.9 | 1.2 | 1.6 | nd | >3.2 | 3.1 |
| p Value | 0.88 | 0.24 | 0.85 | 0.053 | 0.77 | 0.34 | nd | <0.32 | 0.34 |
| 95% CI of | 0.39 | 0.61 | 0.42 | 0.99 | 0.35 | 0.60 | nd | >0.32 | 0.31 |
| OR Quart 4 | 2.2 | 7.4 | 2.9 | 8.4 | 4.1 | 4.4 | nd | na | 31 |

| Neural cell adhesion molecule 1 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 2250 | 3580 | 2250 | 2690 | 2250 | 2950 |
| Average | 2910 | 3890 | 2910 | 4150 | 2910 | 3090 |
| Stdev | 2240 | 4020 | 2240 | 6560 | 2240 | 1780 |
| p (t-test) | | 3.9E−4 | | 6.5E−4 | | 0.59 |
| Min | 6.83 | 221 | 6.83 | 216 | 6.83 | 293 |
| Max | 22000 | 40700 | 22000 | 55700 | 22000 | 6560 |
| n (Samp) | 463 | 119 | 463 | 128 | 463 | 47 |
| n (Patient) | 223 | 119 | 223 | 128 | 223 | 47 |
| sCr only | | | | | | |
| Median | 2830 | 2300 | 2830 | 2420 | 2830 | 1930 |
| Average | 3460 | 2540 | 3460 | 3220 | 3460 | 2360 |
| Stdev | 3360 | 1640 | 3360 | 2380 | 3360 | 1600 |
| p (t-test) | | 0.085 | | 0.63 | | 0.097 |
| Min | 6.83 | 221 | 6.83 | 216 | 6.83 | 387 |
| Max | 55700 | 6210 | 55700 | 10800 | 55700 | 6110 |
| n (Samp) | 1014 | 40 | 1014 | 46 | 1014 | 26 |
| n (Patient) | 373 | 40 | 373 | 46 | 373 | 26 |
| UO only | | | | | | |
| Median | 2400 | 3900 | 2400 | 2850 | 2400 | 2920 |
| Average | 2980 | 4670 | 2980 | 4590 | 2980 | 3220 |
| Stdev | 2070 | 4820 | 2070 | 7080 | 2070 | 1960 |
| p (t-test) | | 4.3E−8 | | 4.0E−5 | | 0.45 |
| Min | 173 | 506 | 173 | 224 | 173 | 293 |
| Max | 11700 | 40700 | 11700 | 55700 | 11700 | 9700 |
| n (Samp) | 436 | 107 | 436 | 117 | 436 | 44 |
| n (Patient) | 173 | 107 | 173 | 117 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.62 | 0.40 | 0.66 | 0.56 | 0.48 | 0.58 | 0.56 | 0.37 | 0.56 |
| SE | 0.030 | 0.048 | 0.031 | 0.029 | 0.044 | 0.031 | 0.045 | 0.059 | 0.047 |
| p | 1.2E−4 | 0.043 | 2.3E−7 | 0.026 | 0.61 | 0.0086 | 0.20 | 0.025 | 0.21 |
| nCohort 1 | 463 | 1014 | 436 | 463 | 1014 | 436 | 463 | 1014 | 436 |
| nCohort 2 | 119 | 40 | 107 | 128 | 46 | 117 | 47 | 26 | 44 |
| Cutoff 1 | 2270 | 1150 | 2690 | 1950 | 1680 | 2080 | 2150 | 1190 | 2250 |
| Sens 1 | 71% | 70% | 70% | 70% | 72% | 70% | 70% | 73% | 70% |
| Spec 1 | 51% | 14% | 56% | 42% | 25% | 43% | 48% | 14% | 46% |
| Cutoff 2 | 1550 | 994 | 2000 | 1250 | 1110 | 1560 | 1500 | 1110 | 1650 |
| Sens 2 | 81% | 80% | 80% | 80% | 80% | 80% | 81% | 81% | 82% |
| Spec 2 | 30% | 11% | 41% | 20% | 13% | 30% | 29% | 13% | 32% |
| Cutoff 3 | 919 | 830 | 1450 | 898 | 883 | 1030 | 485 | 491 | 881 |
| Sens 3 | 91% | 90% | 91% | 91% | 91% | 91% | 91% | 92% | 91% |
| Spec 3 | 11% | 7% | 27% | 11% | 8% | 14% | 3% | 2% | 10% |
| Cutoff 4 | 3530 | 4050 | 3620 | 3530 | 4050 | 3620 | 3530 | 4050 | 3620 |
| Sens 4 | 51% | 18% | 56% | 37% | 33% | 38% | 38% | 15% | 36% |
| Spec 4 | 70% | 70% | 70% | 70% | 70% | 70% | 70% | 70% | 70% |
| Cutoff 5 | 4180 | 4930 | 4360 | 4180 | 4930 | 4360 | 4180 | 4930 | 4360 |
| Sens 5 | 32% | 8% | 34% | 30% | 22% | 32% | 28% | 8% | 25% |
| Spec 5 | 80% | 80% | 80% | 80% | 80% | 80% | 80% | 80% | 80% |
| Cutoff 6 | 5630 | 6450 | 6000 | 5630 | 6450 | 6000 | 5630 | 6450 | 6000 |
| Sens 6 | 17% | 0% | 23% | 20% | 9% | 20% | 9% | 0% | 9% |
| Spec 6 | 90% | 90% | 90% | 90% | 90% | 90% | 90% | 90% | 90% |
| OR Quart 2 | 1.2 | 1.5 | 1.3 | 0.99 | 0.74 | 1.4 | 1.1 | 1.0 | 1.3 |
| p Value | 0.63 | 0.43 | 0.47 | 0.98 | 0.51 | 0.27 | 0.83 | 1.0 | 0.61 |
| 95% CI of | 0.61 | 0.53 | 0.63 | 0.55 | 0.31 | 0.76 | 0.44 | 0.25 | 0.47 |
| OR Quart 2 | 2.3 | 4.3 | 2.8 | 1.8 | 1.8 | 2.6 | 2.8 | 4.0 | 3.6 |
| OR Quart 3 | 2.0 | 1.7 | 2.8 | 1.1 | 1.0 | 1.4 | 1.6 | 2.0 | 2.5 |
| p Value | 0.034 | 0.31 | 0.0032 | 0.79 | 1.0 | 0.27 | 0.28 | 0.25 | 0.055 |
| 95% CI of | 1.1 | 0.61 | 1.4 | 0.61 | 0.44 | 0.76 | 0.68 | 0.60 | 0.98 |
| OR Quart 3 | 3.6 | 4.7 | 5.5 | 1.9 | 2.3 | 2.6 | 3.9 | 6.8 | 6.3 |
| OR Quart 4 | 3.0 | 2.6 | 3.9 | 1.9 | 1.1 | 2.3 | 1.6 | 2.6 | 1.8 |
| p Value | 3.7E−4 | 0.052 | 6.4E−5 | 0.017 | 0.84 | 0.0072 | 0.29 | 0.12 | 0.24 |
| 95% CI of | 1.6 | 0.99 | 2.0 | 1.1 | 0.49 | 1.2 | 0.67 | 0.79 | 0.68 |
| OR Quart 4 | 5.4 | 6.8 | 7.5 | 3.3 | 2.4 | 4.1 | 3.9 | 8.3 | 4.7 |

-continued

| Platelet-derived growth factor subunit B (dimer) | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.961 | 1.70 | 0.961 | 1.70 | 0.961 | 1.75 |
| Average | 3.43 | 3.67 | 3.43 | 14.0 | 3.43 | 4.02 |
| Stdev | 15.8 | 10.6 | 15.8 | 102 | 15.8 | 7.14 |
| p (t-test) | | 0.90 | | 0.060 | | 0.81 |
| Min | 0.00246 | 0.00313 | 0.00246 | 0.00408 | 0.00246 | 0.00683 |
| Max | 270 | 86.2 | 270 | 935 | 270 | 34.8 |
| n (Samp) | 365 | 70 | 365 | 84 | 365 | 41 |
| n (Patient) | 191 | 70 | 191 | 84 | 191 | 41 |
| sCr only | | | | | | |
| Median | 1.06 | 2.21 | 1.06 | 2.31 | 1.06 | 2.18 |
| Average | 4.26 | 6.20 | 4.26 | 3.16 | 4.26 | 4.35 |
| Stdev | 35.9 | 16.9 | 35.9 | 3.24 | 35.9 | 7.82 |
| p (t-test) | | 0.79 | | 0.86 | | 0.99 |
| Min | 0.00246 | 0.0144 | 0.00246 | 0.0140 | 0.00246 | 0.00408 |
| Max | 935 | 86.2 | 935 | 16.9 | 935 | 34.8 |
| n (Samp) | 754 | 25 | 754 | 32 | 754 | 21 |
| n (Patient) | 295 | 25 | 295 | 32 | 295 | 21 |
| UO only | | | | | | |
| Median | 1.14 | 1.82 | 1.14 | 1.77 | 1.14 | 1.63 |
| Average | 3.66 | 3.62 | 3.66 | 15.7 | 3.66 | 3.35 |
| Stdev | 16.6 | 7.97 | 16.6 | 106 | 16.6 | 5.16 |
| p (t-test) | | 0.99 | | 0.054 | | 0.91 |
| Min | 0.00246 | 0.00313 | 0.00246 | 0.00408 | 0.00246 | 0.00683 |
| Max | 270 | 59.1 | 270 | 935 | 270 | 22.1 |
| n (Samp) | 317 | 65 | 317 | 77 | 317 | 36 |
| n (Patient) | 136 | 65 | 136 | 77 | 136 | 36 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.60 | 0.66 | 0.60 | 0.60 | 0.67 | 0.58 | 0.59 | 0.64 | 0.56 |
| SE | 0.038 | 0.060 | 0.040 | 0.036 | 0.053 | 0.037 | 0.049 | 0.066 | 0.052 |
| p | 0.0078 | 0.0097 | 0.010 | 0.0046 | 0.0015 | 0.027 | 0.057 | 0.030 | 0.25 |
| nCohort 1 | 365 | 754 | 317 | 365 | 754 | 317 | 365 | 754 | 317 |
| nCohort 2 | 70 | 25 | 65 | 84 | 32 | 77 | 41 | 21 | 36 |
| Cutoff 1 | 0.718 | 1.09 | 1.14 | 0.901 | 1.39 | 0.965 | 0.392 | 1.24 | 0.353 |
| Sens 1 | 70% | 72% | 71% | 70% | 72% | 70% | 71% | 71% | 72% |
| Spec 1 | 40% | 51% | 50% | 48% | 57% | 46% | 30% | 54% | 27% |
| Cutoff 2 | 0.483 | 0.737 | 0.536 | 0.273 | 0.465 | 0.162 | 0.286 | 0.869 | 0.232 |
| Sens 2 | 80% | 80% | 80% | 81% | 81% | 81% | 80% | 81% | 81% |
| Spec 2 | 32% | 39% | 32% | 25% | 31% | 21% | 26% | 44% | 22% |
| Cutoff 3 | 0.0238 | 0.477 | 0.0238 | 0.0238 | 0.278 | 0.0238 | 0.0244 | 0.0244 | 0.0140 |
| Sens 3 | 94% | 92% | 95% | 93% | 91% | 91% | 90% | 90% | 92% |
| Spec 3 | 17% | 31% | 15% | 17% | 25% | 15% | 20% | 19% | 11% |
| Cutoff 4 | 1.79 | 1.99 | 1.99 | 1.79 | 1.99 | 1.99 | 1.79 | 1.99 | 1.99 |
| Sens 4 | 47% | 64% | 49% | 48% | 62% | 45% | 46% | 62% | 42% |
| Spec 4 | 70% | 70% | 70% | 70% | 70% | 70% | 70% | 70% | 70% |
| Cutoff 5 | 2.54 | 3.02 | 3.08 | 2.54 | 3.02 | 3.08 | 2.54 | 3.02 | 3.08 |
| Sens 5 | 34% | 32% | 31% | 31% | 44% | 25% | 39% | 38% | 31% |
| Spec 5 | 80% | 80% | 80% | 80% | 80% | 80% | 80% | 80% | 80% |
| Cutoff 6 | 4.63 | 4.73 | 5.05 | 4.63 | 4.73 | 5.05 | 4.63 | 4.73 | 5.05 |
| Sens 6 | 13% | 20% | 14% | 15% | 19% | 13% | 15% | 10% | 17% |
| Spec 6 | 90% | 90% | 90% | 90% | 90% | 90% | 90% | 90% | 90% |
| OR Quart 2 | 0.99 | 2.5 | 1.6 | 0.57 | 0.74 | 0.66 | 0.99 | 0.99 | 0.47 |
| p Value | 0.98 | 0.27 | 0.30 | 0.17 | 0.70 | 0.30 | 0.98 | 0.99 | 0.19 |
| 95% CI of | 0.42 | 0.48 | 0.67 | 0.26 | 0.16 | 0.30 | 0.36 | 0.20 | 0.15 |
| OR Quart 2 | 2.3 | 13 | 3.7 | 1.3 | 3.4 | 1.5 | 2.7 | 5.0 | 1.4 |
| OR Quart 3 | 1.9 | 3.0 | 1.9 | 1.6 | 2.9 | 1.4 | 1.0 | 1.7 | 0.78 |
| p Value | 0.098 | 0.18 | 0.15 | 0.18 | 0.077 | 0.37 | 1.0 | 0.48 | 0.62 |
| 95% CI of | 0.89 | 0.61 | 0.80 | 0.81 | 0.89 | 0.68 | 0.36 | 0.39 | 0.29 |
| OR Quart 3 | 4.1 | 15 | 4.3 | 3.1 | 9.1 | 2.8 | 2.8 | 7.1 | 2.1 |
| OR Quart 4 | 2.4 | 6.3 | 2.7 | 1.8 | 3.7 | 1.7 | 2.3 | 3.4 | 1.3 |
| p Value | 0.023 | 0.017 | 0.017 | 0.079 | 0.024 | 0.13 | 0.063 | 0.064 | 0.52 |
| 95% CI of | 1.1 | 1.4 | 1.2 | 0.93 | 1.2 | 0.85 | 0.95 | 0.93 | 0.55 |
| OR Quart 4 | 5.0 | 29 | 6.0 | 3.5 | 11 | 3.4 | 5.7 | 13 | 3.2 |

-continued

| Thyroxine-binding globulin | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.0694 | 0.0901 | 0.0694 | 0.106 | 0.0694 | 0.148 |
| Average | 0.182 | 0.240 | 0.182 | 0.238 | 0.182 | 0.169 |
| Stdev | 0.262 | 0.381 | 0.262 | 0.515 | 0.262 | 0.173 |
| p (t-test) | | 0.20 | | 0.24 | | 0.80 |
| Min | 0.000191 | 8.30E−5 | 0.000191 | 0.000156 | 0.000191 | 0.00190 |
| Max | 1.59 | 1.86 | 1.59 | 3.60 | 1.59 | 0.775 |
| n (Samp) | 255 | 48 | 255 | 56 | 255 | 27 |
| n (Patient) | 103 | 48 | 103 | 56 | 103 | 27 |
| sCr only | | | | | | |
| Median | 0.0777 | 0.0623 | 0.0777 | 0.0721 | 0.0777 | 0.0390 |
| Average | 0.189 | 0.0799 | 0.189 | 0.162 | 0.189 | 0.0671 |
| Stdev | 0.308 | 0.0770 | 0.308 | 0.219 | 0.308 | 0.0674 |
| p (t-test) | | 0.16 | | 0.70 | | 0.15 |
| Min | 0.000191 | 8.30E−5 | 0.000191 | 0.000156 | 0.000191 | 0.00190 |
| Max | 3.60 | 0.250 | 3.60 | 0.792 | 3.60 | 0.218 |
| n (Samp) | 447 | 16 | 447 | 20 | 447 | 13 |
| n (Patient) | 170 | 16 | 170 | 20 | 170 | 13 |
| UO only | | | | | | |
| Median | 0.0675 | 0.0555 | 0.0675 | 0.114 | 0.0675 | 0.149 |
| Average | 0.172 | 0.241 | 0.172 | 0.249 | 0.172 | 0.178 |
| Stdev | 0.259 | 0.391 | 0.259 | 0.537 | 0.259 | 0.177 |
| p (t-test) | | 0.14 | | 0.14 | | 0.91 |
| Min | 0.000191 | 0.00106 | 0.000191 | 0.00324 | 0.000191 | 0.00366 |
| Max | 1.59 | 1.86 | 1.59 | 3.60 | 1.59 | 0.775 |
| n (Samp) | 218 | 46 | 218 | 51 | 218 | 25 |
| n (Patient) | 87 | 46 | 87 | 51 | 87 | 25 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.52 | 0.41 | 0.51 | 0.52 | 0.47 | 0.53 | 0.57 | 0.37 | 0.60 |
| SE | 0.046 | 0.076 | 0.047 | 0.043 | 0.067 | 0.045 | 0.060 | 0.084 | 0.063 |
| p | 0.66 | 0.24 | 0.83 | 0.69 | 0.68 | 0.47 | 0.28 | 0.12 | 0.098 |
| nCohort 1 | 255 | 447 | 218 | 255 | 447 | 218 | 255 | 447 | 218 |
| nCohort 2 | 48 | 16 | 46 | 56 | 20 | 51 | 27 | 13 | 25 |
| Cutoff 1 | 0.0279 | 0.0196 | 0.0169 | 0.0293 | 0.0357 | 0.0287 | 0.0617 | 0.0196 | 0.0694 |
| Sens 1 | 71% | 75% | 72% | 71% | 70% | 71% | 70% | 77% | 72% |
| Spec 1 | 30% | 23% | 22% | 31% | 33% | 32% | 47% | 23% | 52% |
| Cutoff 2 | 0.0150 | 0.0157 | 0.0138 | 0.0194 | 0.0187 | 0.0164 | 0.0471 | 0.00877 | 0.0547 |
| Sens 2 | 81% | 81% | 80% | 80% | 80% | 80% | 81% | 85% | 80% |
| Spec 2 | 20% | 20% | 20% | 22% | 22% | 22% | 41% | 15% | 46% |
| Cutoff 3 | 0.00405 | 0.00990 | 0.00446 | 0.00715 | 0.00325 | 0.0100 | 0.00715 | 0.00319 | 0.0138 |
| Sens 3 | 92% | 94% | 91% | 91% | 90% | 90% | 93% | 92% | 92% |
| Spec 3 | 7% | 16% | 8% | 14% | 6% | 16% | 14% | 6% | 20% |
| Cutoff 4 | 0.193 | 0.198 | 0.174 | 0.193 | 0.198 | 0.174 | 0.193 | 0.198 | 0.174 |
| Sens 4 | 35% | 12% | 39% | 30% | 25% | 37% | 33% | 8% | 44% |
| Spec 4 | 70% | 70% | 70% | 70% | 70% | 70% | 70% | 70% | 70% |
| Cutoff 5 | 0.274 | 0.290 | 0.248 | 0.274 | 0.290 | 0.248 | 0.274 | 0.290 | 0.248 |
| Sens 5 | 23% | 0% | 28% | 21% | 15% | 25% | 11% | 0% | 16% |
| Spec 5 | 80% | 80% | 80% | 80% | 80% | 80% | 80% | 80% | 80% |
| Cutoff 6 | 0.448 | 0.466 | 0.418 | 0.448 | 0.466 | 0.418 | 0.448 | 0.466 | 0.418 |
| Sens 6 | 19% | 0% | 20% | 12% | 10% | 12% | 7% | 0% | 8% |
| Spec 6 | 90% | 90% | 90% | 90% | 90% | 90% | 90% | 90% | 90% |
| OR Quart 2 | 0.64 | 5.2 | 0.54 | 0.74 | 1.5 | 0.59 | 2.1 | >5.2 | 1.7 |
| p Value | 0.34 | 0.14 | 0.18 | 0.49 | 0.52 | 0.26 | 0.32 | <0.13 | 0.48 |
| 95% CI of | 0.26 | 0.60 | 0.22 | 0.31 | 0.42 | 0.23 | 0.49 | >0.60 | 0.39 |
| OR Quart 2 | 1.6 | 45 | 1.3 | 1.7 | 5.6 | 1.5 | 8.6 | na | 7.4 |
| OR Quart 3 | 0.89 | 5.2 | 0.40 | 1.3 | 1.3 | 1.0 | 4.6 | >4.1 | 3.3 |
| p Value | 0.80 | 0.14 | 0.067 | 0.45 | 0.73 | 1.0 | 0.022 | <0.21 | 0.086 |
| 95% CI of | 0.38 | 0.60 | 0.15 | 0.62 | 0.33 | 0.43 | 1.2 | >0.46 | 0.84 |
| OR Quart 3 | 2.1 | 45 | 1.1 | 3.0 | 4.8 | 2.3 | 17 | na | 13 |
| OR Quart 4 | 1.1 | 5.2 | 1.0 | 0.90 | 1.3 | 0.98 | 2.1 | >4.1 | 2.9 |
| p Value | 0.86 | 0.13 | 1.0 | 0.80 | 0.72 | 0.96 | 0.32 | <0.21 | 0.13 |
| 95% CI of | 0.47 | 0.60 | 0.44 | 0.39 | 0.33 | 0.43 | 0.49 | >0.46 | 0.72 |
| OR Quart 4 | 2.5 | 45 | 2.3 | 2.1 | 4.9 | 2.3 | 8.6 | na | 11 |

-continued

| Pigment epithelium-derived factor | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 3.04 | 4.18 | 3.04 | 2.78 | 3.04 | 3.54 |
| Average | 20.4 | 23.7 | 20.4 | 22.4 | 20.4 | 17.8 |
| Stdev | 49.4 | 52.1 | 49.4 | 51.0 | 49.4 | 34.6 |
| p (t-test) | | 0.52 | | 0.68 | | 0.72 |
| Min | 0.000563 | 0.0167 | 0.000563 | 0.00102 | 0.000563 | 0.159 |
| Max | 400 | 302 | 400 | 400 | 400 | 171 |
| n (Samp) | 463 | 119 | 463 | 128 | 463 | 47 |
| n (Patient) | 223 | 119 | 223 | 128 | 223 | 47 |
| sCr only | | | | | | |
| Median | 3.10 | 3.91 | 3.10 | 3.28 | 3.10 | 2.70 |
| Average | 18.7 | 25.3 | 18.7 | 27.7 | 18.7 | 25.4 |
| Stdev | 45.5 | 64.6 | 45.5 | 53.3 | 45.5 | 50.3 |
| p (t-test) | | 0.38 | | 0.19 | | 0.46 |
| Min | 0.000401 | 0.115 | 0.000401 | 0.0102 | 0.000401 | 0.00102 |
| Max | 400 | 361 | 400 | 302 | 400 | 218 |
| n (Samp) | 1015 | 40 | 1015 | 46 | 1015 | 26 |
| n (Patient) | 374 | 40 | 374 | 46 | 374 | 26 |
| UO only | | | | | | |
| Median | 3.33 | 4.99 | 3.33 | 3.59 | 3.33 | 6.11 |
| Average | 24.7 | 27.8 | 24.7 | 29.2 | 24.7 | 22.5 |
| Stdev | 54.1 | 56.4 | 54.1 | 65.5 | 54.1 | 41.4 |
| p (t-test) | | 0.60 | | 0.44 | | 0.80 |
| Min | 0.000563 | 0.0167 | 0.000563 | 0.00102 | 0.000563 | 0.189 |
| Max | 400 | 302 | 400 | 400 | 400 | 171 |
| n (Samp) | 436 | 107 | 436 | 117 | 436 | 44 |
| n (Patient) | 173 | 107 | 173 | 117 | 173 | 44 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.55 | 0.52 | 0.56 | 0.51 | 0.54 | 0.52 | 0.54 | 0.50 | 0.55 |
| SE | 0.030 | 0.047 | 0.032 | 0.029 | 0.044 | 0.030 | 0.045 | 0.058 | 0.047 |
| p | 0.081 | 0.73 | 0.055 | 0.70 | 0.43 | 0.61 | 0.39 | 0.94 | 0.29 |
| nCohort 1 | 463 | 1015 | 436 | 463 | 1015 | 436 | 463 | 1015 | 436 |
| nCohort 2 | 119 | 40 | 107 | 128 | 46 | 117 | 47 | 26 | 44 |
| Cutoff 1 | 1.88 | 1.94 | 2.14 | 1.13 | 0.884 | 1.45 | 1.56 | 0.913 | 2.03 |
| Sens 1 | 71% | 70% | 70% | 70% | 72% | 70% | 70% | 73% | 70% |
| Spec 1 | 41% | 40% | 41% | 31% | 25% | 33% | 38% | 26% | 40% |
| Cutoff 2 | 0.861 | 0.565 | 1.30 | 0.602 | 0.596 | 0.751 | 0.863 | 0.514 | 0.874 |
| Sens 2 | 81% | 80% | 80% | 80% | 80% | 81% | 81% | 81% | 82% |
| Spec 2 | 26% | 17% | 30% | 21% | 18% | 20% | 26% | 15% | 22% |
| Cutoff 3 | 0.329 | 0.169 | 0.596 | 0.283 | 0.132 | 0.320 | 0.361 | 0.185 | 0.681 |
| Sens 3 | 91% | 90% | 91% | 91% | 91% | 91% | 91% | 92% | 91% |
| Spec 3 | 11% | 5% | 16% | 10% | 4% | 8% | 13% | 6% | 19% |
| Cutoff 4 | 9.21 | 8.99 | 11.3 | 9.21 | 8.99 | 11.3 | 9.21 | 8.99 | 11.3 |
| Sens 4 | 36% | 30% | 40% | 32% | 41% | 34% | 30% | 31% | 36% |
| Spec 4 | 70% | 70% | 70% | 70% | 70% | 70% | 70% | 70% | 70% |
| Cutoff 5 | 19.2 | 18.7 | 27.1 | 19.2 | 18.7 | 27.1 | 19.2 | 18.7 | 27.1 |
| Sens 5 | 27% | 18% | 23% | 26% | 37% | 24% | 23% | 23% | 18% |
| Spec 5 | 80% | 80% | 80% | 80% | 80% | 80% | 80% | 80% | 80% |
| Cutoff 6 | 52.9 | 45.1 | 83.6 | 52.9 | 45.1 | 83.6 | 52.9 | 45.1 | 83.6 |
| Sens 6 | 11% | 15% | 8% | 12% | 20% | 9% | 9% | 19% | 9% |
| Spec 6 | 90% | 90% | 90% | 90% | 90% | 90% | 90% | 90% | 90% |
| OR Quart 2 | 1.3 | 0.79 | 1.6 | 0.99 | 0.76 | 1.2 | 1.5 | 1.2 | 0.89 |
| p Value | 0.37 | 0.63 | 0.16 | 0.98 | 0.52 | 0.55 | 0.36 | 0.77 | 0.81 |
| 95% CI of | 0.72 | 0.31 | 0.84 | 0.57 | 0.33 | 0.67 | 0.61 | 0.39 | 0.35 |
| OR Quart 2 | 2.4 | 2.0 | 3.0 | 1.7 | 1.8 | 2.1 | 3.9 | 3.5 | 2.3 |
| OR Quart 3 | 1.4 | 1.1 | 1.4 | 0.67 | 0.30 | 0.95 | 1.8 | 1.0 | 1.2 |
| p Value | 0.29 | 0.83 | 0.27 | 0.18 | 0.036 | 0.88 | 0.19 | 0.99 | 0.65 |
| 95% CI of | 0.76 | 0.46 | 0.76 | 0.37 | 0.096 | 0.52 | 0.74 | 0.32 | 0.51 |
| OR Quart 3 | 2.5 | 2.6 | 2.8 | 1.2 | 0.92 | 1.7 | 4.6 | 3.2 | 2.9 |
| OR Quart 4 | 1.8 | 1.1 | 2.0 | 1.2 | 1.5 | 1.3 | 1.7 | 1.2 | 1.3 |
| p Value | 0.047 | 0.83 | 0.025 | 0.52 | 0.28 | 0.40 | 0.27 | 0.77 | 0.51 |
| 95% CI of | 1.0 | 0.46 | 1.1 | 0.70 | 0.72 | 0.72 | 0.67 | 0.39 | 0.56 |
| OR Quart 4 | 3.2 | 2.6 | 3.8 | 2.0 | 3.1 | 2.3 | 4.2 | 3.5 | 3.2 |

-continued

| Tumor necrosis factor receptor superfamily member 8 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 15.0 | 24.9 | 15.0 | 19.7 | 15.0 | 30.0 |
| Average | 25.2 | 35.9 | 25.2 | 27.2 | 25.2 | 32.8 |
| Stdev | 36.7 | 35.9 | 36.7 | 24.9 | 36.7 | 25.6 |
| p (t-test) | | 0.020 | | 0.63 | | 0.26 |
| Min | 0.0493 | 0.0493 | 0.0493 | 0.121 | 0.0493 | 0.196 |
| Max | 277 | 176 | 277 | 111 | 277 | 110 |
| n (Samp) | 217 | 91 | 217 | 96 | 217 | 32 |
| n (Patient) | 128 | 91 | 128 | 96 | 128 | 32 |
| sCr only | | | | | | |
| Median | 19.5 | 19.8 | 19.5 | 30.5 | 19.5 | 33.4 |
| Average | 31.1 | 29.5 | 31.1 | 43.0 | 31.1 | 38.0 |
| Stdev | 48.0 | 28.0 | 48.0 | 60.6 | 48.0 | 31.6 |
| p (t-test) | | 0.86 | | 0.18 | | 0.55 |
| Min | 0.0493 | 0.121 | 0.0493 | 0.121 | 0.0493 | 0.0561 |
| Max | 554 | 126 | 554 | 353 | 554 | 110 |
| n (Samp) | 517 | 28 | 517 | 33 | 517 | 18 |
| n (Patient) | 242 | 28 | 242 | 33 | 242 | 18 |
| UO only | | | | | | |
| Median | 13.2 | 26.6 | 13.2 | 19.0 | 13.2 | 18.8 |
| Average | 23.7 | 37.3 | 23.7 | 26.7 | 23.7 | 27.7 |
| Stdev | 36.2 | 36.1 | 36.2 | 25.8 | 36.2 | 24.0 |
| p (t-test) | | 0.0040 | | 0.47 | | 0.55 |
| Min | 0.0493 | 0.0493 | 0.0493 | 0.196 | 0.0493 | 0.196 |
| Max | 277 | 176 | 277 | 126 | 277 | 111 |
| n (Samp) | 227 | 81 | 227 | 86 | 227 | 31 |
| n (Patient) | 122 | 81 | 122 | 86 | 122 | 31 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.63 | 0.54 | 0.66 | 0.57 | 0.62 | 0.58 | 0.65 | 0.61 | 0.62 |
| SE | 0.036 | 0.057 | 0.037 | 0.036 | 0.054 | 0.037 | 0.056 | 0.072 | 0.057 |
| p | 4.6E−4 | 0.46 | 1.4E−5 | 0.047 | 0.025 | 0.022 | 0.0079 | 0.14 | 0.037 |
| nCohort 1 | 217 | 517 | 227 | 217 | 517 | 227 | 217 | 517 | 227 |
| nCohort 2 | 91 | 28 | 81 | 96 | 33 | 86 | 32 | 18 | 31 |
| Cutoff 1 | 12.5 | 12.5 | 12.5 | 9.84 | 19.8 | 8.69 | 18.3 | 18.3 | 12.4 |
| Sens 1 | 71% | 71% | 70% | 71% | 73% | 71% | 72% | 72% | 71% |
| Spec 1 | 47% | 39% | 49% | 36% | 52% | 39% | 53% | 46% | 48% |
| Cutoff 2 | 8.52 | 5.14 | 7.30 | 5.14 | 12.3 | 5.14 | 12.1 | 5.76 | 7.30 |
| Sens 2 | 80% | 89% | 80% | 81% | 82% | 81% | 81% | 83% | 81% |
| Spec 2 | 35% | 21% | 39% | 27% | 37% | 30% | 43% | 23% | 39% |
| Cutoff 3 | 4.86 | 0.811 | 4.86 | 2.45 | 5.09 | 2.45 | 6.53 | 0.196 | 5.14 |
| Sens 3 | 90% | 96% | 90% | 91% | 94% | 91% | 91% | 94% | 90% |
| Spec 3 | 23% | 11% | 24% | 20% | 20% | 22% | 30% | 8% | 30% |
| Cutoff 4 | 27.0 | 32.9 | 25.8 | 27.0 | 32.9 | 25.8 | 27.0 | 32.9 | 25.8 |
| Sens 4 | 45% | 36% | 53% | 39% | 39% | 41% | 53% | 50% | 45% |
| Spec 4 | 70% | 71% | 70% | 70% | 71% | 70% | 70% | 71% | 70% |
| Cutoff 5 | 35.9 | 42.2 | 34.0 | 35.9 | 42.2 | 34.0 | 35.9 | 42.2 | 34.0 |
| Sens 5 | 38% | 29% | 43% | 33% | 30% | 31% | 41% | 33% | 29% |
| Spec 5 | 80% | 80% | 81% | 80% | 80% | 81% | 80% | 80% | 81% |
| Cutoff 6 | 53.5 | 62.7 | 50.8 | 53.5 | 62.7 | 50.8 | 53.5 | 62.7 | 50.8 |
| Sens 6 | 20% | 14% | 21% | 15% | 12% | 13% | 12% | 22% | 10% |
| Spec 6 | 90% | 90% | 91% | 90% | 90% | 91% | 90% | 90% | 91% |
| OR Quart 2 | 1.3 | 1.2 | 2.3 | 1.5 | 1.2 | 2.2 | 3.8 | 0.49 | 3.3 |
| p Value | 0.56 | 0.78 | 0.061 | 0.29 | 0.74 | 0.044 | 0.10 | 0.41 | 0.087 |
| 95% CI of | 0.58 | 0.38 | 0.96 | 0.73 | 0.33 | 1.0 | 0.76 | 0.088 | 0.84 |
| OR Quart 2 | 2.7 | 3.6 | 5.5 | 3.0 | 4.8 | 4.6 | 19 | 2.7 | 13 |
| OR Quart 3 | 1.8 | 1.2 | 2.7 | 1.1 | 3.2 | 1.3 | 5.1 | 1.2 | 2.5 |
| p Value | 0.14 | 0.78 | 0.027 | 0.85 | 0.049 | 0.55 | 0.043 | 0.74 | 0.20 |
| 95% CI of | 0.84 | 0.38 | 1.1 | 0.52 | 1.0 | 0.58 | 1.1 | 0.33 | 0.62 |
| OR Quart 3 | 3.7 | 3.6 | 6.3 | 2.2 | 10 | 2.8 | 25 | 4.8 | 10 |
| OR Quart 4 | 3.4 | 1.3 | 6.0 | 2.1 | 3.2 | 2.8 | 8.6 | 1.8 | 4.6 |
| p Value | 7.7E−4 | 0.59 | 2.3E−5 | 0.032 | 0.051 | 0.0061 | 0.0059 | 0.37 | 0.023 |
| 95% CI of | 1.7 | 0.45 | 2.6 | 1.1 | 1.00 | 1.3 | 1.9 | 0.51 | 1.2 |
| OR Quart 4 | 7.1 | 4.0 | 14 | 4.2 | 10 | 5.8 | 40 | 6.2 | 17 |

-continued

| | Alpha-fetoprotein | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.00520 | 0.00428 | 0.00520 | 0.00587 | 0.00520 | 0.00587 |
| Average | 0.0545 | 0.0877 | 0.0545 | 0.0927 | 0.0545 | 0.0161 |
| Stdev | 0.124 | 0.239 | 0.124 | 0.347 | 0.124 | 0.0327 |
| p (t-test) | | 0.13 | | 0.18 | | 0.12 |
| Min | 0.000463 | 0.000463 | 0.000463 | 0.000463 | 0.000463 | 0.000523 |
| Max | 0.803 | 1.74 | 0.803 | 2.85 | 0.803 | 0.118 |
| n (Samp) | 194 | 86 | 194 | 76 | 194 | 26 |
| n (Patient) | 123 | 86 | 123 | 76 | 123 | 26 |
| sCr only | | | | | | |
| Median | 0.00520 | 0.00508 | 0.00520 | 0.00428 | 0.00520 | 0.00546 |
| Average | 0.0560 | 0.170 | 0.0560 | 0.0759 | 0.0560 | 0.0270 |
| Stdev | 0.186 | 0.369 | 0.186 | 0.199 | 0.186 | 0.0391 |
| p (t-test) | | 0.0052 | | 0.58 | | 0.53 |
| Min | 0.000463 | 0.000463 | 0.000463 | 0.000463 | 0.000463 | 0.000523 |
| Max | 2.85 | 1.74 | 2.85 | 0.889 | 2.85 | 0.109 |
| n (Samp) | 428 | 26 | 428 | 28 | 428 | 16 |
| n (Patient) | 210 | 26 | 210 | 28 | 210 | 16 |
| UO only | | | | | | |
| Median | 0.00505 | 0.00428 | 0.00505 | 0.00624 | 0.00505 | 0.00587 |
| Average | 0.0557 | 0.0575 | 0.0557 | 0.0924 | 0.0557 | 0.107 |
| Stdev | 0.132 | 0.144 | 0.132 | 0.343 | 0.132 | 0.346 |
| p (t-test) | | 0.92 | | 0.19 | | 0.14 |
| Min | 0.000463 | 0.000463 | 0.000463 | 0.000463 | 0.000463 | 0.000463 |
| Max | 0.803 | 0.840 | 0.803 | 2.85 | 0.803 | 1.74 |
| n (Samp) | 210 | 78 | 210 | 72 | 210 | 27 |
| n (Patient) | 119 | 78 | 119 | 72 | 119 | 27 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.46 | 0.52 | 0.46 | 0.50 | 0.41 | 0.57 | 0.46 | 0.51 | 0.52 |
| SE | 0.038 | 0.059 | 0.039 | 0.039 | 0.058 | 0.040 | 0.061 | 0.074 | 0.060 |
| p | 0.25 | 0.79 | 0.28 | 0.99 | 0.11 | 0.074 | 0.47 | 0.86 | 0.77 |
| nCohort 1 | 194 | 428 | 210 | 194 | 428 | 210 | 194 | 428 | 210 |
| nCohort 2 | 86 | 26 | 78 | 76 | 28 | 72 | 26 | 16 | 27 |
| Cutoff 1 | 0.00296 | 0.00296 | 0.00296 | 0.00367 | 0.00132 | 0.00428 | 0.00367 | 0.00367 | 0.00423 |
| Sens 1 | 74% | 73% | 72% | 71% | 86% | 71% | 73% | 75% | 70% |
| Spec 1 | 19% | 21% | 21% | 30% | 13% | 42% | 30% | 32% | 32% |
| Cutoff 2 | 0.00132 | 0.00132 | 0.00132 | 0.000523 | 0.00132 | 0.00296 | 0.000523 | 0.00132 | 0.000523 |
| Sens 2 | 81% | 85% | 81% | 87% | 86% | 81% | 96% | 94% | 93% |
| Spec 2 | 12% | 13% | 17% | 12% | 13% | 21% | 12% | 13% | 17% |
| Cutoff 3 | 0.000463 | 0 | 0.000463 | 0 | 0 | 0.000463 | 0.000523 | 0.00132 | 0.000523 |
| Sens 3 | 91% | 100% | 92% | 100% | 100% | 92% | 96% | 94% | 93% |
| Spec 3 | 5% | 0% | 10% | 0% | 0% | 10% | 12% | 13% | 17% |
| Cutoff 4 | 0.0385 | 0.00660 | 0.0128 | 0.0385 | 0.00660 | 0.0128 | 0.0385 | 0.00660 | 0.0128 |
| Sens 4 | 29% | 35% | 27% | 30% | 18% | 43% | 12% | 31% | 22% |
| Spec 4 | 71% | 71% | 70% | 71% | 71% | 70% | 71% | 71% | 70% |
| Cutoff 5 | 0.0728 | 0.0499 | 0.0641 | 0.0728 | 0.0499 | 0.0641 | 0.0728 | 0.0499 | 0.0641 |
| Sens 5 | 20% | 31% | 18% | 20% | 18% | 28% | 12% | 25% | 22% |
| Spec 5 | 81% | 80% | 80% | 81% | 80% | 80% | 81% | 80% | 80% |
| Cutoff 6 | 0.176 | 0.162 | 0.176 | 0.176 | 0.162 | 0.176 | 0.176 | 0.162 | 0.176 |
| Sens 6 | 14% | 31% | 10% | 8% | 14% | 8% | 0% | 0% | 7% |
| Spec 6 | 90% | 91% | 90% | 90% | 91% | 90% | 90% | 91% | 90% |
| OR Quart 2 | 0.56 | 0.84 | 0.57 | 1.1 | 1.0 | 0.98 | 4.8 | 1.0 | 0.22 |
| p Value | 0.13 | 0.76 | 0.17 | 0.88 | 1.0 | 0.97 | 0.020 | 1.0 | 0.066 |
| 95% CI of | 0.26 | 0.27 | 0.26 | 0.49 | 0.28 | 0.43 | 1.3 | 0.24 | 0.045 |
| OR Quart 2 | 1.2 | 2.6 | 1.3 | 2.3 | 3.6 | 2.2 | 18 | 4.1 | 1.1 |
| OR Quart 3 | 1.0 | 0.70 | 1.2 | 1.3 | 1.6 | 1.8 | 1.4 | 1.0 | 1.5 |
| p Value | 1.0 | 0.55 | 0.59 | 0.44 | 0.40 | 0.12 | 0.70 | 1.0 | 0.45 |
| 95% CI of | 0.49 | 0.22 | 0.60 | 0.63 | 0.52 | 0.85 | 0.29 | 0.24 | 0.54 |
| OR Quart 3 | 2.0 | 2.3 | 2.5 | 2.9 | 5.2 | 4.0 | 6.4 | 4.1 | 3.9 |
| OR Quart 4 | 1.1 | 1.1 | 1.1 | 1.2 | 2.1 | 1.8 | 2.5 | 1.0 | 0.71 |
| p Value | 0.72 | 0.80 | 0.71 | 0.60 | 0.19 | 0.14 | 0.20 | 1.0 | 0.55 |
| 95% CI of | 0.56 | 0.40 | 0.56 | 0.57 | 0.69 | 0.83 | 0.62 | 0.24 | 0.23 |
| OR Quart 4 | 2.3 | 3.3 | 2.3 | 2.6 | 6.3 | 3.9 | 10 | 4.1 | 2.2 |

| Apolipoprotein E | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 3.26 | 2.40 | 3.26 | 2.03 | 3.26 | 2.72 |
| Average | 27.3 | 21.6 | 27.3 | 25.4 | 27.3 | 7.72 |
| Stdev | 162 | 164 | 162 | 183 | 162 | 12.5 |
| p (t-test) | | 0.71 | | 0.90 | | 0.40 |
| Min | 0.000147 | 0.00122 | 0.000147 | 0.000147 | 0.000147 | 0.000147 |
| Max | 2160 | 1960 | 2160 | 2140 | 2160 | 63.1 |
| n (Samp) | 499 | 143 | 499 | 143 | 499 | 48 |
| n (Patient) | 235 | 143 | 235 | 143 | 235 | 48 |
| sCr only | | | | | | |
| Median | 2.68 | 1.25 | 2.68 | 1.18 | 2.68 | 2.72 |
| Average | 22.5 | 3.42 | 22.5 | 5.41 | 22.5 | 8.50 |
| Stdev | 142 | 6.10 | 142 | 9.08 | 142 | 16.4 |
| p (t-test) | | 0.36 | | 0.39 | | 0.60 |
| Min | 0.000147 | 0.000147 | 0.000147 | 0.000147 | 0.000147 | 0.000147 |
| Max | 2160 | 33.8 | 2160 | 37.9 | 2160 | 82.5 |
| n (Samp) | 1100 | 46 | 1100 | 51 | 1100 | 28 |
| n (Patient) | 397 | 46 | 397 | 51 | 397 | 28 |
| UO only | | | | | | |
| Median | 2.97 | 3.06 | 2.97 | 2.03 | 2.97 | 2.24 |
| Average | 22.4 | 25.0 | 22.4 | 26.8 | 22.4 | 7.59 |
| Stdev | 131 | 173 | 131 | 190 | 131 | 13.1 |
| p (t-test) | | 0.85 | | 0.75 | | 0.44 |
| Min | 0.000147 | 0.00122 | 0.000147 | 0.000147 | 0.000147 | 0.00122 |
| Max | 2140 | 1960 | 2140 | 2140 | 2140 | 63.1 |
| n (Samp) | 487 | 130 | 487 | 133 | 487 | 47 |
| n (Patient) | 190 | 130 | 190 | 133 | 190 | 47 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.46 | 0.37 | 0.49 | 0.45 | 0.41 | 0.45 | 0.48 | 0.48 | 0.46 |
| SE | 0.028 | 0.045 | 0.029 | 0.028 | 0.043 | 0.029 | 0.044 | 0.056 | 0.045 |
| p | 0.20 | 0.0027 | 0.80 | 0.073 | 0.042 | 0.082 | 0.62 | 0.75 | 0.34 |
| nCohort 1 | 499 | 1100 | 487 | 499 | 1100 | 487 | 499 | 1100 | 487 |
| nCohort 2 | 143 | 46 | 130 | 143 | 51 | 133 | 48 | 28 | 47 |
| Cutoff 1 | 0.858 | 0.393 | 0.882 | 0.737 | 0.628 | 0.737 | 0.942 | 1.06 | 0.711 |
| Sens 1 | 71% | 72% | 70% | 71% | 71% | 71% | 71% | 71% | 70% |
| Spec 1 | 26% | 17% | 27% | 24% | 23% | 23% | 30% | 32% | 22% |
| Cutoff 2 | 0.467 | 0.103 | 0.554 | 0.411 | 0.404 | 0.393 | 0.211 | 0.103 | 0.211 |
| Sens 2 | 80% | 80% | 80% | 80% | 80% | 80% | 81% | 82% | 81% |
| Spec 2 | 19% | 8% | 19% | 18% | 17% | 15% | 12% | 8% | 11% |
| Cutoff 3 | 0.0862 | 0.0258 | 0.130 | 0.0999 | 0.0258 | 0.103 | 0.0520 | 0.00238 | 0.0263 |
| Sens 3 | 91% | 91% | 90% | 90% | 90% | 90% | 92% | 93% | 91% |
| Spec 3 | 8% | 6% | 10% | 9% | 6% | 10% | 8% | 4% | 8% |
| Cutoff 4 | 7.57 | 7.31 | 6.96 | 7.57 | 7.31 | 6.96 | 7.57 | 7.31 | 6.96 |
| Sens 4 | 27% | 13% | 33% | 22% | 20% | 23% | 31% | 29% | 30% |
| Spec 4 | 70% | 70% | 70% | 70% | 70% | 70% | 70% | 70% | 70% |
| Cutoff 5 | 13.3 | 12.7 | 11.4 | 13.3 | 12.7 | 11.4 | 13.3 | 12.7 | 11.4 |
| Sens 5 | 17% | 4% | 22% | 17% | 16% | 18% | 17% | 14% | 19% |
| Spec 5 | 81% | 80% | 80% | 81% | 80% | 80% | 81% | 80% | 80% |
| Cutoff 6 | 30.2 | 27.2 | 28.8 | 30.2 | 27.2 | 28.8 | 30.2 | 27.2 | 28.8 |
| Sens 6 | 8% | 2% | 10% | 6% | 6% | 6% | 6% | 7% | 9% |
| Spec 6 | 90% | 90% | 90% | 90% | 90% | 90% | 90% | 90% | 90% |
| OR Quart 2 | 1.2 | 2.6 | 0.74 | 1.2 | 1.4 | 1.1 | 0.59 | 1.3 | 0.83 |
| p Value | 0.56 | 0.12 | 0.28 | 0.55 | 0.49 | 0.66 | 0.26 | 0.59 | 0.67 |
| 95% CI of | 0.68 | 0.79 | 0.43 | 0.68 | 0.55 | 0.64 | 0.24 | 0.46 | 0.34 |
| OR Quart 2 | 2.0 | 8.3 | 1.3 | 2.1 | 3.5 | 2.0 | 1.5 | 3.9 | 2.0 |
| OR Quart 3 | 1.3 | 3.6 | 0.68 | 1.6 | 1.8 | 1.4 | 1.1 | 1.2 | 0.73 |
| p Value | 0.34 | 0.025 | 0.17 | 0.079 | 0.20 | 0.26 | 0.84 | 0.78 | 0.50 |
| 95% CI of | 0.76 | 1.2 | 0.39 | 0.95 | 0.74 | 0.79 | 0.49 | 0.39 | 0.30 |
| OR Quart 3 | 2.2 | 11 | 1.2 | 2.8 | 4.3 | 2.4 | 2.4 | 3.5 | 1.8 |
| OR Quart 4 | 1.4 | 4.8 | 1.0 | 1.7 | 2.3 | 1.7 | 1.0 | 1.2 | 1.4 |
| p Value | 0.27 | 0.0053 | 0.97 | 0.056 | 0.050 | 0.056 | 0.98 | 0.78 | 0.41 |
| 95% CI of | 0.79 | 1.6 | 0.60 | 0.99 | 1.0 | 0.99 | 0.45 | 0.39 | 0.63 |
| OR Quart 4 | 2.3 | 14 | 1.7 | 2.9 | 5.5 | 2.9 | 2.3 | 3.5 | 3.1 |

-continued

| | Apolipoprotein(a) | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 1.92 | 2.90 | 1.92 | 2.91 | 1.92 | 2.09 |
| Average | 26.2 | 147 | 26.2 | 48.0 | 26.2 | 32.2 |
| Stdev | 128 | 1540 | 128 | 402 | 128 | 151 |
| p (t-test) | | 0.092 | | 0.31 | | 0.77 |
| Min | 0.00770 | 0.00479 | 0.00770 | 0.00241 | 0.00770 | 0.00838 |
| Max | 1510 | 17500 | 1510 | 4580 | 1510 | 1000 |
| n (Samp) | 471 | 129 | 471 | 133 | 471 | 45 |
| n (Patient) | 230 | 129 | 230 | 133 | 230 | 45 |
| sCr only | | | | | | |
| Median | 2.04 | 1.80 | 2.04 | 2.90 | 2.04 | 3.02 |
| Average | 45.0 | 4.31 | 45.0 | 9.65 | 45.0 | 11.7 |
| Stdev | 578 | 9.90 | 578 | 30.9 | 578 | 31.2 |
| p (t-test) | | 0.64 | | 0.67 | | 0.77 |
| Min | 0.00241 | 0.00770 | 0.00241 | 0.00241 | 0.00241 | 0.00838 |
| Max | 17500 | 60.7 | 17500 | 215 | 17500 | 161 |
| n (Samp) | 1040 | 43 | 1040 | 49 | 1040 | 26 |
| n (Patient) | 391 | 43 | 391 | 49 | 391 | 26 |
| UO only | | | | | | |
| Median | 2.11 | 3.31 | 2.11 | 2.86 | 2.11 | 2.04 |
| Average | 20.0 | 172 | 20.0 | 50.6 | 20.0 | 30.5 |
| Stdev | 111 | 1630 | 111 | 420 | 111 | 153 |
| p (t-test) | | 0.049 | | 0.16 | | 0.57 |
| Min | 0.00770 | 0.00479 | 0.00770 | 0.00241 | 0.00770 | 0.00790 |
| Max | 1510 | 17500 | 1510 | 4580 | 1510 | 1000 |
| n (Samp) | 457 | 115 | 457 | 122 | 457 | 43 |
| n (Patient) | 185 | 115 | 185 | 122 | 185 | 43 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.58 | 0.46 | 0.61 | 0.58 | 0.53 | 0.58 | 0.53 | 0.59 | 0.51 |
| SE | 0.029 | 0.046 | 0.031 | 0.029 | 0.043 | 0.030 | 0.046 | 0.059 | 0.046 |
| p | 0.0097 | 0.40 | 4.2E−4 | 0.0068 | 0.48 | 0.0099 | 0.50 | 0.13 | 0.84 |
| nCohort 1 | 471 | 1040 | 457 | 471 | 1040 | 457 | 471 | 1040 | 457 |
| nCohort 2 | 129 | 43 | 115 | 133 | 49 | 122 | 45 | 26 | 43 |
| Cutoff 1 | 1.51 | 0.917 | 1.95 | 1.67 | 0.863 | 1.65 | 1.16 | 1.67 | 1.19 |
| Sens 1 | 71% | 72% | 70% | 71% | 71% | 72% | 71% | 73% | 72% |
| Spec 1 | 42% | 29% | 49% | 46% | 27% | 44% | 34% | 45% | 33% |
| Cutoff 2 | 0.977 | 0.556 | 1.23 | 1.16 | 0.108 | 1.24 | 0.766 | 1.65 | 0.766 |
| Sens 2 | 81% | 81% | 80% | 80% | 82% | 80% | 80% | 81% | 81% |
| Spec 2 | 31% | 22% | 33% | 34% | 12% | 33% | 27% | 45% | 26% |
| Cutoff 3 | 0.108 | 0.108 | 0.496 | 0.108 | 0.0112 | 0.430 | 0.479 | 0.369 | 0.479 |
| Sens 3 | 92% | 91% | 90% | 90% | 92% | 90% | 93% | 92% | 93% |
| Spec 3 | 14% | 12% | 22% | 14% | 4% | 17% | 19% | 15% | 18% |
| Cutoff 4 | 3.77 | 3.78 | 3.85 | 3.77 | 3.78 | 3.85 | 3.77 | 3.78 | 3.85 |
| Sens 4 | 39% | 23% | 43% | 37% | 37% | 36% | 31% | 42% | 23% |
| Spec 4 | 70% | 70% | 70% | 70% | 70% | 70% | 70% | 70% | 70% |
| Cutoff 5 | 5.63 | 5.65 | 5.30 | 5.63 | 5.65 | 5.30 | 5.63 | 5.65 | 5.30 |
| Sens 5 | 22% | 12% | 30% | 28% | 33% | 26% | 20% | 23% | 19% |
| Spec 5 | 80% | 80% | 80% | 80% | 80% | 80% | 80% | 80% | 80% |
| Cutoff 6 | 16.0 | 18.3 | 12.9 | 16.0 | 18.3 | 12.9 | 16.0 | 18.3 | 12.9 |
| Sens 6 | 12% | 7% | 17% | 11% | 8% | 11% | 13% | 15% | 14% |
| Spec 6 | 90% | 90% | 90% | 90% | 90% | 90% | 90% | 90% | 90% |
| OR Quart 2 | 1.4 | 1.9 | 1.8 | 1.1 | 0.28 | 1.6 | 1.2 | 1.2 | 2.0 |
| p Value | 0.28 | 0.18 | 0.098 | 0.76 | 0.024 | 0.17 | 0.64 | 0.74 | 0.13 |
| 95% CI of | 0.76 | 0.75 | 0.90 | 0.60 | 0.089 | 0.83 | 0.50 | 0.33 | 0.81 |
| OR Quart 2 | 2.6 | 4.8 | 3.5 | 2.0 | 0.85 | 2.9 | 3.1 | 4.7 | 4.9 |
| OR Quart 3 | 2.2 | 1.9 | 2.4 | 2.1 | 1.0 | 2.0 | 1.5 | 1.8 | 1.4 |
| p Value | 0.0072 | 0.18 | 0.0088 | 0.0093 | 1.0 | 0.020 | 0.38 | 0.37 | 0.48 |
| 95% CI of | 1.2 | 0.75 | 1.2 | 1.2 | 0.47 | 1.1 | 0.62 | 0.51 | 0.55 |
| OR Quart 3 | 4.0 | 4.8 | 4.6 | 3.7 | 2.1 | 3.7 | 3.6 | 6.1 | 3.6 |
| OR Quart 4 | 2.2 | 1.5 | 3.1 | 1.9 | 1.2 | 2.1 | 1.4 | 2.5 | 1.1 |
| p Value | 0.0072 | 0.46 | 5.2E−4 | 0.026 | 0.59 | 0.014 | 0.50 | 0.12 | 0.80 |
| 95% CI of | 1.2 | 0.54 | 1.6 | 1.1 | 0.59 | 1.2 | 0.56 | 0.79 | 0.42 |
| OR Quart 4 | 4.0 | 3.9 | 5.8 | 3.4 | 2.5 | 3.9 | 3.4 | 8.2 | 3.0 |

FIG. 2: Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | Complement C4-B | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 16.8 | 30.7 | 16.8 | 30.3 | 16.8 | 11.2 |
| Average | 54.2 | 59.9 | 54.2 | 69.1 | 54.2 | 35.1 |
| Stdev | 132 | 84.9 | 132 | 155 | 132 | 61.6 |
| p (t-test) | | 0.74 | | 0.37 | | 0.37 |
| Min | 0.00329 | 0.161 | 0.00329 | 0.211 | 0.00329 | 0.00263 |
| Max | 2000 | 417 | 2000 | 1150 | 2000 | 341 |
| n (Samp) | 927 | 62 | 927 | 70 | 927 | 39 |
| n (Patient) | 360 | 62 | 360 | 70 | 360 | 39 |
| sCr only | | | | | | |
| Median | 17.8 | 6.31 | 17.8 | 5.52 | 17.8 | 17.8 |
| Average | 59.9 | 13.8 | 59.9 | 29.0 | 59.9 | 40.1 |
| Stdev | 146 | 17.1 | 146 | 47.7 | 146 | 51.7 |
| p (t-test) | | 0.22 | | 0.37 | | 0.58 |
| Min | 0.00329 | 0.161 | 0.00329 | 0.211 | 0.00329 | 0.448 |
| Max | 2000 | 47.7 | 2000 | 173 | 2000 | 146 |
| n (Samp) | 1230 | 15 | 1230 | 18 | 1230 | 17 |
| n (Patient) | 440 | 15 | 440 | 18 | 440 | 17 |
| UO only | | | | | | |
| Median | 17.8 | 30.6 | 17.8 | 33.3 | 17.8 | 15.3 |
| Average | 55.4 | 63.6 | 55.4 | 72.3 | 55.4 | 39.5 |
| Stdev | 134 | 87.3 | 134 | 162 | 134 | 63.7 |
| p (t-test) | | 0.65 | | 0.34 | | 0.49 |
| Min | 0.00329 | 0.754 | 0.00329 | 0.383 | 0.00329 | 0.00263 |
| Max | 2000 | 417 | 2000 | 1150 | 2000 | 341 |
| n (Samp) | 815 | 57 | 815 | 63 | 815 | 34 |
| n (Patient) | 282 | 57 | 282 | 63 | 282 | 34 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.57 | 0.33 | 0.59 | 0.55 | 0.41 | 0.56 | 0.45 | 0.47 | 0.48 |
| SE | 0.039 | 0.077 | 0.041 | 0.037 | 0.071 | 0.039 | 0.048 | 0.072 | 0.051 |
| p | 0.071 | 0.027 | 0.031 | 0.13 | 0.20 | 0.10 | 0.29 | 0.71 | 0.69 |
| nCohort 1 | 927 | 1230 | 815 | 927 | 1230 | 815 | 927 | 1230 | 815 |
| nCohort 2 | 62 | 15 | 57 | 70 | 18 | 63 | 39 | 17 | 34 |
| Cutoff 1 | 10.5 | 2.00 | 13.2 | 6.41 | 4.28 | 7.34 | 3.33 | 6.89 | 4.30 |
| Sens 1 | 71% | 73% | 70% | 70% | 72% | 71% | 72% | 71% | 71% |
| Spec 1 | 41% | 15% | 43% | 32% | 25% | 33% | 22% | 31% | 25% |
| Cutoff 2 | 4.21 | 0.968 | 8.26 | 4.21 | 3.21 | 3.60 | 1.74 | 1.49 | 2.00 |
| Sens 2 | 81% | 80% | 81% | 80% | 83% | 81% | 82% | 82% | 82% |
| Spec 2 | 26% | 8% | 35% | 26% | 20% | 21% | 13% | 11% | 14% |
| Cutoff 3 | 0.990 | 0.587 | 2.46 | 1.70 | 1.66 | 1.74 | 0.752 | 0.544 | 1.66 |
| Sens 3 | 90% | 93% | 91% | 90% | 94% | 90% | 92% | 94% | 91% |
| Spec 3 | 8% | 4% | 16% | 13% | 12% | 13% | 6% | 4% | 12% |
| Cutoff 4 | 38.7 | 42.6 | 41.5 | 38.7 | 42.6 | 41.5 | 38.7 | 42.6 | 41.5 |
| Sens 4 | 44% | 13% | 40% | 40% | 22% | 43% | 26% | 35% | 32% |
| Spec 4 | 70% | 70% | 70% | 70% | 70% | 70% | 70% | 70% | 70% |
| Cutoff 5 | 61.6 | 68.8 | 65.8 | 61.6 | 68.8 | 65.8 | 61.6 | 68.8 | 65.8 |
| Sens 5 | 29% | 0% | 30% | 29% | 17% | 24% | 21% | 18% | 21% |
| Spec 5 | 80% | 80% | 80% | 80% | 80% | 80% | 80% | 80% | 80% |
| Cutoff 6 | 130 | 141 | 130 | 130 | 141 | 130 | 130 | 141 | 130 |
| Sens 6 | 11% | 0% | 12% | 14% | 6% | 14% | 8% | 6% | 6% |
| Spec 6 | 90% | 90% | 90% | 90% | 90% | 90% | 90% | 90% | 90% |
| OR Quart 2 | 1.1 | >4.1 | 1.4 | 1.0 | 1.0 | 0.91 | 0.59 | 1.3 | 0.77 |
| p Value | 0.84 | <0.21 | 0.50 | 1.0 | 1.0 | 0.83 | 0.32 | 0.74 | 0.62 |
| 95% CI of OR Quart 2 | 0.49 | >0.45 | 0.56 | 0.47 | 0.20 | 0.41 | 0.21 | 0.33 | 0.28 |
| | 2.4 | na | 3.3 | 2.1 | 5.0 | 2.1 | 1.7 | 4.7 | 2.1 |
| OR Quart 3 | 1.4 | >5.1 | 1.7 | 1.3 | 2.4 | 1.2 | 1.1 | 0.75 | 1.0 |
| p Value | 0.44 | <0.14 | 0.21 | 0.47 | 0.22 | 0.70 | 0.82 | 0.70 | 0.99 |
| 95% CI of OR Quart 3 | 0.63 | >0.59 | 0.73 | 0.64 | 0.61 | 0.54 | 0.46 | 0.17 | 0.39 |
| | 2.9 | na | 4.0 | 2.7 | 9.2 | 2.5 | 2.7 | 3.4 | 2.6 |
| OR Quart 4 | 1.8 | >6.1 | 2.5 | 1.8 | 1.7 | 1.9 | 1.2 | 1.3 | 1.0 |

-continued

| | | | | | | | | | |
|---|---|---|---|---|---|---|---|---|---|
| p Value | 0.11 | <0.094 | 0.027 | 0.098 | 0.48 | 0.088 | 0.66 | 0.73 | 0.99 |
| 95% CI of | 0.87 | >0.73 | 1.1 | 0.90 | 0.40 | 0.91 | 0.52 | 0.33 | 0.39 |
| OR Quart 4 | 3.8 | na | 5.5 | 3.5 | 7.1 | 3.8 | 2.9 | 4.7 | 2.6 |

C-C motif chemokine 7

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.584 | 0.662 | 0.584 | 0.643 | 0.584 | 0.584 |
| Average | 1.89 | 5.43 | 1.89 | 2.29 | 1.89 | 3.19 |
| Stdev | 9.38 | 13.3 | 9.38 | 6.39 | 9.38 | 7.98 |
| p (t-test) | | 0.0054 | | 0.73 | | 0.39 |
| Min | 0.146 | 0.146 | 0.146 | 0.146 | 0.146 | 0.264 |
| Max | 163 | 61.7 | 163 | 45.7 | 163 | 33.9 |
| n (Samp) | 930 | 62 | 930 | 70 | 930 | 39 |
| n (Patient) | 361 | 62 | 361 | 70 | 361 | 39 |
| sCr only | | | | | | |
| Median | 0.584 | 0.812 | 0.584 | 0.637 | 0.584 | 0.816 |
| Average | 2.24 | 8.59 | 2.24 | 5.64 | 2.24 | 3.49 |
| Stdev | 12.2 | 18.9 | 12.2 | 14.5 | 12.2 | 8.42 |
| p (t-test) | | 0.046 | | 0.24 | | 0.67 |
| Min | 0.146 | 0.264 | 0.146 | 0.282 | 0.146 | 0.264 |
| Max | 291 | 69.7 | 291 | 61.7 | 291 | 33.9 |
| n (Samp) | 1234 | 15 | 1234 | 18 | 1234 | 17 |
| n (Patient) | 441 | 15 | 441 | 18 | 441 | 17 |
| UO only | | | | | | |
| Median | 0.625 | 0.662 | 0.625 | 0.662 | 0.625 | 0.584 |
| Average | 2.01 | 8.67 | 2.01 | 4.29 | 2.01 | 2.87 |
| Stdev | 9.92 | 25.3 | 9.92 | 15.7 | 9.92 | 7.34 |
| p (t-test) | | 2.7E−5 | | 0.095 | | 0.62 |
| Min | 0.146 | 0.146 | 0.146 | 0.146 | 0.146 | 0.264 |
| Max | 163 | 166 | 163 | 114 | 163 | 33.0 |
| n (Samp) | 819 | 57 | 819 | 63 | 819 | 34 |
| n (Patient) | 283 | 57 | 283 | 63 | 283 | 34 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.63 | 0.65 | 0.61 | 0.56 | 0.59 | 0.54 | 0.56 | 0.64 | 0.52 |
| SE | 0.039 | 0.078 | 0.041 | 0.037 | 0.071 | 0.038 | 0.048 | 0.073 | 0.051 |
| p | 0.0012 | 0.059 | 0.0085 | 0.12 | 0.18 | 0.31 | 0.22 | 0.063 | 0.74 |
| nCohort 1 | 930 | 1234 | 819 | 930 | 1234 | 819 | 930 | 1234 | 819 |
| nCohort 2 | 62 | 15 | 57 | 70 | 18 | 63 | 39 | 17 | 34 |
| Cutoff 1 | 0.551 | 0.512 | 0.515 | 0.320 | 0.336 | 0.320 | 0.385 | 0.584 | 0.385 |
| Sens 1 | 77% | 73% | 77% | 73% | 78% | 73% | 72% | 82% | 71% |
| Spec 1 | 50% | 44% | 46% | 32% | 34% | 29% | 41% | 52% | 37% |
| Cutoff 2 | 0.336 | 0.424 | 0.336 | 0.319 | 0.320 | 0.319 | 0.336 | 0.584 | 0.336 |
| Sens 2 | 81% | 80% | 81% | 86% | 83% | 87% | 85% | 82% | 85% |
| Spec 2 | 36% | 39% | 34% | 28% | 30% | 26% | 36% | 52% | 34% |
| Cutoff 3 | 0.319 | 0.320 | 0.319 | 0.301 | 0.301 | 0.301 | 0.319 | 0.301 | 0.320 |
| Sens 3 | 92% | 93% | 93% | 96% | 94% | 95% | 92% | 94% | 91% |
| Spec 3 | 23% | 30% | 21% | 17% | 17% | 17% | 23% | 17% | 29% |
| Cutoff 4 | 1.04 | 1.04 | 1.04 | 1.04 | 1.04 | 1.04 | 1.04 | 1.04 | 1.04 |
| Sens 4 | 37% | 47% | 35% | 27% | 39% | 25% | 21% | 29% | 18% |
| Spec 4 | 74% | 72% | 72% | 74% | 72% | 72% | 74% | 72% | 72% |
| Cutoff 5 | 1.12 | 1.12 | 1.12 | 1.12 | 1.12 | 1.15 | 1.12 | 1.12 | 1.15 |
| Sens 5 | 37% | 47% | 32% | 26% | 39% | 22% | 21% | 24% | 18% |
| Spec 5 | 82% | 81% | 84% | 82% | 81% | 84% | 82% | 81% | 84% |
| Cutoff 6 | 1.59 | 1.59 | 1.59 | 1.59 | 1.59 | 1.59 | 1.59 | 1.59 | 1.59 |
| Sens 6 | 16% | 20% | 19% | 10% | 22% | 11% | 13% | 12% | 12% |
| Spec 6 | 94% | 94% | 94% | 94% | 94% | 94% | 94% | 94% | 94% |
| OR Quart 2 | 2.6 | 4.0 | 3.0 | 2.2 | 1.7 | 2.8 | 5.6 | 0 | 6.1 |
| p Value | 0.052 | 0.21 | 0.024 | 0.046 | 0.48 | 0.017 | 0.0065 | na | 0.0044 |
| 95% CI of | 0.99 | 0.45 | 1.2 | 1.0 | 0.40 | 1.2 | 1.6 | na | 1.8 |
| OR Quart 2 | 6.8 | 36 | 7.7 | 4.8 | 7.1 | 6.4 | 20 | na | 21 |
| OR Quart 3 | 3.2 | 3.0 | 2.4 | 2.2 | 1.0 | 2.5 | 4.2 | 5.1 | 2.7 |
| p Value | 0.017 | 0.34 | 0.075 | 0.046 | 1.0 | 0.034 | 0.029 | 0.036 | 0.14 |
| 95% CI of | 1.2 | 0.31 | 0.91 | 1.0 | 0.20 | 1.1 | 1.2 | 1.1 | 0.71 |
| OR Quart 3 | 8.1 | 29 | 6.4 | 4.8 | 5.0 | 5.9 | 15 | 24 | 10 |
| OR Quart 4 | 4.1 | 7.1 | 3.6 | 1.9 | 2.4 | 1.9 | 2.7 | 2.5 | 2.0 |
| p Value | 0.0025 | 0.067 | 0.0075 | 0.12 | 0.22 | 0.14 | 0.14 | 0.27 | 0.32 |

-continued

| | | | | | | | | | |
|---|---|---|---|---|---|---|---|---|---|
| 95% CI of | 1.6 | 0.87 | 1.4 | 0.84 | 0.61 | 0.80 | 0.71 | 0.48 | 0.50 |
| OR Quart 4 | 10 | 58 | 9.1 | 4.1 | 9.2 | 4.6 | 10 | 13 | 8.2 |

Vascular endothelial growth factor receptor 3

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 304 | 364 | 304 | 318 | 304 | 316 |
| Average | 314 | 398 | 314 | 379 | 314 | 354 |
| Stdev | 214 | 273 | 214 | 378 | 214 | 221 |
| p (t-test) | | 0.013 | | 0.056 | | 0.34 |
| Min | 1.37 | 81.1 | 1.37 | 1.37 | 1.37 | 3.04 |
| Max | 2070 | 1700 | 2070 | 2750 | 2070 | 913 |
| n (Samp) | 470 | 47 | 470 | 53 | 470 | 28 |
| n (Patient) | 239 | 47 | 239 | 53 | 239 | 28 |
| sCr only | | | | | | |
| Median | 318 | 354 | 318 | 351 | 318 | 512 |
| Average | 340 | 395 | 340 | 335 | 340 | 495 |
| Stdev | 248 | 284 | 248 | 113 | 248 | 264 |
| p (t-test) | | 0.51 | | 0.95 | | 0.040 |
| Min | 1.37 | 76.2 | 1.37 | 145 | 1.37 | 161 |
| Max | 2750 | 901 | 2750 | 512 | 2750 | 913 |
| n (Samp) | 630 | 9 | 630 | 10 | 630 | 11 |
| n (Patient) | 293 | 9 | 293 | 10 | 293 | 11 |
| UO only | | | | | | |
| Median | 308 | 364 | 308 | 315 | 308 | 318 |
| Average | 322 | 394 | 322 | 384 | 322 | 367 |
| Stdev | 217 | 274 | 217 | 402 | 217 | 225 |
| p (t-test) | | 0.042 | | 0.091 | | 0.31 |
| Min | 1.37 | 81.1 | 1.37 | 1.37 | 1.37 | 3.04 |
| Max | 2070 | 1700 | 2070 | 2750 | 2070 | 901 |
| n (Samp) | 438 | 43 | 438 | 47 | 438 | 25 |
| n (Patient) | 209 | 43 | 209 | 47 | 209 | 25 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.59 | 0.54 | 0.58 | 0.55 | 0.54 | 0.54 | 0.54 | 0.68 | 0.55 |
| SE | 0.045 | 0.099 | 0.047 | 0.043 | 0.094 | 0.045 | 0.057 | 0.090 | 0.061 |
| p | 0.039 | 0.66 | 0.083 | 0.22 | 0.69 | 0.38 | 0.45 | 0.043 | 0.41 |
| nCohort 1 | 470 | 630 | 438 | 470 | 630 | 438 | 470 | 630 | 438 |
| nCohort 2 | 47 | 9 | 43 | 53 | 10 | 47 | 28 | 11 | 25 |
| Cutoff 1 | 249 | 247 | 242 | 249 | 305 | 249 | 249 | 264 | 277 |
| Sens 1 | 70% | 78% | 72% | 72% | 70% | 70% | 71% | 73% | 72% |
| Spec 1 | 39% | 35% | 36% | 39% | 47% | 37% | 39% | 40% | 44% |
| Cutoff 2 | 178 | 76.8 | 178 | 174 | 230 | 171 | 166 | 249 | 242 |
| Sens 2 | 83% | 89% | 81% | 81% | 80% | 81% | 82% | 82% | 80% |
| Spec 2 | 25% | 11% | 23% | 24% | 33% | 22% | 24% | 37% | 36% |
| Cutoff 3 | 163 | 74.3 | 163 | 74.3 | 208 | 61.2 | 120 | 166 | 120 |
| Sens 3 | 91% | 100% | 91% | 91% | 90% | 94% | 93% | 91% | 92% |
| Spec 3 | 22% | 9% | 20% | 11% | 29% | 9% | 15% | 20% | 13% |
| Cutoff 4 | 397 | 414 | 397 | 397 | 414 | 397 | 397 | 414 | 397 |
| Sens 4 | 38% | 22% | 42% | 38% | 30% | 38% | 29% | 64% | 28% |
| Spec 4 | 71% | 71% | 70% | 71% | 71% | 70% | 71% | 71% | 70% |
| Cutoff 5 | 445 | 469 | 445 | 445 | 469 | 445 | 445 | 469 | 445 |
| Sens 5 | 28% | 22% | 30% | 26% | 10% | 32% | 25% | 55% | 24% |
| Spec 5 | 81% | 80% | 81% | 81% | 80% | 81% | 81% | 80% | 81% |
| Cutoff 6 | 534 | 574 | 537 | 534 | 574 | 537 | 534 | 574 | 537 |
| Sens 6 | 19% | 22% | 19% | 11% | 0% | 13% | 14% | 36% | 16% |
| Spec 6 | 90% | 90% | 91% | 90% | 90% | 91% | 90% | 90% | 91% |
| OR Quart 2 | 1.3 | 0.49 | 0.68 | 1.1 | 3.0 | 0.91 | 1.2 | 1.0 | 1.2 |
| p Value | 0.63 | 0.57 | 0.45 | 0.84 | 0.34 | 0.83 | 0.79 | 1.0 | 0.77 |
| 95% CI of | 0.48 | 0.044 | 0.25 | 0.46 | 0.31 | 0.38 | 0.38 | 0.14 | 0.36 |
| OR Quart 2 | 3.3 | 5.5 | 1.9 | 2.6 | 30 | 2.1 | 3.6 | 7.2 | 4.0 |
| OR Quart 3 | 2.0 | 2.0 | 1.2 | 1.3 | 5.1 | 0.64 | 1.4 | 0 | 1.6 |
| p Value | 0.13 | 0.42 | 0.65 | 0.54 | 0.14 | 0.35 | 0.58 | na | 0.40 |
| 95% CI of | 0.81 | 0.36 | 0.51 | 0.56 | 0.59 | 0.25 | 0.46 | na | 0.52 |
| OR Quart 3 | 4.9 | 11 | 2.9 | 3.0 | 44 | 1.6 | 4.0 | na | 5.1 |
| OR Quart 4 | 1.8 | 0.99 | 1.4 | 1.5 | 1.0 | 1.4 | 1.2 | 3.6 | 1.2 |

-continued

| | | | | | | | | | |
|---|---|---|---|---|---|---|---|---|---|
| p Value | 0.19 | 0.99 | 0.40 | 0.32 | 1.0 | 0.44 | 0.79 | 0.11 | 0.77 |
| 95% CI of | 0.74 | 0.14 | 0.61 | 0.67 | 0.062 | 0.62 | 0.38 | 0.73 | 0.36 |
| OR Quart 4 | 4.5 | 7.1 | 3.4 | 3.4 | 16 | 3.0 | 3.6 | 18 | 4.0 |

Interferon alpha-2

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.0967 | 0.104 | 0.0967 | 0.0974 | 0.0967 | 0.122 |
| Average | 7.76 | 13.4 | 7.76 | 8.07 | 7.76 | 11.1 |
| Stdev | 17.7 | 23.4 | 17.7 | 17.5 | 17.7 | 16.9 |
| p (t-test) | | 0.018 | | 0.89 | | 0.24 |
| Min | 0.0238 | 0.0348 | 0.0238 | 0.0348 | 0.0238 | 0.0348 |
| Max | 126 | 99.7 | 126 | 77.3 | 126 | 74.5 |
| n (Samp) | 930 | 62 | 930 | 70 | 930 | 39 |
| n (Patient) | 361 | 62 | 361 | 70 | 361 | 39 |
| sCr only | | | | | | |
| Median | 0.0967 | 0.0724 | 0.0967 | 0.0864 | 0.0967 | 0.0967 |
| Average | 7.73 | 4.18 | 7.73 | 9.65 | 7.73 | 7.16 |
| Stdev | 18.1 | 13.1 | 18.1 | 22.9 | 18.1 | 12.2 |
| p (t-test) | | 0.45 | | 0.66 | | 0.90 |
| Min | 0.0238 | 0.0238 | 0.0238 | 0.0348 | 0.0238 | 0.0369 |
| Max | 126 | 50.5 | 126 | 77.3 | 126 | 39.0 |
| n (Samp) | 1234 | 15 | 1234 | 18 | 1234 | 17 |
| n (Patient) | 441 | 15 | 441 | 18 | 441 | 17 |
| UO only | | | | | | |
| Median | 0.0967 | 0.104 | 0.0967 | 0.0974 | 0.0967 | 1.02 |
| Average | 7.47 | 15.1 | 7.47 | 6.62 | 7.47 | 12.4 |
| Stdev | 17.2 | 24.8 | 17.2 | 14.3 | 17.2 | 18.2 |
| p (t-test) | | 0.0019 | | 0.70 | | 0.10 |
| Min | 0.0238 | 0.0348 | 0.0238 | 0.0348 | 0.0238 | 0.0348 |
| Max | 126 | 99.7 | 126 | 66.2 | 126 | 74.5 |
| n (Samp) | 819 | 57 | 819 | 63 | 819 | 34 |
| n (Patient) | 283 | 57 | 283 | 63 | 283 | 34 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.57 | 0.40 | 0.59 | 0.55 | 0.48 | 0.55 | 0.60 | 0.57 | 0.61 |
| SE | 0.039 | 0.078 | 0.041 | 0.037 | 0.069 | 0.039 | 0.049 | 0.073 | 0.052 |
| p | 0.062 | 0.19 | 0.036 | 0.19 | 0.83 | 0.16 | 0.041 | 0.31 | 0.039 |
| nCohort 1 | 930 | 1234 | 819 | 930 | 1234 | 819 | 930 | 1234 | 819 |
| nCohort 2 | 62 | 15 | 57 | 70 | 18 | 63 | 39 | 17 | 34 |
| Cutoff 1 | 0.0724 | 0.0606 | 0.0724 | 0.0754 | 0.0435 | 0.0754 | 0.0754 | 0.0754 | 0.0815 |
| Sens 1 | 71% | 73% | 72% | 70% | 78% | 75% | 72% | 76% | 71% |
| Spec 1 | 40% | 26% | 38% | 44% | 19% | 42% | 44% | 45% | 47% |
| Cutoff 2 | 0.0656 | 0.0369 | 0.0656 | 0.0709 | 0.0398 | 0.0709 | 0.0435 | 0.0724 | 0.0435 |
| Sens 2 | 84% | 80% | 82% | 81% | 83% | 83% | 82% | 82% | 82% |
| Spec 2 | 29% | 11% | 27% | 36% | 15% | 34% | 19% | 41% | 17% |
| Cutoff 3 | 0.0398 | 0.0238 | 0.0398 | 0.0398 | 0.0369 | 0.0398 | 0.0369 | 0.0398 | 0.0369 |
| Sens 3 | 92% | 93% | 91% | 93% | 94% | 94% | 92% | 94% | 91% |
| Spec 3 | 14% | 3% | 12% | 14% | 11% | 12% | 10% | 15% | 10% |
| Cutoff 4 | 0.311 | 0.311 | 0.311 | 0.311 | 0.311 | 0.311 | 0.311 | 0.311 | 0.311 |
| Sens 4 | 34% | 13% | 39% | 24% | 17% | 25% | 49% | 35% | 50% |
| Spec 4 | 73% | 74% | 73% | 73% | 74% | 73% | 73% | 74% | 73% |
| Cutoff 5 | 10.9 | 10.8 | 9.93 | 10.9 | 10.8 | 9.93 | 10.9 | 10.8 | 9.93 |
| Sens 5 | 32% | 13% | 37% | 20% | 17% | 21% | 38% | 29% | 44% |
| Spec 5 | 80% | 80% | 80% | 80% | 80% | 80% | 80% | 80% | 80% |
| Cutoff 6 | 30.2 | 29.7 | 30.0 | 30.2 | 29.7 | 30.0 | 30.2 | 29.7 | 30.0 |
| Sens 6 | 19% | 7% | 21% | 11% | 17% | 8% | 13% | 6% | 15% |
| Spec 6 | 90% | 90% | 90% | 90% | 90% | 90% | 90% | 90% | 90% |
| OR Quart 2 | 2.0 | 1.0 | 1.5 | 1.4 | 2.0 | 1.6 | 0.62 | 3.0 | 0.56 |
| p Value | 0.090 | 1.00 | 0.31 | 0.44 | 0.32 | 0.29 | 0.40 | 0.18 | 0.37 |
| 95% CI of | 0.90 | 0.14 | 0.67 | 0.63 | 0.50 | 0.67 | 0.20 | 0.61 | 0.16 |
| OR Quart 2 | 4.3 | 7.2 | 3.5 | 2.9 | 8.1 | 3.7 | 1.9 | 15 | 2.0 |
| OR Quart 3 | 1.2 | 3.6 | 1.1 | 2.2 | 1.0 | 2.9 | 1.3 | 2.0 | 1.1 |
| p Value | 0.66 | 0.11 | 0.82 | 0.030 | 1.0 | 0.0089 | 0.63 | 0.42 | 0.79 |
| 95% CI of | 0.51 | 0.74 | 0.46 | 1.1 | 0.20 | 1.3 | 0.49 | 0.36 | 0.41 |
| OR Quart 3 | 2.9 | 17 | 2.7 | 4.5 | 5.0 | 6.3 | 3.3 | 11 | 3.2 |
| OR Quart 4 | 2.2 | 2.0 | 2.2 | 1.4 | 2.0 | 1.8 | 2.1 | 2.5 | 2.2 |
| p Value | 0.046 | 0.42 | 0.045 | 0.34 | 0.32 | 0.16 | 0.10 | 0.27 | 0.089 |

-continued

| | | | | | | | | | |
|---|---|---|---|---|---|---|---|---|---|
| 95% CI of | 1.0 | 0.37 | 1.0 | 0.68 | 0.50 | 0.79 | 0.87 | 0.48 | 0.89 |
| OR Quart 4 | 4.8 | 11 | 4.8 | 3.1 | 8.1 | 4.2 | 4.9 | 13 | 5.6 |

Insulin-like growth factor-binding protein 4

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.733 | 0.441 | 0.733 | 0.923 | 0.733 | 0.660 |
| Average | 1.83 | 1.47 | 1.83 | 2.61 | 1.83 | 0.852 |
| Stdev | 6.92 | 2.61 | 6.92 | 4.90 | 6.92 | 0.999 |
| p (t-test) | | 0.77 | | 0.49 | | 0.53 |
| Min | 0.0319 | 0.0319 | 0.0319 | 0.0319 | 0.0319 | 0.0319 |
| Max | 85.6 | 13.8 | 85.6 | 28.0 | 85.6 | 3.77 |
| n (Samp) | 322 | 31 | 322 | 40 | 322 | 20 |
| n (Patient) | 185 | 31 | 185 | 40 | 185 | 20 |
| sCr only | | | | | | |
| Median | nd | nd | 0.733 | 0.733 | 0.733 | 1.80 |
| Average | nd | nd | 1.77 | 2.04 | 1.77 | 2.08 |
| Stdev | nd | nd | 6.31 | 3.45 | 6.31 | 2.18 |
| p (t-test) | nd | nd | | 0.91 | | 0.89 |
| Min | nd | nd | 0.0319 | 0.0319 | 0.0319 | 0.0612 |
| Max | nd | nd | 85.6 | 9.68 | 85.6 | 6.53 |
| n (Samp) | nd | nd | 416 | 7 | 416 | 8 |
| n (Patient) | nd | nd | 221 | 7 | 221 | 8 |
| UO only | | | | | | |
| Median | 0.733 | 0.419 | 0.733 | 0.923 | 0.733 | 0.733 |
| Average | 1.91 | 1.67 | 1.91 | 2.55 | 1.91 | 0.946 |
| Stdev | 7.28 | 3.20 | 7.28 | 4.93 | 7.28 | 1.21 |
| p (t-test) | | 0.86 | | 0.60 | | 0.57 |
| Min | 0.0319 | 0.0319 | 0.0319 | 0.0319 | 0.0319 | 0.0319 |
| Max | 85.6 | 13.8 | 85.6 | 28.0 | 85.6 | 4.20 |
| n (Samp) | 290 | 30 | 290 | 37 | 290 | 19 |
| n (Patient) | 158 | 30 | 158 | 37 | 158 | 19 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.52 | nd | 0.52 | 0.58 | 0.54 | 0.59 | 0.48 | 0.66 | 0.48 |
| SE | 0.055 | nd | 0.056 | 0.050 | 0.11 | 0.052 | 0.067 | 0.11 | 0.069 |
| p | 0.69 | nd | 0.78 | 0.10 | 0.75 | 0.081 | 0.72 | 0.13 | 0.74 |
| nCohort 1 | 322 | nd | 290 | 322 | 416 | 290 | 322 | 416 | 290 |
| nCohort 2 | 31 | nd | 30 | 40 | 7 | 37 | 20 | 8 | 19 |
| Cutoff 1 | 0.184 | nd | 0.141 | 0.390 | 0.390 | 0.390 | 0.0439 | 0.390 | 0.0439 |
| Sens 1 | 71% | nd | 70% | 72% | 71% | 73% | 85% | 75% | 84% |
| Spec 1 | 29% | nd | 30% | 37% | 38% | 38% | 11% | 38% | 12% |
| Cutoff 2 | 0.0585 | nd | 0.0585 | 0.184 | 0.184 | 0.0585 | 0.0439 | 0.141 | 0.0439 |
| Sens 2 | 81% | nd | 80% | 80% | 86% | 86% | 85% | 88% | 84% |
| Spec 2 | 15% | nd | 15% | 29% | 30% | 15% | 11% | 30% | 12% |
| Cutoff 3 | 0 | nd | 0 | 0.0439 | 0 | 0.0439 | 0 | 0.0585 | 0 |
| Sens 3 | 100% | nd | 100% | 92% | 100% | 92% | 100% | 100% | 100% |
| Spec 3 | 0% | nd | 0% | 11% | 0% | 12% | 0% | 18% | 0% |
| Cutoff 4 | 0.957 | nd | 0.957 | 0.957 | 0.957 | 0.957 | 0.957 | 0.957 | 0.957 |
| Sens 4 | 32% | nd | 30% | 35% | 29% | 35% | 25% | 50% | 26% |
| Spec 4 | 76% | nd | 76% | 76% | 75% | 76% | 76% | 75% | 76% |
| Cutoff 5 | 1.37 | nd | 1.27 | 1.37 | 1.46 | 1.27 | 1.37 | 1.46 | 1.27 |
| Sens 5 | 26% | nd | 23% | 35% | 29% | 35% | 20% | 50% | 21% |
| Spec 5 | 80% | nd | 80% | 80% | 80% | 80% | 80% | 80% | 80% |
| Cutoff 6 | 3.09 | nd | 3.12 | 3.09 | 3.30 | 3.12 | 3.09 | 3.30 | 3.12 |
| Sens 6 | 10% | nd | 10% | 22% | 14% | 22% | 5% | 12% | 11% |
| Spec 6 | 90% | nd | 90% | 90% | 90% | 90% | 90% | 90% | 90% |
| OR Quart 2 | 1.0 | nd | 1.8 | 1.6 | 3.0 | 0.85 | 1.0 | 2.0 | 0.80 |
| p Value | 1.0 | nd | 0.30 | 0.34 | 0.34 | 0.77 | 0.98 | 0.57 | 0.75 |
| 95% CI of | 0.36 | nd | 0.61 | 0.60 | 0.31 | 0.29 | 0.28 | 0.18 | 0.21 |
| OR Quart 2 | 2.8 | nd | 5.1 | 4.4 | 30 | 2.5 | 3.6 | 23 | 3.1 |
| OR Quart 3 | 0.60 | nd | 0.82 | 1.2 | 0.99 | 1.1 | 0.59 | 1.0 | 0.59 |
| p Value | 0.39 | nd | 0.76 | 0.79 | 0.99 | 0.82 | 0.47 | 1.0 | 0.48 |
| 95% CI of | 0.19 | nd | 0.24 | 0.40 | 0.061 | 0.41 | 0.14 | 0.062 | 0.14 |

|  | | | | | | | | | |
|---|---|---|---|---|---|---|---|---|---|
| OR Quart 3 | 1.9 | nd | 2.8 | 3.3 | 16 | 3.1 | 2.5 | 16 | 2.6 |
| OR Quart 4 | 1.3 | nd | 1.6 | 2.2 | 2.0 | 1.7 | 1.5 | 4.1 | 1.5 |
| p Value | 0.64 | nd | 0.42 | 0.12 | 0.57 | 0.26 | 0.54 | 0.21 | 0.53 |
| 95% CI of | 0.47 | nd | 0.53 | 0.83 | 0.18 | 0.67 | 0.44 | 0.45 | 0.44 |
| OR Quart 4 | 3.4 | nd | 4.6 | 5.6 | 22 | 4.4 | 4.8 | 37 | 4.8 |

Insulin-like growth factor-binding protein 5

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 0.0682 | 0.397 | 0.0682 | 0.0682 | 0.0682 | 0.248 |
| Average | 0.587 | 1.22 | 0.587 | 0.858 | 0.587 | 0.859 |
| Stdev | 1.27 | 2.20 | 1.27 | 1.63 | 1.27 | 1.19 |
| p (t-test) |  | 0.014 |  | 0.22 |  | 0.35 |
| Min | 0.0116 | 0.0116 | 0.0116 | 0.0116 | 0.0116 | 0.0116 |
| Max | 9.43 | 10.0 | 9.43 | 8.53 | 9.43 | 3.48 |
| n (Samp) | 323 | 31 | 323 | 40 | 323 | 20 |
| n (Patient) | 186 | 31 | 186 | 40 | 186 | 20 |
| sCr only | | | | | | |
| Median | nd | nd | 0.0682 | 0.0407 | 0.0682 | 0.811 |
| Average | nd | nd | 0.624 | 0.664 | 0.624 | 1.23 |
| Stdev | nd | nd | 1.30 | 1.15 | 1.30 | 1.34 |
| p (t-test) | nd | nd |  | 0.94 |  | 0.19 |
| Min | nd | nd | 0.0116 | 0.0116 | 0.0116 | 0.0393 |
| Max | nd | nd | 9.43 | 2.99 | 9.43 | 3.48 |
| n (Samp) | nd | nd | 417 | 7 | 417 | 8 |
| n (Patient) | nd | nd | 222 | 7 | 222 | 8 |
| UO only | | | | | | |
| Median | 0.0682 | 0.397 | 0.0682 | 0.0682 | 0.0682 | 0.0938 |
| Average | 0.598 | 0.937 | 0.598 | 0.815 | 0.598 | 1.22 |
| Stdev | 1.39 | 1.50 | 1.39 | 1.64 | 1.39 | 2.37 |
| p (t-test) |  | 0.21 |  | 0.38 |  | 0.073 |
| Min | 0.0116 | 0.0116 | 0.0116 | 0.0116 | 0.0116 | 0.0116 |
| Max | 10.3 | 5.59 | 10.3 | 8.53 | 10.3 | 10.0 |
| n (Samp) | 291 | 30 | 291 | 37 | 291 | 19 |
| n (Patient) | 159 | 30 | 159 | 37 | 159 | 19 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.64 | nd | 0.64 | 0.52 | 0.48 | 0.51 | 0.61 | 0.73 | 0.59 |
| SE | 0.056 | nd | 0.057 | 0.049 | 0.11 | 0.051 | 0.069 | 0.10 | 0.071 |
| p | 0.0099 | nd | 0.012 | 0.66 | 0.84 | 0.83 | 0.12 | 0.026 | 0.22 |
| nCohort 1 | 323 | nd | 291 | 323 | 417 | 291 | 323 | 417 | 291 |
| nCohort 2 | 31 | nd | 30 | 40 | 7 | 37 | 20 | 8 | 19 |
| Cutoff 1 | 0.0544 | nd | 0.0544 | 0.0262 | 0.0262 | 0.0262 | 0.0400 | 0.0838 | 0.0358 |
| Sens 1 | 81% | nd | 80% | 75% | 71% | 73% | 75% | 75% | 79% |
| Spec 1 | 48% | nd | 48% | 23% | 23% | 22% | 38% | 59% | 35% |
| Cutoff 2 | 0.0544 | nd | 0.0544 | 0.0116 | 0.0116 | 0.0116 | 0.0358 | 0.0544 | 0.0262 |
| Sens 2 | 81% | nd | 80% | 90% | 86% | 89% | 85% | 88% | 84% |
| Spec 2 | 48% | nd | 48% | 11% | 12% | 12% | 36% | 46% | 22% |
| Cutoff 3 | 0 | nd | 0 | 0.0116 | 0 | 0 | 0.0116 | 0.0358 | 0 |
| Sens 3 | 100% | nd | 100% | 90% | 100% | 100% | 90% | 100% | 100% |
| Spec 3 | 0% | nd | 0% | 11% | 0% | 0% | 11% | 34% | 0% |
| Cutoff 4 | 0.397 | nd | 0.232 | 0.397 | 0.397 | 0.232 | 0.397 | 0.397 | 0.232 |
| Sens 4 | 39% | nd | 57% | 32% | 29% | 35% | 30% | 50% | 47% |
| Spec 4 | 79% | nd | 70% | 79% | 77% | 70% | 79% | 77% | 70% |
| Cutoff 5 | 0.518 | nd | 0.397 | 0.518 | 0.689 | 0.397 | 0.518 | 0.689 | 0.397 |
| Sens 5 | 35% | nd | 40% | 32% | 29% | 30% | 30% | 50% | 32% |
| Spec 5 | 80% | nd | 81% | 80% | 80% | 81% | 80% | 80% | 81% |
| Cutoff 6 | 1.99 | nd | 1.99 | 1.99 | 2.04 | 1.99 | 1.99 | 2.04 | 1.99 |
| Sens 6 | 16% | nd | 13% | 12% | 14% | 11% | 25% | 25% | 26% |
| Spec 6 | 91% | nd | 90% | 91% | 90% | 90% | 91% | 90% | 90% |
| OR Quart 2 | 0.78 | nd | 0.19 | 0.69 | 0.50 | 0.78 | 1.3 | >1.0 | 1.7 |
| p Value | 0.72 | nd | 0.13 | 0.45 | 0.57 | 0.62 | 0.71 | <0.99 | 0.48 |
| 95% CI of | 0.20 | nd | 0.022 | 0.26 | 0.044 | 0.29 | 0.29 | >0.062 | 0.39 |
| OR Quart 2 | 3.0 | nd | 1.7 | 1.8 | 5.5 | 2.1 | 6.1 | na | 7.3 |
| OR Quart 3 | 2.1 | nd | 2.6 | 0.69 | 1.0 | 0.78 | 1.3 | >3.1 | 1.0 |
| p Value | 0.19 | nd | 0.081 | 0.45 | 1.0 | 0.62 | 0.71 | <0.33 | 1.0 |
| 95% CI of | 0.70 | nd | 0.89 | 0.26 | 0.14 | 0.29 | 0.29 | >0.32 | 0.20 |
| OR Quart 3 | 6.5 | nd | 7.9 | 1.8 | 7.2 | 2.1 | 6.1 | na | 5.1 |

-continued

| | | | | | | | | | |
|---|---|---|---|---|---|---|---|---|---|
| OR Quart 4 | 2.6 | nd | 2.6 | 1.2 | 1.0 | 1.1 | 3.2 | >4.1 | 2.8 |
| p Value | 0.087 | nd | 0.086 | 0.68 | 1.0 | 0.82 | 0.090 | <0.21 | 0.14 |
| 95% CI of | 0.87 | nd | 0.87 | 0.51 | 0.14 | 0.45 | 0.83 | >0.45 | 0.72 |
| OR Quart 4 | 7.7 | nd | 7.8 | 2.8 | 7.2 | 2.8 | 12 | na | 11 |

Immunoglogulin G4

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 209 | 304 | 209 | 353 | 209 | 170 |
| Average | 471 | 576 | 471 | 661 | 471 | 294 |
| Stdev | 682 | 766 | 682 | 753 | 682 | 441 |
| p (t-test) | | 0.24 | | 0.025 | | 0.11 |
| Min | 0.00862 | 5.90 | 0.00862 | 2.63 | 0.00862 | 0.203 |
| Max | 2400 | 2400 | 2400 | 2400 | 2400 | 2400 |
| n (Samp) | 922 | 62 | 922 | 70 | 922 | 39 |
| n (Patient) | 358 | 62 | 358 | 70 | 358 | 39 |
| sCr only | | | | | | |
| Median | 219 | 288 | 219 | 330 | 219 | 354 |
| Average | 499 | 473 | 499 | 635 | 499 | 492 |
| Stdev | 704 | 698 | 704 | 799 | 704 | 600 |
| p (t-test) | | 0.89 | | 0.42 | | 0.97 |
| Min | 0.00642 | 27.3 | 0.00642 | 11.5 | 0.00642 | 8.44 |
| Max | 2400 | 2400 | 2400 | 2400 | 2400 | 2400 |
| n (Samp) | 1225 | 15 | 1225 | 18 | 1225 | 17 |
| n (Patient) | 438 | 15 | 438 | 18 | 438 | 17 |
| UO only | | | | | | |
| Median | 227 | 336 | 227 | 384 | 227 | 201 |
| Average | 487 | 639 | 487 | 743 | 487 | 364 |
| Stdev | 688 | 802 | 688 | 797 | 688 | 519 |
| p (t-test) | | 0.11 | | 0.0050 | | 0.30 |
| Min | 0.00962 | 5.90 | 0.00962 | 2.63 | 0.00962 | 0.203 |
| Max | 2400 | 2400 | 2400 | 2400 | 2400 | 2400 |
| n (Samp) | 810 | 57 | 810 | 63 | 810 | 34 |
| n (Patient) | 280 | 57 | 280 | 63 | 280 | 34 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.56 | 0.51 | 0.58 | 0.60 | 0.54 | 0.62 | 0.45 | 0.54 | 0.47 |
| SE | 0.039 | 0.076 | 0.041 | 0.037 | 0.070 | 0.039 | 0.048 | 0.072 | 0.051 |
| p | 0.11 | 0.88 | 0.055 | 0.0084 | 0.52 | 0.0019 | 0.28 | 0.55 | 0.60 |
| nCohort 1 | 922 | 1225 | 810 | 922 | 1225 | 810 | 922 | 1225 | 810 |
| nCohort 2 | 62 | 15 | 57 | 70 | 18 | 63 | 39 | 17 | 34 |
| Cutoff 1 | 174 | 143 | 189 | 146 | 103 | 182 | 75.7 | 118 | 78.5 |
| Sens 1 | 71% | 73% | 70% | 70% | 72% | 71% | 72% | 71% | 71% |
| Spec 1 | 46% | 38% | 46% | 41% | 31% | 46% | 28% | 34% | 27% |
| Cutoff 2 | 45.1 | 108 | 57.6 | 103 | 34.8 | 112 | 53.9 | 53.9 | 67.5 |
| Sens 2 | 81% | 80% | 81% | 80% | 83% | 81% | 82% | 82% | 82% |
| Spec 2 | 20% | 32% | 23% | 32% | 15% | 33% | 22% | 21% | 25% |
| Cutoff 3 | 28.9 | 36.0 | 28.0 | 27.6 | 21.7 | 81.1 | 10.6 | 11.0 | 26.3 |
| Sens 3 | 90% | 93% | 91% | 90% | 94% | 90% | 92% | 94% | 91% |
| Spec 3 | 13% | 15% | 12% | 13% | 10% | 27% | 6% | 6% | 11% |
| Cutoff 4 | 389 | 416 | 409 | 389 | 416 | 409 | 389 | 416 | 409 |
| Sens 4 | 37% | 20% | 42% | 46% | 39% | 48% | 23% | 41% | 26% |
| Spec 4 | 70% | 70% | 70% | 70% | 70% | 70% | 70% | 70% | 70% |
| Cutoff 5 | 581 | 622 | 609 | 581 | 622 | 609 | 581 | 622 | 609 |
| Sens 5 | 21% | 13% | 25% | 33% | 28% | 38% | 8% | 29% | 12% |
| Spec 5 | 80% | 80% | 80% | 80% | 80% | 80% | 80% | 80% | 80% |
| Cutoff 6 | 1540 | 2060 | 1570 | 1540 | 2060 | 1570 | 1540 | 2060 | 1570 |
| Sens 6 | 15% | 7% | 16% | 16% | 11% | 17% | 3% | 6% | 6% |
| Spec 6 | 90% | 90% | 90% | 90% | 90% | 90% | 90% | 90% | 90% |
| OR Quart 2 | 0.70 | 1.0 | 0.65 | 2.0 | 0.75 | 2.8 | 1.9 | 0.75 | 2.0 |
| p Value | 0.40 | 1.0 | 0.36 | 0.11 | 0.70 | 0.035 | 0.22 | 0.70 | 0.20 |
| 95% CI of | 0.31 | 0.20 | 0.26 | 0.85 | 0.17 | 1.1 | 0.68 | 0.17 | 0.69 |
| OR Quart 2 | 1.6 | 5.0 | 1.6 | 4.5 | 3.4 | 7.3 | 5.2 | 3.4 | 6.1 |
| OR Quart 3 | 1.5 | 2.4 | 1.6 | 2.0 | 1.00 | 2.4 | 2.2 | 1.3 | 2.5 |
| p Value | 0.29 | 0.22 | 0.20 | 0.11 | 1.00 | 0.075 | 0.11 | 0.74 | 0.093 |
| 95% CI of | 0.72 | 0.61 | 0.77 | 0.85 | 0.25 | 0.91 | 0.84 | 0.33 | 0.86 |
| OR Quart 3 | 3.0 | 9.2 | 3.4 | 4.5 | 4.0 | 6.4 | 6.0 | 4.7 | 7.2 |
| OR Quart 4 | 1.3 | 0.66 | 1.5 | 3.2 | 1.8 | 5.0 | 1.5 | 1.2 | 1.4 |

-continued

| | | | | | | | | | |
|---|---|---|---|---|---|---|---|---|---|
| p Value | 0.47 | 0.66 | 0.26 | 0.0030 | 0.37 | 5.2E−4 | 0.43 | 0.74 | 0.56 |
| 95% CI of | 0.64 | 0.11 | 0.72 | 1.5 | 0.51 | 2.0 | 0.53 | 0.33 | 0.44 |
| OR Quart 4 | 2.7 | 4.0 | 3.3 | 7.1 | 6.1 | 12 | 4.4 | 4.7 | 4.5 |

Interleukin-21

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 8.31 | 3.89 | 8.31 | 5.21 | 8.31 | 4.89 |
| Average | 11.3 | 7.73 | 11.3 | 7.98 | 11.3 | 7.18 |
| Stdev | 11.5 | 9.96 | 11.5 | 8.29 | 11.5 | 6.85 |
| p (t-test) | | 0.018 | | 0.019 | | 0.028 |
| Min | 0.00404 | 0.00761 | 0.00404 | 0.00404 | 0.00404 | 0.0177 |
| Max | 87.9 | 56.2 | 87.9 | 33.5 | 87.9 | 27.6 |
| n (Samp) | 928 | 62 | 928 | 70 | 928 | 39 |
| n (Patient) | 361 | 62 | 361 | 70 | 361 | 39 |
| sCr only | | | | | | |
| Median | 7.64 | 8.82 | 7.64 | 7.31 | 7.64 | 5.50 |
| Average | 10.7 | 15.1 | 10.7 | 9.85 | 10.7 | 10.5 |
| Stdev | 11.4 | 15.6 | 11.4 | 8.89 | 11.4 | 9.11 |
| p (t-test) | | 0.14 | | 0.76 | | 0.96 |
| Min | 0.00404 | 0.418 | 0.00404 | 0.0537 | 0.00404 | 1.29 |
| Max | 105 | 56.2 | 105 | 29.9 | 105 | 27.6 |
| n (Samp) | 1232 | 15 | 1232 | 18 | 1232 | 17 |
| n (Patient) | 441 | 15 | 441 | 18 | 441 | 17 |
| UO only | | | | | | |
| Median | 8.23 | 3.57 | 8.23 | 4.60 | 8.23 | 3.75 |
| Average | 11.0 | 6.36 | 11.0 | 7.33 | 11.0 | 6.34 |
| Stdev | 11.1 | 6.83 | 11.1 | 7.99 | 11.1 | 6.02 |
| p (t-test) | | 0.0020 | | 0.011 | | 0.016 |
| Min | 0.00404 | 0.00761 | 0.00404 | 0.00404 | 0.00404 | 0.0177 |
| Max | 87.9 | 26.7 | 87.9 | 33.5 | 87.9 | 19.3 |
| n (Samp) | 817 | 57 | 817 | 63 | 817 | 34 |
| n (Patient) | 283 | 57 | 283 | 63 | 283 | 34 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.40 | 0.58 | 0.38 | 0.42 | 0.50 | 0.41 | 0.41 | 0.53 | 0.39 |
| SE | 0.039 | 0.078 | 0.041 | 0.037 | 0.069 | 0.039 | 0.049 | 0.072 | 0.052 |
| p | 0.0075 | 0.29 | 0.0030 | 0.031 | 0.95 | 0.015 | 0.058 | 0.68 | 0.031 |
| nCohort 1 | 928 | 1232 | 817 | 928 | 1232 | 817 | 928 | 1232 | 817 |
| nCohort 2 | 62 | 15 | 57 | 70 | 18 | 63 | 39 | 17 | 34 |
| Cutoff 1 | 1.78 | 3.73 | 1.78 | 2.09 | 3.24 | 1.37 | 2.16 | 3.10 | 2.55 |
| Sens 1 | 71% | 73% | 70% | 70% | 72% | 71% | 72% | 71% | 71% |
| Spec 1 | 20% | 34% | 21% | 23% | 32% | 18% | 24% | 31% | 27% |
| Cutoff 2 | 1.26 | 3.01 | 1.04 | 1.13 | 2.34 | 1.04 | 0.728 | 2.18 | 0.386 |
| Sens 2 | 81% | 80% | 81% | 80% | 83% | 81% | 82% | 82% | 82% |
| Spec 2 | 16% | 31% | 16% | 16% | 26% | 16% | 13% | 25% | 12% |
| Cutoff 3 | 0.161 | 1.29 | 0.161 | 0.527 | 0.0537 | 0.527 | 0.0528 | 1.58 | 0.0528 |
| Sens 3 | 92% | 93% | 91% | 90% | 94% | 90% | 92% | 94% | 91% |
| Spec 3 | 9% | 18% | 10% | 12% | 7% | 13% | 6% | 21% | 7% |
| Cutoff 4 | 14.4 | 13.5 | 14.2 | 14.4 | 13.5 | 14.2 | 14.4 | 13.5 | 14.2 |
| Sens 4 | 18% | 47% | 14% | 21% | 33% | 19% | 15% | 35% | 15% |
| Spec 4 | 70% | 70% | 70% | 70% | 70% | 70% | 70% | 70% | 70% |
| Cutoff 5 | 18.6 | 17.9 | 18.6 | 18.6 | 17.9 | 18.6 | 18.6 | 17.9 | 18.6 |
| Sens 5 | 16% | 47% | 11% | 13% | 17% | 11% | 8% | 24% | 6% |
| Spec 5 | 80% | 80% | 80% | 80% | 80% | 80% | 80% | 80% | 80% |
| Cutoff 6 | 25.8 | 24.7 | 25.4 | 25.8 | 24.7 | 25.4 | 25.8 | 24.7 | 25.4 |
| Sens 6 | 5% | 20% | 2% | 4% | 11% | 5% | 3% | 12% | 0% |
| Spec 6 | 90% | 90% | 90% | 90% | 90% | 90% | 90% | 90% | 90% |
| OR Quart 2 | 0.90 | 2.5 | 2.1 | 1.8 | 2.0 | 1.9 | 4.2 | 0.80 | 3.1 |
| p Value | 0.82 | 0.27 | 0.15 | 0.15 | 0.33 | 0.18 | 0.029 | 0.74 | 0.094 |
| 95% CI of | 0.36 | 0.48 | 0.76 | 0.80 | 0.50 | 0.75 | 1.2 | 0.21 | 0.82 |
| OR Quart 2 | 2.3 | 13 | 5.6 | 4.2 | 8.1 | 4.9 | 15 | 3.0 | 12 |
| OR Quart 3 | 2.4 | 0.50 | 3.6 | 2.7 | 1.7 | 3.2 | 4.2 | 0.60 | 4.2 |
| p Value | 0.023 | 0.57 | 0.0075 | 0.013 | 0.48 | 0.0091 | 0.029 | 0.48 | 0.029 |
| 95% CI of | 1.1 | 0.045 | 1.4 | 1.2 | 0.40 | 1.3 | 1.2 | 0.14 | 1.2 |
| OR Quart 3 | 5.2 | 5.5 | 9.1 | 6.0 | 7.1 | 7.7 | 15 | 2.5 | 15 |
| OR Quart 4 | 2.1 | 3.5 | 3.4 | 2.6 | 1.3 | 3.4 | 4.2 | 1.00 | 3.5 |
| p Value | 0.063 | 0.12 | 0.011 | 0.019 | 0.71 | 0.0062 | 0.028 | 1.00 | 0.062 |

|  | | | | | | | | | |
|---|---|---|---|---|---|---|---|---|---|
| 95% CI of | 0.96 | 0.73 | 1.3 | 1.2 | 0.30 | 1.4 | 1.2 | 0.29 | 0.94 |
| OR Quart 4 | 4.6 | 17 | 8.7 | 5.8 | 6.0 | 8.1 | 15 | 3.5 | 13 |

| Interleukin-23 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 304 | 141 | 304 | 222 | 304 | 79.6 |
| Average | 548 | 252 | 548 | 379 | 548 | 292 |
| Stdev | 730 | 346 | 730 | 415 | 730 | 518 |
| p (t-test) | | 0.0016 | | 0.056 | | 0.030 |
| Min | 0.491 | 0.491 | 0.491 | 0.564 | 0.491 | 0.491 |
| Max | 8520 | 1350 | 8520 | 1540 | 8520 | 2340 |
| n (Samp) | 928 | 62 | 928 | 70 | 928 | 39 |
| n (Patient) | 361 | 62 | 361 | 70 | 361 | 39 |
| sCr only | | | | | | |
| Median | 246 | 105 | 246 | 293 | 246 | 190 |
| Average | 499 | 379 | 499 | 399 | 499 | 407 |
| Stdev | 691 | 583 | 691 | 423 | 691 | 494 |
| p (t-test) | | 0.50 | | 0.54 | | 0.58 |
| Min | 0.491 | 0.491 | 0.491 | 0.564 | 0.491 | 0.651 |
| Max | 8520 | 2120 | 8520 | 1370 | 8520 | 1820 |
| n (Samp) | 1232 | 15 | 1232 | 18 | 1232 | 17 |
| n (Patient) | 441 | 15 | 441 | 18 | 441 | 17 |
| UO only | | | | | | |
| Median | 311 | 141 | 311 | 173 | 311 | 75.4 |
| Average | 552 | 248 | 552 | 335 | 552 | 232 |
| Stdev | 733 | 341 | 733 | 398 | 733 | 466 |
| p (t-test) | | 0.0020 | | 0.020 | | 0.012 |
| Min | 0.491 | 0.491 | 0.491 | 0.564 | 0.491 | 0.491 |
| Max | 8520 | 1350 | 8520 | 1540 | 8520 | 2340 |
| n (Samp) | 817 | 57 | 817 | 63 | 817 | 34 |
| n (Patient) | 283 | 57 | 283 | 63 | 283 | 34 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.37 | 0.43 | 0.36 | 0.47 | 0.49 | 0.44 | 0.36 | 0.50 | 0.32 |
| SE | 0.039 | 0.077 | 0.041 | 0.036 | 0.069 | 0.039 | 0.049 | 0.071 | 0.052 |
| p | 8.8E-4 | 0.35 | 6.3E-4 | 0.36 | 0.87 | 0.097 | 0.0040 | 0.97 | 6.3E-4 |
| nCohort 1 | 928 | 1232 | 817 | 928 | 1232 | 817 | 928 | 1232 | 817 |
| nCohort 2 | 62 | 15 | 57 | 70 | 18 | 63 | 39 | 17 | 34 |
| Cutoff 1 | 1.06 | 1.05 | 1.06 | 48.7 | 1.21 | 16.8 | 1.06 | 79.3 | 1.06 |
| Sens 1 | 71% | 73% | 70% | 70% | 72% | 71% | 72% | 71% | 71% |
| Spec 1 | 18% | 19% | 18% | 29% | 24% | 25% | 18% | 35% | 18% |
| Cutoff 2 | 0.754 | 0.754 | 0.754 | 1.21 | 1.08 | 1.08 | 0.754 | 1.41 | 0.754 |
| Sens 2 | 87% | 87% | 84% | 80% | 83% | 81% | 82% | 82% | 82% |
| Spec 2 | 10% | 11% | 10% | 21% | 20% | 18% | 10% | 26% | 10% |
| Cutoff 3 | 0.682 | 0.682 | 0.643 | 0.844 | 0.682 | 0.844 | 0.552 | 0.844 | 0.552 |
| Sens 3 | 92% | 93% | 91% | 91% | 94% | 90% | 92% | 94% | 91% |
| Spec 3 | 6% | 6% | 4% | 13% | 6% | 13% | 1% | 14% | 1% |
| Cutoff 4 | 640 | 583 | 647 | 640 | 583 | 647 | 640 | 583 | 647 |
| Sens 4 | 13% | 27% | 11% | 26% | 39% | 19% | 13% | 29% | 6% |
| Spec 4 | 70% | 70% | 70% | 70% | 70% | 70% | 70% | 70% | 70% |
| Cutoff 5 | 923 | 857 | 935 | 923 | 857 | 935 | 923 | 857 | 935 |
| Sens 5 | 10% | 13% | 9% | 11% | 11% | 10% | 10% | 18% | 6% |
| Spec 5 | 80% | 80% | 80% | 80% | 80% | 80% | 80% | 80% | 80% |
| Cutoff 6 | 1520 | 1380 | 1460 | 1520 | 1380 | 1460 | 1520 | 1380 | 1460 |
| Sens 6 | 0% | 7% | 0% | 3% | 0% | 3% | 5% | 6% | 3% |
| Spec 6 | 90% | 90% | 90% | 90% | 90% | 90% | 90% | 90% | 90% |
| OR Quart 2 | 1.2 | 0.66 | 1.4 | 1.9 | 0.80 | 2.2 | 2.0 | 0.60 | 3.1 |
| p Value | 0.79 | 0.66 | 0.58 | 0.098 | 0.74 | 0.070 | 0.25 | 0.48 | 0.17 |
| 95% CI of | 0.41 | 0.11 | 0.46 | 0.89 | 0.21 | 0.94 | 0.60 | 0.14 | 0.61 |
| OR Quart 2 | 3.2 | 4.0 | 4.0 | 4.0 | 3.0 | 5.3 | 6.8 | 2.5 | 15 |
| OR Quart 3 | 3.7 | 1.7 | 3.8 | 2.1 | 0.60 | 2.8 | 2.8 | 1.2 | 5.7 |
| p Value | 0.0030 | 0.48 | 0.0051 | 0.052 | 0.48 | 0.016 | 0.078 | 0.76 | 0.024 |
| 95% CI of | 1.6 | 0.40 | 1.5 | 0.99 | 0.14 | 1.2 | 0.89 | 0.36 | 1.3 |
| OR Quart 3 | 8.7 | 7.1 | 9.5 | 4.4 | 2.5 | 6.5 | 9.0 | 4.0 | 26 |

-continued

| | | | | | | | | | |
|---|---|---|---|---|---|---|---|---|---|
| OR Quart 4 | 3.5 | 1.7 | 4.0 | 1.6 | 1.2 | 2.2 | 4.2 | 0.60 | 8.0 |
| p Value | 0.0042 | 0.48 | 0.0033 | 0.24 | 0.76 | 0.070 | 0.011 | 0.48 | 0.0061 |
| 95% CI of | 1.5 | 0.40 | 1.6 | 0.73 | 0.36 | 0.94 | 1.4 | 0.14 | 1.8 |
| OR Quart 4 | 8.4 | 7.1 | 10 | 3.5 | 4.0 | 5.3 | 13 | 2.5 | 36 |

Interleukin-28A

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 16.3 | 11.6 | 16.3 | 22.4 | 16.3 | 6.62 |
| Average | 34.6 | 24.2 | 34.6 | 32.9 | 34.6 | 18.5 |
| Stdev | 45.7 | 33.4 | 45.7 | 37.2 | 45.7 | 24.7 |
| p (t-test) | | 0.080 | | 0.76 | | 0.029 |
| Min | 0.0254 | 0.0517 | 0.0254 | 0.0495 | 0.0254 | 0.0517 |
| Max | 587 | 164 | 587 | 156 | 587 | 82.9 |
| n (Samp) | 928 | 62 | 928 | 70 | 928 | 39 |
| n (Patient) | 361 | 62 | 361 | 70 | 361 | 39 |
| sCr only | | | | | | |
| Median | 14.7 | 20.2 | 14.7 | 26.1 | 14.7 | 22.5 |
| Average | 32.5 | 29.6 | 32.5 | 36.7 | 32.5 | 27.9 |
| Stdev | 43.6 | 31.8 | 43.6 | 38.1 | 43.6 | 28.4 |
| p (t-test) | | 0.80 | | 0.68 | | 0.67 |
| Min | 0.0254 | 0.0777 | 0.0254 | 0.0517 | 0.0254 | 0.155 |
| Max | 587 | 105 | 587 | 131 | 587 | 82.9 |
| n (Samp) | 1232 | 15 | 1232 | 18 | 1232 | 17 |
| n (Patient) | 441 | 15 | 441 | 18 | 441 | 17 |
| UO only | | | | | | |
| Median | 18.7 | 8.37 | 18.7 | 14.6 | 18.7 | 3.36 |
| Average | 35.5 | 22.9 | 35.5 | 28.2 | 35.5 | 14.5 |
| Stdev | 46.4 | 33.0 | 46.4 | 34.9 | 46.4 | 19.7 |
| p (t-test) | | 0.044 | | 0.22 | | 0.0088 |
| Min | 0.0254 | 0.0517 | 0.0254 | 0.0495 | 0.0254 | 0.0517 |
| Max | 587 | 164 | 587 | 156 | 587 | 70.2 |
| n (Samp) | 817 | 57 | 817 | 63 | 817 | 34 |
| n (Patient) | 283 | 57 | 283 | 63 | 283 | 34 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.45 | 0.53 | 0.43 | 0.52 | 0.57 | 0.48 | 0.41 | 0.54 | 0.38 |
| SE | 0.039 | 0.076 | 0.041 | 0.036 | 0.071 | 0.038 | 0.049 | 0.072 | 0.052 |
| p | 0.20 | 0.70 | 0.097 | 0.59 | 0.34 | 0.54 | 0.081 | 0.62 | 0.018 |
| nCohort 1 | 928 | 1232 | 817 | 928 | 1232 | 817 | 928 | 1232 | 817 |
| nCohort 2 | 62 | 15 | 57 | 70 | 18 | 63 | 39 | 17 | 34 |
| Cutoff 1 | 0.194 | 4.33 | 0.194 | 8.60 | 16.3 | 0.243 | 0.194 | 4.11 | 0.194 |
| Sens 1 | 74% | 73% | 74% | 70% | 72% | 71% | 72% | 71% | 71% |
| Spec 1 | 24% | 39% | 24% | 41% | 52% | 28% | 24% | 38% | 24% |
| Cutoff 2 | 0.176 | 3.53 | 0.176 | 0.194 | 7.98 | 0.184 | 0.142 | 0.184 | 0.0896 |
| Sens 2 | 84% | 80% | 84% | 80% | 83% | 81% | 82% | 82% | 88% |
| Spec 2 | 22% | 38% | 21% | 24% | 41% | 22% | 18% | 25% | 14% |
| Cutoff 3 | 0.0896 | 0.0896 | 0.0896 | 0.142 | 0.0854 | 0.0854 | 0.0854 | 0.176 | 0.0854 |
| Sens 3 | 90% | 93% | 91% | 90% | 94% | 90% | 97% | 94% | 97% |
| Spec 3 | 14% | 15% | 14% | 18% | 12% | 12% | 12% | 23% | 12% |
| Cutoff 4 | 47.5 | 44.0 | 50.6 | 47.5 | 44.0 | 50.6 | 47.5 | 44.0 | 50.6 |
| Sens 4 | 16% | 33% | 14% | 24% | 22% | 19% | 15% | 29% | 9% |
| Spec 4 | 70% | 70% | 70% | 70% | 70% | 70% | 70% | 70% | 70% |
| Cutoff 5 | 65.2 | 61.1 | 66.6 | 65.2 | 61.1 | 66.6 | 65.2 | 61.1 | 66.6 |
| Sens 5 | 10% | 20% | 11% | 19% | 22% | 14% | 8% | 12% | 3% |
| Spec 5 | 80% | 80% | 80% | 80% | 80% | 80% | 80% | 80% | 80% |
| Cutoff 6 | 90.8 | 88.8 | 91.5 | 90.8 | 88.8 | 91.5 | 90.8 | 88.8 | 91.5 |
| Sens 6 | 5% | 7% | 4% | 9% | 11% | 6% | 0% | 0% | 0% |
| Spec 6 | 90% | 90% | 90% | 90% | 90% | 90% | 90% | 90% | 90% |
| OR Quart 2 | 1.8 | 2.0 | 2.4 | 1.1 | 0.66 | 1.9 | 1.8 | 1.3 | 5.2 |
| p Value | 0.17 | 0.42 | 0.059 | 0.72 | 0.65 | 0.098 | 0.28 | 0.70 | 0.035 |
| 95% CI of | 0.79 | 0.36 | 0.97 | 0.56 | 0.11 | 0.89 | 0.60 | 0.30 | 1.1 |
| OR Quart 2 | 3.9 | 11 | 6.0 | 2.3 | 4.0 | 4.1 | 5.5 | 6.0 | 24 |
| OR Quart 3 | 1.6 | 2.5 | 2.4 | 1.6 | 3.1 | 1.5 | 2.9 | 2.0 | 4.1 |
| p Value | 0.23 | 0.27 | 0.061 | 0.18 | 0.096 | 0.32 | 0.044 | 0.32 | 0.076 |
| 95% CI of | 0.73 | 0.48 | 0.96 | 0.81 | 0.82 | 0.68 | 1.0 | 0.50 | 0.86 |
| OR Quart 3 | 3.7 | 13 | 5.9 | 3.1 | 11 | 3.3 | 8.2 | 8.1 | 20 |
| OR Quart 4 | 2.0 | 2.0 | 2.7 | 1.00 | 1.3 | 1.5 | 2.3 | 1.3 | 7.5 |

-continued

| | | | | | | | | | |
|---|---|---|---|---|---|---|---|---|---|
| p Value | 0.088 | 0.42 | 0.028 | 0.99 | 0.71 | 0.32 | 0.13 | 0.71 | 0.0084 |
| 95% CI of | 0.90 | 0.36 | 1.1 | 0.48 | 0.30 | 0.68 | 0.78 | 0.30 | 1.7 |
| OR Quart 4 | 4.4 | 11 | 6.7 | 2.1 | 6.0 | 3.3 | 6.6 | 6.0 | 33 |

Interleukin-33

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 43.8 | 20.7 | 43.8 | 37.6 | 43.8 | 25.0 |
| Average | 60.0 | 31.0 | 60.0 | 44.0 | 60.0 | 34.4 |
| Stdev | 64.2 | 30.3 | 64.2 | 41.1 | 64.2 | 39.8 |
| p (t-test) | | 4.5E−4 | | 0.041 | | 0.014 |
| Min | 0.0232 | 0.0360 | 0.0232 | 0.0232 | 0.0232 | 0.0554 |
| Max | 958 | 112 | 958 | 235 | 958 | 148 |
| n (Samp) | 928 | 62 | 928 | 70 | 928 | 39 |
| n (Patient) | 361 | 62 | 361 | 70 | 361 | 39 |
| sCr only | | | | | | |
| Median | 41.0 | 33.6 | 41.0 | 43.0 | 41.0 | 26.5 |
| Average | 56.3 | 42.0 | 56.3 | 44.8 | 56.3 | 50.6 |
| Stdev | 61.2 | 34.0 | 61.2 | 34.6 | 61.2 | 47.5 |
| p (t-test) | | 0.37 | | 0.43 | | 0.70 |
| Min | 0.0232 | 3.22 | 0.0232 | 0.0591 | 0.0232 | 0.111 |
| Max | 958 | 109 | 958 | 117 | 958 | 146 |
| n (Samp) | 1232 | 15 | 1232 | 18 | 1232 | 17 |
| n (Patient) | 441 | 15 | 441 | 18 | 441 | 17 |
| UO only | | | | | | |
| Median | 43.9 | 17.8 | 43.9 | 32.9 | 43.9 | 19.2 |
| Average | 60.2 | 29.1 | 60.2 | 41.1 | 60.2 | 32.0 |
| Stdev | 65.3 | 29.7 | 65.3 | 41.1 | 65.3 | 38.0 |
| p (t-test) | | 3.8E−4 | | 0.023 | | 0.013 |
| Min | 0.0232 | 0.0360 | 0.0232 | 0.0232 | 0.0232 | 0.0554 |
| Max | 958 | 112 | 958 | 235 | 958 | 148 |
| n (Samp) | 817 | 57 | 817 | 63 | 817 | 34 |
| n (Patient) | 283 | 57 | 283 | 63 | 283 | 34 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.36 | 0.46 | 0.34 | 0.44 | 0.48 | 0.41 | 0.36 | 0.49 | 0.34 |
| SE | 0.039 | 0.076 | 0.040 | 0.037 | 0.069 | 0.039 | 0.049 | 0.071 | 0.052 |
| p | 2.1E−4 | 0.64 | 5.1E−5 | 0.091 | 0.77 | 0.028 | 0.0046 | 0.89 | 0.0028 |
| nCohort 1 | 928 | 1232 | 817 | 928 | 1232 | 817 | 928 | 1232 | 817 |
| nCohort 2 | 62 | 15 | 57 | 70 | 18 | 63 | 39 | 17 | 34 |
| Cutoff 1 | 10.4 | 14.5 | 7.17 | 16.2 | 23.2 | 14.5 | 7.06 | 17.0 | 7.06 |
| Sens 1 | 71% | 73% | 70% | 70% | 72% | 71% | 72% | 71% | 71% |
| Spec 1 | 21% | 26% | 18% | 26% | 34% | 24% | 18% | 29% | 18% |
| Cutoff 2 | 4.04 | 14.2 | 2.67 | 12.4 | 13.6 | 8.99 | 2.98 | 10.4 | 0.0768 |
| Sens 2 | 81% | 80% | 81% | 80% | 83% | 81% | 82% | 82% | 82% |
| Spec 2 | 15% | 26% | 14% | 23% | 25% | 19% | 15% | 22% | 9% |
| Cutoff 3 | 0.0837 | 10.4 | 0.0558 | 0.106 | 0.0749 | 0.106 | 0.0686 | 5.13 | 0.0686 |
| Sens 3 | 90% | 93% | 91% | 91% | 94% | 90% | 95% | 94% | 94% |
| Spec 3 | 11% | 22% | 4% | 11% | 9% | 11% | 6% | 17% | 6% |
| Cutoff 4 | 78.3 | 73.3 | 77.4 | 78.3 | 73.3 | 77.4 | 78.3 | 73.3 | 77.4 |
| Sens 4 | 8% | 20% | 7% | 16% | 22% | 13% | 13% | 24% | 12% |
| Spec 4 | 70% | 70% | 70% | 70% | 70% | 70% | 70% | 70% | 70% |
| Cutoff 5 | 99.1 | 93.9 | 98.2 | 99.1 | 93.9 | 98.2 | 99.1 | 93.9 | 98.2 |
| Sens 5 | 5% | 13% | 4% | 9% | 11% | 6% | 10% | 24% | 9% |
| Spec 5 | 80% | 80% | 80% | 80% | 80% | 80% | 80% | 80% | 80% |
| Cutoff 6 | 135 | 127 | 135 | 135 | 127 | 135 | 135 | 127 | 135 |
| Sens 6 | 0% | 0% | 0% | 1% | 0% | 2% | 5% | 6% | 6% |
| Spec 6 | 90% | 90% | 90% | 90% | 90% | 90% | 90% | 90% | 90% |
| OR Quart 2 | 3.9 | 2.0 | 4.9 | 3.2 | 2.0 | 2.8 | 1.8 | 1.0 | 2.0 |
| p Value | 0.016 | 0.42 | 0.013 | 0.0092 | 0.32 | 0.035 | 0.37 | 1.00 | 0.32 |
| 95% CI of | 1.3 | 0.37 | 1.4 | 1.3 | 0.50 | 1.1 | 0.51 | 0.25 | 0.50 |
| OR Quart 2 | 12 | 11 | 17 | 7.7 | 8.2 | 7.3 | 6.1 | 4.0 | 8.2 |
| OR Quart 3 | 4.8 | 3.0 | 5.7 | 3.2 | 2.0 | 3.6 | 2.8 | 1.3 | 2.7 |
| p Value | 0.0053 | 0.18 | 0.0064 | 0.0094 | 0.32 | 0.0075 | 0.078 | 0.73 | 0.14 |
| 95% CI of | 1.6 | 0.61 | 1.6 | 1.3 | 0.50 | 1.4 | 0.89 | 0.33 | 0.71 |
| OR Quart 3 | 14 | 15 | 20 | 7.6 | 8.1 | 9.1 | 9.0 | 4.7 | 10 |
| OR Quart 4 | 6.9 | 1.5 | 8.9 | 3.2 | 1.0 | 3.8 | 4.5 | 1.0 | 6.1 |
| p Value | 4.2E−4 | 0.65 | 4.2E−4 | 0.0092 | 1.00 | 0.0051 | 0.0075 | 1.00 | 0.0043 |

-continued

| | | | | | | | | | |
|---|---|---|---|---|---|---|---|---|---|
| 95% CI of | 2.4 | 0.25 | 2.6 | 1.3 | 0.20 | 1.5 | 1.5 | 0.25 | 1.8 |
| OR Quart 4 | 20 | 9.1 | 30 | 7.7 | 5.0 | 9.5 | 14 | 4.0 | 21 |

Interleukin-4 receptor alpha chain

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 46.5 | 47.2 | 46.5 | 69.4 | 46.5 | 48.6 |
| Average | 56.0 | 57.0 | 56.0 | 76.7 | 56.0 | 50.1 |
| Stdev | 49.4 | 56.5 | 49.4 | 60.5 | 49.4 | 32.8 |
| p (t-test) | | 0.89 | | 0.0057 | | 0.54 |
| Min | 0.839 | 2.31 | 0.839 | 2.31 | 0.839 | 4.67 |
| Max | 297 | 293 | 297 | 239 | 297 | 122 |
| n (Samp) | 460 | 46 | 460 | 51 | 460 | 28 |
| n (Patient) | 234 | 46 | 234 | 51 | 234 | 28 |
| sCr only | | | | | | |
| Median | 47.8 | 24.4 | 47.8 | 76.6 | 47.8 | 85.3 |
| Average | 58.1 | 40.6 | 58.1 | 68.4 | 58.1 | 82.2 |
| Stdev | 53.5 | 34.4 | 53.5 | 58.4 | 53.5 | 46.3 |
| p (t-test) | | 0.33 | | 0.53 | | 0.14 |
| Min | 0.839 | 10.3 | 0.839 | 4.67 | 0.839 | 10.3 |
| Max | 299 | 97.7 | 299 | 200 | 299 | 154 |
| n (Samp) | 617 | 9 | 617 | 11 | 617 | 11 |
| n (Patient) | 287 | 9 | 287 | 11 | 287 | 11 |
| UO only | | | | | | |
| Median | 46.2 | 49.3 | 46.2 | 68.0 | 46.2 | 49.3 |
| Average | 56.2 | 60.7 | 56.2 | 75.6 | 56.2 | 50.8 |
| Stdev | 50.8 | 57.8 | 50.8 | 60.5 | 50.8 | 32.2 |
| p (t-test) | | 0.59 | | 0.017 | | 0.60 |
| Min | 0.839 | 2.31 | 0.839 | 2.31 | 0.839 | 4.67 |
| Max | 297 | 293 | 297 | 239 | 297 | 122 |
| n (Samp) | 431 | 42 | 431 | 45 | 431 | 25 |
| n (Patient) | 206 | 42 | 206 | 45 | 206 | 25 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.50 | 0.45 | 0.51 | 0.61 | 0.56 | 0.60 | 0.50 | 0.67 | 0.51 |
| SE | 0.045 | 0.100 | 0.047 | 0.044 | 0.090 | 0.047 | 0.056 | 0.090 | 0.060 |
| p | 0.97 | 0.60 | 0.75 | 0.012 | 0.53 | 0.025 | 0.94 | 0.057 | 0.81 |
| nCohort 1 | 460 | 617 | 431 | 460 | 617 | 431 | 460 | 617 | 431 |
| nCohort 2 | 46 | 9 | 42 | 51 | 11 | 45 | 28 | 11 | 25 |
| Cutoff 1 | 11.8 | 11.8 | 19.1 | 35.1 | 24.0 | 35.1 | 38.0 | 67.2 | 38.0 |
| Sens 1 | 80% | 89% | 71% | 71% | 73% | 71% | 71% | 73% | 72% |
| Spec 1 | 25% | 24% | 33% | 42% | 34% | 42% | 42% | 64% | 43% |
| Cutoff 2 | 11.8 | 11.8 | 11.3 | 11.8 | 11.8 | 11.8 | 11.8 | 41.5 | 19.1 |
| Sens 2 | 80% | 89% | 81% | 86% | 82% | 84% | 86% | 82% | 80% |
| Spec 2 | 25% | 24% | 21% | 25% | 24% | 25% | 25% | 46% | 33% |
| Cutoff 3 | 7.93 | 9.16 | 6.56 | 11.3 | 6.56 | 9.16 | 9.16 | 11.8 | 10.3 |
| Sens 3 | 91% | 100% | 93% | 90% | 91% | 91% | 93% | 91% | 92% |
| Spec 3 | 13% | 12% | 6% | 20% | 6% | 13% | 13% | 24% | 20% |
| Cutoff 4 | 75.2 | 75.2 | 75.2 | 75.2 | 75.2 | 75.2 | 75.2 | 75.2 | 75.2 |
| Sens 4 | 24% | 22% | 26% | 45% | 55% | 40% | 18% | 64% | 16% |
| Spec 4 | 71% | 71% | 71% | 71% | 71% | 71% | 71% | 71% | 71% |
| Cutoff 5 | 93.9 | 95.7 | 93.9 | 93.9 | 95.7 | 93.9 | 93.9 | 95.7 | 93.9 |
| Sens 5 | 22% | 11% | 24% | 31% | 18% | 33% | 14% | 45% | 12% |
| Spec 5 | 80% | 80% | 80% | 80% | 80% | 80% | 80% | 80% | 80% |
| Cutoff 6 | 116 | 126 | 122 | 116 | 126 | 122 | 116 | 126 | 122 |
| Sens 6 | 17% | 0% | 17% | 20% | 9% | 18% | 7% | 18% | 0% |
| Spec 6 | 90% | 90% | 90% | 90% | 90% | 90% | 90% | 90% | 90% |
| OR Quart 2 | 1.3 | 1.0 | 1.2 | 1.5 | 1.0 | 1.0 | 2.3 | 2.0 | 2.8 |
| p Value | 0.50 | 0.99 | 0.64 | 0.46 | 1.0 | 1.0 | 0.16 | 0.57 | 0.14 |
| 95% CI of | 0.57 | 0.14 | 0.50 | 0.54 | 0.14 | 0.34 | 0.70 | 0.18 | 0.72 |
| OR Quart 2 | 3.2 | 7.2 | 3.1 | 3.9 | 7.2 | 2.9 | 7.8 | 22 | 11 |
| OR Quart 3 | 1.4 | 2.0 | 1.4 | 2.3 | 1.5 | 2.3 | 2.9 | 3.0 | 3.6 |
| p Value | 0.39 | 0.42 | 0.49 | 0.084 | 0.65 | 0.080 | 0.073 | 0.34 | 0.059 |
| 95% CI of | 0.62 | 0.37 | 0.55 | 0.89 | 0.25 | 0.91 | 0.90 | 0.31 | 0.95 |
| OR Quart 3 | 3.4 | 11 | 3.4 | 5.8 | 9.2 | 5.9 | 9.5 | 30 | 13 |
| OR Quart 4 | 0.90 | 0.50 | 1.1 | 3.0 | 2.0 | 2.5 | 1.0 | 5.1 | 1.3 |

|  |  |  |  |  |  |  |  |  |
|---|---|---|---|---|---|---|---|---|
| p Value | 0.83 | 0.57 | 0.83 | 0.018 | 0.42 | 0.054 | 1.0 | 0.14 | 0.70 |
| 95% CI of | 0.35 | 0.045 | 0.43 | 1.2 | 0.37 | 0.98 | 0.24 | 0.59 | 0.29 |
| OR Quart 4 | 2.3 | 5.6 | 2.8 | 7.4 | 11 | 6.3 | 4.1 | 44 | 6.2 |

Vascular endothelial growth factor receptor 2

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 545 | 857 | 545 | 746 | 545 | 455 |
| Average | 735 | 1230 | 735 | 997 | 735 | 642 |
| Stdev | 803 | 1210 | 803 | 952 | 803 | 706 |
| p (t-test) |  | 1.7E-4 |  | 0.030 |  | 0.56 |
| Min | 0.218 | 1.48 | 0.218 | 0.218 | 0.218 | 1.48 |
| Max | 7140 | 5940 | 7140 | 4750 | 7140 | 2820 |
| n (Samp) | 462 | 46 | 462 | 51 | 462 | 27 |
| n (Patient) | 235 | 46 | 235 | 51 | 235 | 27 |
| sCr only | | | | | | |
| Median | 651 | 806 | 651 | 658 | 651 | 609 |
| Average | 863 | 1060 | 863 | 954 | 863 | 522 |
| Stdev | 917 | 1180 | 917 | 975 | 917 | 406 |
| p (t-test) |  | 0.53 |  | 0.76 |  | 0.22 |
| Min | 0.218 | 1.48 | 0.218 | 1.48 | 0.218 | 1.48 |
| Max | 7140 | 3710 | 7140 | 2870 | 7140 | 1350 |
| n (Samp) | 618 | 9 | 618 | 10 | 618 | 11 |
| n (Patient) | 288 | 9 | 288 | 10 | 288 | 11 |
| UO only | | | | | | |
| Median | 539 | 932 | 539 | 825 | 539 | 495 |
| Average | 732 | 1240 | 732 | 1040 | 732 | 714 |
| Stdev | 805 | 1170 | 805 | 967 | 805 | 722 |
| p (t-test) |  | 2.4E-4 |  | 0.018 |  | 0.91 |
| Min | 0.218 | 10.8 | 0.218 | 0.218 | 0.218 | 1.48 |
| Max | 7140 | 5940 | 7140 | 4750 | 7140 | 2820 |
| n (Samp) | 433 | 42 | 433 | 45 | 433 | 24 |
| n (Patient) | 207 | 42 | 207 | 45 | 207 | 24 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.64 | 0.54 | 0.66 | 0.60 | 0.53 | 0.61 | 0.46 | 0.41 | 0.50 |
| SE | 0.046 | 0.099 | 0.048 | 0.044 | 0.093 | 0.046 | 0.058 | 0.091 | 0.061 |
| p | 0.0017 | 0.72 | 8.4E-4 | 0.028 | 0.78 | 0.017 | 0.53 | 0.30 | 1.00 |
| nCohort 1 | 462 | 618 | 433 | 462 | 618 | 433 | 462 | 618 | 433 |
| nCohort 2 | 46 | 9 | 42 | 51 | 10 | 45 | 27 | 11 | 24 |
| Cutoff 1 | 566 | 189 | 581 | 421 | 421 | 577 | 159 | 164 | 237 |
| Sens 1 | 72% | 78% | 71% | 71% | 70% | 71% | 70% | 73% | 71% |
| Spec 1 | 51% | 22% | 53% | 43% | 38% | 52% | 23% | 20% | 29% |
| Cutoff 2 | 292 | 152 | 333 | 304 | 354 | 228 | 106 | 134 | 106 |
| Sens 2 | 80% | 89% | 81% | 80% | 80% | 80% | 81% | 82% | 83% |
| Spec 2 | 34% | 20% | 37% | 35% | 35% | 27% | 20% | 18% | 18% |
| Cutoff 3 | 113 | 1.48 | 185 | 129 | 321 | 123 | 1.48 | 35.7 | 1.48 |
| Sens 3 | 91% | 100% | 90% | 90% | 90% | 91% | 100% | 91% | 100% |
| Spec 3 | 20% | 8% | 24% | 21% | 32% | 19% | 10% | 12% | 9% |
| Cutoff 4 | 907 | 1070 | 903 | 907 | 1070 | 903 | 907 | 1070 | 903 |
| Sens 4 | 48% | 33% | 50% | 39% | 20% | 44% | 26% | 9% | 29% |
| Spec 4 | 70% | 70% | 70% | 70% | 70% | 70% | 70% | 70% | 70% |
| Cutoff 5 | 1190 | 1410 | 1180 | 1190 | 1410 | 1180 | 1190 | 1410 | 1180 |
| Sens 5 | 33% | 33% | 36% | 29% | 20% | 33% | 22% | 0% | 25% |
| Spec 5 | 80% | 80% | 80% | 80% | 80% | 80% | 80% | 80% | 80% |
| Cutoff 6 | 1660 | 1850 | 1650 | 1660 | 1850 | 1650 | 1660 | 1850 | 1650 |
| Sens 6 | 26% | 11% | 24% | 12% | 20% | 11% | 7% | 0% | 8% |
| Spec 6 | 90% | 90% | 90% | 90% | 90% | 90% | 90% | 90% | 90% |
| OR Quart 2 | 0.87 | 0.33 | 1.4 | 1.3 | 4.1 | 0.60 | 0.83 | 2.0 | 0.83 |
| p Value | 0.79 | 0.34 | 0.57 | 0.63 | 0.21 | 0.39 | 0.77 | 0.57 | 0.77 |
| 95% CI of | 0.30 | 0.034 | 0.44 | 0.48 | 0.45 | 0.19 | 0.25 | 0.18 | 0.25 |
| OR Quart 2 | 2.5 | 3.2 | 4.6 | 3.3 | 37 | 1.9 | 2.8 | 23 | 2.8 |
| OR Quart 3 | 1.7 | 0.66 | 2.8 | 2.1 | 3.0 | 2.0 | 1.2 | 4.1 | 1.2 |
| p Value | 0.26 | 0.65 | 0.061 | 0.092 | 0.34 | 0.13 | 0.76 | 0.21 | 0.76 |
| 95% CI of | 0.68 | 0.11 | 0.96 | 0.88 | 0.31 | 0.81 | 0.39 | 0.45 | 0.39 |
| OR Quart 3 | 4.2 | 4.0 | 8.0 | 5.2 | 30 | 4.9 | 3.6 | 37 | 3.7 |

-continued

| | | | | | | | | | |
|---|---|---|---|---|---|---|---|---|---|
| OR Quart 4 | 2.5 | 0.99 | 3.8 | 2.3 | 2.0 | 2.3 | 1.6 | 4.1 | 1.0 |
| p Value | 0.043 | 0.99 | 0.012 | 0.067 | 0.57 | 0.066 | 0.42 | 0.21 | 0.99 |
| 95% CI of | 1.0 | 0.20 | 1.3 | 0.95 | 0.18 | 0.95 | 0.54 | 0.45 | 0.32 |
| OR Quart 4 | 5.9 | 5.0 | 11 | 5.5 | 22 | 5.5 | 4.5 | 37 | 3.2 |

Neural cell adhesion molecule 1

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 2640 | 3420 | 2640 | 2770 | 2640 | 2260 |
| Average | 3270 | 3890 | 3270 | 4280 | 3270 | 2770 |
| Stdev | 2970 | 2700 | 2970 | 6730 | 2970 | 2190 |
| p (t-test) | | 0.11 | | 0.015 | | 0.30 |
| Min | 6.83 | 85.5 | 6.83 | 375 | 6.83 | 138 |
| Max | 48400 | 15000 | 48400 | 55700 | 48400 | 9700 |
| n (Samp) | 926 | 62 | 926 | 70 | 926 | 39 |
| n (Patient) | 359 | 62 | 359 | 70 | 359 | 39 |
| sCr only | | | | | | |
| Median | 2800 | 2420 | 2800 | 2590 | 2800 | 2370 |
| Average | 3450 | 2380 | 3450 | 3790 | 3450 | 3200 |
| Stdev | 3250 | 1460 | 3250 | 2950 | 3250 | 2300 |
| p (t-test) | | 0.20 | | 0.66 | | 0.75 |
| Min | 6.83 | 301 | 6.83 | 921 | 6.83 | 932 |
| Max | 55700 | 4670 | 55700 | 10800 | 55700 | 8410 |
| n (Samp) | 1229 | 15 | 1229 | 18 | 1229 | 17 |
| n (Patient) | 439 | 15 | 439 | 18 | 439 | 17 |
| UO only | | | | | | |
| Median | 2730 | 4020 | 2730 | 3060 | 2730 | 2460 |
| Average | 3320 | 4690 | 3320 | 4760 | 3320 | 2920 |
| Stdev | 2980 | 4040 | 2980 | 7510 | 2980 | 2190 |
| p (t-test) | | 0.0011 | | 0.0016 | | 0.44 |
| Min | 0.234 | 85.5 | 0.234 | 375 | 0.234 | 138 |
| Max | 48400 | 26600 | 48400 | 55700 | 48400 | 9700 |
| n (Samp) | 814 | 57 | 814 | 63 | 814 | 34 |
| n (Patient) | 281 | 57 | 281 | 63 | 281 | 34 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.58 | 0.39 | 0.63 | 0.54 | 0.53 | 0.55 | 0.43 | 0.47 | 0.45 |
| SE | 0.039 | 0.078 | 0.041 | 0.036 | 0.070 | 0.039 | 0.049 | 0.072 | 0.052 |
| p | 0.040 | 0.16 | 0.0016 | 0.30 | 0.70 | 0.24 | 0.16 | 0.71 | 0.34 |
| nCohort 1 | 926 | 1229 | 814 | 926 | 1229 | 814 | 926 | 1229 | 814 |
| nCohort 2 | 62 | 15 | 57 | 70 | 18 | 63 | 39 | 17 | 34 |
| Cutoff 1 | 2290 | 1120 | 2720 | 2030 | 2080 | 2030 | 1250 | 1670 | 1650 |
| Sens 1 | 71% | 73% | 70% | 70% | 72% | 71% | 72% | 71% | 71% |
| Spec 1 | 44% | 14% | 50% | 37% | 35% | 34% | 17% | 26% | 26% |
| Cutoff 2 | 1570 | 849 | 1960 | 1210 | 1700 | 1210 | 962 | 965 | 1180 |
| Sens 2 | 81% | 80% | 81% | 80% | 83% | 81% | 82% | 82% | 82% |
| Spec 2 | 26% | 8% | 32% | 17% | 27% | 16% | 11% | 10% | 15% |
| Cutoff 3 | 863 | 615 | 1210 | 1040 | 1080 | 986 | 402 | 950 | 402 |
| Sens 3 | 90% | 93% | 91% | 90% | 94% | 90% | 92% | 94% | 91% |
| Spec 3 | 9% | 4% | 16% | 13% | 13% | 11% | 2% | 10% | 2% |
| Cutoff 4 | 3860 | 4020 | 3910 | 3860 | 4020 | 3910 | 3860 | 4020 | 3910 |
| Sens 4 | 44% | 7% | 51% | 37% | 39% | 40% | 21% | 35% | 21% |
| Spec 4 | 70% | 70% | 70% | 70% | 70% | 70% | 70% | 70% | 70% |
| Cutoff 5 | 4660 | 4940 | 4740 | 4660 | 4940 | 4740 | 4660 | 4940 | 4740 |
| Sens 5 | 34% | 0% | 42% | 29% | 28% | 32% | 18% | 24% | 18% |
| Spec 5 | 80% | 80% | 80% | 80% | 80% | 80% | 80% | 80% | 80% |
| Cutoff 6 | 6190 | 6480 | 6230 | 6190 | 6480 | 6230 | 6190 | 6480 | 6230 |
| Sens 6 | 21% | 0% | 25% | 17% | 17% | 17% | 8% | 6% | 9% |
| Spec 6 | 90% | 90% | 90% | 90% | 90% | 90% | 90% | 90% | 90% |
| OR Quart 2 | 0.83 | 6.1 | 1.5 | 1.1 | 2.0 | 1.3 | 0.88 | 0.16 | 1.1 |
| p Value | 0.66 | 0.095 | 0.37 | 0.71 | 0.33 | 0.45 | 0.80 | 0.096 | 0.79 |
| 95% CI of | 0.35 | 0.73 | 0.61 | 0.56 | 0.50 | 0.63 | 0.31 | 0.020 | 0.41 |
| OR Quart 2 | 1.9 | 51 | 3.8 | 2.3 | 8.1 | 2.8 | 2.5 | 1.4 | 3.2 |
| OR Quart 3 | 1.4 | 2.0 | 1.5 | 1.1 | 1.3 | 0.92 | 1.5 | 0.83 | 1.4 |
| p Value | 0.34 | 0.57 | 0.37 | 0.85 | 0.71 | 0.84 | 0.36 | 0.76 | 0.46 |
| 95% CI of | 0.68 | 0.18 | 0.61 | 0.52 | 0.30 | 0.41 | 0.62 | 0.25 | 0.54 |
| OR Quart 3 | 3.1 | 22 | 3.8 | 2.2 | 6.0 | 2.1 | 3.8 | 2.8 | 3.9 |
| OR Quart 4 | 2.0 | 6.1 | 3.4 | 1.5 | 1.7 | 1.7 | 1.5 | 0.83 | 1.3 |
| p Value | 0.058 | 0.095 | 0.0036 | 0.23 | 0.48 | 0.16 | 0.36 | 0.77 | 0.61 |

-continued

| | | | | | | | | |
|---|---|---|---|---|---|---|---|---|
| 95% CI of | 0.98 | 0.73 | 1.5 | 0.77 | 0.40 | 0.82 | 0.62 | 0.25 | 0.47 |
| OR Quart 4 | 4.1 | 51 | 7.7 | 3.0 | 7.1 | 3.4 | 3.8 | 2.8 | 3.6 |

Platelet-derived growth factor subunit B (dimer)

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 1.16 | 2.27 | 1.16 | 1.69 | 1.16 | 2.14 |
| Average | 3.31 | 3.21 | 3.31 | 22.5 | 3.31 | 2.17 |
| Stdev | 12.7 | 4.27 | 12.7 | 137 | 12.7 | 1.82 |
| p (t-test) | | 0.96 | | 5.2E−4 | | 0.64 |
| Min | 0.00246 | 0.00313 | 0.00246 | 0.00408 | 0.00246 | 0.00313 |
| Max | 270 | 24.9 | 270 | 935 | 270 | 8.46 |
| n (Samp) | 691 | 36 | 691 | 46 | 691 | 28 |
| n (Patient) | 280 | 36 | 280 | 46 | 280 | 28 |
| sCr only | | | | | | |
| Median | 1.17 | 2.02 | 1.17 | 2.53 | 1.17 | 2.18 |
| Average | 4.08 | 2.61 | 4.08 | 5.64 | 4.08 | 2.38 |
| Stdev | 33.0 | 1.80 | 33.0 | 8.01 | 33.0 | 2.33 |
| p (t-test) | | 0.90 | | 0.87 | | 0.85 |
| Min | 0.00246 | 0.709 | 0.00246 | 0.00741 | 0.00246 | 0.166 |
| Max | 935 | 5.92 | 935 | 26.6 | 935 | 8.93 |
| n (Samp) | 899 | 8 | 899 | 12 | 899 | 13 |
| n (Patient) | 335 | 8 | 335 | 12 | 335 | 13 |
| UO only | | | | | | |
| Median | 1.24 | 2.75 | 1.24 | 1.69 | 1.24 | 2.10 |
| Average | 3.34 | 4.89 | 3.34 | 25.0 | 3.34 | 2.26 |
| Stdev | 13.1 | 10.4 | 13.1 | 142 | 13.1 | 1.83 |
| p (t-test) | | 0.49 | | 4.8E−4 | | 0.68 |
| Min | 0.00246 | 0.00313 | 0.00246 | 0.00408 | 0.00246 | 0.00313 |
| Max | 270 | 59.1 | 270 | 935 | 270 | 8.46 |
| n (Samp) | 581 | 35 | 581 | 43 | 581 | 25 |
| n (Patient) | 208 | 35 | 208 | 43 | 208 | 25 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.64 | 0.67 | 0.63 | 0.57 | 0.68 | 0.55 | 0.59 | 0.60 | 0.60 |
| SE | 0.051 | 0.11 | 0.052 | 0.045 | 0.086 | 0.047 | 0.058 | 0.084 | 0.061 |
| p | 0.0079 | 0.10 | 0.011 | 0.12 | 0.036 | 0.30 | 0.12 | 0.24 | 0.11 |
| nCohort 1 | 691 | 899 | 581 | 691 | 899 | 581 | 691 | 899 | 581 |
| nCohort 2 | 36 | 8 | 35 | 46 | 12 | 43 | 28 | 13 | 25 |
| Cutoff 1 | 1.39 | 1.39 | 1.66 | 0.943 | 1.26 | 0.536 | 0.884 | 0.505 | 1.04 |
| Sens 1 | 72% | 75% | 71% | 72% | 75% | 72% | 71% | 77% | 72% |
| Spec 1 | 56% | 55% | 58% | 45% | 53% | 30% | 43% | 31% | 45% |
| Cutoff 2 | 0.621 | 1.14 | 0.506 | 0.447 | 1.18 | 0.0558 | 0.393 | 0.365 | 0.742 |
| Sens 2 | 81% | 88% | 80% | 80% | 83% | 81% | 82% | 85% | 80% |
| Spec 2 | 34% | 49% | 30% | 29% | 50% | 18% | 28% | 27% | 36% |
| Cutoff 3 | 0.0183 | 0.708 | 0.0183 | 0.0140 | 1.09 | 0.0140 | 0.361 | 0.361 | 0.392 |
| Sens 3 | 92% | 100% | 91% | 98% | 92% | 98% | 93% | 92% | 92% |
| Spec 3 | 13% | 36% | 13% | 10% | 48% | 10% | 27% | 27% | 27% |
| Cutoff 4 | 2.13 | 2.17 | 2.22 | 2.13 | 2.17 | 2.22 | 2.13 | 2.17 | 2.22 |
| Sens 4 | 53% | 38% | 57% | 39% | 58% | 35% | 50% | 54% | 44% |
| Spec 4 | 70% | 70% | 70% | 70% | 70% | 70% | 70% | 70% | 70% |
| Cutoff 5 | 3.13 | 3.13 | 3.15 | 3.13 | 3.13 | 3.15 | 3.13 | 3.13 | 3.15 |
| Sens 5 | 36% | 38% | 40% | 28% | 42% | 28% | 21% | 23% | 24% |
| Spec 5 | 80% | 80% | 80% | 80% | 80% | 80% | 80% | 80% | 80% |
| Cutoff 6 | 5.18 | 5.05 | 5.21 | 5.18 | 5.05 | 5.21 | 5.18 | 5.05 | 5.21 |
| Sens 6 | 14% | 12% | 17% | 9% | 25% | 12% | 4% | 8% | 4% |
| Spec 6 | 90% | 90% | 90% | 90% | 90% | 90% | 90% | 90% | 90% |
| OR Quart 2 | 0.99 | >2.0 | 0.66 | 0.88 | 1.00 | 0.79 | 4.7 | 4.1 | 3.1 |
| p Value | 0.99 | <0.57 | 0.52 | 0.80 | 1.00 | 0.63 | 0.051 | 0.21 | 0.17 |
| 95% CI of | 0.28 | >0.18 | 0.18 | 0.33 | 0.062 | 0.30 | 0.99 | 0.45 | 0.61 |
| OR Quart 2 | 3.5 | na | 2.4 | 2.3 | 16 | 2.1 | 22 | 37 | 15 |
| OR Quart 3 | 1.8 | >3.0 | 1.9 | 1.6 | 4.0 | 1.1 | 3.1 | 2.0 | 4.7 |
| p Value | 0.29 | <0.34 | 0.22 | 0.29 | 0.21 | 0.82 | 0.18 | 0.57 | 0.050 |
| 95% CI of | 0.60 | >0.31 | 0.68 | 0.68 | 0.45 | 0.46 | 0.61 | 0.18 | 1.0 |
| OR Quart 3 | 5.6 | na | 5.3 | 3.8 | 36 | 2.7 | 15 | 22 | 22 |

-continued

| | | | | | | | | | |
|---|---|---|---|---|---|---|---|---|---|
| OR Quart 4 | 3.6 | >3.0 | 2.5 | 1.7 | 6.1 | 1.4 | 5.8 | 6.1 | 4.1 |
| p Value | 0.013 | <0.34 | 0.072 | 0.21 | 0.095 | 0.40 | 0.024 | 0.094 | 0.076 |
| 95% CI of | 1.3 | >0.31 | 0.92 | 0.73 | 0.73 | 0.62 | 1.3 | 0.73 | 0.86 |
| OR Quart 4 | 10 | na | 6.6 | 4.0 | 51 | 3.3 | 26 | 51 | 20 |

Corticotropin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.00163 | 0.00162 | 0.00163 | 0.00208 | 0.00163 | 0.00175 |
| Average | 0.00229 | 0.00185 | 0.00229 | 0.00430 | 0.00229 | 0.00180 |
| Stdev | 0.00404 | 0.00124 | 0.00404 | 0.00727 | 0.00404 | 0.000819 |
| p (t-test) | | 0.61 | | 0.018 | | 0.63 |
| Min | 3.92E−6 | 0.000273 | 3.92E−6 | 0.000388 | 3.92E−6 | 0.000570 |
| Max | 0.0489 | 0.00666 | 0.0489 | 0.0377 | 0.0489 | 0.00318 |
| n (Samp) | 249 | 22 | 249 | 32 | 249 | 16 |
| n (Patient) | 162 | 22 | 162 | 32 | 162 | 16 |
| sCr only | | | | | | |
| Median | nd | nd | 0.00163 | 0.00293 | 0.00163 | 0.00274 |
| Average | nd | nd | 0.00223 | 0.00603 | 0.00223 | 0.00742 |
| Stdev | nd | nd | 0.00365 | 0.00820 | 0.00365 | 0.0134 |
| p (t-test) | nd | nd | | 0.015 | | 9.1E−4 |
| Min | nd | nd | 3.92E−6 | 0.00134 | 3.92E−6 | 0.00109 |
| Max | nd | nd | 0.0489 | 0.0224 | 0.0489 | 0.0377 |
| n (Samp) | nd | nd | 315 | 6 | 315 | 7 |
| n (Patient) | nd | nd | 189 | 6 | 189 | 7 |
| UO only | | | | | | |
| Median | 0.00163 | 0.00162 | 0.00163 | 0.00204 | 0.00163 | 0.00160 |
| Average | 0.00239 | 0.00186 | 0.00239 | 0.00374 | 0.00239 | 0.00300 |
| Stdev | 0.00430 | 0.00126 | 0.00430 | 0.00680 | 0.00430 | 0.00542 |
| p (t-test) | | 0.57 | | 0.14 | | 0.60 |
| Min | 0.000355 | 0.000273 | 0.000355 | 0.000388 | 0.000355 | 0.000570 |
| Max | 0.0489 | 0.00666 | 0.0489 | 0.0377 | 0.0489 | 0.0224 |
| n (Samp) | 217 | 22 | 217 | 29 | 217 | 15 |
| n (Patient) | 135 | 22 | 135 | 29 | 135 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.48 | nd | 0.47 | 0.62 | 0.66 | 0.60 | 0.50 | 0.73 | 0.47 |
| SE | 0.065 | nd | 0.066 | 0.056 | 0.12 | 0.059 | 0.075 | 0.11 | 0.078 |
| p | 0.79 | nd | 0.66 | 0.025 | 0.18 | 0.085 | 0.97 | 0.038 | 0.69 |
| nCohort 1 | 249 | nd | 217 | 249 | 315 | 217 | 249 | 315 | 217 |
| nCohort 2 | 22 | nd | 22 | 32 | 6 | 29 | 16 | 7 | 15 |
| Cutoff 1 | 0.00134 | nd | 0.00134 | 0.00149 | 0.00134 | 0.00149 | 0.00111 | 0.00212 | 0.00111 |
| Sens 1 | 77% | nd | 73% | 72% | 83% | 72% | 75% | 71% | 73% |
| Spec 1 | 33% | nd | 32% | 42% | 32% | 41% | 22% | 69% | 23% |
| Cutoff 2 | 0.00106 | nd | 0.00106 | 0.00124 | 0.00134 | 0.00111 | 0.00109 | 0.00201 | 0.00109 |
| Sens 2 | 86% | nd | 86% | 81% | 83% | 83% | 81% | 86% | 80% |
| Spec 2 | 20% | nd | 21% | 32% | 32% | 23% | 21% | 65% | 22% |
| Cutoff 3 | 0.000794 | nd | 0.000794 | 0.00109 | 0.00124 | 0.000888 | 0.000523 | 0.00106 | 0.000523 |
| Sens 3 | 91% | nd | 91% | 91% | 100% | 93% | 100% | 100% | 100% |
| Spec 3 | 10% | nd | 9% | 21% | 31% | 15% | 7% | 19% | 6% |
| Cutoff 4 | 0.00222 | nd | 0.00227 | 0.00222 | 0.00222 | 0.00227 | 0.00222 | 0.00222 | 0.00227 |
| Sens 4 | 23% | nd | 27% | 47% | 50% | 41% | 31% | 57% | 20% |
| Spec 4 | 70% | nd | 70% | 70% | 70% | 70% | 70% | 70% | 70% |
| Cutoff 5 | 0.00282 | nd | 0.00282 | 0.00282 | 0.00274 | 0.00282 | 0.00282 | 0.00274 | 0.00282 |
| Sens 5 | 9% | nd | 9% | 34% | 50% | 28% | 12% | 43% | 13% |
| Spec 5 | 80% | nd | 81% | 80% | 80% | 81% | 80% | 80% | 81% |
| Cutoff 6 | 0.00362 | nd | 0.00380 | 0.00362 | 0.00352 | 0.00380 | 0.00362 | 0.00352 | 0.00380 |
| Sens 6 | 5% | nd | 5% | 28% | 50% | 14% | 0% | 14% | 7% |
| Spec 6 | 91% | nd | 91% | 91% | 90% | 91% | 91% | 90% | 91% |
| OR Quart 2 | 2.5 | nd | 4.5 | 1.0 | >3.1 | 0.39 | 1.0 | 0 | 1.0 |
| p Value | 0.20 | nd | 0.066 | 1.0 | <0.33 | 0.19 | 0.98 | na | 1.0 |
| 95% CI of | 0.62 | nd | 0.91 | 0.31 | >0.32 | 0.097 | 0.24 | na | 0.19 |
| OR Quart 2 | 10 | nd | 22 | 3.3 | na | 1.6 | 4.2 | na | 5.2 |
| OR Quart 3 | 2.5 | nd | 3.2 | 1.4 | >0 | 1.3 | 0.75 | 2.0 | 1.4 |
| p Value | 0.20 | nd | 0.16 | 0.57 | <na | 0.59 | 0.71 | 0.57 | 0.70 |
| 95% CI of | 0.62 | nd | 0.62 | 0.45 | >na | 0.46 | 0.16 | 0.18 | 0.29 |
| OR Quart 3 | 10 | nd | 17 | 4.2 | na | 3.8 | 3.5 | 23 | 6.4 |
| OR Quart 4 | 1.7 | nd | 3.3 | 2.2 | >3.1 | 1.5 | 1.3 | 4.1 | 1.7 |
| p Value | 0.46 | nd | 0.16 | 0.15 | <0.33 | 0.46 | 0.71 | 0.21 | 0.47 |

-continued

| | | | | | | | | | |
|---|---|---|---|---|---|---|---|---|---|
| 95% CI of | 0.40 | nd | 0.63 | 0.77 | >0.31 | 0.53 | 0.33 | 0.45 | 0.39 |
| OR Quart 4 | 7.6 | nd | 17 | 6.1 | na | 4.2 | 5.0 | 38 | 7.6 |

| Thyroxine-binding globulin | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.0709 | 0.0370 | 0.0709 | 0.0576 | 0.0709 | 0.136 |
| Average | 0.176 | 0.107 | 0.176 | 0.246 | 0.176 | 0.165 |
| Stdev | 0.265 | 0.203 | 0.265 | 0.631 | 0.265 | 0.173 |
| p (t-test) | | 0.20 | | 0.21 | | 0.86 |
| Min | 8.30E−5 | 0.000476 | 8.30E−5 | 0.00330 | 8.30E−5 | 0.00324 |
| Max | 1.86 | 0.885 | 1.86 | 3.60 | 1.86 | 0.602 |
| n (Samp) | 421 | 25 | 421 | 32 | 421 | 17 |
| n (Patient) | 165 | 25 | 165 | 32 | 165 | 17 |
| sCr only | | | | | | |
| Median | nd | nd | 0.0749 | 0.0237 | 0.0749 | 0.0201 |
| Average | nd | nd | 0.178 | 0.130 | 0.178 | 0.0811 |
| Stdev | nd | nd | 0.294 | 0.177 | 0.294 | 0.107 |
| p (t-test) | nd | nd | | 0.67 | | 0.38 |
| Min | nd | nd | 8.30E−5 | 0.00330 | 8.30E−5 | 0.00324 |
| Max | nd | nd | 3.60 | 0.466 | 3.60 | 0.250 |
| n (Samp) | nd | nd | 511 | 7 | 511 | 7 |
| n (Patient) | nd | nd | 198 | 7 | 198 | 7 |
| UO only | | | | | | |
| Median | 0.0686 | 0.0423 | 0.0686 | 0.0428 | 0.0686 | 0.142 |
| Average | 0.178 | 0.119 | 0.178 | 0.251 | 0.178 | 0.173 |
| Stdev | 0.272 | 0.204 | 0.272 | 0.661 | 0.272 | 0.168 |
| p (t-test) | | 0.28 | | 0.24 | | 0.94 |
| Min | 0.000191 | 0.000476 | 0.000191 | 0.00343 | 0.000191 | 0.00768 |
| Max | 1.86 | 0.885 | 1.86 | 3.60 | 1.86 | 0.602 |
| n (Samp) | 357 | 25 | 357 | 29 | 357 | 17 |
| n (Patient) | 135 | 25 | 135 | 29 | 135 | 17 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.38 | nd | 0.41 | 0.49 | 0.42 | 0.49 | 0.56 | 0.38 | 0.60 |
| SE | 0.061 | nd | 0.062 | 0.053 | 0.11 | 0.056 | 0.073 | 0.11 | 0.074 |
| p | 0.058 | nd | 0.15 | 0.88 | 0.47 | 0.85 | 0.41 | 0.28 | 0.19 |
| nCohort 1 | 421 | nd | 357 | 421 | 511 | 357 | 421 | 511 | 357 |
| nCohort 2 | 25 | nd | 25 | 32 | 7 | 29 | 17 | 7 | 17 |
| Cutoff 1 | 0.0145 | nd | 0.0131 | 0.0184 | 0.00990 | 0.0184 | 0.0617 | 0.0187 | 0.109 |
| Sens 1 | 72% | nd | 72% | 72% | 71% | 72% | 71% | 71% | 71% |
| Spec 1 | 20% | nd | 18% | 23% | 16% | 23% | 47% | 23% | 59% |
| Cutoff 2 | 0.0112 | nd | 0.00915 | 0.00971 | 0.00423 | 0.0158 | 0.0353 | 0.0145 | 0.0497 |
| Sens 2 | 80% | nd | 80% | 81% | 86% | 83% | 82% | 86% | 82% |
| Spec 2 | 17% | nd | 16% | 16% | 8% | 21% | 33% | 20% | 43% |
| Cutoff 3 | 0.00446 | nd | 0.00423 | 0.00556 | 0.00325 | 0.00556 | 0.00767 | 0.00319 | 0.0196 |
| Sens 3 | 92% | nd | 92% | 91% | 100% | 93% | 94% | 100% | 94% |
| Spec 3 | 9% | nd | 8% | 11% | 6% | 11% | 14% | 6% | 24% |
| Cutoff 4 | 0.179 | nd | 0.179 | 0.179 | 0.179 | 0.179 | 0.179 | 0.179 | 0.179 |
| Sens 4 | 16% | nd | 20% | 34% | 29% | 34% | 24% | 29% | 24% |
| Spec 4 | 70% | nd | 70% | 70% | 70% | 70% | 70% | 70% | 70% |
| Cutoff 5 | 0.251 | nd | 0.249 | 0.251 | 0.259 | 0.249 | 0.251 | 0.259 | 0.249 |
| Sens 5 | 8% | nd | 8% | 28% | 29% | 28% | 18% | 0% | 18% |
| Spec 5 | 80% | nd | 80% | 80% | 80% | 80% | 80% | 80% | 80% |
| Cutoff 6 | 0.434 | nd | 0.466 | 0.434 | 0.422 | 0.466 | 0.434 | 0.422 | 0.466 |
| Sens 6 | 8% | nd | 8% | 9% | 14% | 7% | 12% | 0% | 12% |
| Spec 6 | 90% | nd | 90% | 90% | 90% | 90% | 90% | 90% | 90% |
| OR Quart 2 | 3.1 | nd | 2.5 | 0.43 | 0.50 | 0.38 | 0.99 | 0 | 1.5 |
| p Value | 0.17 | nd | 0.20 | 0.13 | 0.57 | 0.11 | 0.99 | na | 0.66 |
| 95% CI of | 0.62 | nd | 0.62 | 0.15 | 0.045 | 0.11 | 0.20 | na | 0.24 |
| OR Quart 2 | 16 | nd | 9.8 | 1.3 | 5.6 | 1.3 | 5.0 | na | 9.2 |
| OR Quart 3 | 3.1 | nd | 1.7 | 0.43 | 0.50 | 0.47 | 2.8 | 0.50 | 4.9 |
| p Value | 0.17 | nd | 0.47 | 0.13 | 0.57 | 0.19 | 0.14 | 0.57 | 0.047 |

-continued

| | | | | | | | | | |
|---|---|---|---|---|---|---|---|---|---|
| 95% CI of | 0.61 | nd | 0.40 | 0.15 | 0.044 | 0.16 | 0.72 | 0.044 | 1.0 |
| OR Quart 3 | 16 | nd | 7.3 | 1.3 | 5.5 | 1.4 | 11 | 5.5 | 23 |
| OR Quart 4 | 6.0 | nd | 3.6 | 1.0 | 1.5 | 1.0 | 0.99 | 2.0 | 1.5 |
| p Value | 0.021 | nd | 0.055 | 0.98 | 0.65 | 0.98 | 0.99 | 0.41 | 0.66 |
| 95% CI of | 1.3 | nd | 0.97 | 0.42 | 0.25 | 0.40 | 0.20 | 0.37 | 0.24 |
| OR Quart 4 | 28 | nd | 14 | 2.4 | 9.3 | 2.6 | 5.0 | 11 | 9.2 |

Tumor necrosis factor receptor superfamily member 8

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 18.5 | 33.8 | 18.5 | 26.4 | 18.5 | 18.6 |
| Average | 24.9 | 46.9 | 24.9 | 36.4 | 24.9 | 27.1 |
| Stdev | 30.5 | 60.4 | 30.5 | 36.8 | 30.5 | 27.6 |
| p (t-test) | | 3.0E−5 | | 0.010 | | 0.70 |
| Min | 0.0493 | 0.121 | 0.0493 | 0.0561 | 0.0493 | 0.0688 |
| Max | 277 | 350 | 277 | 158 | 277 | 111 |
| n (Samp) | 473 | 47 | 473 | 54 | 473 | 28 |
| n (Patient) | 240 | 47 | 240 | 54 | 240 | 28 |
| sCr only | | | | | | |
| Median | 19.8 | 12.5 | 19.8 | 32.3 | 19.8 | 38.9 |
| Average | 31.0 | 23.4 | 31.0 | 59.4 | 31.0 | 32.8 |
| Stdev | 46.2 | 25.8 | 46.2 | 98.6 | 46.2 | 21.4 |
| p (t-test) | | 0.62 | | 0.050 | | 0.90 |
| Min | 0.0493 | 0.196 | 0.0493 | 12.1 | 0.0493 | 0.0688 |
| Max | 554 | 63.3 | 554 | 353 | 554 | 59.7 |
| n (Samp) | 634 | 9 | 634 | 11 | 634 | 11 |
| n (Patient) | 295 | 9 | 295 | 11 | 295 | 11 |
| UO only | | | | | | |
| Median | 16.9 | 35.1 | 16.9 | 26.4 | 16.9 | 18.8 |
| Average | 24.3 | 49.2 | 24.3 | 37.3 | 24.3 | 27.5 |
| Stdev | 31.1 | 62.2 | 31.1 | 38.9 | 31.1 | 28.0 |
| p (t-test) | | 9.9E−6 | | 0.0075 | | 0.62 |
| Min | 0.0493 | 0.121 | 0.0493 | 0.0561 | 0.0493 | 0.196 |
| Max | 277 | 350 | 277 | 158 | 277 | 111 |
| n (Samp) | 441 | 43 | 441 | 48 | 441 | 25 |
| n (Patient) | 210 | 43 | 210 | 48 | 210 | 25 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.64 | 0.45 | 0.67 | 0.60 | 0.65 | 0.60 | 0.53 | 0.61 | 0.55 |
| SE | 0.045 | 0.100 | 0.047 | 0.043 | 0.091 | 0.045 | 0.057 | 0.091 | 0.061 |
| p | 0.0018 | 0.59 | 2.9E−4 | 0.021 | 0.098 | 0.028 | 0.59 | 0.24 | 0.37 |
| nCohort 1 | 473 | 634 | 441 | 473 | 634 | 441 | 473 | 634 | 441 |
| nCohort 2 | 47 | 9 | 43 | 54 | 11 | 48 | 28 | 11 | 25 |
| Cutoff 1 | 15.4 | 5.09 | 15.4 | 12.3 | 23.1 | 9.75 | 8.69 | 18.3 | 10.4 |
| Sens 1 | 70% | 78% | 72% | 70% | 73% | 71% | 71% | 73% | 72% |
| Spec 1 | 48% | 19% | 49% | 40% | 56% | 35% | 31% | 46% | 36% |
| Cutoff 2 | 6.53 | 1.18 | 12.1 | 5.14 | 18.5 | 5.09 | 5.76 | 9.75 | 6.53 |
| Sens 2 | 81% | 89% | 81% | 83% | 82% | 81% | 82% | 82% | 84% |
| Spec 2 | 27% | 12% | 41% | 23% | 47% | 23% | 25% | 30% | 29% |
| Cutoff 3 | 1.18 | 0.121 | 5.14 | 1.80 | 13.6 | 1.18 | 0.196 | 5.76 | 0.196 |
| Sens 3 | 94% | 100% | 91% | 91% | 91% | 94% | 93% | 91% | 96% |
| Spec 3 | 14% | 6% | 25% | 16% | 43% | 15% | 9% | 23% | 11% |
| Cutoff 4 | 29.5 | 32.9 | 27.0 | 29.5 | 32.9 | 27.0 | 29.5 | 32.9 | 27.0 |
| Sens 4 | 55% | 33% | 60% | 48% | 27% | 48% | 39% | 55% | 40% |
| Spec 4 | 70% | 71% | 70% | 70% | 71% | 70% | 70% | 71% | 70% |
| Cutoff 5 | 38.9 | 42.2 | 37.4 | 38.9 | 42.2 | 37.4 | 38.9 | 42.2 | 37.4 |
| Sens 5 | 43% | 33% | 49% | 35% | 27% | 42% | 25% | 45% | 24% |
| Spec 5 | 81% | 80% | 80% | 81% | 80% | 80% | 81% | 80% | 80% |
| Cutoff 6 | 53.5 | 63.6 | 53.5 | 53.5 | 63.6 | 53.5 | 53.5 | 63.6 | 53.5 |
| Sens 6 | 26% | 0% | 26% | 20% | 9% | 21% | 7% | 0% | 8% |
| Spec 6 | 90% | 90% | 90% | 90% | 90% | 90% | 90% | 90% | 90% |
| OR Quart 2 | 1.8 | 0 | 2.3 | 0.89 | >3.1 | 0.89 | 1.4 | 1.0 | 1.8 |
| p Value | 0.24 | na | 0.13 | 0.81 | <0.34 | 0.81 | 0.56 | 1.0 | 0.37 |
| 95% CI of | 0.68 | na | 0.78 | 0.37 | >0.31 | 0.35 | 0.44 | 0.14 | 0.51 |
| OR Quart 2 | 4.7 | na | 6.9 | 2.2 | na | 2.3 | 4.6 | 7.2 | 6.3 |
| OR Quart 3 | 0.70 | 0.66 | 1.0 | 1.1 | >5.2 | 0.79 | 1.6 | 0.50 | 1.3 |
| p Value | 0.56 | 0.65 | 1.0 | 0.84 | <0.14 | 0.62 | 0.40 | 0.57 | 0.73 |
| 95% CI of | 0.22 | 0.11 | 0.28 | 0.46 | >0.60 | 0.30 | 0.52 | 0.045 | 0.33 |
| OR Quart 3 | 2.3 | 4.0 | 3.5 | 2.6 | na | 2.1 | 5.2 | 5.5 | 4.8 |

-continued

| | | | | | | | | | |
|---|---|---|---|---|---|---|---|---|---|
| OR Quart 4 | 3.8 | 1.4 | 5.2 | 2.1 | >3.0 | 2.3 | 1.6 | 3.1 | 2.3 |
| p Value | 0.0032 | 0.70 | 0.0014 | 0.066 | <0.34 | 0.041 | 0.41 | 0.18 | 0.17 |
| 95% CI of | 1.6 | 0.30 | 1.9 | 0.95 | >0.31 | 1.0 | 0.52 | 0.61 | 0.70 |
| OR Quart 4 | 9.2 | 6.1 | 14 | 4.5 | na | 5.1 | 5.1 | 15 | 7.8 |

Alpha-fetoprotein

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.00508 | 0.00505 | 0.00508 | 0.00587 | 0.00508 | 0.00428 |
| Average | 0.0492 | 0.0230 | 0.0492 | 0.109 | 0.0492 | 0.0706 |
| Stdev | 0.117 | 0.0651 | 0.117 | 0.406 | 0.117 | 0.242 |
| p (t-test) | | 0.17 | | 0.021 | | 0.40 |
| Min | 0.000463 | 0.000463 | 0.000463 | 0.000463 | 0.000463 | 0.000463 |
| Max | 0.889 | 0.280 | 0.889 | 2.85 | 0.889 | 1.25 |
| n (Samp) | 407 | 39 | 407 | 50 | 407 | 27 |
| n (Patient) | 214 | 39 | 214 | 50 | 214 | 27 |
| sCr only | | | | | | |
| Median | nd | nd | 0.00505 | 0.00624 | 0.00505 | 0.00286 |
| Average | nd | nd | 0.0563 | 0.0846 | 0.0563 | 0.0277 |
| Stdev | nd | nd | 0.178 | 0.126 | 0.178 | 0.0583 |
| p (t-test) | nd | nd | | 0.62 | | 0.60 |
| Min | nd | nd | 0.000463 | 0.000463 | 0.000463 | 0.000463 |
| Max | nd | nd | 2.85 | 0.317 | 2.85 | 0.185 |
| n (Samp) | nd | nd | 535 | 10 | 535 | 11 |
| n (Patient) | nd | nd | 256 | 10 | 256 | 11 |
| UO only | | | | | | |
| Median | 0.00505 | 0.00505 | 0.00505 | 0.00587 | 0.00505 | 0.00428 |
| Average | 0.0537 | 0.0230 | 0.0537 | 0.111 | 0.0537 | 0.0739 |
| Stdev | 0.148 | 0.0651 | 0.148 | 0.418 | 0.148 | 0.251 |
| p (t-test) | | 0.20 | | 0.058 | | 0.53 |
| Min | 0.000463 | 0.000463 | 0.000463 | 0.000463 | 0.000463 | 0.000463 |
| Max | 1.74 | 0.280 | 1.74 | 2.85 | 1.74 | 1.25 |
| n (Samp) | 380 | 39 | 380 | 47 | 380 | 25 |
| n (Patient) | 189 | 39 | 189 | 47 | 189 | 25 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.42 | nd | 0.42 | 0.52 | 0.57 | 0.53 | 0.43 | 0.38 | 0.44 |
| SE | 0.050 | nd | 0.050 | 0.044 | 0.095 | 0.045 | 0.059 | 0.091 | 0.061 |
| p | 0.100 | nd | 0.13 | 0.57 | 0.43 | 0.53 | 0.22 | 0.19 | 0.31 |
| nCohort 1 | 407 | nd | 380 | 407 | 535 | 380 | 407 | 535 | 380 |
| nCohort 2 | 39 | nd | 39 | 50 | 10 | 47 | 27 | 11 | 25 |
| Cutoff 1 | 0.00132 | nd | 0.00132 | 0.00296 | 0.00483 | 0.00296 | 0.00132 | 0.00132 | 0.00132 |
| Sens 1 | 87% | nd | 87% | 78% | 70% | 77% | 81% | 91% | 80% |
| Spec 1 | 14% | nd | 15% | 19% | 44% | 20% | 14% | 15% | 15% |
| Cutoff 2 | 0.00132 | nd | 0.00132 | 0.00132 | 0.00296 | 0.00132 | 0.00132 | 0.00132 | 0.00132 |
| Sens 2 | 87% | nd | 87% | 84% | 80% | 83% | 81% | 91% | 80% |
| Spec 2 | 14% | nd | 15% | 14% | 22% | 15% | 14% | 15% | 15% |
| Cutoff 3 | 0 | nd | 0 | 0.000463 | 0.000463 | 0.000463 | 0.000463 | 0.00132 | 0.000463 |
| Sens 3 | 100% | nd | 100% | 92% | 90% | 91% | 93% | 91% | 92% |
| Spec 3 | 0% | nd | 0% | 8% | 9% | 9% | 8% | 15% | 9% |
| Cutoff 4 | 0.0128 | nd | 0.00660 | 0.0128 | 0.00660 | 0.00660 | 0.0128 | 0.00660 | 0.00660 |
| Sens 4 | 10% | nd | 10% | 40% | 40% | 40% | 22% | 18% | 24% |
| Spec 4 | 70% | nd | 71% | 70% | 72% | 71% | 70% | 72% | 71% |
| Cutoff 5 | 0.0613 | nd | 0.0613 | 0.0613 | 0.0499 | 0.0613 | 0.0613 | 0.0499 | 0.0613 |
| Sens 5 | 8% | nd | 8% | 24% | 30% | 23% | 19% | 18% | 16% |
| Spec 5 | 80% | nd | 80% | 80% | 80% | 80% | 80% | 80% | 80% |
| Cutoff 6 | 0.141 | nd | 0.131 | 0.141 | 0.154 | 0.131 | 0.141 | 0.154 | 0.131 |
| Sens 6 | 8% | nd | 8% | 16% | 30% | 15% | 11% | 9% | 12% |
| Spec 6 | 90% | nd | 90% | 90% | 90% | 90% | 90% | 90% | 90% |
| OR Quart 2 | 5.2 | nd | 5.2 | 1.2 | 1.0 | 0.99 | 1.4 | 0.50 | 1.4 |
| p Value | 0.011 | nd | 0.011 | 0.67 | 1.0 | 0.98 | 0.54 | 0.57 | 0.54 |
| 95% CI of | 1.5 | nd | 1.5 | 0.52 | 0.14 | 0.41 | 0.44 | 0.045 | 0.44 |
| OR Quart 2 | 19 | nd | 19 | 2.8 | 7.2 | 2.4 | 4.7 | 5.6 | 4.7 |
| OR Quart 3 | 3.6 | nd | 3.6 | 1.2 | 1.0 | 0.99 | 0.59 | 1.0 | 0.80 |
| p Value | 0.059 | nd | 0.058 | 0.67 | 1.0 | 0.98 | 0.48 | 1.0 | 0.74 |
| 95% CI of | 0.95 | nd | 0.96 | 0.52 | 0.14 | 0.41 | 0.14 | 0.14 | 0.21 |
| OR Quart 3 | 13 | nd | 13 | 2.8 | 7.2 | 2.4 | 2.5 | 7.2 | 3.1 |
| OR Quart 4 | 4.4 | nd | 4.4 | 1.2 | 2.0 | 1.3 | 2.6 | 3.1 | 1.9 |
| p Value | 0.025 | nd | 0.024 | 0.68 | 0.42 | 0.54 | 0.083 | 0.17 | 0.27 |

-continued

| | | | | | | | | | |
|---|---|---|---|---|---|---|---|---|---|
| 95% CI of | 1.2 | nd | 1.2 | 0.51 | 0.36 | 0.56 | 0.88 | 0.62 | 0.61 |
| OR Quart 4 | 16 | nd | 16 | 2.8 | 11 | 3.0 | 7.7 | 16 | 5.9 |

Apolipoprotein E

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 2.68 | 1.90 | 2.68 | 1.73 | 2.68 | 1.37 |
| Average | 21.4 | 9.42 | 21.4 | 34.9 | 21.4 | 4.56 |
| Stdev | 132 | 20.1 | 132 | 239 | 132 | 12.4 |
| p (t-test) | | 0.45 | | 0.41 | | 0.39 |
| Min | 0.000147 | 0.00122 | 0.000147 | 0.000147 | 0.000147 | 0.000147 |
| Max | 2160 | 135 | 2160 | 2140 | 2160 | 83.4 |
| n (Samp) | 1008 | 70 | 1008 | 80 | 1008 | 46 |
| n (Patient) | 386 | 70 | 386 | 80 | 386 | 46 |
| sCr only | | | | | | |
| Median | 2.56 | 0.695 | 2.56 | 1.07 | 2.56 | 1.79 |
| Average | 20.2 | 1.91 | 20.2 | 3.33 | 20.2 | 3.52 |
| Stdev | 129 | 3.03 | 129 | 6.71 | 129 | 4.87 |
| p (t-test) | | 0.57 | | 0.55 | | 0.56 |
| Min | 0.000147 | 0.00154 | 0.000147 | 0.000147 | 0.000147 | 0.000147 |
| Max | 2160 | 10.5 | 2160 | 28.7 | 2160 | 19.7 |
| n (Samp) | 1344 | 16 | 1344 | 21 | 1344 | 20 |
| n (Patient) | 472 | 16 | 472 | 21 | 472 | 20 |
| UO only | | | | | | |
| Median | 2.57 | 3.56 | 2.57 | 1.85 | 2.57 | 1.41 |
| Average | 19.5 | 11.2 | 19.5 | 38.5 | 19.5 | 4.94 |
| Stdev | 120 | 22.0 | 120 | 250 | 120 | 13.3 |
| p (t-test) | | 0.58 | | 0.24 | | 0.44 |
| Min | 0.000147 | 0.00122 | 0.000147 | 0.000147 | 0.000147 | 0.00328 |
| Max | 2140 | 135 | 2140 | 2140 | 2140 | 83.4 |
| n (Samp) | 900 | 65 | 900 | 73 | 900 | 40 |
| n (Patient) | 310 | 65 | 310 | 73 | 310 | 40 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.47 | 0.29 | 0.50 | 0.45 | 0.34 | 0.47 | 0.37 | 0.40 | 0.39 |
| SE | 0.036 | 0.074 | 0.037 | 0.034 | 0.066 | 0.036 | 0.045 | 0.067 | 0.048 |
| p | 0.36 | 0.0050 | 0.94 | 0.13 | 0.016 | 0.37 | 0.0052 | 0.15 | 0.027 |
| nCohort 1 | 1008 | 1344 | 900 | 1008 | 1344 | 900 | 1008 | 1344 | 900 |
| nCohort 2 | 70 | 16 | 65 | 80 | 21 | 73 | 46 | 20 | 40 |
| Cutoff 1 | 0.809 | 0.201 | 0.825 | 0.551 | 0.423 | 0.422 | 0.505 | 0.757 | 0.515 |
| Sens 1 | 70% | 75% | 71% | 70% | 71% | 71% | 72% | 70% | 70% |
| Spec 1 | 26% | 12% | 26% | 20% | 18% | 16% | 19% | 26% | 19% |
| Cutoff 2 | 0.393 | 0.130 | 0.393 | 0.153 | 0.260 | 0.153 | 0.172 | 0.178 | 0.177 |
| Sens 2 | 80% | 81% | 80% | 80% | 81% | 81% | 83% | 80% | 80% |
| Spec 2 | 16% | 10% | 16% | 10% | 13% | 10% | 11% | 12% | 10% |
| Cutoff 3 | 0.103 | 0.00323 | 0.103 | 0.00463 | 0.00129 | 0.0258 | 0.0258 | 0.0258 | 0.0994 |
| Sens 3 | 90% | 94% | 91% | 90% | 90% | 90% | 93% | 95% | 90% |
| Spec 3 | 9% | 5% | 9% | 6% | 2% | 7% | 6% | 6% | 9% |
| Cutoff 4 | 7.24 | 6.96 | 6.93 | 7.24 | 6.96 | 6.93 | 7.24 | 6.96 | 6.93 |
| Sens 4 | 33% | 12% | 37% | 26% | 14% | 29% | 15% | 20% | 15% |
| Spec 4 | 70% | 70% | 70% | 70% | 70% | 70% | 70% | 70% | 70% |
| Cutoff 5 | 12.6 | 12.4 | 11.5 | 12.6 | 12.4 | 11.5 | 12.6 | 12.4 | 11.5 |
| Sens 5 | 17% | 0% | 28% | 22% | 10% | 26% | 7% | 5% | 10% |
| Spec 5 | 80% | 80% | 80% | 80% | 80% | 80% | 80% | 80% | 80% |
| Cutoff 6 | 28.1 | 26.8 | 27.0 | 28.1 | 26.8 | 27.0 | 28.1 | 26.8 | 27.0 |
| Sens 6 | 6% | 0% | 11% | 9% | 5% | 10% | 2% | 0% | 2% |
| Spec 6 | 90% | 90% | 90% | 90% | 90% | 90% | 90% | 90% | 90% |
| OR Quart 2 | 0.63 | 3.0 | 0.87 | 0.94 | 2.0 | 0.79 | 1.5 | 2.5 | 1.5 |
| p Value | 0.22 | 0.34 | 0.71 | 0.86 | 0.42 | 0.50 | 0.43 | 0.27 | 0.43 |
| 95% CI of | 0.31 | 0.31 | 0.43 | 0.48 | 0.37 | 0.40 | 0.53 | 0.49 | 0.53 |
| OR Quart 2 | 1.3 | 29 | 1.8 | 1.8 | 11 | 1.6 | 4.3 | 13 | 4.3 |
| OR Quart 3 | 0.84 | 3.0 | 0.63 | 0.78 | 3.0 | 0.53 | 2.4 | 3.6 | 1.7 |
| p Value | 0.61 | 0.34 | 0.25 | 0.48 | 0.17 | 0.10 | 0.076 | 0.12 | 0.31 |
| 95% CI of | 0.43 | 0.31 | 0.29 | 0.39 | 0.61 | 0.25 | 0.91 | 0.73 | 0.61 |
| OR Quart 3 | 1.6 | 29 | 1.4 | 1.6 | 15 | 1.1 | 6.4 | 17 | 4.7 |

-continued

| | | | | | | | | | |
|---|---|---|---|---|---|---|---|---|---|
| OR Quart 4 | 1.0 | 9.2 | 1.3 | 1.5 | 4.6 | 1.3 | 3.0 | 3.0 | 2.6 |
| p Value | 0.99 | 0.036 | 0.41 | 0.17 | 0.052 | 0.35 | 0.024 | 0.18 | 0.052 |
| 95% CI of | 0.53 | 1.2 | 0.68 | 0.83 | 0.99 | 0.73 | 1.2 | 0.61 | 0.99 |
| OR Quart 4 | 1.9 | 73 | 2.5 | 2.8 | 21 | 2.5 | 7.7 | 15 | 6.8 |

Apolipoprotein (a)

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 2.16 | 2.88 | 2.16 | 3.39 | 2.16 | 2.04 |
| Average | 46.7 | 10.1 | 46.7 | 23.9 | 46.7 | 5.40 |
| Stdev | 602 | 22.6 | 602 | 97.8 | 602 | 13.0 |
| p (t-test) | | 0.62 | | 0.74 | | 0.66 |
| Min | 0.00241 | 0.00241 | 0.00241 | 0.00838 | 0.00241 | 0.00838 |
| Max | 17500 | 118 | 17500 | 802 | 17500 | 75.7 |
| n (Samp) | 953 | 65 | 953 | 75 | 953 | 41 |
| n (Patient) | 381 | 65 | 381 | 75 | 381 | 41 |
| sCr only | | | | | | |
| Median | 2.09 | 1.68 | 2.09 | 3.09 | 2.09 | 2.25 |
| Average | 39.7 | 3.70 | 39.7 | 5.16 | 39.7 | 11.5 |
| Stdev | 523 | 6.91 | 523 | 8.41 | 523 | 21.6 |
| p (t-test) | | 0.80 | | 0.77 | | 0.81 |
| Min | 0.00241 | 0.0122 | 0.00241 | 0.00479 | 0.00241 | 0.00838 |
| Max | 17500 | 27.0 | 17500 | 37.7 | 17500 | 91.1 |
| n (Samp) | 1273 | 14 | 1273 | 20 | 1273 | 19 |
| n (Patient) | 466 | 14 | 466 | 20 | 466 | 19 |
| UO only | | | | | | |
| Median | 2.19 | 2.95 | 2.19 | 3.88 | 2.19 | 2.13 |
| Average | 46.2 | 20.7 | 46.2 | 26.4 | 46.2 | 6.18 |
| Stdev | 637 | 81.1 | 637 | 102 | 637 | 14.0 |
| p (t-test) | | 0.76 | | 0.80 | | 0.71 |
| Min | 0.00241 | 0.00241 | 0.00241 | 0.00838 | 0.00241 | 0.0122 |
| Max | 17500 | 618 | 17500 | 802 | 17500 | 75.7 |
| n (Samp) | 845 | 61 | 845 | 68 | 845 | 35 |
| n (Patient) | 305 | 61 | 305 | 68 | 305 | 35 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.56 | 0.45 | 0.59 | 0.60 | 0.54 | 0.64 | 0.49 | 0.53 | 0.54 |
| SE | 0.038 | 0.080 | 0.039 | 0.036 | 0.066 | 0.037 | 0.046 | 0.068 | 0.051 |
| p | 0.10 | 0.49 | 0.020 | 0.0058 | 0.58 | 2.2E−4 | 0.89 | 0.64 | 0.44 |
| nCohort 1 | 953 | 1273 | 845 | 953 | 1273 | 845 | 953 | 1273 | 845 |
| nCohort 2 | 65 | 14 | 61 | 75 | 20 | 68 | 41 | 19 | 35 |
| Cutoff 1 | 1.40 | 0.892 | 1.82 | 1.65 | 1.65 | 1.82 | 1.18 | 0.971 | 1.38 |
| Sens 1 | 71% | 71% | 70% | 71% | 70% | 71% | 71% | 74% | 71% |
| Spec 1 | 39% | 28% | 46% | 44% | 44% | 46% | 33% | 30% | 38% |
| Cutoff 2 | 0.917 | 0.108 | 0.977 | 1.20 | 0.751 | 1.26 | 0.826 | 0.0122 | 0.977 |
| Sens 2 | 80% | 86% | 80% | 80% | 80% | 81% | 80% | 84% | 80% |
| Spec 2 | 28% | 11% | 31% | 34% | 25% | 35% | 26% | 6% | 31% |
| Cutoff 3 | 0.108 | 0.0847 | 0.108 | 0.0847 | 0.0140 | 0.509 | 0.182 | 0.00790 | 0.699 |
| Sens 3 | 91% | 93% | 92% | 91% | 90% | 91% | 90% | 100% | 91% |
| Spec 3 | 13% | 11% | 12% | 12% | 7% | 22% | 14% | 1% | 25% |
| Cutoff 4 | 3.89 | 3.89 | 3.74 | 3.89 | 3.89 | 3.74 | 3.89 | 3.89 | 3.74 |
| Sens 4 | 37% | 14% | 43% | 44% | 40% | 53% | 24% | 42% | 31% |
| Spec 4 | 70% | 70% | 70% | 70% | 70% | 70% | 70% | 70% | 70% |
| Cutoff 5 | 5.71 | 5.71 | 5.25 | 5.71 | 5.71 | 5.25 | 5.71 | 5.71 | 5.25 |
| Sens 5 | 25% | 7% | 28% | 31% | 15% | 40% | 12% | 37% | 20% |
| Spec 5 | 80% | 80% | 80% | 80% | 80% | 80% | 80% | 80% | 80% |
| Cutoff 6 | 17.0 | 18.8 | 13.7 | 17.0 | 18.8 | 13.7 | 17.0 | 18.8 | 13.7 |
| Sens 6 | 15% | 7% | 18% | 15% | 5% | 19% | 5% | 16% | 6% |
| Spec 6 | 90% | 90% | 90% | 90% | 90% | 90% | 90% | 90% | 90% |
| OR Quart 2 | 1.1 | 2.0 | 1.1 | 1.4 | 1.0 | 1.8 | 1.0 | 0.80 | 4.0 |
| p Value | 0.85 | 0.42 | 0.83 | 0.42 | 1.0 | 0.20 | 0.99 | 0.74 | 0.016 |
| 95% CI of | 0.48 | 0.37 | 0.46 | 0.62 | 0.25 | 0.74 | 0.39 | 0.21 | 1.3 |
| OR Quart 2 | 2.4 | 11 | 2.6 | 3.1 | 4.0 | 4.4 | 2.6 | 3.0 | 12 |
| OR Quart 3 | 1.7 | 2.0 | 2.0 | 2.1 | 1.5 | 2.1 | 1.8 | 0.40 | 1.5 |
| p Value | 0.15 | 0.42 | 0.089 | 0.052 | 0.53 | 0.100 | 0.16 | 0.27 | 0.53 |
| 95% CI of | 0.82 | 0.37 | 0.90 | 0.99 | 0.42 | 0.87 | 0.79 | 0.076 | 0.42 |
| OR Quart 3 | 3.6 | 11 | 4.4 | 4.4 | 5.4 | 5.0 | 4.2 | 2.1 | 5.4 |
| OR Quart 4 | 1.7 | 2.0 | 2.2 | 2.6 | 1.5 | 4.1 | 0.77 | 1.6 | 2.6 |
| p Value | 0.15 | 0.42 | 0.046 | 0.0090 | 0.53 | 5.2E−4 | 0.62 | 0.40 | 0.12 |

-continued

| | | | | | | | | | |
|---|---|---|---|---|---|---|---|---|---|
| 95% CI of OR Quart 4 | 0.82–3.6 | 0.37–11 | 1.0–4.8 | 1.3–5.4 | 0.42–5.4 | 1.9–9.3 | 0.28–2.1 | 0.52–5.0 | 0.79–8.3 |

FIG. 3: Comparison of marker levels in urine samples collected within 12 hours of reaching stage R from Cohort 1 (patients that reached, but did not progress beyond, RIFLE stage R) and from Cohort 2 (patients that reached RIFLE stage I or F).

| C-C motif chemokine 7 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.737 | 0.625 | 0.515 | 0.428 | 0.816 | 0.625 |
| Average | 3.18 | 2.02 | 2.28 | 1.04 | 3.91 | 1.08 |
| Stdev | 15.8 | 5.30 | 6.57 | 1.96 | 17.8 | 1.64 |
| p (t-test) | | 0.63 | | 0.49 | | 0.38 |
| Min | 0.146 | 0.146 | 0.146 | 0.146 | 0.146 | 0.264 |
| Max | 161 | 33.0 | 33.0 | 7.75 | 161 | 7.33 |
| n (Samp) | 124 | 45 | 49 | 14 | 97 | 31 |
| n (Patient) | 124 | 45 | 49 | 14 | 97 | 31 |

| At Enrollment | | | |
|---|---|---|---|
| | sCr or UO | sCr only | UO only |
| AUC | 0.45 | 0.44 | 0.40 |
| SE | 0.051 | 0.089 | 0.060 |
| p | 0.37 | 0.48 | 0.086 |
| nCohort 1 | 124 | 49 | 97 |
| nCohort 2 | 45 | 14 | 31 |
| Cutoff 1 | 0.341 | 0.319 | 0.515 |
| Sens 1 | 71% | 79% | 71% |
| Spec 1 | 25% | 20% | 27% |
| Cutoff 2 | 0.320 | 0.146 | 0.336 |
| Sens 2 | 80% | 93% | 81% |
| Spec 2 | 19% | 6% | 20% |
| Cutoff 3 | 0.264 | 0.146 | 0.319 |
| Sens 3 | 91% | 93% | 90% |
| Spec 3 | 6% | 6% | 11% |
| Cutoff 4 | 1.04 | 0.812 | 1.15 |
| Sens 4 | 22% | 21% | 13% |
| Spec 4 | 73% | 73% | 77% |
| Cutoff 5 | 1.15 | 1.04 | 1.29 |
| Sens 5 | 20% | 14% | 10% |
| Spec 5 | 81% | 84% | 82% |
| Cutoff 6 | 1.59 | 1.59 | 6.92 |
| Sens 6 | 11% | 7% | 3% |
| Spec 6 | 92% | 92% | 91% |
| OR Quart 2 | 0.78 | 1.4 | 2.3 |
| p Value | 0.64 | 0.67 | 0.21 |
| 95% CI of OR Quart 2 | 0.27–2.2 | 0.27–7.8 | 0.62–8.7 |
| OR Quart 3 | 2.0 | 1.0 | 3.2 |
| p Value | 0.14 | 1.0 | 0.078 |
| 95% CI of OR Quart 3 | 0.79–5.2 | 0.17–5.9 | 0.88–12 |
| OR Quart 4 | 1.2 | 1.6 | 2.7 |
| p Value | 0.75 | 0.60 | 0.13 |
| 95% CI of OR Quart 4 | 0.44–3.1 | 0.29–8.6 | 0.75–10 |

| Interleukin-33 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 22.3 | 38.9 | 18.4 | 33.3 | 23.5 | 39.6 |
| Average | 34.5 | 48.9 | 32.2 | 42.7 | 36.8 | 54.2 |
| Stdev | 34.0 | 41.1 | 33.2 | 33.6 | 37.8 | 42.3 |
| p (t-test) | | 0.023 | | 0.30 | | 0.032 |
| Min | 0.0232 | 0.0591 | 0.0232 | 0.0591 | 0.0232 | 0.0645 |

-continued

| | | | | | | |
|---|---|---|---|---|---|---|
| Max | 138 | 148 | 138 | 136 | 203 | 148 |
| n (Samp) | 124 | 45 | 49 | 14 | 97 | 31 |
| n (Patient) | 124 | 45 | 49 | 14 | 97 | 31 |

| | At Enrollment | | |
|---|---|---|---|
| | sCr or UO | sCr only | UO only |
| AUC | 0.61 | 0.62 | 0.64 |
| SE | 0.051 | 0.089 | 0.060 |
| p | 0.028 | 0.16 | 0.020 |
| nCohort 1 | 124 | 49 | 97 |
| nCohort 2 | 45 | 14 | 31 |
| Cutoff 1 | 23.5 | 22.7 | 26.3 |
| Sens 1 | 71% | 71% | 71% |
| Spec 1 | 52% | 55% | 54% |
| Cutoff 2 | 14.6 | 18.6 | 19.4 |
| Sens 2 | 80% | 86% | 81% |
| Spec 2 | 40% | 53% | 46% |
| Cutoff 3 | 0.0879 | 12.9 | 13.7 |
| Sens 3 | 91% | 93% | 90% |
| Spec 3 | 14% | 39% | 37% |
| Cutoff 4 | 48.0 | 46.3 | 53.0 |
| Sens 4 | 33% | 36% | 39% |
| Spec 4 | 70% | 71% | 70% |
| Cutoff 5 | 65.3 | 59.3 | 70.3 |
| Sens 5 | 29% | 14% | 29% |
| Spec 5 | 81% | 82% | 80% |
| Cutoff 6 | 82.3 | 80.5 | 88.8 |
| Sens 6 | 18% | 7% | 19% |
| Spec 6 | 90% | 92% | 91% |
| OR Quart 2 | 1.4 | 3.2 | 3.2 |
| p Value | 0.58 | 0.34 | 0.11 |
| 95% CI of | 0.46 | 0.30 | 0.77 |
| OR Quart 2 | 4.1 | 35 | 14 |
| OR Quart 3 | 3.1 | 8.4 | 3.8 |
| p Value | 0.031 | 0.066 | 0.066 |
| 95% CI of | 1.1 | 0.87 | 0.92 |
| OR Quart 3 | 8.6 | 81 | 16 |
| OR Quart 4 | 2.2 | 4.7 | 5.1 |
| p Value | 0.15 | 0.19 | 0.023 |
| 95% CI of | 0.77 | 0.46 | 1.3 |
| OR Quart 4 | 6.1 | 48 | 20 |

| | Interleukin-4 receptor alpha chain | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 46.2 | 69.6 | 47.1 | 80.3 | 46.2 | 69.6 |
| Average | 56.0 | 74.5 | 53.5 | 62.1 | 60.2 | 80.6 |
| Stdev | 50.9 | 55.4 | 37.9 | 40.8 | 56.9 | 62.8 |
| p (t-test) | | 0.081 | | 0.54 | | 0.15 |
| Min | 2.31 | 7.12 | 2.31 | 4.67 | 2.31 | 10.3 |
| Max | 256 | 239 | 122 | 119 | 256 | 239 |
| n (Samp) | 90 | 34 | 34 | 10 | 71 | 22 |
| n (Patient) | 90 | 34 | 34 | 10 | 71 | 22 |

| | At Enrollment | | |
|---|---|---|---|
| | sCr or UO | sCr only | UO only |
| AUC | 0.63 | 0.57 | 0.63 |
| SE | 0.058 | 0.11 | 0.071 |
| p | 0.027 | 0.50 | 0.066 |
| nCohort 1 | 90 | 34 | 71 |
| nCohort 2 | 34 | 10 | 22 |
| Cutoff 1 | 40.7 | 49.3 | 25.4 |
| Sens 1 | 71% | 70% | 73% |
| Spec 1 | 39% | 56% | 37% |
| Cutoff 2 | 12.4 | 11.7 | 20.5 |
| Sens 2 | 82% | 80% | 82% |
| Spec 2 | 33% | 26% | 35% |
| Cutoff 3 | 11.8 | 4.67 | 11.8 |
| Sens 3 | 91% | 90% | 91% |
| Spec 3 | 28% | 6% | 25% |
| Cutoff 4 | 69.4 | 79.9 | 68.1 |
| Sens 4 | 50% | 50% | 55% |

|  | | | |
|---|---|---|---|
| Spec 4 | 70% | 71% | 70% |
| Cutoff 5 | 93.9 | 94.4 | 105 |
| Sens 5 | 35% | 10% | 27% |
| Spec 5 | 80% | 82% | 80% |
| Cutoff 6 | 115 | 104 | 137 |
| Sens 6 | 15% | 10% | 14% |
| Spec 6 | 90% | 91% | 90% |
| OR Quart 2 | 2.3 | 0.45 | 3.7 |
| p Value | 0.21 | 0.54 | 0.14 |
| 95% CI of | 0.63 | 0.035 | 0.66 |
| OR Quart 2 | 8.8 | 5.8 | 21 |
| OR Quart 3 | 3.2 | 2.6 | 3.7 |
| p Value | 0.077 | 0.35 | 0.14 |
| 95% CI of | 0.88 | 0.36 | 0.66 |
| OR Quart 3 | 12 | 18 | 21 |
| OR Quart 4 | 4.3 | 1.7 | 5.2 |
| p Value | 0.026 | 0.61 | 0.053 |
| 95% CI of | 1.2 | 0.22 | 0.98 |
| OR Quart 4 | 15 | 13 | 28 |

Lutropin subunit beta

|  | sCr or UO | | sCr only | | UO only | |
|---|---|---|---|---|---|---|
|  | Cohort 1 | Cohort 2 | Cohort 1 | Cohort 2 | Cohort 1 | Cohort 2 |
| Median | 16.9 | 10.4 | nd | nd | 20.2 | 27.2 |
| Average | 45.9 | 40.9 | nd | nd | 41.3 | 64.1 |
| Stdev | 67.7 | 70.4 | nd | nd | 61.1 | 97.6 |
| p (t-test) |  | 0.75 | nd | nd |  | 0.27 |
| Min | 0.211 | 0.0858 | nd | nd | 0.311 | 0.0858 |
| Max | 268 | 277 | nd | nd | 268 | 325 |
| n (Samp) | 54 | 28 | nd | nd | 40 | 20 |
| n (Patient) | 54 | 28 | nd | nd | 40 | 20 |

|  | At Enrollment | | |
|---|---|---|---|
|  | sCr or UO | sCr only | UO only |
| AUC | 0.45 | nd | 0.52 |
| SE | 0.068 | nd | 0.080 |
| p | 0.42 | nd | 0.77 |
| nCohort 1 | 54 | nd | 40 |
| nCohort 2 | 28 | nd | 20 |
| Cutoff 1 | 4.22 | nd | 8.91 |
| Sens 1 | 71% | nd | 70% |
| Spec 1 | 24% | nd | 40% |
| Cutoff 2 | 2.03 | nd | 4.22 |
| Sens 2 | 82% | nd | 80% |
| Spec 2 | 19% | nd | 20% |
| Cutoff 3 | 0.388 | nd | 0.388 |
| Sens 3 | 93% | nd | 90% |
| Spec 3 | 7% | nd | 8% |
| Cutoff 4 | 42.8 | nd | 43.5 |
| Sens 4 | 25% | nd | 35% |
| Spec 4 | 70% | nd | 70% |
| Cutoff 5 | 68.4 | nd | 59.7 |
| Sens 5 | 14% | nd | 25% |
| Spec 5 | 81% | nd | 80% |
| Cutoff 6 | 162 | nd | 76.4 |
| Sens 6 | 7% | nd | 20% |
| Spec 6 | 91% | nd | 90% |
| OR Quart 2 | 1.3 | nd | 0.38 |
| p Value | 0.66 | nd | 0.24 |
| 95% CI of | 0.36 | nd | 0.073 |
| OR Quart 2 | 5.0 | nd | 1.9 |
| OR Quart 3 | 1.2 | nd | 1.0 |
| p Value | 0.74 | nd | 1.0 |
| 95% CI of | 0.34 | nd | 0.23 |
| OR Quart 3 | 4.6 | nd | 4.3 |
| OR Quart 4 | 1.7 | nd | 0.75 |
| p Value | 0.44 | nd | 0.71 |
| 95% CI of | 0.45 | nd | 0.17 |
| OR Quart 4 | 6.1 | nd | 3.3 |

-continued

| Platelet-derived growth factor subunit B (dimer) | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 1.82 | 2.07 | 2.78 | 1.24 | 1.71 | 1.76 |
| Average | 3.46 | 2.36 | 5.94 | 1.92 | 2.45 | 2.25 |
| Stdev | 9.80 | 2.42 | 15.1 | 2.62 | 2.77 | 2.39 |
| p (t-test) | | 0.53 | | 0.41 | | 0.76 |
| Min | 0.00313 | 0.00369 | 0.0244 | 0.0144 | 0.00313 | 0.00369 |
| Max | 86.2 | 10.8 | 86.2 | 8.93 | 17.1 | 10.8 |
| n (Samp) | 77 | 33 | 31 | 10 | 61 | 24 |
| n (Patient) | 77 | 33 | 31 | 10 | 61 | 24 |

| | At Enrollment | | |
|---|---|---|---|
| | sCr or UO | sCr only | UO only |
| AUC | 0.48 | 0.25 | 0.49 |
| SE | 0.061 | 0.097 | 0.070 |
| p | 0.73 | 0.0084 | 0.84 |
| nCohort 1 | 77 | 31 | 61 |
| nCohort 2 | 33 | 10 | 24 |
| Cutoff 1 | 0.484 | 0.463 | 0.545 |
| Sens 1 | 73% | 70% | 71% |
| Spec 1 | 18% | 3% | 21% |
| Cutoff 2 | 0.365 | 0.0244 | 0.365 |
| Sens 2 | 82% | 80% | 83% |
| Spec 2 | 17% | 3% | 20% |
| Cutoff 3 | 0.0144 | 0 | 0.0244 |
| Sens 3 | 91% | 100% | 92% |
| Spec 3 | 3% | 0% | 11% |
| Cutoff 4 | 3.07 | 3.71 | 3.00 |
| Sens 4 | 27% | 10% | 29% |
| Spec 4 | 70% | 71% | 70% |
| Cutoff 5 | 3.71 | 4.20 | 3.42 |
| Sens 5 | 21% | 10% | 25% |
| Spec 5 | 81% | 81% | 80% |
| Cutoff 6 | 6.35 | 8.43 | 5.18 |
| Sens 6 | 6% | 10% | 4% |
| Spec 6 | 91% | 90% | 90% |
| OR Quart 2 | 0.89 | 1.1 | 1.1 |
| p Value | 0.84 | 0.94 | 0.92 |
| 95% CI of OR Quart 2 | 0.28 | 0.060 | 0.28 |
| | 2.8 | 20 | 4.0 |
| OR Quart 3 | 0.46 | 4.3 | 0.63 |
| p Value | 0.22 | 0.25 | 0.53 |
| 95% CI of OR Quart 3 | 0.13 | 0.37 | 0.15 |
| | 1.6 | 50 | 2.6 |
| OR Quart 4 | 1.5 | 10 | 1.6 |
| p Value | 0.51 | 0.060 | 0.45 |
| 95% CI of OR Quart 4 | 0.48 | 0.91 | 0.45 |
| | 4.4 | 110 | 5.9 |

| Corticotropin | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.00163 | 0.00194 | nd | nd | 0.00163 | 0.00171 |
| Average | 0.00250 | 0.00276 | nd | nd | 0.00260 | 0.00164 |
| Stdev | 0.00498 | 0.00438 | nd | nd | 0.00550 | 0.000678 |
| p (t-test) | | 0.82 | nd | nd | | 0.49 |
| Min | 3.92E−6 | 0.000355 | nd | nd | 0.000355 | 0.000355 |
| Max | 0.0373 | 0.0224 | nd | nd | 0.0373 | 0.00282 |
| n (Samp) | 53 | 23 | nd | nd | 43 | 16 |
| n (Patient) | 53 | 23 | nd | nd | 43 | 16 |

| | At Enrollment | | |
|---|---|---|---|
| | sCr or UO | sCr only | UO only |
| AUC | 0.53 | nd | 0.47 |
| SE | 0.073 | nd | 0.086 |
| p | 0.66 | nd | 0.73 |
| nCohort 1 | 53 | nd | 43 |
| nCohort 2 | 23 | nd | 16 |

-continued

| | | | |
|---|---|---|---|
| Cutoff 1 | 0.00119 | nd | 0.00134 |
| Sens 1 | 74% | nd | 75% |
| Spec 1 | 30% | nd | 35% |
| Cutoff 2 | 0.00111 | nd | 0.00111 |
| Sens 2 | 87% | nd | 81% |
| Spec 2 | 23% | nd | 21% |
| Cutoff 3 | 0.000909 | nd | 0.000355 |
| Sens 3 | 91% | nd | 94% |
| Spec 3 | 23% | nd | 5% |
| Cutoff 4 | 0.00222 | nd | 0.00222 |
| Sens 4 | 26% | nd | 12% |
| Spec 4 | 72% | nd | 72% |
| Cutoff 5 | 0.00291 | nd | 0.00256 |
| Sens 5 | 13% | nd | 12% |
| Spec 5 | 85% | nd | 81% |
| Cutoff 6 | 0.00362 | nd | 0.00304 |
| Sens 6 | 13% | nd | 0% |
| Spec 6 | 91% | nd | 91% |
| OR Quart 2 | 1.0 | nd | 4.3 |
| p Value | 1.0 | nd | 0.11 |
| 95% CI of | 0.24 | nd | 0.71 |
| OR Quart 2 | 4.2 | nd | 27 |
| OR Quart 3 | 1.6 | nd | 2.4 |
| p Value | 0.49 | nd | 0.37 |
| 95% CI of | 0.41 | nd | 0.36 |
| OR Quart 3 | 6.5 | nd | 15 |
| OR Quart 4 | 1.3 | nd | 2.6 |
| p Value | 0.72 | nd | 0.32 |
| 95% CI of | 0.32 | nd | 0.39 |
| OR Quart 4 | 5.3 | nd | 17 |

Thyroxine-binding globulin

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.0750 | 0.136 | nd | nd | 0.0894 | 0.150 |
| Average | 0.225 | 0.184 | nd | nd | 0.263 | 0.191 |
| Stdev | 0.373 | 0.205 | nd | nd | 0.411 | 0.184 |
| p (t-test) | | 0.62 | nd | nd | | 0.50 |
| Min | 8.30E−5 | 0.00330 | nd | nd | 0.00106 | 0.00330 |
| Max | 1.86 | 0.748 | nd | nd | 1.86 | 0.564 |
| n (Samp) | 52 | 23 | nd | nd | 43 | 16 |
| n (Patient) | 52 | 23 | nd | nd | 43 | 16 |

At Enrollment

| | sCr or UO | sCr only | UO only |
|---|---|---|---|
| AUC | 0.52 | nd | 0.51 |
| SE | 0.073 | nd | 0.085 |
| p | 0.83 | nd | 0.93 |
| nCohort 1 | 52 | nd | 43 |
| nCohort 2 | 23 | nd | 16 |
| Cutoff 1 | 0.0183 | nd | 0.0179 |
| Sens 1 | 74% | nd | 75% |
| Spec 1 | 27% | nd | 28% |
| Cutoff 2 | 0.0138 | nd | 0.0119 |
| Sens 2 | 83% | nd | 81% |
| Spec 2 | 19% | nd | 21% |
| Cutoff 3 | 0.00575 | nd | 0.00330 |
| Sens 3 | 91% | nd | 94% |
| Spec 3 | 12% | nd | 5% |
| Cutoff 4 | 0.212 | nd | 0.296 |
| Sens 4 | 35% | nd | 31% |
| Spec 4 | 71% | nd | 72% |
| Cutoff 5 | 0.369 | nd | 0.468 |
| Sens 5 | 13% | nd | 12% |
| Spec 5 | 83% | nd | 81% |
| Cutoff 6 | 0.486 | nd | 0.792 |
| Sens 6 | 9% | nd | 0% |
| Spec 6 | 90% | nd | 91% |
| OR Quart 2 | 0.93 | nd | 0.62 |
| p Value | 0.92 | nd | 0.59 |
| 95% CI of | 0.22 | nd | 0.11 |
| OR Quart 2 | 4.0 | nd | 3.5 |
| OR Quart 3 | 1.5 | nd | 1.7 |
| p Value | 0.56 | nd | 0.52 |

-continued

|  | | | | | |
|---|---|---|---|---|---|
| 95% CI of | 0.38 | | nd | | 0.35 |
| OR Quart 3 | 6.1 | | nd | | 7.9 |
| OR Quart 4 | 1.2 | | nd | | 0.62 |
| p Value | 0.80 | | nd | | 0.59 |
| 95% CI of | 0.29 | | nd | | 0.11 |
| OR Quart 4 | 4.9 | | nd | | 3.5 |

Alpha-fetoprotein

|  | sCr or UO | | sCr only | | UO only | |
|---|---|---|---|---|---|---|
|  | Cohort 1 | Cohort 2 | Cohort 1 | Cohort 2 | Cohort 1 | Cohort 2 |
| Median | 0.00505 | 0.00587 | 0.00428 | 0.0385 | 0.00486 | 0.00587 |
| Average | 0.0525 | 0.122 | 0.0656 | 0.297 | 0.0435 | 0.0801 |
| Stdev | 0.106 | 0.321 | 0.126 | 0.568 | 0.0900 | 0.196 |
| p (t-test) | | 0.083 | | 0.037 | | 0.22 |
| Min | 0.000463 | 0.000463 | 0.000463 | 0.000523 | 0.000463 | 0.000463 |
| Max | 0.585 | 1.74 | 0.585 | 1.74 | 0.507 | 0.840 |
| n (Samp) | 79 | 40 | 31 | 9 | 62 | 31 |
| n (Patient) | 79 | 40 | 31 | 9 | 62 | 31 |

At Enrollment

|  | sCr or UO | sCr only | UO only |
|---|---|---|---|
| AUC | 0.50 | 0.67 | 0.50 |
| SE | 0.056 | 0.11 | 0.064 |
| p | 0.99 | 0.12 | 0.96 |
| nCohort 1 | 79 | 31 | 62 |
| nCohort 2 | 40 | 9 | 31 |
| Cutoff 1 | 0.00286 | 0.00483 | 0.00132 |
| Sens 1 | 70% | 78% | 74% |
| Spec 1 | 18% | 55% | 15% |
| Cutoff 2 | 0.000463 | 0.000523 | 0.000463 |
| Sens 2 | 85% | 89% | 90% |
| Spec 2 | 8% | 19% | 6% |
| Cutoff 3 | 0 | 0.000463 | 0.000463 |
| Sens 3 | 100% | 100% | 90% |
| Spec 3 | 0% | 19% | 6% |
| Cutoff 4 | 0.0499 | 0.0671 | 0.00660 |
| Sens 4 | 25% | 44% | 32% |
| Spec 4 | 72% | 71% | 71% |
| Cutoff 5 | 0.0728 | 0.107 | 0.0613 |
| Sens 5 | 22% | 44% | 19% |
| Spec 5 | 81% | 81% | 81% |
| Cutoff 6 | 0.198 | 0.236 | 0.130 |
| Sens 6 | 10% | 22% | 16% |
| Spec 6 | 91% | 90% | 90% |
| OR Quart 2 | 0.43 | 0 | 2.2 |
| p Value | 0.14 | na | 0.19 |
| 95% CI of | 0.14 | na | 0.67 |
| OR Quart 2 | 1.3 | na | 7.4 |
| OR Quart 3 | 0.82 | 1.7 | 0.36 |
| p Value | 0.71 | 0.61 | 0.19 |
| 95% CI of | 0.29 | 0.22 | 0.081 |
| OR Quart 3 | 2.3 | 13 | 1.6 |
| OR Quart 4 | 0.71 | 2.7 | 1.9 |
| p Value | 0.52 | 0.34 | 0.31 |
| 95% CI of | 0.25 | 0.36 | 0.56 |
| OR Quart 4 | 2.0 | 20 | 6.2 |

Apolipoprotein E

|  | sCr or UO | | sCr only | | UO only | |
|---|---|---|---|---|---|---|
|  | Cohort 1 | Cohort 2 | Cohort 1 | Cohort 2 | Cohort 1 | Cohort 2 |
| Median | 3.11 | 1.74 | 1.37 | 1.13 | 4.13 | 1.77 |
| Average | 24.3 | 6.24 | 8.39 | 3.15 | 27.8 | 6.55 |
| Stdev | 169 | 12.6 | 34.1 | 6.55 | 190 | 13.7 |
| p (t-test) | | 0.41 | | 0.55 | | 0.46 |
| Min | 0.00102 | 0.000147 | 0.000147 | 0.000147 | 0.00122 | 0.00129 |
| Max | 1960 | 83.4 | 254 | 26.8 | 1960 | 83.4 |
| n (Samp) | 137 | 59 | 56 | 16 | 107 | 43 |
| n (Patient) | 137 | 59 | 56 | 16 | 107 | 43 |

-continued

|  | At Enrollment | | |
| --- | --- | --- | --- |
|  | sCr or UO | sCr only | UO only |
| AUC | 0.45 | 0.44 | 0.42 |
| SE | 0.045 | 0.083 | 0.053 |
| p | 0.24 | 0.46 | 0.15 |
| nCohort 1 | 137 | 56 | 107 |
| nCohort 2 | 59 | 16 | 43 |
| Cutoff 1 | 0.957 | 0.177 | 1.00 |
| Sens 1 | 71% | 75% | 72% |
| Spec 1 | 34% | 23% | 31% |
| Cutoff 2 | 0.551 | 0.0954 | 0.551 |
| Sens 2 | 81% | 81% | 81% |
| Spec 2 | 20% | 16% | 17% |
| Cutoff 3 | 0.0862 | 0.00122 | 0.0954 |
| Sens 3 | 92% | 94% | 91% |
| Spec 3 | 9% | 5% | 7% |
| Cutoff 4 | 7.35 | 3.25 | 9.11 |
| Sens 4 | 19% | 25% | 19% |
| Spec 4 | 70% | 71% | 71% |
| Cutoff 5 | 14.2 | 4.55 | 17.3 |
| Sens 5 | 12% | 12% | 12% |
| Spec 5 | 80% | 80% | 80% |
| Cutoff 6 | 25.4 | 14.2 | 30.5 |
| Sens 6 | 7% | 6% | 2% |
| Spec 6 | 91% | 91% | 91% |
| OR Quart 2 | 1.9 | 1.4 | 1.2 |
| p Value | 0.17 | 0.67 | 0.74 |
| 95% CI of OR Quart 2 | 0.76 4.7 | 0.27 7.5 | 0.41 3.6 |
| OR Quart 3 | 2.3 | 1.4 | 2.4 |
| p Value | 0.077 | 0.67 | 0.084 |
| 95% CI of OR Quart 3 | 0.92 5.6 | 0.27 7.5 | 0.89 6.8 |
| OR Quart 4 | 1.7 | 1.9 | 1.6 |
| p Value | 0.25 | 0.43 | 0.39 |
| 95% CI of OR Quart 4 | 0.68 4.3 | 0.38 9.6 | 0.55 4.5 |

FIG. 4: Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| | Complement C4-B | | | | | |
| --- | --- | --- | --- | --- | --- | --- |
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 24.7 | 74.8 | 24.7 | 63.2 | 24.7 | 53.0 |
| Average | 80.6 | 110 | 80.6 | 103 | 80.6 | 92.3 |
| Stdev | 182 | 165 | 182 | 163 | 182 | 110 |
| p (t-test) | | 0.41 | | 0.52 | | 0.80 |
| Min | 0.00607 | 0.499 | 0.00607 | 0.499 | 0.00607 | 3.05 |
| Max | 1950 | 827 | 1950 | 827 | 1950 | 425 |
| n (Samp) | 223 | 30 | 223 | 30 | 223 | 16 |
| n (Patient) | 223 | 30 | 223 | 30 | 223 | 16 |
| sCr only | | | | | | |
| Median | 35.2 | 71.6 | 35.2 | 71.6 | 35.2 | 71.6 |
| Average | 106 | 101 | 106 | 101 | 106 | 115 |
| Stdev | 206 | 118 | 206 | 118 | 206 | 142 |
| p (t-test) | | 0.94 | | 0.94 | | 0.90 |
| Min | 0.00607 | 0.499 | 0.00607 | 0.499 | 0.00607 | 17.0 |
| Max | 2000 | 425 | 2000 | 425 | 2000 | 425 |
| n (Samp) | 374 | 13 | 374 | 13 | 374 | 7 |
| n (Patient) | 374 | 13 | 374 | 13 | 374 | 7 |
| UO only | | | | | | |
| Median | 28.0 | 78.0 | 28.0 | 71.6 | 28.0 | 63.2 |
| Average | 88.7 | 111 | 88.7 | 103 | 88.7 | 84.8 |
| Stdev | 187 | 169 | 187 | 168 | 187 | 72.8 |

-continued

| | | | | | | | | | |
|---|---|---|---|---|---|---|---|---|---|
| p (t-test) | | 0.59 | | | 0.73 | | | 0.94 | |
| Min | 0.00329 | 0.904 | | 0.00329 | 0.672 | | 0.00329 | 3.05 | |
| Max | 1950 | 827 | | 1950 | 827 | | 1950 | 236 | |
| n (Samp) | 173 | 23 | | 173 | 23 | | 173 | 14 | |
| n (Patient) | 173 | 23 | | 173 | 23 | | 173 | 14 | |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.60 | 0.55 | 0.60 | 0.59 | 0.55 | 0.58 | 0.63 | 0.64 | 0.61 |
| SE | 0.058 | 0.084 | 0.066 | 0.058 | 0.084 | 0.066 | 0.077 | 0.11 | 0.083 |
| p | 0.080 | 0.54 | 0.12 | 0.14 | 0.54 | 0.20 | 0.085 | 0.22 | 0.18 |
| nCohort 1 | 223 | 374 | 173 | 223 | 374 | 173 | 223 | 374 | 173 |
| nCohort 2 | 30 | 13 | 23 | 30 | 13 | 23 | 16 | 7 | 14 |
| Cutoff 1 | 16.9 | 17.0 | 16.9 | 16.9 | 17.0 | 16.9 | 17.8 | 47.7 | 30.8 |
| Sens 1 | 70% | 77% | 74% | 70% | 77% | 74% | 75% | 71% | 71% |
| Spec 1 | 44% | 34% | 38% | 44% | 34% | 38% | 45% | 56% | 51% |
| Cutoff 2 | 8.71 | 5.52 | 8.98 | 5.52 | 5.52 | 8.71 | 17.0 | 32.9 | 16.9 |
| Sens 2 | 80% | 85% | 83% | 80% | 85% | 83% | 81% | 86% | 86% |
| Spec 2 | 35% | 19% | 27% | 26% | 19% | 27% | 44% | 48% | 38% |
| Cutoff 3 | 2.76 | 0.923 | 4.28 | 2.22 | 0.923 | 2.76 | 4.27 | 17.0 | 4.27 |
| Sens 3 | 90% | 92% | 91% | 90% | 92% | 91% | 94% | 100% | 93% |
| Spec 3 | 16% | 4% | 17% | 13% | 4% | 10% | 22% | 34% | 16% |
| Cutoff 4 | 57.6 | 87.6 | 63.7 | 57.6 | 87.6 | 63.7 | 57.6 | 87.6 | 63.7 |
| Sens 4 | 53% | 38% | 57% | 50% | 38% | 52% | 44% | 29% | 50% |
| Spec 4 | 70% | 70% | 71% | 70% | 70% | 71% | 70% | 70% | 71% |
| Cutoff 5 | 106 | 150 | 128 | 106 | 150 | 128 | 106 | 150 | 128 |
| Sens 5 | 37% | 23% | 35% | 33% | 23% | 30% | 31% | 14% | 36% |
| Spec 5 | 80% | 80% | 80% | 80% | 80% | 80% | 80% | 80% | 80% |
| Cutoff 6 | 213 | 260 | 229 | 213 | 260 | 229 | 213 | 260 | 229 |
| Sens 6 | 10% | 8% | 9% | 7% | 8% | 4% | 12% | 14% | 7% |
| Spec 6 | 90% | 90% | 90% | 90% | 90% | 90% | 90% | 90% | 90% |
| OR Quart 2 | 1.4 | 0.65 | 1.7 | 1.0 | 0.65 | 1.0 | 1.5 | >2.0 | 0.98 |
| p Value | 0.55 | 0.64 | 0.47 | 1.0 | 0.64 | 1.0 | 0.66 | <0.56 | 0.98 |
| 95% CI of | 0.43 | 0.11 | 0.39 | 0.30 | 0.11 | 0.24 | 0.24 | >0.18 | 0.13 |
| OR Quart 2 | 4.8 | 4.0 | 7.7 | 3.3 | 4.0 | 4.2 | 9.3 | na | 7.3 |
| OR Quart 3 | 0.79 | 1.3 | 2.1 | 0.82 | 1.3 | 1.9 | 2.0 | >3.1 | 2.0 |
| p Value | 0.73 | 0.71 | 0.30 | 0.75 | 0.71 | 0.34 | 0.42 | <0.33 | 0.42 |
| 95% CI of | 0.20 | 0.29 | 0.50 | 0.24 | 0.29 | 0.51 | 0.36 | >0.32 | 0.36 |
| OR Quart 3 | 3.1 | 6.1 | 9.1 | 2.8 | 6.1 | 6.9 | 12 | na | 12 |
| OR Quart 4 | 3.2 | 1.3 | 3.4 | 2.4 | 1.3 | 2.2 | 3.8 | >2.0 | 3.2 |
| p Value | 0.034 | 0.71 | 0.077 | 0.095 | 0.71 | 0.23 | 0.11 | <0.57 | 0.17 |
| 95% CI of | 1.1 | 0.29 | 0.87 | 0.86 | 0.29 | 0.61 | 0.75 | >0.18 | 0.61 |
| OR Quart 4 | 9.7 | 6.1 | 14 | 6.8 | 6.1 | 7.8 | 19 | na | 17 |

| C-C motif chemokine 26 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.0402 | 0.0421 | 0.0402 | 0.0405 | 0.0402 | 0.0379 |
| Average | 0.0784 | 1.93 | 0.0784 | 1.93 | 0.0784 | 0.0347 |
| Stdev | 0.610 | 8.08 | 0.610 | 8.08 | 0.610 | 0.0128 |
| p (t-test) | | 7.9E−4 | | 8.0E−4 | | 0.78 |
| Min | 0.00872 | 0.00872 | 0.00872 | 0.00872 | 0.00872 | 0.0195 |
| Max | 9.14 | 42.3 | 9.14 | 42.3 | 9.14 | 0.0526 |
| n (Samp) | 223 | 30 | 223 | 30 | 223 | 16 |
| n (Patient) | 223 | 30 | 223 | 30 | 223 | 16 |
| sCr only | | | | | | |
| Median | 0.0438 | 0.0402 | 0.0438 | 0.0402 | 0.0438 | 0.0443 |
| Average | 0.408 | 0.0374 | 0.408 | 0.0359 | 0.408 | 0.0393 |
| Stdev | 3.41 | 0.0150 | 3.41 | 0.0152 | 3.41 | 0.0124 |
| p (t-test) | | 0.70 | | 0.69 | | 0.78 |
| Min | 0.00872 | 0.00872 | 0.00872 | 0.00872 | 0.00872 | 0.0195 |
| Max | 42.3 | 0.0633 | 42.3 | 0.0633 | 42.3 | 0.0526 |
| n (Samp) | 375 | 13 | 375 | 13 | 375 | 7 |
| n (Patient) | 375 | 13 | 375 | 13 | 375 | 7 |
| UO only | | | | | | |
| Median | 0.0443 | 0.0433 | 0.0443 | 0.0433 | 0.0443 | 0.0363 |
| Average | 0.0482 | 2.91 | 0.0482 | 2.83 | 0.0482 | 0.0340 |
| Stdev | 0.0942 | 9.28 | 0.0942 | 9.23 | 0.0942 | 0.0117 |
| p (t-test) | | 5.6E−5 | | 7.9E−5 | | 0.57 |

-continued

|     |         |        |         |        |         |        |
|-----|---------|--------|---------|--------|---------|--------|
| Min | 0.00872 | 0.0196 | 0.00872 | 0.0196 | 0.00872 | 0.0196 |
| Max | 1.25    | 42.3   | 1.25    | 42.3   | 1.25    | 0.0525 |
| n (Samp)    | 173 | 23 | 173 | 23 | 173 | 14 |
| n (Patient) | 173 | 23 | 173 | 23 | 173 | 14 |

|            | 0 hr prior to AKI stage ||| 24 hr prior to AKI stage ||| 48 hr prior to AKI stage |||
|------------|-----------|----------|---------|-----------|----------|---------|-----------|----------|---------|
|            | sCr or UO | sCr only | UO only | sCr or UO | sCr only | UO only | sCr or UO | sCr only | UO only |
| AUC        | 0.55   | 0.44   | 0.53   | 0.51   | 0.42   | 0.48   | 0.47   | 0.47   | 0.38   |
| SE         | 0.057  | 0.084  | 0.065  | 0.057  | 0.084  | 0.065  | 0.076  | 0.11   | 0.083  |
| p          | 0.37   | 0.48   | 0.62   | 0.85   | 0.37   | 0.81   | 0.66   | 0.79   | 0.15   |
| nCohort 1  | 223    | 375    | 173    | 223    | 375    | 173    | 223    | 375    | 173    |
| nCohort 2  | 30     | 13     | 23     | 30     | 13     | 23     | 16     | 7      | 14     |
| Cutoff 1   | 0.0311 | 0.0240 | 0.0386 | 0.0235 | 0.0235 | 0.0232 | 0.0232 | 0.0433 | 0.0232 |
| Sens 1     | 70%    | 77%    | 74%    | 73%    | 77%    | 78%    | 75%    | 71%    | 79%    |
| Spec 1     | 47%    | 30%    | 41%    | 39%    | 27%    | 28%    | 39%    | 47%    | 28%    |
| Cutoff 2   | 0.0232 | 0.0232 | 0.0232 | 0.0231 | 0.0232 | 0.0231 | 0.0196 | 0.0232 | 0.0196 |
| Sens 2     | 83%    | 85%    | 87%    | 80%    | 85%    | 83%    | 81%    | 86%    | 86%    |
| Spec 2     | 39%    | 27%    | 28%    | 32%    | 27%    | 23%    | 15%    | 27%    | 13%    |
| Cutoff 3   | 0.0196 | 0.0188 | 0.0231 | 0.0195 | 0.0188 | 0.0196 | 0.0195 | 0.0188 | 0.0195 |
| Sens 3     | 90%    | 92%    | 91%    | 93%    | 92%    | 91%    | 94%    | 100%   | 100%   |
| Spec 3     | 15%    | 8%     | 23%    | 15%    | 8%     | 13%    | 15%    | 8%     | 13%    |
| Cutoff 4   | 0.0504 | 0.0525 | 0.0525 | 0.0504 | 0.0525 | 0.0525 | 0.0504 | 0.0525 | 0.0525 |
| Sens 4     | 23%    | 15%    | 22%    | 20%    | 15%    | 17%    | 12%    | 14%    | 0%     |
| Spec 4     | 78%    | 76%    | 77%    | 78%    | 76%    | 77%    | 78%    | 76%    | 77%    |
| Cutoff 5   | 0.0525 | 0.0526 | 0.0526 | 0.0525 | 0.0526 | 0.0526 | 0.0525 | 0.0526 | 0.0526 |
| Sens 5     | 20%    | 8%     | 22%    | 17%    | 8%     | 17%    | 6%     | 0%     | 0%     |
| Spec 5     | 85%    | 82%    | 86%    | 85%    | 82%    | 86%    | 85%    | 82%    | 86%    |
| Cutoff 6   | 0.0628 | 0.0628 | 0.0628 | 0.0628 | 0.0628 | 0.0628 | 0.0628 | 0.0628 | 0.0628 |
| Sens 6     | 17%    | 8%     | 22%    | 13%    | 8%     | 17%    | 0%     | 0%     | 0%     |
| Spec 6     | 95%    | 90%    | 92%    | 95%    | 90%    | 92%    | 95%    | 90%    | 92%    |
| OR Quart 2 | 2.5    | 1.5    | 4.4    | 1.4    | 1.5    | 0.78   | 3.2    | 3.1    | 3.1    |
| p Value    | 0.15   | 0.65   | 0.030  | 0.57   | 0.65   | 0.73   | 0.16   | 0.33   | 0.33   |
| 95% CI of  | 0.72   | 0.25   | 1.2    | 0.45   | 0.25   | 0.20   | 0.62   | 0.32   | 0.31   |
| OR Quart 2 | 8.4    | 9.3    | 17     | 4.2    | 9.3    | 3.1    | 17     | 30     | 31     |
| OR Quart 3 | 2.8    | 3.1    | 1.0    | 1.8    | 3.1    | 2.3    | 2.1    | 2.0    | 8.0    |
| p Value    | 0.099  | 0.17   | 1.0    | 0.29   | 0.17   | 0.17   | 0.41   | 0.57   | 0.056  |
| 95% CI of  | 0.82   | 0.62   | 0.19   | 0.61   | 0.62   | 0.71   | 0.36   | 0.18   | 0.95   |
| OR Quart 3 | 9.4    | 16     | 5.2    | 5.3    | 16     | 7.2    | 12     | 23     | 68     |
| OR Quart 4 | 1.8    | 1.0    | 2.1    | 0.98   | 1.0    | 0.78   | 2.1    | 1.0    | 3.2    |
| p Value    | 0.36   | 1.0    | 0.30   | 0.98   | 1.0    | 0.73   | 0.40   | 0.99   | 0.32   |
| 95% CI of  | 0.50   | 0.14   | 0.50   | 0.30   | 0.14   | 0.20   | 0.37   | 0.062  | 0.32   |
| OR Quart 4 | 6.5    | 7.2    | 9.1    | 3.2    | 7.2    | 3.1    | 12     | 16     | 32     |

C-C motif chemokine 7

|             | 0 hr prior to AKI stage || 24 hr prior to AKI stage || 48 hr prior to AKI stage ||
|-------------|----------|----------|----------|----------|----------|----------|
|             | Cohort 1 | Cohort 2 | Cohort 1 | Cohort 2 | Cohort 1 | Cohort 2 |
| sCr or UO   |          |          |          |          |          |          |
| Median      | 0.662    | 1.22     | 0.662    | 0.812    | 0.662    | 0.625    |
| Average     | 2.62     | 17.1     | 2.62     | 9.44     | 2.62     | 11.0     |
| Stdev       | 9.67     | 24.1     | 9.67     | 18.5     | 9.67     | 22.3     |
| p (t-test)  |          | 4.3E−9   |          | 0.0017   |          | 0.0035   |
| Min         | 0.146    | 0.188    | 0.146    | 0.188    | 0.146    | 0.319    |
| Max         | 125      | 82.4     | 125      | 82.4     | 125      | 82.4     |
| n (Samp)    | 223      | 30       | 223      | 30       | 223      | 16       |
| n (Patient) | 223      | 30       | 223      | 30       | 223      | 16       |
| sCr only    |          |          |          |          |          |          |
| Median      | 0.816    | 1.29     | 0.816    | 1.15     | 0.816    | 0.625    |
| Average     | 3.99     | 34.0     | 3.99     | 12.4     | 3.99     | 7.89     |
| Stdev       | 19.3     | 80.2     | 19.3     | 20.1     | 19.3     | 13.3     |
| p (t-test)  |          | 8.9E−6   |          | 0.12     |          | 0.59     |
| Min         | 0.146    | 0.188    | 0.146    | 0.188    | 0.146    | 0.319    |
| Max         | 291      | 293      | 291      | 67.6     | 291      | 33.9     |
| n (Samp)    | 375      | 13       | 375      | 13       | 375      | 7        |
| n (Patient) | 375      | 13       | 375      | 13       | 375      | 7        |
| UO only     |          |          |          |          |          |          |
| Median      | 0.816    | 1.15     | 0.816    | 0.812    | 0.816    | 0.625    |
| Average     | 3.35     | 26.1     | 3.35     | 14.4     | 3.35     | 8.82     |
| Stdev       | 10.9     | 40.2     | 10.9     | 29.5     | 10.9     | 22.9     |
| p (t-test)  |          | 7.5E−9   |          | 5.7E−4   |          | 0.11     |
| Min         | 0.146    | 0.341    | 0.146    | 0.319    | 0.146    | 0.341    |

-continued

|   | | | | | | |
|---|---|---|---|---|---|---|
| Max | 125 | 166 | 125 | 114 | 125 | 82.4 |
| n (Samp) | 173 | 23 | 173 | 23 | 173 | 14 |
| n (Patient) | 173 | 23 | 173 | 23 | 173 | 14 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.72 | 0.64 | 0.67 | 0.62 | 0.60 | 0.54 | 0.59 | 0.50 | 0.46 |
| SE | 0.055 | 0.084 | 0.065 | 0.058 | 0.084 | 0.065 | 0.077 | 0.11 | 0.082 |
| p | 9.6E−5 | 0.088 | 0.0087 | 0.038 | 0.26 | 0.50 | 0.22 | 1.00 | 0.62 |
| nCohort 1 | 223 | 375 | 173 | 223 | 375 | 173 | 223 | 375 | 173 |
| nCohort 2 | 30 | 13 | 23 | 30 | 13 | 23 | 16 | 7 | 14 |
| Cutoff 1 | 0.584 | 0.380 | 0.584 | 0.515 | 0.380 | 0.515 | 0.483 | 0.336 | 0.515 |
| Sens 1 | 73% | 77% | 78% | 70% | 77% | 74% | 75% | 86% | 71% |
| Spec 1 | 46% | 29% | 31% | 43% | 29% | 29% | 43% | 22% | 29% |
| Cutoff 2 | 0.483 | 0.336 | 0.515 | 0.406 | 0.336 | 0.499 | 0.380 | 0.336 | 0.380 |
| Sens 2 | 83% | 85% | 83% | 80% | 85% | 83% | 81% | 86% | 86% |
| Spec 2 | 43% | 22% | 29% | 41% | 22% | 28% | 41% | 22% | 25% |
| Cutoff 3 | 0.380 | 0.319 | 0.499 | 0.320 | 0.319 | 0.320 | 0.320 | 0.319 | 0.320 |
| Sens 3 | 90% | 92% | 91% | 90% | 92% | 96% | 94% | 100% | 100% |
| Spec 3 | 41% | 12% | 28% | 31% | 12% | 20% | 31% | 12% | 20% |
| Cutoff 4 | 1.04 | 1.15 | 1.29 | 1.04 | 1.15 | 1.29 | 1.04 | 1.15 | 1.29 |
| Sens 4 | 60% | 54% | 43% | 40% | 46% | 26% | 31% | 29% | 14% |
| Spec 4 | 74% | 74% | 77% | 74% | 74% | 77% | 74% | 74% | 77% |
| Cutoff 5 | 1.29 | 1.29 | 1.59 | 1.29 | 1.29 | 1.59 | 1.29 | 1.29 | 1.59 |
| Sens 5 | 43% | 46% | 43% | 27% | 38% | 26% | 25% | 29% | 14% |
| Spec 5 | 84% | 81% | 87% | 84% | 81% | 87% | 84% | 81% | 87% |
| Cutoff 6 | 1.59 | 7.96 | 13.6 | 1.59 | 7.96 | 13.6 | 1.59 | 7.96 | 13.6 |
| Sens 6 | 43% | 46% | 43% | 27% | 38% | 26% | 25% | 29% | 14% |
| Spec 6 | 90% | 90% | 97% | 90% | 90% | 97% | 90% | 90% | 97% |
| OR Quart 2 | 5.1 | 1.5 | 3.9 | 4.2 | 2.0 | 2.5 | 8.9 | 0.32 | 1.0 |
| p Value | 0.043 | 0.65 | 0.100 | 0.033 | 0.42 | 0.15 | 0.042 | 0.33 | 1.0 |
| 95% CI of | 1.1 | 0.25 | 0.77 | 1.1 | 0.37 | 0.72 | 1.1 | 0.033 | 0.13 |
| OR Quart 2 | 25 | 9.3 | 20 | 16 | 11 | 8.9 | 74 | 3.2 | 7.4 |
| OR Quart 3 | 1.0 | 0.49 | 2.1 | 1.4 | 0.49 | 1.0 | 2.0 | 0.33 | 3.9 |
| p Value | 1.0 | 0.57 | 0.41 | 0.70 | 0.57 | 1.0 | 0.58 | 0.34 | 0.099 |
| 95% CI of | 0.14 | 0.044 | 0.36 | 0.29 | 0.044 | 0.24 | 0.18 | 0.033 | 0.77 |
| OR Quart 3 | 7.3 | 5.5 | 12 | 6.3 | 5.5 | 4.2 | 23 | 3.2 | 20 |
| OR Quart 4 | 11 | 3.7 | 6.0 | 4.6 | 3.1 | 1.6 | 5.3 | 0.65 | 1.6 |
| p Value | 0.0019 | 0.11 | 0.026 | 0.023 | 0.17 | 0.51 | 0.13 | 0.64 | 0.63 |
| 95% CI of | 2.4 | 0.75 | 1.2 | 1.2 | 0.62 | 0.41 | 0.60 | 0.11 | 0.25 |
| OR Quart 4 | 50 | 18 | 29 | 17 | 16 | 5.9 | 47 | 4.0 | 9.9 |

Vascular endothelial growth factor receptor 3

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 343 | 467 | 343 | 414 | 343 | 414 |
| Average | 340 | 507 | 340 | 494 | 340 | 470 |
| Stdev | 278 | 193 | 278 | 207 | 278 | 270 |
| p (t-test) |  | 0.0076 |  | 0.017 |  | 0.11 |
| Min | 1.37 | 166 | 1.37 | 166 | 1.37 | 3.04 |
| Max | 2070 | 913 | 2070 | 913 | 2070 | 913 |
| n (Samp) | 128 | 22 | 128 | 21 | 128 | 13 |
| n (Patient) | 128 | 22 | 128 | 21 | 128 | 13 |
| sCr only | | | | | | |
| Median | 397 | 414 | 397 | 401 | nd | nd |
| Average | 405 | 524 | 405 | 494 | nd | nd |
| Stdev | 292 | 206 | 292 | 232 | nd | nd |
| p (t-test) |  | 0.26 |  | 0.40 | nd | nd |
| Min | 1.37 | 362 | 1.37 | 249 | nd | nd |
| Max | 2750 | 913 | 2750 | 913 | nd | nd |
| n (Samp) | 240 | 8 | 240 | 8 | nd | nd |
| n (Patient) | 240 | 8 | 240 | 8 | nd | nd |
| UO only | | | | | | |
| Median | 356 | 509 | 356 | 511 | 356 | 406 |
| Average | 362 | 511 | 362 | 508 | 362 | 437 |
| Stdev | 286 | 188 | 286 | 193 | 286 | 245 |
| p (t-test) |  | 0.039 |  | 0.049 |  | 0.38 |
| Min | 1.37 | 166 | 1.37 | 166 | 1.37 | 3.04 |
| Max | 2070 | 835 | 2070 | 835 | 2070 | 835 |

-continued

| | | | | | | |
|---|---|---|---|---|---|---|
| n (Samp) | 122 | 17 | 122 | 16 | 122 | 12 |
| n (Patient) | 122 | 17 | 122 | 16 | 122 | 12 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.74 | 0.66 | 0.73 | 0.71 | 0.60 | 0.72 | 0.65 | nd | 0.60 |
| SE | 0.064 | 0.11 | 0.073 | 0.067 | 0.11 | 0.075 | 0.086 | nd | 0.090 |
| p | 1.5E-4 | 0.15 | 0.0014 | 0.0017 | 0.37 | 0.0031 | 0.083 | nd | 0.24 |
| nCohort 1 | 128 | 240 | 122 | 128 | 240 | 122 | 128 | nd | 122 |
| nCohort 2 | 22 | 8 | 17 | 21 | 8 | 16 | 13 | nd | 12 |
| Cutoff 1 | 397 | 397 | 407 | 364 | 358 | 397 | 354 | nd | 354 |
| Sens 1 | 73% | 75% | 71% | 71% | 75% | 75% | 77% | nd | 75% |
| Spec 1 | 65% | 51% | 63% | 58% | 43% | 61% | 53% | nd | 50% |
| Cutoff 2 | 364 | 366 | 364 | 337 | 295 | 364 | 242 | nd | 236 |
| Sens 2 | 82% | 88% | 82% | 81% | 88% | 81% | 85% | nd | 83% |
| Spec 2 | 58% | 47% | 53% | 49% | 31% | 53% | 36% | nd | 30% |
| Cutoff 3 | 337 | 358 | 236 | 247 | 247 | 236 | 145 | nd | 145 |
| Sens 3 | 91% | 100% | 94% | 90% | 100% | 94% | 92% | nd | 92% |
| Spec 3 | 49% | 43% | 30% | 36% | 25% | 30% | 24% | nd | 20% |
| Cutoff 4 | 425 | 486 | 441 | 425 | 486 | 441 | 425 | nd | 441 |
| Sens 4 | 50% | 38% | 59% | 48% | 38% | 56% | 38% | nd | 33% |
| Spec 4 | 70% | 72% | 70% | 70% | 72% | 70% | 70% | nd | 70% |
| Cutoff 5 | 475 | 534 | 475 | 475 | 534 | 475 | 475 | nd | 475 |
| Sens 5 | 50% | 38% | 59% | 48% | 38% | 56% | 38% | nd | 33% |
| Spec 5 | 81% | 82% | 80% | 81% | 82% | 80% | 81% | nd | 80% |
| Cutoff 6 | 534 | 651 | 574 | 534 | 651 | 574 | 534 | nd | 574 |
| Sens 6 | 36% | 25% | 29% | 33% | 25% | 31% | 38% | nd | 33% |
| Spec 6 | 91% | 90% | 90% | 91% | 90% | 90% | 91% | nd | 90% |
| OR Quart 2 | 3.1 | >2.1 | 3.1 | 4.4 | 2.0 | 3.1 | 0.49 | nd | 0.97 |
| p Value | 0.34 | <0.56 | 0.34 | 0.20 | 0.57 | 0.34 | 0.56 | nd | 0.98 |
| 95% CI of | 0.31 | >0.18 | 0.31 | 0.46 | 0.18 | 0.31 | 0.042 | nd | 0.13 |
| OR Quart 2 | 31 | na | 31 | 41 | 23 | 31 | 5.6 | nd | 7.3 |
| OR Quart 3 | 8.4 | >3.2 | 3.1 | 7.0 | 2.0 | 3.2 | 2.8 | nd | 2.1 |
| p Value | 0.052 | <0.33 | 0.34 | 0.080 | 0.57 | 0.33 | 0.25 | nd | 0.40 |
| 95% CI of | 0.98 | >0.32 | 0.31 | 0.79 | 0.18 | 0.32 | 0.50 | nd | 0.36 |
| OR Quart 3 | 72 | na | 31 | 61 | 23 | 32 | 15 | nd | 13 |
| OR Quart 4 | 15 | >3.2 | 13 | 13 | 3.1 | 11 | 2.7 | nd | 2.1 |
| p Value | 0.012 | <0.33 | 0.017 | 0.018 | 0.33 | 0.025 | 0.26 | nd | 0.42 |
| 95% CI of | 1.8 | >0.32 | 1.6 | 1.6 | 0.31 | 1.4 | 0.48 | nd | 0.35 |
| OR Quart 4 | 120 | na | 110 | 110 | 31 | 96 | 15 | nd | 12 |

| Interferon alpha-2 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.122 | 3.93 | 0.122 | 2.03 | 0.122 | 9.04 |
| Average | 13.0 | 10.4 | 13.0 | 9.15 | 13.0 | 13.7 |
| Stdev | 22.3 | 12.8 | 22.3 | 12.4 | 22.3 | 13.6 |
| p (t-test) | | 0.53 | | 0.36 | | 0.90 |
| Min | 0.0369 | 0.0450 | 0.0369 | 0.0398 | 0.0369 | 0.0450 |
| Max | 126 | 34.7 | 126 | 34.7 | 126 | 34.7 |
| n (Samp) | 223 | 30 | 223 | 30 | 223 | 16 |
| n (Patient) | 223 | 30 | 223 | 30 | 223 | 16 |
| sCr only | | | | | | |
| Median | 0.122 | 5.88 | 0.122 | 2.21 | 0.122 | 0.122 |
| Average | 14.5 | 10.5 | 14.5 | 8.16 | 14.5 | 9.54 |
| Stdev | 24.0 | 12.9 | 24.0 | 11.6 | 24.0 | 13.9 |
| p (t-test) | | 0.55 | | 0.34 | | 0.59 |
| Min | 0.0238 | 0.0450 | 0.0238 | 0.0450 | 0.0238 | 0.0398 |
| Max | 126 | 34.7 | 126 | 34.7 | 126 | 34.7 |
| n (Samp) | 375 | 13 | 375 | 13 | 375 | 7 |
| n (Patient) | 375 | 13 | 375 | 13 | 375 | 7 |
| UO only | | | | | | |
| Median | 0.311 | 5.47 | 0.311 | 2.39 | 0.311 | 10.8 |
| Average | 14.4 | 11.0 | 14.4 | 10.7 | 14.4 | 15.1 |
| Stdev | 22.4 | 12.9 | 22.4 | 13.0 | 22.4 | 13.8 |
| p (t-test) | | 0.48 | | 0.45 | | 0.91 |
| Min | 0.0348 | 0.0672 | 0.0348 | 0.0398 | 0.0348 | 0.104 |

-continued

| | | | | | | | | |
|---|---|---|---|---|---|---|---|---|
| Max | 126 | 34.7 | 126 | 34.7 | 126 | 34.7 | | |
| n (Samp) | 173 | 23 | 173 | 23 | 173 | 14 | | |
| n (Patient) | 173 | 23 | 173 | 23 | 173 | 14 | | |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.58 | 0.57 | 0.53 | 0.54 | 0.52 | 0.51 | 0.65 | 0.46 | 0.64 |
| SE | 0.058 | 0.084 | 0.065 | 0.057 | 0.083 | 0.064 | 0.077 | 0.11 | 0.083 |
| p | 0.19 | 0.43 | 0.67 | 0.48 | 0.77 | 0.93 | 0.055 | 0.76 | 0.095 |
| nCohort 1 | 223 | 375 | 173 | 223 | 375 | 173 | 223 | 375 | 173 |
| nCohort 2 | 30 | 13 | 23 | 30 | 13 | 23 | 16 | 7 | 14 |
| Cutoff 1 | 0.0974 | 0.0974 | 0.0974 | 0.0974 | 0.0967 | 0.0974 | 1.45 | 0.0802 | 2.24 |
| Sens 1 | 77% | 77% | 78% | 70% | 77% | 74% | 75% | 71% | 71% |
| Spec 1 | 42% | 39% | 30% | 42% | 34% | 30% | 59% | 33% | 57% |
| Cutoff 2 | 0.0967 | 0.0967 | 0.0967 | 0.0802 | 0.0724 | 0.0802 | 0.112 | 0.0418 | 1.45 |
| Sens 2 | 83% | 85% | 83% | 80% | 85% | 83% | 81% | 86% | 86% |
| Spec 2 | 34% | 34% | 25% | 33% | 24% | 24% | 48% | 13% | 54% |
| Cutoff 3 | 0.0606 | 0.0754 | 0.0606 | 0.0606 | 0.0656 | 0.0606 | 0.0974 | 0.0369 | 0.0974 |
| Sens 3 | 97% | 92% | 100% | 90% | 92% | 91% | 94% | 100% | 100% |
| Spec 3 | 22% | 27% | 14% | 22% | 18% | 14% | 42% | 5% | 30% |
| Cutoff 4 | 16.0 | 17.0 | 20.3 | 16.0 | 17.0 | 20.3 | 16.0 | 17.0 | 20.3 |
| Sens 4 | 30% | 31% | 30% | 27% | 23% | 30% | 38% | 29% | 43% |
| Spec 4 | 70% | 70% | 71% | 70% | 70% | 71% | 70% | 70% | 71% |
| Cutoff 5 | 25.6 | 30.0 | 29.7 | 25.6 | 30.0 | 29.7 | 25.6 | 30.0 | 29.7 |
| Sens 5 | 20% | 15% | 13% | 17% | 8% | 13% | 31% | 14% | 21% |
| Spec 5 | 80% | 80% | 80% | 80% | 80% | 80% | 80% | 80% | 80% |
| Cutoff 6 | 40.0 | 47.3 | 41.7 | 40.0 | 47.3 | 41.7 | 40.0 | 47.3 | 41.7 |
| Sens 6 | 0% | 0% | 0% | 0% | 0% | 0% | 0% | 0% | 0% |
| Spec 6 | 90% | 90% | 90% | 90% | 90% | 90% | 90% | 90% | 90% |
| OR Quart 2 | 1.4 | 3.1 | 1.0 | 1.4 | 1.0 | 0.78 | 3.1 | 3.1 | >2.0 |
| p Value | 0.55 | 0.34 | 1.0 | 0.55 | 1.0 | 0.73 | 0.34 | 0.33 | <0.56 |
| 95% CI of | 0.43 | 0.31 | 0.24 | 0.43 | 0.14 | 0.20 | 0.31 | 0.32 | >0.18 |
| OR Quart 2 | 4.8 | 30 | 4.2 | 4.8 | 7.2 | 3.1 | 30 | 30 | na |
| OR Quart 3 | 1.9 | 6.3 | 2.5 | 2.2 | 3.7 | 1.7 | 6.4 | 1.0 | >8.0 |
| p Value | 0.26 | 0.090 | 0.15 | 0.18 | 0.11 | 0.38 | 0.089 | 1.0 | <0.056 |
| 95% CI of | 0.61 | 0.75 | 0.72 | 0.70 | 0.75 | 0.52 | 0.75 | 0.062 | >0.95 |
| OR Quart 3 | 6.1 | 54 | 8.9 | 6.8 | 18 | 5.7 | 55 | 16 | na |
| OR Quart 4 | 1.9 | 3.1 | 1.6 | 1.7 | 1.0 | 1.2 | 6.4 | 2.0 | >5.5 |
| p Value | 0.28 | 0.34 | 0.51 | 0.40 | 1.0 | 0.75 | 0.089 | 0.56 | <0.13 |
| 95% CI of | 0.60 | 0.31 | 0.41 | 0.51 | 0.14 | 0.35 | 0.75 | 0.18 | >0.61 |
| OR Quart 4 | 6.0 | 30 | 5.9 | 5.4 | 7.2 | 4.3 | 55 | 23 | na |

| Insulin-like growth factor-binding protein 4 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.923 | 2.85 | 0.923 | 2.84 | 0.923 | 2.33 |
| Average | 1.70 | 4.02 | 1.70 | 3.86 | 1.70 | 2.23 |
| Stdev | 5.34 | 3.59 | 5.34 | 3.69 | 5.34 | 1.89 |
| p (t-test) | | 0.13 | | 0.16 | | 0.78 |
| Min | 0.0439 | 0.0558 | 0.0439 | 0.0558 | 0.0439 | 0.0558 |
| Max | 53.9 | 11.4 | 53.9 | 11.4 | 53.9 | 5.52 |
| n (Samp) | 109 | 13 | 109 | 13 | 109 | 8 |
| n (Patient) | 109 | 13 | 109 | 13 | 109 | 8 |
| sCr only | | | | | | |
| Median | 0.923 | 2.85 | 0.923 | 0.923 | nd | nd |
| Average | 2.46 | 3.66 | 2.46 | 3.36 | nd | nd |
| Stdev | 8.16 | 3.70 | 8.16 | 3.86 | nd | nd |
| p (t-test) | | 0.70 | | 0.77 | nd | nd |
| Min | 0.0319 | 0.0558 | 0.0319 | 0.0558 | nd | nd |
| Max | 85.6 | 9.68 | 85.6 | 9.68 | nd | nd |
| n (Samp) | 184 | 7 | 184 | 7 | nd | nd |
| n (Patient) | 184 | 7 | 184 | 7 | nd | nd |
| UO only | | | | | | |
| Median | 0.923 | 4.65 | 0.923 | 4.65 | 0.923 | 2.43 |
| Average | 1.65 | 4.84 | 1.65 | 4.84 | 1.65 | 2.53 |
| Stdev | 5.56 | 3.27 | 5.56 | 3.27 | 5.56 | 1.97 |
| p (t-test) | | 0.11 | | 0.11 | | 0.70 |
| Min | 0.0439 | 0.957 | 0.0439 | 0.957 | 0.0439 | 0.0558 |
| Max | 53.9 | 11.4 | 53.9 | 11.4 | 53.9 | 5.52 |

-continued

| | | | | | | | | | |
|---|---|---|---|---|---|---|---|---|---|
| n (Samp) | 99 | 8 | 99 | 8 | 99 | 6 | | | |
| n (Patient) | 99 | 8 | 99 | 8 | 99 | 6 | | | |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.75 | 0.62 | 0.92 | 0.71 | 0.55 | 0.92 | 0.67 | nd | 0.74 |
| SE | 0.081 | 0.12 | 0.068 | 0.084 | 0.11 | 0.068 | 0.11 | nd | 0.12 |
| p | 0.0016 | 0.30 | 8.9E-10 | 0.010 | 0.65 | 8.9E-10 | 0.11 | nd | 0.046 |
| nCohort 1 | 109 | 184 | 99 | 109 | 184 | 99 | 109 | nd | 99 |
| nCohort 2 | 13 | 7 | 8 | 13 | 7 | 8 | 8 | nd | 6 |
| Cutoff 1 | 0.923 | 0.733 | 2.44 | 0.733 | 0.670 | 2.44 | 0.923 | nd | 0.923 |
| Sens 1 | 77% | 71% | 75% | 77% | 71% | 75% | 75% | nd | 83% |
| Spec 1 | 64% | 41% | 91% | 43% | 34% | 91% | 64% | nd | 65% |
| Cutoff 2 | 0.733 | 0.0558 | 1.94 | 0.670 | 0.0558 | 1.94 | 0.0558 | nd | 0.923 |
| Sens 2 | 85% | 86% | 88% | 85% | 86% | 88% | 88% | nd | 83% |
| Spec 2 | 43% | 6% | 89% | 36% | 6% | 89% | 6% | nd | 65% |
| Cutoff 3 | 0.0558 | 0.0439 | 0.923 | 0.0558 | 0.0439 | 0.923 | 0.0439 | nd | 0.0439 |
| Sens 3 | 92% | 100% | 100% | 92% | 100% | 100% | 100% | nd | 100% |
| Spec 3 | 6% | 1% | 65% | 6% | 1% | 65% | 1% | nd | 1% |
| Cutoff 4 | 0.957 | 1.17 | 0.957 | 0.957 | 1.17 | 0.957 | 0.957 | nd | 0.957 |
| Sens 4 | 69% | 57% | 88% | 62% | 43% | 88% | 62% | nd | 67% |
| Spec 4 | 73% | 71% | 74% | 73% | 71% | 74% | 73% | nd | 74% |
| Cutoff 5 | 1.46 | 2.33 | 1.46 | 1.46 | 2.33 | 1.46 | 1.46 | nd | 1.46 |
| Sens 5 | 69% | 57% | 88% | 62% | 43% | 88% | 62% | nd | 67% |
| Spec 5 | 81% | 80% | 82% | 81% | 80% | 82% | 81% | nd | 82% |
| Cutoff 6 | 2.50 | 3.90 | 2.44 | 2.50 | 3.90 | 2.44 | 2.50 | nd | 2.44 |
| Sens 6 | 62% | 43% | 75% | 54% | 43% | 75% | 50% | nd | 50% |
| Spec 6 | 91% | 90% | 91% | 91% | 90% | 91% | 91% | nd | 91% |
| OR Quart 2 | 0.47 | 0.48 | >0 | 0.97 | 0.98 | >0 | 0 | nd | 0 |
| p Value | 0.54 | 0.55 | <na | 0.97 | 0.98 | <na | na | nd | na |
| 95% CI of | 0.040 | 0.042 | >na | 0.13 | 0.13 | >na | na | nd | na |
| OR Quart 2 | 5.4 | 5.5 | na | 7.3 | 7.2 | na | na | nd | na |
| OR Quart 3 | 0.48 | 0 | >1.0 | 0.48 | 0 | >1.0 | 0.48 | nd | 1.0 |
| p Value | 0.56 | na | <1.0 | 0.56 | na | <1.0 | 0.56 | nd | 1.0 |
| 95% CI of | 0.041 | na | >0.059 | 0.041 | na | >0.059 | 0.041 | nd | 0.059 |
| OR Quart 3 | 5.6 | na | na | 5.6 | na | na | 5.6 | nd | 17 |
| OR Quart 4 | 5.7 | 2.0 | >9.1 | 4.9 | 1.5 | >9.1 | 2.7 | nd | 4.3 |
| p Value | 0.036 | 0.42 | <0.047 | 0.059 | 0.67 | <0.047 | 0.26 | nd | 0.20 |
| 95% CI of | 1.1 | 0.36 | >1.0 | 0.94 | 0.24 | >1.0 | 0.48 | nd | 0.45 |
| OR Quart 4 | 29 | 12 | na | 25 | 9.4 | na | 15 | nd | 42 |

| Insulin-like growth factor-binding protein 5 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.0682 | 1.58 | 0.0682 | 1.22 | 0.0682 | 2.34 |
| Average | 0.622 | 1.87 | 0.622 | 1.55 | 0.622 | 2.16 |
| Stdev | 1.19 | 1.87 | 1.19 | 1.80 | 1.19 | 2.03 |
| p (t-test) | | 0.0012 | | 0.014 | | 0.0011 |
| Min | 0.0210 | 0.0210 | 0.0210 | 0.0210 | 0.0210 | 0.0393 |
| Max | 5.79 | 5.59 | 5.79 | 5.59 | 5.79 | 5.59 |
| n (Samp) | 109 | 13 | 109 | 13 | 109 | 8 |
| n (Patient) | 109 | 13 | 109 | 13 | 109 | 8 |
| sCr only | | | | | | |
| Median | 0.0994 | 1.22 | 0.0994 | 0.0938 | nd | nd |
| Average | 0.941 | 1.76 | 0.941 | 1.18 | nd | nd |
| Stdev | 1.65 | 1.83 | 1.65 | 1.60 | nd | nd |
| p (t-test) | | 0.20 | | 0.70 | nd | nd |
| Min | 0.0116 | 0.0210 | 0.0116 | 0.0210 | nd | nd |
| Max | 9.43 | 4.11 | 9.43 | 3.48 | nd | nd |
| n (Samp) | 184 | 7 | 184 | 7 | nd | nd |
| n (Patient) | 184 | 7 | 184 | 7 | nd | nd |
| UO only | | | | | | |
| Median | 0.0682 | 1.68 | 0.0682 | 1.68 | 0.0682 | 2.34 |
| Average | 0.567 | 1.92 | 0.567 | 1.92 | 0.567 | 2.29 |
| Stdev | 1.10 | 1.98 | 1.10 | 1.98 | 1.10 | 2.14 |
| p (t-test) | | 0.0024 | | 0.0024 | | 7.0E-4 |

-continued

| | | | | | | |
|---|---|---|---|---|---|---|
| Min | 0.0210 | 0.0210 | 0.0210 | 0.0210 | 0.0210 | 0.0393 |
| Max | 5.79 | 5.59 | 5.79 | 5.59 | 5.79 | 5.59 |
| n (Samp) | 100 | 8 | 100 | 8 | 100 | 6 |
| n (Patient) | 100 | 8 | 100 | 8 | 100 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.67 | 0.61 | 0.65 | 0.61 | 0.50 | 0.65 | 0.74 | nd | 0.73 |
| SE | 0.086 | 0.12 | 0.11 | 0.087 | 0.11 | 0.11 | 0.10 | nd | 0.12 |
| p | 0.055 | 0.33 | 0.16 | 0.21 | 0.97 | 0.16 | 0.022 | nd | 0.054 |
| nCohort 1 | 109 | 184 | 100 | 109 | 184 | 100 | 109 | nd | 100 |
| nCohort 2 | 13 | 7 | 8 | 13 | 7 | 8 | 8 | nd | 6 |
| Cutoff 1 | 0.0358 | 0.0682 | 0.0358 | 0.0358 | 0.0358 | 0.0358 | 0.0682 | nd | 0.0400 |
| Sens 1 | 85% | 71% | 88% | 77% | 71% | 88% | 75% | nd | 83% |
| Spec 1 | 29% | 46% | 26% | 29% | 22% | 26% | 54% | nd | 28% |
| Cutoff 2 | 0.0358 | 0.0358 | 0.0358 | 0.0255 | 0.0255 | 0.0358 | 0.0400 | nd | 0.0400 |
| Sens 2 | 85% | 86% | 88% | 85% | 86% | 88% | 88% | nd | 83% |
| Spec 2 | 29% | 22% | 26% | 19% | 14% | 26% | 32% | nd | 28% |
| Cutoff 3 | 0 | 0.0116 | 0 | 0 | 0.0116 | 0 | 0.0358 | nd | 0.0358 |
| Sens 3 | 100% | 100% | 100% | 100% | 100% | 100% | 100% | nd | 100% |
| Spec 3 | 0% | 1% | 0% | 0% | 1% | 0% | 29% | nd | 26% |
| Cutoff 4 | 0.397 | 0.558 | 0.397 | 0.397 | 0.558 | 0.397 | 0.397 | nd | 0.397 |
| Sens 4 | 62% | 57% | 62% | 54% | 43% | 62% | 62% | nd | 67% |
| Spec 4 | 76% | 70% | 78% | 76% | 70% | 78% | 76% | nd | 78% |
| Cutoff 5 | 0.593 | 1.58 | 0.465 | 0.593 | 1.58 | 0.465 | 0.593 | nd | 0.465 |
| Sens 5 | 62% | 43% | 62% | 54% | 29% | 62% | 62% | nd | 67% |
| Spec 5 | 81% | 80% | 80% | 81% | 80% | 80% | 81% | nd | 80% |
| Cutoff 6 | 2.38 | 3.03 | 1.76 | 2.38 | 3.03 | 1.76 | 2.38 | nd | 1.76 |
| Sens 6 | 38% | 43% | 50% | 31% | 29% | 50% | 50% | nd | 67% |
| Spec 6 | 91% | 90% | 90% | 91% | 90% | 90% | 91% | nd | 90% |
| OR Quart 2 | 0.97 | 0.48 | 2.1 | 0.62 | 0.31 | 2.1 | >2.1 | nd | >2.1 |
| p Value | 0.97 | 0.55 | 0.56 | 0.62 | 0.32 | 0.56 | <0.54 | nd | <0.56 |
| 95% CI of | 0.13 | 0.042 | 0.18 | 0.096 | 0.031 | 0.18 | >0.18 | nd | >0.18 |
| OR Quart 2 | 7.3 | 5.5 | 24 | 4.0 | 3.1 | 24 | na | nd | na |
| OR Quart 3 | 0.48 | 0 | 0 | 0.31 | 0 | 0 | >1.0 | nd | >0 |
| p Value | 0.56 | na | na | 0.32 | na | na | <0.98 | nd | <na |
| 95% CI of | 0.041 | na | na | 0.030 | na | na | >0.062 | nd | >na |
| OR Quart 3 | 5.6 | na | na | 3.2 | na | na | na | nd | na |
| OR Quart 4 | 4.9 | 2.0 | 5.9 | 2.6 | 0.98 | 5.9 | >5.8 | nd | >4.5 |
| p Value | 0.059 | 0.42 | 0.12 | 0.20 | 0.98 | 0.12 | <0.12 | nd | <0.19 |
| 95% CI of | 0.94 | 0.36 | 0.64 | 0.61 | 0.19 | 0.64 | >0.63 | nd | >0.47 |
| OR Quart 4 | 25 | 12 | 54 | 11 | 5.1 | 54 | na | nd | na |

| Interleukin-21 | | | | | |
|---|---|---|---|---|---|
| 0 hr prior to AKI stage | | 24 hr prior to AKI stage | | 48 hr prior to AKI stage | |
| Cohort 1 | Cohort 2 | Cohort 1 | Cohort 2 | Cohort 1 | Cohort 2 |
| sCr or UO | | | | | |
| Median 13.0 | 9.95 | 13.0 | 7.46 | 13.0 | 9.22 |
| Average 15.4 | 11.4 | 15.4 | 9.90 | 15.4 | 10.5 |
| Stdev 13.1 | 9.82 | 13.1 | 9.70 | 13.1 | 12.0 |
| p (t-test) | 0.11 | | 0.027 | | 0.14 |
| Min 0.0191 | 0.0219 | 0.0191 | 0.0219 | 0.0191 | 0.0177 |
| Max 87.9 | 49.5 | 87.9 | 49.5 | 87.9 | 49.5 |
| n (Samp) 223 | 30 | 223 | 30 | 223 | 16 |
| n (Patient) 223 | 30 | 223 | 30 | 223 | 16 |
| sCr only | | | | | |
| Median 13.0 | 8.34 | 13.0 | 8.34 | 13.0 | 6.02 |
| Average 15.9 | 12.5 | 15.9 | 12.2 | 15.9 | 13.7 |
| Stdev 13.8 | 12.3 | 13.8 | 12.5 | 13.8 | 16.7 |
| p (t-test) | 0.37 | | 0.33 | | 0.68 |
| Min 0.0122 | 2.66 | 0.0122 | 2.65 | 0.0122 | 2.35 |
| Max 87.9 | 49.5 | 87.9 | 49.5 | 87.9 | 49.5 |
| n (Samp) 375 | 13 | 375 | 13 | 375 | 7 |
| n (Patient) 375 | 13 | 375 | 13 | 375 | 7 |
| UO only | | | | | |
| Median 12.6 | 8.82 | 12.6 | 6.02 | 12.6 | 8.02 |
| Average 15.2 | 10.3 | 15.2 | 8.31 | 15.2 | 7.93 |
| Stdev 12.9 | 6.93 | 12.9 | 6.17 | 12.9 | 6.07 |
| p (t-test) | 0.071 | | 0.012 | | 0.037 |
| Min 0.0160 | 0.0219 | 0.0160 | 0.0219 | 0.0160 | 0.0177 |
| Max 87.9 | 24.2 | 87.9 | 20.6 | 87.9 | 17.2 |

-continued

| | | | | | | | | | |
|---|---|---|---|---|---|---|---|---|---|
| n (Samp) | 173 | 23 | 173 | 23 | 173 | 14 | | | |
| n (Patient) | 173 | 23 | 173 | 23 | 173 | 14 | | | |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.41 | 0.42 | 0.39 | 0.36 | 0.41 | 0.33 | 0.36 | 0.42 | 0.32 |
| SE | 0.058 | 0.084 | 0.066 | 0.057 | 0.084 | 0.065 | 0.077 | 0.11 | 0.081 |
| p | 0.12 | 0.34 | 0.10 | 0.015 | 0.26 | 0.0091 | 0.059 | 0.46 | 0.025 |
| nCohort 1 | 223 | 375 | 173 | 223 | 375 | 173 | 223 | 375 | 173 |
| nCohort 2 | 30 | 13 | 23 | 30 | 13 | 23 | 16 | 7 | 14 |
| Cutoff 1 | 5.82 | 5.90 | 5.32 | 3.89 | 5.44 | 3.50 | 2.73 | 5.44 | 2.95 |
| Sens 1 | 70% | 77% | 74% | 70% | 77% | 74% | 75% | 71% | 71% |
| Spec 1 | 26% | 27% | 25% | 20% | 26% | 16% | 15% | 26% | 14% |
| Cutoff 2 | 3.89 | 5.44 | 3.50 | 2.73 | 4.24 | 2.35 | 2.61 | 2.61 | 0.0975 |
| Sens 2 | 80% | 85% | 83% | 80% | 85% | 83% | 81% | 86% | 86% |
| Spec 2 | 20% | 26% | 16% | 15% | 21% | 12% | 14% | 13% | 3% |
| Cutoff 3 | 2.73 | 4.24 | 2.22 | 2.22 | 2.65 | 0.689 | 0.0191 | 2.34 | 0.0191 |
| Sens 3 | 90% | 92% | 91% | 90% | 92% | 91% | 94% | 100% | 93% |
| Spec 3 | 15% | 21% | 12% | 13% | 13% | 5% | 0% | 12% | 1% |
| Cutoff 4 | 19.2 | 19.3 | 19.6 | 19.2 | 19.3 | 19.6 | 19.2 | 19.3 | 19.6 |
| Sens 4 | 20% | 15% | 17% | 13% | 15% | 9% | 6% | 14% | 0% |
| Spec 4 | 70% | 70% | 71% | 70% | 70% | 71% | 70% | 70% | 71% |
| Cutoff 5 | 24.9 | 25.4 | 24.9 | 24.9 | 25.4 | 24.9 | 24.9 | 25.4 | 24.9 |
| Sens 5 | 3% | 8% | 0% | 3% | 8% | 0% | 6% | 14% | 0% |
| Spec 5 | 80% | 80% | 80% | 80% | 80% | 80% | 80% | 80% | 80% |
| Cutoff 6 | 31.3 | 33.5 | 31.2 | 31.3 | 33.5 | 31.2 | 31.3 | 33.5 | 31.2 |
| Sens 6 | 3% | 8% | 0% | 3% | 8% | 0% | 6% | 14% | 0% |
| Spec 6 | 91% | 90% | 90% | 91% | 90% | 90% | 91% | 90% | 90% |
| OR Quart 2 | 0.66 | 3.1 | 6.7 | 1.0 | 3.1 | 6.7 | 4.2 | 2.0 | >3.2 |
| p Value | 0.53 | 0.34 | 0.084 | 0.98 | 0.34 | 0.084 | 0.20 | 0.56 | <0.32 |
| 95% CI of | 0.18 | 0.31 | 0.77 | 0.24 | 0.31 | 0.77 | 0.46 | 0.18 | >0.32 |
| OR Quart 2 | 2.4 | 30 | 58 | 4.3 | 30 | 58 | 39 | 23 | na |
| OR Quart 3 | 2.3 | 7.5 | 12 | 3.2 | 6.3 | 9.4 | 5.4 | 2.0 | >6.9 |
| p Value | 0.12 | 0.062 | 0.019 | 0.060 | 0.090 | 0.039 | 0.13 | 0.57 | <0.080 |
| 95% CI of | 0.80 | 0.90 | 1.5 | 0.95 | 0.75 | 1.1 | 0.61 | 0.18 | >0.79 |
| OR Quart 3 | 6.5 | 62 | 100 | 11 | 54 | 78 | 47 | 23 | na |
| OR Quart 4 | 1.4 | 2.0 | 6.7 | 3.2 | 3.1 | 9.4 | 6.7 | 2.0 | >5.7 |
| p Value | 0.55 | 0.57 | 0.084 | 0.060 | 0.34 | 0.039 | 0.083 | 0.56 | <0.12 |
| 95% CI of | 0.46 | 0.18 | 0.77 | 0.95 | 0.31 | 1.1 | 0.78 | 0.18 | >0.64 |
| OR Quart 4 | 4.3 | 23 | 58 | 11 | 30 | 78 | 57 | 23 | na |

| Interleukin-23 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 583 | 447 | 583 | 304 | 583 | 562 |
| Average | 800 | 615 | 800 | 483 | 800 | 666 |
| Stdev | 942 | 593 | 942 | 512 | 942 | 597 |
| p (t-test) | | 0.30 | | 0.072 | | 0.58 |
| Min | 0.643 | 0.552 | 0.643 | 0.552 | 0.643 | 0.564 |
| Max | 8520 | 2120 | 8520 | 2000 | 8520 | 2000 |
| n (Samp) | 223 | 30 | 223 | 30 | 223 | 16 |
| n (Patient) | 223 | 30 | 223 | 30 | 223 | 16 |
| sCr only | | | | | | |
| Median | 588 | 389 | 588 | 229 | 588 | 279 |
| Average | 798 | 520 | 798 | 475 | 798 | 633 |
| Stdev | 890 | 559 | 890 | 579 | 890 | 747 |
| p (t-test) | | 0.26 | | 0.20 | | 0.63 |
| Min | 0.552 | 0.552 | 0.552 | 0.552 | 0.552 | 1.09 |
| Max | 8520 | 2000 | 8520 | 2000 | 8520 | 2000 |
| n (Samp) | 375 | 13 | 375 | 13 | 375 | 7 |
| n (Patient) | 375 | 13 | 375 | 13 | 375 | 7 |
| UO only | | | | | | |
| Median | 652 | 420 | 652 | 329 | 652 | 562 |
| Average | 870 | 608 | 870 | 457 | 870 | 587 |
| Stdev | 990 | 598 | 990 | 474 | 990 | 521 |
| p (t-test) | | 0.22 | | 0.050 | | 0.29 |
| Min | 0.564 | 0.552 | 0.564 | 0.552 | 0.564 | 0.552 |

-continued

| | | | | | | | | | |
|---|---|---|---|---|---|---|---|---|---|
| Max | 8520 | 2120 | 8520 | 1450 | 8520 | 1450 | | | |
| n (Samp) | 173 | 23 | 173 | 23 | 173 | 14 | | | |
| n (Patient) | 173 | 23 | 173 | 23 | 173 | 14 | | | |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.45 | 0.41 | 0.41 | 0.39 | 0.38 | 0.34 | 0.48 | 0.45 | 0.41 |
| SE | 0.057 | 0.084 | 0.066 | 0.058 | 0.084 | 0.065 | 0.076 | 0.11 | 0.083 |
| p | 0.39 | 0.28 | 0.19 | 0.059 | 0.17 | 0.015 | 0.80 | 0.65 | 0.30 |
| nCohort 1 | 223 | 375 | 173 | 223 | 375 | 173 | 223 | 375 | 173 |
| nCohort 2 | 30 | 13 | 23 | 30 | 13 | 23 | 16 | 7 | 14 |
| Cutoff 1 | 233 | 152 | 129 | 135 | 136 | 1.61 | 233 | 152 | 214 |
| Sens 1 | 70% | 77% | 74% | 70% | 77% | 74% | 75% | 71% | 71% |
| Spec 1 | 32% | 26% | 17% | 24% | 24% | 10% | 32% | 26% | 28% |
| Cutoff 2 | 129 | 84.5 | 0.967 | 1.61 | 1.61 | 0.967 | 152 | 1.61 | 0.967 |
| Sens 2 | 80% | 85% | 83% | 80% | 85% | 83% | 81% | 86% | 86% |
| Spec 2 | 24% | 19% | 5% | 14% | 14% | 5% | 26% | 14% | 5% |
| Cutoff 3 | 0.967 | 1.09 | 0.682 | 0.967 | 1.09 | 0.682 | 0.967 | 1.06 | 0.552 |
| Sens 3 | 90% | 92% | 91% | 90% | 92% | 91% | 94% | 100% | 93% |
| Spec 3 | 9% | 11% | 2% | 9% | 11% | 2% | 9% | 10% | 0% |
| Cutoff 4 | 952 | 977 | 983 | 952 | 977 | 983 | 952 | 977 | 983 |
| Sens 4 | 27% | 15% | 26% | 17% | 15% | 17% | 31% | 29% | 29% |
| Spec 4 | 70% | 70% | 71% | 70% | 70% | 71% | 70% | 70% | 71% |
| Cutoff 5 | 1390 | 1360 | 1390 | 1390 | 1360 | 1390 | 1390 | 1360 | 1390 |
| Sens 5 | 10% | 8% | 9% | 7% | 8% | 4% | 12% | 14% | 7% |
| Spec 5 | 80% | 80% | 80% | 80% | 80% | 80% | 80% | 80% | 80% |
| Cutoff 6 | 1830 | 1900 | 1960 | 1830 | 1900 | 1960 | 1830 | 1900 | 1960 |
| Sens 6 | 7% | 8% | 4% | 3% | 8% | 0% | 6% | 14% | 0% |
| Spec 6 | 90% | 90% | 90% | 90% | 90% | 90% | 90% | 90% | 90% |
| OR Quart 2 | 0.86 | 1.0 | 0.47 | 1.2 | 1.0 | 0.73 | 1.0 | 0.50 | 0.48 |
| p Value | 0.79 | 1.0 | 0.30 | 0.73 | 1.0 | 0.70 | 1.0 | 0.57 | 0.41 |
| 95% CI of | 0.27 | 0.14 | 0.11 | 0.36 | 0.14 | 0.16 | 0.24 | 0.045 | 0.083 |
| OR Quart 2 | 2.7 | 7.2 | 2.0 | 4.3 | 7.2 | 3.5 | 4.2 | 5.6 | 2.7 |
| OR Quart 3 | 1.5 | 3.1 | 1.2 | 2.0 | 2.6 | 1.6 | 1.3 | 1.0 | 1.0 |
| p Value | 0.42 | 0.17 | 0.77 | 0.25 | 0.26 | 0.51 | 0.73 | 1.0 | 1.0 |
| 95% CI of | 0.55 | 0.62 | 0.37 | 0.62 | 0.49 | 0.41 | 0.32 | 0.14 | 0.23 |
| OR Quart 3 | 4.3 | 16 | 3.9 | 6.2 | 14 | 5.9 | 5.0 | 7.2 | 4.3 |
| OR Quart 4 | 1.0 | 1.5 | 1.2 | 2.2 | 2.0 | 2.9 | 0.75 | 1.0 | 1.0 |
| p Value | 0.98 | 0.65 | 0.77 | 0.17 | 0.42 | 0.093 | 0.71 | 0.99 | 0.97 |
| 95% CI of | 0.34 | 0.25 | 0.37 | 0.72 | 0.37 | 0.84 | 0.16 | 0.14 | 0.24 |
| OR Quart 4 | 3.1 | 9.3 | 3.9 | 6.9 | 11 | 9.9 | 3.5 | 7.3 | 4.4 |

Interleukin-28A

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 34.2 | 30.9 | 34.2 | 26.9 | 34.2 | 25.5 |
| Average | 48.6 | 42.1 | 48.6 | 34.5 | 48.6 | 42.0 |
| Stdev | 50.2 | 41.0 | 50.2 | 38.4 | 50.2 | 46.6 |
| p (t-test) | | 0.50 | | 0.14 | | 0.61 |
| Min | 0.0495 | 0.0996 | 0.0495 | 0.0854 | 0.0495 | 0.155 |
| Max | 228 | 186 | 228 | 186 | 228 | 186 |
| n (Samp) | 223 | 30 | 223 | 30 | 223 | 16 |
| n (Patient) | 223 | 30 | 223 | 30 | 223 | 16 |
| sCr only | | | | | | |
| Median | 38.8 | 28.9 | 38.8 | 27.7 | 38.8 | 26.1 |
| Average | 51.6 | 43.5 | 51.6 | 40.0 | 51.6 | 50.8 |
| Stdev | 50.3 | 50.2 | 50.3 | 50.9 | 50.3 | 67.4 |
| p (t-test) | | 0.57 | | 0.41 | | 0.96 |
| Min | 0.0254 | 0.0996 | 0.0254 | 0.0996 | 0.0254 | 0.0860 |
| Max | 235 | 186 | 235 | 186 | 235 | 186 |
| n (Samp) | 375 | 13 | 375 | 13 | 375 | 7 |
| n (Patient) | 375 | 13 | 375 | 13 | 375 | 7 |
| UO only | | | | | | |
| Median | 40.0 | 29.2 | 40.0 | 24.2 | 40.0 | 24.5 |
| Average | 54.0 | 38.1 | 54.0 | 29.4 | 54.0 | 32.2 |
| Stdev | 52.2 | 33.0 | 52.2 | 27.4 | 52.2 | 28.1 |
| p (t-test) | | 0.16 | | 0.028 | | 0.12 |
| Min | 0.0517 | 0.204 | 0.0517 | 0.0777 | 0.0517 | 0.155 |

-continued

|  | | | | | | |
|---|---|---|---|---|---|---|
| Max | 228 | 127 | 228 | 91.0 | 228 | 91.0 |
| n (Samp) | 173 | 23 | 173 | 23 | 173 | 14 |
| n (Patient) | 173 | 23 | 173 | 23 | 173 | 14 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.49 | 0.45 | 0.44 | 0.43 | 0.43 | 0.37 | 0.48 | 0.46 | 0.41 |
| SE | 0.057 | 0.083 | 0.066 | 0.057 | 0.084 | 0.066 | 0.075 | 0.11 | 0.083 |
| p | 0.86 | 0.57 | 0.37 | 0.25 | 0.39 | 0.045 | 0.84 | 0.76 | 0.25 |
| nCohort 1 | 223 | 375 | 173 | 223 | 375 | 173 | 223 | 375 | 173 |
| nCohort 2 | 30 | 13 | 23 | 30 | 13 | 23 | 16 | 7 | 14 |
| Cutoff 1 | 21.6 | 14.7 | 18.7 | 14.1 | 10.1 | 0.932 | 18.7 | 10.1 | 18.7 |
| Sens 1 | 70% | 77% | 74% | 70% | 77% | 74% | 75% | 71% | 71% |
| Spec 1 | 40% | 33% | 32% | 35% | 30% | 22% | 38% | 30% | 32% |
| Cutoff 2 | 10.1 | 10.1 | 1.80 | 0.198 | 1.55 | 0.198 | 10.1 | 1.55 | 2.62 |
| Sens 2 | 80% | 85% | 83% | 83% | 85% | 83% | 81% | 86% | 86% |
| Spec 2 | 33% | 30% | 22% | 16% | 23% | 11% | 33% | 23% | 23% |
| Cutoff 3 | 0.198 | 0.131 | 0.198 | 0.131 | 0.131 | 0.0854 | 0.198 | 0.0854 | 0.198 |
| Sens 3 | 93% | 92% | 100% | 90% | 92% | 91% | 94% | 100% | 93% |
| Spec 3 | 16% | 11% | 8% | 14% | 11% | 8% | 16% | 7% | 11% |
| Cutoff 4 | 65.2 | 70.9 | 78.3 | 65.2 | 70.9 | 78.3 | 65.2 | 70.9 | 78.3 |
| Sens 4 | 23% | 15% | 9% | 17% | 15% | 4% | 25% | 29% | 7% |
| Spec 4 | 70% | 70% | 71% | 70% | 70% | 71% | 70% | 70% | 71% |
| Cutoff 5 | 92.2 | 94.0 | 96.2 | 92.2 | 94.0 | 96.2 | 92.2 | 94.0 | 96.2 |
| Sens 5 | 7% | 8% | 4% | 3% | 8% | 0% | 6% | 14% | 0% |
| Spec 5 | 80% | 80% | 80% | 80% | 80% | 80% | 80% | 80% | 80% |
| Cutoff 6 | 120 | 123 | 120 | 120 | 123 | 120 | 120 | 123 | 120 |
| Sens 6 | 7% | 8% | 4% | 3% | 8% | 0% | 6% | 14% | 0% |
| Spec 6 | 90% | 90% | 90% | 90% | 90% | 90% | 90% | 90% | 90% |
| OR Quart 2 | 3.8 | 1.0 | 3.3 | 5.2 | 0.49 | 6.7 | 2.1 | 0 | 3.1 |
| p Value | 0.050 | 1.0 | 0.16 | 0.041 | 0.57 | 0.084 | 0.41 | na | 0.33 |
| 95% CI of | 1.0 | 0.14 | 0.63 | 1.1 | 0.044 | 0.77 | 0.36 | na | 0.31 |
| OR Quart 2 | 15 | 7.2 | 17 | 25 | 5.5 | 58 | 12 | na | 31 |
| OR Quart 3 | 4.3 | 3.7 | 6.0 | 6.6 | 3.7 | 11 | 4.5 | 1.5 | 8.0 |
| p Value | 0.031 | 0.11 | 0.026 | 0.017 | 0.11 | 0.027 | 0.066 | 0.65 | 0.056 |
| 95% CI of | 1.1 | 0.75 | 1.2 | 1.4 | 0.75 | 1.3 | 0.91 | 0.25 | 0.95 |
| OR Quart 3 | 16 | 18 | 29 | 31 | 18 | 89 | 22 | 9.3 | 68 |
| OR Quart 4 | 2.1 | 1.0 | 2.7 | 4.5 | 1.5 | 8.0 | 1.0 | 1.0 | 3.2 |
| p Value | 0.30 | 1.0 | 0.25 | 0.064 | 0.65 | 0.056 | 0.99 | 0.99 | 0.32 |
| 95% CI of | 0.51 | 0.14 | 0.49 | 0.92 | 0.25 | 0.95 | 0.14 | 0.14 | 0.32 |
| OR Quart 4 | 9.0 | 7.2 | 14 | 22 | 9.3 | 68 | 7.5 | 7.3 | 32 |

| | Interleukin-33 | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 69.0 | 48.4 | 69.0 | 43.9 | 69.0 | 54.0 |
| Average | 83.7 | 58.2 | 83.7 | 52.1 | 83.7 | 61.6 |
| Stdev | 88.6 | 45.1 | 88.6 | 44.4 | 88.6 | 44.2 |
| p (t-test) | | 0.12 | | 0.056 | | 0.32 |
| Min | 0.0360 | 0.0523 | 0.0360 | 0.0232 | 0.0360 | 0.0523 |
| Max | 958 | 170 | 958 | 170 | 958 | 136 |
| n (Samp) | 223 | 30 | 223 | 30 | 223 | 16 |
| n (Patient) | 223 | 30 | 223 | 30 | 223 | 16 |
| sCr only | | | | | | |
| Median | 68.9 | 45.5 | 68.9 | 38.8 | 68.9 | 57.9 |
| Average | 82.6 | 57.8 | 82.6 | 55.5 | 82.6 | 58.4 |
| Stdev | 79.9 | 46.6 | 79.9 | 47.9 | 79.9 | 39.9 |
| p (t-test) | | 0.27 | | 0.22 | | 0.42 |
| Min | 0.0232 | 1.78 | 0.0232 | 1.78 | 0.0232 | 14.4 |
| Max | 958 | 170 | 958 | 170 | 958 | 135 |
| n (Samp) | 375 | 13 | 375 | 13 | 375 | 7 |
| n (Patient) | 375 | 13 | 375 | 13 | 375 | 7 |
| UO only | | | | | | |
| Median | 71.8 | 50.0 | 71.8 | 43.5 | 71.8 | 48.0 |
| Average | 91.0 | 53.0 | 91.0 | 45.9 | 91.0 | 55.6 |
| Stdev | 95.6 | 42.0 | 95.6 | 39.6 | 95.6 | 43.3 |
| p (t-test) | | 0.061 | | 0.027 | | 0.17 |
| Min | 0.0447 | 0.0436 | 0.0447 | 0.0232 | 0.0447 | 0.0523 |
| Max | 958 | 136 | 958 | 136 | 958 | 136 |

-continued

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| n (Samp) | 173 | 23 | 173 | 23 | 173 | 14 | | | |
| n (Patient) | 173 | 23 | 173 | 23 | 173 | 14 | | | |
| AUC | 0.41 | 0.40 | 0.36 | 0.37 | 0.38 | 0.31 | 0.44 | 0.41 | 0.37 |
| SE | 0.058 | 0.084 | 0.065 | 0.057 | 0.084 | 0.064 | 0.077 | 0.11 | 0.083 |
| p | 0.14 | 0.24 | 0.029 | 0.027 | 0.17 | 0.0032 | 0.41 | 0.45 | 0.11 |
| nCohort 1 | 223 | 375 | 173 | 223 | 375 | 173 | 223 | 375 | 173 |
| nCohort 2 | 30 | 13 | 23 | 30 | 13 | 23 | 16 | 7 | 14 |
| Cutoff 1 | 33.2 | 33.2 | 14.4 | 24.0 | 23.7 | 14.4 | 43.4 | 38.4 | 43.4 |
| Sens 1 | 70% | 77% | 74% | 70% | 77% | 74% | 75% | 71% | 71% |
| Spec 1 | 27% | 26% | 12% | 20% | 19% | 12% | 35% | 31% | 31% |
| Cutoff 2 | 14.9 | 23.7 | 12.3 | 14.9 | 22.0 | 2.92 | 38.4 | 23.7 | 0.0743 |
| Sens 2 | 80% | 85% | 83% | 80% | 85% | 83% | 81% | 86% | 86% |
| Spec 2 | 15% | 19% | 12% | 15% | 18% | 6% | 32% | 19% | 3% |
| Cutoff 3 | 2.92 | 20.9 | 0.0743 | 0.172 | 12.9 | 0.0447 | 0.0558 | 12.9 | 0.0558 |
| Sens 3 | 90% | 92% | 91% | 90% | 92% | 91% | 94% | 100% | 93% |
| Spec 3 | 9% | 17% | 3% | 8% | 13% | 1% | 4% | 13% | 1% |
| Cutoff 4 | 103 | 103 | 115 | 103 | 103 | 115 | 103 | 103 | 115 |
| Sens 4 | 23% | 15% | 9% | 17% | 15% | 9% | 25% | 14% | 14% |
| Spec 4 | 70% | 70% | 71% | 70% | 70% | 71% | 70% | 70% | 71% |
| Cutoff 5 | 127 | 127 | 130 | 127 | 127 | 130 | 127 | 127 | 130 |
| Sens 5 | 10% | 15% | 4% | 10% | 15% | 4% | 12% | 14% | 7% |
| Spec 5 | 80% | 80% | 80% | 80% | 80% | 80% | 80% | 80% | 80% |
| Cutoff 6 | 159 | 157 | 176 | 159 | 157 | 176 | 159 | 157 | 176 |
| Sens 6 | 3% | 8% | 0% | 3% | 8% | 0% | 0% | 0% | 0% |
| Spec 6 | 90% | 90% | 90% | 90% | 90% | 90% | 90% | 90% | 90% |
| OR Quart 2 | 2.2 | 1.0 | 3.3 | 1.6 | 1.0 | 2.7 | 1.4 | 2.0 | 1.0 |
| p Value | 0.22 | 1.0 | 0.16 | 0.50 | 1.0 | 0.25 | 0.70 | 0.56 | 1.0 |
| 95% CI of | 0.62 | 0.14 | 0.63 | 0.42 | 0.14 | 0.49 | 0.29 | 0.18 | 0.13 |
| OR Quart 2 | 7.7 | 7.2 | 17 | 5.9 | 7.2 | 14 | 6.3 | 23 | 7.4 |
| OR Quart 3 | 2.5 | 3.1 | 3.3 | 2.5 | 2.6 | 2.7 | 2.1 | 2.0 | 3.3 |
| p Value | 0.15 | 0.17 | 0.16 | 0.15 | 0.26 | 0.25 | 0.31 | 0.57 | 0.16 |
| 95% CI of | 0.73 | 0.62 | 0.63 | 0.73 | 0.49 | 0.49 | 0.50 | 0.18 | 0.63 |
| OR Quart 3 | 8.6 | 16 | 17 | 8.6 | 14 | 14 | 8.9 | 23 | 17 |
| OR Quart 4 | 2.5 | 1.5 | 5.3 | 3.2 | 2.0 | 6.8 | 1.0 | 2.0 | 2.1 |
| p Value | 0.15 | 0.65 | 0.040 | 0.060 | 0.42 | 0.016 | 0.98 | 0.56 | 0.39 |
| 95% CI of | 0.73 | 0.25 | 1.1 | 0.95 | 0.37 | 1.4 | 0.20 | 0.18 | 0.37 |
| OR Quart 4 | 8.6 | 9.3 | 26 | 11 | 11 | 33 | 5.3 | 23 | 12 |

| Vascular endothelial growth factor receptor 2 | | | | | | |
| --- | --- | --- | --- | --- | --- | --- |
|  | 0 hr prior to AKI stage | | 24 hr prior to AKI stage | | 48 hr prior to AKI stage | |
|  | Cohort 1 | Cohort 2 | Cohort 1 | Cohort 2 | Cohort 1 | Cohort 2 |
| sCr or UO | | | | | | |
| Median | 412 | 1060 | 412 | 830 | 412 | 752 |
| Average | 634 | 1330 | 634 | 1160 | 634 | 1150 |
| Stdev | 691 | 962 | 691 | 784 | 691 | 885 |
| p (t-test) |  | 7.5E−5 |  | 0.0019 |  | 0.018 |
| Min | 0.218 | 106 | 0.218 | 106 | 0.218 | 27.3 |
| Max | 4170 | 4230 | 4170 | 2820 | 4170 | 2820 |
| n (Samp) | 124 | 22 | 124 | 21 | 124 | 12 |
| n (Patient) | 124 | 22 | 124 | 21 | 124 | 12 |
| sCr only | | | | | | |
| Median | 692 | 1320 | 692 | 939 | nd | nd |
| Average | 955 | 1350 | 955 | 1200 | nd | nd |
| Stdev | 940 | 841 | 940 | 817 | nd | nd |
| p (t-test) |  | 0.24 |  | 0.47 | nd | nd |
| Min | 0.218 | 122 | 0.218 | 122 | nd | nd |
| Max | 5940 | 2630 | 5940 | 2630 | nd | nd |
| n (Samp) | 236 | 8 | 236 | 8 | nd | nd |
| n (Patient) | 236 | 8 | 236 | 8 | nd | nd |
| UO only | | | | | | |
| Median | 488 | 1050 | 488 | 939 | 488 | 757 |
| Average | 706 | 1350 | 706 | 1200 | 706 | 1120 |
| Stdev | 774 | 1010 | 774 | 811 | 774 | 878 |
| p (t-test) |  | 0.0025 |  | 0.017 |  | 0.097 |
| Min | 0.218 | 106 | 0.218 | 106 | 0.218 | 27.3 |

|  |  |  |  |  |  |  |  |  |
|---|---|---|---|---|---|---|---|---|
| Max | 4210 | 4230 | 4210 | 2820 | 4210 | 2820 | | |
| n (Samp) | 120 | 17 | 120 | 16 | 120 | 11 | | |
| n (Patient) | 120 | 17 | 120 | 16 | 120 | 11 | | |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.76 | 0.67 | 0.75 | 0.74 | 0.63 | 0.73 | 0.72 | nd | 0.69 |
| SE | 0.062 | 0.11 | 0.071 | 0.065 | 0.11 | 0.075 | 0.086 | nd | 0.092 |
| p | 2.8E−5 | 0.11 | 5.4E−4 | 3.0E−4 | 0.23 | 0.0025 | 0.012 | nd | 0.040 |
| nCohort 1 | 124 | 236 | 120 | 124 | 236 | 120 | 124 | nd | 120 |
| nCohort 2 | 22 | 8 | 17 | 21 | 8 | 16 | 12 | nd | 11 |
| Cutoff 1 | 734 | 825 | 747 | 734 | 741 | 734 | 623 | nd | 626 |
| Sens 1 | 73% | 75% | 71% | 71% | 75% | 75% | 75% | nd | 73% |
| Spec 1 | 72% | 59% | 69% | 72% | 53% | 69% | 62% | nd | 61% |
| Cutoff 2 | 623 | 606 | 626 | 623 | 606 | 626 | 606 | nd | 623 |
| Sens 2 | 82% | 88% | 82% | 81% | 88% | 81% | 83% | nd | 82% |
| Spec 2 | 62% | 44% | 61% | 62% | 44% | 61% | 61% | nd | 60% |
| Cutoff 3 | 508 | 113 | 508 | 508 | 113 | 508 | 508 | nd | 508 |
| Sens 3 | 91% | 100% | 94% | 90% | 100% | 94% | 92% | nd | 91% |
| Spec 3 | 57% | 15% | 53% | 57% | 15% | 53% | 57% | nd | 53% |
| Cutoff 4 | 708 | 1220 | 757 | 708 | 1220 | 757 | 708 | nd | 757 |
| Sens 4 | 73% | 50% | 65% | 71% | 38% | 62% | 58% | nd | 45% |
| Spec 4 | 70% | 70% | 70% | 70% | 70% | 70% | 70% | nd | 70% |
| Cutoff 5 | 1130 | 1600 | 1220 | 1130 | 1600 | 1220 | 1130 | nd | 1220 |
| Sens 5 | 45% | 38% | 41% | 33% | 38% | 31% | 33% | nd | 27% |
| Spec 5 | 81% | 81% | 80% | 81% | 81% | 80% | 81% | nd | 80% |
| Cutoff 6 | 1630 | 2040 | 1660 | 1630 | 2040 | 1660 | 1630 | nd | 1660 |
| Sens 6 | 27% | 25% | 24% | 24% | 12% | 19% | 25% | nd | 18% |
| Spec 6 | 90% | 90% | 90% | 90% | 90% | 90% | 90% | nd | 90% |
| OR Quart 2 | 0 | 1.0 | 1.0 | 0 | 1.0 | 1.0 | 0 | nd | 0 |
| p Value | na | 1.0 | 1.0 | na | 1.0 | 1.0 | na | nd | na |
| 95% CI of | na | 0.061 | 0.060 | na | 0.061 | 0.060 | na | nd | na |
| OR Quart 2 | na | 16 | 17 | na | 16 | 17 | na | nd | na |
| OR Quart 3 | 6.5 | 2.0 | 10 | 5.7 | 3.1 | 12 | 7.1 | nd | 8.3 |
| p Value | 0.022 | 0.57 | 0.034 | 0.035 | 0.33 | 0.023 | 0.078 | nd | 0.054 |
| 95% CI of | 1.3 | 0.18 | 1.2 | 1.1 | 0.31 | 1.4 | 0.80 | nd | 0.96 |
| OR Quart 3 | 32 | 23 | 86 | 28 | 31 | 100 | 62 | nd | 72 |
| OR Quart 4 | 6.3 | 4.2 | 8.2 | 6.3 | 3.1 | 5.7 | 5.7 | nd | 3.1 |
| p Value | 0.024 | 0.20 | 0.055 | 0.024 | 0.33 | 0.12 | 0.12 | nd | 0.34 |
| 95% CI of | 1.3 | 0.46 | 0.96 | 1.3 | 0.31 | 0.63 | 0.63 | nd | 0.31 |
| OR Quart 4 | 31 | 39 | 71 | 31 | 31 | 52 | 52 | nd | 31 |

| Lutropin subunit beta | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 23.7 | 9.51 | 23.7 | 9.51 | 23.7 | 8.03 |
| Average | 76.3 | 57.0 | 76.3 | 57.0 | 76.3 | 79.4 |
| Stdev | 120 | 111 | 120 | 111 | 120 | 135 |
| p (t-test) | | 0.58 | | 0.58 | | 0.94 |
| Min | 0.0297 | 0.341 | 0.0297 | 0.341 | 0.0297 | 0.505 |
| Max | 400 | 393 | 400 | 393 | 400 | 393 |
| n (Samp) | 68 | 14 | 68 | 14 | 68 | 9 |
| n (Patient) | 68 | 14 | 68 | 14 | 68 | 9 |
| sCr only | | | | | | |
| Median | 29.6 | 37.1 | 29.6 | 37.1 | 29.6 | 46.2 |
| Average | 78.0 | 86.3 | 78.0 | 86.3 | 78.0 | 118 |
| Stdev | 110 | 132 | 110 | 132 | 110 | 154 |
| p (t-test) | | 0.83 | | 0.83 | | 0.40 |
| Min | 0.0297 | 0.341 | 0.0297 | 0.341 | 0.0297 | 4.62 |
| Max | 400 | 393 | 400 | 393 | 400 | 393 |
| n (Samp) | 128 | 9 | 128 | 9 | 128 | 6 |
| n (Patient) | 128 | 9 | 128 | 9 | 128 | 6 |
| UO only | | | | | | |
| Median | 26.4 | 4.44 | 26.4 | 4.44 | nd | nd |
| Average | 85.1 | 9.51 | 85.1 | 9.51 | nd | nd |
| Stdev | 120 | 12.7 | 120 | 12.7 | nd | nd |
| p (t-test) | | 0.10 | | 0.10 | nd | nd |

-continued

|   | | | | | | | |
|---|---|---|---|---|---|---|---|
| Min | 0.0297 | 0.505 | 0.0297 | 0.505 | nd | nd |
| Max | 400 | 37.1 | 400 | 37.1 | nd | nd |
| n (Samp) | 72 | 7 | 72 | 7 | nd | nd |
| n (Patient) | 72 | 7 | 72 | 7 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.42 | 0.52 | 0.25 | 0.42 | 0.52 | 0.25 | 0.46 | 0.59 | nd |
| SE | 0.087 | 0.10 | 0.11 | 0.087 | 0.10 | 0.11 | 0.10 | 0.12 | nd |
| p | 0.36 | 0.84 | 0.021 | 0.36 | 0.84 | 0.021 | 0.73 | 0.46 | nd |
| nCohort 1 | 68 | 128 | 72 | 68 | 128 | 72 | 68 | 128 | nd |
| nCohort 2 | 14 | 9 | 7 | 14 | 9 | 7 | 9 | 6 | nd |
| Cutoff 1 | 4.35 | 7.97 | 3.37 | 4.35 | 7.97 | 3.37 | 4.35 | 7.97 | nd |
| Sens 1 | 71% | 78% | 71% | 71% | 78% | 71% | 78% | 83% | nd |
| Spec 1 | 21% | 30% | 19% | 21% | 30% | 19% | 21% | 30% | nd |
| Cutoff 2 | 0.933 | 4.00 | 0.840 | 0.933 | 4.00 | 0.840 | 4.00 | 7.97 | nd |
| Sens 2 | 86% | 89% | 86% | 86% | 89% | 86% | 89% | 83% | nd |
| Spec 2 | 12% | 19% | 12% | 12% | 19% | 12% | 21% | 30% | nd |
| Cutoff 3 | 0.341 | 0.311 | 0.422 | 0.341 | 0.311 | 0.422 | 0.234 | 4.00 | nd |
| Sens 3 | 93% | 100% | 100% | 93% | 100% | 100% | 100% | 100% | nd |
| Spec 3 | 6% | 6% | 8% | 6% | 6% | 8% | 6% | 19% | nd |
| Cutoff 4 | 43.9 | 63.3 | 68.2 | 43.9 | 63.3 | 68.2 | 43.9 | 63.3 | nd |
| Sens 4 | 29% | 22% | 0% | 29% | 22% | 0% | 33% | 33% | nd |
| Spec 4 | 71% | 70% | 71% | 71% | 70% | 71% | 71% | 70% | nd |
| Cutoff 5 | 134 | 139 | 151 | 134 | 139 | 151 | 134 | 139 | nd |
| Sens 5 | 14% | 22% | 0% | 14% | 22% | 0% | 22% | 33% | nd |
| Spec 5 | 81% | 80% | 81% | 81% | 80% | 81% | 81% | 80% | nd |
| Cutoff 6 | 315 | 275 | 311 | 315 | 275 | 311 | 315 | 275 | nd |
| Sens 6 | 7% | 11% | 0% | 7% | 11% | 0% | 11% | 17% | nd |
| Spec 6 | 91% | 91% | 90% | 91% | 91% | 90% | 91% | 91% | nd |
| OR Quart 2 | 0.67 | 1.0 | >1.1 | 0.67 | 1.0 | >1.1 | 1.1 | 0.97 | nd |
| p Value | 0.68 | 1.0 | <0.97 | 0.68 | 1.0 | <0.97 | 0.96 | 0.98 | nd |
| 95% CI of | 0.099 | 0.13 | >0.061 | 0.099 | 0.13 | >0.061 | 0.13 | 0.058 | nd |
| OR Quart 2 | 4.5 | 7.5 | na | 4.5 | 7.5 | na | 8.4 | 16 | nd |
| OR Quart 3 | 1.0 | 1.5 | >2.2 | 1.0 | 1.5 | >2.2 | 0.50 | 2.1 | nd |
| p Value | 1.0 | 0.64 | <0.53 | 1.0 | 0.64 | <0.53 | 0.59 | 0.56 | nd |
| 95% CI of | 0.18 | 0.24 | >0.19 | 0.18 | 0.24 | >0.19 | 0.042 | 0.18 | nd |
| OR Quart 3 | 5.6 | 9.9 | na | 5.6 | 9.9 | na | 6.0 | 24 | nd |
| OR Quart 4 | 2.6 | 0.97 | >5.3 | 2.6 | 0.97 | >5.3 | 2.4 | 2.0 | nd |
| p Value | 0.23 | 0.98 | <0.15 | 0.23 | 0.98 | <0.15 | 0.35 | 0.58 | nd |
| 95% CI of | 0.54 | 0.13 | >0.54 | 0.54 | 0.13 | >0.54 | 0.38 | 0.17 | nd |
| OR Quart 4 | 12 | 7.3 | na | 12 | 7.3 | na | 15 | 23 | nd |

| Neural cell adhesion molecule 1 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 2810 | 4940 | 2810 | 4490 | 2810 | 3900 |
| Average | 3350 | 6880 | 3350 | 6380 | 3350 | 4540 |
| Stdev | 2580 | 9710 | 2580 | 9720 | 2580 | 2430 |
| p (t-test) | | 1.4E-5 | | 1.8E-4 | | 0.076 |
| Min | 6.83 | 161 | 6.83 | 142 | 6.83 | 1650 |
| Max | 22000 | 55700 | 22000 | 55700 | 22000 | 9700 |
| n (Samp) | 223 | 30 | 223 | 30 | 223 | 16 |
| n (Patient) | 223 | 30 | 223 | 30 | 223 | 16 |
| sCr only | | | | | | |
| Median | 3740 | 4080 | 3740 | 4080 | 3740 | 5050 |
| Average | 4460 | 4520 | 4460 | 4470 | 4460 | 5230 |
| Stdev | 4470 | 2200 | 4470 | 2240 | 4470 | 1940 |
| p (t-test) | | 0.96 | | 0.99 | | 0.65 |
| Min | 6.83 | 161 | 6.83 | 142 | 6.83 | 2880 |
| Max | 55700 | 7860 | 55700 | 7860 | 55700 | 7860 |
| n (Samp) | 373 | 13 | 373 | 13 | 373 | 7 |
| n (Patient) | 373 | 13 | 373 | 13 | 373 | 7 |
| UO only | | | | | | |
| Median | 3210 | 5230 | 3210 | 5050 | 3210 | 4490 |
| Average | 3630 | 8840 | 3630 | 8180 | 3630 | 4640 |
| Stdev | 2320 | 11500 | 2320 | 11600 | 2320 | 2470 |
| p (t-test) | | 3.6E-7 | | 8.1E-6 | | 0.12 |
| Min | 485 | 1700 | 485 | 1120 | 485 | 1650 |
| Max | 11700 | 55700 | 11700 | 55700 | 11700 | 9700 |

-continued

| | | | | | | | | | |
|---|---|---|---|---|---|---|---|---|---|
| n (Samp) | 173 | 23 | | 173 | 23 | | 173 | 14 | |
| n (Patient) | 173 | 23 | | 173 | 23 | | 173 | 14 | |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.72 | 0.58 | 0.74 | 0.67 | 0.57 | 0.68 | 0.67 | 0.66 | 0.63 |
| SE | 0.055 | 0.084 | 0.062 | 0.057 | 0.084 | 0.065 | 0.076 | 0.11 | 0.083 |
| p | 5.5E−5 | 0.37 | 8.9E−5 | 0.0033 | 0.42 | 0.0065 | 0.030 | 0.16 | 0.12 |
| nCohort 1 | 223 | 373 | 173 | 223 | 373 | 173 | 223 | 373 | 173 |
| nCohort 2 | 30 | 13 | 23 | 30 | 13 | 23 | 16 | 7 | 14 |
| Cutoff 1 | 3720 | 3410 | 3940 | 2810 | 2870 | 2690 | 2870 | 3970 | 2990 |
| Sens 1 | 70% | 77% | 74% | 70% | 77% | 74% | 75% | 71% | 71% |
| Spec 1 | 65% | 46% | 65% | 51% | 37% | 44% | 53% | 56% | 49% |
| Cutoff 2 | 2870 | 2870 | 2990 | 2210 | 2810 | 2160 | 2690 | 3720 | 1720 |
| Sens 2 | 80% | 85% | 83% | 80% | 85% | 83% | 81% | 86% | 86% |
| Spec 2 | 53% | 37% | 49% | 41% | 36% | 36% | 49% | 50% | 22% |
| Cutoff 3 | 2170 | 2200 | 2160 | 1720 | 2200 | 1720 | 1700 | 2870 | 1700 |
| Sens 3 | 90% | 92% | 91% | 90% | 92% | 91% | 94% | 100% | 93% |
| Spec 3 | 41% | 27% | 36% | 27% | 27% | 22% | 26% | 37% | 21% |
| Cutoff 4 | 3930 | 5290 | 4360 | 3930 | 5290 | 4360 | 3930 | 5290 | 4360 |
| Sens 4 | 63% | 31% | 65% | 57% | 31% | 61% | 50% | 29% | 50% |
| Spec 4 | 70% | 70% | 71% | 70% | 70% | 71% | 70% | 70% | 71% |
| Cutoff 5 | 4960 | 6450 | 5580 | 4960 | 6450 | 5580 | 4960 | 6450 | 5580 |
| Sens 5 | 50% | 23% | 48% | 47% | 23% | 43% | 38% | 29% | 36% |
| Spec 5 | 80% | 80% | 80% | 80% | 80% | 80% | 80% | 80% | 80% |
| Cutoff 6 | 6160 | 7690 | 6670 | 6160 | 7690 | 6670 | 6160 | 7690 | 6670 |
| Sens 6 | 33% | 15% | 35% | 30% | 15% | 35% | 25% | 29% | 21% |
| Spec 6 | 90% | 90% | 90% | 90% | 90% | 90% | 90% | 90% | 90% |
| OR Quart 2 | 1.4 | 4.1 | 1.5 | 2.5 | 4.1 | 1.0 | 3.1 | >2.0 | 0.64 |
| p Value | 0.70 | 0.21 | 0.65 | 0.20 | 0.21 | 1.0 | 0.34 | <0.56 | 0.63 |
| 95% CI of | 0.29 | 0.45 | 0.24 | 0.62 | 0.45 | 0.24 | 0.31 | >0.18 | 0.10 |
| OR Quart 2 | 6.3 | 37 | 9.6 | 10 | 37 | 4.2 | 30 | na | 4.0 |
| OR Quart 3 | 2.5 | 5.2 | 3.9 | 1.7 | 5.2 | 1.3 | 5.3 | >3.1 | 1.3 |
| p Value | 0.20 | 0.13 | 0.100 | 0.47 | 0.13 | 0.73 | 0.13 | <0.33 | 0.72 |
| 95% CI of | 0.62 | 0.60 | 0.77 | 0.39 | 0.60 | 0.32 | 0.60 | >0.32 | 0.28 |
| OR Quart 3 | 10 | 46 | 20 | 7.5 | 46 | 5.1 | 47 | na | 6.3 |
| OR Quart 4 | 6.7 | 3.0 | 6.8 | 6.1 | 3.0 | 2.9 | 7.7 | >2.0 | 1.7 |
| p Value | 0.0040 | 0.34 | 0.016 | 0.0061 | 0.34 | 0.093 | 0.061 | <0.56 | 0.48 |
| 95% CI of | 1.8 | 0.31 | 1.4 | 1.7 | 0.31 | 0.84 | 0.91 | >0.18 | 0.38 |
| OR Quart 4 | 24 | 30 | 33 | 22 | 30 | 9.9 | 64 | na | 7.6 |

| Platelet-derived growth factor subunit B (dimer) | | | | | |
|---|---|---|---|---|---|
| 0 hr prior to AKI stage | | 24 hr prior to AKI stage | | 48 hr prior to AKI stage | |
| Cohort 1 | Cohort 2 | Cohort 1 | Cohort 2 | Cohort 1 | Cohort 2 |
| sCr or UO | | | | | |
| Median | | | | | |
| 1.35 | 3.57 | 1.35 | 3.33 | 1.35 | 3.23 |
| Average | | | | | |
| 5.15 | 52.4 | 5.15 | 52.1 | 5.15 | 4.20 |
| Stdev | | | | | |
| 21.4 | 208 | 21.4 | 208 | 21.4 | 3.82 |
| p (t-test) | | | | | |
| | 0.0026 | | 0.0028 | | 0.88 |
| Min | | | | | |
| 0.00246 | 0.283 | 0.00246 | 0.166 | 0.00246 | 0.283 |
| Max | | | | | |
| 270 | 935 | 270 | 935 | 270 | 12.9 |
| n (Samp) | 191 | 20 | 191 | 20 | 191 | 11 |
| n (Patient) | 191 | 20 | 191 | 20 | 191 | 11 |
| sCr only | | | | | |
| Median | 1.68 | 4.25 | 1.68 | 3.52 | 1.68 | 2.23 |
| Average | 8.22 | 7.08 | 8.22 | 5.72 | 8.22 | 4.46 |
| Stdev | 57.1 | 6.03 | 57.1 | 5.43 | 57.1 | 5.26 |
| p (t-test) | | 0.95 | | 0.89 | | 0.87 |
| Min | 0.00246 | 0.283 | 0.00246 | 0.283 | 0.00246 | 0.166 |
| Max | 935 | 16.9 | 935 | 16.9 | 935 | 12.9 |
| n (Samp) | 295 | 10 | 295 | 10 | 295 | 6 |
| n (Patient) | 295 | 10 | 295 | 10 | 295 | 6 |
| UO only | | | | | |
| Median | 1.81 | 4.34 | 1.81 | 3.71 | 1.81 | 3.71 |
| Average | 6.27 | 71.8 | 6.27 | 69.4 | 6.27 | 4.77 |
| Stdev | 24.9 | 239 | 24.9 | 240 | 24.9 | 3.98 |
| p (t-test) | | 0.0021 | | 0.0031 | | 0.86 |

-continued

| | | | | | | |
|---|---|---|---|---|---|---|
| Min | 0.00246 | 0.401 | 0.00246 | 0.166 | 0.00246 | 0.401 |
| Max | 270 | 935 | 270 | 935 | 270 | 12.9 |
| n (Samp) | 136 | 15 | 136 | 15 | 136 | 9 |
| n (Patient) | 136 | 15 | 136 | 15 | 136 | 9 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.75 | 0.75 | 0.76 | 0.71 | 0.71 | 0.69 | 0.68 | 0.55 | 0.69 |
| SE | 0.065 | 0.091 | 0.075 | 0.068 | 0.093 | 0.079 | 0.091 | 0.12 | 0.10 |
| p | 1.3E−4 | 0.0059 | 6.1E−4 | 0.0024 | 0.023 | 0.014 | 0.050 | 0.69 | 0.060 |
| nCohort 1 | 191 | 295 | 136 | 191 | 295 | 136 | 191 | 295 | 136 |
| nCohort 2 | 20 | 10 | 15 | 20 | 10 | 15 | 11 | 6 | 9 |
| Cutoff 1 | 2.84 | 3.05 | 3.16 | 2.40 | 2.50 | 2.37 | 2.40 | 0.279 | 2.37 |
| Sens 1 | 70% | 70% | 73% | 70% | 70% | 73% | 73% | 83% | 78% |
| Spec 1 | 75% | 71% | 74% | 71% | 65% | 65% | 71% | 15% | 65% |
| Cutoff 2 | 2.13 | 2.50 | 2.84 | 1.39 | 2.13 | 1.39 | 0.903 | 0.279 | 0.903 |
| Sens 2 | 80% | 80% | 80% | 80% | 80% | 80% | 82% | 83% | 89% |
| Spec 2 | 67% | 65% | 69% | 51% | 60% | 44% | 37% | 15% | 29% |
| Cutoff 3 | 0.903 | 2.13 | 0.903 | 0.392 | 2.01 | 0.392 | 0.392 | 0.132 | 0.392 |
| Sens 3 | 90% | 90% | 93% | 90% | 90% | 93% | 91% | 100% | 100% |
| Spec 3 | 37% | 60% | 29% | 20% | 58% | 16% | 20% | 13% | 16% |
| Cutoff 4 | 2.30 | 3.00 | 2.99 | 2.30 | 3.00 | 2.99 | 2.30 | 3.00 | 2.99 |
| Sens 4 | 75% | 70% | 73% | 70% | 60% | 67% | 73% | 50% | 67% |
| Spec 4 | 70% | 70% | 71% | 70% | 70% | 71% | 70% | 70% | 71% |
| Cutoff 5 | 3.30 | 3.77 | 3.85 | 3.30 | 3.77 | 3.85 | 3.30 | 3.77 | 3.85 |
| Sens 5 | 55% | 60% | 53% | 50% | 50% | 47% | 45% | 33% | 44% |
| Spec 5 | 80% | 80% | 80% | 80% | 80% | 80% | 80% | 80% | 80% |
| Cutoff 6 | 5.81 | 7.01 | 6.04 | 5.81 | 7.01 | 6.04 | 5.81 | 7.01 | 6.04 |
| Sens 6 | 25% | 40% | 33% | 25% | 30% | 33% | 18% | 33% | 22% |
| Spec 6 | 90% | 90% | 90% | 90% | 90% | 90% | 90% | 90% | 90% |
| OR Quart 2 | 0.48 | 0 | 0.97 | 0.64 | 0 | 0.97 | 0.48 | 0.49 | 1.0 |
| p Value | 0.55 | na | 0.98 | 0.63 | na | 0.98 | 0.55 | 0.57 | 1.0 |
| 95% CI of | 0.042 | na | 0.059 | 0.10 | na | 0.13 | 0.042 | 0.044 | 0.060 |
| OR Quart 2 | 5.5 | na | 16 | 4.0 | na | 7.3 | 5.5 | 5.6 | 17 |
| OR Quart 3 | 2.6 | 3.1 | 5.5 | 1.3 | 4.2 | 1.5 | 1.0 | 0.49 | 2.1 |
| p Value | 0.27 | 0.33 | 0.13 | 0.72 | 0.21 | 0.67 | 1.0 | 0.57 | 0.56 |
| 95% CI of | 0.48 | 0.31 | 0.61 | 0.28 | 0.45 | 0.24 | 0.14 | 0.044 | 0.18 |
| OR Quart 3 | 14 | 30 | 49 | 6.3 | 38 | 9.5 | 7.4 | 5.6 | 24 |
| OR Quart 4 | 7.3 | 6.3 | 9.6 | 4.3 | 5.2 | 4.7 | 3.2 | 0.99 | 5.5 |
| p Value | 0.012 | 0.091 | 0.038 | 0.034 | 0.14 | 0.063 | 0.17 | 0.99 | 0.13 |
| 95% CI of | 1.5 | 0.74 | 1.1 | 1.1 | 0.59 | 0.92 | 0.61 | 0.14 | 0.61 |
| OR Quart 4 | 35 | 54 | 81 | 16 | 46 | 24 | 17 | 7.2 | 49 |

Corticotropin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.00187 | 0.00448 | 0.00187 | 0.00448 | 0.00187 | 0.00227 |
| Average | 0.00264 | 0.00863 | 0.00264 | 0.00863 | 0.00264 | 0.00340 |
| Stdev | 0.00485 | 0.0109 | 0.00485 | 0.0109 | 0.00485 | 0.00271 |
| p (t-test) | | 9.1E−4 | | 9.1E−4 | | 0.68 |
| Min | 0.000316 | 0.00109 | 0.000316 | 0.00109 | 0.000316 | 0.00111 |
| Max | 0.0489 | 0.0377 | 0.0489 | 0.0377 | 0.0489 | 0.00909 |
| n (Samp) | 99 | 12 | 99 | 12 | 99 | 7 |
| n (Patient) | 99 | 12 | 99 | 12 | 99 | 7 |
| sCr only | | | | | | |
| Median | 0.00205 | 0.00713 | 0.00205 | 0.00713 | nd | nd |
| Average | 0.00292 | 0.0133 | 0.00292 | 0.0133 | nd | nd |
| Stdev | 0.00497 | 0.0141 | 0.00497 | 0.0141 | nd | nd |
| p (t-test) | | 1.0E−5 | | 1.0E−5 | nd | nd |
| Min | 0.000316 | 0.00109 | 0.000316 | 0.00109 | nd | nd |
| Max | 0.0489 | 0.0377 | 0.0489 | 0.0377 | nd | nd |
| n (Samp) | 160 | 6 | 160 | 6 | nd | nd |
| n (Patient) | 160 | 6 | 160 | 6 | nd | nd |
| UO only | | | | | | |
| Median | 0.00182 | 0.00425 | 0.00182 | 0.00425 | 0.00182 | 0.00219 |
| Average | 0.00266 | 0.00883 | 0.00266 | 0.00883 | 0.00266 | 0.00333 |
| Stdev | 0.00519 | 0.0121 | 0.00519 | 0.0121 | 0.00519 | 0.00296 |
| p (t-test) | | 0.0066 | | 0.0066 | | 0.76 |
| Min | 0.000388 | 0.00136 | 0.000388 | 0.00136 | 0.000388 | 0.00111 |
| Max | 0.0489 | 0.0377 | 0.0489 | 0.0377 | 0.0489 | 0.00909 |

-continued

| | | | | | | |
|---|---|---|---|---|---|---|
| n (Samp) | 86 | 8 | 86 | 8 | 86 | 6 |
| n (Patient) | 86 | 8 | 86 | 8 | 86 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.78 | 0.82 | 0.79 | 0.78 | 0.82 | 0.79 | 0.65 | nd | 0.62 |
| SE | 0.081 | 0.11 | 0.097 | 0.081 | 0.11 | 0.097 | 0.12 | nd | 0.13 |
| p | 5.8E-4 | 0.0026 | 0.0027 | 5.8E-4 | 0.0026 | 0.0027 | 0.19 | nd | 0.33 |
| nCohort 1 | 99 | 160 | 86 | 99 | 160 | 86 | 99 | nd | 86 |
| nCohort 2 | 12 | 6 | 8 | 12 | 6 | 8 | 7 | nd | 6 |
| Cutoff 1 | 0.00217 | 0.00415 | 0.00217 | 0.00217 | 0.00415 | 0.00217 | 0.00210 | nd | 0.00159 |
| Sens 1 | 75% | 83% | 75% | 75% | 83% | 75% | 71% | nd | 83% |
| Spec 1 | 61% | 91% | 62% | 61% | 91% | 62% | 60% | nd | 44% |
| Cutoff 2 | 0.00210 | 0.00415 | 0.00206 | 0.00210 | 0.00415 | 0.00206 | 0.00159 | nd | 0.00159 |
| Sens 2 | 83% | 83% | 88% | 83% | 83% | 88% | 86% | nd | 83% |
| Spec 2 | 60% | 91% | 60% | 60% | 91% | 60% | 38% | nd | 44% |
| Cutoff 3 | 0.00124 | 0.00106 | 0.00124 | 0.00124 | 0.00106 | 0.00124 | 0.00109 | nd | 0.00109 |
| Sens 3 | 92% | 100% | 100% | 92% | 100% | 100% | 100% | nd | 100% |
| Spec 3 | 30% | 11% | 31% | 30% | 11% | 31% | 15% | nd | 19% |
| Cutoff 4 | 0.00275 | 0.00275 | 0.00274 | 0.00275 | 0.00275 | 0.00274 | 0.00275 | nd | 0.00274 |
| Sens 4 | 67% | 83% | 62% | 67% | 83% | 62% | 43% | nd | 33% |
| Spec 4 | 72% | 71% | 71% | 72% | 71% | 71% | 72% | nd | 71% |
| Cutoff 5 | 0.00307 | 0.00306 | 0.00285 | 0.00307 | 0.00306 | 0.00285 | 0.00307 | nd | 0.00285 |
| Sens 5 | 67% | 83% | 62% | 67% | 83% | 62% | 43% | nd | 33% |
| Spec 5 | 81% | 80% | 80% | 81% | 80% | 80% | 81% | nd | 80% |
| Cutoff 6 | 0.00380 | 0.00404 | 0.00412 | 0.00380 | 0.00404 | 0.00412 | 0.00380 | nd | 0.00412 |
| Sens 6 | 58% | 83% | 50% | 58% | 83% | 50% | 29% | nd | 17% |
| Spec 6 | 91% | 90% | 91% | 91% | 90% | 91% | 91% | nd | 91% |
| OR Quart 2 | 0.96 | 0 | >1.0 | 0.96 | 0 | >1.0 | 0.96 | nd | 1.0 |
| p Value | 0.98 | na | <1.0 | 0.98 | na | <1.0 | 0.98 | nd | 1.0 |
| 95% CI of | 0.057 | na | >0.059 | 0.057 | na | >0.059 | 0.057 | nd | 0.059 |
| OR Quart 2 | 16 | na | na | 16 | na | na | 16 | nd | 17 |
| OR Quart 3 | 2.0 | 0 | >2.2 | 2.0 | 0 | >2.2 | 2.1 | nd | 2.1 |
| p Value | 0.58 | na | <0.53 | 0.58 | na | <0.53 | 0.56 | nd | 0.56 |
| 95% CI of | 0.17 | na | >0.18 | 0.17 | na | >0.18 | 0.18 | nd | 0.18 |
| OR Quart 3 | 23 | na | na | 23 | na | na | 25 | nd | 25 |
| OR Quart 4 | 10 | 5.4 | >6.1 | 10 | 5.4 | >6.1 | 3.1 | nd | 2.1 |
| p Value | 0.034 | 0.13 | <0.11 | 0.034 | 0.13 | <0.11 | 0.34 | nd | 0.56 |
| 95% CI of | 1.2 | 0.60 | >0.65 | 1.2 | 0.60 | >0.65 | 0.30 | nd | 0.18 |
| OR Quart 4 | 90 | 48 | na | 90 | 48 | na | 32 | nd | 25 |

| Thyroxine-binding globulin | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.155 | 0.225 | 0.155 | 0.197 | 0.155 | 0.159 |
| Average | 0.268 | 0.589 | 0.268 | 0.610 | 0.268 | 0.451 |
| Stdev | 0.327 | 0.955 | 0.327 | 0.988 | 0.327 | 0.621 |
| p (t-test) | | 0.011 | | 0.0091 | | 0.16 |
| Min | 0.000191 | 0.00635 | 0.000191 | 0.00635 | 0.000191 | 0.0485 |
| Max | 1.59 | 3.60 | 1.59 | 3.60 | 1.59 | 1.88 |
| n (Samp) | 103 | 15 | 103 | 14 | 103 | 8 |
| n (Patient) | 103 | 15 | 103 | 14 | 103 | 8 |
| sCr only | | | | | | |
| Median | 0.182 | 0.225 | 0.182 | 0.225 | nd | nd |
| Average | 0.313 | 0.470 | 0.313 | 0.470 | nd | nd |
| Stdev | 0.425 | 0.648 | 0.425 | 0.648 | nd | nd |
| p (t-test) | | 0.35 | | 0.35 | nd | nd |
| Min | 0.000191 | 0.00635 | 0.000191 | 0.00635 | nd | nd |
| Max | 3.60 | 1.88 | 3.60 | 1.88 | nd | nd |
| n (Samp) | 170 | 7 | 170 | 7 | nd | nd |
| n (Patient) | 170 | 7 | 170 | 7 | nd | nd |
| UO only | | | | | | |
| Median | 0.155 | 0.234 | 0.155 | 0.225 | 0.155 | 0.128 |
| Average | 0.252 | 0.637 | 0.252 | 0.676 | 0.252 | 0.260 |
| Stdev | 0.323 | 1.07 | 0.323 | 1.13 | 0.323 | 0.269 |
| p (t-test) | | 0.012 | | 0.0088 | | 0.95 |

-continued

|  | | | | | | |
|---|---|---|---|---|---|---|
| Min | 0.000191 | 0.0485 | 0.000191 | 0.0485 | 0.000191 | 0.0485 |
| Max | 1.59 | 3.60 | 1.59 | 3.60 | 1.59 | 0.607 |
| n (Samp) | 87 | 10 | 87 | 9 | 87 | 6 |
| n (Patient) | 87 | 10 | 87 | 9 | 87 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.61 | 0.57 | 0.66 | 0.60 | 0.57 | 0.65 | 0.59 | nd | 0.54 |
| SE | 0.082 | 0.11 | 0.098 | 0.085 | 0.11 | 0.10 | 0.11 | nd | 0.12 |
| p | 0.19 | 0.57 | 0.10 | 0.25 | 0.57 | 0.16 | 0.43 | nd | 0.74 |
| nCohort 1 | 103 | 170 | 87 | 103 | 170 | 87 | 103 | nd | 87 |
| nCohort 2 | 15 | 7 | 10 | 14 | 7 | 9 | 8 | nd | 6 |
| Cutoff 1 | 0.135 | 0.163 | 0.135 | 0.135 | 0.163 | 0.104 | 0.103 | nd | 0.0496 |
| Sens 1 | 73% | 71% | 70% | 71% | 71% | 78% | 75% | nd | 83% |
| Spec 1 | 46% | 46% | 48% | 46% | 46% | 43% | 41% | nd | 30% |
| Cutoff 2 | 0.103 | 0.136 | 0.104 | 0.0496 | 0.136 | 0.0496 | 0.0496 | nd | 0.0496 |
| Sens 2 | 80% | 86% | 80% | 86% | 86% | 89% | 88% | nd | 83% |
| Spec 2 | 41% | 42% | 43% | 29% | 42% | 30% | 29% | nd | 30% |
| Cutoff 3 | 0.0462 | 0.00446 | 0.0927 | 0.0462 | 0.00446 | 0.0462 | 0.0462 | nd | 0.0462 |
| Sens 3 | 93% | 100% | 90% | 93% | 100% | 100% | 100% | nd | 100% |
| Spec 3 | 27% | 5% | 40% | 27% | 5% | 29% | 27% | nd | 29% |
| Cutoff 4 | 0.313 | 0.356 | 0.249 | 0.313 | 0.356 | 0.249 | 0.313 | nd | 0.249 |
| Sens 4 | 33% | 29% | 40% | 36% | 29% | 44% | 38% | nd | 33% |
| Spec 4 | 71% | 70% | 70% | 71% | 70% | 70% | 71% | nd | 70% |
| Cutoff 5 | 0.407 | 0.448 | 0.368 | 0.407 | 0.448 | 0.368 | 0.407 | nd | 0.368 |
| Sens 5 | 33% | 29% | 40% | 36% | 29% | 44% | 38% | nd | 33% |
| Spec 5 | 81% | 80% | 80% | 81% | 80% | 80% | 81% | nd | 80% |
| Cutoff 6 | 0.693 | 0.750 | 0.693 | 0.693 | 0.750 | 0.693 | 0.693 | nd | 0.693 |
| Sens 6 | 13% | 14% | 10% | 14% | 14% | 11% | 12% | nd | 0% |
| Spec 6 | 90% | 90% | 91% | 90% | 90% | 91% | 90% | nd | 91% |
| OR Quart 2 | 7.0 | 2.0 | >4.8 | 5.8 | 2.0 | >4.8 | >4.5 | nd | >4.8 |
| p Value | 0.081 | 0.56 | <0.18 | 0.12 | 0.56 | <0.18 | <0.19 | nd | <0.17 |
| 95% CI of | 0.79 | 0.18 | >0.50 | 0.64 | 0.18 | >0.50 | >0.47 | nd | >0.50 |
| OR Quart 2 | 62 | 23 | na | 53 | 23 | na | na | nd | na |
| OR Quart 3 | 3.2 | 2.0 | >2.2 | 3.2 | 2.0 | >1.0 | >1.0 | nd | >0 |
| p Value | 0.32 | 0.56 | <0.54 | 0.32 | 0.56 | <0.98 | <1.0 | nd | <na |
| 95% CI of | 0.32 | 0.18 | >0.18 | 0.32 | 0.18 | >0.062 | >0.059 | nd | >na |
| OR Quart 3 | 33 | 23 | na | 33 | 23 | na | na | nd | na |
| OR Quart 4 | 5.6 | 2.0 | >4.6 | 5.6 | 2.0 | >4.8 | >3.2 | nd | >2.1 |
| p Value | 0.13 | 0.58 | <0.19 | 0.13 | 0.58 | <0.18 | <0.32 | nd | <0.56 |
| 95% CI of | 0.61 | 0.17 | >0.47 | 0.61 | 0.17 | >0.50 | >0.32 | nd | >0.18 |
| OR Quart 4 | 51 | 23 | na | 51 | 23 | na | na | nd | na |

Pigment epithelium-derived factor

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 3.77 | 40.6 | 3.77 | 34.8 | 3.77 | 14.1 |
| Average | 25.0 | 61.2 | 25.0 | 54.2 | 25.0 | 42.7 |
| Stdev | 52.8 | 66.7 | 52.8 | 60.6 | 52.8 | 58.4 |
| p (t-test) | | 7.5E-4 | | 0.0056 | | 0.20 |
| Min | 0.00100 | 0.121 | 0.00100 | 0.0312 | 0.00100 | 0.683 |
| Max | 400 | 218 | 400 | 218 | 400 | 218 |
| n (Samp) | 223 | 30 | 223 | 30 | 223 | 16 |
| n (Patient) | 223 | 30 | 223 | 30 | 223 | 16 |
| sCr only | | | | | | |
| Median | 5.82 | 58.3 | 5.82 | 47.1 | 5.82 | 70.8 |
| Average | 28.4 | 66.5 | 28.4 | 62.7 | 28.4 | 79.6 |
| Stdev | 55.5 | 66.4 | 55.5 | 68.0 | 55.5 | 71.7 |
| p (t-test) | | 0.016 | | 0.030 | | 0.017 |
| Min | 0.00100 | 0.121 | 0.00100 | 0.0312 | 0.00100 | 2.29 |
| Max | 400 | 218 | 400 | 218 | 400 | 218 |
| n (Samp) | 374 | 13 | 374 | 13 | 374 | 7 |
| n (Patient) | 374 | 13 | 374 | 13 | 374 | 7 |
| UO only | | | | | | |
| Median | 5.79 | 44.2 | 5.79 | 44.2 | 5.79 | 10.0 |
| Average | 30.8 | 73.7 | 30.8 | 66.7 | 30.8 | 42.8 |
| Stdev | 60.5 | 79.4 | 60.5 | 73.2 | 60.5 | 61.7 |
| p (t-test) | | 0.0024 | | 0.0099 | | 0.48 |
| Min | 0.00106 | 2.09 | 0.00106 | 2.00 | 0.00106 | 0.683 |

-continued

|  |  |  |  |  |  |  |
|---|---|---|---|---|---|---|
| Max | 400 | 250 | 400 | 250 | 400 | 218 |
| n (Samp) | 173 | 23 | 173 | 23 | 173 | 14 |
| n (Patient) | 173 | 23 | 173 | 23 | 173 | 14 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.74 | 0.73 | 0.74 | 0.71 | 0.70 | 0.71 | 0.67 | 0.79 | 0.62 |
| SE | 0.054 | 0.081 | 0.062 | 0.055 | 0.082 | 0.063 | 0.076 | 0.10 | 0.083 |
| p | 8.8E−6 | 0.0053 | 1.2E−4 | 1.1E−4 | 0.014 | 7.3E−4 | 0.028 | 0.0041 | 0.15 |
| nCohort 1 | 223 | 374 | 173 | 223 | 374 | 173 | 223 | 374 | 173 |
| nCohort 2 | 30 | 13 | 23 | 30 | 13 | 23 | 16 | 7 | 14 |
| Cutoff 1 | 8.99 | 7.75 | 8.99 | 7.24 | 6.55 | 7.24 | 3.22 | 56.9 | 6.44 |
| Sens 1 | 70% | 77% | 74% | 70% | 77% | 74% | 75% | 71% | 71% |
| Spec 1 | 62% | 55% | 59% | 59% | 52% | 55% | 47% | 87% | 53% |
| Cutoff 2 | 6.55 | 6.55 | 6.44 | 3.77 | 4.09 | 3.77 | 3.11 | 18.0 | 3.11 |
| Sens 2 | 80% | 85% | 83% | 80% | 85% | 83% | 81% | 86% | 86% |
| Spec 2 | 57% | 52% | 53% | 50% | 45% | 47% | 46% | 67% | 40% |
| Cutoff 3 | 2.56 | 2.25 | 3.11 | 2.19 | 2.25 | 2.14 | 1.56 | 2.25 | 1.56 |
| Sens 3 | 90% | 92% | 91% | 90% | 92% | 91% | 94% | 100% | 93% |
| Spec 3 | 42% | 32% | 40% | 39% | 32% | 31% | 33% | 32% | 24% |
| Cutoff 4 | 17.4 | 21.1 | 20.5 | 17.4 | 21.1 | 20.5 | 17.4 | 21.1 | 20.5 |
| Sens 4 | 63% | 69% | 65% | 60% | 62% | 61% | 50% | 71% | 43% |
| Spec 4 | 70% | 70% | 71% | 70% | 70% | 71% | 70% | 70% | 71% |
| Cutoff 5 | 27.6 | 32.9 | 37.5 | 27.6 | 32.9 | 37.5 | 27.6 | 32.9 | 37.5 |
| Sens 5 | 57% | 62% | 52% | 53% | 54% | 52% | 38% | 71% | 36% |
| Spec 5 | 80% | 80% | 80% | 80% | 80% | 80% | 80% | 80% | 80% |
| Cutoff 6 | 70.1 | 81.7 | 105 | 70.1 | 81.7 | 105 | 70.1 | 81.7 | 105 |
| Sens 6 | 33% | 23% | 30% | 33% | 23% | 30% | 31% | 29% | 14% |
| Spec 6 | 90% | 90% | 90% | 90% | 90% | 90% | 90% | 90% | 90% |
| OR Quart 2 | 5.3 | 0.99 | >5.6 | 7.8 | 2.0 | >6.8 | 4.1 | >1.0 | 0.98 |
| p Value | 0.13 | 0.99 | <0.12 | 0.059 | 0.57 | <0.081 | 0.21 | <0.99 | 0.98 |
| 95% CI of | 0.61 | 0.061 | >0.63 | 0.92 | 0.18 | >0.79 | 0.45 | >0.062 | 0.13 |
| OR Quart 2 | 47 | 16 | na | 65 | 22 | na | 38 | na | 7.3 |
| OR Quart 3 | 7.8 | 2.0 | >5.6 | 6.5 | 2.0 | >4.4 | 4.1 | >1.0 | 2.6 |
| p Value | 0.059 | 0.57 | <0.12 | 0.087 | 0.57 | <0.20 | 0.21 | <0.99 | 0.27 |
| 95% CI of | 0.92 | 0.18 | >0.63 | 0.76 | 0.18 | >0.47 | 0.45 | >0.062 | 0.48 |
| OR Quart 3 | 65 | 22 | na | 56 | 22 | na | 38 | na | 14 |
| OR Quart 4 | 22 | 9.7 | >18 | 21 | 8.5 | >18 | 7.7 | >5.2 | 2.6 |
| p Value | 0.0030 | 0.033 | <0.0068 | 0.0039 | 0.045 | <0.0068 | 0.061 | <0.13 | 0.27 |
| 95% CI of | 2.9 | 1.2 | >2.2 | 2.6 | 1.0 | >2.2 | 0.91 | >0.60 | 0.48 |
| OR Quart 4 | 170 | 78 | na | 160 | 70 | na | 64 | na | 14 |

| Tumor necrosis factor receptor superfamily member 8 | | | | | | |
|---|---|---|---|---|---|---|
|  | 0 hr prior to AKI stage | | 24 hr prior to AKI stage | | 48 hr prior to AKI stage | |
|  | Cohort 1 | Cohort 2 | Cohort 1 | Cohort 2 | Cohort 1 | Cohort 2 |
| sCr or UO |  |  |  |  |  |  |
| Median | 21.7 | 39.4 | 21.7 | 38.9 | 21.7 | 38.9 |
| Average | 30.9 | 55.9 | 30.9 | 54.7 | 30.9 | 34.7 |
| Stdev | 38.1 | 68.3 | 38.1 | 69.1 | 38.1 | 22.0 |
| p (t-test) |  | 0.012 |  | 0.018 |  | 0.72 |
| Min | 0.0561 | 4.17 | 0.0561 | 4.17 | 0.0561 | 0.196 |
| Max | 277 | 353 | 277 | 353 | 277 | 68.6 |
| n (Samp) | 128 | 24 | 128 | 23 | 128 | 13 |
| n (Patient) | 128 | 24 | 128 | 23 | 128 | 13 |
| sCr only |  |  |  |  |  |  |
| Median | 27.0 | 43.9 | 27.0 | 43.9 | nd | nd |
| Average | 43.4 | 75.5 | 43.4 | 75.5 | nd | nd |
| Stdev | 61.9 | 105 | 61.9 | 105 | nd | nd |
| p (t-test) |  | 0.14 |  | 0.14 | nd | nd |
| Min | 0.0561 | 25.7 | 0.0561 | 25.7 | nd | nd |
| Max | 554 | 353 | 554 | 353 | nd | nd |
| n (Samp) | 242 | 9 | 242 | 9 | nd | nd |
| n (Patient) | 242 | 9 | 242 | 9 | nd | nd |
| UO only |  |  |  |  |  |  |
| Median | 19.9 | 39.4 | 19.9 | 38.9 | 19.9 | 33.1 |
| Average | 30.3 | 44.9 | 30.3 | 42.6 | 30.3 | 33.8 |
| Stdev | 39.0 | 29.0 | 39.0 | 26.7 | 39.0 | 22.8 |

-continued

|  |  |  |  |  |  |  |
|---|---|---|---|---|---|---|
| p (t-test) |  | 0.13 |  | 0.21 |  | 0.76 |
| Min | 0.0561 | 4.17 | 0.0561 | 4.17 | 0.0561 | 0.196 |
| Max | 277 | 117 | 277 | 102 | 277 | 68.6 |
| n (Samp) | 122 | 18 | 122 | 17 | 122 | 12 |
| n (Patient) | 122 | 18 | 122 | 17 | 122 | 12 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.71 | 0.69 | 0.71 | 0.70 | 0.69 | 0.69 | 0.61 | nd | 0.61 |
| SE | 0.063 | 0.100 | 0.072 | 0.065 | 0.100 | 0.075 | 0.087 | nd | 0.090 |
| p | 8.7E−4 | 0.062 | 0.0028 | 0.0025 | 0.062 | 0.0096 | 0.20 | nd | 0.22 |
| nCohort 1 | 128 | 242 | 122 | 128 | 242 | 122 | 128 | nd | 122 |
| nCohort 2 | 24 | 9 | 18 | 23 | 9 | 17 | 13 | nd | 12 |
| Cutoff 1 | 30.9 | 31.1 | 30.2 | 27.2 | 31.1 | 27.2 | 15.0 | nd | 15.0 |
| Sens 1 | 71% | 78% | 72% | 74% | 78% | 71% | 77% | nd | 75% |
| Spec 1 | 66% | 57% | 67% | 61% | 57% | 64% | 38% | nd | 39% |
| Cutoff 2 | 26.3 | 26.3 | 24.9 | 24.9 | 26.3 | 24.5 | 12.7 | nd | 12.7 |
| Sens 2 | 83% | 89% | 83% | 83% | 89% | 82% | 85% | nd | 83% |
| Spec 2 | 58% | 49% | 57% | 55% | 49% | 55% | 34% | nd | 35% |
| Cutoff 3 | 24.5 | 25.6 | 5.76 | 19.5 | 25.6 | 5.76 | 6.53 | nd | 6.53 |
| Sens 3 | 92% | 100% | 94% | 91% | 100% | 94% | 92% | nd | 92% |
| Spec 3 | 54% | 45% | 16% | 46% | 45% | 16% | 14% | nd | 17% |
| Cutoff 4 | 34.0 | 42.3 | 32.9 | 34.0 | 42.3 | 32.9 | 34.0 | nd | 32.9 |
| Sens 4 | 62% | 56% | 67% | 57% | 56% | 59% | 54% | nd | 50% |
| Spec 4 | 70% | 70% | 71% | 70% | 70% | 71% | 70% | nd | 71% |
| Cutoff 5 | 47.1 | 53.5 | 41.1 | 47.1 | 53.5 | 41.1 | 47.1 | nd | 41.1 |
| Sens 5 | 29% | 22% | 39% | 30% | 22% | 41% | 31% | nd | 42% |
| Spec 5 | 80% | 80% | 80% | 80% | 80% | 80% | 80% | nd | 80% |
| Cutoff 6 | 58.1 | 90.9 | 56.7 | 58.1 | 90.9 | 56.7 | 58.1 | nd | 56.7 |
| Sens 6 | 21% | 11% | 22% | 22% | 11% | 24% | 15% | nd | 17% |
| Spec 6 | 91% | 90% | 90% | 91% | 90% | 90% | 91% | nd | 90% |
| OR Quart 2 | 1.0 | >2.0 | 0.49 | 1.5 | >2.0 | 0.47 | 1.0 | nd | 0.97 |
| p Value | 1.0 | <0.57 | 0.56 | 0.67 | <0.57 | 0.55 | 1.0 | nd | 0.98 |
| 95% CI of | 0.13 | >0.18 | 0.042 | 0.24 | >0.18 | 0.041 | 0.13 | nd | 0.13 |
| OR Quart 2 | 7.5 | na | 5.6 | 9.5 | na | 5.4 | 7.5 | nd | 7.3 |
| OR Quart 3 | 6.4 | >4.2 | 3.4 | 4.7 | >4.2 | 3.3 | 1.5 | nd | 1.0 |
| p Value | 0.022 | <0.20 | 0.15 | 0.063 | <0.20 | 0.16 | 0.64 | nd | 1.0 |
| 95% CI of | 1.3 | >0.46 | 0.64 | 0.92 | >0.46 | 0.62 | 0.24 | nd | 0.13 |
| OR Quart 3 | 32 | na | 18 | 24 | na | 18 | 9.9 | nd | 7.6 |
| OR Quart 4 | 6.4 | >3.1 | 5.7 | 6.2 | >3.1 | 4.7 | 3.3 | nd | 3.3 |
| p Value | 0.022 | <0.33 | 0.035 | 0.025 | <0.33 | 0.062 | 0.16 | nd | 0.16 |
| 95% CI of | 1.3 | >0.31 | 1.1 | 1.3 | >0.31 | 0.93 | 0.62 | nd | 0.62 |
| OR Quart 4 | 32 | na | 29 | 31 | na | 24 | 18 | nd | 18 |

| Alpha-fetoprotein | | | | | | |
|---|---|---|---|---|---|---|
|  | 0 hr prior to AKI stage | | 24 hr prior to AKI stage | | 48 hr prior to AKI stage | |
|  | Cohort 1 | Cohort 2 | Cohort 1 | Cohort 2 | Cohort 1 | Cohort 2 |
| sCr or UO |  |  |  |  |  |  |
| Median | 0.00587 | 0.142 | 0.00587 | 0.142 | 0.00587 | 0.0837 |
| Average | 0.0687 | 0.323 | 0.0687 | 0.323 | 0.0687 | 0.116 |
| Stdev | 0.133 | 0.650 | 0.133 | 0.650 | 0.133 | 0.157 |
| p (t-test) |  | 1.6E−4 |  | 1.6E−4 |  | 0.23 |
| Min | 0.000523 | 0.000523 | 0.000523 | 0.000523 | 0.000523 | 0.000463 |
| Max | 0.803 | 2.85 | 0.803 | 2.85 | 0.803 | 0.537 |
| n (Samp) | 123 | 18 | 123 | 18 | 123 | 13 |
| n (Patient) | 123 | 18 | 123 | 18 | 123 | 13 |
| sCr only |  |  |  |  |  |  |
| Median | 0.00660 | 0.189 | 0.00660 | 0.189 | 0.00660 | 0.107 |
| Average | 0.0908 | 0.188 | 0.0908 | 0.188 | 0.0908 | 0.158 |
| Stdev | 0.246 | 0.162 | 0.246 | 0.162 | 0.246 | 0.189 |
| p (t-test) |  | 0.20 |  | 0.20 |  | 0.45 |
| Min | 0.000523 | 0.000523 | 0.000523 | 0.000523 | 0.000523 | 0.000523 |
| Max | 2.85 | 0.537 | 2.85 | 0.537 | 2.85 | 0.537 |
| n (Samp) | 210 | 11 | 210 | 11 | 210 | 8 |
| n (Patient) | 210 | 11 | 210 | 11 | 210 | 8 |
| UO only |  |  |  |  |  |  |
| Median | 0.00587 | 0.123 | 0.00587 | 0.123 | 0.00587 | 0.0604 |
| Average | 0.0775 | 0.406 | 0.0775 | 0.406 | 0.0775 | 0.0703 |
| Stdev | 0.151 | 0.870 | 0.151 | 0.870 | 0.151 | 0.0706 |
| p (t-test) |  | 3.8E−4 |  | 3.8E−4 |  | 0.89 |
| Min | 0.000463 | 0.00286 | 0.000463 | 0.00286 | 0.000463 | 0.000463 |

-continued

|  | | | | | | |
|---|---|---|---|---|---|---|
| Max | 0.803 | 2.85 | 0.803 | 2.85 | 0.803 | 0.189 |
| n (Samp) | 119 | 10 | 119 | 10 | 119 | 8 |
| n (Patient) | 119 | 10 | 119 | 10 | 119 | 8 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.73 | 0.71 | 0.70 | 0.73 | 0.71 | 0.70 | 0.55 | 0.58 | 0.52 |
| SE | 0.071 | 0.090 | 0.096 | 0.071 | 0.090 | 0.096 | 0.086 | 0.11 | 0.11 |
| p | 0.0011 | 0.021 | 0.040 | 0.0011 | 0.021 | 0.040 | 0.59 | 0.48 | 0.84 |
| nCohort 1 | 123 | 210 | 119 | 123 | 210 | 119 | 123 | 210 | 119 |
| nCohort 2 | 18 | 11 | 10 | 18 | 11 | 10 | 13 | 8 | 8 |
| Cutoff 1 | 0.0728 | 0.0880 | 0.0728 | 0.0728 | 0.0880 | 0.0728 | 0.00296 | 0.00296 | 0.00296 |
| Sens 1 | 72% | 73% | 70% | 72% | 73% | 70% | 77% | 75% | 75% |
| Spec 1 | 76% | 78% | 76% | 76% | 78% | 76% | 11% | 10% | 10% |
| Cutoff 2 | 0.0309 | 0.0309 | 0.0309 | 0.0309 | 0.0309 | 0.0309 | 0.000523 | 0.00132 | 0.000523 |
| Sens 2 | 83% | 82% | 80% | 83% | 82% | 80% | 85% | 88% | 88% |
| Spec 2 | 59% | 57% | 61% | 59% | 57% | 61% | 2% | 3% | 5% |
| Cutoff 3 | 0.000523 | 0.00132 | 0.00296 | 0.000523 | 0.00132 | 0.00296 | 0.000463 | 0 | 0 |
| Sens 3 | 94% | 91% | 90% | 94% | 91% | 90% | 92% | 100% | 100% |
| Spec 3 | 2% | 3% | 10% | 2% | 3% | 10% | 0% | 0% | 0% |
| Cutoff 4 | 0.0499 | 0.0728 | 0.0613 | 0.0499 | 0.0728 | 0.0613 | 0.0499 | 0.0728 | 0.0613 |
| Sens 4 | 72% | 73% | 70% | 72% | 73% | 70% | 54% | 62% | 50% |
| Spec 4 | 71% | 73% | 71% | 71% | 73% | 71% | 71% | 73% | 71% |
| Cutoff 5 | 0.0842 | 0.112 | 0.0880 | 0.0842 | 0.112 | 0.0880 | 0.0842 | 0.112 | 0.0880 |
| Sens 5 | 67% | 64% | 60% | 67% | 64% | 60% | 46% | 50% | 38% |
| Spec 5 | 80% | 80% | 81% | 80% | 80% | 81% | 80% | 80% | 81% |
| Cutoff 6 | 0.198 | 0.213 | 0.259 | 0.198 | 0.213 | 0.259 | 0.198 | 0.213 | 0.259 |
| Sens 6 | 33% | 36% | 20% | 33% | 36% | 20% | 15% | 25% | 0% |
| Spec 6 | 91% | 90% | 91% | 91% | 90% | 91% | 91% | 90% | 91% |
| OR Quart 2 | 0 | 0 | 0 | 0 | 0 | 0 | 0 | 0 | 0 |
| p Value | na | na | na | na | na | na | na | na | na |
| 95% CI of | na | na | na | na | na | na | na | na | na |
| OR Quart 2 | na | na | na | na | na | na | na | na | na |
| OR Quart 3 | 1.0 | 0.49 | 0.48 | 1.0 | 0.49 | 0.48 | 0.18 | 0 | 0.30 |
| p Value | 1.0 | 0.57 | 0.56 | 1.0 | 0.57 | 0.56 | 0.12 | na | 0.31 |
| 95% CI of | 0.19 | 0.043 | 0.042 | 0.19 | 0.043 | 0.042 | 0.019 | na | 0.030 |
| OR Quart 3 | 5.3 | 5.6 | 5.6 | 5.3 | 5.6 | 5.6 | 1.6 | na | 3.1 |
| OR Quart 4 | 5.3 | 4.4 | 4.0 | 5.3 | 4.4 | 4.0 | 1.5 | 1.7 | 1.3 |
| p Value | 0.017 | 0.068 | 0.099 | 0.017 | 0.068 | 0.099 | 0.53 | 0.48 | 0.72 |
| 95% CI of | 1.4 | 0.89 | 0.77 | 1.4 | 0.89 | 0.77 | 0.43 | 0.39 | 0.27 |
| OR Quart 4 | 21 | 22 | 21 | 21 | 22 | 21 | 5.3 | 7.5 | 6.5 |

| Apolipoprotein E | | | | | | |
|---|---|---|---|---|---|---|
|  | 0 hr prior to AKI stage | | 24 hr prior to AKI stage | | 48 hr prior to AKI stage | |
|  | Cohort 1 | Cohort 2 | Cohort 1 | Cohort 2 | Cohort 1 | Cohort 2 |
| sCr or UO | | | | | | |
| Median | 5.23 | 5.48 | 5.23 | 4.43 | 5.23 | 4.43 |
| Average | 43.6 | 94.8 | 43.6 | 90.7 | 43.6 | 10.3 |
| Stdev | 222 | 370 | 222 | 371 | 222 | 18.1 |
| p (t-test) |  | 0.25 |  | 0.29 |  | 0.49 |
| Min | 0.000147 | 0.00247 | 0.000147 | 0.00247 | 0.000147 | 0.211 |
| Max | 2160 | 2140 | 2160 | 2140 | 2160 | 82.5 |
| n (Samp) | 235 | 35 | 235 | 35 | 235 | 21 |
| n (Patient) | 235 | 35 | 235 | 35 | 235 | 21 |
| sCr only | | | | | | |
| Median | 5.95 | 3.82 | 5.95 | 3.60 | 5.95 | 3.60 |
| Average | 46.5 | 39.7 | 46.5 | 39.0 | 46.5 | 4.20 |
| Stdev | 226 | 143 | 226 | 143 | 226 | 3.93 |
| p (t-test) |  | 0.90 |  | 0.89 |  | 0.54 |
| Min | 0.000147 | 0.500 | 0.000147 | 0.290 | 0.000147 | 0.556 |
| Max | 2160 | 594 | 2160 | 594 | 2160 | 12.3 |
| n (Samp) | 397 | 17 | 397 | 17 | 397 | 11 |
| n (Patient) | 397 | 17 | 397 | 17 | 397 | 11 |
| UO only | | | | | | |
| Median | 5.32 | 6.96 | 5.32 | 5.48 | 5.32 | 4.87 |
| Average | 38.7 | 110 | 38.7 | 104 | 38.7 | 12.2 |
| Stdev | 192 | 425 | 192 | 425 | 192 | 20.5 |
| p (t-test) |  | 0.15 |  | 0.19 |  | 0.58 |

-continued

| | | | | | | |
|---|---|---|---|---|---|---|
| Min | 0.000147 | 0.00247 | 0.000147 | 0.00247 | 0.000147 | 0.211 |
| Max | 2140 | 2140 | 2140 | 2140 | 2140 | 82.5 |
| n (Samp) | 190 | 25 | 190 | 25 | 190 | 16 |
| n (Patient) | 190 | 25 | 190 | 25 | 190 | 16 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.52 | 0.40 | 0.54 | 0.48 | 0.37 | 0.51 | 0.47 | 0.34 | 0.47 |
| SE | 0.053 | 0.074 | 0.063 | 0.053 | 0.074 | 0.062 | 0.067 | 0.091 | 0.076 |
| p | 0.78 | 0.16 | 0.54 | 0.75 | 0.088 | 0.87 | 0.63 | 0.077 | 0.72 |
| nCohort 1 | 235 | 397 | 190 | 235 | 397 | 190 | 235 | 397 | 190 |
| nCohort 2 | 35 | 17 | 25 | 35 | 17 | 25 | 21 | 11 | 16 |
| Cutoff 1 | 1.82 | 1.06 | 3.39 | 1.82 | 1.06 | 3.25 | 3.25 | 0.890 | 3.25 |
| Sens 1 | 71% | 71% | 72% | 71% | 71% | 72% | 71% | 73% | 75% |
| Spec 1 | 26% | 17% | 37% | 26% | 17% | 34% | 35% | 14% | 34% |
| Cutoff 2 | 0.882 | 0.692 | 1.06 | 0.626 | 0.609 | 0.626 | 1.76 | 0.626 | 2.00 |
| Sens 2 | 80% | 82% | 80% | 80% | 82% | 80% | 81% | 82% | 81% |
| Spec 2 | 17% | 12% | 15% | 14% | 11% | 9% | 25% | 11% | 23% |
| Cutoff 3 | 0.460 | 0.554 | 0.380 | 0.380 | 0.380 | 0.380 | 0.882 | 0.609 | 0.500 |
| Sens 3 | 91% | 94% | 92% | 91% | 94% | 92% | 90% | 91% | 94% |
| Spec 3 | 11% | 10% | 7% | 10% | 8% | 7% | 17% | 11% | 8% |
| Cutoff 4 | 11.3 | 14.7 | 11.3 | 11.3 | 14.7 | 11.3 | 11.3 | 14.7 | 11.3 |
| Sens 4 | 34% | 6% | 40% | 29% | 6% | 36% | 19% | 0% | 25% |
| Spec 4 | 70% | 70% | 70% | 70% | 70% | 70% | 70% | 70% | 70% |
| Cutoff 5 | 19.4 | 24.7 | 22.9 | 19.4 | 24.7 | 22.9 | 19.4 | 24.7 | 22.9 |
| Sens 5 | 23% | 6% | 32% | 20% | 6% | 28% | 14% | 0% | 19% |
| Spec 5 | 80% | 80% | 80% | 80% | 80% | 80% | 80% | 80% | 80% |
| Cutoff 6 | 59.6 | 64.4 | 57.8 | 59.6 | 64.4 | 57.8 | 59.6 | 64.4 | 57.8 |
| Sens 6 | 14% | 6% | 20% | 11% | 6% | 12% | 5% | 0% | 6% |
| Spec 6 | 90% | 90% | 90% | 90% | 90% | 90% | 90% | 90% | 90% |
| OR Quart 2 | 0.86 | 6.4 | 0.53 | 0.76 | 5.3 | 0.67 | 2.5 | >4.2 | 1.4 |
| p Value | 0.77 | 0.089 | 0.33 | 0.62 | 0.13 | 0.52 | 0.20 | <0.21 | 0.68 |
| 95% CI of | 0.31 | 0.75 | 0.14 | 0.27 | 0.60 | 0.20 | 0.62 | >0.46 | 0.30 |
| OR Quart 2 | 2.4 | 54 | 1.9 | 2.2 | 46 | 2.3 | 10 | na | 6.5 |
| OR Quart 3 | 0.87 | 3.1 | 0.67 | 1.1 | 4.1 | 0.67 | 2.1 | >2.0 | 1.7 |
| p Value | 0.80 | 0.34 | 0.52 | 0.80 | 0.21 | 0.52 | 0.31 | <0.56 | 0.47 |
| 95% CI of | 0.32 | 0.31 | 0.20 | 0.43 | 0.45 | 0.20 | 0.50 | >0.18 | 0.39 |
| OR Quart 3 | 2.4 | 30 | 2.3 | 3.0 | 38 | 2.3 | 8.8 | na | 7.7 |
| OR Quart 4 | 1.1 | 7.5 | 1.3 | 1.0 | 7.5 | 1.1 | 1.7 | >5.3 | 1.4 |
| p Value | 0.83 | 0.062 | 0.62 | 0.97 | 0.062 | 0.81 | 0.47 | <0.13 | 0.68 |
| 95% CI of | 0.42 | 0.91 | 0.45 | 0.38 | 0.91 | 0.38 | 0.39 | >0.60 | 0.30 |
| OR Quart 4 | 2.9 | 62 | 3.8 | 2.7 | 62 | 3.4 | 7.5 | na | 6.5 |

| | Apolipoprotein(a) | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 2.89 | 5.31 | 2.89 | 5.01 | 2.89 | 5.01 |
| Average | 45.1 | 70.6 | 45.1 | 67.4 | 45.1 | 18.3 |
| Stdev | 176 | 234 | 176 | 234 | 176 | 34.3 |
| p (t-test) | | 0.45 | | 0.51 | | 0.49 |
| Min | 0.00770 | 0.123 | 0.00770 | 0.0122 | 0.00770 | 0.0122 |
| Max | 1510 | 1170 | 1510 | 1170 | 1510 | 118 |
| n (Samp) | 230 | 35 | 230 | 35 | 230 | 21 |
| n (Patient) | 230 | 35 | 230 | 35 | 230 | 21 |
| sCr only | | | | | | |
| Median | 3.62 | 7.43 | 3.62 | 5.47 | 3.62 | 7.43 |
| Average | 93.7 | 10.7 | 93.7 | 9.98 | 93.7 | 11.5 |
| Stdev | 910 | 12.9 | 910 | 13.1 | 910 | 15.4 |
| p (t-test) | | 0.71 | | 0.70 | | 0.76 |
| Min | 0.00479 | 1.16 | 0.00479 | 0.0122 | 0.00479 | 1.16 |
| Max | 17500 | 54.1 | 17500 | 54.1 | 17500 | 54.1 |
| n (Samp) | 391 | 17 | 391 | 17 | 391 | 11 |
| n (Patient) | 391 | 17 | 391 | 17 | 391 | 11 |
| UO only | | | | | | |
| Median | 3.46 | 5.31 | 3.46 | 5.31 | 3.46 | 5.16 |
| Average | 39.4 | 119 | 39.4 | 91.2 | 39.4 | 20.4 |
| Stdev | 166 | 293 | 166 | 275 | 166 | 37.7 |
| p (t-test) | | 0.045 | | 0.18 | | 0.65 |
| Min | 0.00790 | 0.123 | 0.00790 | 0.0122 | 0.00790 | 0.0122 |
| Max | 1510 | 1170 | 1510 | 1170 | 1510 | 118 |

|  |  |  |  |  |  |  |  |  |  |
|---|---|---|---|---|---|---|---|---|---|
| n (Samp) | 185 | 25 | 185 | 25 | 185 | 16 | | | |
| n (Patient) | 185 | 25 | 185 | 25 | 185 | 16 | | | |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.62 | 0.60 | 0.60 | 0.59 | 0.55 | 0.58 | 0.59 | 0.58 | 0.56 |
| SE | 0.054 | 0.074 | 0.063 | 0.054 | 0.073 | 0.063 | 0.068 | 0.091 | 0.077 |
| p | 0.024 | 0.20 | 0.11 | 0.10 | 0.49 | 0.21 | 0.20 | 0.39 | 0.46 |
| nCohort 1 | 230 | 391 | 185 | 230 | 391 | 185 | 230 | 391 | 185 |
| nCohort 2 | 35 | 17 | 25 | 35 | 17 | 25 | 21 | 11 | 16 |
| Cutoff 1 | 2.20 | 4.09 | 1.80 | 1.80 | 3.14 | 1.80 | 1.95 | 3.14 | 1.24 |
| Sens 1 | 71% | 71% | 72% | 71% | 71% | 72% | 71% | 73% | 75% |
| Spec 1 | 43% | 55% | 33% | 39% | 43% | 33% | 40% | 43% | 19% |
| Cutoff 2 | 1.25 | 1.61 | 1.24 | 1.25 | 1.25 | 1.24 | 1.25 | 1.61 | 1.16 |
| Sens 2 | 83% | 82% | 80% | 80% | 82% | 80% | 81% | 82% | 81% |
| Spec 2 | 26% | 28% | 19% | 26% | 20% | 19% | 26% | 28% | 19% |
| Cutoff 3 | 1.07 | 1.16 | 0.751 | 0.123 | 0.893 | 0.123 | 1.07 | 1.25 | 0.123 |
| Sens 3 | 91% | 94% | 92% | 91% | 94% | 92% | 90% | 91% | 94% |
| Spec 3 | 23% | 19% | 15% | 12% | 16% | 8% | 23% | 20% | 8% |
| Cutoff 4 | 5.04 | 7.01 | 5.73 | 5.04 | 7.01 | 5.73 | 5.04 | 7.01 | 5.73 |
| Sens 4 | 51% | 53% | 48% | 49% | 47% | 44% | 48% | 55% | 38% |
| Spec 4 | 70% | 70% | 70% | 70% | 70% | 70% | 70% | 70% | 70% |
| Cutoff 5 | 9.17 | 16.0 | 9.17 | 9.17 | 16.0 | 9.17 | 9.17 | 16.0 | 9.17 |
| Sens 5 | 37% | 24% | 40% | 31% | 24% | 36% | 29% | 27% | 31% |
| Spec 5 | 80% | 80% | 80% | 80% | 80% | 80% | 80% | 80% | 80% |
| Cutoff 6 | 61.4 | 61.4 | 52.0 | 61.4 | 61.4 | 52.0 | 61.4 | 61.4 | 52.0 |
| Sens 6 | 11% | 0% | 20% | 9% | 0% | 12% | 10% | 0% | 12% |
| Spec 6 | 90% | 90% | 90% | 90% | 90% | 90% | 90% | 90% | 90% |
| OR Quart 2 | 1.0 | 0.66 | 0.63 | 0.69 | 0.49 | 0.63 | 0.72 | 0.99 | 0.18 |
| p Value | 1.0 | 0.65 | 0.49 | 0.55 | 0.42 | 0.49 | 0.68 | 0.99 | 0.13 |
| 95% CI of | 0.31 | 0.11 | 0.17 | 0.21 | 0.088 | 0.17 | 0.16 | 0.14 | 0.021 |
| OR Quart 2 | 3.3 | 4.0 | 2.4 | 2.3 | 2.7 | 2.4 | 3.4 | 7.2 | 1.6 |
| OR Quart 3 | 1.4 | 2.1 | 0.64 | 1.5 | 1.5 | 0.82 | 1.5 | 1.5 | 0.78 |
| p Value | 0.57 | 0.32 | 0.51 | 0.44 | 0.52 | 0.75 | 0.53 | 0.65 | 0.73 |
| 95% CI of | 0.45 | 0.50 | 0.17 | 0.54 | 0.42 | 0.23 | 0.41 | 0.25 | 0.20 |
| OR Quart 3 | 4.2 | 8.5 | 2.4 | 4.2 | 5.6 | 2.9 | 5.7 | 9.3 | 3.1 |
| OR Quart 4 | 2.9 | 2.1 | 2.0 | 2.0 | 1.3 | 1.8 | 2.1 | 2.0 | 1.2 |
| p Value | 0.041 | 0.32 | 0.21 | 0.16 | 0.73 | 0.30 | 0.24 | 0.42 | 0.78 |
| 95% CI of | 1.0 | 0.50 | 0.68 | 0.75 | 0.33 | 0.60 | 0.60 | 0.36 | 0.34 |
| OR Quart 4 | 8.0 | 8.5 | 5.9 | 5.5 | 4.8 | 5.3 | 7.4 | 11 | 4.2 |

FIG. 5: Comparison of marker levels in EDTA samples collected from Cohort 1 (patients that did not progress beyond RIFLE stage 0) and in EDTA samples collected from subjects at 0, 24 hours, and 48 hours prior to reaching stage R, I or F in Cohort 2.

| | Complement C4-B | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | 65500 | 78300 | 65500 | 83200 | 65500 | 65900 |
| Average | 72500 | 79400 | 72500 | 78500 | 72500 | 73500 |
| Stdev | 40600 | 45100 | 40600 | 38300 | 40600 | 36100 |
| p(t-test) | | 0.32 | | 0.37 | | 0.91 |
| Min | 305 | 1250 | 305 | 10700 | 305 | 21500 |
| Max | 203000 | 223000 | 203000 | 188000 | 203000 | 140000 |
| n (Samp) | 121 | 53 | 121 | 53 | 121 | 26 |
| n (Patient) | 87 | 53 | 87 | 53 | 87 | 26 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 70800 | 87600 | 70800 | 93700 | 70800 | 90200 |
| Average | 77800 | 83300 | 77800 | 91300 | 77800 | 84300 |
| Stdev | 42600 | 39300 | 42600 | 43900 | 42600 | 46200 |
| p(t-test) | | 0.61 | | 0.23 | | 0.64 |
| Min | 305 | 7620 | 305 | 5510 | 305 | 10700 |

-continued

|  |  |  |  |  |  |  |
|---|---|---|---|---|---|---|
| Max | 223000 | 144000 | 223000 | 161000 | 223000 | 140000 |
| n (Samp) | 288 | 16 | 288 | 15 | 288 | 10 |
| n (Patient) | 161 | 16 | 161 | 15 | 161 | 10 |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 65500 | 64200 | 65500 | 77100 | 65500 | 62800 |
| Average | 71100 | 78000 | 71100 | 75500 | 71100 | 67500 |
| Stdev | 36500 | 48100 | 36500 | 38900 | 36500 | 32700 |
| p(t-test) |  | 0.33 |  | 0.46 |  | 0.67 |
| Min | 305 | 1250 | 305 | 10700 | 305 | 21500 |
| Max | 160000 | 223000 | 160000 | 188000 | 160000 | 136000 |
| n (Samp) | 125 | 43 | 125 | 54 | 125 | 23 |
| n (Patient) | 80 | 43 | 80 | 54 | 80 | 23 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.55 | 0.56 | 0.53 | 0.56 | 0.62 | 0.53 | 0.51 | 0.56 | 0.47 |
| SE | 0.048 | 0.076 | 0.052 | 0.048 | 0.079 | 0.047 | 0.063 | 0.096 | 0.066 |
| p | 0.34 | 0.43 | 0.57 | 0.23 | 0.13 | 0.55 | 0.83 | 0.53 | 0.66 |
| nCohort 1 | 121 | 288 | 125 | 121 | 288 | 125 | 121 | 288 | 125 |
| nCohort 2 | 53 | 16 | 43 | 53 | 15 | 54 | 26 | 10 | 23 |
| Cutoff 1 | 47600 | 68900 | 46200 | 51400 | 79100 | 49100 | 49100 | 66700 | 40700 |
| Sens 1 | 72% | 75% | 72% | 72% | 73% | 70% | 73% | 70% | 74% |
| Spec 1 | 31% | 49% | 29% | 36% | 57% | 32% | 33% | 49% | 21% |
| Cutoff 2 | 39400 | 46200 | 36700 | 43600 | 77900 | 41700 | 39400 | 42000 | 38300 |
| Sens 2 | 81% | 81% | 81% | 81% | 80% | 81% | 81% | 80% | 83% |
| Spec 2 | 21% | 26% | 18% | 27% | 55% | 22% | 21% | 23% | 19% |
| Cutoff 3 | 29600 | 20400 | 21400 | 25500 | 5890 | 25500 | 29100 | 25600 | 29100 |
| Sens 3 | 91% | 94% | 91% | 91% | 93% | 91% | 92% | 90% | 91% |
| Spec 3 | 10% | 4% | 6% | 7% | 2% | 6% | 8% | 7% | 7% |
| Cutoff 4 | 86800 | 99700 | 87900 | 86800 | 99700 | 87900 | 86800 | 99700 | 87900 |
| Sens 4 | 42% | 38% | 40% | 43% | 40% | 35% | 35% | 40% | 26% |
| Spec 4 | 70% | 70% | 70% | 70% | 70% | 70% | 70% | 70% | 70% |
| Cutoff 5 | 105000 | 113000 | 100000 | 105000 | 113000 | 100000 | 105000 | 113000 | 100000 |
| Sens 5 | 23% | 19% | 33% | 23% | 33% | 26% | 27% | 40% | 22% |
| Spec 5 | 80% | 80% | 80% | 80% | 80% | 80% | 80% | 80% | 80% |
| Cutoff 6 | 132000 | 133000 | 129000 | 132000 | 133000 | 129000 | 132000 | 133000 | 129000 |
| Sens 6 | 13% | 12% | 14% | 6% | 13% | 6% | 8% | 10% | 4% |
| Spec 6 | 90% | 90% | 90% | 90% | 90% | 90% | 90% | 90% | 90% |
| OR Quart 2 | 0.97 | 0.66 | 1.0 | 1.2 | 0.49 | 1.1 | 1.2 | 0.32 | 0.81 |
| p Value | 0.95 | 0.65 | 1.0 | 0.67 | 0.56 | 0.87 | 0.80 | 0.33 | 0.74 |
| 95% CI of | 0.38 | 0.11 | 0.38 | 0.47 | 0.043 | 0.43 | 0.35 | 0.033 | 0.22 |
| OR Quart2 | 2.5 | 4.1 | 2.6 | 3.3 | 5.5 | 2.7 | 3.9 | 3.1 | 2.9 |
| OR Quart 3 | 1.0 | 2.5 | 0.47 | 1.8 | 3.7 | 1.1 | 0.78 | 0.66 | 0.81 |
| p Value | 1.0 | 0.20 | 0.18 | 0.24 | 0.11 | 0.87 | 0.71 | 0.65 | 0.74 |
| 95% CI of | 0.39 | 0.61 | 0.16 | 0.69 | 0.74 | 0.43 | 0.22 | 0.11 | 0.22 |
| OR Quart3 | 2.6 | 9.9 | 1.4 | 4.6 | 18 | 2.7 | 2.8 | 4.1 | 2.9 |
| OR Quart 4 | 1.6 | 1.4 | 1.6 | 1.9 | 2.6 | 1.5 | 1.4 | 1.3 | 1.2 |
| p Value | 0.29 | 0.70 | 0.35 | 0.18 | 0.27 | 0.40 | 0.59 | 0.71 | 0.76 |
| 95% CI of | 0.66 | 0.29 | 0.62 | 0.74 | 0.48 | 0.60 | 0.43 | 0.29 | 0.36 |
| OR Quart4 | 4.0 | 6.3 | 4.0 | 4.8 | 14 | 3.6 | 4.5 | 6.2 | 4.0 |

| C-C motif chemokine 26 | | | | | | |
|---|---|---|---|---|---|---|
|  | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | 0.725 | 1.25 | 0.725 | 1.62 | 0.725 | 5.42 |
| Average | 12.8 | 5.27 | 12.8 | 8.50 | 12.8 | 11.0 |
| Stdev | 65.9 | 10.1 | 65.9 | 14.0 | 65.9 | 15.6 |
| p(t-test) |  | 0.45 |  | 0.68 |  | 0.91 |
| Min | 0.0121 | 0.0232 | 0.0121 | 0.0121 | 0.0121 | 0.0339 |
| Max | 468 | 55.4 | 468 | 51.1 | 468 | 53.5 |
| n (Samp) | 93 | 45 | 93 | 42 | 93 | 18 |
| n (Patient) | 64 | 45 | 64 | 42 | 64 | 18 |

|  | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 0.785 | 3.74 | 0.785 | 3.16 | 0.785 | 4.75 |
| Average | 8.23 | 7.35 | 8.23 | 11.6 | 8.23 | 12.3 |
| Stdev | 43.2 | 9.45 | 43.2 | 16.6 | 43.2 | 18.3 |

-continued

|  | 0 hr prior to AKI stage | | 0 hr prior to AKI stage | | 24 hr prior to AKI stage | | 24 hr prior to AKI stage | | 48 hr prior to AKI stage | | 48 hr prior to AKI stage | |
|---|---|---|---|---|---|---|---|---|---|---|---|---|
| p(t-test) |  | 0.94 |  |  |  | 0.74 |  |  |  | 0.78 |  |  |
| Min | 0.0121 | 0.0121 |  |  | 0.0121 | 0.0232 |  |  | 0.0121 | 0.0121 |  |  |
| Max | 468 | 29.4 |  |  | 468 | 51.1 |  |  | 468 | 50.9 |  |  |
| n (Samp) | 224 | 14 |  |  | 224 | 18 |  |  | 224 | 9 |  |  |
| n (Patient) | 131 | 14 |  |  | 131 | 18 |  |  | 131 | 9 |  |  |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.0587 | 0.725 | 0.0587 | 1.48 | 0.0587 | 5.00 |
| Average | 12.3 | 3.90 | 12.3 | 6.69 | 12.3 | 8.29 |
| Stdev | 63.1 | 9.51 | 63.1 | 11.4 | 63.1 | 13.5 |
| p(t-test) |  | 0.42 |  | 0.57 |  | 0.81 |
| Min | 0.0121 | 0.0232 | 0.0121 | 0.0121 | 0.0121 | 0.0325 |
| Max | 468 | 55.4 | 468 | 46.1 | 468 | 53.5 |
| n (Samp) | 102 | 37 | 102 | 41 | 102 | 15 |
| n (Patient) | 63 | 37 | 63 | 41 | 63 | 15 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.56 | 0.60 | 0.55 | 0.60 | 0.68 | 0.58 | 0.76 | 0.64 | 0.68 |
| SE | 0.053 | 0.082 | 0.056 | 0.054 | 0.072 | 0.054 | 0.070 | 0.10 | 0.080 |
| p | 0.23 | 0.25 | 0.41 | 0.068 | 0.015 | 0.14 | 2.3E-4 | 0.17 | 0.029 |
| nCohort 1 | 93 | 224 | 102 | 93 | 224 | 102 | 93 | 224 | 102 |
| nCohort 2 | 45 | 14 | 37 | 42 | 18 | 41 | 18 | 9 | 15 |
| Cutoff 1 | 0.0339 | 0.0503 | 0.0339 | 0.0339 | 1.25 | 0.0339 | 4.62 | 0.0503 | 0.0587 |
| Sens 1 | 82% | 71% | 81% | 81% | 72% | 73% | 72% | 78% | 73% |
| Spec 1 | 25% | 41% | 27% | 25% | 56% | 27% | 80% | 41% | 51% |
| Cutoff 2 | 0.0339 | 0.0232 | 0.0339 | 0.0339 | 0.652 | 0.0325 | 1.84 | 0.0339 | 0.0339 |
| Sens 2 | 82% | 93% | 81% | 81% | 83% | 85% | 83% | 89% | 80% |
| Spec 2 | 25% | 4% | 27% | 25% | 47% | 25% | 67% | 25% | 27% |
| Cutoff 3 | 0.0232 | 0.0232 | 0.0232 | 0.0232 | 0.0339 | 0.0232 | 0.0325 | 0 | 0.0325 |
| Sens 3 | 98% | 93% | 97% | 93% | 94% | 93% | 100% | 100% | 93% |
| Spec 3 | 5% | 4% | 5% | 5% | 25% | 5% | 22% | 0% | 25% |
| Cutoff 4 | 2.43 | 3.90 | 2.43 | 2.43 | 3.90 | 2.43 | 2.43 | 3.90 | 2.43 |
| Sens 4 | 36% | 50% | 27% | 43% | 44% | 44% | 78% | 56% | 67% |
| Spec 4 | 71% | 70% | 72% | 71% | 70% | 72% | 71% | 70% | 72% |
| Cutoff 5 | 5.00 | 6.86 | 5.00 | 5.00 | 6.86 | 5.00 | 5.00 | 6.86 | 5.00 |
| Sens 5 | 29% | 43% | 19% | 31% | 33% | 32% | 50% | 33% | 40% |
| Spec 5 | 83% | 81% | 82% | 83% | 81% | 82% | 83% | 81% | 82% |
| Cutoff 6 | 10.6 | 10.7 | 13.4 | 10.6 | 10.7 | 13.4 | 10.6 | 10.7 | 13.4 |
| Sens 6 | 13% | 21% | 5% | 24% | 28% | 15% | 28% | 33% | 13% |
| Spec 6 | 91% | 90% | 90% | 91% | 90% | 90% | 91% | 90% | 90% |
| OR Quart 2 | 1.4 | 0.64 | 1.1 | 1.1 | 0.98 | 1.5 | 0.46 | 2.0 | 1.6 |
| p Value | 0.48 | 0.64 | 0.82 | 0.83 | 0.99 | 0.44 | 0.54 | 0.57 | 0.64 |
| 95% CI of | 0.52 | 0.10 | 0.36 | 0.37 | 0.13 | 0.51 | 0.039 | 0.18 | 0.24 |
| OR Quart2 | 4.1 | 4.0 | 3.6 | 3.4 | 7.2 | 4.6 | 5.4 | 23 | 10 |
| OR Quart 3 | 1.0 | 0.65 | 2.3 | 1.5 | 3.2 | 1.3 | 2.7 | 2.0 | 0.48 |
| p Value | 1.0 | 0.65 | 0.13 | 0.46 | 0.16 | 0.61 | 0.26 | 0.57 | 0.56 |
| 95% CI of | 0.34 | 0.11 | 0.78 | 0.51 | 0.62 | 0.43 | 0.48 | 0.18 | 0.041 |
| OR Quart3 | 2.9 | 4.1 | 6.7 | 4.4 | 17 | 4.1 | 15 | 23 | 5.6 |
| OR Quart 4 | 2.1 | 2.5 | 1.3 | 2.2 | 4.4 | 2.9 | 6.9 | 4.1 | 5.8 |
| p Value | 0.16 | 0.21 | 0.61 | 0.14 | 0.069 | 0.052 | 0.020 | 0.21 | 0.035 |
| 95% CI of | 0.76 | 0.61 | 0.43 | 0.77 | 0.89 | 0.99 | 1.4 | 0.45 | 1.1 |
| OR Quart4 | 5.7 | 10 | 4.1 | 6.2 | 22 | 8.3 | 36 | 38 | 30 |

C-C motif chemokine 7

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.620 | 0.512 | 0.620 | 0.804 | 0.620 | 0.512 |
| Average | 8.13 | 7.46 | 8.13 | 10.4 | 8.13 | 12.7 |
| Stdev | 22.1 | 14.3 | 22.1 | 15.1 | 22.1 | 21.1 |
| p(t-test) |  | 0.85 |  | 0.55 |  | 0.42 |
| Min | 0.193 | 0.193 | 0.193 | 0.193 | 0.193 | 0.193 |
| Max | 128 | 79.4 | 128 | 60.8 | 128 | 75.6 |
| n (Samp) | 94 | 45 | 94 | 42 | 94 | 18 |
| n (Patient) | 65 | 45 | 65 | 42 | 65 | 18 |

-continued

| sCr only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 0.620 | 0.712 | 0.620 | 0.620 | 0.620 | 0.512 |
| Average | 9.35 | 5.26 | 9.35 | 23.9 | 9.35 | 11.1 |
| Stdev | 24.0 | 8.50 | 24.0 | 54.7 | 24.0 | 25.1 |
| p(t-test) | | 0.53 | | 0.031 | | 0.83 |
| Min | 0.193 | 0.193 | 0.193 | 0.193 | 0.193 | 0.193 |
| Max | 181 | 26.1 | 181 | 219 | 181 | 75.6 |
| n (Samp) | 225 | 14 | 225 | 18 | 225 | 9 |
| n (Patient) | 132 | 14 | 132 | 18 | 132 | 9 |

| UO only | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 0.620 | 0.512 | 0.620 | 0.804 | 0.620 | 0.512 |
| Average | 6.86 | 7.17 | 6.86 | 11.9 | 6.86 | 8.74 |
| Stdev | 20.9 | 15.2 | 20.9 | 17.6 | 20.9 | 15.0 |
| p(t-test) | | 0.93 | | 0.18 | | 0.74 |
| Min | 0.193 | 0.193 | 0.193 | 0.193 | 0.193 | 0.193 |
| Max | 128 | 79.4 | 128 | 67.3 | 128 | 48.7 |
| n (Samp) | 103 | 37 | 103 | 41 | 103 | 15 |
| n (Patient) | 64 | 37 | 64 | 41 | 64 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.49 | 0.50 | 0.50 | 0.58 | 0.52 | 0.64 | 0.57 | 0.49 | 0.57 |
| SE | 0.053 | 0.080 | 0.056 | 0.054 | 0.072 | 0.053 | 0.076 | 0.099 | 0.082 |
| p | 0.87 | 0.95 | 0.95 | 0.16 | 0.73 | 0.010 | 0.34 | 0.90 | 0.40 |
| nCohort 1 | 94 | 225 | 103 | 94 | 225 | 103 | 94 | 225 | 103 |
| nCohort 2 | 45 | 14 | 37 | 42 | 18 | 41 | 18 | 9 | 15 |
| Cutoff 1 | 0.193 | 0.308 | 0.193 | 0.193 | 0.193 | 0.308 | 0.308 | 0.308 | 0.308 |
| Sens 1 | 76% | 71% | 76% | 88% | 78% | 80% | 94% | 78% | 87% |
| Spec 1 | 18% | 30% | 20% | 18% | 19% | 38% | 34% | 30% | 38% |
| Cutoff 2 | 0 | 0.193 | 0 | 0.193 | 0 | 0.308 | 0.308 | 0.193 | 0.308 |
| Sens 2 | 100% | 86% | 100% | 88% | 100% | 80% | 94% | 89% | 87% |
| Spec 2 | 0% | 19% | 0% | 18% | 0% | 38% | 34% | 19% | 38% |
| Cutoff 3 | 0 | 0 | 0 | 0 | 0 | 0.193 | 0.308 | 0 | 0.193 |
| Sens 3 | 100% | 100% | 100% | 100% | 100% | 93% | 94% | 100% | 93% |
| Spec 3 | 0% | 0% | 0% | 0% | 0% | 20% | 34% | 0% | 20% |
| Cutoff 4 | 0.804 | 2.71 | 0.804 | 0.804 | 2.71 | 0.804 | 0.804 | 2.71 | 0.804 |
| Sens 4 | 36% | 29% | 32% | 45% | 44% | 46% | 39% | 22% | 33% |
| Spec 4 | 70% | 70% | 75% | 70% | 70% | 75% | 70% | 70% | 75% |
| Cutoff 5 | 8.42 | 9.52 | 5.10 | 8.42 | 9.52 | 5.10 | 8.42 | 9.52 | 5.10 |
| Sens 5 | 31% | 29% | 27% | 38% | 39% | 41% | 33% | 22% | 33% |
| Spec 5 | 84% | 80% | 81% | 84% | 80% | 81% | 84% | 80% | 81% |
| Cutoff 6 | 19.2 | 28.8 | 14.4 | 19.2 | 28.8 | 14.4 | 19.2 | 28.8 | 14.4 |
| Sens 6 | 13% | 0% | 16% | 21% | 17% | 29% | 28% | 11% | 20% |
| Spec 6 | 90% | 90% | 90% | 90% | 90% | 90% | 90% | 90% | 90% |
| OR Quart 2 | 0.38 | 0.72 | 0.45 | 0.86 | 1.5 | 1.2 | 15 | 1.0 | 8.5 |
| p Value | 0.072 | 0.68 | 0.17 | 0.79 | 0.53 | 0.78 | 0.013 | 0.99 | 0.053 |
| 95% CI of | 0.13 | 0.15 | 0.15 | 0.30 | 0.41 | 0.39 | 1.8 | 0.14 | 0.98 |
| OR Quart2 | 1.1 | 3.4 | 1.4 | 2.5 | 5.7 | 3.5 | 130 | 7.5 | 74 |
| OR Quart 3 | 0.69 | 0.72 | 0.55 | 0.62 | 0.23 | 1.0 | 0 | 1.5 | 2.1 |
| p Value | 0.46 | 0.68 | 0.28 | 0.40 | 0.20 | 1.0 | na | 0.65 | 0.56 |
| 95% CI of | 0.26 | 0.15 | 0.18 | 0.20 | 0.025 | 0.33 | na | 0.25 | 0.18 |
| OR Quart3 | 1.8 | 3.4 | 1.6 | 1.9 | 2.2 | 3.0 | na | 9.5 | 24 |
| OR Quart 4 | 0.93 | 0.98 | 1.3 | 2.1 | 1.8 | 2.8 | 9.0 | 1.0 | 5.6 |
| p Value | 0.88 | 0.98 | 0.61 | 0.14 | 0.36 | 0.049 | 0.047 | 0.99 | 0.13 |
| 95% CI of | 0.35 | 0.23 | 0.48 | 0.79 | 0.50 | 1.0 | 1.0 | 0.14 | 0.61 |
| OR Quart4 | 2.4 | 4.1 | 3.5 | 5.8 | 6.6 | 7.8 | 79 | 7.5 | 51 |

Thyrotropin

| sCr or UO | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 1.37 | 1.65 | 1.37 | 1.55 | 1.37 | 1.52 |
| Average | 2.10 | 3.14 | 2.10 | 2.51 | 2.10 | 2.57 |
| Stdev | 2.10 | 4.63 | 2.10 | 2.75 | 2.10 | 3.77 |
| p(t-test) | | 0.092 | | 0.35 | | 0.42 |

-continued

|  | | | | | | |
|---|---|---|---|---|---|---|
| Min | 0.0304 | 0.0228 | 0.0304 | 0.174 | 0.0304 | 0.101 |
| Max | 9.94 | 20.0 | 9.94 | 12.1 | 9.94 | 14.7 |
| n (Samp) | 85 | 35 | 85 | 42 | 85 | 25 |
| n (Patient) | 75 | 35 | 75 | 42 | 75 | 25 |

|  | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 1.55 | 2.14 | 1.55 | 1.82 | 1.55 | 1.36 |
| Average | 3.21 | 3.62 | 3.21 | 2.43 | 3.21 | 1.69 |
| Stdev | 5.66 | 5.87 | 5.66 | 2.33 | 5.66 | 1.27 |
| p(t-test) |  | 0.82 |  | 0.65 |  | 0.45 |
| Min | 0.0304 | 0.0228 | 0.0304 | 0.244 | 0.0304 | 0.101 |
| Max | 60.1 | 20.0 | 60.1 | 8.20 | 60.1 | 3.88 |
| n (Samp) | 201 | 10 | 201 | 11 | 201 | 8 |
| n (Patient) | 132 | 10 | 132 | 11 | 132 | 8 |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 1.37 | 1.65 | 1.37 | 1.40 | 1.37 | 1.16 |
| Average | 2.63 | 2.84 | 2.63 | 2.61 | 2.63 | 2.64 |
| Stdev | 3.37 | 3.87 | 3.37 | 2.99 | 3.37 | 4.07 |
| p(t-test) |  | 0.79 |  | 0.97 |  | 0.99 |
| Min | 0.0304 | 0.0956 | 0.0304 | 0.174 | 0.0304 | 0.106 |
| Max | 20.0 | 19.8 | 20.0 | 12.1 | 20.0 | 14.7 |
| n (Samp) | 77 | 29 | 77 | 43 | 77 | 21 |
| n (Patient) | 64 | 29 | 64 | 43 | 64 | 21 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.53 | 0.52 | 0.52 | 0.53 | 0.52 | 0.51 | 0.49 | 0.47 | 0.47 |
| SE | 0.059 | 0.095 | 0.063 | 0.055 | 0.091 | 0.055 | 0.066 | 0.11 | 0.072 |
| p | 0.57 | 0.80 | 0.78 | 0.57 | 0.80 | 0.84 | 0.91 | 0.75 | 0.64 |
| nCohort 1 | 85 | 201 | 77 | 85 | 201 | 77 | 85 | 201 | 77 |
| nCohort 2 | 35 | 10 | 29 | 42 | 11 | 43 | 25 | 8 | 21 |
| Cutoff 1 | 0.568 | 1.25 | 0.568 | 0.785 | 1.25 | 0.785 | 0.714 | 1.13 | 0.714 |
| Sens 1 | 71% | 70% | 72% | 71% | 73% | 72% | 72% | 75% | 71% |
| Spec 1 | 26% | 45% | 26% | 33% | 45% | 35% | 29% | 43% | 30% |
| Cutoff 2 | 0.395 | 1.00 | 0.383 | 0.463 | 0.645 | 0.463 | 0.463 | 0.787 | 0.463 |
| Sens 2 | 80% | 80% | 83% | 81% | 82% | 81% | 80% | 88% | 81% |
| Spec 2 | 20% | 39% | 18% | 22% | 28% | 23% | 22% | 34% | 23% |
| Cutoff 3 | 0.268 | 0.380 | 0.268 | 0.395 | 0.418 | 0.341 | 0.106 | 0.0956 | 0.216 |
| Sens 3 | 91% | 90% | 93% | 90% | 91% | 91% | 92% | 100% | 90% |
| Spec 3 | 13% | 16% | 12% | 20% | 18% | 16% | 6% | 3% | 10% |
| Cutoff 4 | 2.84 | 3.09 | 3.18 | 2.84 | 3.09 | 3.18 | 2.84 | 3.09 | 3.18 |
| Sens 4 | 34% | 20% | 24% | 29% | 27% | 28% | 24% | 25% | 19% |
| Spec 4 | 71% | 70% | 70% | 71% | 70% | 70% | 71% | 70% | 70% |
| Cutoff 5 | 3.68 | 4.30 | 3.82 | 3.68 | 4.30 | 3.82 | 3.68 | 4.30 | 3.82 |
| Sens 5 | 26% | 10% | 24% | 21% | 18% | 23% | 20% | 0% | 19% |
| Spec 5 | 80% | 80% | 81% | 80% | 80% | 81% | 80% | 80% | 81% |
| Cutoff 6 | 4.63 | 7.46 | 6.31 | 4.63 | 7.46 | 6.31 | 4.63 | 7.46 | 6.31 |
| Sens 6 | 14% | 10% | 10% | 17% | 9% | 14% | 8% | 0% | 10% |
| Spec 6 | 91% | 90% | 91% | 91% | 90% | 91% | 91% | 90% | 91% |
| OR Quart | 20.71 | 0.98 | 0.78 | 1.3 | 1.5 | 1.2 | 1.3 | 3.2 | 1.8 |
| p Value | 0.56 | 0.98 | 0.69 | 0.65 | 0.65 | 0.79 | 0.70 | 0.32 | 0.44 |
| 95% CI of | 0.22 | 0.13 | 0.22 | 0.44 | 0.25 | 0.40 | 0.37 | 0.32 | 0.43 |
| OR Quart2 | 2.2 | 7.2 | 2.7 | 3.7 | 9.5 | 3.3 | 4.5 | 32 | 7.2 |
| OR Quart 3 | 1.2 | 2.0 | 1.4 | 1.3 | 2.1 | 1.3 | 1.0 | 3.2 | 1.7 |
| p Value | 0.78 | 0.42 | 0.55 | 0.65 | 0.41 | 0.59 | 1.0 | 0.32 | 0.48 |
| 95% CI of | 0.39 | 0.36 | 0.44 | 0.44 | 0.36 | 0.46 | 0.28 | 0.32 | 0.41 |
| OR Quart3 | 3.5 | 12 | 4.7 | 3.7 | 12 | 3.8 | 3.6 | 32 | 6.8 |
| OR Quart 4 | 1.0 | 0.98 | 0.95 | 1.3 | 1.0 | 1.0 | 1.0 | 1.0 | 1.4 |
| p Value | 1.0 | 0.98 | 0.93 | 0.65 | 1.0 | 1.0 | 0.94 | 0.99 | 0.66 |
| 95% CI of | 0.33 | 0.13 | 0.28 | 0.44 | 0.14 | 0.34 | 0.29 | 0.062 | 0.32 |
| OR Quart4 | 3.0 | 7.2 | 3.2 | 3.7 | 7.4 | 2.9 | 3.8 | 17 | 5.9 |

Vascular endothelial growth factor receptor 3

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 5470 | 5330 | 5470 | 5760 | 5470 | 6250 |
| Average | 6870 | 8430 | 6870 | 7300 | 6870 | 6400 |

-continued

|  | | | | | | |
|---|---|---|---|---|---|---|
| Stdev | 5340 | 7900 | 5340 | 5490 | 5340 | 2520 |
| p(t-test) |  | 0.17 |  | 0.66 |  | 0.72 |
| Min | 219 | 1360 | 219 | 1000 | 219 | 2840 |
| Max | 29400 | 43200 | 29400 | 26900 | 29400 | 12100 |
| n (Samp) | 94 | 45 | 94 | 42 | 94 | 18 |
| n (Patient) | 65 | 45 | 65 | 42 | 65 | 18 |

|  | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 6210 | 5870 | 6210 | 5070 | 6210 | 3710 |
| Average | 7000 | 8490 | 7000 | 7680 | 7000 | 4330 |
| Stdev | 5110 | 7420 | 5110 | 6800 | 5110 | 2310 |
| p(t-test) |  | 0.30 |  | 0.60 |  | 0.12 |
| Min | 219 | 4080 | 219 | 1280 | 219 | 1030 |
| Max | 43200 | 32800 | 43200 | 26900 | 43200 | 8610 |
| n (Samp) | 225 | 14 | 225 | 18 | 225 | 9 |
| n (Patient) | 132 | 14 | 132 | 18 | 132 | 9 |

|  | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 5640 | 5240 | 5640 | 5950 | 5640 | 6330 |
| Average | 7340 | 7870 | 7340 | 6590 | 7340 | 6900 |
| Stdev | 6250 | 7620 | 6250 | 4150 | 6250 | 2300 |
| p(t-test) |  | 0.68 |  | 0.48 |  | 0.78 |
| Min | 219 | 1360 | 219 | 924 | 219 | 2840 |
| Max | 32800 | 43200 | 32800 | 16600 | 32800 | 12100 |
| n (Samp) | 103 | 37 | 103 | 41 | 103 | 15 |
| n (Patient) | 64 | 37 | 64 | 41 | 64 | 15 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.56 | 0.56 | 0.51 | 0.52 | 0.48 | 0.49 | 0.54 | 0.32 | 0.58 |
| SE | 0.053 | 0.082 | 0.056 | 0.054 | 0.072 | 0.054 | 0.076 | 0.10 | 0.082 |
| p | 0.24 | 0.47 | 0.83 | 0.74 | 0.80 | 0.85 | 0.57 | 0.074 | 0.32 |
| nCohort 1 | 94 | 225 | 103 | 94 | 225 | 103 | 94 | 225 | 103 |
| nCohort 2 | 45 | 14 | 37 | 42 | 18 | 41 | 18 | 9 | 15 |
| Cutoff 1 | 4260 | 5140 | 4160 | 3490 | 4050 | 3400 | 4580 | 3020 | 5450 |
| Sens 1 | 71% | 71% | 70% | 71% | 72% | 71% | 72% | 78% | 73% |
| Spec 1 | 35% | 40% | 29% | 27% | 31% | 22% | 38% | 17% | 49% |
| Cutoff 2 | 3620 | 4120 | 3440 | 2930 | 3440 | 2580 | 3700 | 3010 | 5360 |
| Sens 2 | 80% | 86% | 81% | 81% | 83% | 80% | 83% | 89% | 80% |
| Spec 2 | 30% | 31% | 22% | 18% | 23% | 12% | 32% | 17% | 49% |
| Cutoff 3 | 2930 | 4080 | 2580 | 2070 | 1720 | 1720 | 2930 | 1010 | 4530 |
| Sens 3 | 91% | 93% | 92% | 90% | 94% | 90% | 94% | 100% | 93% |
| Spec 3 | 18% | 31% | 12% | 11% | 7% | 7% | 18% | 4% | 31% |
| Cutoff 4 | 7770 | 8350 | 7770 | 7770 | 8350 | 7770 | 7770 | 8350 | 7770 |
| Sens 4 | 40% | 29% | 35% | 38% | 22% | 37% | 28% | 11% | 33% |
| Spec 4 | 70% | 71% | 71% | 70% | 71% | 71% | 70% | 71% | 71% |
| Cutoff 5 | 9000 | 9630 | 8980 | 9000 | 9630 | 8980 | 9000 | 9630 | 8980 |
| Sens 5 | 27% | 21% | 24% | 31% | 22% | 32% | 11% | 0% | 13% |
| Spec 5 | 81% | 80% | 81% | 81% | 80% | 81% | 81% | 80% | 81% |
| Cutoff 6 | 13200 | 11800 | 13800 | 13200 | 11800 | 13800 | 13200 | 11800 | 13800 |
| Sens 6 | 11% | 7% | 11% | 10% | 17% | 5% | 0% | 0% | 0% |
| Spec 6 | 90% | 90% | 90% | 90% | 90% | 90% | 90% | 90% | 90% |
| OR Quart | 22.4 | >7.8 | 1.3 | 1.1 | 0.74 | 0.51 | 1.8 | >2.1 | 4.3 |
| p Value | 0.092 | <0.059 | 0.60 | 0.79 | 0.70 | 0.20 | 0.45 | <0.55 | 0.20 |
| 95% CI of | 0.86 | >0.93 | 0.47 | 0.41 | 0.16 | 0.18 | 0.39 | >0.19 | 0.45 |
| OR Quart2 | 6.9 | na | 3.8 | 3.2 | 3.4 | 1.4 | 8.4 | na | 41 |
| OR Quart | 30.81 | >4.2 | 0.48 | 0.74 | 1.8 | 0.43 | 2.3 | >3.2 | 8.9 |
| p Value | 0.72 | <0.20 | 0.24 | 0.58 | 0.35 | 0.12 | 0.28 | <0.33 | 0.048 |
| 95% CI of | 0.26 | >0.46 | 0.14 | 0.25 | 0.51 | 0.15 | 0.51 | >0.32 | 1.0 |
| OR Quart3 | 2.6 | na | 1.6 | 2.2 | 6.7 | 1.2 | 10 | na | 78 |
| OR Quart | 42.4 | >3.1 | 1.5 | 1.5 | 1.0 | 1.0 | 1.4 | >4.4 | 3.1 |
| p Value | 0.092 | <0.33 | 0.44 | 0.44 | 0.98 | 1.0 | 0.69 | <0.19 | 0.34 |
| 95% CI of | 0.86 | >0.31 | 0.54 | 0.54 | 0.24 | 0.38 | 0.28 | >0.47 | 0.30 |
| OR Quart4 | 6.9 | na | 4.2 | 4.1 | 4.3 | 2.6 | 6.9 | na | 32 |

-continued

| | Interferon alpha-2 | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | 9.44 | 17.2 | 9.44 | 13.4 | 9.44 | 23.0 |
| Average | 17.1 | 19.3 | 17.1 | 16.9 | 17.1 | 22.5 |
| Stdev | 29.3 | 19.4 | 29.3 | 16.2 | 29.3 | 10.6 |
| p(t-test) | | 0.64 | | 0.97 | | 0.44 |
| Min | 0.0320 | 0.0627 | 0.0320 | 0.0320 | 0.0320 | 0.0627 |
| Max | 223 | 108 | 223 | 67.7 | 223 | 44.7 |
| n (Samp) | 94 | 45 | 94 | 42 | 94 | 18 |
| n (Patient) | 65 | 45 | 65 | 42 | 65 | 18 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 13.5 | 10.2 | 13.5 | 11.2 | 13.5 | 11.8 |
| Average | 18.1 | 17.0 | 18.1 | 23.4 | 18.1 | 15.4 |
| Stdev | 24.6 | 27.7 | 24.6 | 39.4 | 24.6 | 10.2 |
| p(t-test) | | 0.87 | | 0.40 | | 0.74 |
| Min | 0.0320 | 0.0627 | 0.0320 | 0.0320 | 0.0320 | 5.14 |
| Max | 223 | 108 | 223 | 163 | 223 | 35.3 |
| n (Samp) | 225 | 14 | 225 | 18 | 225 | 9 |
| n (Patient) | 132 | 14 | 132 | 18 | 132 | 9 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 7.03 | 17.2 | 7.03 | 13.5 | 7.03 | 24.2 |
| Average | 15.4 | 18.8 | 15.4 | 17.0 | 15.4 | 22.0 |
| Stdev | 29.5 | 14.7 | 29.5 | 14.9 | 29.5 | 12.8 |
| p(t-test) | | 0.50 | | 0.74 | | 0.39 |
| Min | 0.0320 | 0.0627 | 0.0320 | 0.0320 | 0.0320 | 0.0627 |
| Max | 223 | 49.9 | 223 | 52.4 | 223 | 44.7 |
| n (Samp) | 103 | 37 | 103 | 41 | 103 | 15 |
| n (Patient) | 64 | 37 | 64 | 41 | 64 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.58 | 0.46 | 0.64 | 0.54 | 0.46 | 0.61 | 0.71 | 0.54 | 0.73 |
| SE | 0.053 | 0.081 | 0.055 | 0.054 | 0.072 | 0.054 | 0.073 | 0.10 | 0.078 |
| p | 0.13 | 0.60 | 0.013 | 0.43 | 0.59 | 0.041 | 0.0036 | 0.71 | 0.0035 |
| nCohort 1 | 94 | 225 | 103 | 94 | 225 | 103 | 94 | 225 | 103 |
| nCohort 2 | 45 | 14 | 37 | 42 | 18 | 41 | 18 | 9 | 15 |
| Cutoff 1 | 5.80 | 4.47 | 6.46 | 3.73 | 0.0324 | 7.03 | 19.0 | 7.76 | 19.0 |
| Sens 1 | 71% | 71% | 70% | 71% | 89% | 71% | 72% | 78% | 73% |
| Spec 1 | 40% | 33% | 49% | 33% | 2% | 50% | 70% | 40% | 77% |
| Cutoff 2 | 3.73 | 0.0764 | 3.73 | 0.0627 | 0.0324 | 0.0997 | 13.5 | 5.98 | 13.5 |
| Sens 2 | 80% | 93% | 81% | 86% | 89% | 80% | 83% | 89% | 80% |
| Spec 2 | 33% | 17% | 38% | 16% | 2% | 27% | 60% | 37% | 65% |
| Cutoff 3 | 0.0324 | 0.0764 | 0.0324 | 0.0324 | 0.0320 | 0.0627 | 5.80 | 4.65 | 0.0627 |
| Sens 3 | 100% | 93% | 100% | 95% | 94% | 93% | 94% | 100% | 93% |
| Spec 3 | 2% | 17% | 2% | 2% | 1% | 17% | 40% | 34% | 17% |
| Cutoff 4 | 19.0 | 23.2 | 14.8 | 19.0 | 23.2 | 14.8 | 19.0 | 23.2 | 14.8 |
| Sens 4 | 42% | 14% | 62% | 38% | 28% | 49% | 72% | 22% | 73% |
| Spec 4 | 70% | 71% | 71% | 70% | 71% | 71% | 70% | 71% | 71% |
| Cutoff 5 | 26.9 | 29.0 | 20.8 | 26.9 | 29.0 | 20.8 | 26.9 | 29.0 | 20.8 |
| Sens 5 | 27% | 14% | 41% | 26% | 28% | 37% | 28% | 11% | 67% |
| Spec 5 | 81% | 80% | 82% | 81% | 80% | 82% | 81% | 80% | 82% |
| Cutoff 6 | 36.4 | 39.9 | 29.4 | 36.4 | 39.9 | 29.4 | 36.4 | 39.9 | 29.4 |
| Sens 6 | 18% | 7% | 24% | 10% | 11% | 20% | 6% | 0% | 33% |
| Spec 6 | 90% | 90% | 90% | 90% | 90% | 90% | 90% | 90% | 90% |
| OR Quart | 20.96 | 2.1 | 0.83 | 0.74 | 0.58 | 1.0 | 2.1 | >5.4 | 0.47 |
| p Value | 0.94 | 0.41 | 0.76 | 0.58 | 0.47 | 1.0 | 0.56 | <0.13 | 0.54 |
| 95% CI of | 0.33 | 0.36 | 0.25 | 0.25 | 0.13 | 0.33 | 0.18 | >0.61 | 0.040 |
| OR Quart2 | 2.8 | 12 | 2.8 | 2.2 | 2.5 | 3.0 | 24 | na | 5.4 |
| OR Quart 3 | 1.6 | 2.1 | 1.4 | 1.3 | 0.79 | 1.2 | 9.0 | >3.2 | 1.0 |
| p Value | 0.34 | 0.41 | 0.57 | 0.60 | 0.73 | 0.78 | 0.047 | <0.32 | 1.0 |
| 95% CI of | 0.59 | 0.36 | 0.45 | 0.47 | 0.20 | 0.39 | 1.0 | >0.32 | 0.13 |
| OR Quart3 | 4.6 | 12 | 4.3 | 3.6 | 3.1 | 3.5 | 79 | na | 7.6 |

-continued

| | | | | | | | | | |
|---|---|---|---|---|---|---|---|---|---|
| OR Quart 4 | 1.9 | 2.1 | 3.0 | 1.3 | 1.2 | 2.8 | 11 | >1.0 | 6.8 |
| p Value | 0.24 | 0.40 | 0.043 | 0.60 | 0.73 | 0.049 | 0.031 | <1.0 | 0.021 |
| 95% CI of | 0.67 | 0.37 | 1.0 | 0.47 | 0.36 | 1.0 | 1.2 | >0.061 | 1.3 |
| OR Quart4 | 5.1 | 12 | 8.7 | 3.6 | 4.3 | 7.8 | 93 | na | 34 |

Insulin-like growth factor-binding protein 4

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 2.93 | 3.18 | 2.93 | 2.93 | 2.93 | 2.93 |
| Average | 14.5 | 13.6 | 14.5 | 10.9 | 14.5 | 6.68 |
| Stdev | 26.1 | 14.8 | 26.1 | 12.5 | 26.1 | 7.82 |
| p(t-test) | | 0.82 | | 0.35 | | 0.14 |
| Min | 0.0862 | 0.572 | 0.0862 | 0.572 | 0.0862 | 0.572 |
| Max | 158 | 57.3 | 158 | 52.0 | 158 | 24.1 |
| n (Samp) | 119 | 52 | 119 | 53 | 119 | 26 |
| n (Patient) | 87 | 52 | 87 | 53 | 87 | 26 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 2.93 | 8.11 | 2.93 | 2.93 | 2.93 | 2.93 |
| Average | 12.8 | 13.3 | 12.8 | 13.1 | 12.8 | 10.2 |
| Stdev | 19.6 | 13.6 | 19.6 | 15.9 | 19.6 | 11.9 |
| p(t-test) | | 0.92 | | 0.95 | | 0.68 |
| Min | 0.0862 | 0.572 | 0.0862 | 0.572 | 0.0862 | 0.572 |
| Max | 158 | 46.7 | 158 | 52.0 | 158 | 30.5 |
| n (Samp) | 283 | 16 | 283 | 14 | 283 | 10 |
| n (Patient) | 161 | 16 | 161 | 14 | 161 | 10 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 3.29 | 3.18 | 3.29 | 2.93 | 3.29 | 2.93 |
| Average | 15.0 | 13.6 | 15.0 | 9.49 | 15.0 | 6.86 |
| Stdev | 25.6 | 14.9 | 25.6 | 10.6 | 25.6 | 7.85 |
| p(t-test) | | 0.74 | | 0.13 | | 0.13 |
| Min | 0.0728 | 0.572 | 0.0728 | 0.572 | 0.0728 | 0.572 |
| Max | 158 | 57.3 | 158 | 33.5 | 158 | 21.7 |
| n (Samp) | 123 | 42 | 123 | 54 | 123 | 23 |
| n (Patient) | 80 | 42 | 80 | 54 | 80 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.57 | 0.55 | 0.55 | 0.52 | 0.54 | 0.48 | 0.50 | 0.53 | 0.45 |
| SE | 0.048 | 0.076 | 0.052 | 0.048 | 0.081 | 0.047 | 0.063 | 0.095 | 0.067 |
| p | 0.16 | 0.52 | 0.30 | 0.68 | 0.66 | 0.69 | 0.95 | 0.76 | 0.42 |
| nCohort 1 | 119 | 283 | 123 | 119 | 283 | 123 | 119 | 283 | 123 |
| nCohort 2 | 52 | 16 | 42 | 53 | 14 | 54 | 26 | 10 | 23 |
| Cutoff 1 | 0.971 | 0.971 | 0.971 | 0.971 | 0.971 | 0.971 | 0.971 | 2.43 | 0.572 |
| Sens 1 | 79% | 81% | 81% | 72% | 86% | 72% | 77% | 70% | 87% |
| Spec 1 | 36% | 29% | 33% | 36% | 29% | 33% | 36% | 41% | 15% |
| Cutoff 2 | 0.572 | 0.971 | 0.971 | 0.572 | 0.971 | 0.572 | 0.572 | 0.971 | 0.572 |
| Sens 2 | 88% | 81% | 81% | 83% | 86% | 83% | 92% | 90% | 87% |
| Spec 2 | 16% | 29% | 33% | 16% | 29% | 15% | 16% | 29% | 15% |
| Cutoff 3 | 0.0862 | 0.0862 | 0.572 | 0.0862 | 0.0862 | 0.0862 | 0.572 | 0.971 | 0.0862 |
| Sens 3 | 100% | 100% | 90% | 100% | 100% | 100% | 92% | 90% | 100% |
| Spec 3 | 1% | 0% | 15% | 1% | 0% | 2% | 16% | 29% | 2% |
| Cutoff 4 | 14.4 | 17.1 | 16.6 | 14.4 | 17.1 | 16.6 | 14.4 | 17.1 | 16.6 |
| Sens 4 | 40% | 38% | 43% | 28% | 29% | 22% | 23% | 30% | 17% |
| Spec 4 | 71% | 70% | 72% | 71% | 70% | 72% | 71% | 70% | 72% |
| Cutoff 5 | 23.1 | 23.1 | 23.1 | 23.1 | 23.1 | 23.1 | 23.1 | 23.1 | 23.1 |
| Sens 5 | 25% | 31% | 24% | 21% | 29% | 17% | 4% | 30% | 0% |
| Spec 5 | 81% | 81% | 80% | 81% | 81% | 80% | 81% | 81% | 80% |
| Cutoff 6 | 36.9 | 31.3 | 34.8 | 36.9 | 31.3 | 34.8 | 36.9 | 31.3 | 34.8 |
| Sens 6 | 8% | 6% | 10% | 2% | 14% | 0% | 0% | 0% | 0% |
| Spec 6 | 92% | 90% | 90% | 92% | 90% | 90% | 92% | 90% | 90% |
| OR Quart 2 | 2.8 | 3.1 | 1.9 | 0.79 | 2.1 | 1.4 | 2.8 | 4.2 | 1.0 |
| p Value | 0.042 | 0.17 | 0.21 | 0.63 | 0.41 | 0.44 | 0.12 | 0.21 | 0.97 |
| 95% CI of | 1.0 | 0.61 | 0.69 | 0.31 | 0.37 | 0.57 | 0.76 | 0.46 | 0.24 |
| OR Quart2 | 7.4 | 16 | 5.3 | 2.0 | 12 | 3.7 | 9.9 | 38 | 4.5 |
| OR Quart 3 | 1.6 | 0.99 | 1.3 | 1.5 | 2.1 | 1.8 | 2.8 | 2.0 | 2.7 |
| p Value | 0.34 | 0.99 | 0.59 | 0.37 | 0.41 | 0.22 | 0.12 | 0.57 | 0.14 |

-continued

| | | | | | | | | | |
|---|---|---|---|---|---|---|---|---|---|
| 95% CI of | 0.59 | 0.14 | 0.47 | 0.62 | 0.37 | 0.71 | 0.76 | 0.18 | 0.74 |
| OR Quart3 | 4.6 | 7.2 | 3.8 | 3.7 | 12 | 4.4 | 9.9 | 23 | 9.5 |
| OR Quart 4 | 2.3 | 3.1 | 1.5 | 0.89 | 2.0 | 1.3 | 1.0 | 3.0 | 1.6 |
| p Value | 0.10 | 0.17 | 0.47 | 0.81 | 0.42 | 0.59 | 0.97 | 0.34 | 0.47 |
| 95% CI of | 0.84 | 0.61 | 0.52 | 0.35 | 0.36 | 0.51 | 0.24 | 0.31 | 0.42 |
| OR Quart4 | 6.1 | 16 | 4.1 | 2.3 | 11 | 3.3 | 4.5 | 30 | 6.4 |

| Insulin-like growth factor-binding protein 5 | | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | 21.0 | 5.45 | 21.0 | 9.99 | 21.0 | 24.0 |
| Average | 37.8 | 33.6 | 37.8 | 36.6 | 37.8 | 41.1 |
| Stdev | 49.2 | 53.3 | 49.2 | 55.6 | 49.2 | 48.4 |
| p(t-test) | | 0.62 | | 0.89 | | 0.75 |
| Min | 0.204 | 0.204 | 0.204 | 0.204 | 0.204 | 0.204 |
| Max | 257 | 189 | 257 | 228 | 257 | 149 |
| n (Samp) | 119 | 52 | 119 | 53 | 119 | 26 |
| n (Patient) | 87 | 52 | 87 | 53 | 87 | 26 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 14.7 | 0.763 | 14.7 | 0.763 | 14.7 | 6.07 |
| Average | 34.2 | 29.8 | 34.2 | 44.9 | 34.2 | 45.5 |
| Stdev | 47.7 | 51.3 | 47.7 | 66.8 | 47.7 | 62.9 |
| p(t-test) | | 0.72 | | 0.42 | | 0.47 |
| Min | 0.204 | 0.222 | 0.204 | 0.316 | 0.204 | 0.222 |
| Max | 257 | 151 | 257 | 177 | 257 | 149 |
| n (Samp) | 283 | 16 | 283 | 14 | 283 | 10 |
| n (Patient) | 161 | 16 | 161 | 14 | 161 | 10 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 8.50 | 5.45 | 8.50 | 11.4 | 8.50 | 8.58 |
| Average | 30.2 | 34.4 | 30.2 | 34.0 | 30.2 | 33.3 |
| Stdev | 47.5 | 53.1 | 47.5 | 50.4 | 47.5 | 44.1 |
| p(t-test) | | 0.64 | | 0.63 | | 0.78 |
| Min | 0.204 | 0.204 | 0.204 | 0.204 | 0.204 | 0.204 |
| Max | 257 | 189 | 257 | 228 | 257 | 149 |
| n (Samp) | 123 | 42 | 123 | 54 | 123 | 23 |
| n (Patient) | 80 | 42 | 80 | 54 | 80 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.44 | 0.44 | 0.51 | 0.46 | 0.52 | 0.51 | 0.54 | 0.53 | 0.55 |
| SE | 0.048 | 0.076 | 0.052 | 0.048 | 0.080 | 0.047 | 0.063 | 0.094 | 0.067 |
| p | 0.25 | 0.47 | 0.89 | 0.40 | 0.80 | 0.79 | 0.57 | 0.77 | 0.43 |
| nCohort 1 | 119 | 283 | 123 | 119 | 283 | 123 | 119 | 283 | 123 |
| nCohort 2 | 52 | 16 | 42 | 53 | 14 | 54 | 26 | 10 | 23 |
| Cutoff 1 | 0.357 | 0.316 | 0.357 | 0.316 | 0.357 | 0.316 | 0.696 | 0.357 | 0.488 |
| Sens 1 | 73% | 75% | 71% | 75% | 71% | 70% | 73% | 70% | 74% |
| Spec 1 | 22% | 22% | 28% | 18% | 26% | 24% | 32% | 26% | 41% |
| Cutoff 2 | 0.222 | 0.222 | 0.222 | 0.222 | 0.316 | 0.222 | 0.357 | 0.316 | 0.222 |
| Sens 2 | 87% | 81% | 86% | 87% | 93% | 83% | 81% | 90% | 91% |
| Spec 2 | 16% | 16% | 20% | 16% | 22% | 20% | 22% | 22% | 20% |
| Cutoff 3 | 0.204 | 0.204 | 0.204 | 0.204 | 0.316 | 0.204 | 0.222 | 0.316 | 0.222 |
| Sens 3 | 94% | 100% | 93% | 96% | 93% | 96% | 96% | 90% | 91% |
| Spec 3 | 4% | 5% | 5% | 4% | 22% | 5% | 16% | 22% | 20% |
| Cutoff 4 | 47.6 | 41.5 | 36.4 | 47.6 | 41.5 | 36.4 | 47.6 | 41.5 | 36.4 |
| Sens 4 | 19% | 31% | 29% | 26% | 36% | 28% | 35% | 30% | 30% |
| Spec 4 | 71% | 70% | 71% | 71% | 70% | 71% | 71% | 70% | 71% |
| Cutoff 5 | 64.4 | 61.4 | 49.7 | 64.4 | 61.4 | 49.7 | 64.4 | 61.4 | 49.7 |
| Sens 5 | 15% | 19% | 21% | 19% | 29% | 26% | 27% | 30% | 30% |
| Spec 5 | 81% | 80% | 80% | 81% | 80% | 80% | 81% | 80% | 80% |
| Cutoff 6 | 97.6 | 97.6 | 80.9 | 97.6 | 97.6 | 80.9 | 97.6 | 97.6 | 80.9 |
| Sens 6 | 13% | 12% | 17% | 15% | 21% | 13% | 19% | 30% | 13% |
| Spec 6 | 91% | 90% | 90% | 91% | 90% | 90% | 91% | 90% | 90% |
| OR Quart 2 | 1.3 | 0.66 | 1.0 | 0.89 | 1.0 | 0.57 | 1.5 | 1.0 | 1.2 |
| p Value | 0.62 | 0.65 | 1.0 | 0.81 | 1.0 | 0.24 | 0.53 | 1.0 | 0.78 |
| 95% CI of | 0.48 | 0.11 | 0.38 | 0.34 | 0.24 | 0.22 | 0.43 | 0.20 | 0.33 |
| OR Quart2 | 3.4 | 4.1 | 2.7 | 2.3 | 4.2 | 1.5 | 5.2 | 5.1 | 4.3 |

-continued

| | | | | | | | | | |
|---|---|---|---|---|---|---|---|---|---|
| OR Quart 3 | 2.0 | 2.5 | 0.88 | 1.2 | 0.24 | 1.0 | 1.2 | 0.32 | 1.0 |
| p Value | 0.16 | 0.20 | 0.80 | 0.64 | 0.21 | 1.0 | 0.74 | 0.33 | 1.0 |
| 95% CI of | 0.76 | 0.61 | 0.33 | 0.50 | 0.026 | 0.41 | 0.34 | 0.033 | 0.26 |
| OR Quart3 | 5.0 | 9.9 | 2.4 | 3.1 | 2.2 | 2.4 | 4.5 | 3.2 | 3.8 |
| OR Quart 4 | 1.6 | 1.4 | 0.85 | 1.5 | 1.2 | 0.87 | 1.7 | 0.99 | 1.4 |
| p Value | 0.30 | 0.69 | 0.75 | 0.36 | 0.75 | 0.76 | 0.39 | 0.99 | 0.56 |
| 95% CI of | 0.63 | 0.30 | 0.32 | 0.62 | 0.32 | 0.36 | 0.50 | 0.19 | 0.41 |
| OR Quart4 | 4.3 | 6.4 | 2.3 | 3.8 | 4.9 | 2.1 | 5.8 | 5.1 | 5.1 |

Immunoglogulin G4

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 416000 | 348000 | 416000 | 364000 | 416000 | 325000 |
| Average | 815000 | 435000 | 815000 | 451000 | 815000 | 395000 |
| Stdev | 1020000 | 366000 | 1020000 | 338000 | 1020000 | 384000 |
| p(t-test) | | 0.033 | | 0.035 | | 0.20 |
| Min | 15300 | 2000 | 15300 | 14400 | 15300 | 18500 |
| Max | 5190000 | 1690000 | 5190000 | 1480000 | 5190000 | 1070000 |
| n (Samp) | 94 | 35 | 94 | 37 | 94 | 10 |
| n (Patient) | 67 | 35 | 67 | 37 | 67 | 10 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 364000 | 506000 | 364000 | 357000 | nd | nd |
| Average | 626000 | 585000 | 626000 | 454000 | nd | nd |
| Stdev | 765000 | 449000 | 765000 | 347000 | nd | nd |
| p(t-test) | | 0.87 | | 0.53 | nd | nd |
| Min | 2000 | 61100 | 2000 | 58300 | nd | nd |
| Max | 5190000 | 1690000 | 5190000 | 939000 | nd | nd |
| n (Samp) | 205 | 10 | 205 | 8 | nd | nd |
| n (Patient) | 126 | 10 | 126 | 8 | nd | nd |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 417000 | 328000 | 417000 | 409000 | 417000 | 385000 |
| Average | 719000 | 486000 | 719000 | 585000 | 719000 | 434000 |
| Stdev | 858000 | 677000 | 858000 | 651000 | 858000 | 371000 |
| p(t-test) | | 0.19 | | 0.40 | | 0.26 |
| Min | 15300 | 2000 | 15300 | 14400 | 15300 | 18500 |
| Max | 5140000 | 3560000 | 5140000 | 3700000 | 5140000 | 1070000 |
| n (Samp) | 101 | 28 | 101 | 36 | 101 | 12 |
| n (Patient) | 65 | 28 | 65 | 36 | 65 | 12 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.42 | 0.57 | 0.40 | 0.44 | 0.48 | 0.48 | 0.37 | nd | 0.41 |
| SE | 0.058 | 0.096 | 0.063 | 0.057 | 0.11 | 0.056 | 0.099 | nd | 0.091 |
| p | 0.15 | 0.49 | 0.11 | 0.32 | 0.82 | 0.77 | 0.18 | nd | 0.30 |
| nCohort 1 | 94 | 205 | 101 | 94 | 205 | 101 | 94 | nd | 101 |
| nCohort 2 | 35 | 10 | 28 | 37 | 8 | 36 | 10 | nd | 12 |
| Cutoff 1 | 191000 | 402000 | 186000 | 277000 | 250000 | 299000 | 71200 | nd | 71200 |
| Sens 1 | 71% | 70% | 71% | 70% | 75% | 72% | 70% | nd | 75% |
| Spec 1 | 30% | 53% | 28% | 40% | 34% | 40% | 13% | nd | 11% |
| Cutoff 2 | 83300 | 347000 | 56300 | 164000 | 90700 | 245000 | 37500 | nd | 37500 |
| Sens 2 | 80% | 80% | 82% | 81% | 88% | 81% | 80% | nd | 83% |
| Spec 2 | 16% | 49% | 7% | 26% | 18% | 34% | 5% | nd | 4% |
| Cutoff 3 | 33600 | 191000 | 15300 | 38600 | 58100 | 38600 | 18500 | nd | 18500 |
| Sens 3 | 91% | 90% | 93% | 92% | 100% | 92% | 90% | nd | 92% |
| Spec 3 | 4% | 29% | 1% | 5% | 12% | 4% | 1% | nd | 1% |
| Cutoff 4 | 977000 | 705000 | 884000 | 977000 | 705000 | 884000 | 977000 | nd | 884000 |
| Sens 4 | 3% | 20% | 14% | 5% | 25% | 19% | 10% | nd | 8% |
| Spec 4 | 70% | 70% | 70% | 70% | 70% | 70% | 70% | nd | 70% |
| Cutoff 5 | 1370000 | 977000 | 1080000 | 1370000 | 977000 | 1080000 | 1370000 | nd | 1080000 |
| Sens 5 | 3% | 10% | 4% | 3% | 0% | 8% | 0% | nd | 0% |
| Spec 5 | 81% | 80% | 80% | 81% | 80% | 80% | 81% | nd | 80% |
| Cutoff 6 | 2130000 | 1380000 | 1590000 | 2130000 | 1380000 | 1590000 | 2130000 | nd | 1590000 |
| Sens 6 | 0% | 10% | 4% | 0% | 0% | 3% | 0% | nd | 0% |
| Spec 6 | 90% | 90% | 90% | 90% | 90% | 90% | 90% | nd | 90% |
| OR Quart 2 | 6.8 | 2.0 | 2.0 | 4.7 | 1.0 | 1.9 | 3.3 | nd | 4.7 |
| p Value | 0.0063 | 0.58 | 0.30 | 0.016 | 0.98 | 0.25 | 0.32 | nd | 0.18 |

-continued

| | | | | | | | | | |
|---|---|---|---|---|---|---|---|---|---|
| 95% CI of | 1.7 | 0.18 | 0.53 | 1.3 | 0.14 | 0.64 | 0.32 | nd | 0.49 |
| OR Quart2 | 27 | 23 | 7.8 | 17 | 7.5 | 5.7 | 34 | nd | 45 |
| OR Quart 3 | 5.2 | 6.5 | 2.8 | 4.1 | 1.0 | 1.9 | 2.1 | nd | 3.4 |
| p Value | 0.020 | 0.088 | 0.12 | 0.027 | 0.98 | 0.25 | 0.56 | nd | 0.31 |
| 95% CI of | 1.3 | 0.75 | 0.77 | 1.2 | 0.14 | 0.64 | 0.18 | nd | 0.33 |
| OR Quart3 | 21 | 56 | 10 | 15 | 7.5 | 5.7 | 25 | nd | 34 |
| OR Quart 4 | 3.3 | 0.98 | 2.4 | 2.4 | 1.0 | 1.0 | 4.5 | nd | 4.7 |
| p Value | 0.099 | 0.99 | 0.19 | 0.19 | 0.98 | 0.95 | 0.19 | nd | 0.18 |
| 95% CI of | 0.80 | 0.060 | 0.65 | 0.65 | 0.14 | 0.32 | 0.47 | nd | 0.49 |
| OR Quart4 | 14 | 16 | 9.0 | 9.0 | 7.5 | 3.4 | 44 | nd | 45 |

Interleukin-21

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.694 | 0.220 | 0.694 | 0.631 | 0.694 | 1.76 |
| Average | 62.7 | 2.10 | 62.7 | 2.18 | 62.7 | 2.97 |
| Stdev | 560 | 4.20 | 560 | 3.76 | 560 | 4.00 |
| p(t-test) | | 0.47 | | 0.49 | | 0.65 |
| Min | 0.0102 | 0.0102 | 0.0102 | 0.0102 | 0.0102 | 0.0102 |
| Max | 5430 | 18.3 | 5430 | 15.6 | 5430 | 14.3 |
| n (Samp) | 94 | 45 | 94 | 42 | 94 | 18 |
| n (Patient) | 65 | 45 | 65 | 42 | 65 | 18 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 0.430 | 1.62 | 0.430 | 1.56 | 0.430 | 1.36 |
| Average | 27.5 | 4.80 | 27.5 | 4.77 | 27.5 | 3.68 |
| Stdev | 362 | 6.58 | 362 | 7.34 | 362 | 5.30 |
| p(t-test) | | 0.82 | | 0.79 | | 0.84 |
| Min | 0.0102 | 0.0102 | 0.0102 | 0.0257 | 0.0102 | 0.0102 |
| Max | 5430 | 18.3 | 5430 | 26.6 | 5430 | 14.3 |
| n (Samp) | 225 | 14 | 225 | 18 | 225 | 9 |
| n (Patient) | 132 | 14 | 132 | 18 | 132 | 9 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.829 | 0.174 | 0.829 | 0.630 | 0.829 | 0.829 |
| Average | 57.9 | 1.06 | 57.9 | 1.90 | 57.9 | 2.24 |
| Stdev | 535 | 2.03 | 535 | 3.33 | 535 | 3.16 |
| p(t-test) | | 0.52 | | 0.50 | | 0.69 |
| Min | 0.0102 | 0.0102 | 0.0102 | 0.0102 | 0.0102 | 0.0102 |
| Max | 5430 | 8.97 | 5430 | 16.0 | 5430 | 11.5 |
| n (Samp) | 103 | 37 | 103 | 41 | 103 | 15 |
| n (Patient) | 64 | 37 | 64 | 41 | 64 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.45 | 0.58 | 0.37 | 0.52 | 0.68 | 0.47 | 0.62 | 0.63 | 0.54 |
| SE | 0.053 | 0.082 | 0.055 | 0.054 | 0.072 | 0.054 | 0.076 | 0.10 | 0.081 |
| p | 0.37 | 0.33 | 0.020 | 0.70 | 0.011 | 0.56 | 0.099 | 0.20 | 0.63 |
| nCohort 1 | 94 | 225 | 103 | 94 | 225 | 103 | 94 | 225 | 103 |
| nCohort 2 | 45 | 14 | 37 | 42 | 18 | 41 | 18 | 9 | 15 |
| Cutoff 1 | 0.0154 | 0.0154 | 0.0154 | 0.0257 | 0.231 | 0.0257 | 0.605 | 0.783 | 0.430 |
| Sens 1 | 76% | 79% | 70% | 74% | 72% | 71% | 78% | 78% | 73% |
| Spec 1 | 19% | 22% | 14% | 33% | 48% | 32% | 50% | 59% | 46% |
| Cutoff 2 | 0.0142 | 0.0142 | 0.0102 | 0.0182 | 0.174 | 0.0154 | 0.430 | 0.0182 | 0.174 |
| Sens 2 | 82% | 86% | 89% | 83% | 89% | 85% | 83% | 89% | 80% |
| Spec 2 | 15% | 14% | 5% | 24% | 43% | 14% | 49% | 29% | 36% |
| Cutoff 3 | 0.0102 | 0.0102 | 0 | 0.0142 | 0.0257 | 0.0142 | 0.0142 | 0 | 0.0142 |
| Sens 3 | 91% | 93% | 100% | 93% | 94% | 93% | 94% | 100% | 93% |
| Spec 3 | 10% | 9% | 0% | 15% | 39% | 11% | 15% | 0% | 11% |
| Cutoff 4 | 1.77 | 1.61 | 2.03 | 1.77 | 1.61 | 2.03 | 1.77 | 1.61 | 2.03 |
| Sens 4 | 29% | 50% | 19% | 31% | 39% | 24% | 50% | 44% | 20% |
| Spec 4 | 70% | 71% | 72% | 70% | 71% | 72% | 70% | 71% | 72% |
| Cutoff 5 | 2.93 | 2.46 | 3.18 | 2.93 | 2.46 | 3.18 | 2.93 | 2.46 | 3.18 |
| Sens 5 | 16% | 43% | 8% | 24% | 39% | 17% | 22% | 22% | 20% |
| Spec 5 | 81% | 80% | 81% | 81% | 80% | 81% | 81% | 80% | 81% |
| Cutoff 6 | 10.6 | 5.00 | 14.5 | 10.6 | 5.00 | 14.5 | 10.6 | 5.00 | 14.5 |
| Sens 6 | 7% | 29% | 0% | 7% | 28% | 2% | 11% | 22% | 0% |
| Spec 6 | 90% | 90% | 90% | 90% | 90% | 90% | 90% | 90% | 90% |

-continued

| | | | | | | | | | |
|---|---|---|---|---|---|---|---|---|---|
| OR Quart 2 | 0.57 | 0.47 | 1.4 | 1.5 | >6.5 | 1.0 | 2.2 | 0.98 | 3.4 |
| p Value | 0.29 | 0.40 | 0.55 | 0.43 | <0.087 | 1.0 | 0.40 | 0.99 | 0.16 |
| 95% CI of | 0.20 | 0.083 | 0.44 | 0.54 | >0.76 | 0.34 | 0.36 | 0.060 | 0.62 |
| OR Quart2 | 1.6 | 2.7 | 4.7 | 4.3 | na | 2.9 | 13 | 16 | 18 |
| OR Quart 3 | 1.1 | 0.23 | 2.2 | 1.0 | >5.4 | 1.5 | 4.3 | 4.2 | 2.2 |
| p Value | 0.80 | 0.20 | 0.17 | 1.0 | <0.13 | 0.44 | 0.086 | 0.20 | 0.40 |
| 95% CI of | 0.43 | 0.025 | 0.71 | 0.34 | >0.61 | 0.54 | 0.81 | 0.46 | 0.36 |
| OR Quart3 | 3.0 | 2.1 | 6.9 | 2.9 | na | 4.2 | 23 | 39 | 13 |
| OR Quart 4 | 1.0 | 1.8 | 2.5 | 1.5 | >7.8 | 1.3 | 2.8 | 3.1 | 1.5 |
| p Value | 0.93 | 0.36 | 0.11 | 0.43 | <0.059 | 0.60 | 0.24 | 0.34 | 0.67 |
| 95% CI of | 0.39 | 0.50 | 0.82 | 0.54 | >0.93 | 0.47 | 0.50 | 0.31 | 0.23 |
| OR Quart4 | 2.8 | 6.6 | 7.7 | 4.3 | na | 3.7 | 16 | 30 | 9.7 |

Interleukin-23

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.886 | 1.10 | 0.886 | 1.10 | 0.886 | 6.06 |
| Average | 1780 | 3580 | 1780 | 4170 | 1780 | 1560 |
| Stdev | 10800 | 15400 | 10800 | 15900 | 10800 | 4960 |
| p(t-test) | | 0.43 | | 0.31 | | 0.93 |
| Min | 0.257 | 0.257 | 0.257 | 0.257 | 0.257 | 0.603 |
| Max | 100000 | 100000 | 100000 | 100000 | 100000 | 20500 |
| n (Samp) | 93 | 45 | 93 | 42 | 93 | 18 |
| n (Patient) | 64 | 45 | 64 | 42 | 64 | 18 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 1.10 | 0.886 | 1.10 | 1.10 | 1.10 | 0.603 |
| Average | 2750 | 3820 | 2750 | 8680 | 2750 | 2270 |
| Stdev | 14900 | 7430 | 14900 | 23800 | 14900 | 6820 |
| p(t-test) | | 0.79 | | 0.12 | | 0.92 |
| Min | 0.257 | 0.257 | 0.257 | 0.257 | 0.257 | 0.257 |
| Max | 100000 | 20000 | 100000 | 100000 | 100000 | 20500 |
| n (Samp) | 224 | 14 | 224 | 18 | 224 | 9 |
| n (Patient) | 131 | 14 | 131 | 18 | 131 | 9 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.995 | 1.10 | 0.995 | 1.10 | 0.995 | 44.5 |
| Average | 2480 | 2920 | 2480 | 3160 | 2480 | 511 |
| Stdev | 11000 | 16400 | 11000 | 15600 | 11000 | 1650 |
| p(t-test) | | 0.86 | | 0.77 | | 0.49 |
| Min | 0.257 | 0.257 | 0.257 | 0.257 | 0.257 | 0.603 |
| Max | 100000 | 100000 | 100000 | 100000 | 100000 | 6480 |
| n (Samp) | 102 | 37 | 102 | 41 | 102 | 15 |
| n (Patient) | 63 | 37 | 63 | 41 | 63 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.52 | 0.50 | 0.49 | 0.55 | 0.60 | 0.53 | 0.55 | 0.34 | 0.60 |
| SE | 0.053 | 0.080 | 0.056 | 0.054 | 0.073 | 0.054 | 0.076 | 0.10 | 0.082 |
| p | 0.74 | 0.98 | 0.79 | 0.32 | 0.17 | 0.56 | 0.51 | 0.11 | 0.24 |
| nCohort 1 | 93 | 224 | 102 | 93 | 224 | 102 | 93 | 224 | 102 |
| nCohort 2 | 45 | 14 | 37 | 42 | 18 | 41 | 18 | 9 | 15 |
| Cutoff 1 | 0.603 | 0.603 | 0.603 | 0.603 | 0.770 | 0.603 | 0.257 | 0.257 | 0.653 |
| Sens 1 | 78% | 79% | 76% | 79% | 78% | 80% | 100% | 89% | 80% |
| Spec 1 | 25% | 22% | 24% | 25% | 38% | 24% | 18% | 13% | 41% |
| Cutoff 2 | 0.257 | 0.257 | 0.257 | 0.257 | 0.257 | 0.603 | 0.257 | 0.257 | 0.653 |
| Sens 2 | 84% | 86% | 84% | 81% | 83% | 80% | 100% | 89% | 80% |
| Spec 2 | 18% | 13% | 19% | 18% | 13% | 24% | 18% | 13% | 41% |
| Cutoff 3 | 0 | 0 | 0 | 0 | 0 | 0 | 0.257 | 0 | 0.257 |
| Sens 3 | 100% | 100% | 100% | 100% | 100% | 100% | 100% | 100% | 100% |
| Spec 3 | 0% | 0% | 0% | 0% | 0% | 0% | 18% | 0% | 19% |
| Cutoff 4 | 11.0 | 44.5 | 55.0 | 11.0 | 44.5 | 55.0 | 11.0 | 44.5 | 55.0 |
| Sens 4 | 31% | 29% | 27% | 43% | 44% | 34% | 44% | 11% | 47% |
| Spec 4 | 71% | 71% | 71% | 71% | 71% | 71% | 71% | 71% | 71% |
| Cutoff 5 | 501 | 267 | 530 | 501 | 267 | 530 | 501 | 267 | 530 |
| Sens 5 | 16% | 29% | 8% | 29% | 39% | 24% | 11% | 11% | 7% |
| Spec 5 | 81% | 80% | 80% | 81% | 80% | 80% | 81% | 80% | 80% |
| Cutoff 6 | 1500 | 1040 | 2000 | 1500 | 1040 | 2000 | 1500 | 1040 | 2000 |

-continued

| | | | | | | | | | |
|---|---|---|---|---|---|---|---|---|---|
| Sens 6 | 11% | 29% | 5% | 14% | 33% | 12% | 11% | 11% | 7% |
| Spec 6 | 90% | 90% | 90% | 90% | 90% | 90% | 90% | 90% | 90% |
| OR Quart 2 | 1.1 | 1.7 | 2.9 | 1.1 | 0.72 | 1.7 | 0.34 | 1.0 | 1.6 |
| p Value | 0.86 | 0.48 | 0.065 | 0.85 | 0.68 | 0.33 | 0.22 | 0.99 | 0.64 |
| 95% CI of | 0.39 | 0.39 | 0.94 | 0.38 | 0.16 | 0.59 | 0.060 | 0.062 | 0.24 |
| OR Quart2 | 3.1 | 7.4 | 8.7 | 3.2 | 3.4 | 4.8 | 1.9 | 17 | 10 |
| OR Quart 3 | 1.9 | 0.65 | 1.7 | 1.3 | 0.74 | 1.5 | 1.5 | 2.1 | 4.3 |
| p Value | 0.21 | 0.65 | 0.38 | 0.65 | 0.70 | 0.47 | 0.56 | 0.56 | 0.087 |
| 95% CI of | 0.70 | 0.11 | 0.52 | 0.45 | 0.16 | 0.51 | 0.40 | 0.18 | 0.81 |
| OR Quart3 | 5.2 | 4.1 | 5.3 | 3.6 | 3.4 | 4.3 | 5.3 | 23 | 23 |
| OR Quart 4 | 0.83 | 1.3 | 1.7 | 1.5 | 2.1 | 1.3 | 0.73 | 5.5 | 1.5 |
| p Value | 0.73 | 0.71 | 0.35 | 0.48 | 0.24 | 0.63 | 0.67 | 0.13 | 0.67 |
| 95% CI of | 0.29 | 0.29 | 0.54 | 0.51 | 0.60 | 0.44 | 0.17 | 0.62 | 0.23 |
| OR Quart4 | 2.4 | 6.2 | 5.6 | 4.1 | 7.4 | 3.8 | 3.1 | 48 | 9.7 |

Interleukin-28A

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.168 | 0.265 | 0.168 | 0.265 | 0.168 | 12.7 |
| Average | 60.1 | 15.3 | 60.1 | 13.9 | 60.1 | 26.7 |
| Stdev | 387 | 47.2 | 387 | 41.9 | 387 | 54.8 |
| p(t-test) | | 0.44 | | 0.44 | | 0.72 |
| Min | 0.0727 | 0.0727 | 0.0727 | 0.0727 | 0.0727 | 0.148 |
| Max | 3150 | 246 | 3150 | 243 | 3150 | 235 |
| n (Samp) | 93 | 45 | 93 | 42 | 93 | 18 |
| n (Patient) | 64 | 45 | 64 | 42 | 64 | 18 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 0.195 | 0.230 | 0.195 | 0.265 | 0.195 | 0.265 |
| Average | 28.7 | 36.9 | 28.7 | 136 | 28.7 | 31.0 |
| Stdev | 250 | 80.9 | 250 | 470 | 250 | 77.2 |
| p(t-test) | | 0.90 | | 0.11 | | 0.98 |
| Min | 0.0727 | 0.0727 | 0.0727 | 0.148 | 0.0727 | 0.0727 |
| Max | 3150 | 246 | 3150 | 2000 | 3150 | 235 |
| n (Samp) | 224 | 14 | 224 | 18 | 224 | 9 |
| n (Patient) | 131 | 14 | 131 | 18 | 131 | 9 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.168 | 0.265 | 0.168 | 0.265 | 0.168 | 0.265 |
| Average | 57.5 | 4.69 | 57.5 | 7.99 | 57.5 | 13.5 |
| Stdev | 370 | 10.1 | 370 | 16.8 | 370 | 18.3 |
| p(t-test) | | 0.39 | | 0.39 | | 0.65 |
| Min | 0.0727 | 0.0727 | 0.0727 | 0.0727 | 0.0727 | 0.0727 |
| Max | 3150 | 49.8 | 3150 | 92.3 | 3150 | 62.9 |
| n (Samp) | 102 | 37 | 102 | 41 | 102 | 15 |
| n (Patient) | 63 | 37 | 63 | 41 | 63 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.59 | 0.55 | 0.61 | 0.62 | 0.65 | 0.62 | 0.76 | 0.60 | 0.69 |
| SE | 0.053 | 0.082 | 0.056 | 0.054 | 0.073 | 0.053 | 0.069 | 0.10 | 0.080 |
| p | 0.072 | 0.53 | 0.051 | 0.026 | 0.036 | 0.028 | 2.1E−4 | 0.31 | 0.015 |
| nCohort 1 | 93 | 224 | 102 | 93 | 224 | 102 | 93 | 224 | 102 |
| nCohort 2 | 45 | 14 | 37 | 42 | 18 | 41 | 18 | 9 | 15 |
| Cutoff 1 | 0.120 | 0.120 | 0.120 | 0.168 | 0.168 | 0.148 | 0.168 | 0.158 | 0.168 |
| Sens 1 | 91% | 79% | 92% | 71% | 72% | 73% | 89% | 78% | 80% |
| Spec 1 | 19% | 17% | 24% | 54% | 48% | 46% | 54% | 38% | 56% |
| Cutoff 2 | 0.120 | 0 | 0.120 | 0.120 | 0.158 | 0.120 | 0.168 | 0.120 | 0.168 |
| Sens 2 | 91% | 100% | 92% | 88% | 83% | 83% | 89% | 89% | 80% |
| Spec 2 | 19% | 0% | 24% | 19% | 38% | 24% | 54% | 17% | 56% |
| Cutoff 3 | 0.120 | 0 | 0.120 | 0 | 0.120 | 0 | 0.148 | 0 | 0.120 |
| Sens 3 | 91% | 100% | 92% | 100% | 100% | 100% | 94% | 100% | 93% |
| Spec 3 | 19% | 0% | 24% | 0% | 17% | 0% | 41% | 0% | 24% |
| Cutoff 4 | 0.265 | 0.265 | 0.265 | 0.265 | 0.265 | 0.265 | 0.265 | 0.265 | 0.265 |
| Sens 4 | 42% | 36% | 41% | 36% | 39% | 39% | 61% | 44% | 47% |
| Spec 4 | 80% | 71% | 82% | 80% | 71% | 82% | 80% | 71% | 82% |
| Cutoff 5 | 3.03 | 10.2 | 0.265 | 3.03 | 10.2 | 0.265 | 3.03 | 10.2 | 0.265 |
| Sens 5 | 33% | 36% | 41% | 33% | 28% | 39% | 56% | 33% | 47% |

-continued

| | | | | | | | | | |
|---|---|---|---|---|---|---|---|---|---|
| Spec 5 | 81% | 80% | 82% | 81% | 80% | 82% | 81% | 80% | 82% |
| Cutoff 6 | 16.5 | 19.3 | 16.5 | 16.5 | 19.3 | 16.5 | 16.5 | 19.3 | 16.5 |
| Sens 6 | 16% | 29% | 8% | 12% | 28% | 10% | 39% | 22% | 33% |
| Spec 6 | 90% | 90% | 90% | 90% | 90% | 90% | 90% | 90% | 90% |
| OR Quart 2 | 5.0 | 1.3 | 3.4 | 0.81 | >6.5 | 0.47 | >3.2 | 2.0 | 1.0 |
| p Value | 0.011 | 0.71 | 0.056 | 0.72 | <0.087 | 0.22 | <0.32 | 0.57 | 1.0 |
| 95% CI of | 1.4 | 0.29 | 0.97 | 0.26 | >0.76 | 0.14 | >0.32 | 0.18 | 0.060 |
| OR Quart2 | 17 | 6.2 | 12 | 2.6 | na | 1.6 | na | 23 | 17 |
| OR Quart 3 | 3.6 | 0.65 | 1.9 | 1.7 | >6.7 | 1.3 | >5.9 | 3.1 | 7.3 |
| p Value | 0.048 | 0.65 | 0.36 | 0.33 | <0.084 | 0.65 | <0.12 | 0.33 | 0.075 |
| 95% CI of | 1.0 | 0.11 | 0.49 | 0.59 | >0.78 | 0.45 | >0.64 | 0.31 | 0.82 |
| OR Quart3 | 13 | 4.1 | 7.1 | 4.9 | na | 3.6 | na | 31 | 65 |
| OR Quart 4 | 6.3 | 1.7 | 5.6 | 2.5 | >6.5 | 2.3 | >15 | 3.1 | 8.5 |
| p Value | 0.0035 | 0.48 | 0.0063 | 0.090 | <0.087 | 0.10 | <0.013 | 0.34 | 0.053 |
| 95% CI of | 1.8 | 0.39 | 1.6 | 0.87 | >0.76 | 0.85 | >1.8 | 0.31 | 0.98 |
| OR Quart4 | 22 | 7.4 | 19 | 7.0 | na | 6.3 | na | 30 | 74 |

Interleukin-33

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 0.0981 | 0.0981 | 0.0981 | 0.101 | 0.0981 | 0.101 |
| Average | 481 | 183 | 481 | 184 | 481 | 63.4 |
| Stdev | 4130 | 710 | 4130 | 626 | 4130 | 210 |
| p(t-test) | | 0.63 | | 0.64 | | 0.67 |
| Min | 0.0445 | 0.0445 | 0.0445 | 0.0445 | 0.0445 | 0.0445 |
| Max | 40000 | 4440 | 40000 | 3770 | 40000 | 892 |
| n (Samp) | 94 | 45 | 94 | 42 | 94 | 18 |
| n (Patient) | 65 | 45 | 65 | 42 | 65 | 18 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 0.0981 | 0.0762 | 0.0981 | 0.0993 | 0.0981 | 0.101 |
| Average | 327 | 240 | 327 | 844 | 327 | 99.4 |
| Stdev | 2850 | 485 | 2850 | 2870 | 2850 | 297 |
| p(t-test) | | 0.91 | | 0.46 | | 0.81 |
| Min | 0.0445 | 0.0445 | 0.0445 | 0.0445 | 0.0445 | 0.0455 |
| Max | 40000 | 1270 | 40000 | 12300 | 40000 | 892 |
| n (Samp) | 225 | 14 | 225 | 18 | 225 | 9 |
| n (Patient) | 132 | 14 | 132 | 18 | 132 | 9 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 0.0981 | 0.0981 | 0.0981 | 0.101 | 0.0981 | 0.101 |
| Average | 503 | 132 | 503 | 131 | 503 | 16.7 |
| Stdev | 3950 | 730 | 3950 | 595 | 3950 | 38.5 |
| p(t-test) | | 0.57 | | 0.55 | | 0.64 |
| Min | 0.0445 | 0.0445 | 0.0445 | 0.0445 | 0.0445 | 0.0445 |
| Max | 40000 | 4440 | 40000 | 3770 | 40000 | 149 |
| n (Samp) | 103 | 37 | 103 | 41 | 103 | 15 |
| n (Patient) | 64 | 37 | 64 | 41 | 64 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.46 | 0.46 | 0.45 | 0.55 | 0.54 | 0.56 | 0.62 | 0.55 | 0.59 |
| SE | 0.053 | 0.081 | 0.056 | 0.054 | 0.072 | 0.054 | 0.076 | 0.10 | 0.082 |
| p | 0.49 | 0.63 | 0.39 | 0.38 | 0.59 | 0.27 | 0.13 | 0.61 | 0.28 |
| nCohort 1 | 94 | 225 | 103 | 94 | 225 | 103 | 94 | 225 | 103 |
| nCohort 2 | 45 | 14 | 37 | 42 | 18 | 41 | 18 | 9 | 15 |
| Cutoff 1 | 0.0455 | 0.0494 | 0.0455 | 0.0494 | 0.0445 | 0.0494 | 0.0996 | 0.0846 | 0.0996 |
| Sens 1 | 73% | 71% | 73% | 76% | 83% | 83% | 83% | 78% | 73% |
| Spec 1 | 24% | 21% | 23% | 24% | 10% | 23% | 55% | 36% | 60% |
| Cutoff 2 | 0.0445 | 0.0445 | 0.0445 | 0.0445 | 0.0445 | 0.0494 | 0.0996 | 0.0494 | 0.0543 |
| Sens 2 | 89% | 86% | 89% | 95% | 83% | 83% | 83% | 89% | 80% |
| Spec 2 | 11% | 10% | 8% | 11% | 10% | 23% | 55% | 21% | 41% |
| Cutoff 3 | 0 | 0 | 0 | 0.0445 | 0 | 0.0445 | 0 | 0.0445 | 0 |
| Sens 3 | 100% | 100% | 100% | 95% | 100% | 98% | 100% | 100% | 100% |
| Spec 3 | 0% | 0% | 0% | 11% | 0% | 8% | 0% | 10% | 0% |
| Cutoff 4 | 2.20 | 3.29 | 3.29 | 2.20 | 3.29 | 3.29 | 2.20 | 3.29 | 3.29 |
| Sens 4 | 24% | 29% | 19% | 43% | 44% | 39% | 39% | 11% | 40% |
| Spec 4 | 70% | 70% | 71% | 70% | 70% | 71% | 70% | 70% | 71% |

-continued

| | | | | | | | | | |
|---|---|---|---|---|---|---|---|---|---|
| Cutoff 5 | 27.4 | 14.4 | 33.8 | 27.4 | 14.4 | 33.8 | 27.4 | 14.4 | 33.8 |
| Sens 5 | 13% | 29% | 8% | 19% | 28% | 20% | 17% | 11% | 13% |
| Spec 5 | 81% | 80% | 81% | 81% | 80% | 81% | 81% | 80% | 81% |
| Cutoff 6 | 79.4 | 76.8 | 99.5 | 79.4 | 76.8 | 99.5 | 79.4 | 76.8 | 99.5 |
| Sens 6 | 11% | 21% | 5% | 17% | 28% | 15% | 11% | 11% | 7% |
| Spec 6 | 90% | 90% | 90% | 90% | 90% | 90% | 90% | 90% | 90% |
| OR Quart 2 | 1.0 | 0.24 | 1.4 | 0.54 | 0.47 | 1.8 | 1.0 | 2.0 | 0.47 |
| p Value | 1.0 | 0.20 | 0.57 | 0.27 | 0.30 | 0.28 | 1.0 | 0.58 | 0.54 |
| 95% CI of | 0.36 | 0.026 | 0.45 | 0.18 | 0.11 | 0.61 | 0.13 | 0.18 | 0.040 |
| OR Quart2 | 2.7 | 2.2 | 4.3 | 1.6 | 2.0 | 5.4 | 7.6 | 23 | 5.4 |
| OR Quart | 31.1 | 1.0 | 1.8 | 1.0 | 0.31 | 2.1 | 5.2 | 5.4 | 4.3 |
| p Value | 0.80 | 1.0 | 0.28 | 1.0 | 0.16 | 0.19 | 0.051 | 0.13 | 0.087 |
| 95% CI of | 0.42 | 0.24 | 0.61 | 0.36 | 0.059 | 0.71 | 0.99 | 0.61 | 0.81 |
| OR Quart3 | 3.1 | 4.2 | 5.5 | 2.8 | 1.6 | 6.1 | 27 | 48 | 23 |
| OR Quart 4 | 1.0 | 1.3 | 1.6 | 1.3 | 1.2 | 1.8 | 3.5 | 0.98 | 2.7 |
| p Value | 0.93 | 0.71 | 0.41 | 0.61 | 0.79 | 0.28 | 0.14 | 0.99 | 0.26 |
| 95% CI of | 0.38 | 0.33 | 0.53 | 0.48 | 0.37 | 0.61 | 0.65 | 0.060 | 0.48 |
| OR Quart4 | 2.9 | 5.1 | 4.8 | 3.5 | 3.7 | 5.4 | 19 | 16 | 15 |

Vascular endothelial growth factor receptor 2

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 8090 | 7910 | 8090 | 7810 | 8090 | 6760 |
| Average | 11100 | 9090 | 11100 | 9460 | 11100 | 7180 |
| Stdev | 15800 | 5160 | 15800 | 4940 | 15800 | 2560 |
| p(t-test) | | 0.41 | | 0.52 | | 0.30 |
| Min | 3720 | 3140 | 3720 | 4110 | 3720 | 3790 |
| Max | 153000 | 32000 | 153000 | 26100 | 153000 | 14300 |
| n (Samp) | 94 | 45 | 94 | 42 | 94 | 18 |
| n (Patient) | 65 | 45 | 65 | 42 | 65 | 18 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 7990 | 8380 | 7990 | 7560 | 7990 | 6380 |
| Average | 10200 | 10500 | 10200 | 21300 | 10200 | 7330 |
| Stdev | 14900 | 7740 | 14900 | 49000 | 14900 | 2720 |
| p(t-test) | | 0.94 | | 0.020 | | 0.56 |
| Min | 3640 | 3020 | 3640 | 3140 | 3640 | 5310 |
| Max | 166000 | 32000 | 166000 | 216000 | 166000 | 14300 |
| n (Samp) | 225 | 14 | 225 | 18 | 225 | 9 |
| n (Patient) | 132 | 14 | 132 | 18 | 132 | 9 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 1 | Cohort 2 | Cohort 1 |
| Median | 8040 | 7390 | 8040 | 7820 | 8040 | 6900 |
| Average | 11500 | 8180 | 11500 | 8500 | 11500 | 6830 |
| Stdev | 15500 | 3310 | 15500 | 3670 | 15500 | 2010 |
| p(t-test) | | 0.20 | | 0.23 | | 0.25 |
| Min | 3900 | 3140 | 3900 | 4110 | 3900 | 3790 |
| Max | 153000 | 19800 | 153000 | 26100 | 153000 | 11800 |
| n (Samp) | 103 | 37 | 103 | 41 | 103 | 15 |
| n (Patient) | 64 | 37 | 64 | 41 | 64 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.45 | 0.51 | 0.43 | 0.47 | 0.51 | 0.45 | 0.31 | 0.34 | 0.30 |
| SE | 0.053 | 0.080 | 0.056 | 0.054 | 0.071 | 0.054 | 0.074 | 0.10 | 0.079 |
| p | 0.33 | 0.93 | 0.19 | 0.60 | 0.87 | 0.33 | 0.0082 | 0.11 | 0.013 |
| nCohort 1 | 94 | 225 | 103 | 94 | 225 | 103 | 94 | 225 | 103 |
| nCohort 2 | 45 | 14 | 37 | 42 | 18 | 41 | 18 | 9 | 15 |
| Cutoff 1 | 6200 | 6200 | 6340 | 6710 | 6110 | 6690 | 5920 | 6010 | 5440 |
| Sens 1 | 71% | 71% | 70% | 71% | 72% | 71% | 72% | 78% | 73% |
| Spec 1 | 19% | 24% | 23% | 28% | 22% | 30% | 13% | 20% | 11% |
| Cutoff 2 | 5620 | 5310 | 5570 | 6250 | 5560 | 6210 | 5050 | 5920 | 5140 |
| Sens 2 | 80% | 86% | 81% | 81% | 83% | 80% | 83% | 89% | 80% |
| Spec 2 | 10% | 12% | 11% | 19% | 14% | 21% | 6% | 19% | 8% |
| Cutoff 3 | 5230 | 4920 | 5230 | 5070 | 4780 | 5620 | 3900 | 5300 | 4330 |
| Sens 3 | 91% | 93% | 92% | 90% | 94% | 90% | 94% | 100% | 93% |
| Spec 3 | 7% | 7% | 9% | 6% | 6% | 12% | 2% | 11% | 2% |
| Cutoff 4 | 9710 | 9520 | 10000 | 9710 | 9520 | 10000 | 9710 | 9520 | 10000 |

-continued

| | | | | | | | | | |
|---|---|---|---|---|---|---|---|---|---|
| Sens 4 | 29% | 29% | 19% | 26% | 33% | 17% | 11% | 11% | 7% |
| Spec 4 | 70% | 70% | 71% | 70% | 70% | 71% | 70% | 70% | 71% |
| Cutoff 5 | 11000 | 10600 | 11300 | 11000 | 10600 | 11300 | 11000 | 10600 | 11300 |
| Sens 5 | 16% | 21% | 11% | 21% | 33% | 12% | 11% | 11% | 7% |
| Spec 5 | 81% | 80% | 81% | 81% | 80% | 81% | 81% | 80% | 81% |
| Cutoff 6 | 15300 | 14200 | 18800 | 15300 | 14200 | 18800 | 15300 | 14200 | 18800 |
| Sens 6 | 9% | 21% | 3% | 12% | 28% | 2% | 0% | 11% | 0% |
| Spec 6 | 90% | 90% | 90% | 90% | 90% | 90% | 90% | 90% | 90% |
| OR Quart 2 | 1.1 | 0.72 | 1.6 | 0.74 | 0.63 | 1.8 | 0.48 | 0 | 1.0 |
| p Value | 0.79 | 0.68 | 0.41 | 0.58 | 0.49 | 0.28 | 0.56 | na | 0.98 |
| 95% CI of | 0.41 | 0.15 | 0.53 | 0.25 | 0.17 | 0.61 | 0.041 | na | 0.062 |
| OR Quart2 | 3.2 | 3.4 | 4.8 | 2.2 | 2.4 | 5.4 | 5.6 | na | 17 |
| OR Quart | 31.0 | 0.72 | 1.4 | 1.7 | 0.31 | 2.3 | 4.3 | 4.2 | 8.8 |
| p Value | 1.0 | 0.68 | 0.57 | 0.31 | 0.16 | 0.12 | 0.086 | 0.20 | 0.049 |
| 95% CI of | 0.35 | 0.15 | 0.45 | 0.61 | 0.059 | 0.80 | 0.81 | 0.46 | 1.0 |
| OR Quart3 | 2.8 | 3.4 | 4.3 | 4.6 | 1.6 | 6.8 | 23 | 39 | 77 |
| OR Quart | 41.8 | 0.98 | 1.8 | 1.0 | 0.98 | 1.6 | 5.2 | 4.3 | 7.6 |
| p Value | 0.27 | 0.98 | 0.28 | 1.0 | 0.98 | 0.41 | 0.051 | 0.20 | 0.070 |
| 95% CI of | 0.64 | 0.23 | 0.61 | 0.35 | 0.30 | 0.53 | 0.99 | 0.47 | 0.85 |
| OR Quart4 | 4.8 | 4.1 | 5.5 | 2.8 | 3.2 | 4.8 | 27 | 40 | 67 |

| Lutropin subunit beta | | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | 4.52 | 3.87 | 4.52 | 4.46 | 4.52 | 1.63 |
| Average | 7.77 | 7.10 | 7.77 | 5.30 | 7.77 | 2.03 |
| Stdev | 10.8 | 10.6 | 10.8 | 4.52 | 10.8 | 2.17 |
| p(t-test) | | 0.79 | | 0.25 | | 0.14 |
| Min | 0.00783 | 0.0399 | 0.00783 | 0.00467 | 0.00783 | 4.11E-5 |
| Max | 66.0 | 50.0 | 66.0 | 16.5 | 66.0 | 6.33 |
| n (Samp) | 68 | 25 | 68 | 27 | 68 | 8 |
| n (Patient) | 43 | 25 | 43 | 27 | 43 | 8 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 1 | Cohort 2 | Cohort 1 |
| Median | 3.65 | 5.59 | 3.65 | 4.50 | nd | nd |
| Average | 7.37 | 6.27 | 7.37 | 5.90 | nd | nd |
| Stdev | 11.4 | 4.33 | 11.4 | 4.44 | nd | nd |
| p(t-test) | | 0.80 | | 0.74 | nd | nd |
| Min | 4.11E-5 | 1.36 | 4.11E-5 | 1.58 | nd | nd |
| Max | 66.0 | 15.3 | 66.0 | 14.5 | nd | nd |
| n (Samp) | 153 | 7 | 153 | 7 | nd | nd |
| n (Patient) | 89 | 7 | 89 | 7 | nd | nd |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 1 | Cohort 2 | Cohort 1 |
| Median | 4.52 | 3.40 | 4.52 | 4.46 | 4.52 | 1.22 |
| Average | 7.66 | 7.21 | 7.66 | 5.08 | 7.66 | 1.87 |
| Stdev | 10.3 | 11.7 | 10.3 | 4.52 | 10.3 | 2.19 |
| p(t-test) | | 0.87 | | 0.21 | | 0.12 |
| Min | 0.0621 | 0.0399 | 0.0621 | 0.00467 | 0.0621 | 4.11E-5 |
| Max | 66.0 | 50.0 | 66.0 | 16.5 | 66.0 | 6.33 |
| n (Samp) | 76 | 20 | 76 | 27 | 76 | 8 |
| n (Patient) | 43 | 20 | 43 | 27 | 43 | 8 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.46 | 0.63 | 0.42 | 0.48 | 0.59 | 0.45 | 0.26 | nd | 0.23 |
| SE | 0.068 | 0.12 | 0.074 | 0.066 | 0.12 | 0.066 | 0.10 | nd | 0.10 |
| p | 0.58 | 0.26 | 0.30 | 0.78 | 0.42 | 0.46 | 0.024 | nd | 0.0062 |
| nCohort 1 | 68 | 153 | 76 | 68 | 153 | 76 | 68 | nd | 76 |
| nCohort 2 | 25 | 7 | 20 | 27 | 7 | 27 | 8 | nd | 8 |
| Cutoff 1 | 1.85 | 5.10 | 1.85 | 2.38 | 3.52 | 1.54 | 0.471 | nd | 0.471 |
| Sens 1 | 72% | 71% | 70% | 70% | 71% | 70% | 75% | nd | 75% |
| Spec 1 | 34% | 64% | 29% | 35% | 50% | 20% | 9% | nd | 7% |
| Cutoff 2 | 1.17 | 4.12 | 0.544 | 1.40 | 2.38 | 1.32 | 4.11E-5 | nd | 4.11E-5 |
| Sens 2 | 80% | 86% | 80% | 81% | 86% | 81% | 88% | nd | 88% |
| Spec 2 | 25% | 55% | 9% | 25% | 41% | 20% | 0% | nd | 0% |
| Cutoff 3 | 0.218 | 1.17 | 0.134 | 0.218 | 1.54 | 0.158 | 0 | nd | 0 |
| Sens 3 | 92% | 100% | 90% | 93% | 100% | 93% | 100% | nd | 100% |

|  |  |  |  |  |  |  |  |  |  |
|---|---|---|---|---|---|---|---|---|---|
| Spec 3 | 6% | 29% | 4% | 6% | 33% | 4% | 0% | nd | 0% |
| Cutoff 4 | 6.94 | 6.28 | 6.94 | 6.94 | 6.28 | 6.94 | 6.94 | nd | 6.94 |
| Sens 4 | 20% | 29% | 20% | 26% | 29% | 22% | 0% | nd | 0% |
| Spec 4 | 71% | 71% | 71% | 71% | 71% | 71% | 71% | nd | 71% |
| Cutoff 5 | 11.6 | 9.89 | 9.89 | 11.6 | 9.89 | 9.89 | 11.6 | nd | 9.89 |
| Sens 5 | 20% | 14% | 20% | 15% | 14% | 15% | 0% | nd | 0% |
| Spec 5 | 81% | 80% | 80% | 81% | 80% | 80% | 81% | nd | 80% |
| Cutoff 6 | 22.6 | 18.0 | 20.6 | 22.6 | 18.0 | 20.6 | 22.6 | nd | 20.6 |
| Sens 6 | 4% | 0% | 10% | 0% | 0% | 0% | 0% | nd | 0% |
| Spec 6 | 91% | 90% | 91% | 91% | 90% | 91% | 91% | nd | 91% |
| OR Quart | 21.3 | >1.0 | 1.0 | 1.2 | >3.2 | 1.2 | >1.1 | nd | >1.0 |
| p Value | 0.67 | <0.99 | 1.0 | 0.75 | <0.32 | 0.75 | <0.97 | nd | <0.97 |
| 95% CI of | 0.35 | >0.062 | 0.22 | 0.34 | >0.32 | 0.35 | >0.061 | nd | >0.061 |
| OR Quart2 | 5.2 | na | 4.6 | 4.4 | na | 4.3 | na | nd | na |
| OR Quart 3 | 2.0 | >5.7 | 1.7 | 1.5 | >2.1 | 0.79 | >5.1 | nd | >2.2 |
| p Value | 0.29 | <0.12 | 0.48 | 0.53 | <0.55 | 0.73 | <0.17 | nd | <0.53 |
| 95% CI of | 0.55 | >0.64 | 0.40 | 0.43 | >0.18 | 0.21 | >0.51 | nd | >0.19 |
| OR Quart3 | 7.5 | na | 6.9 | 5.3 | na | 3.0 | na | nd | na |
| OR Quart 4 | 1.3 | >1.0 | 1.7 | 1.1 | >2.1 | 1.9 | >3.6 | nd | >6.6 |
| p Value | 0.67 | <0.99 | 0.48 | 0.93 | <0.55 | 0.31 | <0.29 | nd | <0.10 |
| 95% CI of | 0.35 | >0.062 | 0.40 | 0.29 | >0.18 | 0.55 | >0.34 | nd | >0.70 |
| OR Quart4 | 5.2 | na | 6.9 | 3.9 | na | 6.4 | na | nd | na |

Interstitial collagenase

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 54.1 | 65.2 | 54.1 | 46.2 | 54.1 | 92.4 |
| Average | 136 | 206 | 136 | 149 | 136 | 174 |
| Stdev | 174 | 477 | 174 | 202 | 174 | 294 |
| p(t-test) | | 0.16 | | 0.68 | | 0.39 |
| Min | 0.0125 | 0.0125 | 0.0125 | 0.0125 | 0.0125 | 0.0125 |
| Max | 764 | 3260 | 764 | 760 | 764 | 1230 |
| n (Samp) | 121 | 53 | 121 | 52 | 121 | 26 |
| n (Patient) | 87 | 53 | 87 | 52 | 87 | 26 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 53.7 | 73.9 | 53.7 | 65.2 | 53.7 | 56.4 |
| Average | 146 | 98.2 | 146 | 145 | 146 | 121 |
| Stdev | 271 | 103 | 271 | 213 | 271 | 156 |
| p(t-test) | | 0.49 | | 0.99 | | 0.77 |
| Min | 0.0125 | 0.0125 | 0.0125 | 0.0131 | 0.0125 | 0.0125 |
| Max | 3260 | 332 | 3260 | 760 | 3260 | 488 |
| n (Samp) | 287 | 16 | 287 | 15 | 287 | 10 |
| n (Patient) | 161 | 16 | 161 | 15 | 161 | 10 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 47.3 | 82.2 | 47.3 | 54.7 | 47.3 | 110 |
| Average | 113 | 236 | 113 | 149 | 113 | 195 |
| Stdev | 157 | 524 | 157 | 189 | 157 | 309 |
| p(t-test) | | 0.020 | | 0.19 | | 0.056 |
| Min | 0.0125 | 0.0131 | 0.0125 | 0.0125 | 0.0125 | 4.10 |
| Max | 711 | 3260 | 711 | 741 | 711 | 1230 |
| n (Samp) | 125 | 43 | 125 | 53 | 125 | 23 |
| n (Patient) | 80 | 43 | 80 | 53 | 80 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.51 | 0.49 | 0.59 | 0.48 | 0.48 | 0.54 | 0.51 | 0.47 | 0.61 |
| SE | 0.048 | 0.075 | 0.052 | 0.048 | 0.077 | 0.048 | 0.063 | 0.095 | 0.067 |
| p | 0.84 | 0.86 | 0.080 | 0.62 | 0.78 | 0.39 | 0.87 | 0.73 | 0.12 |
| nCohort 1 | 121 | 287 | 125 | 121 | 287 | 125 | 121 | 287 | 125 |
| nCohort 2 | 53 | 16 | 43 | 52 | 15 | 53 | 26 | 10 | 23 |
| Cutoff 1 | 18.5 | 2.35 | 31.6 | 18.2 | 2.08 | 20.2 | 24.3 | 12.0 | 38.7 |
| Sens 1 | 72% | 75% | 72% | 71% | 73% | 72% | 73% | 70% | 74% |
| Spec 1 | 24% | 15% | 39% | 23% | 15% | 33% | 31% | 23% | 43% |
| Cutoff 2 | 5.04 | 2.08 | 17.3 | 1.65 | 1.45 | 8.43 | 10.4 | 0.0270 | 24.3 |
| Sens 2 | 81% | 81% | 81% | 81% | 80% | 81% | 81% | 80% | 83% |
| Spec 2 | 13% | 15% | 30% | 12% | 14% | 23% | 18% | 10% | 37% |

-continued

| | | | | | | | | | |
|---|---|---|---|---|---|---|---|---|---|
| Cutoff 3 | 0.0281 | 0.0243 | 1.65 | 0.0131 | 0.0131 | 0.0270 | 4.08 | 0.0125 | 8.08 |
| Sens 3 | 91% | 94% | 91% | 92% | 93% | 91% | 92% | 90% | 91% |
| Spec 3 | 10% | 7% | 18% | 5% | 6% | 13% | 12% | 1% | 22% |
| Cutoff 4 | 167 | 129 | 105 | 167 | 129 | 105 | 167 | 129 | 105 |
| Sens 4 | 34% | 31% | 47% | 29% | 33% | 34% | 27% | 40% | 52% |
| Spec 4 | 70% | 70% | 70% | 70% | 70% | 70% | 70% | 70% | 70% |
| Cutoff 5 | 232 | 218 | 198 | 232 | 218 | 198 | 232 | 218 | 198 |
| Sens 5 | 21% | 12% | 30% | 25% | 20% | 26% | 12% | 20% | 17% |
| Spec 5 | 80% | 80% | 80% | 80% | 80% | 80% | 80% | 80% | 80% |
| Cutoff 6 | 354 | 406 | 333 | 354 | 406 | 333 | 354 | 406 | 333 |
| Sens 6 | 11% | 0% | 14% | 19% | 13% | 21% | 12% | 10% | 13% |
| Spec 6 | 90% | 90% | 90% | 90% | 90% | 90% | 90% | 90% | 90% |
| OR Quart 2 | 0.48 | 4.4 | 1.3 | 0.92 | 1.0 | 1.1 | 0.97 | 0.24 | 2.6 |
| p Value | 0.14 | 0.069 | 0.60 | 0.87 | 0.98 | 0.87 | 0.96 | 0.21 | 0.19 |
| 95% CI of | 0.18 | 0.89 | 0.47 | 0.36 | 0.24 | 0.43 | 0.28 | 0.027 | 0.63 |
| OR Quart2 | 1.3 | 21 | 3.8 | 2.3 | 4.2 | 2.7 | 3.3 | 2.2 | 11 |
| OR Quart 3 | 1.1 | 0.49 | 1.5 | 0.92 | 0.49 | 1.0 | 1.9 | 0.24 | 2.6 |
| p Value | 0.82 | 0.57 | 0.44 | 0.87 | 0.41 | 1.0 | 0.29 | 0.21 | 0.19 |
| 95% CI of | 0.46 | 0.044 | 0.54 | 0.36 | 0.086 | 0.39 | 0.59 | 0.027 | 0.63 |
| OR Quart3 | 2.7 | 5.6 | 4.2 | 2.3 | 2.7 | 2.6 | 5.8 | 2.2 | 11 |
| OR Quart 4 | 0.78 | 2.6 | 2.1 | 1.3 | 1.3 | 1.5 | 0.61 | 1.0 | 2.2 |
| p Value | 0.59 | 0.25 | 0.14 | 0.59 | 0.72 | 0.40 | 0.47 | 0.98 | 0.29 |
| 95% CI of | 0.32 | 0.50 | 0.78 | 0.52 | 0.33 | 0.60 | 0.16 | 0.24 | 0.50 |
| OR Quart4 | 1.9 | 14 | 5.8 | 3.1 | 5.0 | 3.6 | 2.4 | 4.2 | 9.5 |

Neural cell adhesion molecule 1

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 186000 | 192000 | 186000 | 182000 | 186000 | 174000 |
| Average | 194000 | 192000 | 194000 | 191000 | 194000 | 182000 |
| Stdev | 76100 | 67500 | 76100 | 71400 | 76100 | 61100 |
| p(t-test) | | 0.86 | | 0.86 | | 0.46 |
| Min | 73000 | 63300 | 73000 | 93300 | 73000 | 49200 |
| Max | 520000 | 371000 | 520000 | 506000 | 520000 | 297000 |
| n (Samp) | 120 | 53 | 120 | 53 | 120 | 26 |
| n (Patient) | 86 | 53 | 86 | 53 | 86 | 26 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 181000 | 199000 | 181000 | 206000 | 181000 | 183000 |
| Average | 186000 | 200000 | 186000 | 219000 | 186000 | 189000 |
| Stdev | 67200 | 62800 | 67200 | 99400 | 67200 | 58600 |
| p(t-test) | | 0.44 | | 0.080 | | 0.92 |
| Min | 49200 | 118000 | 49200 | 105000 | 49200 | 108000 |
| Max | 520000 | 316000 | 520000 | 506000 | 520000 | 280000 |
| n (Samp) | 287 | 16 | 287 | 15 | 287 | 10 |
| n (Patient) | 160 | 16 | 160 | 15 | 160 | 10 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 180000 | 182000 | 180000 | 182000 | 180000 | 172000 |
| Average | 191000 | 187000 | 191000 | 184000 | 191000 | 178000 |
| Stdev | 77000 | 69700 | 77000 | 54300 | 77000 | 59400 |
| p(t-test) | | 0.72 | | 0.52 | | 0.44 |
| Min | 73000 | 63300 | 73000 | 93300 | 73000 | 49200 |
| Max | 520000 | 371000 | 520000 | 337000 | 520000 | 297000 |
| n (Samp) | 124 | 43 | 124 | 54 | 124 | 23 |
| n (Patient) | 79 | 43 | 79 | 54 | 79 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.51 | 0.57 | 0.49 | 0.49 | 0.59 | 0.50 | 0.48 | 0.52 | 0.48 |
| SE | 0.048 | 0.076 | 0.051 | 0.048 | 0.079 | 0.047 | 0.063 | 0.094 | 0.066 |
| p | 0.84 | 0.33 | 0.91 | 0.88 | 0.23 | 0.98 | 0.80 | 0.80 | 0.80 |
| nCohort 1 | 120 | 287 | 124 | 120 | 287 | 124 | 120 | 287 | 124 |
| nCohort 2 | 53 | 16 | 43 | 53 | 15 | 54 | 26 | 10 | 23 |
| Cutoff 1 | 151000 | 160000 | 141000 | 161000 | 166000 | 161000 | 147000 | 169000 | 147000 |
| Sens 1 | 72% | 75% | 72% | 72% | 73% | 70% | 73% | 70% | 74% |
| Spec 1 | 31% | 36% | 23% | 36% | 40% | 37% | 26% | 40% | 28% |
| Cutoff 2 | 133000 | 125000 | 119000 | 135000 | 164000 | 133000 | 125000 | 144000 | 125000 |

-continued

| | | | | | | | | | |
|---|---|---|---|---|---|---|---|---|---|
| Sens 2 | 81% | 81% | 81% | 81% | 80% | 81% | 81% | 80% | 83% |
| Spec 2 | 18% | 16% | 11% | 18% | 38% | 21% | 12% | 25% | 15% |
| Cutoff 3 | 105000 | 118000 | 105000 | 111000 | 129000 | 111000 | 115000 | 115000 | 119000 |
| Sens 3 | 91% | 94% | 91% | 91% | 93% | 91% | 92% | 90% | 91% |
| Spec 3 | 8% | 13% | 6% | 8% | 18% | 7% | 10% | 13% | 11% |
| Cutoff 4 | 212000 | 207000 | 209000 | 212000 | 207000 | 209000 | 212000 | 207000 | 209000 |
| Sens 4 | 30% | 44% | 33% | 30% | 47% | 26% | 35% | 30% | 35% |
| Spec 4 | 70% | 70% | 70% | 70% | 70% | 70% | 70% | 70% | 70% |
| Cutoff 5 | 227000 | 227000 | 228000 | 227000 | 227000 | 228000 | 227000 | 227000 | 228000 |
| Sens 5 | 25% | 38% | 21% | 26% | 40% | 24% | 35% | 30% | 35% |
| Spec 5 | 80% | 80% | 81% | 80% | 80% | 81% | 80% | 80% | 81% |
| Cutoff 6 | 262000 | 263000 | 257000 | 262000 | 263000 | 257000 | 262000 | 263000 | 257000 |
| Sens 6 | 13% | 12% | 14% | 8% | 13% | 9% | 12% | 20% | 9% |
| Spec 6 | 90% | 90% | 90% | 90% | 90% | 90% | 90% | 90% | 90% |
| OR Quart 2 | 0.80 | 0.48 | 1.0 | 0.66 | 1.3 | 1.0 | 0.18 | 1.5 | 0.21 |
| p Value | 0.64 | 0.40 | 1.0 | 0.39 | 0.71 | 0.94 | 0.039 | 0.65 | 0.058 |
| 95% CI of | 0.32 | 0.085 | 0.38 | 0.26 | 0.29 | 0.42 | 0.037 | 0.25 | 0.041 |
| OR Quart2 | 2.0 | 2.7 | 2.6 | 1.7 | 6.2 | 2.5 | 0.92 | 9.4 | 1.1 |
| OR Quart 3 | 0.80 | 0.99 | 0.77 | 0.84 | 0.66 | 0.81 | 0.86 | 1.0 | 0.85 |
| p Value | 0.64 | 0.98 | 0.61 | 0.70 | 0.65 | 0.64 | 0.78 | 1.0 | 0.77 |
| 95% CI of | 0.32 | 0.24 | 0.28 | 0.34 | 0.11 | 0.32 | 0.29 | 0.14 | 0.27 |
| OR Quart3 | 2.0 | 4.1 | 2.1 | 2.1 | 4.1 | 2.0 | 2.5 | 7.3 | 2.6 |
| OR Quart | 41.1 | 1.5 | 1.2 | 0.93 | 2.1 | 1.0 | 0.75 | 1.5 | 0.72 |
| p Value | 0.88 | 0.53 | 0.75 | 0.88 | 0.32 | 0.94 | 0.61 | 0.66 | 0.59 |
| 95% CI of | 0.44 | 0.41 | 0.45 | 0.38 | 0.50 | 0.42 | 0.25 | 0.24 | 0.22 |
| OR Quart4 | 2.6 | 5.6 | 3.1 | 2.3 | 8.5 | 2.5 | 2.3 | 9.2 | 2.3 |

| Platelet-derived growth factor subunit B (dimer) | | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | 358 | 321 | 358 | 367 | 358 | 468 |
| Average | 426 | 373 | 426 | 433 | 426 | 470 |
| Stdev | 264 | 206 | 264 | 405 | 264 | 204 |
| p(t-test) | | 0.19 | | 0.89 | | 0.45 |
| Min | 39.4 | 33.7 | 39.4 | 0.189 | 39.4 | 91.4 |
| Max | 1540 | 854 | 1540 | 2690 | 1540 | 836 |
| n (Samp) | 119 | 52 | 119 | 49 | 119 | 24 |
| n (Patient) | 85 | 52 | 85 | 49 | 85 | 24 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 348 | 260 | 348 | 283 | 348 | 425 |
| Average | 399 | 346 | 399 | 503 | 399 | 454 |
| Stdev | 245 | 218 | 245 | 670 | 245 | 238 |
| p(t-test) | | 0.40 | | 0.17 | | 0.49 |
| Min | 0.189 | 43.4 | 0.189 | 33.7 | 0.189 | 129 |
| Max | 1540 | 807 | 1540 | 2690 | 1540 | 836 |
| n (Samp) | 278 | 16 | 278 | 14 | 278 | 10 |
| n (Patient) | 157 | 16 | 157 | 14 | 157 | 10 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 321 | 321 | 321 | 363 | 321 | 463 |
| Average | 378 | 377 | 378 | 399 | 378 | 444 |
| Stdev | 249 | 208 | 249 | 249 | 249 | 209 |
| p(t-test) | | 0.99 | | 0.61 | | 0.25 |
| Min | 28.1 | 33.7 | 28.1 | 0.189 | 28.1 | 48.9 |
| Max | 1540 | 854 | 1540 | 1260 | 1540 | 813 |
| n (Samp) | 123 | 42 | 123 | 50 | 123 | 21 |
| n (Patient) | 78 | 42 | 78 | 50 | 78 | 21 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.45 | 0.44 | 0.52 | 0.47 | 0.45 | 0.53 | 0.58 | 0.58 | 0.61 |
| SE | 0.048 | 0.076 | 0.052 | 0.049 | 0.081 | 0.049 | 0.066 | 0.096 | 0.070 |
| p | 0.31 | 0.43 | 0.72 | 0.54 | 0.54 | 0.56 | 0.21 | 0.42 | 0.11 |
| nCohort 1 | 119 | 278 | 123 | 119 | 278 | 123 | 119 | 278 | 123 |
| nCohort 2 | 52 | 16 | 42 | 49 | 14 | 50 | 24 | 10 | 21 |
| Cutoff 1 | 238 | 194 | 238 | 250 | 220 | 250 | 301 | 277 | 300 |
| Sens 1 | 71% | 75% | 71% | 71% | 71% | 70% | 71% | 70% | 71% |

-continued

| | | | | | | | | | |
|---|---|---|---|---|---|---|---|---|---|
| Spec 1 | 24% | 21% | 32% | 27% | 25% | 35% | 35% | 37% | 45% |
| Cutoff 2 | 218 | 192 | 220 | 202 | 150 | 218 | 259 | 247 | 259 |
| Sens 2 | 81% | 81% | 81% | 82% | 86% | 80% | 83% | 80% | 81% |
| Spec 2 | 22% | 21% | 29% | 19% | 15% | 29% | 32% | 29% | 41% |
| Cutoff 3 | 135 | 117 | 135 | 122 | 145 | 122 | 229 | 242 | 211 |
| Sens 3 | 90% | 94% | 90% | 92% | 93% | 90% | 92% | 90% | 90% |
| Spec 3 | 10% | 11% | 15% | 8% | 14% | 12% | 24% | 28% | 27% |
| Cutoff 4 | 539 | 497 | 475 | 539 | 497 | 475 | 539 | 497 | 475 |
| Sens 4 | 21% | 31% | 24% | 18% | 21% | 34% | 38% | 50% | 43% |
| Spec 4 | 71% | 70% | 71% | 71% | 70% | 71% | 71% | 70% | 71% |
| Cutoff 5 | 618 | 599 | 544 | 618 | 599 | 544 | 618 | 599 | 544 |
| Sens 5 | 13% | 19% | 21% | 16% | 14% | 18% | 21% | 40% | 33% |
| Spec 5 | 81% | 80% | 80% | 81% | 80% | 80% | 81% | 80% | 80% |
| Cutoff 6 | 741 | 721 | 673 | 741 | 721 | 673 | 741 | 721 | 673 |
| Sens 6 | 10% | 6% | 14% | 8% | 14% | 14% | 8% | 10% | 14% |
| Spec 6 | 91% | 90% | 90% | 91% | 90% | 90% | 91% | 90% | 90% |
| OR Quart 2 | 1.3 | 0.75 | 2.5 | 2.9 | 0.66 | 1.1 | 1.2 | 4.2 | 1.4 |
| p Value | 0.63 | 0.71 | 0.081 | 0.035 | 0.65 | 0.80 | 0.76 | 0.21 | 0.69 |
| 95% CI of | 0.49 | 0.16 | 0.89 | 1.1 | 0.11 | 0.42 | 0.31 | 0.46 | 0.28 |
| OR Quart2 | 3.2 | 3.5 | 7.1 | 7.7 | 4.1 | 3.0 | 5.1 | 38 | 6.6 |
| OR Quart 3 | 1.4 | 1.0 | 2.0 | 1.5 | 1.7 | 2.2 | 1.6 | 1.0 | 2.7 |
| p Value | 0.48 | 1.0 | 0.19 | 0.44 | 0.47 | 0.11 | 0.53 | 1.0 | 0.18 |
| 95% CI of | 0.55 | 0.24 | 0.70 | 0.54 | 0.39 | 0.85 | 0.40 | 0.061 | 0.63 |
| OR Quart3 | 3.6 | 4.2 | 5.8 | 4.2 | 7.5 | 5.5 | 6.0 | 16 | 11 |
| OR Quart 4 | 1.5 | 1.3 | 1.3 | 1.9 | 1.4 | 1.2 | 2.6 | 4.2 | 2.7 |
| p Value | 0.43 | 0.72 | 0.62 | 0.21 | 0.70 | 0.67 | 0.15 | 0.21 | 0.18 |
| 95% CI of | 0.57 | 0.33 | 0.44 | 0.69 | 0.29 | 0.47 | 0.71 | 0.46 | 0.63 |
| OR Quart4 | 3.7 | 5.0 | 4.0 | 5.2 | 6.3 | 3.3 | 9.3 | 38 | 11 |

Thyroxine-binding globulin

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 38.2 | 37.2 | 38.2 | 33.1 | 38.2 | 32.2 |
| Average | 39.2 | 36.8 | 39.2 | 34.5 | 39.2 | 34.4 |
| Stdev | 11.0 | 10.3 | 11.0 | 9.68 | 11.0 | 9.33 |
| p(t-test) | | 0.15 | | 0.0040 | | 0.034 |
| Min | 13.4 | 12.8 | 13.4 | 13.9 | 13.4 | 16.3 |
| Max | 75.8 | 56.7 | 75.8 | 56.1 | 75.8 | 51.1 |
| n (Samp) | 262 | 51 | 262 | 55 | 262 | 26 |
| n (Patient) | 110 | 51 | 110 | 55 | 110 | 26 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 36.0 | 33.2 | 36.0 | 33.2 | 36.0 | 33.2 |
| Average | 37.2 | 36.1 | 37.2 | 35.1 | 37.2 | 35.6 |
| Stdev | 11.3 | 10.9 | 11.3 | 9.71 | 11.3 | 7.59 |
| p(t-test) | | 0.69 | | 0.42 | | 0.63 |
| Min | 12.8 | 23.2 | 12.8 | 22.7 | 12.8 | 26.8 |
| Max | 75.8 | 63.7 | 75.8 | 62.0 | 75.8 | 51.1 |
| n (Samp) | 466 | 18 | 466 | 20 | 466 | 13 |
| n (Patient) | 180 | 18 | 180 | 20 | 180 | 13 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 36.8 | 34.2 | 36.8 | 33.2 | 36.8 | 32.1 |
| Average | 38.0 | 35.7 | 38.0 | 34.3 | 38.0 | 34.2 |
| Stdev | 10.4 | 10.8 | 10.4 | 9.95 | 10.4 | 10.2 |
| p(t-test) | | 0.17 | | 0.023 | | 0.099 |
| Min | 13.4 | 12.8 | 13.4 | 13.9 | 13.4 | 16.3 |
| Max | 75.8 | 56.7 | 75.8 | 56.1 | 75.8 | 51.1 |
| n (Samp) | 221 | 50 | 221 | 52 | 221 | 23 |
| n (Patient) | 91 | 50 | 91 | 52 | 91 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.44 | 0.45 | 0.44 | 0.38 | 0.43 | 0.40 | 0.37 | 0.46 | 0.40 |
| SE | 0.045 | 0.071 | 0.046 | 0.043 | 0.068 | 0.045 | 0.061 | 0.083 | 0.065 |
| p | 0.22 | 0.52 | 0.23 | 0.0041 | 0.30 | 0.030 | 0.037 | 0.61 | 0.14 |
| nCohort 1 | 262 | 466 | 221 | 262 | 466 | 221 | 262 | 466 | 221 |
| nCohort 2 | 51 | 18 | 50 | 55 | 20 | 52 | 26 | 13 | 23 |

-continued

| | | | | | | | | | |
|---|---|---|---|---|---|---|---|---|---|
| Cutoff 1 | 29.1 | 28.0 | 29.1 | 28.7 | 28.5 | 27.9 | 28.1 | 29.8 | 28.0 |
| Sens 1 | 71% | 72% | 70% | 71% | 70% | 71% | 73% | 77% | 74% |
| Spec 1 | 19% | 22% | 22% | 18% | 24% | 16% | 15% | 28% | 16% |
| Cutoff 2 | 26.5 | 26.7 | 26.5 | 26.5 | 28.3 | 25.0 | 27.8 | 29.4 | 27.4 |
| Sens 2 | 80% | 83% | 80% | 80% | 80% | 81% | 81% | 85% | 87% |
| Spec 2 | 11% | 18% | 12% | 11% | 23% | 10% | 14% | 27% | 14% |
| Cutoff 3 | 24.2 | 24.4 | 23.7 | 22.5 | 25.7 | 21.4 | 26.5 | 27.8 | 17.9 |
| Sens 3 | 90% | 94% | 90% | 91% | 90% | 90% | 92% | 92% | 91% |
| Spec 3 | 7% | 12% | 6% | 5% | 15% | 4% | 11% | 21% | 2% |
| Cutoff 4 | 44.9 | 43.4 | 43.6 | 44.9 | 43.4 | 43.6 | 44.9 | 43.4 | 43.6 |
| Sens 4 | 25% | 22% | 28% | 18% | 20% | 19% | 19% | 15% | 22% |
| Spec 4 | 70% | 70% | 71% | 70% | 70% | 71% | 70% | 70% | 71% |
| Cutoff 5 | 47.3 | 46.4 | 46.3 | 47.3 | 46.4 | 46.3 | 47.3 | 46.4 | 46.3 |
| Sens 5 | 14% | 17% | 20% | 11% | 10% | 15% | 8% | 15% | 22% |
| Spec 5 | 80% | 80% | 80% | 80% | 80% | 80% | 80% | 80% | 80% |
| Cutoff 6 | 52.5 | 50.3 | 49.9 | 52.5 | 50.3 | 49.9 | 52.5 | 50.3 | 49.9 |
| Sens 6 | 6% | 11% | 10% | 4% | 5% | 6% | 0% | 8% | 9% |
| Spec 6 | 90% | 90% | 90% | 90% | 90% | 90% | 90% | 90% | 90% |
| OR Quart 2 | 1.1 | 1.7 | 0.65 | 1.6 | 0.75 | 1.1 | 0.79 | 1.5 | 0.58 |
| p Value | 0.80 | 0.48 | 0.35 | 0.33 | 0.71 | 0.78 | 0.73 | 0.65 | 0.47 |
| 95% CI of | 0.47 | 0.40 | 0.26 | 0.62 | 0.16 | 0.45 | 0.20 | 0.25 | 0.13 |
| OR Quart2 | 2.6 | 7.3 | 1.6 | 4.2 | 3.4 | 2.9 | 3.1 | 9.2 | 2.5 |
| OR Quart 3 | 0.73 | 1.0 | 0.91 | 1.9 | 1.5 | 1.3 | 1.4 | 3.1 | 1.5 |
| p Value | 0.50 | 1.0 | 0.82 | 0.16 | 0.52 | 0.62 | 0.55 | 0.17 | 0.54 |
| 95% CI of | 0.29 | 0.20 | 0.38 | 0.76 | 0.42 | 0.51 | 0.44 | 0.61 | 0.43 |
| OR Quart3 | 1.8 | 5.1 | 2.2 | 4.9 | 5.5 | 3.2 | 4.8 | 16 | 4.9 |
| OR Quart 4 | 1.6 | 2.4 | 1.3 | 3.3 | 1.8 | 2.3 | 2.2 | 1.0 | 1.7 |
| p Value | 0.29 | 0.21 | 0.50 | 0.0089 | 0.35 | 0.058 | 0.18 | 0.99 | 0.38 |
| 95% CI of | 0.69 | 0.61 | 0.58 | 1.3 | 0.52 | 0.97 | 0.70 | 0.14 | 0.52 |
| OR Quart4 | 3.5 | 9.6 | 3.0 | 7.9 | 6.4 | 5.4 | 6.7 | 7.3 | 5.5 |

Pigment epithelium-derived factor

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 1630 | 1820 | 1630 | 1420 | 1630 | 1640 |
| Average | 1720 | 2180 | 1720 | 1690 | 1720 | 1580 |
| Stdev | 753 | 1290 | 753 | 987 | 753 | 695 |
| p(t-test) | | 0.0042 | | 0.78 | | 0.36 |
| Min | 445 | 317 | 445 | 339 | 445 | 347 |
| Max | 4240 | 5620 | 4240 | 4750 | 4240 | 3400 |
| n (Samp) | 121 | 53 | 121 | 53 | 121 | 26 |
| n (Patient) | 87 | 53 | 87 | 53 | 87 | 26 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 1660 | 1950 | 1660 | 1670 | 1660 | 1960 |
| Average | 1920 | 2130 | 1920 | 1820 | 1920 | 2000 |
| Stdev | 1150 | 1270 | 1150 | 1050 | 1150 | 998 |
| p(t-test) | | 0.47 | | 0.77 | | 0.82 |
| Min | 84.2 | 328 | 84.2 | 629 | 84.2 | 813 |
| Max | 7450 | 4300 | 7450 | 4910 | 7450 | 4360 |
| n (Samp) | 288 | 16 | 288 | 15 | 288 | 10 |
| n (Patient) | 161 | 16 | 161 | 15 | 161 | 10 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 1560 | 1740 | 1560 | 1400 | 1560 | 1510 |
| Average | 1720 | 2200 | 1720 | 1690 | 1720 | 1480 |
| Stdev | 787 | 1320 | 787 | 1020 | 787 | 701 |
| p(t-test) | | 0.0046 | | 0.87 | | 0.19 |
| Min | 328 | 317 | 328 | 339 | 328 | 347 |
| Max | 4510 | 5620 | 4510 | 4750 | 4510 | 3400 |
| n (Samp) | 125 | 43 | 125 | 54 | 125 | 23 |
| n (Patient) | 80 | 43 | 80 | 54 | 80 | 23 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.58 | 0.55 | 0.59 | 0.44 | 0.49 | 0.45 | 0.47 | 0.57 | 0.43 |
| SE | 0.048 | 0.076 | 0.052 | 0.048 | 0.077 | 0.047 | 0.063 | 0.096 | 0.067 |
| p | 0.082 | 0.52 | 0.067 | 0.24 | 0.88 | 0.28 | 0.63 | 0.49 | 0.30 |

-continued

| | | | | | | | | | |
|---|---|---|---|---|---|---|---|---|---|
| nCohort 1 | 121 | 288 | 125 | 121 | 288 | 125 | 121 | 288 | 125 |
| nCohort 2 | 53 | 16 | 43 | 53 | 15 | 54 | 26 | 10 | 23 |
| Cutoff 1 | 1310 | 1170 | 1340 | 1150 | 1280 | 1150 | 1190 | 1770 | 1040 |
| Sens 1 | 72% | 75% | 72% | 72% | 73% | 70% | 73% | 70% | 74% |
| Spec 1 | 32% | 26% | 35% | 22% | 32% | 22% | 27% | 58% | 18% |
| Cutoff 2 | 1060 | 1080 | 1060 | 813 | 1220 | 812 | 1030 | 1450 | 760 |
| Sens 2 | 81% | 81% | 81% | 81% | 80% | 81% | 81% | 80% | 83% |
| Spec 2 | 19% | 22% | 20% | 8% | 29% | 7% | 17% | 41% | 7% |
| Cutoff 3 | 974 | 529 | 999 | 733 | 760 | 677 | 591 | 852 | 529 |
| Sens 3 | 91% | 94% | 91% | 91% | 93% | 91% | 92% | 90% | 91% |
| Spec 3 | 13% | 4% | 15% | 7% | 9% | 6% | 3% | 10% | 2% |
| Cutoff 4 | 1970 | 2080 | 1970 | 1970 | 2080 | 1970 | 1970 | 2080 | 1970 |
| Sens 4 | 45% | 44% | 44% | 25% | 33% | 28% | 27% | 30% | 17% |
| Spec 4 | 70% | 70% | 70% | 70% | 70% | 70% | 70% | 70% | 70% |
| Cutoff 5 | 2210 | 2510 | 2160 | 2210 | 2510 | 2160 | 2210 | 2510 | 2160 |
| Sens 5 | 38% | 31% | 40% | 21% | 13% | 26% | 12% | 10% | 9% |
| Spec 5 | 80% | 80% | 80% | 80% | 80% | 80% | 80% | 80% | 80% |
| Cutoff 6 | 2820 | 3520 | 2830 | 2820 | 3520 | 2830 | 2820 | 3520 | 2830 |
| Sens 6 | 25% | 31% | 23% | 11% | 7% | 13% | 4% | 10% | 4% |
| Spec 6 | 90% | 90% | 90% | 90% | 90% | 90% | 90% | 90% | 90% |
| OR Quart 2 | 0.68 | 0.74 | 0.64 | 0.72 | 1.7 | 0.43 | 2.7 | 0.49 | 1.9 |
| p Value | 0.43 | 0.70 | 0.42 | 0.51 | 0.47 | 0.095 | 0.14 | 0.56 | 0.33 |
| 95% CI of | 0.26 | 0.16 | 0.22 | 0.28 | 0.39 | 0.16 | 0.74 | 0.043 | 0.51 |
| OR Quart2 | 1.8 | 3.4 | 1.9 | 1.9 | 7.4 | 1.2 | 9.5 | 5.5 | 7.2 |
| OR Quart 3 | 0.70 | 1.0 | 0.87 | 1.1 | 1.4 | 0.90 | 1.6 | 2.1 | 1.3 |
| p Value | 0.47 | 1.0 | 0.79 | 0.82 | 0.70 | 0.82 | 0.50 | 0.41 | 0.72 |
| 95% CI of | 0.27 | 0.24 | 0.31 | 0.45 | 0.29 | 0.37 | 0.41 | 0.37 | 0.32 |
| OR Quart3 | 1.8 | 4.2 | 2.4 | 2.8 | 6.3 | 2.2 | 6.2 | 12 | 5.2 |
| OR Quart 4 | 1.9 | 1.3 | 2.2 | 1.4 | 1.0 | 1.3 | 2.0 | 1.5 | 1.9 |
| p Value | 0.15 | 0.73 | 0.11 | 0.45 | 0.99 | 0.60 | 0.31 | 0.66 | 0.33 |
| 95% CI of | 0.80 | 0.33 | 0.85 | 0.58 | 0.20 | 0.53 | 0.53 | 0.24 | 0.51 |
| OR Quart4 | 4.6 | 4.9 | 5.6 | 3.5 | 5.2 | 3.0 | 7.5 | 9.2 | 7.2 |

Tumor necrosis factor receptor superfamily member 8

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | 96.5 | 104 | 96.5 | 122 | 96.5 | 123 |
| Average | 184 | 201 | 184 | 187 | 184 | 122 |
| Stdev | 461 | 420 | 461 | 202 | 461 | 70.9 |
| p(t-test) | | 0.83 | | 0.97 | | 0.57 |
| Min | 12.8 | 19.4 | 12.8 | 12.8 | 12.8 | 4.06 |
| Max | 3360 | 2810 | 3360 | 1040 | 3360 | 288 |
| n (Samp) | 94 | 45 | 94 | 42 | 94 | 18 |
| n (Patient) | 65 | 45 | 65 | 42 | 65 | 18 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 101 | 97.7 | 101 | 163 | 101 | 103 |
| Average | 199 | 192 | 199 | 343 | 199 | 115 |
| Stdev | 425 | 225 | 425 | 395 | 425 | 71.5 |
| p(t-test) | | 0.95 | | 0.17 | | 0.55 |
| Min | 4.06 | 39.7 | 4.06 | 33.2 | 4.06 | 56.2 |
| Max | 3360 | 726 | 3360 | 1460 | 3360 | 288 |
| n (Samp) | 225 | 14 | 225 | 18 | 225 | 9 |
| n (Patient) | 132 | 14 | 132 | 18 | 132 | 9 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 100 | 96.4 | 100 | 101 | 100 | 116 |
| Average | 211 | 184 | 211 | 129 | 211 | 110 |
| Stdev | 468 | 447 | 468 | 102 | 468 | 66.6 |
| p(t-test) | | 0.76 | | 0.27 | | 0.41 |
| Min | 12.8 | 19.4 | 12.8 | 12.8 | 12.8 | 4.06 |
| Max | 3360 | 2810 | 3360 | 595 | 3360 | 208 |
| n (Samp) | 103 | 37 | 103 | 41 | 103 | 15 |
| n (Patient) | 64 | 37 | 64 | 41 | 64 | 15 |

-continued

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | 0.55 | 0.51 | 0.50 | 0.62 | 0.66 | 0.51 | 0.54 | 0.46 | 0.47 |
| SE | 0.053 | 0.080 | 0.056 | 0.054 | 0.072 | 0.054 | 0.076 | 0.10 | 0.081 |
| p | 0.32 | 0.94 | 0.93 | 0.031 | 0.025 | 0.85 | 0.56 | 0.67 | 0.74 |
| nCohort 1 | 94 | 225 | 103 | 94 | 225 | 103 | 94 | 225 | 103 |
| nCohort 2 | 45 | 14 | 37 | 42 | 18 | 41 | 18 | 9 | 15 |
| Cutoff 1 | 76.5 | 76.5 | 75.6 | 96.4 | 104 | 83.2 | 84.9 | 65.4 | 56.2 |
| Sens 1 | 71% | 71% | 70% | 71% | 72% | 71% | 72% | 78% | 73% |
| Spec 1 | 36% | 33% | 33% | 50% | 51% | 40% | 44% | 23% | 18% |
| Cutoff 2 | 74.6 | 62.3 | 73.4 | 83.2 | 82.7 | 68.4 | 56.2 | 56.6 | 54.3 |
| Sens 2 | 80% | 86% | 81% | 81% | 83% | 80% | 83% | 89% | 80% |
| Spec 2 | 34% | 20% | 31% | 41% | 36% | 28% | 19% | 16% | 17% |
| Cutoff 3 | 62.3 | 53.7 | 62.3 | 68.4 | 50.8 | 47.2 | 34.2 | 54.3 | 36.7 |
| Sens 3 | 91% | 93% | 92% | 90% | 94% | 90% | 94% | 100% | 93% |
| Spec 3 | 24% | 13% | 23% | 31% | 12% | 15% | 10% | 14% | 11% |
| Cutoff 4 | 145 | 151 | 149 | 145 | 151 | 149 | 145 | 151 | 149 |
| Sens 4 | 29% | 21% | 19% | 33% | 56% | 20% | 33% | 11% | 40% |
| Spec 4 | 70% | 70% | 71% | 70% | 70% | 71% | 70% | 70% | 71% |
| Cutoff 5 | 178 | 205 | 192 | 178 | 205 | 192 | 178 | 205 | 192 |
| Sens 5 | 16% | 21% | 11% | 24% | 33% | 15% | 22% | 11% | 13% |
| Spec 5 | 81% | 80% | 81% | 81% | 80% | 81% | 81% | 80% | 81% |
| Cutoff 6 | 258 | 285 | 318 | 258 | 285 | 318 | 258 | 285 | 318 |
| Sens 6 | 11% | 21% | 3% | 17% | 33% | 5% | 6% | 11% | 0% |
| Spec 6 | 90% | 91% | 90% | 90% | 91% | 90% | 90% | 91% | 90% |
| OR Quart 2 | 5.5 | 0.72 | 3.2 | 4.1 | 1.5 | 1.8 | 0.17 | 4.3 | 1.0 |
| p Value | 0.0040 | 0.68 | 0.039 | 0.028 | 0.66 | 0.30 | 0.12 | 0.20 | 0.96 |
| 95% CI of | 1.7 | 0.15 | 1.1 | 1.2 | 0.24 | 0.61 | 0.019 | 0.47 | 0.23 |
| OR Quart2 | 17 | 3.4 | 9.8 | 14 | 9.3 | 5.0 | 1.6 | 40 | 4.6 |
| OR Quart 3 | 3.4 | 0.98 | 1.9 | 5.2 | 2.6 | 2.2 | 1.5 | 1.0 | 0.22 |
| p Value | 0.039 | 0.98 | 0.26 | 0.0091 | 0.27 | 0.13 | 0.52 | 1.0 | 0.19 |
| 95% CI of | 1.1 | 0.23 | 0.62 | 1.5 | 0.48 | 0.79 | 0.42 | 0.061 | 0.024 |
| OR Quart3 | 11 | 4.1 | 6.1 | 18 | 14 | 6.3 | 5.6 | 16 | 2.1 |
| OR Quart 4 | 2.3 | 0.72 | 1.2 | 4.1 | 4.4 | 0.84 | 1.0 | 3.2 | 1.7 |
| p Value | 0.17 | 0.68 | 0.76 | 0.028 | 0.069 | 0.77 | 1.0 | 0.32 | 0.45 |
| 95% CI of | 0.70 | 0.15 | 0.36 | 1.2 | 0.89 | 0.27 | 0.25 | 0.32 | 0.42 |
| OR Quart4 | 7.7 | 3.4 | 4.0 | 14 | 22 | 2.6 | 3.9 | 31 | 6.8 |

| Alpha-fetoprotein | | | | | | |
| --- | --- | --- | --- | --- | --- | --- |
|  | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | 0.324 | 0.333 | 0.324 | 0.394 | 0.324 | 0.477 |
| Average | 0.366 | 0.334 | 0.366 | 0.418 | 0.366 | 0.480 |
| Stdev | 0.364 | 0.323 | 0.364 | 0.325 | 0.364 | 0.292 |
| p(t-test) |  | 0.58 |  | 0.37 |  | 0.14 |
| Min | 0.00580 | 0.00580 | 0.00580 | 0.00580 | 0.00580 | 0.00580 |
| Max | 1.81 | 1.31 | 1.81 | 1.53 | 1.81 | 1.42 |
| n (Samp) | 121 | 53 | 121 | 53 | 121 | 26 |
| n (Patient) | 87 | 53 | 87 | 53 | 87 | 26 |
| sCr only | Cohort 1 | Cohort 2 | Cohort 1 | Cohort 2 | Cohort 1 | Cohort 2 |
| Median | 0.329 | 0.438 | 0.329 | 0.547 | 0.329 | 0.484 |
| Average | 0.355 | 0.401 | 0.355 | 0.502 | 0.355 | 0.488 |
| Stdev | 0.344 | 0.363 | 0.344 | 0.401 | 0.344 | 0.316 |
| p(t-test) |  | 0.61 |  | 0.11 |  | 0.23 |
| Min | 0.00580 | 0.00580 | 0.00580 | 0.00580 | 0.00580 | 0.00580 |
| Max | 1.81 | 1.11 | 1.81 | 1.40 | 1.81 | 0.979 |
| n (Samp) | 288 | 16 | 288 | 15 | 288 | 10 |
| n (Patient) | 161 | 16 | 161 | 15 | 161 | 10 |
| UO only | Cohort 1 | Cohort 2 | Cohort 1 | Cohort 2 | Cohort 1 | Cohort 2 |
| Median | 0.309 | 0.289 | 0.309 | 0.400 | 0.309 | 0.445 |
| Average | 0.341 | 0.311 | 0.341 | 0.444 | 0.341 | 0.437 |
| Stdev | 0.366 | 0.308 | 0.366 | 0.352 | 0.366 | 0.303 |
| p(t-test) |  | 0.63 |  | 0.082 |  | 0.24 |
| Min | 0.00580 | 0.00580 | 0.00580 | 0.00580 | 0.00580 | 0.00580 |

-continued

|  | | | | | | | | |
|---|---|---|---|---|---|---|---|---|
| Max | 1.81 | 1.31 | 1.81 | 1.53 | 1.81 | 1.42 | | |
| n (Samp) | 125 | 43 | 125 | 54 | 125 | 23 | | |
| n (Patient) | 80 | 43 | 80 | 54 | 80 | 23 | | |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.48 | 0.56 | 0.49 | 0.57 | 0.61 | 0.60 | 0.64 | 0.65 | 0.62 |
| SE | 0.048 | 0.076 | 0.051 | 0.048 | 0.079 | 0.047 | 0.063 | 0.096 | 0.067 |
| p | 0.70 | 0.47 | 0.81 | 0.16 | 0.18 | 0.028 | 0.029 | 0.12 | 0.073 |
| nCohort 1 | 121 | 288 | 125 | 121 | 288 | 125 | 121 | 288 | 125 |
| nCohort 2 | 53 | 16 | 43 | 53 | 15 | 54 | 26 | 10 | 23 |
| Cutoff 1 | 0.00580 | 0.00580 | 0.00580 | 0.272 | 0.207 | 0.272 | 0.347 | 0.392 | 0.272 |
| Sens 1 | 79% | 88% | 79% | 72% | 73% | 72% | 73% | 70% | 74% |
| Spec 1 | 16% | 16% | 19% | 42% | 39% | 46% | 55% | 62% | 46% |
| Cutoff 2 | 0 | 0.00580 | 0 | 0.00580 | 0 | 0.00580 | 0.272 | 0.387 | 0.173 |
| Sens 2 | 100% | 88% | 100% | 89% | 100% | 93% | 81% | 80% | 83% |
| Spec 2 | 0% | 16% | 0% | 16% | 0% | 19% | 42% | 61% | 42% |
| Cutoff 3 | 0 | 0 | 0 | 0 | 0 | 0.00580 | 0.0850 | 0.00580 | 0.0687 |
| Sens 3 | 100% | 100% | 100% | 100% | 100% | 93% | 92% | 90% | 91% |
| Spec 3 | 0% | 0% | 0% | 0% | 0% | 19% | 31% | 16% | 38% |
| Cutoff 4 | 0.446 | 0.485 | 0.446 | 0.446 | 0.485 | 0.446 | 0.446 | 0.485 | 0.446 |
| Sens 4 | 32% | 50% | 28% | 38% | 60% | 39% | 50% | 50% | 48% |
| Spec 4 | 70% | 70% | 70% | 70% | 70% | 70% | 70% | 70% | 70% |
| Cutoff 5 | 0.607 | 0.585 | 0.588 | 0.607 | 0.585 | 0.588 | 0.607 | 0.585 | 0.588 |
| Sens 5 | 17% | 31% | 14% | 21% | 40% | 26% | 27% | 40% | 22% |
| Spec 5 | 80% | 80% | 80% | 80% | 80% | 80% | 80% | 80% | 80% |
| Cutoff 6 | 0.836 | 0.767 | 0.836 | 0.836 | 0.767 | 0.836 | 0.836 | 0.767 | 0.836 |
| Sens 6 | 8% | 12% | 7% | 8% | 20% | 11% | 8% | 20% | 4% |
| Spec 6 | 90% | 90% | 90% | 90% | 90% | 90% | 90% | 90% | 90% |
| OR Quart 2 | 1.3 | 2.1 | 1.5 | 1.8 | 0.24 | 1.6 | 6.8 | 0 | 8.4 |
| p Value | 0.59 | 0.41 | 0.45 | 0.24 | 0.20 | 0.34 | 0.084 | na | 0.052 |
| 95% CI of | 0.52 | 0.37 | 0.54 | 0.67 | 0.026 | 0.60 | 0.77 | na | 0.98 |
| OR Quart2 | 3.1 | 12 | 4.0 | 5.0 | 2.2 | 4.5 | 59 | na | 72 |
| OR Quart 3 | 0.79 | 2.6 | 1.6 | 2.6 | 0.73 | 2.7 | 13 | 2.1 | 8.4 |
| p Value | 0.63 | 0.26 | 0.32 | 0.058 | 0.69 | 0.043 | 0.018 | 0.41 | 0.052 |
| 95% CI of | 0.31 | 0.49 | 0.61 | 0.97 | 0.16 | 1.0 | 1.6 | 0.37 | 0.98 |
| OR Quart3 | 2.0 | 14 | 4.4 | 6.9 | 3.4 | 7.2 | 110 | 12 | 72 |
| OR Quart 4 | 1.2 | 2.6 | 1.0 | 2.5 | 1.8 | 2.7 | 11 | 2.0 | 9.9 |
| p Value | 0.76 | 0.26 | 1.0 | 0.068 | 0.36 | 0.043 | 0.026 | 0.42 | 0.035 |
| 95% CI of | 0.46 | 0.49 | 0.35 | 0.94 | 0.50 | 1.0 | 1.3 | 0.36 | 1.2 |
| OR Quart4 | 2.9 | 14 | 2.8 | 6.7 | 6.4 | 7.2 | 94 | 11 | 84 |

| Apolipoprotein E | | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | 53900 | 51900 | 53900 | 41500 | 53900 | 28700 |
| Average | 66800 | 69000 | 66800 | 53100 | 66800 | 33700 |
| Stdev | 47000 | 50500 | 47000 | 43200 | 47000 | 20200 |
| p(t-test) | | 0.76 | | 0.051 | | 4.4E−4 |
| Min | 8630 | 13000 | 8630 | 10300 | 8630 | 4980 |
| Max | 260000 | 244000 | 260000 | 232000 | 260000 | 73300 |
| n (Samp) | 145 | 64 | 145 | 62 | 145 | 27 |
| n (Patient) | 111 | 64 | 111 | 62 | 111 | 27 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 49300 | 50300 | 49300 | 51700 | 49300 | 49300 |
| Average | 61100 | 60300 | 61100 | 70300 | 61100 | 47800 |
| Stdev | 44800 | 37100 | 44800 | 61900 | 44800 | 22100 |
| p(t-test) | | 0.94 | | 0.38 | | 0.29 |
| Min | 1940 | 20700 | 1940 | 13500 | 1940 | 4980 |
| Max | 260000 | 147000 | 260000 | 232000 | 260000 | 75700 |
| n (Samp) | 341 | 19 | 341 | 20 | 341 | 13 |
| n (Patient) | 193 | 19 | 193 | 20 | 193 | 13 |

| | 0 hr prior to AKI stage | | 24 hr prior to AKI stage | | 48 hr prior to AKI stage | |
|---|---|---|---|---|---|---|
| UO only | Cohort 1 | Cohort 2 | Cohort 1 | Cohort 2 | Cohort 1 | Cohort 2 |
| Median | 53200 | 49900 | 53200 | 41200 | 53200 | 26000 |
| Average | 64500 | 69900 | 64500 | 45600 | 64500 | 28600 |
| Stdev | 43200 | 52200 | 43200 | 26400 | 43200 | 15400 |

-continued

|  | | | | | | | | | |
|---|---|---|---|---|---|---|---|---|---|
| p(t-test) | | 0.46 | | | 0.0024 | | | 8.5E−5 | |
| Min | 4980 | 13000 | | 4980 | 10300 | | 4980 | 5170 | |
| Max | 218000 | 244000 | | 218000 | 132000 | | 218000 | 68300 | |
| n (Samp) | 151 | 54 | | 151 | 56 | | 151 | 24 | |
| n (Patient) | 103 | 54 | | 103 | 56 | | 103 | 24 | |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.50 | 0.51 | 0.51 | 0.39 | 0.50 | 0.37 | 0.23 | 0.46 | 0.18 |
| SE | 0.043 | 0.068 | 0.046 | 0.044 | 0.067 | 0.045 | 0.056 | 0.083 | 0.055 |
| p | 0.99 | 0.91 | 0.81 | 0.0095 | 0.95 | 0.0039 | 2.0E−6 | 0.65 | 8.4E−9 |
| nCohort 1 | 145 | 341 | 151 | 145 | 341 | 151 | 145 | 341 | 151 |
| nCohort 2 | 64 | 19 | 54 | 62 | 20 | 56 | 27 | 13 | 24 |
| Cutoff 1 | 39600 | 29600 | 39600 | 25800 | 33900 | 27000 | 23900 | 34000 | 19800 |
| Sens 1 | 70% | 74% | 70% | 71% | 70% | 71% | 70% | 77% | 75% |
| Spec 1 | 31% | 22% | 33% | 8% | 29% | 14% | 7% | 30% | 9% |
| Cutoff 2 | 27200 | 25600 | 29100 | 19600 | 20200 | 23500 | 16400 | 28600 | 16500 |
| Sens 2 | 81% | 84% | 81% | 81% | 80% | 80% | 81% | 85% | 83% |
| Spec 2 | 10% | 16% | 17% | 6% | 11% | 10% | 5% | 20% | 7% |
| Cutoff 3 | 20700 | 23900 | 20200 | 14300 | 19100 | 13800 | 8630 | 15100 | 13800 |
| Sens 3 | 91% | 95% | 91% | 90% | 90% | 91% | 93% | 92% | 92% |
| Spec 3 | 6% | 14% | 9% | 3% | 10% | 3% | 1% | 7% | 3% |
| Cutoff 4 | 76000 | 67600 | 76000 | 76000 | 67600 | 76000 | 76000 | 67600 | 76000 |
| Sens 4 | 34% | 32% | 35% | 19% | 35% | 14% | 0% | 23% | 0% |
| Spec 4 | 70% | 70% | 70% | 70% | 70% | 70% | 70% | 70% | 70% |
| Cutoff 5 | 90100 | 86400 | 92000 | 90100 | 86400 | 92000 | 90100 | 86400 | 92000 |
| Sens 5 | 27% | 26% | 26% | 11% | 30% | 4% | 0% | 0% | 0% |
| Spec 5 | 80% | 80% | 80% | 80% | 80% | 80% | 80% | 80% | 80% |
| Cutoff 6 | 131000 | 113000 | 120000 | 131000 | 113000 | 120000 | 131000 | 113000 | 120000 |
| Sens 6 | 12% | 11% | 13% | 6% | 20% | 2% | 0% | 0% | 0% |
| Spec 6 | 90% | 90% | 90% | 90% | 90% | 90% | 90% | 90% | 90% |
| OR Quart 2 | 0.70 | 0.48 | 1.2 | 1.2 | 0.65 | 2.0 | >7.0 | >7.7 | >2.1 |
| p Value | 0.40 | 0.31 | 0.66 | 0.65 | 0.52 | 0.15 | <0.078 | <0.059 | <0.55 |
| 95% CI of | 0.30 | 0.12 | 0.51 | 0.50 | 0.18 | 0.77 | >0.80 | >0.93 | >0.18 |
| OR Quart2 | 1.6 | 2.0 | 2.9 | 3.0 | 2.4 | 5.4 | na | na | na |
| OR Quart 3 | 0.63 | 0.65 | 0.80 | 1.1 | 0.65 | 2.0 | >5.7 | >3.1 | >6.9 |
| p Value | 0.29 | 0.52 | 0.64 | 0.82 | 0.52 | 0.15 | <0.12 | <0.33 | <0.079 |
| 95% CI of | 0.27 | 0.18 | 0.32 | 0.45 | 0.18 | 0.77 | >0.63 | >0.32 | >0.80 |
| OR Quart3 | 1.5 | 2.4 | 2.0 | 2.7 | 2.4 | 5.4 | na | na | na |
| OR Quart 4 | 1.1 | 1.0 | 1.2 | 2.7 | 0.99 | 3.5 | >25 | >3.1 | >26 |
| p Value | 0.89 | 1.0 | 0.70 | 0.020 | 0.98 | 0.0083 | <0.0022 | <0.33 | <0.0021 |
| 95% CI of | 0.47 | 0.31 | 0.50 | 1.2 | 0.31 | 1.4 | >3.2 | >0.32 | >3.3 |
| OR Quart4 | 2.4 | 3.2 | 2.8 | 6.4 | 3.2 | 9.1 | na | na | na |

| Apolipoprotein(a) | | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | 47000 | 38500 | 47000 | 29800 | 47000 | 41500 |
| Average | 76700 | 78000 | 76700 | 72900 | 76700 | 82500 |
| Stdev | 99200 | 105000 | 99200 | 123000 | 99200 | 106000 |
| p(t-test) | | 0.93 | | 0.82 | | 0.78 |
| Min | 7.99 | 1060 | 7.99 | 20.1 | 7.99 | 341 |
| Max | 631000 | 560000 | 631000 | 722000 | 631000 | 382000 |
| n (Samp) | 145 | 64 | 145 | 62 | 145 | 27 |
| n (Patient) | 111 | 64 | 111 | 62 | 111 | 27 |

| | 0 hr prior to AKI stage | | 24 hr prior to AKI stage | | 48 hr prior to AKI stage | |
|---|---|---|---|---|---|---|
| sCr only | Cohort 1 | Cohort 2 | Cohort 1 | Cohort 2 | Cohort 1 | Cohort 2 |
| Median | 41400 | 53200 | 41400 | 46900 | 41400 | 49600 |
| Average | 80100 | 84900 | 80100 | 109000 | 80100 | 94500 |
| Stdev | 102000 | 88500 | 102000 | 167000 | 102000 | 129000 |
| p(t-test) | | 0.84 | | 0.24 | | 0.62 |
| Min | 7.99 | 2390 | 7.99 | 20.1 | 7.99 | 341 |
| Max | 631000 | 309000 | 631000 | 722000 | 631000 | 382000 |
| n (Samp) | 341 | 19 | 341 | 20 | 341 | 13 |
| n (Patient) | 193 | 19 | 193 | 20 | 193 | 13 |

-continued

|  | 0 hr prior to AKI stage | | 24 hr prior to AKI stage | | 48 hr prior to AKI stage | |
| --- | --- | --- | --- | --- | --- | --- |
| UO only | Cohort 1 | Cohort 2 | Cohort 1 | Cohort 2 | Cohort 1 | Cohort 2 |
| Median | 51100 | 29500 | 51100 | 22200 | 51100 | 29300 |
| Average | 75400 | 68600 | 75400 | 61700 | 75400 | 55600 |
| Stdev | 94800 | 104000 | 94800 | 92400 | 94800 | 68400 |
| p(t-test) | | 0.66 | | 0.35 | | 0.33 |
| Min | 7.99 | 1060 | 7.99 | 977 | 7.99 | 1300 |
| Max | 631000 | 560000 | 631000 | 512000 | 631000 | 290000 |
| n (Samp) | 151 | 54 | 151 | 56 | 151 | 24 |
| n (Patient) | 103 | 54 | 103 | 56 | 103 | 24 |

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | 0.49 | 0.55 | 0.43 | 0.44 | 0.53 | 0.41 | 0.49 | 0.49 | 0.43 |
| SE | 0.044 | 0.070 | 0.046 | 0.044 | 0.068 | 0.046 | 0.061 | 0.082 | 0.065 |
| p | 0.75 | 0.48 | 0.12 | 0.20 | 0.63 | 0.052 | 0.88 | 0.89 | 0.27 |
| nCohort 1 | 145 | 341 | 151 | 145 | 341 | 151 | 145 | 341 | 151 |
| nCohort 2 | 64 | 19 | 54 | 62 | 20 | 56 | 27 | 13 | 24 |
| Cutoff 1 | 14100 | 32400 | 11100 | 10500 | 25900 | 8730 | 16800 | 4700 | 15300 |
| Sens 1 | 70% | 74% | 70% | 71% | 70% | 71% | 70% | 77% | 71% |
| Spec 1 | 29% | 45% | 19% | 21% | 40% | 15% | 32% | 11% | 28% |
| Cutoff 2 | 8730 | 15600 | 6840 | 5630 | 15300 | 5630 | 5630 | 4300 | 5630 |
| Sens 2 | 81% | 84% | 81% | 81% | 80% | 80% | 81% | 85% | 83% |
| Spec 2 | 18% | 31% | 11% | 12% | 31% | 9% | 12% | 9% | 9% |
| Cutoff 3 | 4980 | 2640 | 4320 | 2640 | 4700 | 2640 | 1810 | 1680 | 3010 |
| Sens 3 | 91% | 95% | 91% | 90% | 90% | 91% | 93% | 92% | 92% |
| Spec 3 | 8% | 6% | 5% | 6% | 11% | 4% | 6% | 4% | 5% |
| Cutoff 4 | 80900 | 89900 | 81800 | 80900 | 89900 | 81800 | 80900 | 89900 | 81800 |
| Sens 4 | 27% | 32% | 22% | 23% | 30% | 23% | 33% | 31% | 25% |
| Spec 4 | 70% | 70% | 70% | 70% | 70% | 70% | 70% | 70% | 70% |
| Cutoff 5 | 122000 | 125000 | 112000 | 122000 | 125000 | 112000 | 122000 | 125000 | 112000 |
| Sens 5 | 19% | 21% | 19% | 16% | 30% | 18% | 22% | 23% | 17% |
| Spec 5 | 80% | 80% | 80% | 80% | 80% | 80% | 80% | 80% | 80% |
| Cutoff 6 | 209000 | 214000 | 180000 | 209000 | 214000 | 180000 | 209000 | 214000 | 180000 |
| Sens 6 | 11% | 11% | 11% | 10% | 15% | 7% | 11% | 15% | 4% |
| Spec 6 | 90% | 90% | 90% | 90% | 90% | 90% | 90% | 90% | 90% |
| OR Quart | 20.85 | 1.7 | 0.91 | 0.90 | 1.3 | 0.55 | 0.58 | 0.75 | 0.46 |
| p Value | 0.71 | 0.47 | 0.85 | 0.82 | 0.73 | 0.23 | 0.37 | 0.71 | 0.30 |
| 95% CI of | 0.36 | 0.40 | 0.35 | 0.38 | 0.33 | 0.20 | 0.17 | 0.16 | 0.11 |
| OR Quart2 | 2.0 | 7.4 | 2.4 | 2.2 | 4.9 | 1.5 | 1.9 | 3.5 | 2.0 |
| OR Quart 3 | 1.0 | 2.1 | 1.6 | 1.2 | 1.3 | 1.5 | 0.71 | 0.49 | 1.4 |
| p Value | 0.95 | 0.31 | 0.34 | 0.67 | 0.73 | 0.39 | 0.56 | 0.42 | 0.56 |
| 95% CI of | 0.45 | 0.50 | 0.63 | 0.52 | 0.33 | 0.62 | 0.22 | 0.087 | 0.44 |
| OR Quart3 | 2.4 | 8.6 | 3.8 | 2.8 | 4.9 | 3.4 | 2.3 | 2.7 | 4.5 |
| OR Quart 4 | 1.2 | 1.7 | 2.0 | 1.6 | 1.5 | 1.6 | 1.0 | 1.0 | 1.2 |
| p Value | 0.63 | 0.47 | 0.11 | 0.26 | 0.53 | 0.26 | 1.0 | 0.99 | 0.73 |
| 95% CI of | 0.54 | 0.40 | 0.84 | 0.70 | 0.41 | 0.70 | 0.34 | 0.24 | 0.38 |
| OR Quart4 | 2.8 | 7.4 | 4.9 | 3.7 | 5.6 | 3.8 | 3.0 | 4.2 | 4.0 |

FIG. 6: Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| Complement C4-B | | | | | | |
| --- | --- | --- | --- | --- | --- | --- |
|  | 0 hr prior to AKI stage | | 24 hr prior to AKI stage | | 48 hr prior to AKI stage | |
|  | Cohort 1 | Cohort 2 | Cohort 1 | Cohort 2 | Cohort 1 | Cohort 2 |
| sCr or UO | | | | | | |
| Median | 70800 | 86100 | 70800 | 78800 | 70800 | 59900 |
| Average | 76600 | 85000 | 76600 | 83100 | 76600 | 71500 |
| Stdev | 39900 | 53500 | 39900 | 52600 | 39900 | 39100 |
| p (t-test) | | 0.42 | | 0.43 | | 0.58 |
| Min | 305 | 7620 | 305 | 5510 | 305 | 10700 |
| Max | 223000 | 172000 | 223000 | 214000 | 223000 | 140000 |
| n (Samp) | 282 | 16 | 282 | 28 | 282 | 20 |
| n (Patient) | 160 | 16 | 160 | 28 | 160 | 20 |

| sCr only | | | | | | |
|---|---|---|---|---|---|---|
| Median | nd | nd | nd | nd | 72400 | 112000 |
| Average | nd | nd | nd | nd | 77600 | 104000 |
| Stdev | nd | nd | nd | nd | 41600 | 51900 |
| p (t-test) | nd | nd | nd | nd | | 0.13 |
| Min | nd | nd | nd | nd | 305 | 15300 |
| Max | nd | nd | nd | nd | 223000 | 161000 |
| n (Samp) | nd | nd | nd | nd | 353 | 6 |
| n (Patient) | nd | nd | nd | nd | 193 | 6 |
| UO only | | | | | | |
| Median | 66200 | 84700 | 66200 | 67900 | 66200 | 59300 |
| Average | 73700 | 80900 | 73700 | 81800 | 73700 | 69000 |
| Stdev | 38600 | 57100 | 38600 | 54200 | 38600 | 35600 |
| p (t-test) | | 0.53 | | 0.33 | | 0.62 |
| Min | 305 | 7620 | 305 | 5510 | 305 | 10700 |
| Max | 223000 | 172000 | 223000 | 214000 | 223000 | 126000 |
| n (Samp) | 258 | 13 | 258 | 26 | 258 | 17 |
| n (Patient) | 140 | 13 | 140 | 26 | 140 | 17 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.54 | nd | 0.52 | 0.52 | nd | 0.52 | 0.47 | 0.68 | 0.47 |
| SE | 0.076 | nd | 0.083 | 0.058 | nd | 0.060 | 0.068 | 0.12 | 0.073 |
| p | 0.57 | nd | 0.83 | 0.74 | nd | 0.75 | 0.67 | 0.14 | 0.73 |
| nCohort 1 | 282 | nd | 258 | 282 | nd | 258 | 282 | 353 | 258 |
| nCohort 2 | 16 | nd | 13 | 28 | nd | 26 | 20 | 6 | 17 |
| Cutoff 1 | 39400 | nd | 32200 | 46200 | nd | 45900 | 50900 | 81100 | 50900 |
| Sens 1 | 75% | nd | 77% | 71% | nd | 73% | 70% | 83% | 71% |
| Spec 1 | 19% | nd | 13% | 24% | nd | 26% | 30% | 57% | 33% |
| Cutoff 2 | 32200 | nd | 29600 | 34900 | nd | 34900 | 39400 | 81100 | 39400 |
| Sens 2 | 81% | nd | 85% | 82% | nd | 81% | 80% | 83% | 82% |
| Spec 2 | 12% | nd | 10% | 15% | nd | 16% | 19% | 57% | 20% |
| Cutoff 3 | 7620 | nd | 7620 | 23300 | nd | 23300 | 21400 | 13500 | 21400 |
| Sens 3 | 94% | nd | 92% | 93% | nd | 92% | 90% | 100% | 94% |
| Spec 3 | 2% | nd | 3% | 6% | nd | 6% | 5% | 4% | 5% |
| Cutoff 4 | 96100 | nd | 90900 | 96100 | nd | 90900 | 96100 | 100000 | 90900 |
| Sens 4 | 38% | nd | 38% | 36% | nd | 42% | 35% | 50% | 29% |
| Spec 4 | 70% | nd | 70% | 70% | nd | 70% | 70% | 70% | 70% |
| Cutoff 5 | 111000 | nd | 108000 | 111000 | nd | 108000 | 111000 | 113000 | 108000 |
| Sens 5 | 31% | nd | 38% | 32% | nd | 35% | 25% | 50% | 24% |
| Spec 5 | 80% | nd | 80% | 80% | nd | 80% | 80% | 80% | 80% |
| Cutoff 6 | 132000 | nd | 131000 | 132000 | nd | 131000 | 132000 | 132000 | 131000 |
| Sens 6 | 25% | nd | 23% | 14% | nd | 12% | 5% | 33% | 0% |
| Spec 6 | 90% | nd | 90% | 90% | nd | 90% | 90% | 90% | 90% |
| OR Quart 2 | 0.19 | nd | 0.19 | 0.59 | nd | 0.84 | 0.80 | 0 | 0.74 |
| p Value | 0.13 | nd | 0.13 | 0.38 | nd | 0.77 | 0.75 | na | 0.70 |
| 95% CI of | 0.021 | nd | 0.021 | 0.18 | nd | 0.27 | 0.21 | na | 0.16 |
| OR Quart 2 | 1.6 | nd | 1.6 | 1.9 | nd | 2.6 | 3.1 | na | 3.4 |
| OR Quart 3 | 0.79 | nd | 0.38 | 0.73 | nd | 0.40 | 1.0 | 2.0 | 1.5 |
| p Value | 0.73 | nd | 0.25 | 0.58 | nd | 0.20 | 1.0 | 0.57 | 0.51 |
| 95% CI of | 0.20 | nd | 0.070 | 0.24 | nd | 0.100 | 0.28 | 0.18 | 0.42 |
| OR Quart 3 | 3.1 | nd | 2.0 | 2.2 | nd | 1.6 | 3.6 | 22 | 5.7 |
| OR Quart 4 | 1.2 | nd | 0.98 | 1.1 | nd | 1.5 | 1.2 | 3.0 | 1.0 |
| p Value | 0.77 | nd | 0.98 | 0.82 | nd | 0.44 | 0.74 | 0.34 | 0.98 |
| 95% CI of | 0.35 | nd | 0.27 | 0.41 | nd | 0.54 | 0.36 | 0.31 | 0.24 |
| OR Quart 4 | 4.1 | nd | 3.6 | 3.1 | nd | 4.2 | 4.2 | 30 | 4.2 |

C-C motif chemokine 7

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.620 | 0.804 | 0.620 | 0.712 | 0.620 | 0.620 |
| Average | 7.83 | 22.1 | 7.83 | 11.9 | 7.83 | 10.9 |
| Stdev | 19.8 | 46.2 | 19.8 | 21.0 | 19.8 | 18.8 |
| p (t-test) | | 0.015 | | 0.31 | | 0.54 |
| Min | 0.193 | 0.193 | 0.193 | 0.193 | 0.193 | 0.193 |
| Max | 166 | 181 | 166 | 79.4 | 166 | 60.8 |
| n (Samp) | 217 | 16 | 217 | 28 | 217 | 17 |
| n (Patient) | 133 | 16 | 133 | 28 | 133 | 17 |

| UO only | | | | | | |
|---|---|---|---|---|---|---|
| Median | 0.620 | 0.804 | 0.620 | 0.512 | 0.620 | 0.620 |
| Average | 8.13 | 24.1 | 8.13 | 10.6 | 8.13 | 10.8 |
| Stdev | 21.4 | 51.2 | 21.4 | 20.6 | 21.4 | 19.8 |
| p (t-test) | | 0.022 | | 0.56 | | 0.65 |
| Min | 0.193 | 0.193 | 0.193 | 0.193 | 0.193 | 0.193 |
| Max | 166 | 181 | 166 | 79.4 | 166 | 60.8 |
| n (Samp) | 199 | 13 | 199 | 29 | 199 | 15 |
| n (Patient) | 118 | 13 | 118 | 29 | 118 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.58 | nd | 0.56 | 0.52 | nd | 0.51 | 0.57 | nd | 0.55 |
| SE | 0.077 | nd | 0.085 | 0.059 | nd | 0.058 | 0.075 | nd | 0.079 |
| p | 0.30 | nd | 0.48 | 0.69 | nd | 0.93 | 0.37 | nd | 0.57 |
| nCohort 1 | 217 | nd | 199 | 217 | nd | 199 | 217 | nd | 199 |
| nCohort 2 | 16 | nd | 13 | 28 | nd | 29 | 17 | nd | 15 |
| Cutoff 1 | 0.308 | nd | 0 | 0.193 | nd | 0.193 | 0.308 | nd | 0.308 |
| Sens 1 | 75% | nd | 100% | 86% | nd | 86% | 88% | nd | 87% |
| Spec 1 | 30% | nd | 0% | 18% | nd | 20% | 30% | nd | 32% |
| Cutoff 2 | 0 | nd | 0 | 0.193 | nd | 0.193 | 0.308 | nd | 0.308 |
| Sens 2 | 100% | nd | 100% | 86% | nd | 86% | 88% | nd | 87% |
| Spec 2 | 0% | nd | 0% | 18% | nd | 20% | 30% | nd | 32% |
| Cutoff 3 | 0 | nd | 0 | 0 | nd | 0 | 0.193 | nd | 0.193 |
| Sens 3 | 100% | nd | 100% | 100% | nd | 100% | 94% | nd | 93% |
| Spec 3 | 0% | nd | 0% | 0% | nd | 0% | 18% | nd | 20% |
| Cutoff 4 | 2.71 | nd | 2.32 | 2.71 | nd | 2.32 | 2.71 | nd | 2.32 |
| Sens 4 | 44% | nd | 38% | 32% | nd | 34% | 29% | nd | 27% |
| Spec 4 | 71% | nd | 71% | 71% | nd | 71% | 71% | nd | 71% |
| Cutoff 5 | 11.7 | nd | 9.52 | 11.7 | nd | 9.52 | 11.7 | nd | 9.52 |
| Sens 5 | 38% | nd | 31% | 29% | nd | 24% | 29% | nd | 27% |
| Spec 5 | 80% | nd | 81% | 80% | nd | 81% | 80% | nd | 81% |
| Cutoff 6 | 19.2 | nd | 18.9 | 19.2 | nd | 18.9 | 19.2 | nd | 18.9 |
| Sens 6 | 31% | nd | 31% | 25% | nd | 21% | 24% | nd | 20% |
| Spec 6 | 90% | nd | 90% | 90% | nd | 90% | 90% | nd | 90% |
| OR Quart 2 | 0.48 | nd | 0.24 | 0.72 | nd | 1.3 | 8.9 | nd | 3.2 |
| p Value | 0.41 | nd | 0.20 | 0.57 | nd | 0.59 | 0.042 | nd | 0.17 |
| 95% CI of | 0.085 | nd | 0.025 | 0.23 | nd | 0.46 | 1.1 | nd | 0.61 |
| OR Quart 2 | 2.7 | nd | 2.2 | 2.2 | nd | 3.9 | 74 | nd | 17 |
| OR Quart 3 | 1.0 | nd | 1.0 | 0.72 | nd | 0.69 | 3.1 | nd | 1.5 |
| p Value | 1.0 | nd | 1.0 | 0.57 | nd | 0.54 | 0.33 | nd | 0.65 |
| 95% CI of | 0.24 | nd | 0.24 | 0.23 | nd | 0.20 | 0.31 | nd | 0.25 |
| OR Quart 3 | 4.2 | nd | 4.2 | 2.2 | nd | 2.3 | 31 | nd | 9.5 |
| OR Quart 4 | 1.5 | nd | 1.0 | 0.98 | nd | 1.2 | 5.3 | nd | 2.0 |
| p Value | 0.53 | nd | 1.0 | 0.97 | nd | 0.78 | 0.13 | nd | 0.42 |
| 95% CI of | 0.41 | nd | 0.24 | 0.34 | nd | 0.39 | 0.60 | nd | 0.36 |
| OR Quart 4 | 5.7 | nd | 4.2 | 2.8 | nd | 3.5 | 47 | nd | 12 |

Vascular endothelial growth factor receptor 3

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 6100 | 5150 | 6100 | 5290 | 6100 | 5450 |
| Average | 7380 | 6360 | 7380 | 6050 | 7380 | 6270 |
| Stdev | 5900 | 3290 | 5900 | 3460 | 5900 | 3330 |
| p (t-test) | | 0.49 | | 0.24 | | 0.44 |
| Min | 219 | 1190 | 219 | 1360 | 219 | 1500 |
| Max | 43200 | 12400 | 43200 | 16600 | 43200 | 12900 |
| n (Samp) | 217 | 16 | 217 | 28 | 217 | 17 |
| n (Patient) | 133 | 16 | 133 | 28 | 133 | 17 |
| UO only | | | | | | |
| Median | 6100 | 5110 | 6100 | 5810 | 6100 | 5450 |
| Average | 7350 | 6420 | 7350 | 6480 | 7350 | 6490 |
| Stdev | 5870 | 3590 | 5870 | 3710 | 5870 | 3400 |
| p (t-test) | | 0.58 | | 0.44 | | 0.58 |
| Min | 219 | 1190 | 219 | 1360 | 219 | 1500 |
| Max | 43200 | 12400 | 43200 | 16600 | 43200 | 12900 |
| n (Samp) | 199 | 13 | 199 | 29 | 199 | 15 |
| n (Patient) | 118 | 13 | 118 | 29 | 118 | 15 |

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | 0.49 | nd | 0.49 | 0.45 | nd | 0.48 | 0.47 | nd | 0.49 |
| SE | 0.075 | nd | 0.083 | 0.059 | nd | 0.058 | 0.074 | nd | 0.078 |
| p | 0.90 | nd | 0.89 | 0.38 | nd | 0.71 | 0.70 | nd | 0.93 |
| nCohort 1 | 217 | nd | 199 | 217 | nd | 199 | 217 | nd | 199 |
| nCohort 2 | 16 | nd | 13 | 28 | nd | 29 | 17 | nd | 15 |
| Cutoff 1 | 4400 | nd | 4400 | 3920 | nd | 3920 | 3700 | nd | 4610 |
| Sens 1 | 75% | nd | 77% | 71% | nd | 72% | 71% | nd | 73% |
| Spec 1 | 32% | nd | 31% | 28% | nd | 28% | 27% | nd | 34% |
| Cutoff 2 | 4100 | nd | 4050 | 3400 | nd | 3400 | 3140 | nd | 3230 |
| Sens 2 | 81% | nd | 85% | 82% | nd | 83% | 82% | nd | 80% |
| Spec 2 | 29% | nd | 29% | 21% | nd | 21% | 17% | nd | 18% |
| Cutoff 3 | 1630 | nd | 1630 | 1810 | nd | 1810 | 2780 | nd | 2780 |
| Sens 3 | 94% | nd | 92% | 93% | nd | 93% | 94% | nd | 93% |
| Spec 3 | 6% | nd | 6% | 6% | nd | 7% | 12% | nd | 13% |
| Cutoff 4 | 8170 | nd | 8170 | 8170 | nd | 8170 | 8170 | nd | 8170 |
| Sens 4 | 31% | nd | 38% | 21% | nd | 24% | 29% | nd | 33% |
| Spec 4 | 70% | nd | 70% | 70% | nd | 70% | 70% | nd | 70% |
| Cutoff 5 | 9670 | nd | 9630 | 9670 | nd | 9630 | 9670 | nd | 9630 |
| Sens 5 | 25% | nd | 31% | 14% | nd | 17% | 18% | nd | 27% |
| Spec 5 | 80% | nd | 80% | 80% | nd | 80% | 80% | nd | 80% |
| Cutoff 6 | 12600 | nd | 12600 | 12600 | nd | 12600 | 12600 | nd | 12600 |
| Sens 6 | 0% | nd | 0% | 4% | nd | 7% | 6% | nd | 7% |
| Spec 6 | 90% | nd | 90% | 90% | nd | 90% | 90% | nd | 90% |
| OR Quart 2 | 0.39 | nd | 0 | 0.83 | nd | 1.0 | 0.59 | nd | 0.38 |
| p Value | 0.27 | nd | na | 0.77 | nd | 1.0 | 0.48 | nd | 0.27 |
| 95% CI of | 0.072 | nd | na | 0.24 | nd | 0.33 | 0.13 | nd | 0.071 |
| OR Quart 2 | 2.1 | nd | na | 2.9 | nd | 3.1 | 2.6 | nd | 2.1 |
| OR Quart 3 | 1.5 | nd | 1.2 | 1.8 | nd | 1.2 | 0.79 | nd | 0.78 |
| p Value | 0.52 | nd | 0.75 | 0.27 | nd | 0.78 | 0.73 | nd | 0.73 |
| 95% CI of | 0.44 | nd | 0.35 | 0.62 | nd | 0.39 | 0.20 | nd | 0.20 |
| OR Quart 3 | 5.0 | nd | 4.3 | 5.4 | nd | 3.5 | 3.1 | nd | 3.1 |
| OR Quart 4 | 0.39 | nd | 0.38 | 1.2 | nd | 1.0 | 1.0 | nd | 0.80 |
| p Value | 0.27 | nd | 0.26 | 0.75 | nd | 1.0 | 0.98 | nd | 0.75 |
| 95% CI of | 0.072 | nd | 0.070 | 0.38 | nd | 0.33 | 0.28 | nd | 0.20 |
| OR Quart 4 | 2.1 | nd | 2.0 | 3.8 | nd | 3.1 | 3.7 | nd | 3.2 |

Interferon alpha-2

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| Median | 13.4 | 13.5 | 13.4 | 8.40 | 13.4 | 16.4 |
| Average | 17.6 | 19.9 | 17.6 | 14.8 | 17.6 | 16.6 |
| Stdev | 24.2 | 25.8 | 24.2 | 23.0 | 24.2 | 10.9 |
| p (t-test) |  | 0.72 |  | 0.56 |  | 0.86 |
| Min | 0.0320 | 0.0627 | 0.0320 | 0.0627 | 0.0320 | 0.0627 |
| Max | 223 | 95.9 | 223 | 121 | 223 | 35.3 |
| n (Samp) | 217 | 16 | 217 | 28 | 217 | 17 |
| n (Patient) | 133 | 16 | 133 | 28 | 133 | 17 |
| UO only | | | | | | |
| Median | 12.2 | 8.40 | 12.2 | 8.40 | 12.2 | 17.2 |
| Average | 16.8 | 19.1 | 16.8 | 16.5 | 16.8 | 17.7 |
| Stdev | 24.8 | 28.6 | 24.8 | 23.8 | 24.8 | 11.7 |
| p (t-test) |  | 0.75 |  | 0.95 |  | 0.89 |
| Min | 0.0320 | 0.0627 | 0.0320 | 0.0627 | 0.0320 | 0.0627 |
| Max | 223 | 95.9 | 223 | 121 | 223 | 35.3 |
| n (Samp) | 199 | 13 | 199 | 29 | 199 | 15 |
| n (Patient) | 118 | 13 | 118 | 29 | 118 | 15 |

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | 0.51 | nd | 0.49 | 0.46 | nd | 0.50 | 0.56 | nd | 0.60 |
| SE | 0.075 | nd | 0.083 | 0.059 | nd | 0.058 | 0.075 | nd | 0.080 |
| p | 0.89 | nd | 0.87 | 0.45 | nd | 0.97 | 0.45 | nd | 0.21 |
| nCohort 1 | 217 | nd | 199 | 217 | nd | 199 | 217 | nd | 199 |
| nCohort 2 | 16 | nd | 13 | 28 | nd | 29 | 17 | nd | 15 |
| Cutoff 1 | 4.47 | nd | 0.0764 | 4.03 | nd | 4.03 | 9.68 | nd | 9.68 |
| Sens 1 | 75% | nd | 85% | 71% | nd | 72% | 71% | nd | 73% |
| Spec 1 | 34% | nd | 18% | 31% | nd | 34% | 45% | nd | 48% |

-continued

| | | | | | | | | | |
|---|---|---|---|---|---|---|---|---|---|
| Cutoff 2 | 0.0627 | nd | 0.0764 | 0.0627 | nd | 0.0764 | 5.98 | nd | 8.88 |
| Sens 2 | 88% | nd | 85% | 86% | nd | 86% | 82% | nd | 80% |
| Spec 2 | 16% | nd | 18% | 16% | nd | 18% | 38% | nd | 46% |
| Cutoff 3 | 0.0324 | nd | 0.0324 | 0.0324 | nd | 0.0324 | 0.0627 | nd | 0.0764 |
| Sens 3 | 100% | nd | 100% | 100% | nd | 100% | 94% | nd | 93% |
| Spec 3 | 3% | nd | 3% | 3% | nd | 3% | 16% | nd | 18% |
| Cutoff 4 | 23.2 | nd | 20.8 | 23.2 | nd | 20.8 | 23.2 | nd | 20.8 |
| Sens 4 | 19% | nd | 31% | 14% | nd | 28% | 18% | nd | 47% |
| Spec 4 | 71% | nd | 71% | 71% | nd | 71% | 71% | nd | 71% |
| Cutoff 5 | 28.1 | nd | 27.4 | 28.1 | nd | 27.4 | 28.1 | nd | 27.4 |
| Sens 5 | 19% | nd | 15% | 11% | nd | 14% | 18% | nd | 27% |
| Spec 5 | 80% | nd | 80% | 80% | nd | 80% | 80% | nd | 80% |
| Cutoff 6 | 38.0 | nd | 36.7 | 38.0 | nd | 36.7 | 38.0 | nd | 36.7 |
| Sens 6 | 12% | nd | 15% | 4% | nd | 7% | 0% | nd | 0% |
| Spec 6 | 90% | nd | 90% | 90% | nd | 90% | 90% | nd | 90% |
| OR Quart 2 | 1.0 | nd | 1.5 | 1.9 | nd | 1.8 | 2.0 | nd | 1.5 |
| p Value | 1.0 | nd | 0.65 | 0.34 | nd | 0.29 | 0.42 | nd | 0.66 |
| 95% CI of | 0.24 | nd | 0.25 | 0.52 | nd | 0.61 | 0.36 | nd | 0.24 |
| OR Quart 2 | 4.2 | nd | 9.5 | 6.8 | nd | 5.4 | 12 | nd | 9.4 |
| OR Quart 3 | 1.3 | nd | 2.7 | 2.8 | nd | 1.4 | 4.5 | nd | 3.3 |
| p Value | 0.73 | nd | 0.26 | 0.093 | nd | 0.57 | 0.065 | nd | 0.16 |
| 95% CI of | 0.32 | nd | 0.49 | 0.84 | nd | 0.45 | 0.91 | nd | 0.63 |
| OR Quart 3 | 5.0 | nd | 14 | 9.6 | nd | 4.3 | 22 | nd | 17 |
| OR Quart 4 | 0.72 | nd | 1.5 | 1.9 | nd | 0.82 | 1.5 | nd | 2.0 |
| p Value | 0.68 | nd | 0.65 | 0.34 | nd | 0.75 | 0.66 | nd | 0.42 |
| 95% CI of | 0.15 | nd | 0.25 | 0.52 | nd | 0.23 | 0.24 | nd | 0.36 |
| OR Quart 4 | 3.4 | nd | 9.5 | 6.8 | nd | 2.8 | 9.3 | nd | 12 |

| Insulin-like growth factor-binding protein 4 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 2.93 | 20.4 | 2.93 | 8.48 | 2.93 | 2.93 |
| Average | 12.2 | 19.6 | 12.2 | 15.8 | 12.2 | 10.9 |
| Stdev | 19.3 | 15.9 | 19.3 | 17.1 | 19.3 | 11.5 |
| p (t-test) | | 0.15 | | 0.34 | | 0.75 |
| Min | 0.0728 | 2.43 | 0.0728 | 0.572 | 0.0728 | 0.572 |
| Max | 158 | 47.3 | 158 | 57.3 | 158 | 33.5 |
| n (Samp) | 278 | 15 | 278 | 28 | 278 | 20 |
| n (Patient) | 160 | 15 | 160 | 28 | 160 | 20 |
| sCr only | | | | | | |
| Median | nd | nd | nd | nd | 2.93 | 13.3 |
| Average | nd | nd | nd | nd | 12.7 | 13.9 |
| Stdev | nd | nd | nd | nd | 18.5 | 13.3 |
| p (t-test) | nd | nd | nd | nd | | 0.87 |
| Min | nd | nd | nd | nd | 0.0728 | 0.572 |
| Max | nd | nd | nd | nd | 158 | 26.9 |
| n (Samp) | nd | nd | nd | nd | 347 | 6 |
| n (Patient) | nd | nd | nd | nd | 193 | 6 |
| UO only | | | | | | |
| Median | 2.93 | 21.7 | 2.93 | 8.48 | 2.93 | 2.93 |
| Average | 12.2 | 20.2 | 12.2 | 15.2 | 12.2 | 9.66 |
| Stdev | 19.5 | 14.3 | 19.5 | 16.1 | 19.5 | 11.1 |
| p (t-test) | | 0.16 | | 0.45 | | 0.60 |
| Min | 0.0728 | 2.43 | 0.0728 | 0.572 | 0.0728 | 0.572 |
| Max | 158 | 47.3 | 158 | 57.3 | 158 | 33.5 |
| n (Samp) | 254 | 12 | 254 | 26 | 254 | 17 |
| n (Patient) | 140 | 12 | 140 | 26 | 140 | 17 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.68 | nd | 0.71 | 0.58 | nd | 0.57 | 0.54 | 0.54 | 0.51 |
| SE | 0.078 | nd | 0.086 | 0.059 | nd | 0.061 | 0.068 | 0.12 | 0.073 |
| p | 0.018 | nd | 0.015 | 0.19 | nd | 0.23 | 0.60 | 0.76 | 0.84 |
| nCohort 1 | 278 | nd | 254 | 278 | nd | 254 | 278 | 347 | 254 |
| nCohort 2 | 15 | nd | 12 | 28 | nd | 26 | 20 | 6 | 17 |
| Cutoff 1 | 2.43 | nd | 10.7 | 0.971 | nd | 0.971 | 0.971 | 0.971 | 2.43 |
| Sens 1 | 73% | nd | 75% | 79% | nd | 77% | 85% | 83% | 71% |
| Spec 1 | 41% | nd | 61% | 30% | nd | 29% | 30% | 27% | 39% |
| Cutoff 2 | 0.971 | nd | 0.971 | 0.572 | nd | 0.572 | 0.971 | 0.971 | 0.971 |
| Sens 2 | 100% | nd | 100% | 89% | nd | 88% | 85% | 83% | 82% |

-continued

| | | | | | | | | | |
|---|---|---|---|---|---|---|---|---|---|
| Spec 2 | 30% | nd | 29% | 15% | nd | 15% | 30% | 27% | 29% |
| Cutoff 3 | 0.971 | nd | 0.971 | 0.0862 | nd | 0.0862 | 0.572 | 0.0862 | 0.0862 |
| Sens 3 | 100% | nd | 100% | 100% | nd | 100% | 90% | 100% | 100% |
| Spec 3 | 30% | nd | 29% | 1% | nd | 1% | 15% | 1% | 1% |
| Cutoff 4 | 14.4 | nd | 14.4 | 14.4 | nd | 14.4 | 14.4 | 16.6 | 14.4 |
| Sens 4 | 53% | nd | 58% | 46% | nd | 46% | 40% | 50% | 35% |
| Spec 4 | 71% | nd | 71% | 71% | nd | 71% | 71% | 71% | 71% |
| Cutoff 5 | 21.4 | nd | 20.4 | 21.4 | nd | 20.4 | 21.4 | 23.1 | 20.4 |
| Sens 5 | 47% | nd | 50% | 32% | nd | 38% | 25% | 50% | 24% |
| Spec 5 | 81% | nd | 80% | 81% | nd | 80% | 81% | 81% | 80% |
| Cutoff 6 | 30.3 | nd | 28.1 | 30.3 | nd | 28.1 | 30.3 | 31.3 | 28.1 |
| Sens 6 | 27% | nd | 25% | 18% | nd | 23% | 10% | 0% | 12% |
| Spec 6 | 90% | nd | 91% | 90% | nd | 91% | 90% | 90% | 91% |
| OR Quart 2 | >5.4 | nd | >3.1 | 1.2 | nd | 1.4 | 3.7 | 2.0 | 2.8 |
| p Value | <0.13 | nd | <0.33 | 0.77 | nd | 0.55 | 0.11 | 0.57 | 0.14 |
| 95% CI of | >0.61 | nd | >0.31 | 0.35 | nd | 0.44 | 0.74 | 0.18 | 0.72 |
| OR Quart 2 | na | nd | na | 4.1 | nd | 4.8 | 18 | 23 | 11 |
| OR Quart 3 | >2.1 | nd | >2.1 | 1.2 | nd | 0.79 | 2.6 | 0 | 0.65 |
| p Value | <0.56 | nd | <0.56 | 0.75 | nd | 0.73 | 0.26 | na | 0.64 |
| 95% CI of | >0.18 | nd | >0.18 | 0.36 | nd | 0.20 | 0.49 | na | 0.10 |
| OR Quart 3 | na | nd | na | 4.2 | nd | 3.1 | 14 | na | 4.0 |
| OR Quart 4 | >8.8 | nd | >7.7 | 2.4 | nd | 2.2 | 3.1 | 3.0 | 1.3 |
| p Value | <0.042 | nd | <0.060 | 0.13 | nd | 0.18 | 0.17 | 0.34 | 0.71 |
| 95% CI of | >1.1 | nd | >0.92 | 0.78 | nd | 0.70 | 0.61 | 0.31 | 0.29 |
| OR Quart 4 | na | nd | na | 7.2 | nd | 6.7 | 16 | 30 | 6.2 |

| | Insulin-like growth factor-binding protein 5 | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 14.4 | 0.488 | 14.4 | 0.488 | 14.4 | 10.7 |
| Average | 37.5 | 22.2 | 37.5 | 30.1 | 37.5 | 27.4 |
| Stdev | 52.0 | 40.5 | 52.0 | 49.6 | 52.0 | 39.9 |
| p (t-test) | | 0.26 | | 0.47 | | 0.40 |
| Min | 0.204 | 0.222 | 0.204 | 0.204 | 0.204 | 0.222 |
| Max | 257 | 151 | 257 | 177 | 257 | 149 |
| n (Samp) | 278 | 15 | 278 | 28 | 278 | 20 |
| n (Patient) | 160 | 15 | 160 | 28 | 160 | 20 |
| sCr only | | | | | | |
| Median | nd | nd | nd | nd | 12.8 | 20.6 |
| Average | nd | nd | nd | nd | 34.3 | 50.2 |
| Stdev | nd | nd | nd | nd | 48.7 | 64.5 |
| p (t-test) | nd | nd | nd | nd | | 0.43 |
| Min | nd | nd | nd | nd | 0.204 | 0.357 |
| Max | nd | nd | nd | nd | 257 | 149 |
| n (Samp) | nd | nd | nd | nd | 347 | 6 |
| n (Patient) | nd | nd | nd | nd | 193 | 6 |
| UO only | | | | | | |
| Median | 8.54 | 1.20 | 8.54 | 0.488 | 8.54 | 0.488 |
| Average | 32.1 | 15.1 | 32.1 | 24.5 | 32.1 | 14.6 |
| Stdev | 49.2 | 21.2 | 49.2 | 38.7 | 49.2 | 19.0 |
| p (t-test) | | 0.24 | | 0.44 | | 0.15 |
| Min | 0.204 | 0.222 | 0.204 | 0.204 | 0.204 | 0.222 |
| Max | 257 | 66.0 | 257 | 126 | 257 | 51.0 |
| n (Samp) | 254 | 12 | 254 | 26 | 254 | 17 |
| n (Patient) | 140 | 12 | 140 | 26 | 140 | 17 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.41 | nd | 0.44 | 0.43 | nd | 0.44 | 0.46 | 0.59 | 0.42 |
| SE | 0.079 | nd | 0.088 | 0.059 | nd | 0.061 | 0.068 | 0.12 | 0.075 |
| p | 0.27 | nd | 0.47 | 0.23 | nd | 0.35 | 0.51 | 0.46 | 0.29 |
| nCohort 1 | 278 | nd | 254 | 278 | nd | 254 | 278 | 347 | 254 |
| nCohort 2 | 15 | nd | 12 | 28 | nd | 26 | 20 | 6 | 17 |
| Cutoff 1 | 0.316 | nd | 0.316 | 0.316 | nd | 0.222 | 0.316 | 0.357 | 0.222 |
| Sens 1 | 80% | nd | 83% | 71% | nd | 77% | 75% | 83% | 82% |
| Spec 1 | 22% | nd | 25% | 22% | nd | 18% | 22% | 28% | 18% |
| Cutoff 2 | 0.316 | nd | 0.316 | 0.204 | nd | 0.204 | 0.222 | 0.357 | 0.222 |
| Sens 2 | 80% | nd | 83% | 93% | nd | 92% | 85% | 83% | 82% |
| Spec 2 | 22% | nd | 25% | 5% | nd | 6% | 17% | 28% | 18% |
| Cutoff 3 | 0.204 | nd | 0.204 | 0.204 | nd | 0.204 | 0.204 | 0.316 | 0.204 |

-continued

| | | | | | | | | | |
|---|---|---|---|---|---|---|---|---|---|
| Sens 3 | 100% | nd | 100% | 93% | nd | 92% | 100% | 100% | 100% |
| Spec 3 | 5% | nd | 6% | 5% | nd | 6% | 5% | 23% | 6% |
| Cutoff 4 | 43.8 | nd | 35.0 | 43.8 | nd | 35.0 | 43.8 | 40.2 | 35.0 |
| Sens 4 | 13% | nd | 8% | 25% | nd | 31% | 20% | 33% | 24% |
| Spec 4 | 71% | nd | 70% | 71% | nd | 70% | 71% | 70% | 70% |
| Cutoff 5 | 64.4 | nd | 55.8 | 64.4 | nd | 55.8 | 64.4 | 61.6 | 55.8 |
| Sens 5 | 13% | nd | 8% | 18% | nd | 19% | 10% | 33% | 0% |
| Spec 5 | 80% | nd | 80% | 80% | nd | 80% | 80% | 80% | 80% |
| Cutoff 6 | 125 | nd | 105 | 125 | nd | 105 | 125 | 105 | 105 |
| Sens 6 | 7% | nd | 0% | 11% | nd | 8% | 5% | 33% | 0% |
| Spec 6 | 90% | nd | 91% | 90% | nd | 91% | 90% | 90% | 91% |
| OR Quart 2 | 2.1 | nd | 4.3 | 0.83 | nd | 0.65 | 2.1 | >3.1 | 3.2 |
| p Value | 0.40 | nd | 0.20 | 0.77 | nd | 0.51 | 0.30 | <0.33 | 0.16 |
| 95% CI of | 0.37 | nd | 0.46 | 0.24 | nd | 0.17 | 0.51 | >0.32 | 0.62 |
| OR Quart 2 | 12 | nd | 39 | 2.9 | nd | 2.4 | 8.8 | na | 16 |
| OR Quart 3 | 1.0 | nd | 5.3 | 1.0 | nd | 1.4 | 1.7 | >1.0 | 1.5 |
| p Value | 0.99 | nd | 0.13 | 1.0 | nd | 0.57 | 0.47 | <0.99 | 0.65 |
| 95% CI of | 0.14 | nd | 0.60 | 0.31 | nd | 0.45 | 0.39 | >0.062 | 0.25 |
| OR Quart 3 | 7.4 | nd | 47 | 3.2 | nd | 4.2 | 7.4 | na | 9.4 |
| OR Quart 4 | 3.8 | nd | 2.1 | 2.0 | nd | 1.4 | 2.1 | >2.0 | 3.2 |
| p Value | 0.10 | nd | 0.56 | 0.19 | nd | 0.57 | 0.30 | <0.57 | 0.16 |
| 95% CI of | 0.77 | nd | 0.18 | 0.70 | nd | 0.45 | 0.51 | >0.18 | 0.63 |
| OR Quart 4 | 19 | nd | 23 | 5.7 | nd | 4.2 | 8.8 | na | 17 |

Immunoglogulin G4

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 414000 | 444000 | 414000 | 250000 | 414000 | 70300 |
| Average | 667000 | 519000 | 667000 | 415000 | 667000 | 205000 |
| Stdev | 807000 | 481000 | 807000 | 406000 | 807000 | 245000 |
| p (t-test) | | 0.59 | | 0.17 | | 0.11 |
| Min | 2000 | 30100 | 2000 | 4650 | 2000 | 18500 |
| Max | 5190000 | 1210000 | 5190000 | 1350000 | 5190000 | 681000 |
| n (Samp) | 205 | 9 | 205 | 20 | 205 | 8 |
| n (Patient) | 127 | 9 | 127 | 20 | 127 | 8 |
| UO only | | | | | | |
| Median | 412000 | 444000 | 412000 | 250000 | 412000 | 90700 |
| Average | 642000 | 519000 | 642000 | 442000 | 642000 | 227000 |
| Stdev | 750000 | 481000 | 750000 | 418000 | 750000 | 255000 |
| p (t-test) | | 0.63 | | 0.27 | | 0.15 |
| Min | 2000 | 30100 | 2000 | 4650 | 2000 | 18500 |
| Max | 5140000 | 1210000 | 5140000 | 1350000 | 5140000 | 681000 |
| n (Samp) | 191 | 9 | 191 | 18 | 191 | 7 |
| n (Patient) | 113 | 9 | 113 | 18 | 113 | 7 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.46 | nd | 0.47 | 0.39 | nd | 0.42 | 0.24 | nd | 0.27 |
| SE | 0.10 | nd | 0.10 | 0.070 | nd | 0.073 | 0.10 | nd | 0.11 |
| p | 0.71 | nd | 0.73 | 0.12 | nd | 0.26 | 0.0093 | nd | 0.034 |
| nCohort 1 | 205 | nd | 191 | 205 | nd | 191 | 205 | nd | 191 |
| nCohort 2 | 9 | nd | 9 | 20 | nd | 18 | 8 | nd | 7 |
| Cutoff 1 | 83300 | nd | 83300 | 206000 | nd | 206000 | 37500 | nd | 37500 |
| Sens 1 | 78% | nd | 78% | 70% | nd | 72% | 75% | nd | 71% |
| Spec 1 | 14% | nd | 14% | 25% | nd | 27% | 6% | nd | 6% |
| Cutoff 2 | 51700 | nd | 51700 | 59500 | nd | 59500 | 33600 | nd | 33600 |
| Sens 2 | 89% | nd | 89% | 80% | nd | 83% | 88% | nd | 86% |
| Spec 2 | 7% | nd | 7% | 10% | nd | 10% | 5% | nd | 5% |
| Cutoff 3 | 29400 | nd | 29400 | 52400 | nd | 8490 | 17900 | nd | 17900 |
| Sens 3 | 100% | nd | 100% | 90% | nd | 94% | 100% | nd | 100% |
| Spec 3 | 4% | nd | 5% | 7% | nd | 2% | 3% | nd | 3% |
| Cutoff 4 | 731000 | nd | 731000 | 731000 | nd | 731000 | 731000 | nd | 731000 |
| Sens 4 | 33% | nd | 33% | 15% | nd | 17% | 0% | nd | 0% |
| Spec 4 | 70% | nd | 70% | 70% | nd | 70% | 70% | nd | 70% |
| Cutoff 5 | 935000 | nd | 935000 | 935000 | nd | 935000 | 935000 | nd | 935000 |
| Sens 5 | 33% | nd | 33% | 15% | nd | 17% | 0% | nd | 0% |
| Spec 5 | 80% | nd | 80% | 80% | nd | 80% | 80% | nd | 80% |
| Cutoff 6 | 1490000 | nd | 1380000 | 1490000 | nd | 1380000 | 1490000 | nd | 1380000 |
| Sens 6 | 0% | nd | 0% | 0% | nd | 0% | 0% | nd | 0% |
| Spec 6 | 90% | nd | 90% | 90% | nd | 90% | 90% | nd | 90% |
| OR Quart 2 | 0.67 | nd | 0.65 | 1.4 | nd | 1.4 | >2.1 | nd | >2.1 |

| | | | | | | | | | |
|---|---|---|---|---|---|---|---|---|---|
| p Value | 0.66 | nd | 0.65 | 0.68 | nd | 0.68 | <0.55 | nd | <0.54 |
| 95% CI of | 0.11 | nd | 0.10 | 0.30 | nd | 0.30 | >0.19 | nd | >0.19 |
| OR Quart 2 | 4.2 | nd | 4.1 | 6.5 | nd | 6.5 | na | nd | na |
| OR Quart 3 | 0 | nd | 0 | 2.6 | nd | 2.2 | >1.0 | nd | >1.0 |
| p Value | na | nd | na | 0.19 | nd | 0.29 | <0.98 | nd | <0.99 |
| 95% CI of | na | nd | na | 0.63 | nd | 0.51 | >0.063 | nd | >0.062 |
| OR Quart 3 | na | nd | na | 10 | nd | 9.2 | na | nd | na |
| OR Quart 4 | 1.4 | nd | 1.4 | 2.2 | nd | 1.8 | >5.6 | nd | >4.4 |
| p Value | 0.68 | nd | 0.70 | 0.29 | nd | 0.45 | <0.12 | nd | <0.19 |
| 95% CI of | 0.30 | nd | 0.29 | 0.51 | nd | 0.40 | >0.63 | nd | >0.48 |
| OR Quart 4 | 6.5 | nd | 6.4 | 9.1 | nd | 7.8 | na | nd | na |

Interleukin-21

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.430 | 0.784 | 0.430 | 0.630 | 0.430 | 1.63 |
| Average | 28.3 | 2.46 | 28.3 | 2.05 | 28.3 | 11.1 |
| Stdev | 369 | 3.78 | 369 | 3.54 | 369 | 31.5 |
| p (t-test) | | 0.78 | | 0.71 | | 0.85 |
| Min | 0.0102 | 0.0102 | 0.0102 | 0.0102 | 0.0102 | 0.0102 |
| Max | 5430 | 12.6 | 5430 | 15.6 | 5430 | 132 |
| n (Samp) | 217 | 16 | 217 | 28 | 217 | 17 |
| n (Patient) | 133 | 16 | 133 | 28 | 133 | 17 |
| UO only | | | | | | |
| Median | 0.430 | 0.605 | 0.430 | 0.630 | 0.430 | 0.964 |
| Average | 30.7 | 1.70 | 30.7 | 1.61 | 30.7 | 11.4 |
| Stdev | 385 | 2.93 | 385 | 2.31 | 385 | 33.6 |
| p (t-test) | | 0.79 | | 0.68 | | 0.85 |
| Min | 0.0102 | 0.0102 | 0.0102 | 0.0102 | 0.0102 | 0.0102 |
| Max | 5430 | 9.84 | 5430 | 8.04 | 5430 | 132 |
| n (Samp) | 199 | 13 | 199 | 29 | 199 | 15 |
| n (Patient) | 118 | 13 | 118 | 29 | 118 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.53 | nd | 0.46 | 0.50 | nd | 0.50 | 0.62 | nd | 0.58 |
| SE | 0.076 | nd | 0.084 | 0.058 | nd | 0.058 | 0.075 | nd | 0.080 |
| p | 0.67 | nd | 0.67 | 0.97 | nd | 0.94 | 0.11 | nd | 0.33 |
| nCohort 1 | 217 | nd | 199 | 217 | nd | 199 | 217 | nd | 199 |
| nCohort 2 | 16 | nd | 13 | 28 | nd | 29 | 17 | nd | 15 |
| Cutoff 1 | 0.0182 | nd | 0.0154 | 0.0257 | nd | 0.0257 | 0.783 | nd | 0.174 |
| Sens 1 | 75% | nd | 85% | 71% | nd | 72% | 71% | nd | 80% |
| Spec 1 | 26% | nd | 18% | 35% | nd | 36% | 55% | nd | 40% |
| Cutoff 2 | 0.0154 | nd | 0.0154 | 0.0154 | nd | 0.0154 | 0.174 | nd | 0.174 |
| Sens 2 | 88% | nd | 85% | 82% | nd | 83% | 82% | nd | 80% |
| Spec 2 | 18% | nd | 18% | 18% | nd | 18% | 40% | nd | 40% |
| Cutoff 3 | 0 | nd | 0 | 0.0102 | nd | 0.0102 | 0 | nd | 0 |
| Sens 3 | 100% | nd | 100% | 93% | nd | 93% | 100% | nd | 100% |
| Spec 3 | 0% | nd | 0% | 7% | nd | 6% | 0% | nd | 0% |
| Cutoff 4 | 1.89 | nd | 1.89 | 1.89 | nd | 1.89 | 1.89 | nd | 1.89 |
| Sens 4 | 38% | nd | 23% | 29% | nd | 31% | 29% | nd | 27% |
| Spec 4 | 72% | nd | 72% | 72% | nd | 72% | 72% | nd | 72% |
| Cutoff 5 | 2.75 | nd | 2.81 | 2.75 | nd | 2.81 | 2.75 | nd | 2.81 |
| Sens 5 | 19% | nd | 15% | 21% | nd | 17% | 29% | nd | 27% |
| Spec 5 | 80% | nd | 80% | 80% | nd | 80% | 80% | nd | 80% |
| Cutoff 6 | 6.18 | nd | 7.58 | 6.18 | nd | 7.58 | 6.18 | nd | 7.58 |
| Sens 6 | 12% | nd | 8% | 11% | nd | 7% | 29% | nd | 27% |
| Spec 6 | 90% | nd | 90% | 90% | nd | 90% | 90% | nd | 90% |
| OR Quart 2 | 0.48 | nd | 1.4 | 1.2 | nd | 0.69 | 0.32 | nd | 0.64 |
| p Value | 0.41 | nd | 0.70 | 0.77 | nd | 0.54 | 0.32 | nd | 0.63 |
| 95% CI of | 0.085 | nd | 0.29 | 0.38 | nd | 0.20 | 0.032 | nd | 0.10 |
| OR Quart 2 | 2.7 | nd | 6.4 | 3.8 | nd | 2.3 | 3.1 | nd | 4.0 |
| OR Quart 3 | 1.3 | nd | 0.65 | 1.4 | nd | 1.7 | 2.9 | nd | 2.1 |
| p Value | 0.73 | nd | 0.65 | 0.57 | nd | 0.31 | 0.13 | nd | 0.30 |
| 95% CI of | 0.32 | nd | 0.10 | 0.45 | nd | 0.61 | 0.74 | nd | 0.50 |
| OR Quart 3 | 5.0 | nd | 4.1 | 4.3 | nd | 4.8 | 12 | nd | 9.0 |
| OR Quart 4 | 1.2 | nd | 1.4 | 1.2 | nd | 0.84 | 1.7 | nd | 1.3 |
| p Value | 0.75 | nd | 0.70 | 0.79 | nd | 0.77 | 0.48 | nd | 0.72 |
| 95% CI of | 0.32 | nd | 0.29 | 0.37 | nd | 0.26 | 0.39 | nd | 0.28 |
| OR Quart 4 | 4.9 | nd | 6.4 | 3.7 | nd | 2.7 | 7.5 | nd | 6.3 |

| Interleukin-23 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.886 | 1.10 | 0.886 | 1.10 | 0.886 | 1.10 |
| Average | 1270 | 8060 | 1270 | 5040 | 1270 | 13400 |
| Stdev | 7660 | 25000 | 7660 | 19200 | 7660 | 33000 |
| p (t-test) | | 0.0080 | | 0.053 | | 3.5E−5 |
| Min | 0.257 | 0.653 | 0.257 | 0.257 | 0.257 | 0.603 |
| Max | 100000 | 100000 | 100000 | 100000 | 100000 | 100000 |
| n (Samp) | 216 | 16 | 216 | 28 | 216 | 17 |
| n (Patient) | 132 | 16 | 132 | 28 | 132 | 17 |
| UO only | | | | | | |
| Median | 0.886 | 1.10 | 0.886 | 1.10 | 0.886 | 72.6 |
| Average | 1350 | 8370 | 1350 | 4290 | 1350 | 13800 |
| Stdev | 7990 | 27600 | 7990 | 18500 | 7990 | 35000 |
| p (t-test) | | 0.017 | | 0.14 | | 1.2E−4 |
| Min | 0.257 | 0.653 | 0.257 | 0.257 | 0.257 | 0.603 |
| Max | 100000 | 100000 | 100000 | 100000 | 100000 | 100000 |
| n (Samp) | 198 | 13 | 198 | 29 | 198 | 15 |
| n (Patient) | 117 | 13 | 117 | 29 | 117 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.63 | nd | 0.60 | 0.54 | nd | 0.52 | 0.62 | nd | 0.63 |
| SE | 0.077 | nd | 0.085 | 0.059 | nd | 0.058 | 0.075 | nd | 0.080 |
| p | 0.082 | nd | 0.24 | 0.51 | nd | 0.77 | 0.12 | nd | 0.097 |
| nCohort 1 | 216 | nd | 198 | 216 | nd | 198 | 216 | nd | 198 |
| nCohort 2 | 16 | nd | 13 | 28 | nd | 29 | 17 | nd | 15 |
| Cutoff 1 | 0.770 | nd | 0.603 | 0.603 | nd | 0.603 | 0.770 | nd | 0.770 |
| Sens 1 | 75% | nd | 100% | 75% | nd | 72% | 71% | nd | 73% |
| Spec 1 | 41% | nd | 23% | 25% | nd | 23% | 41% | nd | 41% |
| Cutoff 2 | 0.603 | nd | 0.603 | 0 | nd | 0 | 0.603 | nd | 0.603 |
| Sens 2 | 100% | nd | 100% | 100% | nd | 100% | 88% | nd | 93% |
| Spec 2 | 25% | nd | 23% | 0% | nd | 0% | 25% | nd | 23% |
| Cutoff 3 | 0.603 | nd | 0.603 | 0 | nd | 0 | 0.257 | nd | 0.603 |
| Sens 3 | 100% | nd | 100% | 100% | nd | 100% | 100% | nd | 93% |
| Spec 3 | 25% | nd | 23% | 0% | nd | 0% | 15% | nd | 23% |
| Cutoff 4 | 1.10 | nd | 1.10 | 1.10 | nd | 1.10 | 1.10 | nd | 1.10 |
| Sens 4 | 38% | nd | 31% | 43% | nd | 41% | 47% | nd | 53% |
| Spec 4 | 71% | nd | 70% | 71% | nd | 70% | 71% | nd | 70% |
| Cutoff 5 | 179 | nd | 267 | 179 | nd | 267 | 179 | nd | 267 |
| Sens 5 | 25% | nd | 23% | 32% | nd | 24% | 35% | nd | 20% |
| Spec 5 | 80% | nd | 80% | 80% | nd | 80% | 80% | nd | 80% |
| Cutoff 6 | 1040 | nd | 1040 | 1040 | nd | 1040 | 1040 | nd | 1040 |
| Sens 6 | 25% | nd | 23% | 14% | nd | 14% | 24% | nd | 20% |
| Spec 6 | 90% | nd | 90% | 90% | nd | 90% | 90% | nd | 90% |
| OR Quart 2 | >6.7 | nd | >5.4 | 0.84 | nd | 0.71 | 1.5 | nd | 2.1 |
| p Value | <0.083 | nd | <0.13 | 0.77 | nd | 0.55 | 0.65 | nd | 0.41 |
| 95% CI of | >0.78 | nd | >0.61 | 0.27 | nd | 0.23 | 0.25 | nd | 0.36 |
| OR Quart 2 | na | nd | na | 2.7 | nd | 2.2 | 9.5 | nd | 12 |
| OR Quart 3 | >5.5 | nd | >5.4 | 0.69 | nd | 0.58 | 2.6 | nd | 1.5 |
| p Value | <0.13 | nd | <0.13 | 0.54 | nd | 0.36 | 0.26 | nd | 0.65 |
| 95% CI of | >0.62 | nd | >0.61 | 0.21 | nd | 0.18 | 0.49 | nd | 0.25 |
| OR Quart 3 | na | nd | na | 2.3 | nd | 1.9 | 14 | nd | 9.5 |
| OR Quart 4 | >5.5 | nd | >3.1 | 1.5 | nd | 1.3 | 3.8 | nd | 3.2 |
| p Value | <0.13 | nd | <0.33 | 0.43 | nd | 0.64 | 0.11 | nd | 0.17 |
| 95% CI of | >0.62 | nd | >0.31 | 0.54 | nd | 0.46 | 0.75 | nd | 0.61 |
| OR Quart 4 | na | nd | na | 4.3 | nd | 3.5 | 19 | nd | 17 |

| Interleukin-28A | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.195 | 0.148 | 0.195 | 0.265 | 0.195 | 2.92 |
| Average | 31.1 | 18.2 | 31.1 | 12.7 | 31.1 | 26.0 |
| Stdev | 255 | 61.1 | 255 | 45.7 | 255 | 58.2 |
| p (t-test) | | 0.84 | | 0.70 | | 0.93 |

-continued

| | | | | | | |
|---|---|---|---|---|---|---|
| Min | 0.0727 | 0.0727 | 0.0727 | 0.0727 | 0.0727 | 0.0727 |
| Max | 3150 | 246 | 3150 | 243 | 3150 | 235 |
| n (Samp) | 216 | 16 | 216 | 28 | 216 | 17 |
| n (Patient) | 132 | 16 | 132 | 28 | 132 | 17 |
| UO only | | | | | | |
| Median | 0.195 | 0.148 | 0.195 | 0.265 | 0.195 | 0.195 |
| Average | 32.4 | 2.50 | 32.4 | 4.50 | 32.4 | 12.9 |
| Stdev | 266 | 5.90 | 266 | 8.06 | 266 | 23.4 |
| p (t-test) | | 0.69 | | 0.57 | | 0.78 |
| Min | 0.0727 | 0.0727 | 0.0727 | 0.0727 | 0.0727 | 0.0727 |
| Max | 3150 | 20.8 | 3150 | 35.6 | 3150 | 71.6 |
| n (Samp) | 198 | 13 | 198 | 29 | 198 | 15 |
| n (Patient) | 117 | 13 | 117 | 29 | 117 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.43 | nd | 0.35 | 0.54 | nd | 0.58 | 0.60 | nd | 0.57 |
| SE | 0.077 | nd | 0.085 | 0.059 | nd | 0.059 | 0.075 | nd | 0.080 |
| p | 0.34 | nd | 0.081 | 0.45 | nd | 0.17 | 0.16 | nd | 0.35 |
| nCohort 1 | 216 | nd | 198 | 216 | nd | 198 | 216 | nd | 198 |
| nCohort 2 | 16 | nd | 13 | 28 | nd | 29 | 17 | nd | 15 |
| Cutoff 1 | 0 | nd | 0 | 0.158 | nd | 0.158 | 0.158 | nd | 0.158 |
| Sens 1 | 100% | nd | 100% | 71% | nd | 72% | 76% | nd | 73% |
| Spec 1 | 0% | nd | 0% | 38% | nd | 41% | 38% | nd | 41% |
| Cutoff 2 | 0 | nd | 0 | 0.120 | nd | 0.120 | 0.120 | nd | 0.120 |
| Sens 2 | 100% | nd | 100% | 86% | nd | 86% | 82% | nd | 80% |
| Spec 2 | 0% | nd | 0% | 17% | nd | 19% | 17% | nd | 19% |
| Cutoff 3 | 0 | nd | 0 | 0 | nd | 0 | 0 | nd | 0 |
| Sens 3 | 100% | nd | 100% | 100% | nd | 100% | 100% | nd | 100% |
| Spec 3 | 0% | nd | 0% | 0% | nd | 0% | 0% | nd | 0% |
| Cutoff 4 | 0.265 | nd | 0.265 | 0.265 | nd | 0.265 | 0.265 | nd | 0.265 |
| Sens 4 | 38% | nd | 23% | 32% | nd | 34% | 53% | nd | 40% |
| Spec 4 | 71% | nd | 75% | 71% | nd | 75% | 71% | nd | 75% |
| Cutoff 5 | 10.2 | nd | 5.01 | 10.2 | nd | 5.01 | 10.2 | nd | 5.01 |
| Sens 5 | 19% | nd | 15% | 21% | nd | 31% | 41% | nd | 33% |
| Spec 5 | 80% | nd | 80% | 80% | nd | 80% | 80% | nd | 80% |
| Cutoff 6 | 21.9 | nd | 20.8 | 21.9 | nd | 20.8 | 21.9 | nd | 20.8 |
| Sens 6 | 6% | nd | 0% | 7% | nd | 3% | 24% | nd | 20% |
| Spec 6 | 91% | nd | 90% | 91% | nd | 90% | 91% | nd | 90% |
| OR Quart 2 | 0.48 | nd | 0 | 2.2 | nd | 1.8 | 0.74 | nd | 1.7 |
| p Value | 0.41 | nd | na | 0.23 | nd | 0.36 | 0.70 | nd | 0.47 |
| 95% CI of | 0.085 | nd | na | 0.61 | nd | 0.50 | 0.16 | nd | 0.39 |
| OR Quart 2 | 2.7 | nd | na | 7.6 | nd | 6.6 | 3.4 | nd | 7.7 |
| OR Quart 3 | 1.3 | nd | 1.7 | 1.8 | nd | 2.4 | 0.74 | nd | 0.32 |
| p Value | 0.73 | nd | 0.47 | 0.35 | nd | 0.16 | 0.70 | nd | 0.33 |
| 95% CI of | 0.32 | nd | 0.39 | 0.51 | nd | 0.70 | 0.16 | nd | 0.032 |
| OR Quart 3 | 5.0 | nd | 7.7 | 6.7 | nd | 8.4 | 3.4 | nd | 3.2 |
| OR Quart 4 | 1.3 | nd | 1.8 | 2.5 | nd | 2.4 | 1.8 | nd | 2.1 |
| p Value | 0.73 | nd | 0.45 | 0.15 | nd | 0.16 | 0.36 | nd | 0.32 |
| 95% CI of | 0.32 | nd | 0.40 | 0.72 | nd | 0.70 | 0.50 | nd | 0.49 |
| OR Quart 4 | 5.0 | nd | 7.8 | 8.5 | nd | 8.4 | 6.6 | nd | 8.8 |

| Interleukin-33 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.0981 | 0.0981 | 0.0981 | 0.0981 | 0.0981 | 2.20 |
| Average | 244 | 336 | 244 | 222 | 244 | 1080 |
| Stdev | 2720 | 1030 | 2720 | 849 | 2720 | 3330 |
| p (t-test) | | 0.89 | | 0.97 | | 0.23 |
| Min | 0.0445 | 0.0445 | 0.0445 | 0.0445 | 0.0445 | 0.0445 |
| Max | 40000 | 4130 | 40000 | 4440 | 40000 | 13500 |
| n (Samp) | 217 | 16 | 217 | 28 | 217 | 17 |
| n (Patient) | 133 | 16 | 133 | 28 | 133 | 17 |
| UO only | | | | | | |
| Median | 0.0981 | 0.0981 | 0.0981 | 0.0981 | 0.0981 | 2.20 |
| Average | 264 | 351 | 264 | 196 | 264 | 1160 |
| Stdev | 2850 | 1140 | 2850 | 828 | 2850 | 3540 |
| p (t-test) | | 0.91 | | 0.90 | | 0.25 |
| Min | 0.0445 | 0.0445 | 0.0445 | 0.0445 | 0.0445 | 0.0445 |
| Max | 40000 | 4130 | 40000 | 4440 | 40000 | 13500 |

|  | 0 hr prior to AKI stage | | 24 hr prior to AKI stage | | 48 hr prior to AKI stage | |
| --- | --- | --- | --- | --- | --- | --- |
| n (Samp) | 199 | 13 | 199 | 29 | 199 | 15 |
| n (Patient) | 118 | 13 | 118 | 29 | 118 | 15 |

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | 0.53 | nd | 0.52 | 0.51 | nd | 0.52 | 0.64 | nd | 0.66 |
| SE | 0.076 | nd | 0.084 | 0.058 | nd | 0.058 | 0.075 | nd | 0.079 |
| p | 0.72 | nd | 0.81 | 0.82 | nd | 0.79 | 0.053 | nd | 0.042 |
| nCohort 1 | 217 | nd | 199 | 217 | nd | 199 | 217 | nd | 199 |
| nCohort 2 | 16 | nd | 13 | 28 | nd | 29 | 17 | nd | 15 |
| Cutoff 1 | 0.0494 | nd | 0.0494 | 0.0494 | nd | 0.0494 | 0.0996 | nd | 0.0996 |
| Sens 1 | 88% | nd | 92% | 71% | nd | 72% | 71% | nd | 73% |
| Spec 1 | 23% | nd | 21% | 23% | nd | 21% | 57% | nd | 58% |
| Cutoff 2 | 0.0494 | nd | 0.0494 | 0.0445 | nd | 0.0445 | 0.0494 | nd | 0.0846 |
| Sens 2 | 88% | nd | 92% | 93% | nd | 93% | 88% | nd | 80% |
| Spec 2 | 23% | nd | 21% | 10% | nd | 9% | 23% | nd | 39% |
| Cutoff 3 | 0 | nd | 0.0494 | 0.0445 | nd | 0.0445 | 0 | nd | 0.0494 |
| Sens 3 | 100% | nd | 92% | 93% | nd | 93% | 100% | nd | 93% |
| Spec 3 | 0% | nd | 21% | 10% | nd | 9% | 0% | nd | 21% |
| Cutoff 4 | 0.821 | nd | 0.101 | 0.821 | nd | 0.101 | 0.821 | nd | 0.101 |
| Sens 4 | 31% | nd | 31% | 39% | nd | 41% | 59% | nd | 60% |
| Spec 4 | 71% | nd | 70% | 71% | nd | 70% | 71% | nd | 70% |
| Cutoff 5 | 10.4 | nd | 13.1 | 10.4 | nd | 13.1 | 10.4 | nd | 13.1 |
| Sens 5 | 25% | nd | 23% | 25% | nd | 24% | 35% | nd | 33% |
| Spec 5 | 80% | nd | 80% | 80% | nd | 80% | 80% | nd | 80% |
| Cutoff 6 | 58.1 | nd | 58.1 | 58.1 | nd | 58.1 | 58.1 | nd | 58.1 |
| Sens 6 | 25% | nd | 23% | 14% | nd | 14% | 24% | nd | 20% |
| Spec 6 | 90% | nd | 90% | 90% | nd | 90% | 90% | nd | 90% |
| OR Quart 2 | 4.5 | nd | 7.9 | 0.86 | nd | 0.86 | 1.5 | nd | 0.48 |
| p Value | 0.065 | nd | 0.057 | 0.78 | nd | 0.78 | 0.66 | nd | 0.56 |
| 95% CI of | 0.91 | nd | 0.94 | 0.29 | nd | 0.29 | 0.24 | nd | 0.042 |
| OR Quart 2 | 22 | nd | 67 | 2.5 | nd | 2.5 | 9.3 | nd | 5.5 |
| OR Quart 3 | 0.49 | nd | 2.0 | 0.59 | nd | 0.72 | 2.6 | nd | 3.9 |
| p Value | 0.57 | nd | 0.57 | 0.38 | nd | 0.57 | 0.26 | nd | 0.10 |
| 95% CI of | 0.043 | nd | 0.18 | 0.18 | nd | 0.23 | 0.49 | nd | 0.77 |
| OR Quart 3 | 5.6 | nd | 23 | 1.9 | nd | 2.2 | 14 | nd | 20 |
| OR Quart 4 | 2.6 | nd | 3.1 | 0.98 | nd | 1.0 | 3.8 | nd | 2.6 |
| p Value | 0.27 | nd | 0.33 | 0.97 | nd | 1.0 | 0.11 | nd | 0.27 |
| 95% CI of | 0.48 | nd | 0.31 | 0.34 | nd | 0.35 | 0.75 | nd | 0.48 |
| OR Quart 4 | 14 | nd | 31 | 2.8 | nd | 2.9 | 19 | nd | 14 |

| Interleukin-4 receptor alpha chain | | | | | | |
| --- | --- | --- | --- | --- | --- | --- |
|  | 0 hr prior to AKI stage | | 24 hr prior to AKI stage | | 48 hr prior to AKI stage | |
|  | Cohort 1 | Cohort 2 | Cohort 1 | Cohort 2 | Cohort 1 | Cohort 2 |
| sCr or UO | | | | | | |
| Median | 218 | 269 | 218 | 218 | 218 | 228 |
| Average | 288 | 396 | 288 | 297 | 288 | 332 |
| Stdev | 210 | 321 | 210 | 271 | 210 | 233 |
| p (t-test) |  | 0.057 |  | 0.83 |  | 0.40 |
| Min | 49.7 | 111 | 49.7 | 3.27 | 49.7 | 103 |
| Max | 1200 | 1090 | 1200 | 1210 | 1200 | 997 |
| n (Samp) | 217 | 16 | 217 | 28 | 217 | 17 |
| n (Patient) | 133 | 16 | 133 | 28 | 133 | 17 |
| UO only | | | | | | |
| Median | 229 | 298 | 229 | 191 | 229 | 228 |
| Average | 297 | 442 | 297 | 286 | 297 | 341 |
| Stdev | 215 | 336 | 215 | 268 | 215 | 247 |
| p (t-test) |  | 0.024 |  | 0.82 |  | 0.45 |
| Min | 49.7 | 138 | 49.7 | 3.27 | 49.7 | 84.5 |
| Max | 1200 | 1090 | 1200 | 1210 | 1200 | 997 |
| n (Samp) | 199 | 13 | 199 | 29 | 199 | 15 |
| n (Patient) | 118 | 13 | 118 | 29 | 118 | 15 |

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | 0.59 | nd | 0.64 | 0.48 | nd | 0.44 | 0.56 | nd | 0.54 |
| SE | 0.077 | nd | 0.085 | 0.059 | nd | 0.059 | 0.075 | nd | 0.079 |
| p | 0.26 | nd | 0.11 | 0.72 | nd | 0.32 | 0.44 | nd | 0.58 |
| nCohort 1 | 217 | nd | 199 | 217 | nd | 199 | 217 | nd | 199 |
| nCohort 2 | 16 | nd | 13 | 28 | nd | 29 | 17 | nd | 15 |

-continued

| | | | | | | | | | |
|---|---|---|---|---|---|---|---|---|---|
| Cutoff 1 | 195 | nd | 204 | 148 | nd | 142 | 178 | nd | 170 |
| Sens 1 | 75% | nd | 77% | 71% | nd | 72% | 71% | nd | 73% |
| Spec 1 | 43% | nd | 42% | 23% | nd | 19% | 35% | nd | 30% |
| Cutoff 2 | 153 | nd | 195 | 104 | nd | 104 | 165 | nd | 165 |
| Sens 2 | 81% | nd | 85% | 89% | nd | 93% | 82% | nd | 80% |
| Spec 2 | 25% | nd | 40% | 6% | nd | 6% | 30% | nd | 29% |
| Cutoff 3 | 111 | nd | 153 | 83.5 | nd | 104 | 121 | nd | 121 |
| Sens 3 | 94% | nd | 92% | 93% | nd | 93% | 94% | nd | 93% |
| Spec 3 | 6% | nd | 24% | 3% | nd | 6% | 9% | nd | 8% |
| Cutoff 4 | 299 | nd | 317 | 299 | nd | 317 | 299 | nd | 317 |
| Sens 4 | 44% | nd | 46% | 39% | nd | 28% | 47% | nd | 47% |
| Spec 4 | 70% | nd | 70% | 70% | nd | 70% | 70% | nd | 70% |
| Cutoff 5 | 380 | nd | 400 | 380 | nd | 400 | 380 | nd | 400 |
| Sens 5 | 31% | nd | 38% | 18% | nd | 17% | 35% | nd | 33% |
| Spec 5 | 80% | nd | 80% | 80% | nd | 80% | 80% | nd | 80% |
| Cutoff 6 | 529 | nd | 560 | 529 | nd | 560 | 529 | nd | 560 |
| Sens 6 | 25% | nd | 23% | 11% | nd | 10% | 18% | nd | 20% |
| Spec 6 | 90% | nd | 90% | 90% | nd | 90% | 90% | nd | 90% |
| OR Quart 2 | 1.4 | nd | 1.5 | 0.74 | nd | 0.54 | 1.7 | nd | 1.7 |
| p Value | 0.70 | nd | 0.65 | 0.59 | nd | 0.35 | 0.48 | nd | 0.48 |
| 95% CI of | 0.29 | nd | 0.25 | 0.24 | nd | 0.15 | 0.39 | nd | 0.39 |
| OR Quart 2 | 6.4 | nd | 9.5 | 2.3 | nd | 2.0 | 7.5 | nd | 7.5 |
| OR Quart 3 | 1.0 | nd | 1.5 | 0.60 | nd | 1.2 | 1.0 | nd | 0.32 |
| p Value | 1.0 | nd | 0.65 | 0.40 | nd | 0.78 | 1.0 | nd | 0.33 |
| 95% CI of | 0.19 | nd | 0.25 | 0.19 | nd | 0.39 | 0.19 | nd | 0.032 |
| OR Quart 3 | 5.2 | nd | 9.5 | 2.0 | nd | 3.5 | 5.2 | nd | 3.2 |
| OR Quart 4 | 2.1 | nd | 2.7 | 1.2 | nd | 1.5 | 2.1 | nd | 2.1 |
| p Value | 0.32 | nd | 0.26 | 0.77 | nd | 0.43 | 0.32 | nd | 0.32 |
| 95% CI of | 0.49 | nd | 0.49 | 0.42 | nd | 0.53 | 0.49 | nd | 0.49 |
| OR Quart 4 | 8.7 | nd | 14 | 3.3 | nd | 4.3 | 8.7 | nd | 8.8 |

| Vascular endothelial growth factor receptor 2 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 7910 | 9090 | 7910 | 7270 | 7910 | 7250 |
| Average | 9670 | 9560 | 9670 | 8430 | 9670 | 17800 |
| Stdev | 11000 | 4770 | 11000 | 3820 | 11000 | 38600 |
| p (t-test) | | 0.97 | | 0.55 | | 0.028 |
| Min | 3640 | 3140 | 3640 | 4110 | 3640 | 3340 |
| Max | 153000 | 18000 | 153000 | 19800 | 153000 | 166000 |
| n (Samp) | 217 | 16 | 217 | 28 | 217 | 17 |
| n (Patient) | 133 | 16 | 133 | 28 | 133 | 17 |
| UO only | | | | | | |
| Median | 7930 | 9140 | 7930 | 7590 | 7930 | 7250 |
| Average | 9820 | 9510 | 9820 | 8350 | 9820 | 19000 |
| Stdev | 11400 | 4780 | 11400 | 3590 | 11400 | 41100 |
| p (t-test) | | 0.92 | | 0.49 | | 0.025 |
| Min | 3640 | 3140 | 3640 | 4110 | 3640 | 4480 |
| Max | 153000 | 18000 | 153000 | 19800 | 153000 | 166000 |
| n (Samp) | 199 | 13 | 199 | 29 | 199 | 15 |
| n (Patient) | 118 | 13 | 118 | 29 | 118 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.53 | nd | 0.54 | 0.45 | nd | 0.45 | 0.45 | nd | 0.44 |
| SE | 0.076 | nd | 0.084 | 0.059 | nd | 0.059 | 0.075 | nd | 0.079 |
| p | 0.71 | nd | 0.67 | 0.38 | nd | 0.41 | 0.47 | nd | 0.46 |
| nCohort 1 | 217 | nd | 199 | 217 | nd | 199 | 217 | nd | 199 |
| nCohort 2 | 16 | nd | 13 | 28 | nd | 29 | 17 | nd | 15 |
| Cutoff 1 | 5760 | nd | 5620 | 5720 | nd | 5720 | 6010 | nd | 6010 |
| Sens 1 | 75% | nd | 77% | 71% | nd | 72% | 71% | nd | 73% |
| Spec 1 | 15% | nd | 14% | 15% | nd | 15% | 18% | nd | 18% |
| Cutoff 2 | 5620 | nd | 5310 | 5610 | nd | 5610 | 5140 | nd | 5880 |
| Sens 2 | 81% | nd | 85% | 82% | nd | 83% | 82% | nd | 80% |
| Spec 2 | 14% | nd | 9% | 14% | nd | 14% | 8% | nd | 16% |
| Cutoff 3 | 4780 | nd | 4730 | 5140 | nd | 5140 | 4330 | nd | 5030 |
| Sens 3 | 94% | nd | 92% | 93% | nd | 93% | 94% | nd | 93% |
| Spec 3 | 6% | nd | 5% | 8% | nd | 7% | 4% | nd | 6% |
| Cutoff 4 | 9260 | nd | 9260 | 9260 | nd | 9260 | 9260 | nd | 9260 |
| Sens 4 | 44% | nd | 46% | 25% | nd | 24% | 29% | nd | 27% |
| Spec 4 | 70% | nd | 70% | 70% | nd | 70% | 70% | nd | 70% |

| | | | | | | | | | |
|---|---|---|---|---|---|---|---|---|---|
| Cutoff 5 | 10300 | nd | 10500 | 10300 | nd | 10500 | 10300 | nd | 10500 |
| Sens 5 | 25% | nd | 23% | 21% | nd | 21% | 29% | nd | 27% |
| Spec 5 | 80% | nd | 80% | 80% | nd | 80% | 80% | nd | 80% |
| Cutoff 6 | 14000 | nd | 14400 | 14000 | nd | 14400 | 14000 | nd | 14400 |
| Sens 6 | 25% | nd | 23% | 14% | nd | 7% | 18% | nd | 13% |
| Spec 6 | 90% | nd | 90% | 90% | nd | 90% | 90% | nd | 90% |
| OR Quart 2 | 0.15 | nd | 0 | 1.2 | nd | 1.2 | 0.19 | nd | 0.24 |
| p Value | 0.086 | nd | na | 0.75 | nd | 0.77 | 0.13 | nd | 0.21 |
| 95% CI of | 0.018 | nd | na | 0.38 | nd | 0.37 | 0.021 | nd | 0.026 |
| OR Quart 2 | 1.3 | nd | na | 3.8 | nd | 3.8 | 1.7 | nd | 2.2 |
| OR Quart 3 | 0.64 | nd | 0.78 | 0.48 | nd | 0.82 | 0.79 | nd | 1.0 |
| p Value | 0.51 | nd | 0.73 | 0.32 | nd | 0.75 | 0.73 | nd | 1.0 |
| 95% CI of | 0.17 | nd | 0.20 | 0.12 | nd | 0.23 | 0.20 | nd | 0.24 |
| OR Quart 3 | 2.4 | nd | 3.1 | 2.0 | nd | 2.8 | 3.1 | nd | 4.2 |
| OR Quart 4 | 0.80 | nd | 0.78 | 2.3 | nd | 2.0 | 1.5 | nd | 1.6 |
| p Value | 0.73 | nd | 0.73 | 0.12 | nd | 0.19 | 0.52 | nd | 0.49 |
| 95% CI of | 0.23 | nd | 0.20 | 0.80 | nd | 0.70 | 0.44 | nd | 0.42 |
| OR Quart 4 | 2.8 | nd | 3.1 | 6.5 | nd | 5.9 | 5.0 | nd | 6.0 |

Neural cell adhesion molecule 1

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 185000 | 178000 | 185000 | 185000 | 185000 | 165000 |
| Average | 192000 | 187000 | 192000 | 195000 | 192000 | 164000 |
| Stdev | 67100 | 63200 | 67100 | 86900 | 67100 | 55500 |
| p (t-test) | | 0.77 | | 0.84 | | 0.067 |
| Min | 63300 | 93200 | 63300 | 81100 | 63300 | 49200 |
| Max | 520000 | 316000 | 520000 | 506000 | 520000 | 280000 |
| n (Samp) | 281 | 16 | 281 | 28 | 281 | 20 |
| n (Patient) | 159 | 16 | 159 | 28 | 159 | 20 |
| sCr only | | | | | | |
| Median | nd | nd | nd | nd | 181000 | 181000 |
| Average | nd | nd | nd | nd | 187000 | 203000 |
| Stdev | nd | nd | nd | nd | 65700 | 57300 |
| p (t-test) | nd | nd | nd | nd | | 0.55 |
| Min | nd | nd | nd | nd | 49200 | 140000 |
| Max | nd | nd | nd | nd | 520000 | 280000 |
| n (Samp) | nd | nd | nd | nd | 352 | 6 |
| n (Patient) | nd | nd | nd | nd | 192 | 6 |
| UO only | | | | | | |
| Median | 184000 | 172000 | 184000 | 177000 | 184000 | 156000 |
| Average | 191000 | 168000 | 191000 | 173000 | 191000 | 155000 |
| Stdev | 69000 | 51800 | 69000 | 56900 | 69000 | 47600 |
| p (t-test) | | 0.24 | | 0.20 | | 0.032 |
| Min | 63300 | 93200 | 63300 | 81100 | 63300 | 49200 |
| Max | 520000 | 282000 | 520000 | 331000 | 520000 | 230000 |
| n (Samp) | 257 | 13 | 257 | 26 | 257 | 17 |
| n (Patient) | 139 | 13 | 139 | 26 | 139 | 17 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.48 | nd | 0.40 | 0.48 | nd | 0.42 | 0.37 | 0.58 | 0.35 |
| SE | 0.075 | nd | 0.085 | 0.058 | nd | 0.061 | 0.069 | 0.12 | 0.074 |
| p | 0.84 | nd | 0.24 | 0.73 | nd | 0.21 | 0.069 | 0.54 | 0.037 |
| nCohort 1 | 281 | nd | 257 | 281 | nd | 257 | 281 | 352 | 257 |
| nCohort 2 | 16 | nd | 13 | 28 | nd | 26 | 20 | 6 | 17 |
| Cutoff 1 | 152000 | nd | 133000 | 158000 | nd | 130000 | 144000 | 166000 | 144000 |
| Sens 1 | 75% | nd | 77% | 71% | nd | 73% | 70% | 83% | 71% |
| Spec 1 | 29% | nd | 19% | 31% | nd | 18% | 23% | 40% | 25% |
| Cutoff 2 | 133000 | nd | 121000 | 125000 | nd | 121000 | 121000 | 166000 | 107000 |
| Sens 2 | 81% | nd | 85% | 82% | nd | 81% | 80% | 83% | 82% |
| Spec 2 | 18% | nd | 13% | 12% | nd | 13% | 11% | 40% | 8% |
| Cutoff 3 | 95600 | nd | 95600 | 105000 | nd | 105000 | 106000 | 140000 | 91800 |
| Sens 3 | 94% | nd | 92% | 93% | nd | 92% | 90% | 100% | 94% |
| Spec 3 | 4% | nd | 4% | 6% | nd | 7% | 7% | 23% | 3% |
| Cutoff 4 | 214000 | nd | 215000 | 214000 | nd | 215000 | 214000 | 207000 | 215000 |
| Sens 4 | 25% | nd | 8% | 29% | nd | 19% | 15% | 33% | 12% |
| Spec 4 | 70% | nd | 70% | 70% | nd | 70% | 70% | 70% | 70% |
| Cutoff 5 | 233000 | nd | 234000 | 233000 | nd | 234000 | 233000 | 228000 | 234000 |
| Sens 5 | 19% | nd | 8% | 14% | nd | 12% | 10% | 33% | 0% |

-continued

| | | | | | | | | | |
|---|---|---|---|---|---|---|---|---|---|
| Spec 5 | 80% | nd | 80% | 80% | nd | 80% | 80% | 80% | 80% |
| Cutoff 6 | 266000 | nd | 266000 | 266000 | nd | 266000 | 266000 | 262000 | 266000 |
| Sens 6 | 12% | nd | 8% | 11% | nd | 4% | 10% | 33% | 0% |
| Spec 6 | 90% | nd | 90% | 90% | nd | 90% | 90% | 90% | 90% |
| OR Quart 2 | 0.75 | nd | 3.1 | 1.0 | nd | 1.8 | 1.0 | 2.0 | 1.5 |
| p Value | 0.71 | nd | 0.33 | 0.98 | nd | 0.35 | 0.99 | 0.57 | 0.64 |
| 95% CI of | 0.16 | nd | 0.32 | 0.34 | nd | 0.51 | 0.20 | 0.18 | 0.25 |
| OR Quart 2 | 3.5 | nd | 31 | 3.0 | nd | 6.6 | 5.2 | 22 | 9.6 |
| OR Quart 3 | 1.3 | nd | 5.3 | 0.86 | nd | 1.5 | 2.5 | 1.0 | 3.8 |
| p Value | 0.72 | nd | 0.13 | 0.79 | nd | 0.51 | 0.20 | 1.0 | 0.11 |
| 95% CI of | 0.33 | nd | 0.60 | 0.27 | nd | 0.42 | 0.62 | 0.062 | 0.76 |
| OR Quart 3 | 5.0 | nd | 47 | 2.7 | nd | 5.7 | 10 | 16 | 19 |
| OR Quart 4 | 1.0 | nd | 4.3 | 1.2 | nd | 2.5 | 2.5 | 2.0 | 2.7 |
| p Value | 0.98 | nd | 0.20 | 0.77 | nd | 0.15 | 0.20 | 0.57 | 0.25 |
| 95% CI of | 0.24 | nd | 0.46 | 0.40 | nd | 0.72 | 0.62 | 0.18 | 0.50 |
| OR Quart 4 | 4.2 | nd | 39 | 3.4 | nd | 8.4 | 10 | 22 | 14 |

Platelet-derived growth factor subunit B (dimer)

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 357 | 228 | 357 | 346 | 357 | 448 |
| Average | 410 | 280 | 410 | 523 | 410 | 398 |
| Stdev | 246 | 155 | 246 | 668 | 246 | 234 |
| p (t-test) | | 0.039 | | 0.067 | | 0.84 |
| Min | 28.1 | 33.7 | 28.1 | 74.0 | 28.1 | 45.0 |
| Max | 1540 | 601 | 1540 | 2720 | 1540 | 750 |
| n (Samp) | 274 | 16 | 274 | 27 | 274 | 19 |
| n (Patient) | 158 | 16 | 158 | 27 | 158 | 19 |
| sCr only | | | | | | |
| Median | nd | nd | nd | nd | 342 | 357 |
| Average | nd | nd | nd | nd | 391 | 385 |
| Stdev | nd | nd | nd | nd | 245 | 160 |
| p (t-test) | nd | nd | nd | nd | | 0.95 |
| Min | nd | nd | nd | nd | 0.189 | 220 |
| Max | nd | nd | nd | nd | 1540 | 609 |
| n (Samp) | nd | nd | nd | nd | 341 | 6 |
| n (Patient) | nd | nd | nd | nd | 188 | 6 |
| UO only | | | | | | |
| Median | 334 | 224 | 334 | 346 | 334 | 352 |
| Average | 389 | 283 | 389 | 456 | 389 | 385 |
| Stdev | 238 | 171 | 238 | 532 | 238 | 247 |
| p (t-test) | | 0.12 | | 0.25 | | 0.95 |
| Min | 28.1 | 33.7 | 28.1 | 74.0 | 28.1 | 45.0 |
| Max | 1540 | 601 | 1540 | 2720 | 1540 | 750 |
| n (Samp) | 250 | 13 | 250 | 25 | 250 | 16 |
| n (Patient) | 138 | 13 | 138 | 25 | 138 | 16 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.34 | nd | 0.36 | 0.46 | nd | 0.47 | 0.50 | 0.52 | 0.49 |
| SE | 0.076 | nd | 0.085 | 0.059 | nd | 0.061 | 0.069 | 0.12 | 0.075 |
| p | 0.030 | nd | 0.11 | 0.50 | nd | 0.67 | 0.95 | 0.86 | 0.94 |
| nCohort 1 | 274 | nd | 250 | 274 | nd | 250 | 274 | 341 | 250 |
| nCohort 2 | 16 | nd | 13 | 27 | nd | 25 | 19 | 6 | 16 |
| Cutoff 1 | 192 | nd | 171 | 220 | nd | 220 | 242 | 247 | 229 |
| Sens 1 | 75% | nd | 77% | 70% | nd | 72% | 74% | 83% | 75% |
| Spec 1 | 19% | nd | 18% | 23% | nd | 26% | 26% | 31% | 27% |
| Cutoff 2 | 171 | nd | 165 | 155 | nd | 155 | 122 | 247 | 122 |
| Sens 2 | 81% | nd | 85% | 81% | nd | 80% | 84% | 83% | 81% |
| Spec 2 | 16% | nd | 18% | 15% | nd | 16% | 10% | 31% | 11% |
| Cutoff 3 | 138 | nd | 138 | 88.8 | nd | 88.8 | 88.8 | 220 | 88.8 |
| Sens 3 | 94% | nd | 92% | 93% | nd | 92% | 95% | 100% | 94% |
| Spec 3 | 12% | nd | 13% | 5% | nd | 5% | 5% | 27% | 5% |
| Cutoff 4 | 504 | nd | 478 | 504 | nd | 478 | 504 | 496 | 478 |
| Sens 4 | 12% | nd | 23% | 22% | nd | 24% | 42% | 33% | 44% |
| Spec 4 | 70% | nd | 70% | 70% | nd | 70% | 70% | 70% | 70% |
| Cutoff 5 | 613 | nd | 569 | 613 | nd | 569 | 613 | 583 | 569 |
| Sens 5 | 0% | nd | 8% | 22% | nd | 24% | 16% | 17% | 25% |
| Spec 5 | 80% | nd | 80% | 80% | nd | 80% | 80% | 80% | 80% |
| Cutoff 6 | 728 | nd | 697 | 728 | nd | 697 | 728 | 704 | 697 |

-continued

| | | | | | | | | | |
|---|---|---|---|---|---|---|---|---|---|
| Sens 6 | 0% | nd | 0% | 19% | nd | 20% | 11% | 0% | 19% |
| Spec 6 | 90% | nd | 90% | 90% | nd | 90% | 90% | 90% | 90% |
| OR Quart 2 | 4.2 | nd | 1.0 | 1.2 | nd | 1.2 | 1.0 | >3.1 | 0.59 |
| p Value | 0.20 | nd | 1.0 | 0.75 | nd | 0.77 | 0.98 | <0.34 | 0.48 |
| 95% CI of | 0.46 | nd | 0.14 | 0.38 | nd | 0.38 | 0.28 | >0.31 | 0.14 |
| OR Quart 2 | 39 | nd | 7.3 | 3.8 | nd | 3.7 | 3.7 | na | 2.6 |
| OR Quart 3 | 3.1 | nd | 1.5 | 0.83 | nd | 0.82 | 0.80 | >2.0 | 0.79 |
| p Value | 0.33 | nd | 0.65 | 0.77 | nd | 0.75 | 0.75 | <0.57 | 0.73 |
| 95% CI of | 0.31 | nd | 0.25 | 0.24 | nd | 0.24 | 0.21 | >0.18 | 0.20 |
| OR Quart 3 | 30 | nd | 9.4 | 2.9 | nd | 2.8 | 3.1 | na | 3.1 |
| OR Quart 4 | 9.0 | nd | 3.3 | 1.6 | nd | 1.2 | 1.0 | >1.0 | 0.80 |
| p Value | 0.041 | nd | 0.16 | 0.40 | nd | 0.75 | 0.98 | <1.0 | 0.75 |
| 95% CI of | 1.1 | nd | 0.63 | 0.54 | nd | 0.38 | 0.28 | >0.062 | 0.21 |
| OR Quart 4 | 74 | nd | 17 | 4.7 | nd | 3.8 | 3.7 | na | 3.1 |

Corticotropin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.000668 | 0.00344 | 0.000668 | 0.00402 | 0.000668 | 0.00254 |
| Average | 0.00568 | 0.00650 | 0.00568 | 0.00599 | 0.00568 | 0.00960 |
| Stdev | 0.0263 | 0.00561 | 0.0263 | 0.00669 | 0.0263 | 0.0224 |
| p (t-test) | | 0.93 | | 0.96 | | 0.56 |
| Min | 3.38E−6 | 6.17E−6 | 3.38E−6 | 3.38E−6 | 3.38E−6 | 3.38E−6 |
| Max | 0.292 | 0.0140 | 0.292 | 0.0251 | 0.292 | 0.0908 |
| n (Samp) | 197 | 7 | 197 | 20 | 197 | 16 |
| n (Patient) | 131 | 7 | 131 | 20 | 131 | 16 |
| UO only | | | | | | |
| Median | nd | nd | 0.000881 | 0.00389 | 0.000881 | 0.00297 |
| Average | nd | nd | 0.00636 | 0.00721 | 0.00636 | 0.0115 |
| Stdev | nd | nd | 0.0280 | 0.00813 | 0.0280 | 0.0246 |
| p (t-test) | nd | nd | | 0.90 | | 0.52 |
| Min | nd | nd | 3.38E−6 | 3.38E−6 | 3.38E−6 | 3.38E−6 |
| Max | nd | nd | 0.292 | 0.0251 | 0.292 | 0.0908 |
| n (Samp) | nd | nd | 173 | 18 | 173 | 13 |
| n (Patient) | nd | nd | 111 | 18 | 111 | 13 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.74 | nd | nd | 0.67 | nd | 0.67 | 0.56 | nd | 0.63 |
| SE | 0.11 | nd | nd | 0.069 | nd | 0.072 | 0.077 | nd | 0.086 |
| p | 0.026 | nd | nd | 0.016 | nd | 0.016 | 0.46 | nd | 0.12 |
| nCohort 1 | 197 | nd | nd | 197 | nd | 173 | 197 | nd | 173 |
| nCohort 2 | 7 | nd | nd | 20 | nd | 18 | 16 | nd | 13 |
| Cutoff 1 | 0.00317 | nd | nd | 0.000466 | nd | 0.000293 | 4.31E−6 | nd | 0.00192 |
| Sens 1 | 71% | nd | nd | 70% | nd | 72% | 75% | nd | 77% |
| Spec 1 | 76% | nd | nd | 45% | nd | 42% | 16% | nd | 64% |
| Cutoff 2 | 0.00183 | nd | nd | 0.000278 | nd | 0.000278 | 3.38E−6 | nd | 4.31E−6 |
| Sens 2 | 86% | nd | nd | 85% | nd | 89% | 88% | nd | 85% |
| Spec 2 | 66% | nd | nd | 41% | nd | 39% | 5% | nd | 16% |
| Cutoff 3 | 4.31E−6 | nd | nd | 4.31E−6 | nd | 4.31E−6 | 0 | nd | 3.38E−6 |
| Sens 3 | 100% | nd | nd | 90% | nd | 94% | 100% | nd | 92% |
| Spec 3 | 16% | nd | nd | 16% | nd | 16% | 0% | nd | 5% |
| Cutoff 4 | 0.00221 | nd | nd | 0.00221 | nd | 0.00297 | 0.00221 | nd | 0.00297 |
| Sens 4 | 71% | nd | nd | 60% | nd | 61% | 56% | nd | 46% |
| Spec 4 | 70% | nd | nd | 70% | nd | 72% | 70% | nd | 72% |
| Cutoff 5 | 0.00423 | nd | nd | 0.00423 | nd | 0.00486 | 0.00423 | nd | 0.00486 |
| Sens 5 | 43% | nd | nd | 50% | nd | 44% | 31% | nd | 31% |
| Spec 5 | 80% | nd | nd | 80% | nd | 80% | 80% | nd | 80% |
| Cutoff 6 | 0.00829 | nd | nd | 0.00829 | nd | 0.00914 | 0.00829 | nd | 0.00914 |
| Sens 6 | 43% | nd | nd | 35% | nd | 33% | 19% | nd | 23% |
| Spec 6 | 90% | nd | nd | 90% | nd | 90% | 90% | nd | 90% |
| OR Quart 2 | 0 | nd | nd | 1.4 | nd | 2.0 | 0 | nd | 0 |
| p Value | na | nd | nd | 0.70 | nd | 0.42 | na | nd | na |
| 95% CI of | na | nd | nd | 0.29 | nd | 0.36 | na | nd | na |
| OR Quart 2 | na | nd | nd | 6.4 | nd | 12 | na | nd | na |
| OR Quart 3 | 2.0 | nd | nd | 0.65 | nd | 1.5 | 0.64 | nd | 1.7 |
| p Value | 0.57 | nd | nd | 0.65 | nd | 0.67 | 0.51 | nd | 0.46 |
| 95% CI of | 0.18 | nd | nd | 0.10 | nd | 0.24 | 0.17 | nd | 0.39 |
| OR Quart 3 | 23 | nd | nd | 4.1 | nd | 9.4 | 2.4 | nd | 7.8 |
| OR Quart 4 | 4.3 | nd | nd | 4.2 | nd | 5.2 | 0.98 | nd | 1.7 |
| p Value | 0.20 | nd | nd | 0.034 | nd | 0.042 | 0.97 | nd | 0.48 |

| | | | | | | | | | |
|---|---|---|---|---|---|---|---|---|---|
| 95% CI of | 0.46 | nd | nd | 1.1 | nd | 1.1 | 0.29 | nd | 0.38 |
| OR Quart 4 | 39 | nd | nd | 16 | nd | 25 | 3.3 | nd | 7.6 |

Thyroxine-binding globulin

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 36.9 | 34.2 | 36.9 | 29.8 | 36.9 | 30.0 |
| Average | 37.8 | 35.8 | 37.8 | 33.3 | 37.8 | 35.1 |
| Stdev | 10.8 | 10.4 | 10.8 | 12.0 | 10.8 | 12.8 |
| p (t-test) | | 0.36 | | 0.026 | | 0.31 |
| Min | 12.8 | 15.2 | 12.8 | 14.2 | 12.8 | 16.3 |
| Max | 75.8 | 57.7 | 75.8 | 63.7 | 75.8 | 62.0 |
| n (Samp) | 437 | 26 | 437 | 32 | 437 | 17 |
| n (Patient) | 174 | 26 | 174 | 32 | 174 | 17 |
| sCr only | | | | | | |
| Median | 36.2 | 28.7 | 36.2 | 30.3 | 36.2 | 33.2 |
| Average | 37.0 | 31.4 | 37.0 | 33.8 | 37.0 | 34.0 |
| Stdev | 11.1 | 12.8 | 11.1 | 14.8 | 11.1 | 14.2 |
| p (t-test) | | 0.22 | | 0.42 | | 0.47 |
| Min | 12.8 | 18.0 | 12.8 | 15.9 | 12.8 | 15.2 |
| Max | 75.8 | 56.0 | 75.8 | 63.7 | 75.8 | 62.0 |
| n (Samp) | 535 | 6 | 535 | 8 | 535 | 7 |
| n (Patient) | 207 | 6 | 207 | 8 | 207 | 7 |
| UO only | | | | | | |
| Median | 35.6 | 32.5 | 35.6 | 28.5 | 35.6 | 30.0 |
| Average | 36.9 | 34.7 | 36.9 | 31.9 | 36.9 | 34.0 |
| Stdev | 10.6 | 9.63 | 10.6 | 10.5 | 10.6 | 12.5 |
| p (t-test) | | 0.30 | | 0.011 | | 0.26 |
| Min | 12.8 | 15.2 | 12.8 | 14.2 | 12.8 | 16.3 |
| Max | 75.8 | 57.7 | 75.8 | 57.0 | 75.8 | 56.0 |
| n (Samp) | 363 | 26 | 363 | 31 | 363 | 17 |
| n (Patient) | 141 | 26 | 141 | 31 | 141 | 17 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.44 | 0.32 | 0.43 | 0.36 | 0.39 | 0.34 | 0.42 | 0.40 | 0.42 |
| SE | 0.060 | 0.12 | 0.060 | 0.054 | 0.11 | 0.055 | 0.074 | 0.11 | 0.074 |
| p | 0.28 | 0.15 | 0.24 | 0.013 | 0.29 | 0.0049 | 0.31 | 0.36 | 0.26 |
| nCohort 1 | 437 | 535 | 363 | 437 | 535 | 363 | 437 | 535 | 363 |
| nCohort 2 | 26 | 6 | 26 | 32 | 8 | 31 | 17 | 7 | 17 |
| Cutoff 1 | 28.4 | 26.8 | 28.4 | 25.7 | 28.4 | 26.4 | 28.2 | 29.8 | 27.4 |
| Sens 1 | 73% | 83% | 73% | 72% | 75% | 71% | 71% | 71% | 71% |
| Spec 1 | 19% | 18% | 21% | 12% | 24% | 15% | 19% | 28% | 16% |
| Cutoff 2 | 27.6 | 26.8 | 27.6 | 23.9 | 22.2 | 24.7 | 23.8 | 26.9 | 22.2 |
| Sens 2 | 85% | 83% | 81% | 81% | 88% | 81% | 82% | 86% | 82% |
| Spec 2 | 17% | 18% | 18% | 8% | 8% | 11% | 8% | 18% | 6% |
| Cutoff 3 | 26.5 | 17.9 | 26.5 | 20.5 | 15.8 | 20.5 | 19.6 | 15.0 | 19.6 |
| Sens 3 | 92% | 100% | 92% | 91% | 100% | 90% | 94% | 100% | 94% |
| Spec 3 | 14% | 4% | 15% | 5% | 3% | 6% | 4% | 1% | 4% |
| Cutoff 4 | 43.6 | 42.9 | 42.2 | 43.6 | 42.9 | 42.2 | 43.6 | 42.9 | 42.2 |
| Sens 4 | 19% | 17% | 23% | 19% | 25% | 16% | 29% | 14% | 35% |
| Spec 4 | 70% | 71% | 71% | 70% | 71% | 71% | 70% | 71% | 71% |
| Cutoff 5 | 46.7 | 46.3 | 46.0 | 46.7 | 46.3 | 46.0 | 46.7 | 46.3 | 46.0 |
| Sens 5 | 15% | 17% | 15% | 12% | 12% | 10% | 18% | 14% | 18% |
| Spec 5 | 80% | 80% | 80% | 80% | 80% | 80% | 80% | 80% | 80% |
| Cutoff 6 | 50.4 | 50.1 | 49.7 | 50.4 | 50.1 | 49.7 | 50.4 | 50.1 | 49.7 |
| Sens 6 | 12% | 17% | 8% | 9% | 12% | 6% | 12% | 14% | 18% |
| Spec 6 | 90% | 90% | 90% | 90% | 90% | 90% | 90% | 90% | 90% |
| OR Quart 2 | 0.79 | 0 | 1.3 | 1.0 | 0 | 1.5 | 0.75 | 1.0 | 0.39 |
| p Value | 0.73 | na | 0.72 | 0.99 | na | 0.51 | 0.71 | 1.00 | 0.26 |
| 95% CI of | 0.21 | na | 0.33 | 0.32 | na | 0.42 | 0.16 | 0.062 | 0.073 |
| OR Quart 2 | 3.0 | na | 4.9 | 3.2 | na | 5.7 | 3.4 | 16 | 2.0 |
| OR Quart 3 | 1.6 | 2.0 | 2.1 | 0.66 | 1.0 | 1.3 | 1.0 | 3.0 | 0.39 |
| p Value | 0.40 | 0.57 | 0.24 | 0.53 | 1.0 | 0.73 | 1.0 | 0.34 | 0.26 |
| 95% CI of | 0.52 | 0.18 | 0.61 | 0.18 | 0.14 | 0.33 | 0.24 | 0.31 | 0.073 |
| OR Quart 3 | 5.2 | 23 | 7.3 | 2.4 | 7.2 | 4.9 | 4.1 | 30 | 2.0 |
| OR Quart 4 | 1.9 | 3.1 | 2.4 | 3.0 | 2.0 | 4.6 | 1.5 | 2.0 | 1.7 |
| p Value | 0.27 | 0.33 | 0.16 | 0.029 | 0.41 | 0.0081 | 0.51 | 0.57 | 0.39 |

-continued

| | | | | | | | | | |
|---|---|---|---|---|---|---|---|---|---|
| 95% CI of | 0.61 | 0.32 | 0.71 | 1.1 | 0.37 | 1.5 | 0.42 | 0.18 | 0.52 |
| OR Quart 4 | 5.8 | 30 | 8.1 | 7.8 | 11 | 14 | 5.6 | 23 | 5.3 |

Tumor necrosis factor receptor superfamily member 8

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 101 | 105 | 101 | 98.7 | 101 | 69.9 |
| Average | 201 | 193 | 201 | 156 | 201 | 244 |
| Stdev | 415 | 178 | 415 | 144 | 415 | 637 |
| p (t-test) | | 0.94 | | 0.57 | | 0.69 |
| Min | 12.8 | 53.7 | 12.8 | 12.8 | 12.8 | 4.06 |
| Max | 3360 | 611 | 3360 | 595 | 3360 | 2700 |
| n (Samp) | 217 | 16 | 217 | 28 | 217 | 17 |
| n (Patient) | 133 | 16 | 133 | 28 | 133 | 17 |
| UO only | | | | | | |
| Median | 101 | 105 | 101 | 104 | 101 | 67.7 |
| Average | 205 | 201 | 205 | 148 | 205 | 250 |
| Stdev | 431 | 189 | 431 | 137 | 431 | 680 |
| p (t-test) | | 0.98 | | 0.48 | | 0.71 |
| Min | 12.8 | 53.7 | 12.8 | 12.8 | 12.8 | 4.06 |
| Max | 3360 | 611 | 3360 | 595 | 3360 | 2700 |
| n (Samp) | 199 | 13 | 199 | 29 | 199 | 15 |
| n (Patient) | 118 | 13 | 118 | 29 | 118 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.57 | nd | 0.58 | 0.49 | nd | 0.49 | 0.38 | nd | 0.34 |
| SE | 0.077 | nd | 0.085 | 0.058 | nd | 0.058 | 0.075 | nd | 0.079 |
| p | 0.39 | nd | 0.32 | 0.85 | nd | 0.89 | 0.12 | nd | 0.042 |
| nCohort 1 | 217 | nd | 199 | 217 | nd | 199 | 217 | nd | 199 |
| nCohort 2 | 16 | nd | 13 | 28 | nd | 29 | 17 | nd | 15 |
| Cutoff 1 | 75.4 | nd | 75.4 | 65.4 | nd | 68.4 | 47.2 | nd | 47.2 |
| Sens 1 | 75% | nd | 77% | 71% | nd | 72% | 71% | nd | 73% |
| Spec 1 | 29% | nd | 30% | 24% | nd | 26% | 13% | nd | 13% |
| Cutoff 2 | 74.6 | nd | 74.6 | 54.3 | nd | 54.3 | 37.8 | nd | 37.8 |
| Sens 2 | 81% | nd | 85% | 86% | nd | 86% | 82% | nd | 80% |
| Spec 2 | 29% | nd | 29% | 15% | nd | 15% | 9% | nd | 10% |
| Cutoff 3 | 53.7 | nd | 64.9 | 36.7 | nd | 36.7 | 36.7 | nd | 36.7 |
| Sens 3 | 94% | nd | 92% | 93% | nd | 93% | 94% | nd | 93% |
| Spec 3 | 15% | nd | 23% | 8% | nd | 9% | 8% | nd | 9% |
| Cutoff 4 | 148 | nd | 148 | 148 | nd | 148 | 148 | nd | 148 |
| Sens 4 | 38% | nd | 38% | 29% | nd | 24% | 24% | nd | 20% |
| Spec 4 | 70% | nd | 70% | 70% | nd | 70% | 70% | nd | 70% |
| Cutoff 5 | 192 | nd | 192 | 192 | nd | 192 | 192 | nd | 192 |
| Sens 5 | 31% | nd | 31% | 29% | nd | 24% | 12% | nd | 7% |
| Spec 5 | 80% | nd | 80% | 80% | nd | 80% | 80% | nd | 80% |
| Cutoff 6 | 285 | nd | 285 | 285 | nd | 285 | 285 | nd | 285 |
| Sens 6 | 19% | nd | 15% | 18% | nd | 14% | 12% | nd | 7% |
| Spec 6 | 90% | nd | 90% | 90% | nd | 90% | 90% | nd | 90% |
| OR Quart 2 | 1.4 | nd | 1.5 | 0.74 | nd | 1.2 | 1.0 | nd | 0.67 |
| p Value | 0.70 | nd | 0.65 | 0.59 | nd | 0.78 | 0.98 | nd | 0.66 |
| 95% CI of | 0.29 | nd | 0.25 | 0.24 | nd | 0.39 | 0.20 | nd | 0.11 |
| OR Quart 2 | 6.4 | nd | 9.5 | 2.3 | nd | 3.5 | 5.3 | nd | 4.2 |
| OR Quart 3 | 1.4 | nd | 2.1 | 0.74 | nd | 0.84 | 1.4 | nd | 1.0 |
| p Value | 0.70 | nd | 0.41 | 0.59 | nd | 0.77 | 0.70 | nd | 1.0 |
| 95% CI of | 0.29 | nd | 0.36 | 0.24 | nd | 0.26 | 0.29 | nd | 0.19 |
| OR Quart 3 | 6.4 | nd | 12 | 2.3 | nd | 2.7 | 6.3 | nd | 5.2 |
| OR Quart 4 | 1.7 | nd | 2.1 | 1.0 | nd | 1.2 | 2.6 | nd | 2.6 |
| p Value | 0.48 | nd | 0.41 | 0.97 | nd | 0.78 | 0.19 | nd | 0.19 |
| 95% CI of | 0.39 | nd | 0.36 | 0.36 | nd | 0.39 | 0.63 | nd | 0.63 |
| OR Quart 4 | 7.5 | nd | 12 | 2.9 | nd | 3.5 | 10 | nd | 11 |

-continued

| | Alpha-fetoprotein | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.321 | 0.00880 | 0.321 | 0.410 | 0.321 | 0.441 |
| Average | 0.350 | 0.327 | 0.350 | 0.470 | 0.350 | 0.497 |
| Stdev | 0.333 | 0.467 | 0.333 | 0.436 | 0.333 | 0.351 |
| p (t-test) | | 0.79 | | 0.078 | | 0.058 |
| Min | 0.00580 | 0.00580 | 0.00580 | 0.00580 | 0.00580 | 0.00580 |
| Max | 1.81 | 1.63 | 1.81 | 1.53 | 1.81 | 1.19 |
| n (Samp) | 282 | 16 | 282 | 28 | 282 | 20 |
| n (Patient) | 160 | 16 | 160 | 28 | 160 | 20 |
| sCr only | | | | | | |
| Median | nd | nd | nd | nd | 0.327 | 0.484 |
| Average | nd | nd | nd | nd | 0.355 | 0.487 |
| Stdev | nd | nd | nd | nd | 0.348 | 0.303 |
| p (t-test) | nd | nd | nd | nd | | 0.35 |
| Min | nd | nd | nd | nd | 0.00580 | 0.00580 |
| Max | nd | nd | nd | nd | 1.81 | 0.924 |
| n (Samp) | nd | nd | nd | nd | 353 | 6 |
| n (Patient) | nd | nd | nd | nd | 193 | 6 |
| UO only | | | | | | |
| Median | 0.321 | 0.00880 | 0.321 | 0.376 | 0.321 | 0.445 |
| Average | 0.342 | 0.279 | 0.342 | 0.438 | 0.342 | 0.527 |
| Stdev | 0.333 | 0.504 | 0.333 | 0.420 | 0.333 | 0.418 |
| p (t-test) | | 0.52 | | 0.18 | | 0.030 |
| Min | 0.00580 | 0.00580 | 0.00580 | 0.00580 | 0.00580 | 0.00580 |
| Max | 1.81 | 1.63 | 1.81 | 1.53 | 1.81 | 1.31 |
| n (Samp) | 258 | 13 | 258 | 26 | 258 | 17 |
| n (Patient) | 140 | 13 | 140 | 26 | 140 | 17 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.43 | nd | 0.38 | 0.58 | nd | 0.56 | 0.64 | 0.64 | 0.65 |
| SE | 0.076 | nd | 0.085 | 0.059 | nd | 0.061 | 0.069 | 0.12 | 0.074 |
| p | 0.38 | nd | 0.15 | 0.19 | nd | 0.31 | 0.035 | 0.26 | 0.050 |
| nCohort 1 | 282 | nd | 258 | 282 | nd | 258 | 282 | 353 | 258 |
| nCohort 2 | 16 | nd | 13 | 28 | nd | 26 | 20 | 6 | 17 |
| Cutoff 1 | 0.00580 | nd | 0 | 0.0947 | nd | 0.00580 | 0.392 | 0.392 | 0.381 |
| Sens 1 | 75% | nd | 100% | 71% | nd | 85% | 70% | 83% | 71% |
| Spec 1 | 16% | nd | 0% | 32% | nd | 17% | 62% | 61% | 59% |
| Cutoff 2 | 0 | nd | 0 | 0.00580 | nd | 0.00580 | 0.221 | 0.392 | 0.00580 |
| Sens 2 | 100% | nd | 100% | 86% | nd | 85% | 80% | 83% | 94% |
| Spec 2 | 0% | nd | 0% | 16% | nd | 17% | 41% | 61% | 17% |
| Cutoff 3 | 0 | nd | 0 | 0 | nd | 0 | 0.00580 | 0 | 0.00580 |
| Sens 3 | 100% | nd | 100% | 100% | nd | 100% | 95% | 100% | 94% |
| Spec 3 | 0% | nd | 0% | 0% | nd | 0% | 16% | 0% | 17% |
| Cutoff 4 | 0.496 | nd | 0.502 | 0.496 | nd | 0.502 | 0.496 | 0.509 | 0.502 |
| Sens 4 | 31% | nd | 23% | 43% | nd | 42% | 45% | 50% | 47% |
| Spec 4 | 70% | nd | 70% | 70% | nd | 70% | 70% | 70% | 70% |
| Cutoff 5 | 0.581 | nd | 0.581 | 0.581 | nd | 0.581 | 0.581 | 0.607 | 0.581 |
| Sens 5 | 25% | nd | 23% | 36% | nd | 35% | 35% | 33% | 41% |
| Spec 5 | 80% | nd | 80% | 80% | nd | 80% | 80% | 80% | 80% |
| Cutoff 6 | 0.767 | nd | 0.767 | 0.767 | nd | 0.767 | 0.767 | 0.803 | 0.767 |
| Sens 6 | 12% | nd | 15% | 21% | nd | 19% | 20% | 17% | 24% |
| Spec 6 | 90% | nd | 90% | 90% | nd | 90% | 90% | 90% | 90% |
| OR Quart 2 | 0.75 | nd | 0.32 | 0.54 | nd | 1.8 | 4.1 | 0 | 4.1 |
| p Value | 0.71 | nd | 0.33 | 0.34 | nd | 0.35 | 0.21 | na | 0.21 |
| 95% CI of | 0.16 | nd | 0.033 | 0.15 | nd | 0.51 | 0.45 | na | 0.45 |
| OR Quart 2 | 3.5 | nd | 3.2 | 1.9 | nd | 6.6 | 38 | na | 38 |
| OR Quart 3 | 0.74 | nd | 1.7 | 0.85 | nd | 1.5 | 7.6 | 3.0 | 5.2 |
| p Value | 0.70 | nd | 0.47 | 0.77 | nd | 0.51 | 0.061 | 0.34 | 0.14 |
| 95% CI of | 0.16 | nd | 0.39 | 0.27 | nd | 0.42 | 0.91 | 0.31 | 0.60 |
| OR Quart 3 | 3.4 | nd | 7.5 | 2.6 | nd | 5.7 | 64 | 30 | 46 |
| OR Quart 4 | 1.6 | nd | 1.4 | 1.6 | nd | 2.4 | 8.7 | 2.0 | 7.6 |
| p Value | 0.50 | nd | 0.68 | 0.33 | nd | 0.16 | 0.044 | 0.57 | 0.062 |
| 95% CI of | 0.42 | nd | 0.30 | 0.60 | nd | 0.71 | 1.1 | 0.18 | 0.90 |
| OR Quart 4 | 5.8 | nd | 6.4 | 4.5 | nd | 8.3 | 71 | 22 | 63 |

-continued

| | Apolipoprotein E | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 51700 | 43400 | 51700 | 47500 | 51700 | 32700 |
| Average | 63800 | 54300 | 63800 | 55300 | 63800 | 37200 |
| Stdev | 46700 | 35100 | 46700 | 43000 | 46700 | 23500 |
| p (t-test) | | 0.30 | | 0.31 | | 0.014 |
| Min | 4980 | 14500 | 4980 | 10500 | 4980 | 1940 |
| Max | 260000 | 141000 | 260000 | 232000 | 260000 | 98400 |
| n (Samp) | 325 | 27 | 325 | 34 | 325 | 19 |
| n (Patient) | 192 | 27 | 192 | 34 | 192 | 19 |
| sCr only | | | | | | |
| Median | nd | nd | 51000 | 50300 | nd | nd |
| Average | nd | nd | 61200 | 86900 | nd | nd |
| Stdev | nd | nd | 44000 | 79800 | nd | nd |
| p (t-test) | nd | nd | | 0.16 | nd | nd |
| Min | nd | nd | 1940 | 27200 | nd | nd |
| Max | nd | nd | 260000 | 232000 | nd | nd |
| n (Samp) | nd | nd | 417 | 6 | nd | nd |
| n (Patient) | nd | nd | 228 | 6 | nd | nd |
| UO only | | | | | | |
| Median | 51100 | 46800 | 51100 | 41600 | 51100 | 30200 |
| Average | 62700 | 55800 | 62700 | 46200 | 62700 | 34900 |
| Stdev | 45100 | 34800 | 45100 | 26700 | 45100 | 22900 |
| p (t-test) | | 0.44 | | 0.037 | | 0.0100 |
| Min | 4980 | 14500 | 4980 | 10500 | 4980 | 1940 |
| Max | 244000 | 141000 | 244000 | 129000 | 244000 | 98400 |
| n (Samp) | 295 | 27 | 295 | 34 | 295 | 18 |
| n (Patient) | 167 | 27 | 167 | 34 | 167 | 18 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.45 | nd | 0.47 | 0.44 | 0.57 | 0.40 | 0.32 | nd | 0.29 |
| SE | 0.059 | nd | 0.059 | 0.053 | 0.12 | 0.054 | 0.069 | nd | 0.070 |
| p | 0.37 | nd | 0.62 | 0.29 | 0.59 | 0.076 | 0.0077 | nd | 0.0033 |
| nCohort 1 | 325 | nd | 295 | 325 | 417 | 295 | 325 | nd | 295 |
| nCohort 2 | 27 | nd | 27 | 34 | 6 | 34 | 19 | nd | 18 |
| Cutoff 1 | 29100 | nd | 30700 | 31300 | 33900 | 29100 | 25600 | nd | 25600 |
| Sens 1 | 70% | nd | 70% | 71% | 83% | 71% | 74% | nd | 72% |
| Spec 1 | 22% | nd | 25% | 26% | 29% | 22% | 17% | nd | 17% |
| Cutoff 2 | 25700 | nd | 25600 | 24700 | 33900 | 20900 | 16700 | nd | 16700 |
| Sens 2 | 81% | nd | 81% | 82% | 83% | 82% | 84% | nd | 83% |
| Spec 2 | 17% | nd | 17% | 16% | 29% | 14% | 9% | nd | 9% |
| Cutoff 3 | 20700 | nd | 20700 | 16700 | 27000 | 16700 | 4980 | nd | 4980 |
| Sens 3 | 93% | nd | 93% | 91% | 100% | 91% | 95% | nd | 94% |
| Spec 3 | 13% | nd | 14% | 9% | 19% | 9% | 0% | nd | 0% |
| Cutoff 4 | 75000 | nd | 75700 | 75000 | 68400 | 75700 | 75000 | nd | 75700 |
| Sens 4 | 19% | nd | 19% | 18% | 33% | 12% | 5% | nd | 6% |
| Spec 4 | 70% | nd | 70% | 70% | 70% | 70% | 70% | nd | 70% |
| Cutoff 5 | 90400 | nd | 90900 | 90400 | 87000 | 90900 | 90400 | nd | 90900 |
| Sens 5 | 11% | nd | 11% | 12% | 33% | 6% | 5% | nd | 6% |
| Spec 5 | 80% | nd | 80% | 80% | 80% | 80% | 80% | nd | 80% |
| Cutoff 6 | 124000 | nd | 121000 | 124000 | 120000 | 121000 | 124000 | nd | 121000 |
| Sens 6 | 7% | nd | 11% | 9% | 33% | 3% | 0% | nd | 0% |
| Spec 6 | 90% | nd | 90% | 90% | 90% | 90% | 90% | nd | 90% |
| OR Quart 2 | 1.4 | nd | 1.7 | 1.9 | 2.0 | 4.1 | 3.1 | nd | 2.1 |
| p Value | 0.55 | nd | 0.38 | 0.27 | 0.57 | 0.035 | 0.34 | nd | 0.56 |
| 95% CI of | 0.44 | nd | 0.53 | 0.61 | 0.18 | 1.1 | 0.31 | nd | 0.18 |
| OR Quart 2 | 4.7 | nd | 5.4 | 5.9 | 22 | 15 | 30 | nd | 23 |
| OR Quart 3 | 1.2 | nd | 1.2 | 2.1 | 0.99 | 2.9 | 7.5 | nd | 6.5 |
| p Value | 0.76 | nd | 0.76 | 0.19 | 0.99 | 0.13 | 0.062 | nd | 0.087 |
| 95% CI of | 0.36 | nd | 0.36 | 0.70 | 0.061 | 0.74 | 0.91 | nd | 0.76 |
| OR Quart 3 | 4.1 | nd | 4.2 | 6.5 | 16 | 11 | 63 | nd | 55 |
| OR Quart 4 | 1.9 | nd | 1.7 | 2.2 | 2.0 | 4.6 | 8.7 | nd | 10 |
| p Value | 0.27 | nd | 0.38 | 0.18 | 0.57 | 0.022 | 0.043 | nd | 0.030 |
| 95% CI of | 0.61 | nd | 0.53 | 0.70 | 0.18 | 1.2 | 1.1 | nd | 1.3 |
| OR Quart 4 | 5.9 | nd | 5.4 | 6.6 | 22 | 17 | 71 | nd | 82 |

Apolipoprotein(a)

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 52400 | 30100 | 52400 | 41200 | 52400 | 15800 |
| Average | 89500 | 61200 | 89500 | 73100 | 89500 | 42400 |
| Stdev | 110000 | 72000 | 110000 | 95100 | 110000 | 58500 |
| p (t-test) | | 0.19 | | 0.41 | | 0.066 |
| Min | 7.99 | 380 | 7.99 | 1030 | 7.99 | 1300 |
| Max | 722000 | 234000 | 722000 | 423000 | 722000 | 187000 |
| n (Samp) | 325 | 27 | 325 | 34 | 325 | 19 |
| n (Patient) | 192 | 27 | 192 | 34 | 192 | 19 |
| sCr only | | | | | | |
| Median | nd | nd | 45000 | 30300 | nd | nd |
| Average | nd | nd | 84100 | 68400 | nd | nd |
| Stdev | nd | nd | 106000 | 83400 | nd | nd |
| p (t-test) | nd | nd | | 0.72 | nd | nd |
| Min | nd | nd | 7.99 | 968 | nd | nd |
| Max | nd | nd | 722000 | 200000 | nd | nd |
| n (Samp) | nd | nd | 417 | 6 | nd | nd |
| n (Patient) | nd | nd | 228 | 6 | nd | nd |
| UO only | | | | | | |
| Median | 47600 | 30100 | 47600 | 31200 | 47600 | 13500 |
| Average | 82800 | 61400 | 82800 | 68900 | 82800 | 41800 |
| Stdev | 102000 | 71900 | 102000 | 95000 | 102000 | 60300 |
| p (t-test) | | 0.28 | | 0.45 | | 0.092 |
| Min | 7.99 | 380 | 7.99 | 1030 | 7.99 | 1300 |
| Max | 631000 | 234000 | 631000 | 423000 | 631000 | 187000 |
| n (Samp) | 295 | 27 | 295 | 34 | 295 | 18 |
| n (Patient) | 167 | 27 | 167 | 34 | 167 | 18 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.41 | nd | 0.42 | 0.44 | 0.44 | 0.44 | 0.32 | nd | 0.32 |
| SE | 0.060 | nd | 0.060 | 0.053 | 0.12 | 0.054 | 0.069 | nd | 0.071 |
| p | 0.12 | nd | 0.20 | 0.29 | 0.60 | 0.23 | 0.0084 | nd | 0.010 |
| nCohort 1 | 325 | nd | 295 | 325 | 417 | 295 | 325 | nd | 295 |
| nCohort 2 | 27 | nd | 27 | 34 | 6 | 34 | 19 | nd | 18 |
| Cutoff 1 | 9720 | nd | 9720 | 14100 | 4320 | 10500 | 3140 | nd | 3010 |
| Sens 1 | 70% | nd | 70% | 71% | 83% | 71% | 74% | nd | 72% |
| Spec 1 | 16% | nd | 17% | 24% | 9% | 19% | 5% | nd | 6% |
| Cutoff 2 | 4320 | nd | 4320 | 6200 | 4320 | 6120 | 2260 | nd | 2260 |
| Sens 2 | 81% | nd | 81% | 82% | 83% | 88% | 84% | nd | 83% |
| Spec 2 | 6% | nd | 7% | 10% | 9% | 11% | 4% | nd | 4% |
| Cutoff 3 | 2710 | nd | 3010 | 5110 | 887 | 5110 | 1680 | nd | 1680 |
| Sens 3 | 93% | nd | 93% | 91% | 100% | 91% | 95% | nd | 94% |
| Spec 3 | 4% | nd | 6% | 7% | 2% | 7% | 4% | nd | 4% |
| Cutoff 4 | 99500 | nd | 92000 | 99500 | 95700 | 92000 | 99500 | nd | 92000 |
| Sens 4 | 22% | nd | 26% | 26% | 33% | 26% | 16% | nd | 22% |
| Spec 4 | 70% | nd | 70% | 70% | 70% | 70% | 70% | nd | 70% |
| Cutoff 5 | 142000 | nd | 128000 | 142000 | 135000 | 128000 | 142000 | nd | 128000 |
| Sens 5 | 15% | nd | 15% | 18% | 33% | 15% | 16% | nd | 17% |
| Spec 5 | 80% | nd | 80% | 80% | 80% | 80% | 80% | nd | 80% |
| Cutoff 6 | 235000 | nd | 219000 | 235000 | 225000 | 219000 | 235000 | nd | 219000 |
| Sens 6 | 0% | nd | 7% | 6% | 0% | 6% | 0% | nd | 0% |
| Spec 6 | 90% | nd | 90% | 90% | 90% | 90% | 90% | nd | 90% |
| OR Quart 2 | 0.82 | nd | 0.83 | 0.42 | 0 | 0.74 | 0.66 | nd | 0.33 |
| p Value | 0.76 | nd | 0.77 | 0.16 | na | 0.59 | 0.65 | nd | 0.34 |
| 95% CI of | 0.24 | nd | 0.24 | 0.12 | na | 0.25 | 0.11 | nd | 0.033 |
| OR Quart 2 | 2.8 | nd | 2.8 | 1.4 | na | 2.2 | 4.0 | nd | 3.2 |
| OR Quart 3 | 1.0 | nd | 1.0 | 1.3 | 1.0 | 1.2 | 1.7 | nd | 1.7 |
| p Value | 1.0 | nd | 1.0 | 0.64 | 1.0 | 0.78 | 0.47 | nd | 0.46 |
| 95% CI of | 0.31 | nd | 0.31 | 0.49 | 0.14 | 0.42 | 0.40 | nd | 0.40 |
| OR Quart 3 | 3.2 | nd | 3.2 | 3.2 | 7.2 | 3.2 | 7.4 | nd | 7.5 |
| OR Quart 4 | 1.8 | nd | 1.8 | 1.1 | 1.0 | 1.5 | 3.2 | nd | 3.3 |
| p Value | 0.30 | nd | 0.29 | 0.79 | 0.99 | 0.45 | 0.087 | nd | 0.082 |
| 95% CI of | 0.61 | nd | 0.62 | 0.44 | 0.14 | 0.55 | 0.84 | nd | 0.86 |
| OR Quart 4 | 5.0 | nd | 5.2 | 3.0 | 7.3 | 3.8 | 12 | nd | 13 |

FIG. 7: Comparison of marker levels in EDTA samples collected within 12 hours of reaching stage R from Cohort 1 (patients that reached, but did not progress beyond, RIFLE stage R) and from Cohort 2 (patients that reached RIFLE stage I or F).

| C-C motif chemokine 7 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.620 | 0.512 | nd | nd | 0.620 | 0.512 |
| Average | 10.9 | 11.4 | nd | nd | 11.2 | 12.4 |
| Stdev | 28.1 | 22.4 | nd | nd | 30.3 | 24.3 |
| p (t-test) | | 0.94 | nd | nd | | 0.90 |
| Min | 0.193 | 0.193 | nd | nd | 0.193 | 0.193 |
| Max | 166 | 79.4 | nd | nd | 166 | 79.4 |
| n (Samp) | 41 | 19 | nd | nd | 31 | 15 |
| n (Patient) | 41 | 19 | nd | nd | 31 | 15 |

| At Enrollment | | | |
|---|---|---|---|
| | sCr or UO | sCr only | UO only |
| AUC | 0.51 | nd | 0.49 |
| SE | 0.081 | nd | 0.092 |
| p | 0.95 | nd | 0.93 |
| nCohort 1 | 41 | nd | 31 |
| nCohort 2 | 19 | nd | 15 |
| Cutoff 1 | 0.193 | nd | 0.193 |
| Sens 1 | 95% | nd | 93% |
| Spec 1 | 20% | nd | 19% |
| Cutoff 2 | 0.193 | nd | 0.193 |
| Sens 2 | 95% | nd | 93% |
| Spec 2 | 20% | nd | 19% |
| Cutoff 3 | 0.193 | nd | 0.193 |
| Sens 3 | 95% | nd | 93% |
| Spec 3 | 20% | nd | 19% |
| Cutoff 4 | 9.43 | nd | 9.43 |
| Sens 4 | 32% | nd | 33% |
| Spec 4 | 71% | nd | 71% |
| Cutoff 5 | 13.9 | nd | 13.9 |
| Sens 5 | 21% | nd | 20% |
| Spec 5 | 80% | nd | 81% |
| Cutoff 6 | 19.6 | nd | 19.6 |
| Sens 6 | 16% | nd | 13% |
| Spec 6 | 90% | nd | 90% |
| OR Quart 2 | 1.0 | nd | 0.75 |
| p Value | 1.0 | nd | 0.75 |
| 95% CI of | 0.22 | nd | 0.13 |
| OR Quart 2 | 4.6 | nd | 4.5 |
| OR Quart 3 | 0.73 | nd | 1.0 |
| p Value | 0.69 | nd | 1.0 |
| 95% CI of | 0.15 | nd | 0.18 |
| OR Quart 3 | 3.5 | nd | 5.5 |
| OR Quart 4 | 1.0 | nd | 1.1 |
| p Value | 1.0 | nd | 0.88 |
| 95% CI of | 0.22 | nd | 0.21 |
| OR Quart 4 | 4.6 | nd | 6.4 |

| Interleukin-33 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.0981 | 0.0981 | nd | nd | 0.0981 | 0.0543 |
| Average | 67.7 | 946 | nd | nd | 3.24 | 1200 |
| Stdev | 275 | 3200 | nd | nd | 8.39 | 3590 |
| p (t-test) | | 0.084 | nd | nd | | 0.067 |
| Min | 0.0445 | 0.0445 | nd | nd | 0.0445 | 0.0445 |
| Max | 1270 | 13500 | nd | nd | 42.0 | 13500 |
| n (Samp) | 41 | 19 | nd | nd | 31 | 15 |
| n (Patient) | 41 | 19 | nd | nd | 31 | 15 |

-continued

|  | At Enrollment | | |
|---|---|---|---|
|  | sCr or UO | sCr only | UO only |
| AUC | 0.48 | nd | 0.48 |
| SE | 0.081 | nd | 0.092 |
| p | 0.82 | nd | 0.84 |
| nCohort 1 | 41 | nd | 31 |
| nCohort 2 | 19 | nd | 15 |
| Cutoff 1 | 0.0445 | nd | 0.0445 |
| Sens 1 | 84% | nd | 87% |
| Spec 1 | 7% | nd | 10% |
| Cutoff 2 | 0.0445 | nd | 0.0445 |
| Sens 2 | 84% | nd | 87% |
| Spec 2 | 7% | nd | 10% |
| Cutoff 3 | 0 | nd | 0 |
| Sens 3 | 100% | nd | 100% |
| Spec 3 | 0% | nd | 0% |
| Cutoff 4 | 0.101 | nd | 0.101 |
| Sens 4 | 37% | nd | 33% |
| Spec 4 | 76% | nd | 81% |
| Cutoff 5 | 9.78 | nd | 0.101 |
| Sens 5 | 21% | nd | 33% |
| Spec 5 | 80% | nd | 81% |
| Cutoff 6 | 17.9 | nd | 9.90 |
| Sens 6 | 16% | nd | 27% |
| Spec 6 | 90% | nd | 90% |
| OR Quart 2 | 1.0 | nd | 0.14 |
| p Value | 1.0 | nd | 0.10 |
| 95% CI of | 0.22 | nd | 0.013 |
| OR Quart 2 | 4.6 | nd | 1.5 |
| OR Quart 3 | 0.31 | nd | 0.47 |
| p Value | 0.21 | nd | 0.39 |
| 95% CI of | 0.049 | nd | 0.082 |
| OR Quart 3 | 1.9 | nd | 2.7 |
| OR Quart 4 | 1.8 | nd | 1.7 |
| p Value | 0.46 | nd | 0.54 |
| 95% CI of | 0.40 | nd | 0.32 |
| OR Quart 4 | 7.7 | nd | 8.8 |

| Interleukin-4 receptor alpha chain | | | | | | |
|---|---|---|---|---|---|---|
|  | sCr or UO | | sCr only | | UO only | |
|  | Cohort 1 | Cohort 2 | Cohort 1 | Cohort 2 | Cohort 1 | Cohort 2 |
| Median | 208 | 186 | nd | nd | 193 | 193 |
| Average | 301 | 235 | nd | nd | 289 | 254 |
| Stdev | 242 | 256 | nd | nd | 245 | 278 |
| p (t-test) |  | 0.34 | nd | nd |  | 0.67 |
| Min | 49.7 | 3.27 | nd | nd | 49.7 | 41.2 |
| Max | 1040 | 1210 | nd | nd | 1040 | 1210 |
| n (Samp) | 41 | 19 | nd | nd | 31 | 15 |
| n (Patient) | 41 | 19 | nd | nd | 31 | 15 |

|  | At Enrollment | | |
|---|---|---|---|
|  | sCr or UO | sCr only | UO only |
| AUC | 0.39 | nd | 0.45 |
| SE | 0.081 | nd | 0.092 |
| p | 0.19 | nd | 0.59 |
| nCohort 1 | 41 | nd | 31 |
| nCohort 2 | 19 | nd | 15 |
| Cutoff 1 | 104 | nd | 108 |
| Sens 1 | 79% | nd | 73% |
| Spec 1 | 7% | nd | 6% |
| Cutoff 2 | 84.5 | nd | 104 |
| Sens 2 | 84% | nd | 87% |
| Spec 2 | 5% | nd | 6% |
| Cutoff 3 | 3.27 | nd | 49.7 |
| Sens 3 | 95% | nd | 93% |
| Spec 3 | 0% | nd | 3% |
| Cutoff 4 | 296 | nd | 234 |
| Sens 4 | 21% | nd | 33% |
| Spec 4 | 71% | nd | 71% |
| Cutoff 5 | 431 | nd | 336 |
| Sens 5 | 5% | nd | 13% |
| Spec 5 | 80% | nd | 81% |

-continued

| | | | |
|---|---|---|---|
| Cutoff 6 | 621 | nd | 621 |
| Sens 6 | 5% | nd | 7% |
| Spec 6 | 90% | nd | 90% |
| OR Quart 2 | 2.0 | nd | 1.1 |
| p Value | 0.41 | nd | 0.88 |
| 95% CI of | 0.38 | nd | 0.21 |
| OR Quart 2 | 11 | nd | 6.4 |
| OR Quart 3 | 1.5 | nd | 0.40 |
| p Value | 0.67 | nd | 0.35 |
| 95% CI of | 0.26 | nd | 0.058 |
| OR Quart 3 | 8.0 | nd | 2.8 |
| OR Quart 4 | 3.5 | nd | 1.7 |
| p Value | 0.13 | nd | 0.55 |
| 95% CI of | 0.69 | nd | 0.31 |
| OR Quart 4 | 18 | nd | 9.0 |

Lutropin subunit beta

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 3.69 | 1.32 | nd | nd | nd | nd |
| Average | 7.27 | 1.57 | nd | nd | nd | nd |
| Stdev | 10.3 | 1.24 | nd | nd | nd | nd |
| p (t-test) | | 0.16 | nd | nd | nd | nd |
| Min | 0.0399 | 0.0768 | nd | nd | nd | nd |
| Max | 50.0 | 3.61 | nd | nd | nd | nd |
| n (Samp) | 30 | 7 | nd | nd | nd | nd |
| n (Patient) | 30 | 7 | nd | nd | nd | nd |

At Enrollment

| | sCr or UO | sCr only | UO only |
|---|---|---|---|
| AUC | 0.28 | nd | nd |
| SE | 0.12 | nd | nd |
| p | 0.057 | nd | nd |
| nCohort 1 | 30 | nd | nd |
| nCohort 2 | 7 | nd | nd |
| Cutoff 1 | 0.565 | nd | nd |
| Sens 1 | 71% | nd | nd |
| Spec 1 | 23% | nd | nd |
| Cutoff 2 | 0.429 | nd | nd |
| Sens 2 | 86% | nd | nd |
| Spec 2 | 17% | nd | nd |
| Cutoff 3 | 0.0621 | nd | nd |
| Sens 3 | 100% | nd | nd |
| Spec 3 | 7% | nd | nd |
| Cutoff 4 | 5.73 | nd | nd |
| Sens 4 | 0% | nd | nd |
| Spec 4 | 70% | nd | nd |
| Cutoff 5 | 14.5 | nd | nd |
| Sens 5 | 0% | nd | nd |
| Spec 5 | 80% | nd | nd |
| Cutoff 6 | 17.8 | nd | nd |
| Sens 6 | 0% | nd | nd |
| Spec 6 | 90% | nd | nd |
| OR Quart 2 | >1.2 | nd | nd |
| p Value | <0.88 | nd | nd |
| 95% CI of | >0.067 | nd | nd |
| OR Quart 2 | na | nd | nd |
| OR Quart 3 | >8.0 | nd | nd |
| p Value | <0.095 | nd | nd |
| 95% CI of | >0.70 | nd | nd |
| OR Quart 3 | na | nd | nd |
| OR Quart 4 | >2.9 | nd | nd |
| p Value | <0.43 | nd | nd |
| 95% CI of | >0.21 | nd | nd |
| OR Quart 4 | na | nd | nd |

Platelet-derived growth factor subunit B (dimer)

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 347 | 370 | nd | nd | 356 | 390 |
| Average | 415 | 392 | nd | nd | 425 | 404 |

-continued

| | | | | | | |
|---|---|---|---|---|---|---|
| Stdev | 228 | 193 | nd | nd | 228 | 215 |
| p (t-test) | | 0.72 | nd | nd | | 0.78 |
| Min | 65.1 | 152 | nd | nd | 65.1 | 152 |
| Max | 960 | 766 | nd | nd | 960 | 766 |
| n (Samp) | 57 | 15 | nd | nd | 43 | 12 |
| n (Patient) | 57 | 15 | nd | nd | 43 | 12 |

| | At Enrollment | | |
|---|---|---|---|
| | sCr or UO | sCr only | UO only |
| AUC | 0.47 | nd | 0.46 |
| SE | 0.085 | nd | 0.096 |
| p | 0.77 | nd | 0.70 |
| nCohort 1 | 57 | nd | 43 |
| nCohort 2 | 15 | nd | 12 |
| Cutoff 1 | 235 | nd | 220 |
| Sens 1 | 73% | nd | 75% |
| Spec 1 | 23% | nd | 16% |
| Cutoff 2 | 220 | nd | 212 |
| Sens 2 | 80% | nd | 83% |
| Spec 2 | 19% | nd | 16% |
| Cutoff 3 | 195 | nd | 192 |
| Sens 3 | 93% | nd | 92% |
| Spec 3 | 19% | nd | 16% |
| Cutoff 4 | 515 | nd | 567 |
| Sens 4 | 20% | nd | 25% |
| Spec 4 | 70% | nd | 72% |
| Cutoff 5 | 609 | nd | 629 |
| Sens 5 | 20% | nd | 17% |
| Spec 5 | 81% | nd | 81% |
| Cutoff 6 | 782 | nd | 779 |
| Sens 6 | 0% | nd | 0% |
| Spec 6 | 91% | nd | 91% |
| OR Quart 2 | 1.9 | nd | 1.0 |
| p Value | 0.43 | nd | 1.0 |
| 95% CI of | 0.38 | nd | 0.16 |
| OR Quart 2 | 9.6 | nd | 6.1 |
| OR Quart 3 | 0.62 | nd | 0.28 |
| p Value | 0.63 | nd | 0.30 |
| 95% CI of | 0.091 | nd | 0.026 |
| OR Quart 3 | 4.3 | nd | 3.1 |
| OR Quart 4 | 1.9 | nd | 2.3 |
| p Value | 0.43 | nd | 0.34 |
| 95% CI of | 0.38 | nd | 0.42 |
| OR Quart 4 | 9.6 | nd | 13 |

| Corticotropin | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.000624 | 0.00327 | nd | nd | 0.000539 | 0.00321 |
| Average | 0.00399 | 0.00614 | nd | nd | 0.00371 | 0.00648 |
| Stdev | 0.00894 | 0.00786 | nd | nd | 0.00924 | 0.00821 |
| p (t-test) | | 0.44 | nd | nd | | 0.42 |
| Min | 3.38E−6 | 4.31E−6 | nd | nd | 3.38E−6 | 0.000293 |
| Max | 0.0483 | 0.0251 | nd | nd | 0.0483 | 0.0251 |
| n (Samp) | 42 | 13 | nd | nd | 33 | 9 |
| n (Patient) | 42 | 13 | nd | nd | 33 | 9 |

| | At Enrollment | | |
|---|---|---|---|
| | sCr or UO | sCr only | UO only |
| AUC | 0.66 | nd | 0.74 |
| SE | 0.091 | nd | 0.10 |
| p | 0.078 | nd | 0.021 |
| nCohort 1 | 42 | nd | 33 |
| nCohort 2 | 13 | nd | 9 |
| Cutoff 1 | 0.000466 | nd | 0.00122 |
| Sens 1 | 77% | nd | 78% |
| Spec 1 | 45% | nd | 61% |
| Cutoff 2 | 0.000261 | nd | 0.000293 |
| Sens 2 | 85% | nd | 89% |
| Spec 2 | 40% | nd | 45% |
| Cutoff 3 | 4.31E−6 | nd | 0.000261 |
| Sens 3 | 92% | nd | 100% |

-continued

|  | | | |
|---|---|---|---|
| Spec 3 | 24% | nd | 42% |
| Cutoff 4 | 0.00201 | nd | 0.00183 |
| Sens 4 | 62% | nd | 67% |
| Spec 4 | 71% | nd | 73% |
| Cutoff 5 | 0.00486 | nd | 0.00329 |
| Sens 5 | 31% | nd | 33% |
| Spec 5 | 81% | nd | 82% |
| Cutoff 6 | 0.00761 | nd | 0.00658 |
| Sens 6 | 31% | nd | 33% |
| Spec 6 | 90% | nd | 91% |
| OR Quart 2 | 0.92 | nd | >2.2 |
| p Value | 0.94 | nd | <0.54 |
| 95% CI of | 0.11 | nd | >0.17 |
| OR Quart 2 | 7.7 | nd | na |
| OR Quart 3 | 2.2 | nd | >4.3 |
| p Value | 0.42 | nd | <0.25 |
| 95% CI of | 0.33 | nd | >0.37 |
| OR Quart 3 | 15 | nd | na |
| OR Quart 4 | 3.1 | nd | >5.7 |
| p Value | 0.24 | nd | <0.15 |
| 95% CI of | 0.47 | nd | >0.52 |
| OR Quart 4 | 20 | nd | na |

| Thyroxine-binding globulin | | | | | |
|---|---|---|---|---|---|
| sCr or UO | | sCr only | | UO only | |
| Cohort 1 | Cohort 2 | Cohort 1 | Cohort 2 | Cohort 1 | Cohort 2 |
| Median | 36.1 | 28.0 | nd | nd | 34.1 | 30.0 |
| Average | 36.5 | 30.9 | nd | nd | 36.1 | 31.3 |
| Stdev | 10.8 | 10.6 | nd | nd | 11.3 | 10.6 |
| p (t-test) | | 0.044 | nd | nd | | 0.14 |
| Min | 12.8 | 14.2 | nd | nd | 12.8 | 14.2 |
| Max | 56.7 | 48.3 | nd | nd | 56.7 | 46.0 |
| n (Samp) | 55 | 22 | nd | nd | 46 | 16 |
| n (Patient) | 55 | 22 | nd | nd | 46 | 16 |

| At Enrollment | | |
|---|---|---|
| sCr or UO | sCr only | UO only |
| AUC | 0.35 | nd | 0.36 |
| SE | 0.072 | nd | 0.084 |
| p | 0.043 | nd | 0.10 |
| nCohort 1 | 55 | nd | 46 |
| nCohort 2 | 22 | nd | 16 |
| Cutoff 1 | 24.7 | nd | 25.2 |
| Sens 1 | 73% | nd | 75% |
| Spec 1 | 15% | nd | 20% |
| Cutoff 2 | 19.7 | nd | 22.8 |
| Sens 2 | 82% | nd | 81% |
| Spec 2 | 7% | nd | 13% |
| Cutoff 3 | 15.8 | nd | 15.4 |
| Sens 3 | 91% | nd | 94% |
| Spec 3 | 5% | nd | 7% |
| Cutoff 4 | 43.0 | nd | 42.3 |
| Sens 4 | 18% | nd | 25% |
| Spec 4 | 71% | nd | 72% |
| Cutoff 5 | 46.9 | nd | 47.1 |
| Sens 5 | 5% | nd | 0% |
| Spec 5 | 80% | nd | 80% |
| Cutoff 6 | 51.0 | nd | 51.0 |
| Sens 6 | 0% | nd | 0% |
| Spec 6 | 91% | nd | 91% |
| OR Quart 2 | 1.1 | nd | 1.1 |
| p Value | 0.94 | nd | 0.93 |
| 95% CI of | 0.23 | nd | 0.18 |
| OR Quart 2 | 5.0 | nd | 6.4 |
| OR Quart 3 | 1.8 | nd | 2.0 |
| p Value | 0.41 | nd | 0.42 |
| 95% CI of | 0.43 | nd | 0.38 |
| OR Quart 3 | 8.0 | nd | 10 |
| OR Quart 4 | 2.9 | nd | 2.2 |
| p Value | 0.14 | nd | 0.36 |
| 95% CI of | 0.70 | nd | 0.42 |
| OR Quart 4 | 12 | nd | 11 |

-continued

Alpha-fetoprotein

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.331 | 0.458 | nd | nd | 0.302 | 0.452 |
| Average | 0.318 | 0.516 | nd | nd | 0.298 | 0.452 |
| Stdev | 0.265 | 0.415 | nd | nd | 0.238 | 0.396 |
| p (t-test) | | 0.023 | nd | nd | | 0.095 |
| Min | 0.00580 | 0.00580 | nd | nd | 0.00580 | 0.00580 |
| Max | 1.11 | 1.31 | nd | nd | 0.997 | 1.31 |
| n (Samp) | 58 | 16 | nd | nd | 44 | 12 |
| n (Patient) | 58 | 16 | nd | nd | 44 | 12 |

At Enrollment

| | sCr or UO | sCr only | UO only |
|---|---|---|---|
| AUC | 0.65 | nd | 0.62 |
| SE | 0.082 | nd | 0.096 |
| p | 0.076 | nd | 0.20 |
| nCohort 1 | 58 | nd | 44 |
| nCohort 2 | 16 | nd | 12 |
| Cutoff 1 | 0.225 | nd | 0.221 |
| Sens 1 | 75% | nd | 75% |
| Spec 1 | 40% | nd | 39% |
| Cutoff 2 | 0.221 | nd | 0.00580 |
| Sens 2 | 81% | nd | 92% |
| Spec 2 | 38% | nd | 14% |
| Cutoff 3 | 0.00580 | nd | 0.00580 |
| Sens 3 | 94% | nd | 92% |
| Spec 3 | 14% | nd | 14% |
| Cutoff 4 | 0.446 | nd | 0.415 |
| Sens 4 | 50% | nd | 50% |
| Spec 4 | 71% | nd | 70% |
| Cutoff 5 | 0.530 | nd | 0.513 |
| Sens 5 | 44% | nd | 50% |
| Spec 5 | 81% | nd | 82% |
| Cutoff 6 | 0.598 | nd | 0.570 |
| Sens 6 | 38% | nd | 33% |
| Spec 6 | 91% | nd | 91% |
| OR Quart 2 | 0.94 | nd | 0.61 |
| p Value | 0.94 | nd | 0.62 |
| 95% CI of | 0.16 | nd | 0.085 |
| OR Quart 2 | 5.4 | nd | 4.4 |
| OR Quart 3 | 1.0 | nd | 0.28 |
| p Value | 1.0 | nd | 0.30 |
| 95% CI of | 0.17 | nd | 0.026 |
| OR Quart 3 | 5.8 | nd | 3.1 |
| OR Quart 4 | 2.9 | nd | 2.8 |
| p Value | 0.18 | nd | 0.23 |
| 95% CI of | 0.62 | nd | 0.52 |
| OR Quart 4 | 14 | nd | 14 |

Apolipoprotein E

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 59000 | 43100 | nd | nd | 59600 | 50600 |
| Average | 74200 | 47600 | nd | nd | 78300 | 50500 |
| Stdev | 52400 | 31200 | nd | nd | 54800 | 34500 |
| p (t-test) | | 0.027 | nd | nd | | 0.054 |
| Min | 12600 | 1940 | nd | nd | 13000 | 1940 |
| Max | 244000 | 120000 | nd | nd | 244000 | 120000 |
| n (Samp) | 68 | 22 | nd | nd | 53 | 17 |
| n (Patient) | 68 | 22 | nd | nd | 53 | 17 |

At Enrollment

| | sCr or UO | sCr only | UO only |
|---|---|---|---|
| AUC | 0.35 | nd | 0.36 |
| SE | 0.071 | nd | 0.081 |
| p | 0.029 | nd | 0.080 |
| nCohort 1 | 68 | nd | 53 |
| nCohort 2 | 22 | nd | 17 |

-continued

| | | | |
|---|---|---|---|
| Cutoff 1 | 23900 | nd | 27300 |
| Sens 1 | 73% | nd | 71% |
| Spec 1 | 13% | nd | 11% |
| Cutoff 2 | 17400 | nd | 14200 |
| Sens 2 | 82% | nd | 82% |
| Spec 2 | 6% | nd | 4% |
| Cutoff 3 | 14100 | nd | 1940 |
| Sens 3 | 91% | nd | 94% |
| Spec 3 | 4% | nd | 0% |
| Cutoff 4 | 85700 | nd | 91600 |
| Sens 4 | 14% | nd | 18% |
| Spec 4 | 71% | nd | 72% |
| Cutoff 5 | 98600 | nd | 98600 |
| Sens 5 | 9% | nd | 12% |
| Spec 5 | 81% | nd | 81% |
| Cutoff 6 | 164000 | nd | 164000 |
| Sens 6 | 0% | nd | 0% |
| Spec 6 | 91% | nd | 91% |
| OR Quart 2 | 1.5 | nd | 1.1 |
| p Value | 0.64 | nd | 0.94 |
| 95% CI of | 0.29 | nd | 0.18 |
| OR Quart 2 | 7.5 | nd | 6.2 |
| OR Quart 3 | 3.6 | nd | 1.4 |
| p Value | 0.094 | nd | 0.67 |
| 95% CI of | 0.80 | nd | 0.27 |
| OR Quart 3 | 16 | nd | 7.5 |
| OR Quart 4 | 3.1 | nd | 3.5 |
| p Value | 0.14 | nd | 0.12 |
| 95% CI of | 0.69 | nd | 0.73 |
| OR Quart 4 | 14 | nd | 17 |

FIG. 8: Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

| | Complement C4-B | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 65500 | 61600 | 65500 | 61600 | nd | nd |
| Average | 73300 | 68700 | 73300 | 68700 | nd | nd |
| Stdev | 40400 | 39200 | 40400 | 39200 | nd | nd |
| p (t-test) | | 0.76 | | 0.76 | nd | nd |
| Min | 641 | 13500 | 641 | 13500 | nd | nd |
| Max | 203000 | 125000 | 203000 | 125000 | nd | nd |
| n (Samp) | 87 | 8 | 87 | 8 | nd | nd |
| n (Patient) | 87 | 8 | 87 | 8 | nd | nd |
| UO only | | | | | | |
| Median | 65700 | 61600 | 65700 | 61600 | nd | nd |
| Average | 71600 | 68700 | 71600 | 68700 | nd | nd |
| Stdev | 35600 | 45800 | 35600 | 45800 | nd | nd |
| p (t-test) | | 0.85 | | 0.85 | nd | nd |
| Min | 641 | 13500 | 641 | 13500 | nd | nd |
| Max | 160000 | 125000 | 160000 | 125000 | nd | nd |
| n (Samp) | 80 | 6 | 80 | 6 | nd | nd |
| n (Patient) | 80 | 6 | 80 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.48 | nd | 0.46 | 0.48 | nd | 0.46 | nd | nd | nd |
| SE | 0.11 | nd | 0.13 | 0.11 | nd | 0.13 | nd | nd | nd |
| p | 0.84 | nd | 0.76 | 0.84 | nd | 0.76 | nd | nd | nd |
| nCohort 1 | 87 | nd | 80 | 87 | nd | 80 | nd | nd | nd |
| nCohort 2 | 8 | nd | 6 | 8 | nd | 6 | nd | nd | nd |
| Cutoff 1 | 57800 | nd | 29600 | 57800 | nd | 29600 | nd | nd | nd |
| Sens 1 | 75% | nd | 83% | 75% | nd | 83% | nd | nd | nd |
| Spec 1 | 41% | nd | 10% | 41% | nd | 10% | nd | nd | nd |
| Cutoff 2 | 29600 | nd | 29600 | 29600 | nd | 29600 | nd | nd | nd |

-continued

| | | | | | | | | | |
|---|---|---|---|---|---|---|---|---|---|
| Sens 2 | 88% | nd | 83% | 88% | nd | 83% | nd | nd | nd |
| Spec 2 | 10% | nd | 10% | 10% | nd | 10% | nd | nd | nd |
| Cutoff 3 | 5890 | nd | 5890 | 5890 | nd | 5890 | nd | nd | nd |
| Sens 3 | 100% | nd | 100% | 100% | nd | 100% | nd | nd | nd |
| Spec 3 | 2% | nd | 2% | 2% | nd | 2% | nd | nd | nd |
| Cutoff 4 | 86300 | nd | 87900 | 86300 | nd | 87900 | nd | nd | nd |
| Sens 4 | 25% | nd | 33% | 25% | nd | 33% | nd | nd | nd |
| Spec 4 | 70% | nd | 70% | 70% | nd | 70% | nd | nd | nd |
| Cutoff 5 | 104000 | nd | 100000 | 104000 | nd | 100000 | nd | nd | nd |
| Sens 5 | 25% | nd | 33% | 25% | nd | 33% | nd | nd | nd |
| Spec 5 | 80% | nd | 80% | 80% | nd | 80% | nd | nd | nd |
| Cutoff 6 | 129000 | nd | 124000 | 129000 | nd | 124000 | nd | nd | nd |
| Sens 6 | 0% | nd | 17% | 0% | nd | 17% | nd | nd | nd |
| Spec 6 | 91% | nd | 90% | 91% | nd | 90% | nd | nd | nd |
| OR Quart 2 | 0.48 | nd | 0 | 0.48 | nd | 0 | nd | nd | nd |
| p Value | 0.56 | nd | na | 0.56 | nd | na | nd | nd | nd |
| 95% CI of | 0.040 | nd | na | 0.040 | nd | na | nd | nd | nd |
| OR Quart 2 | 5.7 | nd | na | 5.7 | nd | na | nd | nd | nd |
| OR Quart 3 | 1.6 | nd | 1.0 | 1.6 | nd | 1.0 | nd | nd | nd |
| p Value | 0.64 | nd | 1.0 | 0.64 | nd | 1.0 | nd | nd | nd |
| 95% CI of | 0.24 | nd | 0.13 | 0.24 | nd | 0.13 | nd | nd | nd |
| OR Quart 3 | 10 | nd | 7.8 | 10 | nd | 7.8 | nd | nd | nd |
| OR Quart 4 | 1.0 | nd | 1.1 | 1.0 | nd | 1.1 | nd | nd | nd |
| p Value | 0.96 | nd | 0.96 | 0.96 | nd | 0.96 | nd | nd | nd |
| 95% CI of | 0.13 | nd | 0.13 | 0.13 | nd | 0.13 | nd | nd | nd |
| OR Quart 4 | 8.1 | nd | 8.2 | 8.1 | nd | 8.2 | nd | nd | nd |

C-C motif chemokine 26

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 1.25 | 4.43 | 1.25 | 4.43 | 1.25 | 6.99 |
| Average | 18.1 | 7.55 | 18.1 | 7.36 | 18.1 | 6.64 |
| Stdev | 79.1 | 9.61 | 79.1 | 9.74 | 79.1 | 6.53 |
| p (t-test) | | 0.65 | | 0.64 | | 0.71 |
| Min | 0.0121 | 0.0232 | 0.0121 | 0.0232 | 0.0121 | 0.652 |
| Max | 468 | 33.0 | 468 | 33.0 | 468 | 18.3 |
| n (Samp) | 64 | 12 | 64 | 12 | 64 | 7 |
| n (Patient) | 64 | 12 | 64 | 12 | 64 | 7 |
| sCr only | | | | | | |
| Median | 1.76 | 1.73 | 1.76 | 0.937 | nd | nd |
| Average | 11.9 | 2.36 | 11.9 | 1.99 | nd | nd |
| Stdev | 55.9 | 2.51 | 55.9 | 2.69 | nd | nd |
| p (t-test) | | 0.68 | | 0.67 | | |
| Min | 0.0121 | 0.0232 | 0.0121 | 0.0232 | nd | nd |
| Max | 468 | 6.99 | 468 | 6.99 | nd | nd |
| n (Samp) | 131 | 6 | 131 | 6 | nd | nd |
| n (Patient) | 131 | 6 | 131 | 6 | nd | nd |
| UO only | | | | | | |
| Median | 1.25 | 7.45 | 1.25 | 7.45 | 1.25 | 7.45 |
| Average | 18.5 | 10.5 | 18.5 | 10.5 | 18.5 | 7.54 |
| Stdev | 79.7 | 10.7 | 79.7 | 10.7 | 79.7 | 6.66 |
| p (t-test) | | 0.78 | | 0.78 | | 0.74 |
| Min | 0.0121 | 0.652 | 0.0121 | 0.652 | 0.0121 | 0.652 |
| Max | 468 | 33.0 | 468 | 33.0 | 468 | 18.3 |
| n (Samp) | 63 | 8 | 63 | 8 | 63 | 6 |
| n (Patient) | 63 | 8 | 63 | 8 | 63 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.63 | 0.46 | 0.73 | 0.59 | 0.38 | 0.73 | 0.65 | nd | 0.69 |
| SE | 0.093 | 0.12 | 0.11 | 0.093 | 0.13 | 0.11 | 0.12 | nd | 0.12 |
| p | 0.15 | 0.74 | 0.029 | 0.33 | 0.36 | 0.029 | 0.19 | nd | 0.12 |
| nCohort 1 | 64 | 131 | 63 | 64 | 131 | 63 | 64 | nd | 63 |
| nCohort 2 | 12 | 6 | 8 | 12 | 6 | 8 | 7 | nd | 6 |
| Cutoff 1 | 0.949 | 0.355 | 5.00 | 0.0587 | 0.0325 | 5.00 | 0.949 | nd | 0.0587 |
| Sens 1 | 75% | 83% | 75% | 83% | 83% | 75% | 71% | nd | 100% |
| Spec 1 | 44% | 33% | 78% | 31% | 7% | 78% | 44% | nd | 35% |
| Cutoff 2 | 0.0587 | 0.355 | 0.0587 | 0.0587 | 0.0325 | 0.0587 | 0.0587 | nd | 0.0587 |
| Sens 2 | 92% | 83% | 100% | 83% | 83% | 100% | 100% | nd | 100% |

-continued

| | | | | | | | | | |
|---|---|---|---|---|---|---|---|---|---|
| Spec 2 | 31% | 33% | 35% | 31% | 7% | 35% | 31% | nd | 35% |
| Cutoff 3 | 0.0587 | 0.0121 | 0.0587 | 0.0232 | 0.0121 | 0.0587 | 0.0587 | nd | 0.0587 |
| Sens 3 | 92% | 100% | 100% | 92% | 100% | 100% | 100% | nd | 100% |
| Spec 3 | 31% | 2% | 35% | 8% | 2% | 35% | 31% | nd | 35% |
| Cutoff 4 | 3.61 | 5.00 | 3.57 | 3.61 | 5.00 | 3.57 | 3.61 | nd | 3.57 |
| Sens 4 | 50% | 17% | 75% | 50% | 17% | 75% | 57% | nd | 67% |
| Spec 4 | 70% | 71% | 71% | 70% | 71% | 71% | 70% | nd | 71% |
| Cutoff 5 | 6.86 | 7.86 | 6.86 | 6.86 | 7.86 | 6.86 | 6.86 | nd | 6.86 |
| Sens 5 | 42% | 0% | 62% | 42% | 0% | 62% | 57% | nd | 67% |
| Spec 5 | 81% | 80% | 81% | 81% | 80% | 81% | 81% | nd | 81% |
| Cutoff 6 | 14.2 | 14.2 | 14.2 | 14.2 | 14.2 | 14.2 | 14.2 | nd | 14.2 |
| Sens 6 | 17% | 0% | 25% | 17% | 0% | 25% | 14% | nd | 17% |
| Spec 6 | 91% | 90% | 90% | 91% | 90% | 90% | 91% | nd | 90% |
| OR Quart 2 | 3.4 | 2.1 | >2.1 | 1.6 | 1.0 | >2.1 | >3.4 | nd | >2.3 |
| p Value | 0.31 | 0.55 | <0.55 | 0.63 | 0.98 | <0.55 | <0.31 | nd | <0.52 |
| 95% CI of | 0.32 | 0.18 | >0.18 | 0.23 | 0.062 | >0.18 | >0.32 | nd | >0.19 |
| OR Quart 2 | 36 | 25 | na | 11 | 17 | na | na | nd | na |
| OR Quart 3 | 3.4 | 2.1 | >1.0 | 1.0 | 2.1 | >1.0 | >0 | nd | >0 |
| p Value | 0.31 | 0.55 | <1.0 | 1.0 | 0.55 | <1.0 | <na | nd | <na |
| 95% CI of | 0.32 | 0.18 | >0.058 | 0.13 | 0.18 | >0.058 | >na | nd | >na |
| OR Quart 3 | 36 | 25 | na | 7.9 | 25 | na | na | nd | na |
| OR Quart 4 | 6.4 | 1.0 | >6.5 | 3.0 | 2.1 | >6.5 | >4.9 | nd | >4.9 |
| p Value | 0.11 | 0.98 | <0.10 | 0.22 | 0.55 | <0.10 | <0.18 | nd | <0.18 |
| 95% CI of | 0.67 | 0.062 | >0.68 | 0.51 | 0.18 | >0.68 | >0.49 | nd | >0.49 |
| OR Quart 4 | 61 | 17 | na | 18 | 25 | na | na | nd | na |

C-C motif chemokine 7

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.804 | 5.45 | 0.804 | 5.45 | 0.804 | 10.4 |
| Average | 11.6 | 36.3 | 11.6 | 36.3 | 11.6 | 12.6 |
| Stdev | 26.0 | 65.4 | 26.0 | 65.4 | 26.0 | 13.3 |
| p (t-test) | | 0.026 | | 0.026 | | 0.92 |
| Min | 0.193 | 0.308 | 0.193 | 0.308 | 0.193 | 0.308 |
| Max | 128 | 219 | 128 | 219 | 128 | 30.8 |
| n (Samp) | 65 | 12 | 65 | 12 | 65 | 7 |
| n (Patient) | 65 | 12 | 65 | 12 | 65 | 7 |
| sCr only | | | | | | |
| Median | 0.804 | 5.45 | 0.804 | 5.45 | nd | nd |
| Average | 13.2 | 22.1 | 13.2 | 22.1 | nd | nd |
| Stdev | 29.3 | 40.6 | 29.3 | 40.6 | nd | nd |
| p (t-test) | | 0.48 | | 0.48 | nd | nd |
| Min | 0.193 | 0.308 | 0.193 | 0.308 | nd | nd |
| Max | 181 | 104 | 181 | 104 | nd | nd |
| n (Samp) | 132 | 6 | 132 | 6 | nd | nd |
| n (Patient) | 132 | 6 | 132 | 6 | nd | nd |
| UO only | | | | | | |
| Median | 0.804 | 5.45 | 0.804 | 5.45 | 0.804 | 5.45 |
| Average | 10.4 | 39.2 | 10.4 | 39.2 | 10.4 | 11.9 |
| Stdev | 25.9 | 75.1 | 25.9 | 75.1 | 25.9 | 14.5 |
| p (t-test) | | 0.028 | | 0.028 | | 0.89 |
| Min | 0.193 | 0.308 | 0.193 | 0.308 | 0.193 | 0.308 |
| Max | 128 | 219 | 128 | 219 | 128 | 30.8 |
| n (Samp) | 64 | 8 | 64 | 8 | 64 | 6 |
| n (Patient) | 64 | 8 | 64 | 8 | 64 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.56 | 0.50 | 0.58 | 0.56 | 0.50 | 0.58 | 0.56 | nd | 0.55 |
| SE | 0.093 | 0.12 | 0.11 | 0.093 | 0.12 | 0.11 | 0.12 | nd | 0.13 |
| p | 0.52 | 1.00 | 0.47 | 0.52 | 1.00 | 0.47 | 0.59 | nd | 0.71 |
| nCohort 1 | 65 | 132 | 64 | 65 | 132 | 64 | 65 | nd | 64 |
| nCohort 2 | 12 | 6 | 8 | 12 | 6 | 8 | 7 | nd | 6 |
| Cutoff 1 | 0.308 | 0.193 | 0.308 | 0.308 | 0.193 | 0.308 | 0.308 | nd | 0.193 |
| Sens 1 | 75% | 100% | 75% | 75% | 100% | 75% | 71% | nd | 100% |
| Spec 1 | 25% | 3% | 28% | 25% | 3% | 28% | 25% | nd | 3% |
| Cutoff 2 | 0.193 | 0.193 | 0.193 | 0.193 | 0.193 | 0.193 | 0.193 | nd | 0.193 |
| Sens 2 | 100% | 100% | 100% | 100% | 100% | 100% | 100% | nd | 100% |
| Spec 2 | 3% | 3% | 3% | 3% | 3% | 3% | 3% | nd | 3% |

-continued

| | | | | | | | | | |
|---|---|---|---|---|---|---|---|---|---|
| Cutoff 3 | 0.193 | 0.193 | 0.193 | 0.193 | 0.193 | 0.193 | 0.193 | nd | 0.193 |
| Sens 3 | 100% | 100% | 100% | 100% | 100% | 100% | 100% | nd | 100% |
| Spec 3 | 3% | 3% | 3% | 3% | 3% | 3% | 3% | nd | 3% |
| Cutoff 4 | 8.40 | 8.42 | 4.51 | 8.40 | 8.42 | 4.51 | 8.40 | nd | 4.51 |
| Sens 4 | 50% | 50% | 50% | 50% | 50% | 50% | 57% | nd | 50% |
| Spec 4 | 71% | 70% | 70% | 71% | 70% | 70% | 71% | nd | 70% |
| Cutoff 5 | 12.2 | 15.3 | 8.42 | 12.2 | 15.3 | 8.42 | 12.2 | nd | 8.42 |
| Sens 5 | 42% | 33% | 50% | 42% | 33% | 50% | 43% | nd | 50% |
| Spec 5 | 80% | 80% | 81% | 80% | 80% | 81% | 80% | nd | 81% |
| Cutoff 6 | 32.2 | 33.2 | 18.9 | 32.2 | 33.2 | 18.9 | 32.2 | nd | 18.9 |
| Sens 6 | 25% | 17% | 38% | 25% | 17% | 38% | 0% | nd | 33% |
| Spec 6 | 91% | 90% | 91% | 91% | 90% | 91% | 91% | nd | 91% |
| OR Quart 2 | 1.0 | 0.50 | 1.0 | 1.0 | 0.50 | 1.0 | 0.47 | nd | 0.44 |
| p Value | 1.0 | 0.58 | 1.0 | 1.0 | 0.58 | 1.0 | 0.55 | nd | 0.52 |
| 95% CI of | 0.17 | 0.043 | 0.13 | 0.17 | 0.043 | 0.13 | 0.039 | nd | 0.036 |
| OR Quart 2 | 5.7 | 5.8 | 8.0 | 5.7 | 5.8 | 8.0 | 5.7 | nd | 5.4 |
| OR Quart 3 | 0 | 0.49 | 0 | 0 | 0.49 | 0 | 0 | nd | 0 |
| p Value | na | 0.56 | na | na | 0.56 | na | na | nd | na |
| 95% CI of | na | 0.042 | na | na | 0.042 | na | na | nd | na |
| OR Quart 3 | na | 5.6 | na | na | 5.6 | na | na | nd | na |
| OR Quart 4 | 2.3 | 1.0 | 2.3 | 2.3 | 1.0 | 2.3 | 2.3 | nd | 1.5 |
| p Value | 0.30 | 0.98 | 0.38 | 0.30 | 0.98 | 0.38 | 0.38 | nd | 0.68 |
| 95% CI of | 0.48 | 0.14 | 0.36 | 0.48 | 0.14 | 0.36 | 0.36 | nd | 0.22 |
| OR Quart 4 | 11 | 7.8 | 14 | 11 | 7.8 | 14 | 14 | nd | 10 |

Vascular endothelial growth factor receptor 3

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 5220 | 5750 | 5220 | 5190 | 5220 | 4620 |
| Average | 7140 | 7290 | 7140 | 7190 | 7140 | 6080 |
| Stdev | 5790 | 4660 | 5790 | 4690 | 5790 | 2970 |
| p (t-test) | | 0.93 | | 0.98 | | 0.64 |
| Min | 565 | 1740 | 565 | 1740 | 565 | 3160 |
| Max | 29400 | 16600 | 29400 | 16600 | 29400 | 10400 |
| n (Samp) | 65 | 12 | 65 | 12 | 65 | 7 |
| n (Patient) | 65 | 12 | 65 | 12 | 65 | 7 |
| sCr only | | | | | | |
| Median | 6370 | 4450 | 6370 | 4280 | nd | nd |
| Average | 7630 | 5070 | 7630 | 4880 | nd | nd |
| Stdev | 5970 | 3070 | 5970 | 3030 | nd | nd |
| p (t-test) | | 0.30 | | 0.27 | nd | nd |
| Min | 565 | 1740 | 565 | 1740 | nd | nd |
| Max | 43200 | 10400 | 43200 | 10400 | nd | nd |
| n (Samp) | 132 | 6 | 132 | 6 | nd | nd |
| n (Patient) | 132 | 6 | 132 | 6 | nd | nd |
| UO only | | | | | | |
| Median | 5340 | 5790 | 5340 | 5790 | 5340 | 4410 |
| Average | 7390 | 7970 | 7390 | 7970 | 7390 | 5350 |
| Stdev | 6200 | 5200 | 6200 | 5200 | 6200 | 2480 |
| p (t-test) | | 0.80 | | 0.80 | | 0.43 |
| Min | 565 | 3160 | 565 | 3160 | 565 | 3160 |
| Max | 32800 | 16600 | 32800 | 16600 | 32800 | 9630 |
| n (Samp) | 64 | 8 | 64 | 8 | 64 | 6 |
| n (Patient) | 64 | 8 | 64 | 8 | 64 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.54 | 0.36 | 0.53 | 0.53 | 0.34 | 0.53 | 0.49 | nd | 0.40 |
| SE | 0.092 | 0.12 | 0.11 | 0.092 | 0.12 | 0.11 | 0.12 | nd | 0.13 |
| p | 0.70 | 0.25 | 0.79 | 0.78 | 0.19 | 0.79 | 0.90 | nd | 0.41 |
| nCohort 1 | 65 | 132 | 64 | 65 | 132 | 64 | 65 | nd | 64 |
| nCohort 2 | 12 | 6 | 8 | 12 | 6 | 8 | 7 | nd | 6 |
| Cutoff 1 | 3920 | 3140 | 3920 | 3920 | 3140 | 3920 | 3920 | nd | 3400 |
| Sens 1 | 75% | 83% | 75% | 75% | 83% | 75% | 71% | nd | 83% |
| Spec 1 | 31% | 16% | 28% | 31% | 16% | 28% | 31% | nd | 20% |
| Cutoff 2 | 3400 | 3140 | 3400 | 3400 | 3140 | 3400 | 3400 | nd | 3400 |
| Sens 2 | 83% | 83% | 88% | 83% | 83% | 88% | 86% | nd | 83% |
| Spec 2 | 23% | 16% | 20% | 23% | 16% | 20% | 23% | nd | 20% |
| Cutoff 3 | 3140 | 1720 | 3140 | 3140 | 1720 | 3140 | 3140 | nd | 3140 |

-continued

| | | | | | | | | | |
|---|---|---|---|---|---|---|---|---|---|
| Sens 3 | 92% | 100% | 100% | 92% | 100% | 100% | 100% | nd | 100% |
| Spec 3 | 17% | 5% | 14% | 17% | 5% | 14% | 17% | nd | 14% |
| Cutoff 4 | 7590 | 8540 | 7610 | 7590 | 8540 | 7610 | 7590 | nd | 7610 |
| Sens 4 | 33% | 17% | 38% | 33% | 17% | 38% | 29% | nd | 17% |
| Spec 4 | 71% | 70% | 70% | 71% | 70% | 70% | 71% | nd | 70% |
| Cutoff 5 | 9000 | 10300 | 9000 | 9000 | 10300 | 9000 | 9000 | nd | 9000 |
| Sens 5 | 33% | 17% | 38% | 33% | 17% | 38% | 29% | nd | 17% |
| Spec 5 | 80% | 80% | 81% | 80% | 80% | 81% | 80% | nd | 81% |
| Cutoff 6 | 13800 | 13200 | 13800 | 13800 | 13200 | 13800 | 13800 | nd | 13800 |
| Sens 6 | 17% | 0% | 25% | 17% | 0% | 25% | 0% | nd | 0% |
| Spec 6 | 91% | 90% | 91% | 91% | 90% | 91% | 91% | nd | 91% |
| OR Quart 2 | 0.63 | 0 | 1.0 | 1.0 | 0 | 1.0 | 0.47 | nd | 1.1 |
| p Value | 0.63 | na | 1.0 | 1.0 | na | 1.0 | 0.55 | nd | 0.97 |
| 95% CI of | 0.092 | na | 0.13 | 0.17 | na | 0.13 | 0.039 | nd | 0.061 |
| OR Quart 2 | 4.3 | na | 8.0 | 5.7 | na | 8.0 | 5.7 | nd | 18 |
| OR Quart 3 | 1.0 | 2.1 | 0.47 | 0.63 | 2.1 | 0.47 | 1.0 | nd | 2.1 |
| p Value | 1.0 | 0.56 | 0.55 | 0.63 | 0.56 | 0.55 | 1.0 | nd | 0.55 |
| 95% CI of | 0.17 | 0.18 | 0.039 | 0.092 | 0.18 | 0.039 | 0.13 | nd | 0.18 |
| OR Quart 3 | 5.7 | 24 | 5.7 | 4.3 | 24 | 5.7 | 8.0 | nd | 26 |
| OR Quart 4 | 1.3 | 3.3 | 1.6 | 1.3 | 3.3 | 1.6 | 1.0 | nd | 2.3 |
| p Value | 0.73 | 0.31 | 0.63 | 0.73 | 0.31 | 0.63 | 1.0 | nd | 0.52 |
| 95% CI of | 0.26 | 0.32 | 0.23 | 0.26 | 0.32 | 0.23 | 0.13 | nd | 0.19 |
| OR Quart 4 | 6.9 | 33 | 11 | 6.9 | 33 | 11 | 8.0 | nd | 28 |

Interferon alpha-2

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 14.0 | 23.9 | 14.0 | 23.9 | 14.0 | 14.0 |
| Average | 22.3 | 34.7 | 22.3 | 34.4 | 22.3 | 16.8 |
| Stdev | 33.5 | 43.9 | 33.5 | 44.0 | 33.5 | 14.9 |
| p (t-test) | | 0.26 | | 0.28 | | 0.67 |
| Min | 0.0320 | 0.209 | 0.0320 | 0.209 | 0.0320 | 0.209 |
| Max | 223 | 163 | 223 | 163 | 223 | 43.4 |
| n (Samp) | 65 | 12 | 65 | 12 | 65 | 7 |
| n (Patient) | 65 | 12 | 65 | 12 | 65 | 7 |
| sCr only | | | | | | |
| Median | 19.5 | 23.7 | 19.5 | 23.7 | nd | nd |
| Average | 23.8 | 20.4 | 23.8 | 19.7 | nd | nd |
| Stdev | 28.3 | 15.7 | 28.3 | 15.2 | nd | nd |
| p (t-test) | | 0.78 | | 0.73 | nd | nd |
| Min | 0.0320 | 0.209 | 0.0320 | 0.209 | nd | nd |
| Max | 223 | 39.2 | 223 | 39.2 | nd | nd |
| n (Samp) | 132 | 6 | 132 | 6 | nd | nd |
| n (Patient) | 132 | 6 | 132 | 6 | nd | nd |
| UO only | | | | | | |
| Median | 13.3 | 23.9 | 13.3 | 23.9 | 13.3 | 10.6 |
| Average | 21.0 | 39.9 | 21.0 | 39.9 | 21.0 | 15.9 |
| Stdev | 35.0 | 53.2 | 35.0 | 53.2 | 35.0 | 16.1 |
| p (t-test) | | 0.18 | | 0.18 | | 0.73 |
| Min | 0.0320 | 0.209 | 0.0320 | 0.209 | 0.0320 | 0.209 |
| Max | 223 | 163 | 223 | 163 | 223 | 43.4 |
| n (Samp) | 64 | 8 | 64 | 8 | 64 | 6 |
| n (Patient) | 64 | 8 | 64 | 8 | 64 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.61 | 0.52 | 0.63 | 0.61 | 0.50 | 0.63 | 0.48 | nd | 0.49 |
| SE | 0.093 | 0.12 | 0.11 | 0.093 | 0.12 | 0.11 | 0.12 | nd | 0.13 |
| p | 0.24 | 0.90 | 0.23 | 0.25 | 0.98 | 0.23 | 0.88 | nd | 0.91 |
| nCohort 1 | 65 | 132 | 64 | 65 | 132 | 64 | 65 | nd | 64 |
| nCohort 2 | 12 | 6 | 8 | 12 | 6 | 8 | 7 | nd | 6 |
| Cutoff 1 | 6.46 | 2.04 | 6.46 | 6.46 | 2.04 | 6.46 | 6.46 | nd | 4.65 |
| Sens 1 | 75% | 83% | 75% | 75% | 83% | 75% | 71% | nd | 83% |
| Spec 1 | 28% | 14% | 31% | 28% | 14% | 31% | 28% | nd | 25% |
| Cutoff 2 | 4.65 | 2.04 | 4.65 | 4.65 | 2.04 | 4.65 | 4.65 | nd | 4.65 |
| Sens 2 | 83% | 83% | 88% | 83% | 83% | 88% | 86% | nd | 83% |
| Spec 2 | 22% | 14% | 25% | 22% | 14% | 25% | 22% | nd | 25% |
| Cutoff 3 | 2.04 | 0.0997 | 0.0997 | 2.04 | 0.0997 | 0.0997 | 0.0997 | nd | 0.0997 |
| Sens 3 | 92% | 100% | 100% | 92% | 100% | 100% | 100% | nd | 100% |

-continued

| | | | | | | | | | |
|---|---|---|---|---|---|---|---|---|---|
| Spec 3 | 15% | 11% | 9% | 15% | 11% | 9% | 8% | nd | 9% |
| Cutoff 4 | 23.8 | 28.0 | 19.0 | 23.8 | 28.0 | 19.0 | 23.8 | nd | 19.0 |
| Sens 4 | 50% | 33% | 62% | 50% | 33% | 62% | 29% | nd | 33% |
| Spec 4 | 71% | 70% | 70% | 71% | 70% | 70% | 71% | nd | 70% |
| Cutoff 5 | 29.2 | 32.9 | 26.8 | 29.2 | 32.9 | 26.8 | 29.2 | nd | 26.8 |
| Sens 5 | 42% | 17% | 38% | 33% | 17% | 38% | 14% | nd | 17% |
| Spec 5 | 80% | 80% | 81% | 80% | 80% | 81% | 80% | nd | 81% |
| Cutoff 6 | 44.4 | 43.4 | 34.3 | 44.4 | 43.4 | 34.3 | 44.4 | nd | 34.3 |
| Sens 6 | 17% | 0% | 38% | 17% | 0% | 38% | 0% | nd | 17% |
| Spec 6 | 92% | 90% | 91% | 92% | 90% | 91% | 92% | nd | 91% |
| OR Quart 2 | 0.30 | 0 | 0.47 | 0.30 | 0 | 0.47 | 3.4 | nd | 0.50 |
| p Value | 0.31 | na | 0.55 | 0.31 | na | 0.55 | 0.31 | nd | 0.59 |
| 95% CI of | 0.028 | na | 0.039 | 0.028 | na | 0.039 | 0.32 | nd | 0.041 |
| OR Quart 2 | 3.1 | na | 5.7 | 3.1 | na | 5.7 | 36 | nd | 6.1 |
| OR Quart 3 | 1.0 | 1.0 | 0.47 | 1.0 | 1.5 | 0.47 | 1.0 | nd | 1.0 |
| p Value | 1.0 | 1.0 | 0.55 | 1.0 | 0.64 | 0.55 | 1.0 | nd | 1.0 |
| 95% CI of | 0.17 | 0.13 | 0.039 | 0.17 | 0.24 | 0.039 | 0.058 | nd | 0.13 |
| OR Quart 3 | 5.7 | 7.5 | 5.7 | 5.7 | 9.9 | 5.7 | 17 | nd | 8.0 |
| OR Quart 4 | 1.8 | 0.97 | 2.3 | 1.8 | 0.47 | 2.3 | 2.1 | nd | 0.50 |
| p Value | 0.48 | 0.98 | 0.38 | 0.48 | 0.55 | 0.38 | 0.55 | nd | 0.59 |
| 95% CI of | 0.36 | 0.13 | 0.36 | 0.36 | 0.041 | 0.36 | 0.18 | nd | 0.041 |
| OR Quart 4 | 8.8 | 7.3 | 14 | 8.8 | 5.4 | 14 | 26 | nd | 6.1 |

Insulin-like growth factor-binding protein 4

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 2.43 | 14.3 | 2.43 | 14.3 | nd | nd |
| Average | 12.0 | 16.2 | 12.0 | 16.2 | nd | nd |
| Stdev | 24.2 | 15.1 | 24.2 | 15.1 | nd | nd |
| p (t-test) | | 0.63 | | 0.63 | nd | nd |
| Min | 0.572 | 0.572 | 0.572 | 0.572 | nd | nd |
| Max | 158 | 33.4 | 158 | 33.4 | nd | nd |
| n (Samp) | 87 | 8 | 87 | 8 | nd | nd |
| n (Patient) | 87 | 8 | 87 | 8 | nd | nd |
| UO only | | | | | | |
| Median | 2.93 | 15.8 | 2.93 | 15.8 | nd | nd |
| Average | 13.3 | 16.8 | 13.3 | 16.8 | nd | nd |
| Stdev | 25.0 | 16.4 | 25.0 | 16.4 | nd | nd |
| p (t-test) | | 0.74 | | 0.74 | nd | nd |
| Min | 0.572 | 0.572 | 0.572 | 0.572 | nd | nd |
| Max | 158 | 33.4 | 158 | 33.4 | nd | nd |
| n (Samp) | 80 | 6 | 80 | 6 | nd | nd |
| n (Patient) | 80 | 6 | 80 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.66 | nd | 0.61 | 0.66 | nd | 0.61 | nd | nd | nd |
| SE | 0.11 | nd | 0.13 | 0.11 | nd | 0.13 | nd | nd | nd |
| p | 0.14 | nd | 0.37 | 0.14 | nd | 0.37 | nd | nd | nd |
| nCohort 1 | 87 | nd | 80 | 87 | nd | 80 | nd | nd | nd |
| nCohort 2 | 8 | nd | 6 | 8 | nd | 6 | nd | nd | nd |
| Cutoff 1 | 2.43 | nd | 0.971 | 2.43 | nd | 0.971 | nd | nd | nd |
| Sens 1 | 75% | nd | 83% | 75% | nd | 83% | nd | nd | nd |
| Spec 1 | 55% | nd | 38% | 55% | nd | 38% | nd | nd | nd |
| Cutoff 2 | 0.971 | nd | 0.971 | 0.971 | nd | 0.971 | nd | nd | nd |
| Sens 2 | 88% | nd | 83% | 88% | nd | 83% | nd | nd | nd |
| Spec 2 | 43% | nd | 38% | 43% | nd | 38% | nd | nd | nd |
| Cutoff 3 | 0 | nd | 0 | 0 | nd | 0 | nd | nd | nd |
| Sens 3 | 100% | nd | 100% | 100% | nd | 100% | nd | nd | nd |
| Spec 3 | 0% | nd | 0% | 0% | nd | 0% | nd | nd | nd |
| Cutoff 4 | 6.75 | nd | 10.7 | 6.75 | nd | 10.7 | nd | nd | nd |
| Sens 4 | 50% | nd | 50% | 50% | nd | 50% | nd | nd | nd |
| Spec 4 | 70% | nd | 70% | 70% | nd | 70% | nd | nd | nd |
| Cutoff 5 | 19.0 | nd | 21.4 | 19.0 | nd | 21.4 | nd | nd | nd |
| Sens 5 | 50% | nd | 50% | 50% | nd | 50% | nd | nd | nd |
| Spec 5 | 80% | nd | 80% | 80% | nd | 80% | nd | nd | nd |
| Cutoff 6 | 31.3 | nd | 34.2 | 31.3 | nd | 34.2 | nd | nd | nd |
| Sens 6 | 25% | nd | 0% | 25% | nd | 0% | nd | nd | nd |
| Spec 6 | 91% | nd | 90% | 91% | nd | 90% | nd | nd | nd |
| OR Quart 2 | 0 | nd | 2.0 | 0 | nd | 2.0 | nd | nd | nd |

-continued

| | | | | | | | | | |
|---|---|---|---|---|---|---|---|---|---|
| p Value | na | nd | 0.58 | na | nd | 0.58 | nd | nd | nd |
| 95% CI of | na | nd | 0.17 | na | nd | 0.17 | nd | nd | nd |
| OR Quart 2 | na | nd | 24 | na | nd | 24 | nd | nd | nd |
| OR Quart 3 | 3.1 | nd | 0 | 3.1 | nd | 0 | nd | nd | nd |
| p Value | 0.34 | nd | na | 0.34 | nd | na | nd | nd | nd |
| 95% CI of | 0.30 | nd | na | 0.30 | nd | na | nd | nd | nd |
| OR Quart 3 | 33 | nd | na | 33 | nd | na | nd | nd | nd |
| OR Quart 4 | 4.4 | nd | 3.2 | 4.4 | nd | 3.2 | nd | nd | nd |
| p Value | 0.20 | nd | 0.34 | 0.20 | nd | 0.34 | nd | nd | nd |
| 95% CI of | 0.45 | nd | 0.30 | 0.45 | nd | 0.30 | nd | nd | nd |
| OR Quart 4 | 43 | nd | 33 | 43 | nd | 33 | nd | nd | nd |

Insulin-like growth factor-binding protein 5

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 34.6 | 48.0 | 34.6 | 48.0 | nd | nd |
| Average | 47.2 | 43.5 | 47.2 | 43.5 | nd | nd |
| Stdev | 52.3 | 42.3 | 52.3 | 42.3 | nd | nd |
| p (t-test) | | 0.85 | | 0.85 | nd | nd |
| Min | 0.204 | 0.204 | 0.204 | 0.204 | nd | nd |
| Max | 257 | 117 | 257 | 117 | nd | nd |
| n (Samp) | 87 | 8 | 87 | 8 | nd | nd |
| n (Patient) | 87 | 8 | 87 | 8 | nd | nd |
| UO only | | | | | | |
| Median | 24.6 | 62.6 | 24.6 | 62.6 | nd | nd |
| Average | 41.6 | 52.3 | 41.6 | 52.3 | nd | nd |
| Stdev | 53.2 | 44.9 | 53.2 | 44.9 | nd | nd |
| p (t-test) | | 0.63 | | 0.63 | nd | nd |
| Min | 0.204 | 0.204 | 0.204 | 0.204 | nd | nd |
| Max | 257 | 117 | 257 | 117 | nd | nd |
| n (Samp) | 80 | 6 | 80 | 6 | nd | nd |
| n (Patient) | 80 | 6 | 80 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.49 | nd | 0.59 | 0.49 | nd | 0.59 | nd | nd | nd |
| SE | 0.11 | nd | 0.13 | 0.11 | nd | 0.13 | nd | nd | nd |
| p | 0.92 | nd | 0.47 | 0.92 | nd | 0.47 | nd | nd | nd |
| nCohort 1 | 87 | nd | 80 | 87 | nd | 80 | nd | nd | nd |
| nCohort 2 | 8 | nd | 6 | 8 | nd | 6 | nd | nd | nd |
| Cutoff 1 | 0.488 | nd | 0.488 | 0.488 | nd | 0.488 | nd | nd | nd |
| Sens 1 | 75% | nd | 83% | 75% | nd | 83% | nd | nd | nd |
| Spec 1 | 18% | nd | 22% | 18% | nd | 22% | nd | nd | nd |
| Cutoff 2 | 0.204 | nd | 0.488 | 0.204 | nd | 0.488 | nd | nd | nd |
| Sens 2 | 88% | nd | 83% | 88% | nd | 83% | nd | nd | nd |
| Spec 2 | 6% | nd | 22% | 6% | nd | 22% | nd | nd | nd |
| Cutoff 3 | 0 | nd | 0 | 0 | nd | 0 | nd | nd | nd |
| Sens 3 | 100% | nd | 100% | 100% | nd | 100% | nd | nd | nd |
| Spec 3 | 0% | nd | 0% | 0% | nd | 0% | nd | nd | nd |
| Cutoff 4 | 59.8 | nd | 47.6 | 59.8 | nd | 47.6 | nd | nd | nd |
| Sens 4 | 50% | nd | 67% | 50% | nd | 67% | nd | nd | nd |
| Spec 4 | 70% | nd | 70% | 70% | nd | 70% | nd | nd | nd |
| Cutoff 5 | 76.0 | nd | 65.5 | 76.0 | nd | 65.5 | nd | nd | nd |
| Sens 5 | 12% | nd | 33% | 12% | nd | 33% | nd | nd | nd |
| Spec 5 | 80% | nd | 80% | 80% | nd | 80% | nd | nd | nd |
| Cutoff 6 | 124 | nd | 97.6 | 124 | nd | 97.6 | nd | nd | nd |
| Sens 6 | 0% | nd | 17% | 0% | nd | 17% | nd | nd | nd |
| Spec 6 | 91% | nd | 90% | 91% | nd | 90% | nd | nd | nd |
| OR Quart 2 | 1.0 | nd | 0.95 | 1.0 | nd | 0.95 | nd | nd | nd |
| p Value | 1.0 | nd | 0.97 | 1.0 | nd | 0.97 | nd | nd | nd |
| 95% CI of | 0.13 | nd | 0.056 | 0.13 | nd | 0.056 | nd | nd | nd |
| OR Quart 2 | 7.7 | nd | 16 | 7.7 | nd | 16 | nd | nd | nd |
| OR Quart 3 | 1.0 | nd | 0 | 1.0 | nd | 0 | nd | nd | nd |
| p Value | 1.0 | nd | na | 1.0 | nd | na | nd | nd | nd |
| 95% CI of | 0.13 | nd | na | 0.13 | nd | na | nd | nd | nd |
| OR Quart 3 | 7.7 | nd | na | 7.7 | nd | na | nd | nd | nd |
| OR Quart 4 | 1.0 | nd | 4.4 | 1.0 | nd | 4.4 | nd | nd | nd |

-continued

| | | | | | | | | | |
|---|---|---|---|---|---|---|---|---|---|
| p Value | 0.96 | nd | 0.20 | 0.96 | nd | 0.20 | nd | nd | nd |
| 95% CI of | 0.13 | nd | 0.45 | 0.13 | nd | 0.45 | nd | nd | nd |
| OR Quart 4 | 8.1 | nd | 44 | 8.1 | nd | 44 | nd | nd | nd |

Interleukin-21

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.783 | 1.89 | 0.783 | 1.75 | 0.783 | 1.89 |
| Average | 88.7 | 4.14 | 88.7 | 3.98 | 88.7 | 2.64 |
| Stdev | 673 | 7.38 | 673 | 7.45 | 673 | 2.51 |
| p (t-test) | | 0.67 | | 0.67 | | 0.74 |
| Min | 0.0102 | 0.0102 | 0.0102 | 0.0102 | 0.0102 | 0.829 |
| Max | 5430 | 26.6 | 5430 | 26.6 | 5430 | 8.25 |
| n (Samp) | 65 | 12 | 65 | 12 | 65 | 7 |
| n (Patient) | 65 | 12 | 65 | 12 | 65 | 7 |
| sCr only | | | | | | |
| Median | 0.783 | 2.01 | 0.783 | 1.80 | nd | nd |
| Average | 45.5 | 2.67 | 45.5 | 2.35 | nd | nd |
| Stdev | 473 | 2.84 | 473 | 3.02 | nd | nd |
| p (t-test) | | 0.83 | | 0.82 | nd | nd |
| Min | 0.0102 | 0.0102 | 0.0102 | 0.0102 | nd | nd |
| Max | 5430 | 8.25 | 5430 | 8.25 | nd | nd |
| n (Samp) | 132 | 6 | 132 | 6 | nd | nd |
| n (Patient) | 132 | 6 | 132 | 6 | nd | nd |
| UO only | | | | | | |
| Median | 1.02 | 1.89 | 1.02 | 1.89 | 1.02 | 1.89 |
| Average | 90.5 | 4.71 | 90.5 | 4.71 | 90.5 | 1.71 |
| Stdev | 678 | 8.88 | 678 | 8.88 | 678 | 0.455 |
| p (t-test) | | 0.72 | | 0.72 | | 0.75 |
| Min | 0.0102 | 0.783 | 0.0102 | 0.783 | 0.0102 | 0.829 |
| Max | 5430 | 26.6 | 5430 | 26.6 | 5430 | 2.03 |
| n (Samp) | 64 | 8 | 64 | 8 | 64 | 6 |
| n (Patient) | 64 | 8 | 64 | 8 | 64 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.69 | 0.66 | 0.66 | 0.65 | 0.59 | 0.66 | 0.74 | nd | 0.65 |
| SE | 0.090 | 0.12 | 0.11 | 0.092 | 0.12 | 0.11 | 0.11 | nd | 0.13 |
| p | 0.038 | 0.19 | 0.14 | 0.10 | 0.45 | 0.14 | 0.034 | nd | 0.23 |
| nCohort 1 | 65 | 132 | 64 | 65 | 132 | 64 | 65 | nd | 64 |
| nCohort 2 | 12 | 6 | 8 | 12 | 6 | 8 | 7 | nd | 6 |
| Cutoff 1 | 1.53 | 1.53 | 1.53 | 0.783 | 0.0314 | 1.53 | 1.79 | nd | 1.53 |
| Sens 1 | 75% | 83% | 75% | 75% | 83% | 75% | 71% | nd | 83% |
| Spec 1 | 71% | 67% | 64% | 51% | 33% | 64% | 74% | nd | 64% |
| Cutoff 2 | 0.783 | 1.53 | 0.783 | 0.605 | 0.0314 | 0.783 | 1.53 | nd | 1.53 |
| Sens 2 | 83% | 83% | 88% | 83% | 83% | 88% | 86% | nd | 83% |
| Spec 2 | 51% | 67% | 45% | 49% | 33% | 45% | 71% | nd | 64% |
| Cutoff 3 | 0.605 | 0.0102 | 0.605 | 0.0314 | 0.0102 | 0.605 | 0.783 | nd | 0.783 |
| Sens 3 | 92% | 100% | 100% | 92% | 100% | 100% | 100% | nd | 100% |
| Spec 3 | 49% | 8% | 44% | 34% | 8% | 44% | 51% | nd | 45% |
| Cutoff 4 | 1.53 | 1.79 | 1.89 | 1.53 | 1.79 | 1.89 | 1.53 | nd | 1.89 |
| Sens 4 | 75% | 67% | 38% | 67% | 50% | 38% | 86% | nd | 33% |
| Spec 4 | 71% | 70% | 70% | 71% | 70% | 70% | 71% | nd | 70% |
| Cutoff 5 | 2.03 | 2.60 | 3.18 | 2.03 | 2.60 | 3.18 | 2.03 | nd | 3.18 |
| Sens 5 | 25% | 17% | 12% | 17% | 17% | 12% | 14% | nd | 0% |
| Spec 5 | 80% | 81% | 81% | 80% | 81% | 81% | 80% | nd | 81% |
| Cutoff 6 | 10.6 | 5.72 | 11.4 | 10.6 | 5.72 | 11.4 | 10.6 | nd | 11.4 |
| Sens 6 | 8% | 17% | 12% | 8% | 17% | 12% | 0% | nd | 0% |
| Spec 6 | 91% | 90% | 91% | 91% | 90% | 91% | 91% | nd | 91% |
| OR Quart 2 | 2.1 | 0 | >2.2 | 3.4 | 0.97 | >2.2 | >1.1 | nd | >1.0 |
| p Value | 0.55 | na | <0.52 | 0.31 | 0.98 | <0.52 | <0.97 | nd | <1.0 |
| 95% CI of | 0.18 | na | >0.19 | 0.32 | 0.058 | >0.19 | >0.061 | nd | >0.058 |
| OR Quart 2 | 26 | na | na | 36 | 16 | na | na | nd | na |
| OR Quart 3 | 4.8 | 2.1 | >6.9 | 4.8 | 2.1 | >6.9 | >5.1 | nd | >7.1 |
| p Value | 0.18 | 0.56 | <0.094 | 0.18 | 0.56 | <0.094 | <0.16 | nd | <0.091 |
| 95% CI of | 0.48 | 0.18 | >0.72 | 0.48 | 0.18 | >0.72 | >0.52 | nd | >0.73 |
| OR Quart 3 | 48 | 24 | na | 48 | 24 | na | na | nd | na |
| OR Quart 4 | 6.0 | 3.1 | >1.1 | 4.5 | 2.0 | >1.1 | >2.2 | nd | >0 |
| p Value | 0.12 | 0.34 | <0.97 | 0.20 | 0.58 | <0.97 | <0.52 | nd | <na |

| | | | | | | | | | |
|---|---|---|---|---|---|---|---|---|---|
| 95% CI of | 0.63 | 0.31 | >0.061 | 0.45 | 0.17 | >0.061 | >0.19 | nd | >na |
| OR Quart 4 | 57 | 31 | na | 45 | 23 | na | na | nd | na |

Interleukin-23

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.995 | 256 | 0.995 | 216 | 0.995 | 22.3 |
| Average | 2550 | 9620 | 2550 | 9610 | 2550 | 1110 |
| Stdev | 13000 | 28600 | 13000 | 28600 | 13000 | 2390 |
| p (t-test) | | 0.17 | | 0.17 | | 0.77 |
| Min | 0.257 | 0.257 | 0.257 | 0.257 | 0.257 | 0.257 |
| Max | 100000 | 100000 | 100000 | 100000 | 100000 | 6480 |
| n (Samp) | 64 | 12 | 64 | 12 | 64 | 7 |
| n (Patient) | 64 | 12 | 64 | 12 | 64 | 7 |
| sCr only | | | | | | |
| Median | 1.10 | 89.5 | 1.10 | 50.3 | nd | nd |
| Average | 3050 | 435 | 3050 | 421 | nd | nd |
| Stdev | 15200 | 637 | 15200 | 644 | nd | nd |
| p (t-test) | | 0.68 | | 0.67 | nd | nd |
| Min | 0.257 | 0.257 | 0.257 | 0.257 | nd | nd |
| Max | 100000 | 1520 | 100000 | 1520 | nd | nd |
| n (Samp) | 131 | 6 | 131 | 6 | nd | nd |
| n (Patient) | 131 | 6 | 131 | 6 | nd | nd |
| UO only | | | | | | |
| Median | 1.10 | 621 | 1.10 | 621 | 1.10 | 178 |
| Average | 3240 | 14200 | 3240 | 14200 | 3240 | 1290 |
| Stdev | 13600 | 34800 | 13600 | 34800 | 13600 | 2560 |
| p (t-test) | | 0.091 | | 0.091 | | 0.73 |
| Min | 0.257 | 0.257 | 0.257 | 0.257 | 0.257 | 0.257 |
| Max | 100000 | 100000 | 100000 | 100000 | 100000 | 6480 |
| n (Samp) | 63 | 8 | 63 | 8 | 63 | 6 |
| n (Patient) | 63 | 8 | 63 | 8 | 63 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.67 | 0.58 | 0.70 | 0.66 | 0.57 | 0.70 | 0.62 | nd | 0.61 |
| SE | 0.092 | 0.12 | 0.11 | 0.092 | 0.12 | 0.11 | 0.12 | nd | 0.13 |
| p | 0.070 | 0.54 | 0.072 | 0.072 | 0.58 | 0.072 | 0.32 | nd | 0.40 |
| nCohort 1 | 64 | 131 | 63 | 64 | 131 | 63 | 64 | nd | 63 |
| nCohort 2 | 12 | 6 | 8 | 12 | 6 | 8 | 7 | nd | 6 |
| Cutoff 1 | 0.886 | 0.770 | 11.0 | 0.886 | 0.770 | 11.0 | 0.886 | nd | 0.603 |
| Sens 1 | 75% | 83% | 75% | 75% | 83% | 75% | 71% | nd | 83% |
| Spec 1 | 50% | 32% | 67% | 50% | 32% | 67% | 50% | nd | 35% |
| Cutoff 2 | 0.770 | 0.770 | 0.603 | 0.770 | 0.770 | 0.603 | 0.770 | nd | 0.603 |
| Sens 2 | 83% | 83% | 88% | 83% | 83% | 88% | 86% | nd | 83% |
| Spec 2 | 36% | 32% | 35% | 36% | 32% | 35% | 36% | nd | 35% |
| Cutoff 3 | 0 | 0 | 0 | 0 | 0 | 0 | 0 | nd | 0 |
| Sens 3 | 100% | 100% | 100% | 100% | 100% | 100% | 100% | nd | 100% |
| Spec 3 | 0% | 0% | 0% | 0% | 0% | 0% | 0% | nd | 0% |
| Cutoff 4 | 55.0 | 138 | 405 | 55.0 | 138 | 405 | 55.0 | nd | 405 |
| Sens 4 | 58% | 50% | 50% | 58% | 33% | 50% | 43% | nd | 33% |
| Spec 4 | 70% | 70% | 71% | 70% | 70% | 71% | 70% | nd | 71% |
| Cutoff 5 | 861 | 637 | 861 | 861 | 637 | 861 | 861 | nd | 861 |
| Sens 5 | 42% | 33% | 50% | 42% | 33% | 50% | 29% | nd | 33% |
| Spec 5 | 81% | 80% | 81% | 81% | 80% | 81% | 81% | nd | 81% |
| Cutoff 6 | 2000 | 1540 | 2000 | 2000 | 1540 | 2000 | 2000 | nd | 2000 |
| Sens 6 | 25% | 0% | 38% | 25% | 0% | 38% | 14% | nd | 17% |
| Spec 6 | 91% | 90% | 90% | 91% | 90% | 90% | 91% | nd | 90% |
| OR Quart 2 | 0.47 | 1.0 | >2.1 | 0.47 | 1.0 | >2.1 | 0.94 | nd | >2.3 |
| p Value | 0.55 | 1.0 | <0.55 | 0.55 | 1.0 | <0.55 | 0.97 | nd | <0.52 |
| 95% CI of | 0.039 | 0.060 | >0.18 | 0.039 | 0.060 | >0.18 | 0.054 | nd | >0.19 |
| OR Quart 2 | 5.7 | 17 | na | 5.7 | 17 | na | 16 | nd | na |
| OR Quart 3 | 2.3 | 2.1 | >2.1 | 2.3 | 2.1 | >2.1 | 3.2 | nd | >2.3 |
| p Value | 0.38 | 0.56 | <0.55 | 0.38 | 0.56 | <0.55 | 0.34 | nd | <0.52 |
| 95% CI of | 0.36 | 0.18 | >0.18 | 0.36 | 0.18 | >0.18 | 0.30 | nd | >0.19 |
| OR Quart 3 | 14 | 24 | na | 14 | 24 | na | 34 | nd | na |

-continued

| | | | | | | | | | |
|---|---|---|---|---|---|---|---|---|---|
| OR Quart 4 | 3.0 | 2.0 | >4.9 | 3.0 | 2.0 | >4.9 | 2.0 | nd | >2.1 |
| p Value | 0.22 | 0.58 | <0.18 | 0.22 | 0.58 | <0.18 | 0.59 | nd | <0.55 |
| 95% CI of | 0.51 | 0.17 | >0.49 | 0.51 | 0.17 | >0.49 | 0.16 | nd | >0.18 |
| OR Quart 4 | 18 | 23 | na | 18 | 23 | na | 24 | nd | na |

Interleukin-28A

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.265 | 12.0 | 0.265 | 12.0 | 0.265 | 7.61 |
| Average | 87.3 | 181 | 87.3 | 181 | 87.3 | 14.1 |
| Stdev | 465 | 574 | 465 | 574 | 465 | 15.5 |
| p (t-test) | | 0.54 | | 0.54 | | 0.68 |
| Min | 0.120 | 0.148 | 0.120 | 0.148 | 0.120 | 0.148 |
| Max | 3150 | 2000 | 3150 | 2000 | 3150 | 35.6 |
| n (Samp) | 64 | 12 | 64 | 12 | 64 | 7 |
| n (Patient) | 64 | 12 | 64 | 12 | 64 | 7 |
| sCr only | | | | | | |
| Median | 0.265 | 0.626 | 0.265 | 0.265 | nd | nd |
| Average | 47.7 | 10.8 | 47.7 | 10.7 | nd | nd |
| Stdev | 326 | 22.2 | 326 | 22.3 | nd | nd |
| p (t-test) | | 0.78 | | 0.78 | nd | nd |
| Min | 0.0727 | 0.148 | 0.0727 | 0.148 | nd | nd |
| Max | 3150 | 55.8 | 3150 | 55.8 | nd | nd |
| n (Samp) | 131 | 6 | 131 | 6 | nd | nd |
| n (Patient) | 131 | 6 | 131 | 6 | nd | nd |
| UO only | | | | | | |
| Median | 0.265 | 21.0 | 0.265 | 21.0 | 0.265 | 16.6 |
| Average | 90.5 | 265 | 90.5 | 265 | 90.5 | 16.4 |
| Stdev | 468 | 703 | 468 | 703 | 468 | 15.6 |
| p (t-test) | | 0.35 | | 0.35 | | 0.70 |
| Min | 0.120 | 0.265 | | 0.265 | 0.120 | 0.265 |
| Max | 3150 | 2000 | 3150 | 2000 | 3150 | 35.6 |
| n (Samp) | 63 | 8 | 63 | 8 | 63 | 6 |
| n (Patient) | 63 | 8 | 63 | 8 | 63 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.73 | 0.57 | 0.82 | 0.70 | 0.52 | 0.82 | 0.68 | nd | 0.78 |
| SE | 0.088 | 0.12 | 0.095 | 0.090 | 0.12 | 0.095 | 0.12 | nd | 0.11 |
| p | 0.0095 | 0.59 | 8.5E−4 | 0.025 | 0.86 | 8.5E−4 | 0.13 | nd | 0.015 |
| nCohort 1 | 64 | 131 | 63 | 64 | 131 | 63 | 64 | nd | 63 |
| nCohort 2 | 12 | 6 | 8 | 12 | 6 | 8 | 7 | nd | 6 |
| Cutoff 1 | 0.195 | 0.195 | 3.03 | 0.195 | 0.168 | 3.03 | 0.195 | nd | 0.195 |
| Sens 1 | 92% | 83% | 75% | 83% | 83% | 75% | 86% | nd | 100% |
| Spec 1 | 41% | 40% | 78% | 41% | 31% | 78% | 41% | nd | 43% |
| Cutoff 2 | 0.195 | 0.195 | 0.195 | 0.195 | 0.168 | 0.195 | 0.195 | nd | 0.195 |
| Sens 2 | 92% | 83% | 100% | 83% | 83% | 100% | 86% | nd | 100% |
| Spec 2 | 41% | 40% | 43% | 41% | 31% | 43% | 41% | nd | 43% |
| Cutoff 3 | 0.195 | 0.120 | 0.195 | 0.168 | 0.120 | 0.195 | 0.120 | nd | 0.195 |
| Sens 3 | 92% | 100% | 100% | 92% | 100% | 100% | 100% | nd | 100% |
| Spec 3 | 41% | 2% | 43% | 34% | 2% | 43% | 2% | nd | 43% |
| Cutoff 4 | 0.265 | 10.2 | 0.265 | 0.265 | 10.2 | 0.265 | 0.265 | nd | 0.265 |
| Sens 4 | 67% | 17% | 75% | 58% | 17% | 75% | 57% | nd | 67% |
| Spec 4 | 70% | 71% | 76% | 70% | 71% | 76% | 70% | nd | 76% |
| Cutoff 5 | 12.3 | 14.3 | 10.8 | 12.3 | 14.3 | 10.8 | 12.3 | nd | 10.8 |
| Sens 5 | 50% | 17% | 62% | 50% | 17% | 62% | 43% | nd | 50% |
| Spec 5 | 81% | 80% | 81% | 81% | 80% | 81% | 81% | nd | 81% |
| Cutoff 6 | 21.6 | 25.6 | 21.6 | 21.6 | 25.6 | 21.6 | 21.6 | nd | 21.6 |
| Sens 6 | 42% | 17% | 50% | 42% | 17% | 50% | 43% | nd | 50% |
| Spec 6 | 91% | 91% | 90% | 91% | 91% | 90% | 91% | nd | 90% |
| OR Quart 2 | 3.4 | 0 | >2.1 | 4.8 | 2.1 | >2.1 | 2.0 | nd | >2.3 |
| p Value | 0.31 | na | <0.55 | 0.18 | 0.56 | <0.55 | 0.59 | nd | <0.52 |
| 95% CI of | 0.32 | na | >0.18 | 0.48 | 0.18 | >0.18 | 0.16 | nd | >0.19 |
| OR Quart 2 | 36 | na | na | 48 | 24 | na | 24 | nd | na |
| OR Quart 3 | 2.1 | 4.4 | >1.0 | 1.0 | 2.1 | >1.0 | 0.94 | nd | >0 |
| p Value | 0.55 | 0.20 | <1.0 | 1.0 | 0.56 | <1.0 | 0.97 | nd | <na |
| 95% CI of | 0.18 | 0.47 | >0.058 | 0.058 | 0.18 | >0.058 | 0.054 | nd | >na |
| OR Quart 3 | 26 | 42 | na | 17 | 24 | na | 16 | nd | na |
| OR Quart 4 | 8.3 | 0.97 | >6.5 | 8.3 | 0.97 | >6.5 | 3.2 | nd | >4.9 |

| | | | | | | | | | |
|---|---|---|---|---|---|---|---|---|---|
| p Value | 0.063 | 0.98 | <0.10 | 0.063 | 0.98 | <0.10 | 0.34 | nd | <0.18 |
| 95% CI of | 0.89 | 0.058 | >0.68 | 0.89 | 0.058 | >0.68 | 0.30 | nd | >0.49 |
| OR Quart 4 | 78 | 16 | na | 78 | 16 | na | 34 | nd | na |

Interleukin-33

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 0.101 | 15.5 | 0.101 | 15.5 | 0.101 | 9.09 |
| Average | 687 | 1070 | 687 | 1070 | 687 | 34.8 |
| Stdev | 4960 | 3520 | 4960 | 3520 | 4960 | 54.3 |
| p (t-test) | | 0.80 | | 0.80 | | 0.73 |
| Min | 0.0445 | 0.0455 | 0.0445 | 0.0455 | 0.0445 | 0.0455 |
| Max | 40000 | 12300 | 40000 | 12300 | 40000 | 149 |
| n (Samp) | 65 | 12 | 65 | 12 | 65 | 7 |
| n (Patient) | 65 | 12 | 65 | 12 | 65 | 7 |
| sCr only | | | | | | |
| Median | 0.101 | 6.17 | 0.101 | 6.17 | nd | nd |
| Average | 489 | 24.6 | 489 | 24.6 | nd | nd |
| Stdev | 3680 | 44.2 | 3680 | 44.2 | nd | nd |
| p (t-test) | | 0.76 | | 0.76 | nd | nd |
| Min | 0.0445 | 0.0455 | 0.0445 | 0.0455 | nd | nd |
| Max | 40000 | 113 | 40000 | 113 | nd | nd |
| n (Samp) | 132 | 6 | 132 | 6 | nd | nd |
| n (Patient) | 132 | 6 | 132 | 6 | nd | nd |
| UO only | | | | | | |
| Median | 0.0981 | 39.7 | 0.0981 | 39.7 | 0.0981 | 12.6 |
| Average | 749 | 1600 | 749 | 1600 | 749 | 39.1 |
| Stdev | 5000 | 4310 | 5000 | 4310 | 5000 | 58.2 |
| p (t-test) | | 0.65 | | 0.65 | | 0.73 |
| Min | 0.0445 | 0.0455 | 0.0445 | 0.0455 | 0.0445 | 0.0455 |
| Max | 40000 | 12300 | 40000 | 12300 | 40000 | 149 |
| n (Samp) | 64 | 8 | 64 | 8 | 64 | 6 |
| n (Patient) | 64 | 8 | 64 | 8 | 64 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.70 | 0.62 | 0.75 | 0.70 | 0.62 | 0.75 | 0.70 | nd | 0.68 |
| SE | 0.090 | 0.12 | 0.10 | 0.090 | 0.12 | 0.10 | 0.12 | nd | 0.13 |
| p | 0.023 | 0.33 | 0.018 | 0.023 | 0.33 | 0.018 | 0.086 | nd | 0.15 |
| nCohort 1 | 65 | 132 | 64 | 65 | 132 | 64 | 65 | nd | 64 |
| nCohort 2 | 12 | 6 | 8 | 12 | 6 | 8 | 7 | nd | 6 |
| Cutoff 1 | 2.20 | 0.0981 | 2.65 | 2.20 | 0.0981 | 2.65 | 2.65 | nd | 2.20 |
| Sens 1 | 75% | 83% | 75% | 75% | 83% | 75% | 71% | nd | 83% |
| Spec 1 | 68% | 42% | 67% | 68% | 42% | 67% | 68% | nd | 67% |
| Cutoff 2 | 0.0981 | 0.0981 | 2.20 | 0.0981 | 0.0981 | 2.20 | 2.20 | nd | 2.20 |
| Sens 2 | 83% | 83% | 88% | 83% | 83% | 88% | 86% | nd | 83% |
| Spec 2 | 46% | 42% | 67% | 46% | 42% | 67% | 68% | nd | 67% |
| Cutoff 3 | 0.0445 | 0.0445 | 0.0445 | 0.0445 | 0.0445 | 0.0445 | 0.0445 | nd | 0.0445 |
| Sens 3 | 100% | 100% | 100% | 100% | 100% | 100% | 100% | nd | 100% |
| Spec 3 | 11% | 8% | 8% | 11% | 8% | 8% | 11% | nd | 8% |
| Cutoff 4 | 4.56 | 7.37 | 4.56 | 4.56 | 7.37 | 4.56 | 4.56 | nd | 4.56 |
| Sens 4 | 58% | 50% | 62% | 58% | 50% | 62% | 57% | nd | 50% |
| Spec 4 | 71% | 70% | 70% | 71% | 70% | 70% | 71% | nd | 70% |
| Cutoff 5 | 20.5 | 27.4 | 31.5 | 20.5 | 27.4 | 31.5 | 20.5 | nd | 31.5 |
| Sens 5 | 50% | 17% | 50% | 50% | 17% | 50% | 43% | nd | 33% |
| Spec 5 | 80% | 80% | 81% | 80% | 80% | 81% | 80% | nd | 81% |
| Cutoff 6 | 89.5 | 89.5 | 99.5 | 89.5 | 89.5 | 99.5 | 89.5 | nd | 99.5 |
| Sens 6 | 33% | 17% | 38% | 33% | 17% | 38% | 14% | nd | 17% |
| Spec 6 | 91% | 90% | 91% | 91% | 90% | 91% | 91% | nd | 91% |
| OR Quart 2 | 2.1 | 0 | >1.1 | 2.1 | 0 | >1.1 | 0 | nd | >1.0 |
| p Value | 0.55 | na | <0.97 | 0.55 | na | <0.97 | na | nd | <1.0 |
| 95% CI of | 0.18 | na | >0.061 | 0.18 | na | >0.061 | na | nd | >0.058 |
| OR Quart 2 | 26 | na | na | 26 | na | na | na | nd | na |
| OR Quart 3 | 3.4 | 3.2 | >3.6 | 3.4 | 3.2 | >3.6 | 3.4 | nd | >2.3 |
| p Value | 0.31 | 0.33 | <0.29 | 0.31 | 0.33 | <0.29 | 0.31 | nd | <0.52 |
| 95% CI of | 0.32 | 0.32 | >0.34 | 0.32 | 0.32 | >0.34 | 0.32 | nd | >0.19 |
| OR Quart 3 | 36 | 32 | na | 36 | 32 | na | 36 | nd | na |
| OR Quart 4 | 7.7 | 2.0 | >5.1 | 7.7 | 2.0 | >5.1 | 3.4 | nd | >3.4 |
| p Value | 0.072 | 0.58 | <0.16 | 0.072 | 0.58 | <0.16 | 0.31 | nd | <0.31 |

| | | | | | | | | | |
|---|---|---|---|---|---|---|---|---|---|
| 95% CI of | 0.83 | 0.17 | >0.52 | 0.83 | 0.17 | >0.52 | 0.32 | nd | >0.32 |
| OR Quart 4 | 72 | 23 | na | 72 | 23 | na | 36 | nd | na |

Vascular endothelial growth factor receptor 2

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 8020 | 7370 | 8020 | 7130 | 8020 | 7560 |
| Average | 11300 | 25200 | 11300 | 25100 | 11300 | 7430 |
| Stdev | 18600 | 60300 | 18600 | 60300 | 18600 | 1750 |
| p (t-test) | | 0.13 | | 0.13 | | 0.59 |
| Min | 3720 | 5310 | 3720 | 5310 | 3720 | 5310 |
| Max | 153000 | 216000 | 153000 | 216000 | 153000 | 10600 |
| n (Samp) | 65 | 12 | 65 | 12 | 65 | 7 |
| n (Patient) | 65 | 12 | 65 | 12 | 65 | 7 |
| sCr only | | | | | | |
| Median | 8020 | 6320 | 8020 | 5950 | nd | nd |
| Average | 11200 | 7000 | 11200 | 6800 | nd | nd |
| Stdev | 19000 | 1860 | 19000 | 1900 | nd | nd |
| p (t-test) | | 0.59 | | 0.57 | nd | nd |
| Min | 3720 | 5750 | 3720 | 5750 | nd | nd |
| Max | 166000 | 10600 | 166000 | 10600 | nd | nd |
| n (Samp) | 132 | 6 | 132 | 6 | nd | nd |
| n (Patient) | 132 | 6 | 132 | 6 | nd | nd |
| UO only | | | | | | |
| Median | 8010 | 7860 | 8010 | 7860 | 8010 | 7130 |
| Average | 11900 | 34100 | 11900 | 34100 | 11900 | 6900 |
| Stdev | 19000 | 73700 | 19000 | 73700 | 19000 | 1150 |
| p (t-test) | | 0.049 | | 0.049 | | 0.53 |
| Min | 3900 | 5310 | 3900 | 5310 | 3900 | 5310 |
| Max | 153000 | 216000 | 153000 | 216000 | 153000 | 8150 |
| n (Samp) | 64 | 8 | 64 | 8 | 64 | 6 |
| n (Patient) | 64 | 8 | 64 | 8 | 64 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.46 | 0.31 | 0.52 | 0.44 | 0.28 | 0.52 | 0.39 | nd | 0.34 |
| SE | 0.093 | 0.12 | 0.11 | 0.093 | 0.12 | 0.11 | 0.12 | nd | 0.13 |
| p | 0.65 | 0.13 | 0.86 | 0.51 | 0.069 | 0.86 | 0.36 | nd | 0.21 |
| nCohort 1 | 65 | 132 | 64 | 65 | 132 | 64 | 65 | nd | 64 |
| nCohort 2 | 12 | 6 | 8 | 12 | 6 | 8 | 7 | nd | 6 |
| Cutoff 1 | 5920 | 5830 | 6660 | 5920 | 5830 | 6660 | 6660 | nd | 5700 |
| Sens 1 | 75% | 83% | 75% | 75% | 83% | 75% | 71% | nd | 83% |
| Spec 1 | 12% | 15% | 33% | 12% | 15% | 33% | 31% | nd | 12% |
| Cutoff 2 | 5750 | 5830 | 5700 | 5750 | 5830 | 5700 | 5310 | nd | 5700 |
| Sens 2 | 83% | 83% | 88% | 83% | 83% | 88% | 86% | nd | 83% |
| Spec 2 | 11% | 15% | 12% | 11% | 15% | 12% | 11% | nd | 12% |
| Cutoff 3 | 5310 | 5720 | 5230 | 5310 | 5720 | 5230 | 5230 | nd | 5230 |
| Sens 3 | 92% | 100% | 100% | 92% | 100% | 100% | 100% | nd | 100% |
| Spec 3 | 11% | 14% | 9% | 11% | 14% | 9% | 11% | nd | 9% |
| Cutoff 4 | 9430 | 9520 | 9430 | 9430 | 9520 | 9430 | 9430 | nd | 9430 |
| Sens 4 | 33% | 17% | 38% | 33% | 17% | 38% | 14% | nd | 0% |
| Spec 4 | 71% | 70% | 70% | 71% | 70% | 70% | 71% | nd | 70% |
| Cutoff 5 | 10800 | 10800 | 11100 | 10800 | 10800 | 11100 | 10800 | nd | 11100 |
| Sens 5 | 17% | 0% | 25% | 17% | 0% | 25% | 0% | nd | 0% |
| Spec 5 | 80% | 80% | 81% | 80% | 80% | 81% | 80% | nd | 81% |
| Cutoff 6 | 13800 | 14200 | 16000 | 13800 | 14200 | 16000 | 13800 | nd | 16000 |
| Sens 6 | 8% | 0% | 12% | 8% | 0% | 12% | 0% | nd | 0% |
| Spec 6 | 91% | 90% | 91% | 91% | 90% | 91% | 91% | nd | 91% |
| OR Quart 2 | 0.67 | 0 | 1.0 | 0.67 | 0 | 1.0 | 1.0 | nd | >1.1 |
| p Value | 0.68 | na | 1.0 | 0.68 | na | 1.0 | 1.0 | nd | <0.94 |
| 95% CI of | 0.099 | na | 0.13 | 0.099 | na | 0.13 | 0.058 | nd | >0.065 |
| OR Quart 2 | 4.5 | na | 8.0 | 4.5 | na | 8.0 | 17 | nd | na |
| OR Quart 3 | 1.1 | 2.1 | 1.0 | 0.67 | 1.0 | 1.0 | 3.4 | nd | >3.6 |
| p Value | 0.95 | 0.56 | 1.0 | 0.68 | 1.0 | 1.0 | 0.31 | nd | <0.29 |
| 95% CI of | 0.19 | 0.18 | 0.13 | 0.099 | 0.060 | 0.13 | 0.32 | nd | >0.34 |

-continued

| | | | | | | | | | |
|---|---|---|---|---|---|---|---|---|---|
| OR Quart 3 | 6.1 | 24 | 8.0 | 4.5 | 17 | 8.0 | 36 | nd | na |
| OR Quart 4 | 1.5 | 3.3 | 1.0 | 2.0 | 4.5 | 1.0 | 2.1 | nd | >2.4 |
| p Value | 0.62 | 0.31 | 1.0 | 0.39 | 0.19 | 1.0 | 0.55 | nd | <0.49 |
| 95% CI of | 0.29 | 0.32 | 0.13 | 0.41 | 0.48 | 0.13 | 0.18 | nd | >0.20 |
| OR Quart 4 | 7.9 | 33 | 8.0 | 10.0 | 43 | 8.0 | 26 | nd | na |

Neural cell adhesion molecule 1

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 189000 | 172000 | 189000 | 172000 | nd | nd |
| Average | 192000 | 180000 | 192000 | 177000 | nd | nd |
| Stdev | 74500 | 49600 | 74500 | 44400 | nd | nd |
| p (t-test) | | 0.65 | | 0.56 | nd | nd |
| Min | 73000 | 111000 | 73000 | 111000 | nd | nd |
| Max | 520000 | 256000 | 520000 | 245000 | nd | nd |
| n (Samp) | 86 | 8 | 86 | 8 | nd | nd |
| n (Patient) | 86 | 8 | 86 | 8 | nd | nd |
| UO only | | | | | | |
| Median | 186000 | 162000 | 186000 | 162000 | nd | nd |
| Average | 193000 | 166000 | 193000 | 166000 | nd | nd |
| Stdev | 78400 | 45100 | 78400 | 45100 | nd | nd |
| p (t-test) | | 0.41 | | 0.41 | nd | nd |
| Min | 73000 | 111000 | 73000 | 111000 | nd | nd |
| Max | 520000 | 245000 | 520000 | 245000 | nd | nd |
| n (Samp) | 79 | 6 | 79 | 6 | nd | nd |
| n (Patient) | 79 | 6 | 79 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.46 | nd | 0.39 | 0.45 | nd | 0.39 | nd | nd | nd |
| SE | 0.11 | nd | 0.13 | 0.11 | nd | 0.13 | nd | nd | nd |
| p | 0.72 | nd | 0.40 | 0.67 | nd | 0.40 | nd | nd | nd |
| nCohort 1 | 86 | nd | 79 | 86 | nd | 79 | nd | nd | nd |
| nCohort 2 | 8 | nd | 6 | 8 | nd | 6 | nd | nd | nd |
| Cutoff 1 | 158000 | nd | 139000 | 158000 | nd | 139000 | nd | nd | nd |
| Sens 1 | 75% | nd | 83% | 75% | nd | 83% | nd | nd | nd |
| Spec 1 | 35% | nd | 23% | 35% | nd | 23% | nd | nd | nd |
| Cutoff 2 | 139000 | nd | 139000 | 139000 | nd | 139000 | nd | nd | nd |
| Sens 2 | 88% | nd | 83% | 88% | nd | 83% | nd | nd | nd |
| Spec 2 | 22% | nd | 23% | 22% | nd | 23% | nd | nd | nd |
| Cutoff 3 | 107000 | nd | 107000 | 107000 | nd | 107000 | nd | nd | nd |
| Sens 3 | 100% | nd | 100% | 100% | nd | 100% | nd | nd | nd |
| Spec 3 | 9% | nd | 9% | 9% | nd | 9% | nd | nd | nd |
| Cutoff 4 | 217000 | nd | 217000 | 217000 | nd | 217000 | nd | nd | nd |
| Sens 4 | 25% | nd | 17% | 25% | nd | 17% | nd | nd | nd |
| Spec 4 | 71% | nd | 71% | 71% | nd | 71% | nd | nd | nd |
| Cutoff 5 | 227000 | nd | 228000 | 227000 | nd | 228000 | nd | nd | nd |
| Sens 5 | 25% | nd | 17% | 25% | nd | 17% | nd | nd | nd |
| Spec 5 | 80% | nd | 81% | 80% | nd | 81% | nd | nd | nd |
| Cutoff 6 | 272000 | nd | 262000 | 272000 | nd | 262000 | nd | nd | nd |
| Sens 6 | 0% | nd | 0% | 0% | nd | 0% | nd | nd | nd |
| Spec 6 | 91% | nd | 91% | 91% | nd | 91% | nd | nd | nd |
| OR Quart 2 | 0.50 | nd | 0 | 0.50 | nd | 0 | nd | nd | nd |
| p Value | 0.58 | nd | na | 0.58 | nd | na | nd | nd | nd |
| 95% CI of | 0.042 | nd | na | 0.042 | nd | na | nd | nd | nd |
| OR Quart 2 | 5.9 | nd | na | 5.9 | nd | na | nd | nd | nd |
| OR Quart 3 | 1.6 | nd | 3.5 | 1.6 | nd | 3.5 | nd | nd | nd |
| p Value | 0.64 | nd | 0.30 | 0.64 | nd | 0.30 | nd | nd | nd |
| 95% CI of | 0.24 | nd | 0.33 | 0.24 | nd | 0.33 | nd | nd | nd |
| OR Quart 3 | 10 | nd | 37 | 10 | nd | 37 | nd | nd | nd |
| OR Quart 4 | 1.0 | nd | 2.2 | 1.0 | nd | 2.2 | nd | nd | nd |
| p Value | 0.96 | nd | 0.53 | 0.96 | nd | 0.53 | nd | nd | nd |
| 95% CI of | 0.13 | nd | 0.19 | 0.13 | nd | 0.19 | nd | nd | nd |
| OR Quart 4 | 8.1 | nd | 26 | 8.1 | nd | 26 | nd | nd | nd |

-continued

| Platelet-derived growth factor subunit B (dimer) | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 468 | 535 | 468 | 535 | nd | nd |
| Average | 494 | 734 | 494 | 734 | nd | nd |
| Stdev | 267 | 833 | 267 | 833 | nd | nd |
| p (t-test) | | 0.064 | | 0.064 | nd | nd |
| Min | 113 | 91.9 | 113 | 91.9 | nd | nd |
| Max | 1540 | 2720 | 1540 | 2720 | nd | nd |
| n (Samp) | 85 | 8 | 85 | 8 | nd | nd |
| n (Patient) | 85 | 8 | 85 | 8 | nd | nd |
| UO only | | | | | | |
| Median | 438 | 535 | 438 | 535 | nd | nd |
| Average | 463 | 485 | 463 | 485 | nd | nd |
| Stdev | 254 | 247 | 254 | 247 | nd | nd |
| p (t-test) | | 0.83 | | 0.83 | nd | nd |
| Min | 113 | 91.9 | 113 | 91.9 | nd | nd |
| Max | 1540 | 721 | 1540 | 721 | nd | nd |
| n (Samp) | 78 | 6 | 78 | 6 | nd | nd |
| n (Patient) | 78 | 6 | 78 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.55 | nd | 0.58 | 0.55 | nd | 0.58 | nd | nd | nd |
| SE | 0.11 | nd | 0.13 | 0.11 | nd | 0.13 | nd | nd | nd |
| p | 0.65 | nd | 0.52 | 0.65 | nd | 0.52 | nd | nd | nd |
| nCohort 1 | 85 | nd | 78 | 85 | nd | 78 | nd | nd | nd |
| nCohort 2 | 8 | nd | 6 | 8 | nd | 6 | nd | nd | nd |
| Cutoff 1 | 326 | nd | 326 | 326 | nd | 326 | nd | nd | nd |
| Sens 1 | 75% | nd | 83% | 75% | nd | 83% | nd | nd | nd |
| Spec 1 | 34% | nd | 41% | 34% | nd | 41% | nd | nd | nd |
| Cutoff 2 | 238 | nd | 326 | 238 | nd | 326 | nd | nd | nd |
| Sens 2 | 88% | nd | 83% | 88% | nd | 83% | nd | nd | nd |
| Spec 2 | 12% | nd | 41% | 12% | nd | 41% | nd | nd | nd |
| Cutoff 3 | 0 | nd | 0 | 0 | nd | 0 | nd | nd | nd |
| Sens 3 | 100% | nd | 100% | 100% | nd | 100% | nd | nd | nd |
| Spec 3 | 0% | nd | 0% | 0% | nd | 0% | nd | nd | nd |
| Cutoff 4 | 595 | nd | 543 | 595 | nd | 543 | nd | nd | nd |
| Sens 4 | 50% | nd | 50% | 50% | nd | 50% | nd | nd | nd |
| Spec 4 | 71% | nd | 71% | 71% | nd | 71% | nd | nd | nd |
| Cutoff 5 | 660 | nd | 618 | 660 | nd | 618 | nd | nd | nd |
| Sens 5 | 38% | nd | 50% | 38% | nd | 50% | nd | nd | nd |
| Spec 5 | 80% | nd | 81% | 80% | nd | 81% | nd | nd | nd |
| Cutoff 6 | 763 | nd | 747 | 763 | nd | 747 | nd | nd | nd |
| Sens 6 | 12% | nd | 0% | 12% | nd | 0% | nd | nd | nd |
| Spec 6 | 91% | nd | 91% | 91% | nd | 91% | nd | nd | nd |
| OR Quart 2 | 1.0 | nd | 2.1 | 1.0 | nd | 2.1 | nd | nd | nd |
| p Value | 1.0 | nd | 0.56 | 1.0 | nd | 0.56 | nd | nd | nd |
| 95% CI of | 0.13 | nd | 0.18 | 0.13 | nd | 0.18 | nd | nd | nd |
| OR Quart 2 | 7.8 | nd | 25 | 7.8 | nd | 25 | nd | nd | nd |
| OR Quart 3 | 0.48 | nd | 0 | 0.48 | nd | 0 | nd | nd | nd |
| p Value | 0.56 | nd | na | 0.56 | nd | na | nd | nd | nd |
| 95% CI of | 0.040 | nd | na | 0.040 | nd | na | nd | nd | nd |
| OR Quart 3 | 5.7 | nd | na | 5.7 | nd | na | nd | nd | nd |
| OR Quart 4 | 1.5 | nd | 3.3 | 1.5 | nd | 3.3 | nd | nd | nd |
| p Value | 0.67 | nd | 0.32 | 0.67 | nd | 0.32 | nd | nd | nd |
| 95% CI of | 0.23 | nd | 0.32 | 0.23 | nd | 0.32 | nd | nd | nd |
| OR Quart 4 | 9.9 | nd | 35 | 9.9 | nd | 35 | nd | nd | nd |

| Corticotropin | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.00105 | 0.00369 | 0.00105 | 0.00369 | nd | nd |
| Average | 0.00913 | 0.00636 | 0.00913 | 0.00636 | nd | nd |

-continued

|  | | | | | | |
|---|---|---|---|---|---|---|
| Stdev | 0.0411 | 0.00856 | 0.0411 | 0.00856 | nd | nd |
| p (t-test) |  | 0.86 |  | 0.86 | nd | nd |
| Min | 3.38E−6 | 3.38E−6 | 3.38E−6 | 3.38E−6 | nd | nd |
| Max | 0.292 | 0.0245 | 0.292 | 0.0245 | nd | nd |
| n (Samp) | 75 | 7 | 75 | 7 | nd | nd |
| n (Patient) | 75 | 7 | 75 | 7 | nd | nd |
| UO only |  |  |  |  |  |  |
| Median | 0.00140 | 0.00367 | 0.00140 | 0.00367 | nd | nd |
| Average | 0.0109 | 0.00681 | 0.0109 | 0.00681 | nd | nd |
| Stdev | 0.0444 | 0.00929 | 0.0444 | 0.00929 | nd | nd |
| p (t-test) |  | 0.82 |  | 0.82 | nd | nd |
| Min | 4.31E−6 | 3.38E−6 | 4.31E−6 | 3.38E−6 | nd | nd |
| Max | 0.292 | 0.0245 | 0.292 | 0.0245 | nd | nd |
| n (Samp) | 64 | 6 | 64 | 6 | nd | nd |
| n (Patient) | 64 | 6 | 64 | 6 | nd | nd |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.65 | nd | 0.59 | 0.65 | nd | 0.59 | nd | nd | nd |
| SE | 0.12 | nd | 0.13 | 0.12 | nd | 0.13 | nd | nd | nd |
| p | 0.21 | nd | 0.49 | 0.21 | nd | 0.49 | nd | nd | nd |
| nCohort 1 | 75 | nd | 64 | 75 | nd | 64 | nd | nd | nd |
| nCohort 2 | 7 | nd | 6 | 7 | nd | 6 | nd | nd | nd |
| Cutoff 1 | 0.00170 | nd | 0.000278 | 0.00170 | nd | 0.000278 | nd | nd | nd |
| Sens 1 | 71% | nd | 83% | 71% | nd | 83% | nd | nd | nd |
| Spec 1 | 64% | nd | 30% | 64% | nd | 30% | nd | nd | nd |
| Cutoff 2 | 0.000278 | nd | 0.000278 | 0.000278 | nd | 0.000278 | nd | nd | nd |
| Sens 2 | 86% | nd | 83% | 86% | nd | 83% | nd | nd | nd |
| Spec 2 | 36% | nd | 30% | 36% | nd | 30% | nd | nd | nd |
| Cutoff 3 | 0 | nd | 0 | 0 | nd | 0 | nd | nd | nd |
| Sens 3 | 100% | nd | 100% | 100% | nd | 100% | nd | nd | nd |
| Spec 3 | 0% | nd | 0% | 0% | nd | 0% | nd | nd | nd |
| Cutoff 4 | 0.00297 | nd | 0.00345 | 0.00297 | nd | 0.00345 | nd | nd | nd |
| Sens 4 | 57% | nd | 50% | 57% | nd | 50% | nd | nd | nd |
| Spec 4 | 71% | nd | 70% | 71% | nd | 70% | nd | nd | nd |
| Cutoff 5 | 0.00423 | nd | 0.00550 | 0.00423 | nd | 0.00550 | nd | nd | nd |
| Sens 5 | 43% | nd | 33% | 43% | nd | 33% | nd | nd | nd |
| Spec 5 | 81% | nd | 81% | 81% | nd | 81% | nd | nd | nd |
| Cutoff 6 | 0.00767 | nd | 0.00859 | 0.00767 | nd | 0.00859 | nd | nd | nd |
| Sens 6 | 29% | nd | 33% | 29% | nd | 33% | nd | nd | nd |
| Spec 6 | 91% | nd | 91% | 91% | nd | 91% | nd | nd | nd |
| OR Quart 2 | 0.95 | nd | 0.94 | 0.95 | nd | 0.94 | nd | nd | nd |
| p Value | 0.97 | nd | 0.97 | 0.97 | nd | 0.97 | nd | nd | nd |
| 95% CI of OR Quart 2 | 0.055 16 | nd nd | 0.054 16 | 0.055 16 | nd nd | 0.054 16 | nd nd | nd nd | nd nd |
| OR Quart 3 | 2.1 | nd | 1.0 | 2.1 | nd | 1.0 | nd | nd | nd |
| p Value | 0.56 | nd | 1.0 | 0.56 | nd | 1.0 | nd | nd | nd |
| 95% CI of OR Quart 3 | 0.18 25 | nd nd | 0.057 17 | 0.18 25 | nd nd | 0.057 17 | nd nd | nd nd | nd nd |
| OR Quart 4 | 3.2 | nd | 3.2 | 3.2 | nd | 3.2 | nd | nd | nd |
| p Value | 0.34 | nd | 0.34 | 0.34 | nd | 0.34 | nd | nd | nd |
| 95% CI of OR Quart 4 | 0.30 33 | nd nd | 0.30 34 | 0.30 33 | nd nd | 0.30 34 | nd nd | nd nd | nd nd |

Thyroxine-binding globulin

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO |  |  |  |  |  |  |
| Median | 43.7 | 29.2 | 43.7 | 28.6 | 43.7 | 42.5 |
| Average | 42.7 | 35.2 | 42.7 | 34.5 | 42.7 | 42.1 |
| Stdev | 12.2 | 13.1 | 12.2 | 13.5 | 12.2 | 14.0 |
| p (t-test) |  | 0.029 |  | 0.017 |  | 0.89 |
| Min | 15.5 | 21.0 | 15.5 | 21.0 | 15.5 | 24.8 |
| Max | 75.8 | 63.7 | 75.8 | 63.7 | 75.8 | 62.0 |
| n (Samp) | 110 | 15 | 110 | 15 | 110 | 8 |
| n (Patient) | 110 | 15 | 110 | 15 | 110 | 8 |
| sCr only |  |  |  |  |  |  |
| Median | 39.3 | 30.1 | 39.3 | 28.6 | nd | nd |
| Average | 41.1 | 40.0 | 41.1 | 38.9 | nd | nd |
| Stdev | 12.1 | 16.1 | 12.1 | 17.1 | nd | nd |

|  |  |  |  |  |  |  |
|---|---|---|---|---|---|---|
| p (t-test) |  | 0.82 |  | 0.65 | nd | nd |
| Min | 14.2 | 23.4 | 14.2 | 22.3 | nd | nd |
| Max | 75.8 | 63.7 | 75.8 | 63.7 | nd | nd |
| n (Samp) | 180 | 7 | 180 | 7 | nd | nd |
| n (Patient) | 180 | 7 | 180 | 7 | nd | nd |
| UO only |  |  |  |  |  |  |
| Median | 43.5 | 28.8 | 43.5 | 28.8 | 43.5 | 32.6 |
| Average | 41.9 | 33.2 | 41.9 | 33.0 | 41.9 | 37.5 |
| Stdev | 11.8 | 11.2 | 11.8 | 11.3 | 11.8 | 12.6 |
| p (t-test) |  | 0.030 |  | 0.026 |  | 0.39 |
| Min | 20.4 | 21.0 | 20.4 | 21.0 | 20.4 | 24.8 |
| Max | 75.8 | 56.1 | 75.8 | 56.1 | 75.8 | 56.1 |
| n (Samp) | 91 | 10 | 91 | 10 | 91 | 6 |
| n (Patient) | 91 | 10 | 91 | 10 | 91 | 6 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.31 | 0.45 | 0.29 | 0.30 | 0.43 | 0.28 | 0.50 | nd | 0.41 |
| SE | 0.080 | 0.11 | 0.095 | 0.079 | 0.11 | 0.095 | 0.11 | nd | 0.13 |
| p | 0.018 | 0.66 | 0.024 | 0.011 | 0.54 | 0.021 | 1.00 | nd | 0.45 |
| nCohort 1 | 110 | 180 | 91 | 110 | 180 | 91 | 110 | nd | 91 |
| nCohort 2 | 15 | 7 | 10 | 15 | 7 | 10 | 8 | nd | 6 |
| Cutoff 1 | 27.9 | 28.5 | 27.9 | 26.5 | 28.2 | 27.4 | 29.2 | nd | 29.1 |
| Sens 1 | 73% | 71% | 70% | 73% | 71% | 70% | 75% | nd | 83% |
| Spec 1 | 11% | 14% | 13% | 8% | 13% | 11% | 15% | nd | 18% |
| Cutoff 2 | 27.4 | 28.2 | 27.4 | 23.7 | 23.3 | 26.8 | 29.1 | nd | 29.1 |
| Sens 2 | 80% | 86% | 80% | 80% | 86% | 80% | 88% | nd | 83% |
| Spec 2 | 9% | 13% | 11% | 5% | 7% | 10% | 15% | nd | 18% |
| Cutoff 3 | 23.3 | 23.3 | 24.6 | 21.0 | 21.0 | 24.6 | 23.7 | nd | 24.6 |
| Sens 3 | 93% | 100% | 90% | 93% | 100% | 90% | 100% | nd | 100% |
| Spec 3 | 5% | 7% | 7% | 2% | 4% | 7% | 5% | nd | 7% |
| Cutoff 4 | 48.0 | 47.1 | 47.2 | 48.0 | 47.1 | 47.2 | 48.0 | nd | 47.2 |
| Sens 4 | 27% | 43% | 20% | 27% | 43% | 20% | 50% | nd | 33% |
| Spec 4 | 70% | 70% | 70% | 70% | 70% | 70% | 70% | nd | 70% |
| Cutoff 5 | 52.3 | 50.1 | 50.4 | 52.3 | 50.1 | 50.4 | 52.3 | nd | 50.4 |
| Sens 5 | 13% | 29% | 10% | 13% | 29% | 10% | 25% | nd | 17% |
| Spec 5 | 80% | 80% | 80% | 80% | 80% | 80% | 80% | nd | 80% |
| Cutoff 6 | 57.6 | 56.1 | 55.2 | 57.6 | 56.1 | 55.2 | 57.6 | nd | 55.2 |
| Sens 6 | 7% | 14% | 10% | 7% | 14% | 10% | 12% | nd | 17% |
| Spec 6 | 90% | 90% | 90% | 90% | 90% | 90% | 90% | nd | 90% |
| OR Quart 2 | 0 | 0 | 0 | 0 | 0 | 0 | 0.32 | nd | 0 |
| p Value | na | na | na | na | na | na | 0.34 | nd | na |
| 95% CI of | na | na | na | na | na | na | 0.031 | nd | na |
| OR Quart 2 | na | na | na | na | na | na | 3.3 | nd | na |
| OR Quart 3 | 0.23 | 0 | 0.50 | 0.23 | 0 | 0.50 | 0.31 | nd | 0.50 |
| p Value | 0.21 | na | 0.58 | 0.21 | na | 0.58 | 0.32 | nd | 0.58 |
| 95% CI of | 0.025 | na | 0.042 | 0.025 | na | 0.042 | 0.030 | nd | 0.042 |
| OR Quart 3 | 2.2 | na | 5.9 | 2.2 | na | 5.9 | 3.2 | nd | 5.9 |
| OR Quart 4 | 3.3 | 1.4 | 4.7 | 3.3 | 1.4 | 4.7 | 1.0 | nd | 1.6 |
| p Value | 0.067 | 0.67 | 0.073 | 0.067 | 0.67 | 0.073 | 0.97 | nd | 0.61 |
| 95% CI of | 0.92 | 0.29 | 0.86 | 0.92 | 0.29 | 0.86 | 0.19 | nd | 0.25 |
| OR Quart 4 | 12 | 6.6 | 25 | 12 | 6.6 | 25 | 5.6 | nd | 11 |

| Pigment epithelium-derived factor | | | | | |
|---|---|---|---|---|---|
| 0 hr prior to AKI stage | | 24 hr prior to AKI stage | | 48 hr prior to AKI stage | |
| Cohort 1 | Cohort 2 | Cohort 1 | Cohort 2 | Cohort 1 | Cohort 2 |

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO |  |  |  |  |  |  |
| Median | 1670 | 1590 | 1670 | 1590 | nd | nd |
| Average | 1710 | 1630 | 1710 | 1590 | nd | nd |
| Stdev | 774 | 749 | 774 | 788 | nd | nd |
| p (t-test) |  | 0.78 |  | 0.67 | nd | nd |
| Min | 445 | 339 | 445 | 339 | nd | nd |
| Max | 4240 | 2850 | 4240 | 2850 | nd | nd |
| n (Samp) | 87 | 8 | 87 | 8 | nd | nd |
| n (Patient) | 87 | 8 | 87 | 8 | nd | nd |
| UO only |  |  |  |  |  |  |
| Median | 1620 | 1850 | 1620 | 1850 | nd | nd |
| Average | 1760 | 1720 | 1760 | 1720 | nd | nd |
| Stdev | 841 | 855 | 841 | 855 | nd | nd |
| p (t-test) |  | 0.93 |  | 0.93 | nd | nd |

-continued

|  | | | | | | |
|---|---|---|---|---|---|---|
| Min | 445 | 339 | 445 | 339 | nd | nd |
| Max | 4510 | 2850 | 4510 | 2850 | nd | nd |
| n (Samp) | 80 | 6 | 80 | 6 | nd | nd |
| n (Patient) | 80 | 6 | 80 | 6 | nd | nd |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.50 | nd | 0.53 | 0.48 | nd | 0.53 | nd | nd | nd |
| SE | 0.11 | nd | 0.12 | 0.11 | nd | 0.12 | nd | nd | nd |
| p | 0.99 | nd | 0.82 | 0.82 | nd | 0.82 | nd | nd | nd |
| nCohort 1 | 87 | nd | 80 | 87 | nd | 80 | nd | nd | nd |
| nCohort 2 | 8 | nd | 6 | 8 | nd | 6 | nd | nd | nd |
| Cutoff 1 | 1280 | nd | 1280 | 1280 | nd | 1280 | nd | nd | nd |
| Sens 1 | 75% | nd | 83% | 75% | nd | 83% | nd | nd | nd |
| Spec 1 | 37% | nd | 34% | 37% | nd | 34% | nd | nd | nd |
| Cutoff 2 | 1170 | nd | 1280 | 756 | nd | 1280 | nd | nd | nd |
| Sens 2 | 88% | nd | 83% | 88% | nd | 83% | nd | nd | nd |
| Spec 2 | 30% | nd | 34% | 9% | nd | 34% | nd | nd | nd |
| Cutoff 3 | 0 | nd | 0 | 0 | nd | 0 | nd | nd | nd |
| Sens 3 | 100% | nd | 100% | 100% | nd | 100% | nd | nd | nd |
| Spec 3 | 0% | nd | 0% | 0% | nd | 0% | nd | nd | nd |
| Cutoff 4 | 2020 | nd | 2030 | 2020 | nd | 2030 | nd | nd | nd |
| Sens 4 | 38% | nd | 50% | 38% | nd | 50% | nd | nd | nd |
| Spec 4 | 70% | nd | 70% | 70% | nd | 70% | nd | nd | nd |
| Cutoff 5 | 2350 | nd | 2350 | 2350 | nd | 2350 | nd | nd | nd |
| Sens 5 | 12% | nd | 17% | 12% | nd | 17% | nd | nd | nd |
| Spec 5 | 80% | nd | 80% | 80% | nd | 80% | nd | nd | nd |
| Cutoff 6 | 2830 | nd | 2880 | 2830 | nd | 2880 | nd | nd | nd |
| Sens 6 | 12% | nd | 0% | 12% | nd | 0% | nd | nd | nd |
| Spec 6 | 91% | nd | 91% | 91% | nd | 91% | nd | nd | nd |
| OR Quart 2 | 3.1 | nd | 0.95 | 3.3 | nd | 0.95 | nd | nd | nd |
| p Value | 0.34 | nd | 0.97 | 0.32 | nd | 0.97 | nd | nd | nd |
| 95% CI of | 0.30 | nd | 0.056 | 0.32 | nd | 0.056 | nd | nd | nd |
| OR Quart 2 | 33 | nd | 16 | 34 | nd | 16 | nd | nd | nd |
| OR Quart 3 | 3.1 | nd | 3.3 | 2.1 | nd | 3.3 | nd | nd | nd |
| p Value | 0.34 | nd | 0.32 | 0.56 | nd | 0.32 | nd | nd | nd |
| 95% CI of | 0.30 | nd | 0.32 | 0.18 | nd | 0.32 | nd | nd | nd |
| OR Quart 3 | 33 | nd | 35 | 25 | nd | 35 | nd | nd | nd |
| OR Quart 4 | 0.96 | nd | 0.95 | 2.2 | nd | 0.95 | nd | nd | nd |
| p Value | 0.98 | nd | 0.97 | 0.53 | nd | 0.97 | nd | nd | nd |
| 95% CI of | 0.056 | nd | 0.056 | 0.18 | nd | 0.056 | nd | nd | nd |
| OR Quart 4 | 16 | nd | 16 | 26 | nd | 16 | nd | nd | nd |

Tumor necrosis factor receptor superfamily member 8

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 104 | 107 | 104 | 107 | 104 | 93.1 |
| Average | 226 | 271 | 226 | 268 | 226 | 166 |
| Stdev | 549 | 403 | 549 | 404 | 549 | 192 |
| p (t-test) |  | 0.78 |  | 0.80 |  | 0.78 |
| Min | 26.3 | 50.0 | 26.3 | 50.0 | 26.3 | 50.0 |
| Max | 3360 | 1460 | 3360 | 1460 | 3360 | 595 |
| n (Samp) | 65 | 12 | 65 | 12 | 65 | 7 |
| n (Patient) | 65 | 12 | 65 | 12 | 65 | 7 |
| sCr only | | | | | | |
| Median | 117 | 100 | 117 | 94.1 | nd | nd |
| Average | 236 | 107 | 236 | 101 | nd | nd |
| Stdev | 507 | 26.7 | 507 | 33.0 | nd | nd |
| p (t-test) |  | 0.54 |  | 0.52 | nd | nd |
| Min | 26.3 | 82.5 | 26.3 | 60.0 | nd | nd |
| Max | 3360 | 152 | 3360 | 152 | nd | nd |
| n (Samp) | 132 | 6 | 132 | 6 | nd | nd |
| n (Patient) | 132 | 6 | 132 | 6 | nd | nd |
| UO only | | | | | | |
| Median | 115 | 107 | 115 | 107 | 115 | 98.7 |
| Average | 260 | 350 | 260 | 350 | 260 | 180 |
| Stdev | 575 | 483 | 575 | 483 | 575 | 206 |
| p (t-test) |  | 0.67 |  | 0.67 |  | 0.74 |
| Min | 30.2 | 50.0 | 30.2 | 50.0 | 30.2 | 50.0 |

|  | | | | | | | | | |
|---|---|---|---|---|---|---|---|---|---|
| Max | 3360 | 1460 | | 3360 | 1460 | | 3360 | | 595 |
| n (Samp) | 64 | 8 | | 64 | 8 | | 64 | | 6 |
| n (Patient) | 64 | 8 | | 64 | 8 | | 64 | | 6 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.56 | 0.42 | 0.56 | 0.54 | 0.38 | 0.56 | 0.48 | nd | 0.46 |
| SE | 0.093 | 0.12 | 0.11 | 0.093 | 0.12 | 0.11 | 0.12 | nd | 0.13 |
| p | 0.49 | 0.54 | 0.62 | 0.66 | 0.34 | 0.62 | 0.86 | nd | 0.78 |
| nCohort 1 | 65 | 132 | 64 | 65 | 132 | 64 | 65 | nd | 64 |
| nCohort 2 | 12 | 6 | 8 | 12 | 6 | 8 | 7 | nd | 6 |
| Cutoff 1 | 89.9 | 83.2 | 89.9 | 83.2 | 75.6 | 89.9 | 83.2 | nd | 83.2 |
| Sens 1 | 75% | 83% | 75% | 75% | 83% | 75% | 71% | nd | 83% |
| Spec 1 | 40% | 28% | 34% | 34% | 27% | 34% | 34% | nd | 28% |
| Cutoff 2 | 83.2 | 83.2 | 83.2 | 75.6 | 75.6 | 83.2 | 75.6 | nd | 83.2 |
| Sens 2 | 83% | 83% | 88% | 83% | 83% | 88% | 86% | nd | 83% |
| Spec 2 | 34% | 28% | 28% | 32% | 27% | 28% | 32% | nd | 28% |
| Cutoff 3 | 75.6 | 75.6 | 43.9 | 56.2 | 56.6 | 43.9 | 47.2 | nd | 43.9 |
| Sens 3 | 92% | 100% | 100% | 92% | 100% | 100% | 100% | nd | 100% |
| Spec 3 | 32% | 27% | 9% | 14% | 11% | 9% | 12% | nd | 9% |
| Cutoff 4 | 165 | 167 | 167 | 165 | 167 | 167 | 165 | nd | 167 |
| Sens 4 | 25% | 0% | 38% | 25% | 0% | 38% | 14% | nd | 17% |
| Spec 4 | 71% | 70% | 70% | 71% | 70% | 70% | 71% | nd | 70% |
| Cutoff 5 | 205 | 217 | 217 | 205 | 217 | 217 | 205 | nd | 217 |
| Sens 5 | 25% | 0% | 38% | 25% | 0% | 38% | 14% | nd | 17% |
| Spec 5 | 82% | 80% | 81% | 82% | 80% | 81% | 82% | nd | 81% |
| Cutoff 6 | 292 | 310 | 323 | 292 | 310 | 323 | 292 | nd | 323 |
| Sens 6 | 25% | 0% | 25% | 25% | 0% | 25% | 14% | nd | 17% |
| Spec 6 | 91% | 90% | 91% | 91% | 90% | 91% | 91% | nd | 91% |
| OR Quart 2 | 4.8 | >2.2 | 4.9 | 1.6 | >2.2 | 4.9 | 2.1 | nd | 1.1 |
| p Value | 0.18 | <0.53 | 0.18 | 0.63 | <0.53 | 0.18 | 0.55 | nd | 0.97 |
| 95% CI of | 0.48 | >0.19 | 0.49 | 0.23 | >0.19 | 0.49 | 0.18 | nd | 0.061 |
| OR Quart 2 | 48 | na | 49 | 11 | na | 49 | 26 | nd | 18 |
| OR Quart 3 | 4.8 | >4.5 | 0 | 2.3 | >3.3 | 0 | 3.4 | nd | 3.4 |
| p Value | 0.18 | <0.19 | na | 0.38 | <0.31 | na | 0.31 | nd | 0.31 |
| 95% CI of | 0.48 | >0.48 | na | 0.36 | >0.32 | na | 0.32 | nd | 0.32 |
| OR Quart 3 | 48 | na | na | 14 | na | na | 36 | nd | 36 |
| OR Quart 4 | 3.2 | >0 | 3.4 | 1.5 | >1.1 | 3.4 | 1.0 | nd | 1.1 |
| p Value | 0.34 | <na | 0.31 | 0.68 | <0.97 | 0.31 | 1.0 | nd | 0.97 |
| 95% CI of | 0.30 | >na | 0.32 | 0.22 | >0.064 | 0.32 | 0.058 | nd | 0.061 |
| OR Quart 4 | 34 | na | 36 | 10 | na | 36 | 17 | nd | 18 |

Alpha-fetoprotein

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 0.381 | 0.719 | 0.381 | 0.719 | nd | nd |
| Average | 0.450 | 0.803 | 0.450 | 0.803 | nd | nd |
| Stdev | 0.361 | 0.466 | 0.361 | 0.466 | nd | nd |
| p (t-test) | | 0.011 | | 0.011 | nd | nd |
| Min | 0.00580 | 0.00880 | 0.00580 | 0.00880 | nd | nd |
| Max | 1.81 | 1.53 | 1.81 | 1.53 | nd | nd |
| n (Samp) | 87 | 8 | 87 | 8 | nd | nd |
| n (Patient) | 87 | 8 | 87 | 8 | nd | nd |
| UO only | | | | | | |
| Median | 0.382 | 0.719 | 0.382 | 0.719 | nd | nd |
| Average | 0.449 | 0.851 | 0.449 | 0.851 | nd | nd |
| Stdev | 0.372 | 0.351 | 0.372 | 0.351 | nd | nd |
| p (t-test) | | 0.012 | | 0.012 | nd | nd |
| Min | 0.00580 | 0.583 | 0.00580 | 0.583 | nd | nd |
| Max | 1.81 | 1.53 | 1.81 | 1.53 | nd | nd |
| n (Samp) | 80 | 6 | 80 | 6 | nd | nd |
| n (Patient) | 80 | 6 | 80 | 6 | nd | nd |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.76 | nd | 0.82 | 0.76 | nd | 0.82 | nd | nd | nd |
| SE | 0.10 | nd | 0.11 | 0.10 | nd | 0.11 | nd | nd | nd |
| p | 0.011 | nd | 0.0024 | 0.011 | nd | 0.0024 | nd | nd | nd |

-continued

| | | | | | | | | | |
|---|---|---|---|---|---|---|---|---|---|
| nCohort 1 | 87 | nd | 80 | 87 | nd | 80 | nd | nd | nd |
| nCohort 2 | 8 | nd | 6 | 8 | nd | 6 | nd | nd | nd |
| Cutoff 1 | 0.620 | nd | 0.620 | 0.620 | nd | 0.620 | nd | nd | nd |
| Sens 1 | 75% | nd | 83% | 75% | nd | 83% | nd | nd | nd |
| Spec 1 | 78% | nd | 76% | 78% | nd | 76% | nd | nd | nd |
| Cutoff 2 | 0.558 | nd | 0.620 | 0.558 | nd | 0.620 | nd | nd | nd |
| Sens 2 | 88% | nd | 83% | 88% | nd | 83% | nd | nd | nd |
| Spec 2 | 74% | nd | 76% | 74% | nd | 76% | nd | nd | nd |
| Cutoff 3 | 0.00580 | nd | 0.558 | 0.00580 | nd | 0.558 | nd | nd | nd |
| Sens 3 | 100% | nd | 100% | 100% | nd | 100% | nd | nd | nd |
| Spec 3 | 2% | nd | 71% | 2% | nd | 71% | nd | nd | nd |
| Cutoff 4 | 0.541 | nd | 0.558 | 0.541 | nd | 0.558 | nd | nd | nd |
| Sens 4 | 88% | nd | 100% | 88% | nd | 100% | nd | nd | nd |
| Spec 4 | 70% | nd | 71% | 70% | nd | 71% | nd | nd | nd |
| Cutoff 5 | 0.705 | nd | 0.741 | 0.705 | nd | 0.741 | nd | nd | nd |
| Sens 5 | 50% | nd | 33% | 50% | nd | 33% | nd | nd | nd |
| Spec 5 | 80% | nd | 80% | 80% | nd | 80% | nd | nd | nd |
| Cutoff 6 | 0.891 | nd | 0.891 | 0.891 | nd | 0.891 | nd | nd | nd |
| Sens 6 | 38% | nd | 33% | 38% | nd | 33% | nd | nd | nd |
| Spec 6 | 91% | nd | 90% | 91% | nd | 90% | nd | nd | nd |
| OR Quart 2 | 0 | nd | >0 | 0 | nd | >0 | nd | nd | nd |
| p Value | na | nd | <na | na | nd | <na | nd | nd | nd |
| 95% CI of | na | nd | >na | na | nd | >na | nd | nd | nd |
| OR Quart 2 | na | nd | na | na | nd | na | nd | nd | nd |
| OR Quart 3 | 2.0 | nd | >2.2 | 2.0 | nd | >2.2 | nd | nd | nd |
| p Value | 0.58 | nd | <0.53 | 0.58 | nd | <0.53 | nd | nd | nd |
| 95% CI of | 0.17 | nd | >0.19 | 0.17 | nd | >0.19 | nd | nd | nd |
| OR Quart 3 | 24 | nd | na | 24 | nd | na | nd | nd | nd |
| OR Quart 4 | 5.8 | nd | >4.7 | 5.8 | nd | >4.7 | nd | nd | nd |
| p Value | 0.12 | nd | <0.19 | 0.12 | nd | <0.19 | nd | nd | nd |
| 95% CI of | 0.62 | nd | >0.48 | 0.62 | nd | >0.48 | nd | nd | nd |
| OR Quart 4 | 54 | nd | na | 54 | nd | na | nd | nd | nd |

Apolipoprotein E

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 55900 | 45300 | 55900 | 44900 | 55900 | 42800 |
| Average | 67400 | 45200 | 67400 | 44600 | 67400 | 40300 |
| Stdev | 48000 | 9980 | 48000 | 11000 | 48000 | 10100 |
| p (t-test) | | 0.11 | | 0.12 | | 0.14 |
| Min | 8630 | 29200 | 8630 | 25800 | 8630 | 22400 |
| Max | 260000 | 59600 | 260000 | 59600 | 260000 | 52300 |
| n (Samp) | 111 | 12 | 111 | 11 | 111 | 7 |
| n (Patient) | 111 | 12 | 111 | 11 | 111 | 7 |
| sCr only | | | | | | |
| Median | 56700 | 46700 | nd | nd | nd | nd |
| Average | 69900 | 47000 | nd | nd | nd | nd |
| Stdev | 49700 | 10900 | nd | nd | nd | nd |
| p (t-test) | | 0.26 | nd | nd | nd | nd |
| Min | 8630 | 29200 | nd | nd | nd | nd |
| Max | 260000 | 59600 | nd | nd | nd | nd |
| n (Samp) | 193 | 6 | nd | nd | nd | nd |
| n (Patient) | 193 | 6 | nd | nd | nd | nd |
| UO only | | | | | | |
| Median | 56300 | 43900 | 56300 | 42800 | 56300 | 42800 |
| Average | 67500 | 43800 | 67500 | 41100 | 67500 | 39400 |
| Stdev | 43600 | 8230 | 43600 | 10200 | 43600 | 10700 |
| p (t-test) | | 0.13 | | 0.091 | | 0.12 |
| Min | 8630 | 31000 | 8630 | 25800 | 8630 | 22400 |
| Max | 218000 | 54900 | 218000 | 54900 | 218000 | 52300 |
| n (Samp) | 103 | 8 | 103 | 8 | 103 | 6 |
| n (Patient) | 103 | 8 | 103 | 8 | 103 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.38 | 0.38 | 0.34 | 0.36 | nd | 0.30 | 0.32 | nd | 0.28 |
| SE | 0.090 | 0.12 | 0.11 | 0.094 | nd | 0.11 | 0.11 | nd | 0.12 |
| p | 0.17 | 0.34 | 0.14 | 0.15 | nd | 0.066 | 0.11 | nd | 0.074 |
| nCohort 1 | 111 | 193 | 103 | 111 | nd | 103 | 111 | nd | 103 |

| | | | | | | | | | |
|---|---|---|---|---|---|---|---|---|---|
| nCohort 2 | 12 | 6 | 8 | 11 | nd | 8 | 7 | nd | 6 |
| Cutoff 1 | 41000 | 41900 | 41000 | 41000 | nd | 33100 | 41000 | nd | 30600 |
| Sens 1 | 75% | 83% | 75% | 73% | nd | 75% | 71% | nd | 83% |
| Spec 1 | 34% | 32% | 33% | 34% | nd | 22% | 34% | nd | 17% |
| Cutoff 2 | 33100 | 41900 | 33100 | 33100 | nd | 30600 | 30600 | nd | 30600 |
| Sens 2 | 83% | 83% | 88% | 82% | nd | 88% | 86% | nd | 83% |
| Spec 2 | 23% | 32% | 22% | 23% | nd | 17% | 19% | nd | 17% |
| Cutoff 3 | 30600 | 28800 | 30600 | 30600 | nd | 25400 | 19800 | nd | 19800 |
| Sens 3 | 92% | 100% | 100% | 91% | nd | 100% | 100% | nd | 100% |
| Spec 3 | 19% | 17% | 17% | 19% | nd | 11% | 7% | nd | 8% |
| Cutoff 4 | 76700 | 79500 | 79500 | 76700 | nd | 79500 | 76700 | nd | 79500 |
| Sens 4 | 0% | 0% | 0% | 0% | nd | 0% | 0% | nd | 0% |
| Spec 4 | 71% | 70% | 72% | 71% | nd | 72% | 71% | nd | 72% |
| Cutoff 5 | 89800 | 93400 | 94900 | 89800 | nd | 94900 | 89800 | nd | 94900 |
| Sens 5 | 0% | 0% | 0% | 0% | nd | 0% | 0% | nd | 0% |
| Spec 5 | 80% | 80% | 81% | 80% | nd | 81% | 80% | nd | 81% |
| Cutoff 6 | 131000 | 139000 | 120000 | 131000 | nd | 120000 | 131000 | nd | 120000 |
| Sens 6 | 0% | 0% | 0% | 0% | nd | 0% | 0% | nd | 0% |
| Spec 6 | 90% | 90% | 90% | 90% | nd | 90% | 90% | nd | 90% |
| OR Quart 2 | >3.3 | >2.1 | >1.0 | >3.4 | nd | >1.0 | >0 | nd | >0 |
| p Value | <0.31 | <0.55 | <0.98 | <0.30 | nd | <0.98 | <na | nd | <na |
| 95% CI of | >0.33 | >0.18 | >0.062 | >0.34 | nd | >0.062 | >na | nd | >na |
| OR Quart 2 | na | na | na | na | nd | na | na | nd | na |
| OR Quart 3 | >7.4 | >3.2 | >6.1 | >6.0 | nd | >4.7 | >6.0 | nd | >4.9 |
| p Value | <0.071 | <0.32 | <0.11 | <0.11 | nd | <0.18 | <0.11 | nd | <0.17 |
| 95% CI of | >0.84 | >0.32 | >0.66 | >0.65 | nd | >0.49 | >0.66 | nd | >0.51 |
| OR Quart 3 | na | na | na | na | nd | na | na | nd | na |
| OR Quart 4 | >3.4 | >1.0 | >2.2 | >3.4 | nd | >3.5 | >2.2 | nd | >2.2 |
| p Value | <0.30 | <0.98 | <0.52 | <0.30 | nd | <0.29 | <0.52 | nd | <0.52 |
| 95% CI of | >0.34 | >0.063 | >0.19 | >0.34 | nd | >0.34 | >0.19 | nd | >0.19 |
| OR Quart 4 | na | na | na | na | nd | na | na | nd | na |

| | Apolipoprotein(a) | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 51300 | 43600 | 51300 | 44500 | 51300 | 94400 |
| Average | 81000 | 62200 | 81000 | 65900 | 81000 | 78300 |
| Stdev | 104000 | 61300 | 104000 | 62900 | 104000 | 47500 |
| p (t-test) | | 0.54 | | 0.64 | | 0.95 |
| Min | 7.99 | 968 | 7.99 | 968 | 7.99 | 2260 |
| Max | 631000 | 200000 | 631000 | 200000 | 631000 | 125000 |
| n (Samp) | 111 | 12 | 111 | 11 | 111 | 7 |
| n (Patient) | 111 | 12 | 111 | 11 | 111 | 7 |
| sCr only | | | | | | |
| Median | 47400 | 43600 | nd | nd | nd | nd |
| Average | 84900 | 45900 | nd | nd | nd | nd |
| Stdev | 109000 | 33900 | nd | nd | nd | nd |
| p (t-test) | | 0.38 | nd | nd | nd | nd |
| Min | 7.99 | 968 | nd | nd | nd | nd |
| Max | 631000 | 94400 | nd | nd | nd | nd |
| n (Samp) | 193 | 6 | nd | nd | nd | nd |
| n (Patient) | 193 | 6 | nd | nd | nd | nd |
| UO only | | | | | | |
| Median | 54000 | 68600 | 54000 | 68600 | 54000 | 104000 |
| Average | 81600 | 76000 | 81600 | 75900 | 81600 | 79300 |
| Stdev | 103000 | 69600 | 103000 | 69700 | 103000 | 52000 |
| p (t-test) | | 0.88 | | 0.88 | | 0.96 |
| Min | 7.99 | 2260 | 7.99 | 2260 | 7.99 | 2260 |
| Max | 631000 | 200000 | 631000 | 200000 | 631000 | 125000 |
| n (Samp) | 103 | 8 | 103 | 8 | 103 | 6 |
| n (Patient) | 103 | 8 | 103 | 8 | 103 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.47 | 0.45 | 0.52 | 0.49 | nd | 0.51 | 0.60 | nd | 0.59 |
| SE | 0.089 | 0.12 | 0.11 | 0.092 | nd | 0.11 | 0.12 | nd | 0.13 |
| p | 0.76 | 0.68 | 0.88 | 0.88 | nd | 0.89 | 0.38 | nd | 0.49 |
| nCohort 1 | 111 | 193 | 103 | 111 | nd | 103 | 111 | nd | 103 |
| nCohort 2 | 12 | 6 | 8 | 11 | nd | 8 | 7 | nd | 6 |

-continued

| | | | | | | | | | |
|---|---|---|---|---|---|---|---|---|---|
| Cutoff 1 | 18200 | 18800 | 26200 | 25100 | nd | 25100 | 69900 | nd | 25100 |
| Sens 1 | 75% | 83% | 75% | 73% | nd | 75% | 71% | nd | 83% |
| Spec 1 | 31% | 33% | 37% | 37% | nd | 36% | 66% | nd | 36% |
| Cutoff 2 | 2260 | 18800 | 2260 | 2260 | nd | 2260 | 25100 | nd | 25100 |
| Sens 2 | 83% | 83% | 88% | 82% | nd | 88% | 86% | nd | 83% |
| Spec 2 | 7% | 33% | 5% | 7% | nd | 5% | 37% | nd | 36% |
| Cutoff 3 | 1680 | 814 | 1680 | 1680 | nd | 1680 | 1680 | nd | 1680 |
| Sens 3 | 92% | 100% | 100% | 91% | nd | 100% | 100% | nd | 100% |
| Spec 3 | 7% | 3% | 5% | 7% | nd | 5% | 7% | nd | 5% |
| Cutoff 4 | 80900 | 85400 | 85400 | 80900 | nd | 85400 | 80900 | nd | 85400 |
| Sens 4 | 33% | 17% | 50% | 36% | nd | 50% | 57% | nd | 67% |
| Spec 4 | 70% | 70% | 71% | 70% | nd | 71% | 70% | nd | 71% |
| Cutoff 5 | 128000 | 129000 | 128000 | 128000 | nd | 128000 | 128000 | nd | 128000 |
| Sens 5 | 8% | 0% | 12% | 9% | nd | 12% | 0% | nd | 0% |
| Spec 5 | 80% | 80% | 81% | 80% | nd | 81% | 80% | nd | 81% |
| Cutoff 6 | 210000 | 221000 | 198000 | 210000 | nd | 198000 | 210000 | nd | 198000 |
| Sens 6 | 0% | 0% | 12% | 0% | nd | 12% | 0% | nd | 0% |
| Spec 6 | 90% | 90% | 90% | 90% | nd | 90% | 90% | nd | 90% |
| OR Quart 2 | 0.64 | >2.1 | 0.96 | 0.67 | nd | 0.96 | 0.97 | nd | 1.0 |
| p Value | 0.64 | <0.55 | 0.97 | 0.67 | nd | 0.97 | 0.98 | nd | 1.0 |
| 95% CI of | 0.100 | >0.18 | 0.13 | 0.10 | nd | 0.13 | 0.058 | nd | 0.059 |
| OR Quart 2 | 4.1 | na | 7.4 | 4.3 | nd | 7.4 | 16 | nd | 17 |
| OR Quart 3 | 1.4 | >3.2 | 0.46 | 1.0 | nd | 0.46 | 2.1 | nd | 1.0 |
| p Value | 0.69 | <0.32 | 0.54 | 1.0 | nd | 0.54 | 0.56 | nd | 1.0 |
| 95% CI of | 0.28 | >0.32 | 0.039 | 0.19 | nd | 0.039 | 0.18 | nd | 0.059 |
| OR Quart 3 | 6.8 | na | 5.4 | 5.4 | nd | 5.4 | 24 | nd | 17 |
| OR Quart 4 | 1.0 | >1.0 | 1.5 | 1.0 | nd | 1.5 | 3.1 | nd | 3.1 |
| p Value | 0.97 | <0.98 | 0.67 | 0.97 | nd | 0.67 | 0.34 | nd | 0.34 |
| 95% CI of | 0.19 | >0.063 | 0.23 | 0.19 | nd | 0.23 | 0.30 | nd | 0.30 |
| OR Quart 4 | 5.6 | na | 9.8 | 5.6 | nd | 9.8 | 32 | nd | 32 |

FIG. 9: Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | C-C motif chemokine 7 | | | | | |
|---|---|---|---|---|---|---|
| | sCr or UO | | | | | |
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 0.584 | 1.22 | 0.584 | 0.618 | 0.584 | 0.623 |
| Average | 1.77 | 17.2 | 1.77 | 4.33 | 1.77 | 8.93 |
| Stdev | 8.21 | 24.8 | 8.21 | 11.0 | 8.21 | 14.1 |
| p(t-test) | | 5.0E−16 | | 0.17 | | 0.0064 |
| Min | 0.146 | 0.188 | 0.146 | 0.319 | 0.146 | 0.319 |
| Max | 163 | 82.4 | 163 | 45.7 | 163 | 33.9 |
| n (Samp) | 1277 | 22 | 1277 | 20 | 1277 | 10 |
| n (Patient) | 452 | 22 | 452 | 20 | 452 | 10 |
| | sCr only | | | | | |
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 0.584 | 1.22 | nd | nd | nd | nd |
| Average | 2.34 | 15.5 | nd | nd | nd | nd |
| Stdev | 12.1 | 24.5 | nd | nd | nd | nd |
| p(t-test) | | 0.0024 | nd | nd | nd | nd |
| Min | 0.146 | 0.188 | nd | nd | nd | nd |
| Max | 291 | 69.7 | nd | nd | nd | nd |
| n (Samp) | 1341 | 8 | nd | nd | nd | nd |
| n (Patient) | 467 | 8 | nd | nd | nd | nd |
| | UO only | | | | | |
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 0.584 | 11.6 | 0.584 | 0.625 | 0.584 | 0.584 |
| Average | 1.81 | 30.2 | 1.81 | 11.2 | 1.81 | 5.17 |
| Stdev | 8.60 | 45.3 | 8.60 | 27.6 | 8.60 | 12.3 |

-continued

|  |  |  |  |  |  |  |  |  |
|---|---|---|---|---|---|---|---|---|
| p(t-test) |  | 1.1E-25 |  | 1.2E-5 |  |  |  | 0.30 |
| Min | 0.146 | 0.515 | 0.146 | 0.319 |  | 0.146 |  | 0.341 |
| Max | 163 | 166 | 163 | 114 |  | 163 |  | 33.0 |
| n (Samp) | 1124 | 14 | 1124 | 19 |  | 1124 |  | 7 |
| n (Patient) | 362 | 14 | 362 | 19 |  | 362 |  | 7 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.75 | 0.70 | 0.78 | 0.54 | nd | 0.54 | 0.60 | nd | 0.53 |
| SE | 0.061 | 0.10 | 0.074 | 0.067 | nd | 0.068 | 0.095 | nd | 0.11 |
| p | 3.5E-5 | 0.054 | 1.6E-4 | 0.53 | nd | 0.58 | 0.28 | nd | 0.76 |
| nCohort 1 | 1277 | 1341 | 1124 | 1277 | nd | 1124 | 1277 | nd | 1124 |
| nCohort 2 | 22 | 8 | 14 | 20 | nd | 19 | 10 | nd | 7 |
| Cutoff 1 | 0.584 | 0.582 | 0.612 | 0.336 | nd | 0.319 | 0.451 | nd | 0.451 |
| Sens 1 | 77% | 75% | 86% | 70% | nd | 89% | 70% | nd | 71% |
| Spec 1 | 52% | 48% | 51% | 34% | nd | 25% | 43% | nd | 41% |
| Cutoff 2 | 0.582 | 0.386 | 0.612 | 0.319 | nd | 0.319 | 0.336 | nd | 0.336 |
| Sens 2 | 86% | 88% | 86% | 90% | nd | 89% | 90% | nd | 100% |
| Spec 2 | 49% | 38% | 51% | 26% | nd | 25% | 34% | nd | 33% |
| Cutoff 3 | 0.512 | 0.146 | 0.582 | 0.319 | nd | 0.301 | 0.336 | nd | 0.336 |
| Sens 3 | 91% | 100% | 93% | 90% | nd | 100% | 90% | nd | 100% |
| Spec 3 | 44% | 4% | 47% | 26% | nd | 17% | 34% | nd | 33% |
| Cutoff 4 | 1.04 | 1.04 | 1.04 | 1.04 | nd | 1.04 | 1.04 | nd | 1.04 |
| Sens 4 | 59% | 62% | 57% | 20% | nd | 21% | 30% | nd | 14% |
| Spec 4 | 73% | 72% | 71% | 73% | nd | 71% | 73% | nd | 71% |
| Cutoff 5 | 1.12 | 1.12 | 1.12 | 1.12 | nd | 1.12 | 1.12 | nd | 1.12 |
| Sens 5 | 59% | 62% | 57% | 20% | nd | 21% | 30% | nd | 14% |
| Spec 5 | 81% | 81% | 80% | 81% | nd | 80% | 81% | nd | 80% |
| Cutoff 6 | 1.59 | 1.59 | 1.59 | 1.59 | nd | 1.59 | 1.59 | nd | 1.59 |
| Sens 6 | 41% | 38% | 50% | 15% | nd | 21% | 30% | nd | 14% |
| Spec 6 | 94% | 93% | 94% | 94% | nd | 94% | 94% | nd | 94% |
| OR Quart 2 | 4.0 | 2.0 | >1.0 | 3.6 | nd | 1.2 | 3.0 | nd | >4.0 |
| p Value | 0.21 | 0.57 | <1.0 | 0.12 | nd | 0.74 | 0.34 | nd | <0.21 |
| 95% CI of | 0.45 | 0.18 | >0.062 | 0.73 | nd | 0.33 | 0.31 | nd | >0.45 |
| OR Quart2 | 36 | 22 | na | 17 | nd | 4.7 | 29 | nd | na |
| OR Quart 3 | 4.0 | 0 | >5.1 | 3.6 | nd | 1.5 | 3.0 | nd | >2.0 |
| p Value | 0.21 | na | <0.14 | 0.12 | nd | 0.53 | 0.34 | nd | <0.57 |
| 95% CI of | 0.45 | na | >0.59 | 0.73 | nd | 0.42 | 0.31 | nd | >0.18 |
| OR Quart3 | 36 | na | na | 17 | nd | 5.4 | 29 | nd | na |
| OR Quart 4 | 13 | 5.0 | >8.2 | 2.0 | nd | 1.00 | 3.0 | nd | >1.0 |
| p Value | 0.012 | 0.14 | <0.048 | 0.42 | nd | 1.00 | 0.34 | nd | <1.0 |
| 95% CI of | 1.8 | 0.59 | >1.0 | 0.36 | nd | 0.25 | 0.31 | nd | >0.062 |
| OR Quart4 | 100 | 43 | na | 11 | nd | 4.0 | 29 | nd | na |

Vascular endothelial growth factor receptor 3 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| Median | 317 | 401 | 317 | 318 | 317 | 247 |
| Average | 334 | 402 | 334 | 351 | 334 | 350 |
| Stdev | 240 | 181 | 240 | 211 | 240 | 334 |
| p(t-test) |  | 0.29 |  | 0.79 |  | 0.87 |
| Min | 1.37 | 81.1 | 1.37 | 1.37 | 1.37 | 3.04 |
| Max | 2750 | 711 | 2750 | 798 | 2750 | 913 |
| n (Samp) | 655 | 14 | 655 | 15 | 655 | 7 |
| n (Patient) | 299 | 14 | 299 | 15 | 299 | 7 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| Median | 318 | 521 | 318 | 328 | nd | nd |
| Average | 341 | 475 | 341 | 359 | nd | nd |
| Stdev | 245 | 178 | 245 | 237 | nd | nd |
| p(t-test) |  | 0.10 |  | 0.81 | nd | nd |
| Min | 1.37 | 166 | 1.37 | 1.37 | nd | nd |
| Max | 2750 | 711 | 2750 | 798 | nd | nd |
| n (Samp) | 597 | 9 | 597 | 12 | nd | nd |
| n (Patient) | 262 | 9 | 262 | 12 | nd | nd |

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | 0.63 | nd | 0.73 | 0.55 | nd | 0.55 | 0.46 | nd | nd |
| SE | 0.081 | nd | 0.096 | 0.077 | nd | 0.086 | 0.11 | nd | nd |
| p | 0.11 | nd | 0.016 | 0.54 | nd | 0.58 | 0.73 | nd | nd |
| nCohort 1 | 655 | nd | 597 | 655 | nd | 597 | 655 | nd | nd |
| nCohort 2 | 14 | nd | 9 | 15 | nd | 12 | 7 | nd | nd |
| Cutoff 1 | 315 | nd | 364 | 273 | nd | 273 | 163 | nd | nd |
| Sens 1 | 71% | nd | 78% | 73% | nd | 75% | 71% | nd | nd |
| Spec 1 | 50% | nd | 62% | 43% | nd | 41% | 19% | nd | nd |
| Cutoff 2 | 247 | nd | 249 | 264 | nd | 171 | 74.3 | nd | nd |
| Sens 2 | 86% | nd | 89% | 80% | nd | 83% | 86% | nd | nd |
| Spec 2 | 35% | nd | 36% | 40% | nd | 20% | 9% | nd | nd |
| Cutoff 3 | 164 | nd | 164 | 0 | nd | 0 | 2.36 | nd | nd |
| Sens 3 | 93% | nd | 100% | 100% | nd | 100% | 100% | nd | nd |
| Spec 3 | 20% | nd | 19% | 0% | nd | 0% | 4% | nd | nd |
| Cutoff 4 | 414 | nd | 414 | 414 | nd | 414 | 414 | nd | nd |
| Sens 4 | 36% | nd | 67% | 33% | nd | 42% | 29% | nd | nd |
| Spec 4 | 72% | nd | 72% | 72% | nd | 72% | 72% | nd | nd |
| Cutoff 5 | 452 | nd | 455 | 452 | nd | 455 | 452 | nd | nd |
| Sens 5 | 36% | nd | 67% | 33% | nd | 42% | 29% | nd | nd |
| Spec 5 | 80% | nd | 80% | 80% | nd | 80% | 80% | nd | nd |
| Cutoff 6 | 542 | nd | 542 | 542 | nd | 542 | 542 | nd | nd |
| Sens 6 | 29% | nd | 44% | 13% | nd | 17% | 29% | nd | nd |
| Spec 6 | 90% | nd | 90% | 90% | nd | 90% | 90% | nd | nd |
| OR Quart 2 | 1.5 | nd | 0.99 | 1.3 | nd | 0.66 | 0.50 | nd | nd |
| p Value | 0.65 | nd | 1.00 | 0.71 | nd | 0.65 | 0.57 | nd | nd |
| 95% CI of OR Quart2 | 0.25 | nd | 0.062 | 0.29 | nd | 0.11 | 0.045 | nd | nd |
|  | 9.2 | nd | 16 | 6.1 | nd | 4.0 | 5.6 | nd | nd |
| OR Quart 3 | 2.0 | nd | 1.0 | 1.0 | nd | 0.66 | 0.50 | nd | nd |
| p Value | 0.42 | nd | 1.0 | 1.0 | nd | 0.65 | 0.57 | nd | nd |
| 95% CI of OR Quart3 | 0.37 | nd | 0.062 | 0.20 | nd | 0.11 | 0.045 | nd | nd |
|  | 11 | nd | 16 | 5.0 | nd | 4.0 | 5.5 | nd | nd |
| OR Quart 4 | 2.5 | nd | 6.2 | 1.7 | nd | 1.7 | 1.5 | nd | nd |
| p Value | 0.27 | nd | 0.094 | 0.48 | nd | 0.48 | 0.65 | nd | nd |
| 95% CI of OR Quart4 | 0.48 | nd | 0.73 | 0.39 | nd | 0.39 | 0.25 | nd | nd |
|  | 13 | nd | 52 | 7.1 | nd | 7.1 | 9.2 | nd | nd |

Interferon alpha-2 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| Median | 0.0967 | 0.0970 | 0.0967 | 0.0974 | 0.0967 | 1.20 |
| Average | 7.83 | 6.68 | 7.83 | 2.57 | 7.83 | 8.13 |
| Stdev | 18.2 | 10.4 | 18.2 | 6.54 | 18.2 | 13.0 |
| p(t-test) |  | 0.77 |  | 0.20 |  | 0.96 |
| Min | 0.0238 | 0.0348 | 0.0238 | 0.0348 | 0.0238 | 0.0418 |
| Max | 126 | 31.4 | 126 | 24.7 | 126 | 34.2 |
| n (Samp) | 1277 | 22 | 1277 | 20 | 1277 | 10 |
| n (Patient) | 452 | 22 | 452 | 20 | 452 | 10 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| Median | 0.0967 | 1.14 | nd | nd | nd | nd |
| Average | 7.67 | 5.56 | nd | nd | nd | nd |
| Stdev | 17.9 | 8.77 | nd | nd | nd | nd |
| p(t-test) |  | 0.74 | nd | nd | nd | nd |
| Min | 0.0238 | 0.0656 | nd | nd | nd | nd |
| Max | 126 | 24.9 | nd | nd | nd | nd |
| n (Samp) | 1341 | 8 | nd | nd | nd | nd |
| n (Patient) | 467 | 8 | nd | nd | nd | nd |

-continued

| | UO only | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 0.0967 | 0.0739 | 0.0967 | 0.0974 | 0.0967 | 2.39 |
| Average | 7.65 | 7.02 | 7.65 | 3.41 | 7.65 | 11.5 |
| Stdev | 17.8 | 11.6 | 17.8 | 7.11 | 17.8 | 14.5 |
| p(t-test) | | 0.89 | | 0.30 | | 0.57 |
| Min | 0.0238 | 0.0348 | 0.0238 | 0.0348 | 0.0238 | 0.104 |
| Max | 126 | 31.4 | 126 | 24.7 | 126 | 34.2 |
| n (Samp) | 1124 | 14 | 1124 | 19 | 1124 | 7 |
| n (Patient) | 362 | 14 | 362 | 19 | 362 | 7 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.56 | 0.58 | 0.49 | 0.50 | nd | 0.49 | 0.69 | nd | 0.76 |
| SE | 0.064 | 0.11 | 0.078 | 0.065 | nd | 0.067 | 0.094 | nd | 0.11 |
| p | 0.34 | 0.48 | 0.94 | 0.94 | nd | 0.89 | 0.045 | nd | 0.017 |
| nCohort 1 | 1277 | 1341 | 1124 | 1277 | nd | 1124 | 1277 | nd | 1124 |
| nCohort 2 | 22 | 8 | 14 | 20 | nd | 19 | 10 | nd | 7 |
| Cutoff 1 | 0.0722 | 0.0672 | 0.0656 | 0.0802 | nd | 0.0722 | 0.114 | nd | 1.81 |
| Sens 1 | 73% | 75% | 79% | 70% | nd | 74% | 70% | nd | 71% |
| Spec 1 | 37% | 33% | 29% | 49% | nd | 36% | 65% | nd | 75% |
| Cutoff 2 | 0.0656 | 0.0656 | 0.0435 | 0.0722 | nd | 0.0398 | 0.0974 | nd | 0.0974 |
| Sens 2 | 91% | 88% | 86% | 80% | nd | 89% | 90% | nd | 100% |
| Spec 2 | 30% | 30% | 18% | 37% | nd | 14% | 57% | nd | 56% |
| Cutoff 3 | 0.0656 | 0.0606 | 0.0238 | 0.0398 | nd | 0.0369 | 0.0974 | nd | 0.0974 |
| Sens 3 | 91% | 100% | 100% | 90% | nd | 95% | 90% | nd | 100% |
| Spec 3 | 30% | 26% | 3% | 15% | nd | 11% | 57% | nd | 56% |
| Cutoff 4 | 0.311 | 0.191 | 0.311 | 0.311 | nd | 0.311 | 0.311 | nd | 0.311 |
| Sens 4 | 41% | 50% | 36% | 15% | nd | 21% | 60% | nd | 71% |
| Spec 4 | 74% | 70% | 74% | 74% | nd | 74% | 74% | nd | 74% |
| Cutoff 5 | 10.8 | 10.4 | 10.9 | 10.8 | nd | 10.9 | 10.8 | nd | 10.9 |
| Sens 5 | 27% | 25% | 29% | 10% | nd | 16% | 30% | nd | 43% |
| Spec 5 | 80% | 80% | 80% | 80% | nd | 80% | 80% | nd | 80% |
| Cutoff 6 | 30.7 | 30.0 | 29.7 | 30.7 | nd | 29.7 | 30.7 | nd | 29.7 |
| Sens 6 | 5% | 0% | 7% | 0% | nd | 0% | 10% | nd | 14% |
| Spec 6 | 90% | 90% | 90% | 90% | nd | 90% | 90% | nd | 90% |
| OR Quart 2 | 4.1 | >4.0 | 0.50 | 0.75 | nd | 1.8 | 0 | nd | >0 |
| p Value | 0.078 | <0.21 | 0.42 | 0.70 | nd | 0.37 | na | nd | <na |
| 95% CI of | 0.86 | >0.45 | 0.091 | 0.17 | nd | 0.51 | na | nd | >na |
| OR Quart2 | 19 | na | 2.7 | 3.4 | nd | 6.1 | na | nd | na |
| OR Quart 3 | 1.5 | >0 | 1.3 | 2.5 | nd | 1.0 | 5.0 | nd | >3.0 |
| p Value | 0.66 | <na | 0.74 | 0.12 | nd | 1.0 | 0.14 | nd | <0.34 |
| 95% CI of | 0.25 | >na | 0.33 | 0.79 | nd | 0.25 | 0.59 | nd | >0.31 |
| OR Quart3 | 9.0 | na | 4.7 | 8.2 | nd | 4.0 | 43 | nd | na |
| OR Quart 4 | 4.6 | >4.0 | 0.75 | 0.75 | nd | 1.0 | 4.0 | nd | >4.0 |
| p Value | 0.053 | <0.21 | 0.71 | 0.70 | nd | 1.00 | 0.21 | nd | <0.21 |
| 95% CI of | 0.98 | >0.45 | 0.17 | 0.17 | nd | 0.25 | 0.45 | nd | >0.45 |
| OR Quart4 | 21 | na | 3.4 | 3.4 | nd | 4.1 | 36 | nd | na |

Insulin-like growth factor-binding protein 4

| | sCr or UO | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 0.733 | 0.968 | 0.733 | 2.01 | nd | nd |
| Average | 1.72 | 1.38 | 1.72 | 4.03 | nd | nd |
| Stdev | 6.16 | 1.15 | 6.16 | 3.96 | nd | nd |
| p(t-test) | | 0.88 | | 0.22 | nd | nd |
| Min | 0.0319 | 0.0558 | 0.0319 | 0.0612 | nd | nd |
| Max | 85.6 | 2.84 | 85.6 | 11.4 | nd | nd |
| n (Samp) | 438 | 8 | 438 | 11 | nd | nd |
| n (Patient) | 226 | 8 | 226 | 11 | nd | nd |

-continued

| | UO only | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | nd | nd | 0.733 | 3.77 | nd | nd |
| Average | nd | nd | 1.77 | 4.23 | nd | nd |
| Stdev | nd | nd | 6.43 | 3.74 | nd | nd |
| p(t-test) | nd | nd | | 0.28 | nd | nd |
| Min | nd | nd | 0.0319 | 0.870 | nd | nd |
| Max | nd | nd | 85.6 | 11.4 | nd | nd |
| n (Samp) | nd | nd | 399 | 8 | nd | nd |
| n (Patient) | nd | nd | 196 | 8 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.64 | nd | nd | 0.75 | nd | 0.82 | nd | nd | nd |
| SE | 0.11 | nd | nd | 0.086 | nd | 0.092 | nd | nd | nd |
| p | 0.18 | nd | nd | 0.0036 | nd | 4.8E−4 | nd | nd | nd |
| nCohort 1 | 438 | nd | nd | 438 | nd | 399 | nd | nd | nd |
| nCohort 2 | 8 | nd | nd | 11 | nd | 8 | nd | nd | nd |
| Cutoff 1 | 0.918 | nd | nd | 0.918 | nd | 0.870 | nd | nd | nd |
| Sens 1 | 75% | nd | nd | 73% | nd | 88% | nd | nd | nd |
| Spec 1 | 57% | nd | nd | 57% | nd | 58% | nd | nd | nd |
| Cutoff 2 | 0.0585 | nd | nd | 0.845 | nd | 0.870 | nd | nd | nd |
| Sens 2 | 88% | nd | nd | 82% | nd | 88% | nd | nd | nd |
| Spec 2 | 18% | nd | nd | 56% | nd | 58% | nd | nd | nd |
| Cutoff 3 | 0.0439 | nd | nd | 0.670 | nd | 0.845 | nd | nd | nd |
| Sens 3 | 100% | nd | nd | 91% | nd | 100% | nd | nd | nd |
| Spec 3 | 12% | nd | nd | 47% | nd | 58% | nd | nd | nd |
| Cutoff 4 | 0.957 | nd | nd | 0.957 | nd | 0.957 | nd | nd | nd |
| Sens 4 | 50% | nd | nd | 55% | nd | 62% | nd | nd | nd |
| Spec 4 | 75% | nd | nd | 75% | nd | 75% | nd | nd | nd |
| Cutoff 5 | 1.46 | nd | nd | 1.46 | nd | 1.46 | nd | nd | nd |
| Sens 5 | 38% | nd | nd | 55% | nd | 62% | nd | nd | nd |
| Spec 5 | 80% | nd | nd | 80% | nd | 80% | nd | nd | nd |
| Cutoff 6 | 3.30 | nd | nd | 3.30 | nd | 3.30 | nd | nd | nd |
| Sens 6 | 0% | nd | nd | 45% | nd | 50% | nd | nd | nd |
| Spec 6 | 90% | nd | nd | 90% | nd | 90% | nd | nd | nd |
| OR Quart 2 | 0 | nd | nd | >1.0 | nd | >0 | nd | nd | nd |
| p Value | na | nd | nd | <0.99 | nd | <na | nd | nd | nd |
| 95% CI of | na | nd | nd | >0.062 | nd | >na | nd | nd | nd |
| OR Quart2 | na | nd | nd | na | nd | na | nd | nd | nd |
| OR Quart 3 | 1.0 | nd | nd | >4.1 | nd | >3.1 | nd | nd | nd |
| p Value | 1.0 | nd | nd | <0.21 | nd | <0.34 | nd | nd | nd |
| 95% CI of | 0.14 | nd | nd | >0.46 | nd | >0.31 | nd | nd | nd |
| OR Quart3 | 7.2 | nd | nd | na | nd | na | nd | nd | nd |
| OR Quart 4 | 2.0 | nd | nd | >6.3 | nd | >5.2 | nd | nd | nd |
| p Value | 0.42 | nd | nd | <0.091 | nd | <0.14 | nd | nd | nd |
| 95% CI of | 0.36 | nd | nd | >0.74 | nd | >0.60 | nd | nd | nd |
| OR Quart4 | 11 | nd | nd | na | nd | na | nd | nd | nd |

| Insulin-like growth factor-binding protein 5 | | | | | | |
|---|---|---|---|---|---|---|
| | sCr or UO | | | | | |
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 0.0682 | 0.811 | 0.0682 | 0.0682 | nd | nd |
| Average | 0.658 | 1.44 | 0.658 | 1.33 | nd | nd |
| Stdev | 1.43 | 1.85 | 1.43 | 1.59 | nd | nd |
| p(t-test) | | 0.13 | | 0.12 | nd | nd |
| Min | 0.0116 | 0.0210 | 0.0116 | 0.0210 | nd | nd |
| Max | 10.3 | 5.59 | 10.3 | 3.92 | nd | nd |
| n (Samp) | 439 | 8 | 439 | 11 | nd | nd |
| n (Patient) | 227 | 8 | 227 | 11 | nd | nd |

-continued

|  | UO only | | | | | |
|---|---|---|---|---|---|---|
|  | 0 hr prior to AKI stage | | 24 hr prior to AKI stage | | 48 hr prior to AKI stage | |
|  | Cohort 1 | Cohort 2 | Cohort 1 | Cohort 2 | Cohort 1 | Cohort 2 |
| Median | nd | nd | 0.0682 | 0.808 | nd | nd |
| Average | nd | nd | 0.652 | 1.45 | nd | nd |
| Stdev | nd | nd | 1.46 | 1.66 | nd | nd |
| p(t-test) | nd | nd |  | 0.13 | nd | nd |
| Min | nd | nd | 0.0116 | 0.0210 | nd | nd |
| Max | nd | nd | 10.3 | 3.92 | nd | nd |
| n (Samp) | nd | nd | 400 | 8 | nd | nd |
| n (Patient) | nd | nd | 197 | 8 | nd | nd |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.72 | nd | nd | 0.57 | nd | 0.57 | nd | nd | nd |
| SE | 0.10 | nd | nd | 0.091 | nd | 0.11 | nd | nd | nd |
| p | 0.038 | nd | nd | 0.43 | nd | 0.50 | nd | nd | nd |
| nCohort 1 | 439 | nd | nd | 439 | nd | 400 | nd | nd | nd |
| nCohort 2 | 8 | nd | nd | 11 | nd | 8 | nd | nd | nd |
| Cutoff 1 | 0.369 | nd | nd | 0.0262 | nd | 0.0116 | nd | nd | nd |
| Sens 1 | 75% | nd | nd | 73% | nd | 100% | nd | nd | nd |
| Spec 1 | 67% | nd | nd | 23% | nd | 14% | nd | nd | nd |
| Cutoff 2 | 0.0544 | nd | nd | 0.0116 | nd | 0.0116 | nd | nd | nd |
| Sens 2 | 88% | nd | nd | 100% | nd | 100% | nd | nd | nd |
| Spec 2 | 46% | nd | nd | 13% | nd | 14% | nd | nd | nd |
| Cutoff 3 | 0.0116 | nd | nd | 0.0116 | nd | 0.0116 | nd | nd | nd |
| Sens 3 | 100% | nd | nd | 100% | nd | 100% | nd | nd | nd |
| Spec 3 | 13% | nd | nd | 13% | nd | 14% | nd | nd | nd |
| Cutoff 4 | 0.397 | nd | nd | 0.397 | nd | 0.397 | nd | nd | nd |
| Sens 4 | 50% | nd | nd | 45% | nd | 50% | nd | nd | nd |
| Spec 4 | 77% | nd | nd | 77% | nd | 78% | nd | nd | nd |
| Cutoff 5 | 0.762 | nd | nd | 0.762 | nd | 0.558 | nd | nd | nd |
| Sens 5 | 50% | nd | nd | 45% | nd | 50% | nd | nd | nd |
| Spec 5 | 80% | nd | nd | 80% | nd | 80% | nd | nd | nd |
| Cutoff 6 | 2.38 | nd | nd | 2.38 | nd | 2.38 | nd | nd | nd |
| Sens 6 | 12% | nd | nd | 36% | nd | 38% | nd | nd | nd |
| Spec 6 | 90% | nd | nd | 90% | nd | 90% | nd | nd | nd |
| OR Quart 2 | 0 | nd | nd | 0.65 | nd | 0.33 | nd | nd | nd |
| p Value | na | nd | nd | 0.65 | nd | 0.34 | nd | nd | nd |
| 95% CI of | na | nd | nd | 0.11 | nd | 0.033 | nd | nd | nd |
| OR Quart2 | na | nd | nd | 4.0 | nd | 3.2 | nd | nd | nd |
| OR Quart 3 | 3.0 | nd | nd | 0.33 | nd | 0 | nd | nd | nd |
| p Value | 0.34 | nd | nd | 0.34 | nd | na | nd | nd | nd |
| 95% CI of | 0.31 | nd | nd | 0.034 | nd | na | nd | nd | nd |
| OR Quart3 | 30 | nd | nd | 3.2 | nd | na | nd | nd | nd |
| OR Quart 4 | 4.1 | nd | nd | 1.7 | nd | 1.3 | nd | nd | nd |
| p Value | 0.21 | nd | nd | 0.48 | nd | 0.70 | nd | nd | nd |
| 95% CI of | 0.45 | nd | nd | 0.39 | nd | 0.29 | nd | nd | nd |
| OR Quart4 | 37 | nd | nd | 7.2 | nd | 6.2 | nd | nd | nd |

Interleukin-33

|  | sCr or UO | | | | | |
|---|---|---|---|---|---|---|
|  | 0 hr prior to AKI stage | | 24 hr prior to AKI stage | | 48 hr prior to AKI stage | |
|  | Cohort 1 | Cohort 2 | Cohort 1 | Cohort 2 | Cohort 1 | Cohort 2 |
| Median | 40.9 | 22.9 | 40.9 | 35.9 | 40.9 | 21.0 |
| Average | 56.0 | 37.6 | 56.0 | 37.0 | 56.0 | 34.9 |
| Stdev | 60.8 | 43.3 | 60.8 | 24.9 | 60.8 | 42.2 |
| p(t-test) |  | 0.16 |  | 0.16 |  | 0.27 |
| Min | 0.0232 | 0.0523 | 0.0232 | 0.0232 | 0.0232 | 0.0688 |
| Max | 958 | 170 | 958 | 84.1 | 958 | 136 |
| n (Samp) | 1275 | 22 | 1275 | 20 | 1275 | 10 |
| n (Patient) | 452 | 22 | 452 | 20 | 452 | 10 |

-continued

| | sCr only | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 40.2 | 28.8 | nd | nd | nd | nd |
| Average | 55.1 | 51.4 | nd | nd | nd | nd |
| Stdev | 59.8 | 57.8 | nd | nd | nd | nd |
| p(t-test) | | 0.86 | nd | nd | nd | nd |
| Min | 0.0232 | 1.78 | nd | nd | nd | nd |
| Max | 958 | 170 | nd | nd | nd | nd |
| n (Samp) | 1339 | 8 | nd | nd | nd | nd |
| n (Patient) | 467 | 8 | nd | nd | nd | nd |

| | UO only | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 41.0 | 19.8 | 41.0 | 27.1 | 41.0 | 41.9 |
| Average | 56.3 | 30.4 | 56.3 | 32.8 | 56.3 | 42.8 |
| Stdev | 62.1 | 31.4 | 62.1 | 27.2 | 62.1 | 49.0 |
| p(t-test) | | 0.12 | | 0.10 | | 0.57 |
| Min | 0.0232 | 0.0436 | 0.0232 | 0.0232 | 0.0232 | 0.0688 |
| Max | 958 | 105 | 958 | 84.1 | 958 | 136 |
| n (Samp) | 1122 | 14 | 1122 | 19 | 1122 | 7 |
| n (Patient) | 362 | 14 | 362 | 19 | 362 | 7 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.40 | 0.48 | 0.36 | 0.43 | nd | 0.39 | 0.39 | nd | 0.43 |
| SE | 0.064 | 0.10 | 0.080 | 0.067 | nd | 0.069 | 0.095 | nd | 0.11 |
| p | 0.13 | 0.84 | 0.080 | 0.33 | nd | 0.12 | 0.23 | nd | 0.52 |
| nCohort 1 | 1275 | 1339 | 1122 | 1275 | nd | 1122 | 1275 | nd | 1122 |
| nCohort 2 | 22 | 8 | 14 | 20 | nd | 19 | 10 | nd | 7 |
| Cutoff 1 | 12.9 | 20.9 | 12.9 | 23.2 | nd | 14.3 | 7.14 | nd | 6.03 |
| Sens 1 | 73% | 75% | 71% | 70% | nd | 74% | 70% | nd | 71% |
| Spec 1 | 25% | 33% | 25% | 34% | nd | 26% | 19% | nd | 17% |
| Cutoff 2 | 4.04 | 14.5 | 0.0558 | 14.9 | nd | 4.04 | 6.03 | nd | 0.0768 |
| Sens 2 | 82% | 88% | 86% | 80% | nd | 84% | 80% | nd | 86% |
| Spec 2 | 16% | 27% | 5% | 26% | nd | 16% | 18% | nd | 10% |
| Cutoff 3 | 0.106 | 1.78 | 0.0518 | 7.14 | nd | 0.0360 | 0.0768 | nd | 0.0686 |
| Sens 3 | 91% | 100% | 93% | 90% | nd | 95% | 90% | nd | 100% |
| Spec 3 | 12% | 14% | 3% | 19% | nd | 2% | 10% | nd | 6% |
| Cutoff 4 | 73.1 | 71.8 | 72.6 | 73.1 | nd | 72.6 | 73.1 | nd | 72.6 |
| Sens 4 | 18% | 25% | 14% | 5% | nd | 5% | 10% | nd | 14% |
| Spec 4 | 70% | 70% | 70% | 70% | nd | 70% | 70% | nd | 70% |
| Cutoff 5 | 93.1 | 92.2 | 93.9 | 93.1 | nd | 93.9 | 93.1 | nd | 93.9 |
| Sens 5 | 14% | 25% | 7% | 0% | nd | 0% | 10% | nd | 14% |
| Spec 5 | 80% | 80% | 80% | 80% | nd | 80% | 80% | nd | 80% |
| Cutoff 6 | 127 | 126 | 127 | 127 | nd | 127 | 127 | nd | 127 |
| Sens 6 | 5% | 12% | 0% | 0% | nd | 0% | 10% | nd | 14% |
| Spec 6 | 90% | 90% | 90% | 90% | nd | 90% | 90% | nd | 90% |
| OR Quart 2 | 1.3 | 0 | 3.0 | 7.1 | nd | 6.1 | 3.0 | nd | 3.0 |
| p Value | 0.70 | na | 0.34 | 0.067 | nd | 0.094 | 0.34 | nd | 0.34 |
| 95% CI of | 0.30 | na | 0.31 | 0.87 | nd | 0.73 | 0.31 | nd | 0.31 |
| OR Quart2 | 6.0 | na | 29 | 58 | nd | 51 | 29 | nd | 29 |
| OR Quart 3 | 3.1 | 2.5 | 5.1 | 9.2 | nd | 7.2 | 2.0 | nd | 0 |
| p Value | 0.095 | 0.27 | 0.14 | 0.036 | nd | 0.066 | 0.57 | nd | na |
| 95% CI of | 0.82 | 0.49 | 0.59 | 1.2 | nd | 0.88 | 0.18 | nd | na |
| OR Quart3 | 11 | 13 | 44 | 73 | nd | 59 | 22 | nd | na |
| OR Quart 4 | 2.0 | 0.50 | 5.1 | 3.0 | nd | 5.1 | 4.1 | nd | 3.0 |
| p Value | 0.32 | 0.57 | 0.14 | 0.34 | nd | 0.14 | 0.21 | nd | 0.34 |
| 95% CI of | 0.50 | 0.045 | 0.59 | 0.31 | nd | 0.59 | 0.45 | nd | 0.31 |
| OR Quart4 | 8.2 | 5.5 | 44 | 29 | nd | 44 | 36 | nd | 29 |

-continued

| | Interleukin-4 receptor alpha chain | | | | | |
|---|---|---|---|---|---|---|
| | sCr or UO | | | | | |
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 46.2 | 65.5 | 46.2 | 87.3 | 46.2 | 66.6 |
| Average | 56.4 | 62.9 | 56.4 | 81.4 | 56.4 | 75.3 |
| Stdev | 51.8 | 42.9 | 51.8 | 55.4 | 51.8 | 24.6 |
| p(t-test) | | 0.63 | | 0.066 | | 0.33 |
| Min | 0.839 | 7.12 | 0.839 | 7.12 | 0.839 | 47.8 |
| Max | 299 | 156 | 299 | 230 | 299 | 119 |
| n (Samp) | 642 | 15 | 642 | 15 | 642 | 7 |
| n (Patient) | 293 | 15 | 293 | 15 | 293 | 7 |

| | UO only | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 46.2 | 66.5 | 46.2 | 77.9 | nd | nd |
| Average | 56.9 | 73.2 | 56.9 | 85.4 | nd | nd |
| Stdev | 52.8 | 49.1 | 52.8 | 58.9 | nd | nd |
| p(t-test) | | 0.36 | | 0.065 | nd | nd |
| Min | 0.839 | 7.12 | 0.839 | 7.12 | nd | nd |
| Max | 299 | 156 | 299 | 230 | nd | nd |
| n (Samp) | 587 | 9 | 587 | 12 | nd | nd |
| n (Patient) | 258 | 9 | 258 | 12 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.57 | nd | 0.61 | 0.66 | nd | 0.67 | 0.69 | nd | nd |
| SE | 0.078 | nd | 0.10 | 0.078 | nd | 0.087 | 0.11 | nd | nd |
| p | 0.37 | nd | 0.29 | 0.042 | nd | 0.057 | 0.089 | nd | nd |
| nCohort 1 | 642 | nd | 587 | 642 | nd | 587 | 642 | nd | nd |
| nCohort 2 | 15 | nd | 9 | 15 | nd | 12 | 7 | nd | nd |
| Cutoff 1 | 50.2 | nd | 59.3 | 59.2 | nd | 59.2 | 60.1 | nd | nd |
| Sens 1 | 73% | nd | 78% | 73% | nd | 75% | 71% | nd | nd |
| Spec 1 | 56% | nd | 62% | 61% | nd | 61% | 63% | nd | nd |
| Cutoff 2 | 11.8 | nd | 6.56 | 50.2 | nd | 50.2 | 59.3 | nd | nd |
| Sens 2 | 80% | nd | 100% | 80% | nd | 83% | 86% | nd | nd |
| Spec 2 | 25% | nd | 6% | 56% | nd | 56% | 62% | nd | nd |
| Cutoff 3 | 6.56 | nd | 6.56 | 11.3 | nd | 11.3 | 46.5 | nd | nd |
| Sens 3 | 100% | nd | 100% | 93% | nd | 92% | 100% | nd | nd |
| Spec 3 | 6% | nd | 6% | 20% | nd | 19% | 51% | nd | nd |
| Cutoff 4 | 75.2 | nd | 74.6 | 75.2 | nd | 74.6 | 75.2 | nd | nd |
| Sens 4 | 27% | nd | 33% | 53% | nd | 50% | 43% | nd | nd |
| Spec 4 | 71% | nd | 70% | 71% | nd | 70% | 71% | nd | nd |
| Cutoff 5 | 94.3 | nd | 94.3 | 94.3 | nd | 94.3 | 94.3 | nd | nd |
| Sens 5 | 20% | nd | 33% | 33% | nd | 42% | 29% | nd | nd |
| Spec 5 | 81% | nd | 80% | 81% | nd | 80% | 81% | nd | nd |
| Cutoff 6 | 122 | nd | 122 | 122 | nd | 122 | 122 | nd | nd |
| Sens 6 | 13% | nd | 11% | 13% | nd | 17% | 0% | nd | nd |
| Spec 6 | 90% | nd | 90% | 90% | nd | 90% | 90% | nd | nd |
| OR Quart 2 | 0.33 | nd | 0 | 0.50 | nd | 0 | >0 | nd | nd |
| p Value | 0.34 | nd | na | 0.57 | nd | na | <na | nd | nd |
| 95% CI of | 0.034 | nd | na | 0.045 | nd | na | >na | nd | nd |
| OR Quart2 | 3.2 | nd | na | 5.5 | nd | na | na | nd | nd |
| OR Quart 3 | 2.8 | nd | 2.0 | 2.0 | nd | 2.0 | >5.2 | nd | nd |
| p Value | 0.14 | nd | 0.42 | 0.42 | nd | 0.42 | <0.14 | nd | nd |
| 95% CI of | 0.72 | nd | 0.37 | 0.37 | nd | 0.36 | >0.60 | nd | nd |
| OR Quart3 | 11 | nd | 11 | 11 | nd | 11 | na | nd | nd |
| OR Quart 4 | 0.99 | nd | 1.5 | 4.1 | nd | 3.1 | >2.0 | nd | nd |
| p Value | 0.99 | nd | 0.65 | 0.076 | nd | 0.17 | <0.57 | nd | nd |
| 95% CI of | 0.20 | nd | 0.25 | 0.86 | nd | 0.61 | >0.18 | nd | nd |
| OR Quart4 | 5.0 | nd | 9.2 | 20 | nd | 15 | na | nd | nd |

-continued

| Vascular endothelial growth factor receptor 2 | | | | | | |
|---|---|---|---|---|---|---|
| sCr or UO | | | | | | |
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 605 | 866 | 605 | 825 | 605 | 561 |
| Average | 804 | 1120 | 804 | 888 | 804 | 829 |
| Stdev | 870 | 1050 | 870 | 798 | 870 | 1040 |
| p(t-test) | | 0.18 | | 0.71 | | 0.94 |
| Min | 0.218 | 106 | 0.218 | 27.3 | 0.218 | 1.48 |
| Max | 7140 | 4230 | 7140 | 2600 | 7140 | 2820 |
| n (Samp) | 644 | 14 | 644 | 15 | 644 | 6 |
| n (Patient) | 294 | 14 | 294 | 15 | 294 | 6 |

| UO only | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 626 | 1390 | 626 | 828 | nd | nd |
| Average | 824 | 1400 | 824 | 915 | nd | nd |
| Stdev | 875 | 1190 | 875 | 879 | nd | nd |
| p(t-test) | | 0.051 | | 0.72 | nd | nd |
| Min | 0.218 | 106 | 0.218 | 27.3 | nd | nd |
| Max | 7140 | 4230 | 7140 | 2600 | nd | nd |
| n (Samp) | 589 | 9 | 589 | 12 | nd | nd |
| n (Patient) | 259 | 9 | 259 | 12 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.62 | nd | 0.69 | 0.55 | nd | 0.53 | 0.48 | nd | nd |
| SE | 0.081 | nd | 0.099 | 0.077 | nd | 0.086 | 0.12 | nd | nd |
| p | 0.15 | nd | 0.058 | 0.52 | nd | 0.73 | 0.86 | nd | nd |
| nCohort 1 | 644 | nd | 589 | 644 | nd | 589 | 644 | nd | nd |
| nCohort 2 | 14 | nd | 9 | 15 | nd | 12 | 6 | nd | nd |
| Cutoff 1 | 626 | nd | 747 | 224 | nd | 182 | 65.6 | nd | nd |
| Sens 1 | 71% | nd | 78% | 73% | nd | 75% | 83% | nd | nd |
| Spec 1 | 51% | nd | 58% | 26% | nd | 21% | 16% | nd | nd |
| Cutoff 2 | 152 | nd | 581 | 182 | nd | 140 | 65.6 | nd | nd |
| Sens 2 | 86% | nd | 89% | 80% | nd | 83% | 83% | nd | nd |
| Spec 2 | 21% | nd | 47% | 23% | nd | 18% | 16% | nd | nd |
| Cutoff 3 | 119 | nd | 106 | 119 | nd | 119 | 1.48 | nd | nd |
| Sens 3 | 93% | nd | 100% | 93% | nd | 92% | 100% | nd | nd |
| Spec 3 | 19% | nd | 16% | 19% | nd | 17% | 8% | nd | nd |
| Cutoff 4 | 981 | nd | 1020 | 981 | nd | 1020 | 981 | nd | nd |
| Sens 4 | 43% | nd | 56% | 40% | nd | 42% | 17% | nd | nd |
| Spec 4 | 70% | nd | 70% | 70% | nd | 70% | 70% | nd | nd |
| Cutoff 5 | 1330 | nd | 1340 | 1330 | nd | 1340 | 1330 | nd | nd |
| Sens 5 | 36% | nd | 56% | 20% | nd | 25% | 17% | nd | nd |
| Spec 5 | 80% | nd | 80% | 80% | nd | 80% | 80% | nd | nd |
| Cutoff 6 | 1740 | nd | 1770 | 1740 | nd | 1770 | 1740 | nd | nd |
| Sens 6 | 14% | nd | 22% | 13% | nd | 17% | 17% | nd | nd |
| Spec 6 | 90% | nd | 90% | 90% | nd | 90% | 90% | nd | nd |
| OR Quart 2 | 0.33 | nd | 0.99 | 0.49 | nd | 0 | 2.0 | nd | nd |
| p Value | 0.34 | nd | 1.00 | 0.42 | nd | na | 0.57 | nd | nd |
| 95% CI of | 0.034 | nd | 0.062 | 0.089 | nd | na | 0.18 | nd | nd |
| OR Quart2 | 3.2 | nd | 16 | 2.7 | nd | na | 23 | nd | nd |
| OR Quart 3 | 1.7 | nd | 2.0 | 1.2 | nd | 0.79 | 1.0 | nd | nd |
| p Value | 0.48 | nd | 0.57 | 0.74 | nd | 0.74 | 1.0 | nd | nd |
| 95% CI of | 0.40 | nd | 0.18 | 0.33 | nd | 0.21 | 0.062 | nd | nd |
| OR Quart3 | 7.2 | nd | 22 | 4.7 | nd | 3.0 | 16 | nd | nd |
| OR Quart 4 | 1.7 | nd | 5.1 | 0.99 | nd | 0.59 | 2.0 | nd | nd |
| p Value | 0.48 | nd | 0.14 | 0.99 | nd | 0.47 | 0.57 | nd | nd |
| 95% CI of | 0.39 | nd | 0.59 | 0.24 | nd | 0.14 | 0.18 | nd | nd |
| OR Quart4 | 7.1 | nd | 44 | 4.0 | nd | 2.5 | 23 | nd | nd |

-continued

| | Lutropin subunit beta | | | | | |
|---|---|---|---|---|---|---|
| | sCr or UO | | | | | |
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | nd | nd | 19.4 | 9.51 | nd | nd |
| Average | nd | nd | 56.4 | 42.0 | nd | nd |
| Stdev | nd | nd | 86.6 | 90.9 | nd | nd |
| p(t-test) | nd | nd | | 0.57 | nd | nd |
| Min | nd | nd | 0.0297 | 0.341 | nd | nd |
| Max | nd | nd | 400 | 325 | nd | nd |
| n (Samp) | nd | nd | 353 | 12 | nd | nd |
| n (Patient) | nd | nd | 165 | 12 | nd | nd |

| | UO only | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | nd | nd | 21.0 | 4.44 | nd | nd |
| Average | nd | nd | 60.2 | 7.20 | nd | nd |
| Stdev | nd | nd | 90.0 | 8.59 | nd | nd |
| p(t-test) | nd | nd | | 0.12 | nd | nd |
| Min | nd | nd | 0.0297 | 0.505 | nd | nd |
| Max | nd | nd | 400 | 24.5 | nd | nd |
| n (Samp) | nd | nd | 352 | 7 | nd | nd |
| n (Patient) | nd | nd | 156 | 7 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | nd | nd | nd | 0.41 | nd | 0.25 | nd | nd | nd |
| SE | nd | nd | nd | 0.088 | nd | 0.11 | nd | nd | nd |
| p | nd | nd | nd | 0.28 | nd | 0.018 | nd | nd | nd |
| nCohort 1 | nd | nd | nd | 353 | nd | 352 | nd | nd | nd |
| nCohort 2 | nd | nd | nd | 12 | nd | 7 | nd | nd | nd |
| Cutoff 1 | nd | nd | nd | 1.09 | nd | 1.09 | nd | nd | nd |
| Sens 1 | nd | nd | nd | 75% | nd | 71% | nd | nd | nd |
| Spec 1 | nd | nd | nd | 12% | nd | 11% | nd | nd | nd |
| Cutoff 2 | nd | nd | nd | 0.840 | nd | 0.840 | nd | nd | nd |
| Sens 2 | nd | nd | nd | 83% | nd | 86% | nd | nd | nd |
| Spec 2 | nd | nd | nd | 10% | nd | 10% | nd | nd | nd |
| Cutoff 3 | nd | nd | nd | 0.463 | nd | 0.463 | nd | nd | nd |
| Sens 3 | nd | nd | nd | 92% | nd | 100% | nd | nd | nd |
| Spec 3 | nd | nd | nd | 9% | nd | 9% | nd | nd | nd |
| Cutoff 4 | nd | nd | nd | 45.5 | nd | 49.1 | nd | nd | nd |
| Sens 4 | nd | nd | nd | 17% | nd | 0% | nd | nd | nd |
| Spec 4 | nd | nd | nd | 70% | nd | 70% | nd | nd | nd |
| Cutoff 5 | nd | nd | nd | 84.1 | nd | 92.0 | nd | nd | nd |
| Sens 5 | nd | nd | nd | 8% | nd | 0% | nd | nd | nd |
| Spec 5 | nd | nd | nd | 80% | nd | 80% | nd | nd | nd |
| Cutoff 6 | nd | nd | nd | 179 | nd | 207 | nd | nd | nd |
| Sens 6 | nd | nd | nd | 8% | nd | 0% | nd | nd | nd |
| Spec 6 | nd | nd | nd | 90% | nd | 90% | nd | nd | nd |
| OR Quart 2 | nd | nd | nd | 1.5 | nd | >1.0 | nd | nd | nd |
| p Value | nd | nd | nd | 0.64 | nd | <0.99 | nd | nd | nd |
| 95% CI of | nd | nd | nd | 0.25 | nd | >0.062 | nd | nd | nd |
| OR Quart2 | nd | nd | nd | 9.4 | nd | na | nd | nd | nd |
| OR Quart 3 | nd | nd | nd | 1.0 | nd | >2.0 | nd | nd | nd |
| p Value | nd | nd | nd | 0.99 | nd | <0.56 | nd | nd | nd |
| 95% CI of | nd | nd | nd | 0.14 | nd | >0.18 | nd | nd | nd |
| OR Quart3 | nd | nd | nd | 7.3 | nd | na | nd | nd | nd |
| OR Quart 4 | nd | nd | nd | 2.6 | nd | >4.2 | nd | nd | nd |
| p Value | nd | nd | nd | 0.26 | nd | <0.20 | nd | nd | nd |
| 95% CI of | nd | nd | nd | 0.49 | nd | >0.46 | nd | nd | nd |
| OR Quart4 | nd | nd | nd | 14 | nd | na | nd | nd | nd |

-continued

| Neural cell adhesion molecule 1 | | | | | | |
|---|---|---|---|---|---|---|
| | sCr or UO | | | | | |
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 2720 | 3990 | 2720 | 2660 | 2720 | 2100 |
| Average | 3320 | 4390 | 3320 | 6260 | 3320 | 2840 |
| Stdev | 2860 | 3520 | 2860 | 11900 | 2860 | 2900 |
| p(t-test) | | 0.085 | | 4.5E−5 | | 0.60 |
| Min | 0.234 | 142 | 0.234 | 375 | 0.234 | 138 |
| Max | 48400 | 15000 | 48400 | 55700 | 48400 | 9700 |
| n (Samp) | 1272 | 22 | 1272 | 20 | 1272 | 10 |
| n (Patient) | 450 | 22 | 450 | 20 | 450 | 10 |

| | sCr only | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 2740 | 2260 | nd | nd | nd | nd |
| Average | 3430 | 2670 | nd | nd | nd | nd |
| Stdev | 3250 | 2170 | nd | nd | nd | nd |
| p(t-test) | | 0.51 | nd | nd | nd | nd |
| Min | 0.234 | 142 | nd | nd | nd | nd |
| Max | 55700 | 6800 | nd | nd | nd | nd |
| n (Samp) | 1336 | 8 | nd | nd | nd | nd |
| n (Patient) | 465 | 8 | nd | nd | nd | nd |

| | UO only | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 2820 | 4560 | 2820 | 4560 | 2820 | 3060 |
| Average | 3380 | 6830 | 3380 | 8190 | 3380 | 3540 |
| Stdev | 2830 | 6750 | 2830 | 12900 | 2830 | 3190 |
| p(t-test) | | 1.1E−5 | | 2.2E−10 | | 0.88 |
| Min | 0.234 | 416 | 0.234 | 375 | 0.234 | 346 |
| Max | 48400 | 26600 | 48400 | 55700 | 48400 | 9700 |
| n (Samp) | 1118 | 14 | 1118 | 19 | 1118 | 7 |
| n (Patient) | 360 | 14 | 360 | 19 | 360 | 7 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.59 | 0.42 | 0.71 | 0.55 | nd | 0.62 | 0.40 | nd | 0.48 |
| SE | 0.064 | 0.11 | 0.079 | 0.067 | nd | 0.069 | 0.095 | nd | 0.11 |
| p | 0.15 | 0.46 | 0.0090 | 0.44 | nd | 0.079 | 0.31 | nd | 0.86 |
| nCohort 1 | 1272 | 1336 | 1118 | 1272 | nd | 1118 | 1272 | nd | 1118 |
| nCohort 2 | 22 | 8 | 14 | 20 | nd | 19 | 10 | nd | 7 |
| Cutoff 1 | 2200 | 1340 | 3860 | 2030 | nd | 2080 | 1180 | nd | 1650 |
| Sens 1 | 73% | 75% | 71% | 70% | nd | 74% | 70% | nd | 71% |
| Spec 1 | 40% | 19% | 68% | 35% | nd | 34% | 16% | nd | 24% |
| Cutoff 2 | 1340 | 623 | 2310 | 1740 | nd | 1740 | 962 | nd | 1180 |
| Sens 2 | 82% | 88% | 86% | 80% | nd | 84% | 80% | nd | 86% |
| Spec 2 | 20% | 5% | 40% | 29% | nd | 26% | 11% | nd | 14% |
| Cutoff 3 | 623 | 85.5 | 1490 | 1110 | nd | 1110 | 341 | nd | 337 |
| Sens 3 | 91% | 100% | 93% | 90% | nd | 95% | 90% | nd | 100% |
| Spec 3 | 5% | 0% | 21% | 15% | nd | 14% | 1% | nd | 1% |
| Cutoff 4 | 3930 | 3980 | 3980 | 3930 | nd | 3980 | 3930 | nd | 3980 |
| Sens 4 | 55% | 12% | 64% | 45% | nd | 58% | 20% | nd | 29% |
| Spec 4 | 70% | 70% | 70% | 70% | nd | 70% | 70% | nd | 70% |
| Cutoff 5 | 4840 | 4910 | 4890 | 4840 | nd | 4890 | 4840 | nd | 4890 |
| Sens 5 | 41% | 12% | 43% | 35% | nd | 42% | 20% | nd | 29% |
| Spec 5 | 80% | 80% | 80% | 80% | nd | 80% | 80% | nd | 80% |
| Cutoff 6 | 6370 | 6470 | 6410 | 6370 | nd | 6410 | 6370 | nd | 6410 |
| Sens 6 | 23% | 12% | 36% | 20% | nd | 32% | 10% | nd | 14% |
| Spec 6 | 90% | 90% | 90% | 90% | nd | 90% | 90% | nd | 90% |
| OR Quart 2 | 0.33 | 2.0 | 0.50 | 1.5 | nd | 1.7 | 1.0 | nd | 1.0 |
| p Value | 0.17 | 0.57 | 0.57 | 0.53 | nd | 0.48 | 1.00 | nd | 1.00 |
| 95% CI of | 0.066 | 0.18 | 0.045 | 0.42 | nd | 0.40 | 0.14 | nd | 0.14 |
| OR Quart2 | 1.6 | 22 | 5.5 | 5.4 | nd | 7.1 | 7.2 | nd | 7.2 |
| OR Quart 3 | 0.83 | 2.0 | 2.0 | 0.50 | nd | 0.33 | 1.0 | nd | 0 |

-continued

| | | | | | | | | | |
|---|---|---|---|---|---|---|---|---|---|
| p Value | 0.76 | 0.57 | 0.42 | 0.42 | nd | 0.34 | 1.0 | nd | na |
| 95% CI of OR Quart3 | 0.25 2.7 | 0.18 22 | 0.37 11 | 0.090 2.7 | nd nd | 0.034 3.2 | 0.14 7.1 | nd nd | na na |
| OR Quart 4 | 1.5 | 3.0 | 3.6 | 2.0 | nd | 3.4 | 2.0 | nd | 1.5 |
| p Value | 0.44 | 0.34 | 0.12 | 0.25 | nd | 0.065 | 0.42 | nd | 0.65 |
| 95% CI of OR Quart4 | 0.53 4.3 | 0.31 29 | 0.73 17 | 0.60 6.8 | nd nd | 0.93 13 | 0.37 11 | nd nd | 0.25 9.1 |

Platelet-derived growth factor subunit B (dimer)

sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 1.19 | 3.23 | 1.19 | 1.55 | 1.19 | 2.47 |
| Average | 3.27 | 6.13 | 3.27 | 68.5 | 3.27 | 1.87 |
| Stdev | 12.5 | 8.36 | 12.5 | 249 | 12.5 | 1.44 |
| p(t-test) | | 0.41 | | 6.0E−14 | | 0.77 |
| Min | 0.00246 | 1.15 | 0.00246 | 0.0144 | 0.00246 | 0.371 |
| Max | 270 | 30.4 | 270 | 935 | 270 | 3.71 |
| n (Samp) | 933 | 13 | 933 | 14 | 933 | 7 |
| n (Patient) | 344 | 13 | 344 | 14 | 344 | 7 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 1.23 | 2.28 | nd | nd | nd | nd |
| Average | 4.24 | 2.60 | nd | nd | nd | nd |
| Stdev | 32.3 | 1.38 | nd | nd | nd | nd |
| p(t-test) | | 0.90 | nd | nd | nd | nd |
| Min | 0.00246 | 1.15 | nd | nd | nd | nd |
| Max | 935 | 4.52 | nd | nd | nd | nd |
| n (Samp) | 970 | 6 | nd | nd | nd | nd |
| n (Patient) | 354 | 6 | nd | nd | nd | nd |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 1.24 | 3.58 | 1.24 | 2.37 | nd | nd |
| Average | 3.30 | 10.3 | 3.30 | 72.4 | nd | nd |
| Stdev | 13.0 | 19.8 | 13.0 | 248 | nd | nd |
| p(t-test) | | 0.13 | | 1.2E−13 | nd | nd |
| Min | 0.00246 | 1.22 | 0.00246 | 0.0144 | nd | nd |
| Max | 270 | 59.1 | 270 | 935 | nd | nd |
| n (Samp) | 800 | 8 | 800 | 14 | nd | nd |
| n (Patient) | 263 | 8 | 263 | 14 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.77 | 0.69 | 0.80 | 0.57 | nd | 0.62 | 0.56 | nd | nd |
| SE | 0.077 | 0.12 | 0.095 | 0.080 | nd | 0.081 | 0.11 | nd | nd |
| p | 4.6E−4 | 0.11 | 0.0018 | 0.40 | nd | 0.14 | 0.59 | nd | nd |
| nCohort 1 | 933 | 970 | 800 | 933 | nd | 800 | 933 | nd | nd |
| nCohort 2 | 13 | 6 | 8 | 14 | nd | 14 | 7 | nd | nd |
| Cutoff 1 | 2.03 | 1.39 | 2.84 | 0.943 | nd | 0.938 | 0.393 | nd | nd |
| Sens 1 | 77% | 83% | 75% | 71% | nd | 71% | 71% | nd | nd |
| Spec 1 | 67% | 54% | 76% | 44% | nd | 43% | 27% | nd | nd |
| Cutoff 2 | 1.39 | 1.39 | 2.03 | 0.162 | nd | 0.162 | 0.392 | nd | nd |
| Sens 2 | 85% | 83% | 88% | 86% | nd | 86% | 86% | nd | nd |
| Spec 2 | 55% | 54% | 66% | 20% | nd | 21% | 27% | nd | nd |
| Cutoff 3 | 1.20 | 1.14 | 1.20 | 0.0140 | nd | 0.0140 | 0.365 | nd | nd |
| Sens 3 | 92% | 100% | 100% | 100% | nd | 100% | 100% | nd | nd |
| Spec 3 | 50% | 48% | 49% | 11% | nd | 12% | 26% | nd | nd |
| Cutoff 4 | 2.18 | 2.23 | 2.22 | 2.18 | nd | 2.22 | 2.18 | nd | nd |
| Sens 4 | 69% | 50% | 75% | 43% | nd | 50% | 57% | nd | nd |
| Spec 4 | 70% | 70% | 70% | 70% | nd | 70% | 70% | nd | nd |
| Cutoff 5 | 3.13 | 3.16 | 3.15 | 3.13 | nd | 3.15 | 3.13 | nd | nd |
| Sens 5 | 54% | 33% | 62% | 29% | nd | 43% | 14% | nd | nd |
| Spec 5 | 80% | 80% | 80% | 80% | nd | 80% | 80% | nd | nd |

-continued

|  | | | | | | | | | |
|---|---|---|---|---|---|---|---|---|---|
| Cutoff 6 | 5.13 | 5.13 | 5.05 | 5.13 | nd | 5.05 | 5.13 | nd | nd |
| Sens 6 | 23% | 0% | 25% | 14% | nd | 29% | 0% | nd | nd |
| Spec 6 | 90% | 90% | 90% | 90% | nd | 90% | 90% | nd | nd |
| OR Quart 2 | >2.0 | >1.0 | >1.0 | 1.00 | nd | 0.66 | >3.0 | nd | nd |
| p Value | <0.57 | <1.00 | <1.00 | 1.00 | nd | 0.65 | <0.34 | nd | nd |
| 95% CI of | >0.18 | >0.062 | >0.062 | 0.20 | nd | 0.11 | >0.31 | nd | nd |
| OR Quart2 | na | na | na | 5.0 | nd | 4.0 | na | nd | nd |
| OR Quart 3 | >3.0 | >3.0 | >1.0 | 1.00 | nd | 0.66 | >1.0 | nd | nd |
| p Value | <0.34 | <0.34 | <1.00 | 1.00 | nd | 0.65 | <1.00 | nd | nd |
| 95% CI of | >0.31 | >0.31 | >0.062 | 0.20 | nd | 0.11 | >0.062 | nd | nd |
| OR Quart3 | na | na | na | 5.0 | nd | 4.0 | na | nd | nd |
| OR Quart 4 | >8.2 | >2.0 | >6.2 | 1.7 | nd | 2.4 | >3.0 | nd | nd |
| p Value | <0.048 | <0.57 | <0.093 | 0.48 | nd | 0.22 | <0.34 | nd | nd |
| 95% CI of | >1.0 | >0.18 | >0.74 | 0.40 | nd | 0.60 | >0.31 | nd | nd |
| OR Quart4 | na | na | na | 7.1 | nd | 9.3 | na | nd | nd |

Corticotropin sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 0.00162 | 0.00162 | 0.00162 | 0.00425 | nd | nd |
| Average | 0.00219 | 0.00196 | 0.00219 | 0.00914 | nd | nd |
| Stdev | 0.00354 | 0.00112 | 0.00354 | 0.0119 | nd | nd |
| p(t-test) | | 0.87 | | 1.1E−7 | nd | nd |
| Min | 3.92E−6 | 0.00109 | 3.92E−6 | 0.000794 | nd | nd |
| Max | 0.0489 | 0.00427 | 0.0489 | 0.0377 | nd | nd |
| n (Samp) | 332 | 7 | 332 | 10 | nd | nd |
| n (Patient) | 193 | 7 | 193 | 10 | nd | nd |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | nd | nd | 0.00163 | 0.00380 | nd | nd |
| Average | nd | nd | 0.00233 | 0.00797 | nd | nd |
| Stdev | nd | nd | 0.00396 | 0.0123 | nd | nd |
| p(t-test) | nd | nd | | 3.4E−4 | nd | nd |
| Min | nd | nd | 0.000273 | 0.000794 | nd | nd |
| Max | nd | nd | 0.0489 | 0.0377 | nd | nd |
| n (Samp) | nd | nd | 290 | 8 | nd | nd |
| n (Patient) | nd | nd | 162 | 8 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.50 | nd | nd | 0.78 | nd | 0.72 | nd | nd | nd |
| SE | 0.11 | nd | nd | 0.087 | nd | 0.10 | nd | nd | nd |
| p | 1.00 | nd | nd | 0.0013 | nd | 0.032 | nd | nd | nd |
| nCohort 1 | 332 | nd | nd | 332 | nd | 290 | nd | nd | nd |
| nCohort 2 | 7 | nd | nd | 10 | nd | 8 | nd | nd | nd |
| Cutoff 1 | 0.00134 | nd | nd | 0.00375 | nd | 0.00229 | nd | nd | nd |
| Sens 1 | 71% | nd | nd | 70% | nd | 75% | nd | nd | nd |
| Spec 1 | 32% | nd | nd | 92% | nd | 72% | nd | nd | nd |
| Cutoff 2 | 0.00106 | nd | nd | 0.00229 | nd | 0.00106 | nd | nd | nd |
| Sens 2 | 100% | nd | nd | 80% | nd | 88% | nd | nd | nd |
| Spec 2 | 19% | nd | nd | 73% | nd | 20% | nd | nd | nd |
| Cutoff 3 | 0.00106 | nd | nd | 0.00106 | nd | 0.000687 | nd | nd | nd |
| Sens 3 | 100% | nd | nd | 90% | nd | 100% | nd | nd | nd |
| Spec 3 | 19% | nd | nd | 19% | nd | 9% | nd | nd | nd |
| Cutoff 4 | 0.00212 | nd | nd | 0.00212 | nd | 0.00218 | nd | nd | nd |
| Sens 4 | 29% | nd | nd | 80% | nd | 75% | nd | nd | nd |
| Spec 4 | 70% | nd | nd | 70% | nd | 70% | nd | nd | nd |
| Cutoff 5 | 0.00274 | nd | nd | 0.00274 | nd | 0.00275 | nd | nd | nd |
| Sens 5 | 14% | nd | nd | 70% | nd | 62% | nd | nd | nd |
| Spec 5 | 80% | nd | nd | 80% | nd | 80% | nd | nd | nd |
| Cutoff 6 | 0.00352 | nd | nd | 0.00352 | nd | 0.00362 | nd | nd | nd |
| Sens 6 | 14% | nd | nd | 70% | nd | 62% | nd | nd | nd |
| Spec 6 | 90% | nd | nd | 90% | nd | 90% | nd | nd | nd |
| OR Quart 2 | 0.49 | nd | nd | 0 | nd | 0 | nd | nd | nd |
| p Value | 0.57 | nd | nd | na | nd | na | nd | nd | nd |
| 95% CI of | 0.044 | nd | nd | na | nd | na | nd | nd | nd |
| OR Quart2 | 5.6 | nd | nd | na | nd | na | nd | nd | nd |

-continued

|  | | | | | | | | | |
|---|---|---|---|---|---|---|---|---|---|
| OR Quart 3 | 1.0 | nd | nd | 0.49 | nd | 0.49 | nd | nd | nd |
| p Value | 1.0 | nd | nd | 0.57 | nd | 0.57 | nd | nd | nd |
| 95% CI of | 0.14 | nd | nd | 0.044 | nd | 0.044 | nd | nd | nd |
| OR Quart3 | 7.3 | nd | nd | 5.6 | nd | 5.6 | nd | nd | nd |
| OR Quart 4 | 1.0 | nd | nd | 3.7 | nd | 2.6 | nd | nd | nd |
| p Value | 0.99 | nd | nd | 0.11 | nd | 0.27 | nd | nd | nd |
| 95% CI of | 0.14 | nd | nd | 0.74 | nd | 0.48 | nd | nd | nd |
| OR Quart4 | 7.4 | nd | nd | 18 | nd | 14 | nd | nd | nd |

Pigment epithelium-derived factor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| Median | 3.21 | 8.76 | 3.21 | 11.6 | 3.21 | 4.86 |
| Average | 20.2 | 39.5 | 20.2 | 41.2 | 20.2 | 21.3 |
| Stdev | 47.4 | 63.3 | 47.4 | 54.0 | 47.4 | 36.7 |
| p(t-test) |  | 0.060 |  | 0.050 |  | 0.94 |
| Min | 0.000401 | 0.0312 | 0.000401 | 0.117 | 0.000401 | 0.00102 |
| Max | 400 | 204 | 400 | 168 | 400 | 115 |
| n (Samp) | 1273 | 22 | 1273 | 20 | 1273 | 10 |
| n (Patient) | 451 | 22 | 451 | 20 | 451 | 10 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| Median | 3.33 | 12.0 | nd | nd | nd | nd |
| Average | 20.9 | 37.0 | nd | nd | nd | nd |
| Stdev | 47.9 | 57.0 | nd | nd | nd | nd |
| p(t-test) |  | 0.34 | nd | nd | nd | nd |
| Min | 0.000401 | 0.0312 | nd | nd | nd | nd |
| Max | 400 | 168 | nd | nd | nd | nd |
| n (Samp) | 1337 | 8 | nd | nd | nd | nd |
| n (Patient) | 466 | 8 | nd | nd | nd | nd |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| Median | 3.46 | 19.8 | 3.46 | 14.9 | 3.46 | 2.22 |
| Average | 22.0 | 53.2 | 22.0 | 55.6 | 22.0 | 26.7 |
| Stdev | 50.6 | 75.1 | 50.6 | 71.6 | 50.6 | 43.3 |
| p(t-test) |  | 0.023 |  | 0.0045 |  | 0.81 |
| Min | 0.000401 | 0.106 | 0.000401 | 0.190 | 0.000401 | 0.644 |
| Max | 400 | 204 | 400 | 250 | 400 | 115 |
| n (Samp) | 1119 | 14 | 1119 | 19 | 1119 | 7 |
| n (Patient) | 361 | 14 | 361 | 19 | 361 | 7 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.62 | 0.64 | 0.66 | 0.64 | nd | 0.68 | 0.52 | nd | 0.53 |
| SE | 0.064 | 0.11 | 0.080 | 0.067 | nd | 0.069 | 0.093 | nd | 0.11 |
| p | 0.069 | 0.19 | 0.048 | 0.033 | nd | 0.0099 | 0.81 | nd | 0.81 |
| nCohort 1 | 1273 | 1337 | 1119 | 1273 | nd | 1119 | 1273 | nd | 1119 |
| nCohort 2 | 22 | 8 | 14 | 20 | nd | 19 | 10 | nd | 7 |
| Cutoff 1 | 2.66 | 4.16 | 3.30 | 2.20 | nd | 2.20 | 1.56 | nd | 1.56 |
| Sens 1 | 73% | 75% | 71% | 70% | nd | 74% | 70% | nd | 71% |
| Spec 1 | 46% | 55% | 49% | 43% | nd | 41% | 36% | nd | 34% |
| Cutoff 2 | 2.01 | 2.29 | 2.01 | 1.99 | nd | 1.99 | 0.682 | nd | 0.682 |
| Sens 2 | 82% | 88% | 86% | 80% | nd | 84% | 80% | nd | 86% |
| Spec 2 | 41% | 43% | 39% | 41% | nd | 39% | 21% | nd | 19% |
| Cutoff 3 | 0.351 | 0.0292 | 0.511 | 1.24 | nd | 1.24 | 0.643 | nd | 0.640 |
| Sens 3 | 91% | 100% | 93% | 90% | nd | 95% | 90% | nd | 100% |
| Spec 3 | 12% | 1% | 14% | 31% | nd | 29% | 20% | nd | 19% |
| Cutoff 4 | 10.1 | 10.5 | 11.0 | 10.1 | nd | 11.0 | 10.1 | nd | 11.0 |
| Sens 4 | 50% | 50% | 57% | 50% | nd | 53% | 40% | nd | 43% |
| Spec 4 | 70% | 70% | 70% | 70% | nd | 70% | 70% | nd | 70% |
| Cutoff 5 | 21.8 | 23.1 | 23.9 | 21.8 | nd | 23.9 | 21.8 | nd | 23.9 |
| Sens 5 | 41% | 38% | 43% | 40% | nd | 47% | 20% | nd | 29% |

-continued

| | | | | | | | | | |
|---|---|---|---|---|---|---|---|---|---|
| Spec 5 | 80% | 80% | 80% | 80% | nd | 80% | 80% | nd | 80% |
| Cutoff 6 | 52.9 | 58.1 | 60.9 | 52.9 | nd | 60.9 | 52.9 | nd | 60.9 |
| Sens 6 | 23% | 25% | 29% | 30% | nd | 32% | 20% | nd | 14% |
| Spec 6 | 90% | 90% | 90% | 90% | nd | 90% | 90% | nd | 90% |
| OR Quart 2 | 0.75 | 1.0 | 1.5 | 2.5 | nd | 5.1 | 0.66 | nd | 1.00 |
| p Value | 0.70 | 1.0 | 0.66 | 0.27 | nd | 0.14 | 0.65 | nd | 1.00 |
| 95% CI of | 0.17 | 0.062 | 0.25 | 0.49 | nd | 0.59 | 0.11 | nd | 0.14 |
| OR Quart2 | 3.4 | 16 | 9.1 | 13 | nd | 44 | 4.0 | nd | 7.1 |
| OR Quart 3 | 1.2 | 2.0 | 0.50 | 2.0 | nd | 4.0 | 0.66 | nd | 0.50 |
| p Value | 0.74 | 0.57 | 0.57 | 0.42 | nd | 0.21 | 0.65 | nd | 0.57 |
| 95% CI of | 0.33 | 0.18 | 0.045 | 0.37 | nd | 0.45 | 0.11 | nd | 0.045 |
| OR Quart3 | 4.7 | 22 | 5.5 | 11 | nd | 36 | 4.0 | nd | 5.5 |
| OR Quart 4 | 2.5 | 4.0 | 4.1 | 4.6 | nd | 9.2 | 1.00 | nd | 1.00 |
| p Value | 0.12 | 0.21 | 0.077 | 0.053 | nd | 0.036 | 1.00 | nd | 1.00 |
| 95% CI of | 0.79 | 0.45 | 0.86 | 0.98 | nd | 1.2 | 0.20 | nd | 0.14 |
| OR Quart4 | 8.2 | 36 | 19 | 21 | nd | 73 | 5.0 | nd | 7.1 |

Tumor necrosis factor receptor superfamily member 8 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 19.5 | 38.9 | 19.5 | 19.6 | 19.5 | 13.2 |
| Average | 29.9 | 57.9 | 29.9 | 29.5 | 29.9 | 23.3 |
| Stdev | 44.8 | 86.8 | 44.8 | 30.1 | 44.8 | 23.1 |
| p(t-test) | | 0.020 | | 0.97 | | 0.70 |
| Min | 0.0493 | 0.121 | 0.0493 | 0.0561 | 0.0493 | 0.196 |
| Max | 554 | 353 | 554 | 102 | 554 | 50.0 |
| n (Samp) | 658 | 15 | 658 | 16 | 658 | 7 |
| n (Patient) | 300 | 15 | 300 | 16 | 300 | 7 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 19.5 | 38.9 | 19.5 | 19.8 | nd | nd |
| Average | 29.9 | 44.8 | 29.9 | 31.2 | nd | nd |
| Stdev | 46.4 | 32.5 | 46.4 | 33.2 | nd | nd |
| p(t-test) | | 0.34 | | 0.92 | nd | nd |
| Min | 0.0493 | 6.52 | 0.0493 | 0.0561 | nd | nd |
| Max | 554 | 117 | 554 | 102 | nd | nd |
| n (Samp) | 600 | 9 | 600 | 13 | nd | nd |
| n (Patient) | 263 | 9 | 263 | 13 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.65 | nd | 0.72 | 0.51 | nd | 0.51 | 0.48 | nd | nd |
| SE | 0.078 | nd | 0.098 | 0.074 | nd | 0.082 | 0.11 | nd | nd |
| p | 0.053 | nd | 0.027 | 0.84 | nd | 0.86 | 0.85 | nd | nd |
| nCohort 1 | 658 | nd | 600 | 658 | nd | 600 | 658 | nd | nd |
| nCohort 2 | 15 | nd | 9 | 16 | nd | 13 | 7 | nd | nd |
| Cutoff 1 | 25.6 | nd | 30.2 | 5.76 | nd | 4.22 | 6.53 | nd | nd |
| Sens 1 | 73% | nd | 78% | 75% | nd | 77% | 71% | nd | nd |
| Spec 1 | 60% | nd | 68% | 23% | nd | 17% | 25% | nd | nd |
| Cutoff 2 | 15.4 | nd | 15.4 | 4.22 | nd | 3.98 | 0.196 | nd | nd |
| Sens 2 | 80% | nd | 89% | 81% | nd | 85% | 86% | nd | nd |
| Spec 2 | 44% | nd | 45% | 16% | nd | 16% | 8% | nd | nd |
| Cutoff 3 | 1.18 | nd | 5.76 | 1.80 | nd | 1.80 | 0.121 | nd | nd |
| Sens 3 | 93% | nd | 100% | 94% | nd | 92% | 100% | nd | nd |
| Spec 3 | 12% | nd | 25% | 15% | nd | 16% | 6% | nd | nd |
| Cutoff 4 | 32.7 | nd | 31.4 | 32.7 | nd | 31.4 | 32.7 | nd | nd |
| Sens 4 | 60% | nd | 67% | 38% | nd | 46% | 43% | nd | nd |
| Spec 4 | 70% | nd | 70% | 70% | nd | 70% | 70% | nd | nd |
| Cutoff 5 | 41.7 | nd | 41.1 | 41.7 | nd | 41.1 | 41.7 | nd | nd |
| Sens 5 | 40% | nd | 33% | 19% | nd | 23% | 43% | nd | nd |
| Spec 5 | 80% | nd | 80% | 80% | nd | 80% | 80% | nd | nd |
| Cutoff 6 | 62.5 | nd | 62.5 | 62.5 | nd | 62.5 | 62.5 | nd | nd |
| Sens 6 | 20% | nd | 22% | 12% | nd | 15% | 0% | nd | nd |
| Spec 6 | 90% | nd | 90% | 90% | nd | 90% | 90% | nd | nd |
| OR Quart 2 | 0.33 | nd | >2.0 | 0.39 | nd | 0.49 | 0 | nd | nd |
| p Value | 0.34 | nd | <0.57 | 0.27 | nd | 0.42 | na | nd | nd |
| 95% CI of | 0.034 | nd | >0.18 | 0.075 | nd | 0.089 | na | nd | nd |

-continued

| | | | | | | | | | |
|---|---|---|---|---|---|---|---|---|---|
| OR Quart2 | 3.2 | nd | na | 2.0 | nd | 2.7 | na | nd | nd |
| OR Quart 3 | 1.0 | nd | >2.0 | 0.80 | nd | 0.49 | 0.67 | nd | nd |
| p Value | 1.0 | nd | <0.57 | 0.74 | nd | 0.42 | 0.66 | nd | nd |
| 95% CI of | 0.20 | nd | >0.18 | 0.21 | nd | 0.089 | 0.11 | nd | nd |
| OR Quart3 | 5.0 | nd | na | 3.0 | nd | 2.7 | 4.0 | nd | nd |
| OR Quart 4 | 2.7 | nd | >5.1 | 0.99 | nd | 1.2 | 0.67 | nd | nd |
| p Value | 0.14 | nd | <0.14 | 0.99 | nd | 0.74 | 0.66 | nd | nd |
| 95% CI of | 0.71 | nd | >0.59 | 0.28 | nd | 0.33 | 0.11 | nd | nd |
| OR Quart4 | 10 | nd | na | 3.5 | nd | 4.7 | 4.0 | nd | nd |

Alpha-fetoprotein sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 0.00505 | 0.00508 | 0.00505 | 0.0385 | 0.00505 | 0.00446 |
| Average | 0.0526 | 0.0780 | 0.0526 | 0.263 | 0.0526 | 0.0371 |
| Stdev | 0.146 | 0.123 | 0.146 | 0.722 | 0.146 | 0.0669 |
| p(t-test) | | 0.59 | | 1.4E−5 | | 0.77 |
| Min | 0.000463 | 0.000463 | 0.000463 | 0.000463 | 0.000463 | 0.000463 |
| Max | 1.74 | 0.296 | 1.74 | 2.85 | 1.74 | 0.185 |
| n (Samp) | 558 | 10 | 558 | 15 | 558 | 8 |
| n (Patient) | 262 | 10 | 262 | 15 | 262 | 8 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | nd | nd | nd | nd | 0.00505 | 0.00286 |
| Average | nd | nd | nd | nd | 0.0577 | 0.0473 |
| Stdev | nd | nd | nd | nd | 0.187 | 0.0760 |
| p(t-test) | nd | nd | nd | nd | | 0.89 |
| Min | nd | nd | nd | nd | 0.000463 | 0.000463 |
| Max | nd | nd | nd | nd | 2.85 | 0.185 |
| n (Samp) | nd | nd | nd | nd | 575 | 6 |
| n (Patient) | nd | nd | nd | nd | 269 | 6 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | nd | nd | 0.00505 | 0.0604 | nd | nd |
| Average | nd | nd | 0.0546 | 0.339 | nd | nd |
| Stdev | nd | nd | 0.151 | 0.885 | nd | nd |
| p(t-test) | nd | nd | | 3.0E−6 | nd | nd |
| Min | nd | nd | 0.000463 | 0.000463 | nd | nd |
| Max | nd | nd | 1.74 | 2.85 | nd | nd |
| n (Samp) | nd | nd | 533 | 10 | nd | nd |
| n (Patient) | nd | nd | 235 | 10 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.50 | nd | nd | 0.60 | nd | 0.58 | 0.46 | 0.40 | nd |
| SE | 0.092 | nd | nd | 0.078 | nd | 0.095 | 0.10 | 0.12 | nd |
| p | 0.97 | nd | nd | 0.22 | nd | 0.39 | 0.74 | 0.40 | nd |
| nCohort 1 | 558 | nd | nd | 558 | nd | 533 | 558 | 575 | nd |
| nCohort 2 | 10 | nd | nd | 15 | nd | 10 | 8 | 6 | nd |
| Cutoff 1 | 0.00132 | nd | nd | 0.00296 | nd | 0.00296 | 0.00132 | 0.00132 | nd |
| Sens 1 | 90% | nd | nd | 73% | nd | 70% | 88% | 83% | nd |
| Spec 1 | 15% | nd | nd | 22% | nd | 23% | 15% | 14% | nd |
| Cutoff 2 | 0.00132 | nd | nd | 0.00132 | nd | 0.00132 | 0.00132 | 0.00132 | nd |
| Sens 2 | 90% | nd | nd | 80% | nd | 80% | 88% | 83% | nd |
| Spec 2 | 15% | nd | nd | 15% | nd | 17% | 15% | 14% | nd |
| Cutoff 3 | 0.00132 | nd | nd | 0 | nd | 0 | 0 | 0 | nd |
| Sens 3 | 90% | nd | nd | 100% | nd | 100% | 100% | 100% | nd |
| Spec 3 | 15% | nd | nd | 0% | nd | 0% | 0% | 0% | nd |
| Cutoff 4 | 0.00660 | nd | nd | 0.00660 | nd | 0.00660 | 0.00660 | 0.00660 | nd |
| Sens 4 | 30% | nd | nd | 60% | nd | 60% | 25% | 33% | nd |
| Spec 4 | 72% | nd | nd | 72% | nd | 73% | 72% | 72% | nd |
| Cutoff 5 | 0.0499 | nd | nd | 0.0499 | nd | 0.0499 | 0.0499 | 0.0499 | nd |

-continued

| | | | | | | | | | |
|---|---|---|---|---|---|---|---|---|---|
| Sens 5 | 30% | nd | nd | 47% | nd | 50% | 25% | 33% | nd |
| Spec 5 | 80% | nd | nd | 80% | nd | 80% | 80% | 80% | nd |
| Cutoff 6 | 0.141 | nd | nd | 0.141 | nd | 0.154 | 0.141 | 0.141 | nd |
| Sens 6 | 30% | nd | nd | 27% | nd | 20% | 12% | 17% | nd |
| Spec 6 | 90% | nd | nd | 90% | nd | 90% | 90% | 90% | nd |
| OR Quart 2 | 0.66 | nd | nd | 0.49 | nd | 0.33 | 1.0 | 0 | nd |
| p Value | 0.65 | nd | nd | 0.42 | nd | 0.33 | 0.99 | na | nd |
| 95% CI of | 0.11 | nd | nd | 0.089 | nd | 0.033 | 0.14 | na | nd |
| OR Quart2 | 4.0 | nd | nd | 2.7 | nd | 3.2 | 7.3 | na | nd |
| OR Quart 3 | 0.33 | nd | nd | 0.24 | nd | 0.33 | 0.50 | 0 | nd |
| p Value | 0.34 | nd | nd | 0.21 | nd | 0.33 | 0.57 | na | nd |
| 95% CI of | 0.034 | nd | nd | 0.027 | nd | 0.033 | 0.045 | na | nd |
| OR Quart3 | 3.2 | nd | nd | 2.2 | nd | 3.2 | 5.5 | na | nd |
| OR Quart 4 | 1.3 | nd | nd | 2.0 | nd | 1.7 | 1.5 | 2.0 | nd |
| p Value | 0.70 | nd | nd | 0.25 | nd | 0.48 | 0.65 | 0.41 | nd |
| 95% CI of | 0.30 | nd | nd | 0.60 | nd | 0.39 | 0.25 | 0.37 | nd |
| OR Quart4 | 6.1 | nd | nd | 6.9 | nd | 7.2 | 9.2 | 11 | nd |

Apolipoprotein E sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 2.46 | 1.66 | 2.46 | 1.59 | 2.46 | 1.96 |
| Average | 18.0 | 33.9 | 18.0 | 99.3 | 18.0 | 3.18 |
| Stdev | 114 | 122 | 114 | 435 | 114 | 3.65 |
| p(t-test) | | 0.50 | | 0.0018 | | 0.64 |
| Min | 0.000147 | 0.00122 | 0.000147 | 0.000147 | 0.000147 | 0.00328 |
| Max | 2160 | 594 | 2160 | 2140 | 2160 | 12.3 |
| n (Samp) | 1388 | 24 | 1388 | 24 | 1388 | 13 |
| n (Patient) | 484 | 24 | 484 | 24 | 484 | 13 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 2.41 | 0.351 | 2.41 | 0.985 | 2.41 | 0.907 |
| Average | 19.4 | 75.3 | 19.4 | 3.39 | 19.4 | 1.85 |
| Stdev | 125 | 210 | 125 | 5.64 | 125 | 2.68 |
| p(t-test) | | 0.21 | | 0.75 | | 0.71 |
| Min | 0.000147 | 0.0847 | 0.000147 | 0.000147 | 0.000147 | 0.0263 |
| Max | 2160 | 594 | 2160 | 14.6 | 2160 | 7.68 |
| n (Samp) | 1455 | 8 | 1455 | 6 | 1455 | 7 |
| n (Patient) | 500 | 8 | 500 | 6 | 500 | 7 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | 2.40 | 1.08 | 2.40 | 3.49 | 2.40 | 3.25 |
| Average | 17.1 | 17.0 | 17.1 | 116 | 17.1 | 4.27 |
| Stdev | 105 | 37.4 | 105 | 464 | 105 | 4.05 |
| p(t-test) | | 1.00 | | 1.7E-4 | | 0.75 |
| Min | 0.000147 | 0.00122 | 0.000147 | 0.00247 | 0.000147 | 0.211 |
| Max | 2140 | 135 | 2140 | 2140 | 2140 | 12.3 |
| n (Samp) | 1246 | 15 | 1246 | 21 | 1246 | 7 |
| n (Patient) | 397 | 15 | 397 | 21 | 397 | 7 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.44 | 0.35 | 0.41 | 0.46 | 0.36 | 0.52 | 0.42 | 0.32 | 0.52 |
| SE | 0.061 | 0.11 | 0.078 | 0.061 | 0.12 | 0.064 | 0.083 | 0.11 | 0.11 |
| p | 0.32 | 0.16 | 0.24 | 0.48 | 0.26 | 0.73 | 0.32 | 0.12 | 0.84 |
| nCohort 1 | 1388 | 1455 | 1246 | 1388 | 1455 | 1246 | 1388 | 1455 | 1246 |
| nCohort 2 | 24 | 8 | 15 | 24 | 6 | 21 | 13 | 7 | 7 |
| Cutoff 1 | 0.404 | 0.201 | 0.172 | 0.309 | 0.260 | 0.422 | 0.207 | 0.624 | 2.00 |
| Sens 1 | 71% | 75% | 73% | 71% | 83% | 71% | 77% | 71% | 71% |
| Spec 1 | 18% | 12% | 11% | 15% | 13% | 18% | 13% | 24% | 45% |
| Cutoff 2 | 0.172 | 0.130 | 0.130 | 0.0258 | 0.260 | 0.130 | 0.0537 | 0.0258 | 1.36 |
| Sens 2 | 83% | 88% | 80% | 83% | 83% | 81% | 85% | 100% | 86% |

-continued

| | | | | | | | | | |
|---|---|---|---|---|---|---|---|---|---|
| Spec 2 | 11% | 10% | 10% | 7% | 13% | 10% | 8% | 7% | 38% |
| Cutoff 3 | 0.00154 | 0.0782 | 0.00129 | 0.00238 | 0 | 0.0258 | 0.0258 | 0.0258 | 0.207 |
| Sens 3 | 92% | 100% | 93% | 92% | 100% | 90% | 92% | 100% | 100% |
| Spec 3 | 3% | 9% | 2% | 4% | 0% | 7% | 7% | 7% | 12% |
| Cutoff 4 | 6.82 | 6.82 | 6.52 | 6.82 | 6.82 | 6.52 | 6.82 | 6.82 | 6.52 |
| Sens 4 | 25% | 12% | 33% | 33% | 17% | 43% | 15% | 14% | 14% |
| Spec 4 | 70% | 70% | 70% | 70% | 70% | 70% | 70% | 70% | 70% |
| Cutoff 5 | 11.8 | 12.1 | 11.3 | 11.8 | 12.1 | 11.3 | 11.8 | 12.1 | 11.3 |
| Sens 5 | 17% | 12% | 20% | 29% | 17% | 38% | 8% | 0% | 14% |
| Spec 5 | 80% | 80% | 80% | 80% | 80% | 80% | 80% | 80% | 80% |
| Cutoff 6 | 25.4 | 26.2 | 24.2 | 25.4 | 26.2 | 24.2 | 25.4 | 26.2 | 24.2 |
| Sens 6 | 12% | 12% | 20% | 17% | 0% | 24% | 0% | 0% | 0% |
| Spec 6 | 90% | 90% | 90% | 90% | 90% | 90% | 90% | 90% | 90% |
| OR Quart 2 | 1.2 | 2.0 | 0.25 | 0.57 | 1.0 | 0.11 | 4.0 | >1.0 | 2.0 |
| p Value | 0.76 | 0.57 | 0.21 | 0.37 | 1.00 | 0.035 | 0.21 | <1.00 | 0.57 |
| 95% CI of | 0.36 | 0.18 | 0.028 | 0.16 | 0.062 | 0.014 | 0.45 | >0.063 | 0.18 |
| OR Quart2 | 4.0 | 22 | 2.2 | 2.0 | 16 | 0.86 | 36 | na | 22 |
| OR Quart 3 | 0.80 | 0 | 0.75 | 0.28 | 1.0 | 0.33 | 4.0 | >3.0 | 3.0 |
| p Value | 0.74 | na | 0.71 | 0.12 | 1.00 | 0.095 | 0.21 | <0.34 | 0.34 |
| 95% CI of | 0.21 | na | 0.17 | 0.058 | 0.062 | 0.087 | 0.45 | >0.31 | 0.31 |
| OR Quart3 | 3.0 | na | 3.4 | 1.4 | 16 | 1.2 | 36 | na | 29 |
| OR Quart 4 | 1.8 | 5.1 | 1.8 | 1.6 | 3.0 | 0.88 | 4.0 | >3.0 | 1.00 |
| p Value | 0.29 | 0.14 | 0.36 | 0.34 | 0.34 | 0.80 | 0.21 | <0.34 | 1.00 |
| 95% CI of | 0.60 | 0.59 | 0.51 | 0.61 | 0.31 | 0.34 | 0.45 | >0.31 | 0.062 |
| OR Quart4 | 5.5 | 44 | 6.1 | 4.1 | 29 | 2.3 | 36 | na | 16 |

FIG. 10: Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.

| | C-C motif chemokine 7 | | | | | | | | |
|---|---|---|---|---|---|---|---|---|---|
| | sCr or UO | | | | | | | | |
| | 0 hr prior to AKI stage | | 24 hr prior to AKI stage | | 48 hr prior to AKI stage | | | | |
| | Cohort 1 | Cohort 2 | Cohort 1 | Cohort 2 | Cohort 1 | | Cohort 2 | | |
| Median | nd | nd | 0.758 | 0.410 | nd | | nd | | |
| Average | nd | nd | 8.98 | 14.0 | nd | | nd | | |
| Stdev | nd | nd | 22.1 | 22.1 | nd | | nd | | |
| p(t-test) | nd | nd | | 0.59 | nd | | nd | | |
| Min | nd | nd | 0.193 | 0.193 | nd | | nd | | |
| Max | nd | nd | 181 | 51.7 | nd | | nd | | |
| n (Samp) | nd | nd | 298 | 6 | nd | | nd | | |
| n (Patient) | nd | nd | 167 | 6 | nd | | nd | | |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | nd | nd | nd | 0.47 | nd | nd | nd | nd | nd |
| SE | nd | nd | nd | 0.12 | nd | nd | nd | nd | nd |
| p | nd | nd | nd | 0.78 | nd | nd | nd | nd | nd |
| nCohort 1 | nd | nd | nd | 298 | nd | nd | nd | nd | nd |
| nCohort2 | nd | nd | nd | 6 | nd | nd | nd | nd | nd |
| Cutoff 1 | nd | nd | nd | 0.193 | nd | nd | nd | nd | nd |
| Sens 1 | nd | nd | nd | 83% | nd | nd | nd | nd | nd |
| Spec 1 | nd | nd | nd | 17% | nd | nd | nd | nd | nd |
| Cutoff 2 | nd | nd | nd | 0.193 | nd | nd | nd | nd | nd |
| Sens 2 | nd | nd | nd | 83% | nd | nd | nd | nd | nd |
| Spec 2 | nd | nd | nd | 17% | nd | nd | nd | nd | nd |
| Cutoff 3 | nd | nd | nd | 0 | nd | nd | nd | nd | nd |
| Sens 3 | nd | nd | nd | 100% | nd | nd | nd | nd | nd |
| Spec 3 | nd | nd | nd | 0% | nd | nd | nd | nd | nd |
| Cutoff 4 | nd | nd | nd | 2.71 | nd | nd | nd | nd | nd |
| Sens 4 | nd | nd | nd | 33% | nd | nd | nd | nd | nd |
| Spec 4 | nd | nd | nd | 70% | nd | nd | nd | nd | nd |
| Cutoff 5 | nd | nd | nd | 13.1 | nd | nd | nd | nd | nd |
| Sens 5 | nd | nd | nd | 33% | nd | nd | nd | nd | nd |
| Spec 5 | nd | nd | nd | 80% | nd | nd | nd | nd | nd |
| Cutoff 6 | nd | nd | nd | 26.6 | nd | nd | nd | nd | nd |
| Sens 6 | nd | nd | nd | 33% | nd | nd | nd | nd | nd |
| Spec 6 | nd | nd | nd | 90% | nd | nd | nd | nd | nd |
| OR Quart 2 | nd | nd | nd | 0 | nd | nd | nd | nd | nd |
| p Value | nd | nd | nd | na | nd | nd | nd | nd | nd |

-continued

| | | | | | | | | | |
|---|---|---|---|---|---|---|---|---|---|
| 95% CI of | nd | nd | nd | na | nd | nd | nd | nd | nd |
| OR Quart2 | nd | nd | nd | na | nd | nd | nd | nd | nd |
| OR Quart 3 | nd | nd | nd | 0.49 | nd | nd | nd | nd | nd |
| p Value | nd | nd | nd | 0.57 | nd | nd | nd | nd | nd |
| 95% CI of | nd | nd | nd | 0.044 | nd | nd | nd | nd | nd |
| OR Quart3 | nd | nd | nd | 5.6 | nd | nd | nd | nd | nd |
| OR Quart 4 | nd | nd | nd | 1.5 | nd | nd | nd | nd | nd |
| p Value | nd | nd | nd | 0.65 | nd | nd | nd | nd | nd |
| 95% CI of | nd | nd | nd | 0.25 | nd | nd | nd | nd | nd |
| OR Quart4 | nd | nd | nd | 9.4 | nd | nd | nd | nd | nd |

Vascular endothelial growth factor receptor 3 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | nd | nd | 6150 | 5990 | nd | nd |
| Average | nd | nd | 7130 | 7240 | nd | nd |
| Stdev | nd | nd | 5340 | 4850 | nd | nd |
| p(t-test) | nd | nd | | 0.96 | nd | nd |
| Min | nd | nd | 219 | 3540 | nd | nd |
| Max | nd | nd | 43200 | 16600 | nd | nd |
| n (Samp) | nd | nd | 298 | 6 | nd | nd |
| n (Patient) | nd | nd | 167 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | nd | nd | nd | 0.50 | nd | nd | nd | nd | nd |
| SE | nd | nd | nd | 0.12 | nd | nd | nd | nd | nd |
| p | nd | nd | nd | 0.98 | nd | nd | nd | nd | nd |
| nCohort 1 | nd | nd | nd | 298 | nd | nd | nd | nd | nd |
| nCohort 2 | nd | nd | nd | 6 | nd | nd | nd | nd | nd |
| Cutoff 1 | nd | nd | nd | 3920 | nd | nd | nd | nd | nd |
| Sens 1 | nd | nd | nd | 83% | nd | nd | nd | nd | nd |
| Spec 1 | nd | nd | nd | 28% | nd | nd | nd | nd | nd |
| Cutoff 2 | nd | nd | nd | 3920 | nd | nd | nd | nd | nd |
| Sens 2 | nd | nd | nd | 83% | nd | nd | nd | nd | nd |
| Spec 2 | nd | nd | nd | 28% | nd | nd | nd | nd | nd |
| Cutoff 3 | nd | nd | nd | 3530 | nd | nd | nd | nd | nd |
| Sens 3 | nd | nd | nd | 100% | nd | nd | nd | nd | nd |
| Spec 3 | nd | nd | nd | 22% | nd | nd | nd | nd | nd |
| Cutoff 4 | nd | nd | nd | 8160 | nd | nd | nd | nd | nd |
| Sens 4 | nd | nd | nd | 17% | nd | nd | nd | nd | nd |
| Spec 4 | nd | nd | nd | 70% | nd | nd | nd | nd | nd |
| Cutoff 5 | nd | nd | nd | 9630 | nd | nd | nd | nd | nd |
| Sens 5 | nd | nd | nd | 17% | nd | nd | nd | nd | nd |
| Spec 5 | nd | nd | nd | 80% | nd | nd | nd | nd | nd |
| Cutoff 6 | nd | nd | nd | 12100 | nd | nd | nd | nd | nd |
| Sens 6 | nd | nd | nd | 17% | nd | nd | nd | nd | nd |
| Spec 6 | nd | nd | nd | 90% | nd | nd | nd | nd | nd |
| OR Quart 2 | nd | nd | nd | 2.0 | nd | nd | nd | nd | nd |
| p Value | nd | nd | nd | 0.57 | nd | nd | nd | nd | nd |
| 95% CI of | nd | nd | nd | 0.18 | nd | nd | nd | nd | nd |
| OR Quart2 | nd | nd | nd | 23 | nd | nd | nd | nd | nd |
| OR Quart 3 | nd | nd | nd | 2.0 | nd | nd | nd | nd | nd |
| p Value | nd | nd | nd | 0.57 | nd | nd | nd | nd | nd |
| 95% CI of | nd | nd | nd | 0.18 | nd | nd | nd | nd | nd |
| OR Quart3 | nd | nd | nd | 23 | nd | nd | nd | nd | nd |
| OR Quart 4 | nd | nd | nd | 1.0 | nd | nd | nd | nd | nd |
| p Value | nd | nd | nd | 1.0 | nd | nd | nd | nd | nd |
| 95% CI of | nd | nd | nd | 0.061 | nd | nd | nd | nd | nd |
| OR Quart4 | nd | nd | nd | 16 | nd | nd | nd | nd | nd |

Interferon alpha-2 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | nd | nd | 12.3 | 6.12 | nd | nd |
| Average | nd | nd | 17.0 | 10.5 | nd | nd |
| Stdev | nd | nd | 23.1 | 12.0 | nd | nd |

-continued

| | | | | | | |
|---|---|---|---|---|---|---|
| p(t-test) | nd | nd | | 0.50 | nd | nd |
| Min | nd | nd | 0.0320 | 0.0627 | nd | nd |
| Max | nd | nd | 223 | 28.5 | nd | nd |
| n (Samp) | nd | nd | 298 | 6 | nd | nd |
| n (Patient) | nd | nd | 167 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | nd | nd | nd | 0.44 | nd | nd | nd | nd | nd |
| SE | nd | nd | nd | 0.12 | nd | nd | nd | nd | nd |
| p | nd | nd | nd | 0.61 | nd | nd | nd | nd | nd |
| nCohort 1 | nd | nd | nd | 298 | nd | nd | nd | nd | nd |
| nCohort 2 | nd | nd | nd | 6 | nd | nd | nd | nd | nd |
| Cutoff 1 | nd | nd | nd | 0.0997 | nd | nd | nd | nd | nd |
| Sens 1 | nd | nd | nd | 83% | nd | nd | nd | nd | nd |
| Spec 1 | nd | nd | nd | 25% | nd | nd | nd | nd | nd |
| Cutoff 2 | nd | nd | nd | 0.0997 | nd | nd | nd | nd | nd |
| Sens 2 | nd | nd | nd | 83% | nd | nd | nd | nd | nd |
| Spec 2 | nd | nd | nd | 25% | nd | nd | nd | nd | nd |
| Cutoff 3 | nd | nd | nd | 0.0324 | nd | nd | nd | nd | nd |
| Sens 3 | nd | nd | nd | 100% | nd | nd | nd | nd | nd |
| Spec 3 | nd | nd | nd | 2% | nd | nd | nd | nd | nd |
| Cutoff 4 | nd | nd | nd | 21.2 | nd | nd | nd | nd | nd |
| Sens 4 | nd | nd | nd | 33% | nd | nd | nd | nd | nd |
| Spec 4 | nd | nd | nd | 70% | nd | nd | nd | nd | nd |
| Cutoff 5 | nd | nd | nd | 27.4 | nd | nd | nd | nd | nd |
| Sens 5 | nd | nd | nd | 17% | nd | nd | nd | nd | nd |
| Spec 5 | nd | nd | nd | 80% | nd | nd | nd | nd | nd |
| Cutoff 6 | nd | nd | nd | 36.4 | nd | nd | nd | nd | nd |
| Sens 6 | nd | nd | nd | 0% | nd | nd | nd | nd | nd |
| Spec 6 | nd | nd | nd | 90% | nd | nd | nd | nd | nd |
| OR Quart 2 | nd | nd | nd | 1.0 | nd | nd | nd | nd | nd |
| p Value | nd | nd | nd | 1.0 | nd | nd | nd | nd | nd |
| 95% CI of | nd | nd | nd | 0.061 | nd | nd | nd | nd | nd |
| OR Quart2 | nd | nd | nd | 16 | nd | nd | nd | nd | nd |
| OR Quart 3 | nd | nd | nd | 3.1 | nd | nd | nd | nd | nd |
| p Value | nd | nd | nd | 0.33 | nd | nd | nd | nd | nd |
| 95% CI of | nd | nd | nd | 0.31 | nd | nd | nd | nd | nd |
| OR Quart3 | nd | nd | nd | 30 | nd | nd | nd | nd | nd |
| OR Quart 4 | nd | nd | nd | 1.0 | nd | nd | nd | nd | nd |
| p Value | nd | nd | nd | 1.0 | nd | nd | nd | nd | nd |
| 95% CI of | nd | nd | nd | 0.061 | nd | nd | nd | nd | nd |
| OR Quart4 | nd | nd | nd | 16 | nd | nd | nd | nd | nd |

Insulin-like growth factor-binding protein 4 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | nd | nd | 2.93 | 4.81 | nd | nd |
| Average | nd | nd | 12.8 | 12.6 | nd | nd |
| Stdev | nd | nd | 18.4 | 14.7 | nd | nd |
| p(t-test) | nd | nd | | 0.98 | nd | nd |
| Min | nd | nd | 0.0728 | 0.572 | nd | nd |
| Max | nd | nd | 158 | 33.4 | nd | nd |
| n (Samp) | nd | nd | 361 | 6 | nd | nd |
| n (Patient) | nd | nd | 197 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | nd | nd | nd | 0.55 | nd | nd | nd | nd | nd |
| SE | nd | nd | nd | 0.12 | nd | nd | nd | nd | nd |
| p | nd | nd | nd | 0.66 | nd | nd | nd | nd | nd |
| nCohort 1 | nd | nd | nd | 361 | nd | nd | nd | nd | nd |
| nCohort 2 | nd | nd | nd | 6 | nd | nd | nd | nd | nd |
| Cutoff 1 | nd | nd | nd | 2.43 | nd | nd | nd | nd | nd |
| Sens 1 | nd | nd | nd | 83% | nd | nd | nd | nd | nd |
| Spec 1 | nd | nd | nd | 38% | nd | nd | nd | nd | nd |
| Cutoff 2 | nd | nd | nd | 2.43 | nd | nd | nd | nd | nd |
| Sens 2 | nd | nd | nd | 83% | nd | nd | nd | nd | nd |
| Spec 2 | nd | nd | nd | 38% | nd | nd | nd | nd | nd |
| Cutoff 3 | nd | nd | nd | 0.0862 | nd | nd | nd | nd | nd |

|  | | | | | | | | | |
|---|---|---|---|---|---|---|---|---|---|
| Sens 3 | nd | nd | nd | 100% | nd | nd | nd | nd | nd |
| Spec 3 | nd | nd | nd | 1% | nd | nd | nd | nd | nd |
| Cutoff 4 | nd | nd | nd | 17.1 | nd | nd | nd | nd | nd |
| Sens 4 | nd | nd | nd | 33% | nd | nd | nd | nd | nd |
| Spec 4 | nd | nd | nd | 70% | nd | nd | nd | nd | nd |
| Cutoff 5 | nd | nd | nd | 23.5 | nd | nd | nd | nd | nd |
| Sens 5 | nd | nd | nd | 33% | nd | nd | nd | nd | nd |
| Spec 5 | nd | nd | nd | 80% | nd | nd | nd | nd | nd |
| Cutoff 6 | nd | nd | nd | 30.5 | nd | nd | nd | nd | nd |
| Sens 6 | nd | nd | nd | 17% | nd | nd | nd | nd | nd |
| Spec 6 | nd | nd | nd | 90% | nd | nd | nd | nd | nd |
| OR Quart 2 | nd | nd | nd | 2.0 | nd | nd | nd | nd | nd |
| p Value | nd | nd | nd | 0.57 | nd | nd | nd | nd | nd |
| 95% CI of | nd | nd | nd | 0.18 | nd | nd | nd | nd | nd |
| OR Quart2 | nd | nd | nd | 22 | nd | nd | nd | nd | nd |
| OR Quart 3 | nd | nd | nd | 0.99 | nd | nd | nd | nd | nd |
| p Value | nd | nd | nd | 0.99 | nd | nd | nd | nd | nd |
| 95% CI of | nd | nd | nd | 0.061 | nd | nd | nd | nd | nd |
| OR Quart3 | nd | nd | nd | 16 | nd | nd | nd | nd | nd |
| OR Quart 4 | nd | nd | nd | 2.0 | nd | nd | nd | nd | nd |
| p Value | nd | nd | nd | 0.57 | nd | nd | nd | nd | nd |
| 95% CI of | nd | nd | nd | 0.18 | nd | nd | nd | nd | nd |
| OR Quart4 | nd | nd | nd | 22 | nd | nd | nd | nd | nd |

Insulin-like growth factor-binding protein 5 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| Median | nd | nd | 11.5 | 0.763 | nd | nd |
| Average | nd | nd | 34.9 | 22.5 | nd | nd |
| Stdev | nd | nd | 49.9 | 34.1 | nd | nd |
| p(t-test) | nd | nd |  | 0.54 | nd | nd |
| Min | nd | nd | 0.204 | 0.204 | nd | nd |
| Max | nd | nd | 257 | 69.8 | nd | nd |
| n (Samp) | nd | nd | 361 | 6 | nd | nd |
| n (Patient) | nd | nd | 197 | 6 | nd | nd |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | nd | nd | nd | 0.44 | nd | nd | nd | nd | nd |
| SE | nd | nd | nd | 0.12 | nd | nd | nd | nd | nd |
| p | nd | nd | nd | 0.61 | nd | nd | nd | nd | nd |
| nCohort 1 | nd | nd | nd | 361 | nd | nd | nd | nd | nd |
| nCohort 2 | nd | nd | nd | 6 | nd | nd | nd | nd | nd |
| Cutoff 1 | nd | nd | nd | 0.222 | nd | nd | nd | nd | nd |
| Sens 1 | nd | nd | nd | 83% | nd | nd | nd | nd | nd |
| Spec 1 | nd | nd | nd | 18% | nd | nd | nd | nd | nd |
| Cutoff 2 | nd | nd | nd | 0.222 | nd | nd | nd | nd | nd |
| Sens 2 | nd | nd | nd | 83% | nd | nd | nd | nd | nd |
| Spec 2 | nd | nd | nd | 18% | nd | nd | nd | nd | nd |
| Cutoff 3 | nd | nd | nd | 0 | nd | nd | nd | nd | nd |
| Sens 3 | nd | nd | nd | 100% | nd | nd | nd | nd | nd |
| Spec 3 | nd | nd | nd | 0% | nd | nd | nd | nd | nd |
| Cutoff 4 | nd | nd | nd | 40.2 | nd | nd | nd | nd | nd |
| Sens 4 | nd | nd | nd | 33% | nd | nd | nd | nd | nd |
| Spec 4 | nd | nd | nd | 70% | nd | nd | nd | nd | nd |
| Cutoff 5 | nd | nd | nd | 62.1 | nd | nd | nd | nd | nd |
| Sens 5 | nd | nd | nd | 33% | nd | nd | nd | nd | nd |
| Spec 5 | nd | nd | nd | 80% | nd | nd | nd | nd | nd |
| Cutoff 6 | nd | nd | nd | 119 | nd | nd | nd | nd | nd |
| Sens 6 | nd | nd | nd | 0% | nd | nd | nd | nd | nd |
| Spec 6 | nd | nd | nd | 90% | nd | nd | nd | nd | nd |
| OR Quart 2 | nd | nd | nd | 0 | nd | nd | nd | nd | nd |
| p Value | nd | nd | nd | na | nd | nd | nd | nd | nd |
| 95% CI of | nd | nd | nd | na | nd | nd | nd | nd | nd |
| OR Quart2 | nd | nd | nd | na | nd | nd | nd | nd | nd |
| OR Quart 3 | nd | nd | nd | 1.0 | nd | nd | nd | nd | nd |
| p Value | nd | nd | nd | 1.0 | nd | nd | nd | nd | nd |
| 95% CI of | nd | nd | nd | 0.14 | nd | nd | nd | nd | nd |
| OR Quart3 | nd | nd | nd | 7.3 | nd | nd | nd | nd | nd |

| | | | | | | | | | |
|---|---|---|---|---|---|---|---|---|---|
| OR Quart 4 | nd | nd | nd | 1.0 | nd | nd | nd | nd | nd |
| p Value | nd | nd | nd | 0.99 | nd | nd | nd | nd | nd |
| 95% CI of | nd | nd | nd | 0.14 | nd | nd | nd | nd | nd |
| OR Quart4 | nd | nd | nd | 7.3 | nd | nd | nd | nd | nd |

Interleukin-33 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | nd | nd | 0.0981 | 5.87 | nd | nd |
| Average | nd | nd | 278 | 36.4 | nd | nd |
| Stdev | nd | nd | 2480 | 73.0 | nd | nd |
| p(t-test) | nd | nd | | 0.81 | nd | nd |
| Min | nd | nd | 0.0445 | 0.0455 | nd | nd |
| Max | nd | nd | 40000 | 184 | nd | nd |
| n (Samp) | nd | nd | 298 | 6 | nd | nd |
| n (Patient) | nd | nd | 167 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | nd | nd | nd | 0.67 | nd | nd | nd | nd | nd |
| SE | nd | nd | nd | 0.12 | nd | nd | nd | nd | nd |
| p | nd | nd | nd | 0.16 | nd | nd | nd | nd | nd |
| nCohort 1 | nd | nd | nd | 298 | nd | nd | nd | nd | nd |
| nCohort 2 | nd | nd | nd | 6 | nd | nd | nd | nd | nd |
| Cutoff 1 | nd | nd | nd | 0.0996 | nd | nd | nd | nd | nd |
| Sens 1 | nd | nd | nd | 83% | nd | nd | nd | nd | nd |
| Spec 1 | nd | nd | nd | 56% | nd | nd | nd | nd | nd |
| Cutoff 2 | nd | nd | nd | 0.0996 | nd | nd | nd | nd | nd |
| Sens 2 | nd | nd | nd | 83% | nd | nd | nd | nd | nd |
| Spec 2 | nd | nd | nd | 56% | nd | nd | nd | nd | nd |
| Cutoff 3 | nd | nd | nd | 0.0445 | nd | nd | nd | nd | nd |
| Sens 3 | nd | nd | nd | 100% | nd | nd | nd | nd | nd |
| Spec 3 | nd | nd | nd | 10% | nd | nd | nd | nd | nd |
| Cutoff 4 | nd | nd | nd | 1.13 | nd | nd | nd | nd | nd |
| Sens 4 | nd | nd | nd | 67% | nd | nd | nd | nd | nd |
| Spec 4 | nd | nd | nd | 70% | nd | nd | nd | nd | nd |
| Cutoff 5 | nd | nd | nd | 13.1 | nd | nd | nd | nd | nd |
| Sens 5 | nd | nd | nd | 33% | nd | nd | nd | nd | nd |
| Spec 5 | nd | nd | nd | 80% | nd | nd | nd | nd | nd |
| Cutoff 6 | nd | nd | nd | 76.8 | nd | nd | nd | nd | nd |
| Sens 6 | nd | nd | nd | 17% | nd | nd | nd | nd | nd |
| Spec 6 | nd | nd | nd | 90% | nd | nd | nd | nd | nd |
| OR Quart 2 | nd | nd | nd | 0 | nd | nd | nd | nd | nd |
| p Value | nd | nd | nd | na | nd | nd | nd | nd | nd |
| 95% CI of | nd | nd | nd | na | nd | nd | nd | nd | nd |
| OR Quart2 | nd | nd | nd | na | nd | nd | nd | nd | nd |
| OR Quart 3 | nd | nd | nd | 2.0 | nd | nd | nd | nd | nd |
| p Value | nd | nd | nd | 0.57 | nd | nd | nd | nd | nd |
| 95% CI of | nd | nd | nd | 0.18 | nd | nd | nd | nd | nd |
| OR Quart3 | nd | nd | nd | 23 | nd | nd | nd | nd | nd |
| OR Quart 4 | nd | nd | nd | 3.1 | nd | nd | nd | nd | nd |
| p Value | nd | nd | nd | 0.33 | nd | nd | nd | nd | nd |
| 95% CI of | nd | nd | nd | 0.31 | nd | nd | nd | nd | nd |
| OR Quart4 | nd | nd | nd | 30 | nd | nd | nd | nd | nd |

Interleukin-4 receptor alpha chain sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | nd | nd | 219 | 275 | nd | nd |
| Average | nd | nd | 294 | 314 | nd | nd |
| Stdev | nd | nd | 230 | 226 | nd | nd |
| p(t-test) | nd | nd | | 0.83 | nd | nd |
| Min | nd | nd | 3.27 | 84.5 | nd | nd |
| Max | nd | nd | 1210 | 646 | nd | nd |
| n (Samp) | nd | nd | 298 | 6 | nd | nd |
| n (Patient) | nd | nd | 167 | 6 | nd | nd |

-continued

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | nd | nd | nd | 0.52 | nd | nd | nd | nd | nd |
| SE | nd | nd | nd | 0.12 | nd | nd | nd | nd | nd |
| p | nd | nd | nd | 0.86 | nd | nd | nd | nd | nd |
| nCohort 1 | nd | nd | nd | 298 | nd | nd | nd | nd | nd |
| nCohort 2 | nd | nd | nd | 6 | nd | nd | nd | nd | nd |
| Cutoff 1 | nd | nd | nd | 104 | nd | nd | nd | nd | nd |
| Sens 1 | nd | nd | nd | 83% | nd | nd | nd | nd | nd |
| Spec 1 | nd | nd | nd | 7% | nd | nd | nd | nd | nd |
| Cutoff 2 | nd | nd | nd | 104 | nd | nd | nd | nd | nd |
| Sens 2 | nd | nd | nd | 83% | nd | nd | nd | nd | nd |
| Spec 2 | nd | nd | nd | 7% | nd | nd | nd | nd | nd |
| Cutoff 3 | nd | nd | nd | 83.5 | nd | nd | nd | nd | nd |
| Sens 3 | nd | nd | nd | 100% | nd | nd | nd | nd | nd |
| Spec 3 | nd | nd | nd | 4% | nd | nd | nd | nd | nd |
| Cutoff 4 | nd | nd | nd | 304 | nd | nd | nd | nd | nd |
| Sens 4 | nd | nd | nd | 50% | nd | nd | nd | nd | nd |
| Spec 4 | nd | nd | nd | 70% | nd | nd | nd | nd | nd |
| Cutoff 5 | nd | nd | nd | 376 | nd | nd | nd | nd | nd |
| Sens 5 | nd | nd | nd | 33% | nd | nd | nd | nd | nd |
| Spec 5 | nd | nd | nd | 80% | nd | nd | nd | nd | nd |
| Cutoff 6 | nd | nd | nd | 554 | nd | nd | nd | nd | nd |
| Sens 6 | nd | nd | nd | 17% | nd | nd | nd | nd | nd |
| Spec 6 | nd | nd | nd | 90% | nd | nd | nd | nd | nd |
| OR Quart 2 | nd | nd | nd | 0.49 | nd | nd | nd | nd | nd |
| p Value | nd | nd | nd | 0.57 | nd | nd | nd | nd | nd |
| 95% CI of OR Quart2 | nd | nd | nd | 0.044 | nd | nd | nd | nd | nd |
|  | nd | nd | nd | 5.6 | nd | nd | nd | nd | nd |
| OR Quart 3 | nd | nd | nd | 0 | nd | nd | nd | nd | nd |
| p Value | nd | nd | nd | na | nd | nd | nd | nd | nd |
| 95% CI of OR Quart3 | nd | nd | nd | na | nd | nd | nd | nd | nd |
|  | nd | nd | nd | na | nd | nd | nd | nd | nd |
| OR Quart 4 | nd | nd | nd | 1.5 | nd | nd | nd | nd | nd |
| p Value | nd | nd | nd | 0.65 | nd | nd | nd | nd | nd |
| 95% CI of OR Quart4 | nd | nd | nd | 0.25 | nd | nd | nd | nd | nd |
|  | nd | nd | nd | 9.4 | nd | nd | nd | nd | nd |

| Vascular endothelial growth factor receptor 2 | | | | | |
| --- | --- | --- | --- | --- | --- |
| sCr or UO | | | | | |
| 0 hr prior to AKI stage | | 24 hr prior to AKI stage | | 48 hr prior to AKI stage | |
| Cohort 1 | Cohort 2 | Cohort 1 | Cohort 2 | Cohort 1 | Cohort 2 |
| Median | nd | nd | 7870 | 7420 | nd | nd |

| | Cohort 1 | Cohort 2 | Cohort 1 | Cohort 2 | Cohort 1 | Cohort 2 |
| --- | --- | --- | --- | --- | --- | --- |
| Median | nd | nd | 7870 | 7420 | nd | nd |
| Average | nd | nd | 9920 | 7340 | nd | nd |
| Stdev | nd | nd | 13200 | 1600 | nd | nd |
| p(t-test) | nd | nd |  | 0.63 | nd | nd |
| Min | nd | nd | 3020 | 5310 | nd | nd |
| Max | nd | nd | 166000 | 9440 | nd | nd |
| n (Samp) | nd | nd | 298 | 6 | nd | nd |
| n (Patient) | nd | nd | 167 | 6 | nd | nd |

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | nd | nd | nd | 0.42 | nd | nd | nd | nd | nd |
| SE | nd | nd | nd | 0.12 | nd | nd | nd | nd | nd |
| p | nd | nd | nd | 0.54 | nd | nd | nd | nd | nd |
| nCohort 1 | nd | nd | nd | 298 | nd | nd | nd | nd | nd |
| nCohort 2 | nd | nd | nd | 6 | nd | nd | nd | nd | nd |
| Cutoff 1 | nd | nd | nd | 5920 | nd | nd | nd | nd | nd |
| Sens 1 | nd | nd | nd | 83% | nd | nd | nd | nd | nd |
| Spec 1 | nd | nd | nd | 20% | nd | nd | nd | nd | nd |
| Cutoff 2 | nd | nd | nd | 5920 | nd | nd | nd | nd | nd |
| Sens 2 | nd | nd | nd | 83% | nd | nd | nd | nd | nd |
| Spec 2 | nd | nd | nd | 20% | nd | nd | nd | nd | nd |
| Cutoff 3 | nd | nd | nd | 5300 | nd | nd | nd | nd | nd |
| Sens 3 | nd | nd | nd | 100% | nd | nd | nd | nd | nd |
| Spec 3 | nd | nd | nd | 11% | nd | nd | nd | nd | nd |
| Cutoff 4 | nd | nd | nd | 9430 | nd | nd | nd | nd | nd |
| Sens 4 | nd | nd | nd | 17% | nd | nd | nd | nd | nd |
| Spec 4 | nd | nd | nd | 70% | nd | nd | nd | nd | nd |
| Cutoff 5 | nd | nd | nd | 10600 | nd | nd | nd | nd | nd |

-continued

| | | | | | | | | | |
|---|---|---|---|---|---|---|---|---|---|
| Sens 5 | nd | nd | nd | 0% | nd | nd | nd | nd | nd |
| Spec 5 | nd | nd | nd | 80% | nd | nd | nd | nd | nd |
| Cutoff 6 | nd | nd | nd | 14300 | nd | nd | nd | nd | nd |
| Sens 6 | nd | nd | nd | 0% | nd | nd | nd | nd | nd |
| Spec 6 | nd | nd | nd | 90% | nd | nd | nd | nd | nd |
| OR Quart 2 | nd | nd | nd | >3.1 | nd | nd | nd | nd | nd |
| p Value | nd | nd | nd | <0.33 | nd | nd | nd | nd | nd |
| 95% CI of | nd | nd | nd | >0.32 | nd | nd | nd | nd | nd |
| OR Quart2 | nd | nd | nd | na | nd | nd | nd | nd | nd |
| OR Quart 3 | nd | nd | nd | >1.0 | nd | nd | nd | nd | nd |
| p Value | nd | nd | nd | <0.99 | nd | nd | nd | nd | nd |
| 95% CI of | nd | nd | nd | >0.062 | nd | nd | nd | nd | nd |
| OR Quart3 | nd | nd | nd | na | nd | nd | nd | nd | nd |
| OR Quart 4 | nd | nd | nd | >2.1 | nd | nd | nd | nd | nd |
| p Value | nd | nd | nd | <0.56 | nd | nd | nd | nd | nd |
| 95% CI of | nd | nd | nd | >0.18 | nd | nd | nd | nd | nd |
| OR Quart4 | nd | nd | nd | na | nd | nd | nd | nd | nd |

Neural cell adhesion molecule 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | nd | nd | 182000 | 166000 | nd | nd |
| Average | nd | nd | 189000 | 177000 | nd | nd |
| Stdev | nd | nd | 70000 | 50000 | nd | nd |
| p(t-test) | nd | nd | | 0.68 | nd | nd |
| Min | nd | nd | 49200 | 125000 | nd | nd |
| Max | nd | nd | 520000 | 245000 | nd | nd |
| n (Samp) | nd | nd | 366 | 6 | nd | nd |
| n (Patient) | nd | nd | 196 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | nd | nd | nd | 0.46 | nd | nd | nd | nd | nd |
| SE | nd | nd | nd | 0.12 | nd | nd | nd | nd | nd |
| p | nd | nd | nd | 0.75 | nd | nd | nd | nd | nd |
| nCohort 1 | nd | nd | nd | 366 | nd | nd | nd | nd | nd |
| nCohort 2 | nd | nd | nd | 6 | nd | nd | nd | nd | nd |
| Cutoff 1 | nd | nd | nd | 131000 | nd | nd | nd | nd | nd |
| Sens 1 | nd | nd | nd | 83% | nd | nd | nd | nd | nd |
| Spec 1 | nd | nd | nd | 19% | nd | nd | nd | nd | nd |
| Cutoff 2 | nd | nd | nd | 131000 | nd | nd | nd | nd | nd |
| Sens 2 | nd | nd | nd | 83% | nd | nd | nd | nd | nd |
| Spec 2 | nd | nd | nd | 19% | nd | nd | nd | nd | nd |
| Cutoff 3 | nd | nd | nd | 125000 | nd | nd | nd | nd | nd |
| Sens 3 | nd | nd | nd | 100% | nd | nd | nd | nd | nd |
| Spec 3 | nd | nd | nd | 15% | nd | nd | nd | nd | nd |
| Cutoff 4 | nd | nd | nd | 209000 | nd | nd | nd | nd | nd |
| Sens 4 | nd | nd | nd | 33% | nd | nd | nd | nd | nd |
| Spec 4 | nd | nd | nd | 70% | nd | nd | nd | nd | nd |
| Cutoff 5 | nd | nd | nd | 230000 | nd | nd | nd | nd | nd |
| Sens 5 | nd | nd | nd | 33% | nd | nd | nd | nd | nd |
| Spec 5 | nd | nd | nd | 80% | nd | nd | nd | nd | nd |
| Cutoff 6 | nd | nd | nd | 268000 | nd | nd | nd | nd | nd |
| Sens 6 | nd | nd | nd | 0% | nd | nd | nd | nd | nd |
| Spec 6 | nd | nd | nd | 90% | nd | nd | nd | nd | nd |
| OR Quart 2 | nd | nd | nd | 0 | nd | nd | nd | nd | nd |
| p Value | nd | nd | nd | na | nd | nd | nd | nd | nd |
| 95% CI of | nd | nd | nd | na | nd | nd | nd | nd | nd |
| OR Quart2 | nd | nd | nd | na | nd | nd | nd | nd | nd |
| OR Quart 3 | nd | nd | nd | 1.0 | nd | nd | nd | nd | nd |
| p Value | nd | nd | nd | 1.0 | nd | nd | nd | nd | nd |
| 95% CI of | nd | nd | nd | 0.14 | nd | nd | nd | nd | nd |
| OR Quart3 | nd | nd | nd | 7.3 | nd | nd | nd | nd | nd |
| OR Quart 4 | nd | nd | nd | 1.0 | nd | nd | nd | nd | nd |
| p Value | nd | nd | nd | 1.0 | nd | nd | nd | nd | nd |
| 95% CI of | nd | nd | nd | 0.14 | nd | nd | nd | nd | nd |
| OR Quart4 | nd | nd | nd | 7.3 | nd | nd | nd | nd | nd |

Platelet-derived growth factor subunit B (dimer)

sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | nd | nd | 337 | 403 | nd | nd |
| Average | nd | nd | 394 | 748 | nd | nd |
| Stdev | nd | nd | 270 | 983 | nd | nd |
| p(t-test) | nd | nd | | 0.0034 | nd | nd |
| Min | nd | nd | 0.189 | 91.9 | nd | nd |
| Max | nd | nd | 2690 | 2720 | nd | nd |
| n (Samp) | nd | nd | 355 | 6 | nd | nd |
| n (Patient) | nd | nd | 192 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | nd | nd | nd | 0.57 | nd | nd | nd | nd | nd |
| SE | nd | nd | nd | 0.12 | nd | nd | nd | nd | nd |
| p | nd | nd | nd | 0.59 | nd | nd | nd | nd | nd |
| nCohort 1 | nd | nd | nd | 355 | nd | nd | nd | nd | nd |
| nCohort 2 | nd | nd | nd | 6 | nd | nd | nd | nd | nd |
| Cutoff 1 | nd | nd | nd | 242 | nd | nd | nd | nd | nd |
| Sens 1 | nd | nd | nd | 83% | nd | nd | nd | nd | nd |
| Spec 1 | nd | nd | nd | 31% | nd | nd | nd | nd | nd |
| Cutoff 2 | nd | nd | nd | 242 | nd | nd | nd | nd | nd |
| Sens 2 | nd | nd | nd | 83% | nd | nd | nd | nd | nd |
| Spec 2 | nd | nd | nd | 31% | nd | nd | nd | nd | nd |
| Cutoff 3 | nd | nd | nd | 91.4 | nd | nd | nd | nd | nd |
| Sens 3 | nd | nd | nd | 100% | nd | nd | nd | nd | nd |
| Spec 3 | nd | nd | nd | 7% | nd | nd | nd | nd | nd |
| Cutoff 4 | nd | nd | nd | 495 | nd | nd | nd | nd | nd |
| Sens 4 | nd | nd | nd | 33% | nd | nd | nd | nd | nd |
| Spec 4 | nd | nd | nd | 70% | nd | nd | nd | nd | nd |
| Cutoff 5 | nd | nd | nd | 581 | nd | nd | nd | nd | nd |
| Sens 5 | nd | nd | nd | 33% | nd | nd | nd | nd | nd |
| Spec 5 | nd | nd | nd | 80% | nd | nd | nd | nd | nd |
| Cutoff 6 | nd | nd | nd | 699 | nd | nd | nd | nd | nd |
| Sens 6 | nd | nd | nd | 17% | nd | nd | nd | nd | nd |
| Spec 6 | nd | nd | nd | 90% | nd | nd | nd | nd | nd |
| OR Quart 2 | nd | nd | nd | 1.0 | nd | nd | nd | nd | nd |
| p Value | nd | nd | nd | 1.0 | nd | nd | nd | nd | nd |
| 95% CI of | nd | nd | nd | 0.062 | nd | nd | nd | nd | nd |
| OR Quart2 | nd | nd | nd | 16 | nd | nd | nd | nd | nd |
| OR Quart 3 | nd | nd | nd | 2.0 | nd | nd | nd | nd | nd |
| p Value | nd | nd | nd | 0.57 | nd | nd | nd | nd | nd |
| 95% CI of | nd | nd | nd | 0.18 | nd | nd | nd | nd | nd |
| OR Quart3 | nd | nd | nd | 23 | nd | nd | nd | nd | nd |
| OR Quart 4 | nd | nd | nd | 2.0 | nd | nd | nd | nd | nd |
| p Value | nd | nd | nd | 0.57 | nd | nd | nd | nd | nd |
| 95% CI of | nd | nd | nd | 0.18 | nd | nd | nd | nd | nd |
| OR Quart4 | nd | nd | nd | 22 | nd | nd | nd | nd | nd |

Pigment epithelium-derived factor sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| Median | nd | nd | 1670 | 1350 | nd | nd |
| Average | nd | nd | 1920 | 1180 | nd | nd |
| Stdev | nd | nd | 1130 | 498 | nd | nd |
| p(t-test) | nd | nd | | 0.11 | nd | nd |
| Min | nd | nd | 84.2 | 339 | nd | nd |
| Max | nd | nd | 7450 | 1650 | nd | nd |
| n (Samp) | nd | nd | 367 | 6 | nd | nd |
| n (Patient) | nd | nd | 197 | 6 | nd | nd |

-continued

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | nd | nd | nd | 0.29 | nd | nd | nd | nd | nd |
| SE | nd | nd | nd | 0.12 | nd | nd | nd | nd | nd |
| p | nd | nd | nd | 0.086 | nd | nd | nd | nd | nd |
| nCohort 1 | nd | nd | nd | 367 | nd | nd | nd | nd | nd |
| nCohort 2 | nd | nd | nd | 6 | nd | nd | nd | nd | nd |
| Cutoff 1 | nd | nd | nd | 823 | nd | nd | nd | nd | nd |
| Sens 1 | nd | nd | nd | 83% | nd | nd | nd | nd | nd |
| Spec 1 | nd | nd | nd | 10% | nd | nd | nd | nd | nd |
| Cutoff 2 | nd | nd | nd | 823 | nd | nd | nd | nd | nd |
| Sens 2 | nd | nd | nd | 83% | nd | nd | nd | nd | nd |
| Spec 2 | nd | nd | nd | 10% | nd | nd | nd | nd | nd |
| Cutoff 3 | nd | nd | nd | 328 | nd | nd | nd | nd | nd |
| Sens 3 | nd | nd | nd | 100% | nd | nd | nd | nd | nd |
| Spec 3 | nd | nd | nd | 1% | nd | nd | nd | nd | nd |
| Cutoff 4 | nd | nd | nd | 2120 | nd | nd | nd | nd | nd |
| Sens 4 | nd | nd | nd | 0% | nd | nd | nd | nd | nd |
| Spec 4 | nd | nd | nd | 70% | nd | nd | nd | nd | nd |
| Cutoff 5 | nd | nd | nd | 2510 | nd | nd | nd | nd | nd |
| Sens 5 | nd | nd | nd | 0% | nd | nd | nd | nd | nd |
| Spec 5 | nd | nd | nd | 80% | nd | nd | nd | nd | nd |
| Cutoff 6 | nd | nd | nd | 3550 | nd | nd | nd | nd | nd |
| Sens 6 | nd | nd | nd | 0% | nd | nd | nd | nd | nd |
| Spec 6 | nd | nd | nd | 90% | nd | nd | nd | nd | nd |
| OR Quart 2 | nd | nd | nd | >0 | nd | nd | nd | nd | nd |
| p Value | nd | nd | nd | <na | nd | nd | nd | nd | nd |
| 95% CI of OR Quart2 | nd | nd | nd | >na na | nd | nd | nd | nd | nd |
| OR Quart 3 | nd | nd | nd | >4.2 | nd | nd | nd | nd | nd |
| p Value | nd | nd | nd | <0.20 | nd | nd | nd | nd | nd |
| 95% CI of OR Quart3 | nd | nd | nd | >0.46 na | nd | nd | nd | nd | nd |
| OR Quart 4 | nd | nd | nd | >2.1 | nd | nd | nd | nd | nd |
| p Value | nd | nd | nd | <0.56 | nd | nd | nd | nd | nd |
| 95% CI of OR Quart4 | nd | nd | nd | >0.18 na | nd | nd | nd | nd | nd |

Tumor necrosis factor receptor superfamily member 8 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| Median | nd | nd | 102 | 71.9 | nd | nd |
| Average | nd | nd | 195 | 189 | nd | nd |
| Stdev | nd | nd | 388 | 223 | nd | nd |
| p(t-test) | nd | nd | 0.97 | | nd | nd |
| Min | nd | nd | 4.06 | 30.8 | nd | nd |
| Max | nd | nd | 3360 | 595 | nd | nd |
| n (Samp) | nd | nd | 298 | 6 | nd | nd |
| n (Patient) | nd | nd | 167 | 6 | nd | nd |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | nd | nd | nd | 0.43 | nd | nd | nd | nd | nd |
| SE | nd | nd | nd | 0.12 | nd | nd | nd | nd | nd |
| p | nd | nd | nd | 0.58 | nd | nd | nd | nd | nd |
| nCohort 1 | nd | nd | nd | 298 | nd | nd | nd | nd | nd |
| nCohort 2 | nd | nd | nd | 6 | nd | nd | nd | nd | nd |
| Cutoff 1 | nd | nd | nd | 54.3 | nd | nd | nd | nd | nd |
| Sens 1 | nd | nd | nd | 83% | nd | nd | nd | nd | nd |
| Spec 1 | nd | nd | nd | 14% | nd | nd | nd | nd | nd |
| Cutoff 2 | nd | nd | nd | 54.3 | nd | nd | nd | nd | nd |
| Sens 2 | nd | nd | nd | 83% | nd | nd | nd | nd | nd |
| Spec 2 | nd | nd | nd | 14% | nd | nd | nd | nd | nd |
| Cutoff 3 | nd | nd | nd | 30.2 | nd | nd | nd | nd | nd |
| Sens 3 | nd | nd | nd | 100% | nd | nd | nd | nd | nd |
| Spec 3 | nd | nd | nd | 4% | nd | nd | nd | nd | nd |
| Cutoff 4 | nd | nd | nd | 149 | nd | nd | nd | nd | nd |
| Sens 4 | nd | nd | nd | 33% | nd | nd | nd | nd | nd |
| Spec 4 | nd | nd | nd | 70% | nd | nd | nd | nd | nd |
| Cutoff 5 | nd | nd | nd | 205 | nd | nd | nd | nd | nd |

-continued

| | | | | | | | | | |
|---|---|---|---|---|---|---|---|---|---|
| Sens 5 | nd | nd | nd | 33% | nd | nd | nd | nd | nd |
| Spec 5 | nd | nd | nd | 81% | nd | nd | nd | nd | nd |
| Cutoff 6 | nd | nd | nd | 305 | nd | nd | nd | nd | nd |
| Sens 6 | nd | nd | nd | 33% | nd | nd | nd | nd | nd |
| Spec 6 | nd | nd | nd | 90% | nd | nd | nd | nd | nd |
| OR Quart 2 | nd | nd | nd | 0 | nd | nd | nd | nd | nd |
| p Value | nd | nd | nd | na | nd | nd | nd | nd | nd |
| 95% CI of OR Quart2 | nd | nd | nd | na na | nd | nd | nd | nd | nd |
| OR Quart 3 | nd | nd | nd | 0.49 | nd | nd | nd | nd | nd |
| p Value | nd | nd | nd | 0.57 | nd | nd | nd | nd | nd |
| 95% CI of OR Quart3 | nd | nd | nd | 0.044 5.6 | nd | nd | nd | nd | nd |
| OR Quart 4 | nd | nd | nd | 1.5 | nd | nd | nd | nd | nd |
| p Value | nd | nd | nd | 0.65 | nd | nd | nd | nd | nd |
| 95% CI of OR Quart4 | nd | nd | nd | 0.25 9.4 | nd | nd | nd | nd | nd |

Alpha-fetoprotein

| | sCr or UO | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | nd | nd | 0.328 | 0.608 | nd | nd |
| Average | nd | nd | 0.351 | 0.738 | nd | nd |
| Stdev | nd | nd | 0.339 | 0.576 | nd | nd |
| p(t-test) | nd | nd | | 0.0065 | nd | nd |
| Min | nd | nd | 0.00580 | 0.00580 | nd | nd |
| Max | nd | nd | 1.81 | 1.53 | nd | nd |
| n (Samp) | nd | nd | 367 | 6 | nd | nd |
| n (Patient) | nd | nd | 197 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | nd | nd | nd | 0.71 | nd | nd | nd | nd | nd |
| SE | nd | nd | nd | 0.12 | nd | nd | nd | nd | nd |
| p | nd | nd | nd | 0.087 | nd | nd | nd | nd | nd |
| nCohort 1 | nd | nd | nd | 367 | nd | nd | nd | nd | nd |
| nCohort 2 | nd | nd | nd | 6 | nd | nd | nd | nd | nd |
| Cutoff 1 | nd | nd | nd | 0.369 | nd | nd | nd | nd | nd |
| Sens 1 | nd | nd | nd | 83% | nd | nd | nd | nd | nd |
| Spec 1 | nd | nd | nd | 57% | nd | nd | nd | nd | nd |
| Cutoff 2 | nd | nd | nd | 0.369 | nd | nd | nd | nd | nd |
| Sens 2 | nd | nd | nd | 83% | nd | nd | nd | nd | nd |
| Spec 2 | nd | nd | nd | 57% | nd | nd | nd | nd | nd |
| Cutoff 3 | nd | nd | nd | 0 | nd | nd | nd | nd | nd |
| Sens 3 | nd | nd | nd | 100% | nd | nd | nd | nd | nd |
| Spec 3 | nd | nd | nd | 0% | nd | nd | nd | nd | nd |
| Cutoff 4 | nd | nd | nd | 0.509 | nd | nd | nd | nd | nd |
| Sens 4 | nd | nd | nd | 67% | nd | nd | nd | nd | nd |
| Spec 4 | nd | nd | nd | 70% | nd | nd | nd | nd | nd |
| Cutoff 5 | nd | nd | nd | 0.598 | nd | nd | nd | nd | nd |
| Sens 5 | nd | nd | nd | 50% | nd | nd | nd | nd | nd |
| Spec 5 | nd | nd | nd | 80% | nd | nd | nd | nd | nd |
| Cutoff 6 | nd | nd | nd | 0.784 | nd | nd | nd | nd | nd |
| Sens 6 | nd | nd | nd | 33% | nd | nd | nd | nd | nd |
| Spec 6 | nd | nd | nd | 90% | nd | nd | nd | nd | nd |
| OR Quart 2 | nd | nd | nd | 0 | nd | nd | nd | nd | nd |
| p Value | nd | nd | nd | na | nd | nd | nd | nd | nd |
| 95% CI of OR Quart2 | nd | nd | nd | na na | nd | nd | nd | nd | nd |
| OR Quart 3 | nd | nd | nd | 1.0 | nd | nd | nd | nd | nd |
| p Value | nd | nd | nd | 1.0 | nd | nd | nd | nd | nd |
| 95% CI of OR Quart3 | nd | nd | nd | 0.062 16 | nd | nd | nd | nd | nd |
| OR Quart 4 | nd | nd | nd | 4.1 | nd | nd | nd | nd | nd |
| p Value | nd | nd | nd | 0.21 | nd | nd | nd | nd | nd |
| 95% CI of OR Quart4 | nd | nd | nd | 0.45 37 | nd | nd | nd | nd | nd |

-continued

| | Apolipoprotein E | | | | | |
|---|---|---|---|---|---|---|
| | sCr or UO | | | | | |
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | 51000 | 28200 | 51000 | 42800 | nd | nd |
| Average | 61600 | 35600 | 61600 | 39400 | nd | nd |
| Stdev | 44300 | 15000 | 44300 | 11700 | nd | nd |
| p(t-test) | | 0.098 | | 0.19 | nd | nd |
| Min | 1940 | 22400 | 1940 | 25800 | nd | nd |
| Max | 260000 | 59600 | 260000 | 54900 | nd | nd |
| n (Samp) | 434 | 8 | 434 | 7 | nd | nd |
| n (Patient) | 233 | 8 | 233 | 7 | nd | nd |

| | UO only | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| Median | nd | nd | 48700 | 37100 | nd | nd |
| Average | nd | nd | 59500 | 38400 | nd | nd |
| Stdev | nd | nd | 42000 | 12400 | nd | nd |
| p(t-test) | nd | nd | | 0.22 | nd | nd |
| Min | nd | nd | 1940 | 25800 | nd | nd |
| Max | nd | nd | 244000 | 54900 | nd | nd |
| n (Samp) | nd | nd | 400 | 6 | nd | nd |
| n (Patient) | nd | nd | 205 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.30 | nd | nd | 0.36 | nd | 0.36 | nd | nd | nd |
| SE | 0.10 | nd | nd | 0.11 | nd | 0.12 | nd | nd | nd |
| p | 0.058 | nd | nd | 0.21 | nd | 0.25 | nd | nd | nd |
| nCohort 1 | 434 | nd | nd | 434 | nd | 400 | nd | nd | nd |
| nCohort 2 | 8 | nd | nd | 7 | nd | 6 | nd | nd | nd |
| Cutoff 1 | 25600 | nd | nd | 31300 | nd | 25800 | nd | nd | nd |
| Sens 1 | 75% | nd | nd | 71% | nd | 83% | nd | nd | nd |
| Spec 1 | 17% | nd | nd | 26% | nd | 19% | nd | nd | nd |
| Cutoff 2 | 23900 | nd | nd | 25800 | nd | 25800 | nd | nd | nd |
| Sens 2 | 88% | nd | nd | 86% | nd | 83% | nd | nd | nd |
| Spec 2 | 15% | nd | nd | 18% | nd | 19% | nd | nd | nd |
| Cutoff 3 | 20900 | nd | nd | 25800 | nd | 25800 | nd | nd | nd |
| Sens 3 | 100% | nd | nd | 100% | nd | 100% | nd | nd | nd |
| Spec 3 | 13% | nd | nd | 18% | nd | 19% | nd | nd | nd |
| Cutoff 4 | 69500 | nd | nd | 69500 | nd | 67600 | nd | nd | nd |
| Sens 4 | 0% | nd | nd | 0% | nd | 0% | nd | nd | nd |
| Spec 4 | 70% | nd | nd | 70% | nd | 70% | nd | nd | nd |
| Cutoff 5 | 87400 | nd | nd | 87400 | nd | 86400 | nd | nd | nd |
| Sens 5 | 0% | nd | nd | 0% | nd | 0% | nd | nd | nd |
| Spec 5 | 80% | nd | nd | 80% | nd | 80% | nd | nd | nd |
| Cutoff 6 | 120000 | nd | nd | 120000 | nd | 110000 | nd | nd | nd |
| Sens 6 | 0% | nd | nd | 0% | nd | 0% | nd | nd | nd |
| Spec 6 | 90% | nd | nd | 90% | nd | 90% | nd | nd | nd |
| OR Quart 2 | >2.1 | nd | nd | >1.0 | nd | >2.1 | nd | nd | nd |
| p Value | <0.56 | nd | nd | <0.99 | nd | <0.56 | nd | nd | nd |
| 95% CI of | >0.18 | nd | nd | >0.063 | nd | >0.18 | nd | nd | nd |
| OR Quart2 | na | nd | nd | na | nd | na | nd | nd | nd |
| OR Quart 3 | >1.0 | nd | nd | >4.2 | nd | >2.0 | nd | nd | nd |
| p Value | <0.99 | nd | nd | <0.20 | nd | <0.56 | nd | nd | nd |
| 95% CI of | >0.062 | nd | nd | >0.46 | nd | >0.18 | nd | nd | nd |
| OR Quart3 | na | nd | nd | na | nd | na | nd | nd | nd |
| OR Quart 4 | >5.3 | nd | nd | >2.1 | nd | >2.1 | nd | nd | nd |
| p Value | <0.13 | nd | nd | <0.56 | nd | <0.56 | nd | nd | nd |
| 95% CI of | >0.61 | nd | nd | >0.18 | nd | >0.18 | nd | nd | nd |
| OR Quart4 | na | nd | nd | na | nd | na | nd | nd | nd |

FIG. 11: Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | Complement C4-B | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 16.6 | 33.8 | 18.1 | 31.8 | 18.9 | 43.7 |
| Average | 59.8 | 80.1 | 63.5 | 70.6 | 59.4 | 84.2 |
| Stdev | 150 | 154 | 154 | 83.8 | 152 | 163 |
| p (t-test) | | 0.25 | | 0.84 | | 0.21 |
| Min | 0.00329 | 0.00263 | 0.00263 | 0.448 | 0.00329 | 0.00263 |
| Max | 1950 | 1150 | 1950 | 245 | 1950 | 1150 |
| n (Samp) | 383 | 92 | 451 | 20 | 296 | 79 |
| n (Patient) | 383 | 92 | 451 | 20 | 296 | 79 |

| | At Enrollment | | |
|---|---|---|---|
| | sCr or UO | sCr only | UO only |
| AUC | 0.59 | 0.57 | 0.60 |
| SE | 0.034 | 0.068 | 0.037 |
| p | 0.0090 | 0.33 | 0.0092 |
| nCohort 1 | 383 | 451 | 296 |
| nCohort 2 | 92 | 20 | 79 |
| Cutoff 1 | 8.26 | 9.33 | 8.97 |
| Sens 1 | 71% | 70% | 71% |
| Spec 1 | 38% | 41% | 38% |
| Cutoff 2 | 4.30 | 4.27 | 5.44 |
| Sens 2 | 80% | 80% | 81% |
| Spec 2 | 25% | 24% | 28% |
| Cutoff 3 | 1.74 | 1.07 | 1.77 |
| Sens 3 | 90% | 90% | 91% |
| Spec 3 | 15% | 9% | 14% |
| Cutoff 4 | 36.7 | 44.0 | 38.7 |
| Sens 4 | 49% | 50% | 51% |
| Spec 4 | 70% | 70% | 70% |
| Cutoff 5 | 62.0 | 65.8 | 62.0 |
| Sens 5 | 34% | 40% | 34% |
| Spec 5 | 80% | 80% | 80% |
| Cutoff 6 | 147 | 150 | 129 |
| Sens 6 | 15% | 20% | 18% |
| Spec 6 | 90% | 90% | 90% |
| OR Quart 2 | 0.93 | 0.58 | 1.1 |
| p Value | 0.84 | 0.47 | 0.72 |
| 95% CI of | 0.46 | 0.14 | 0.54 |
| OR Quart 2 | 1.9 | 2.5 | 2.5 |
| OR Quart 3 | 1.1 | 0.58 | 1.1 |
| p Value | 0.75 | 0.47 | 0.72 |
| 95% CI of | 0.57 | 0.14 | 0.54 |
| OR Quart 3 | 2.2 | 2.5 | 2.5 |
| OR Quart 4 | 2.1 | 1.8 | 2.4 |
| p Value | 0.023 | 0.28 | 0.013 |
| 95% CI of | 1.1 | 0.60 | 1.2 |
| OR Quart 4 | 3.9 | 5.7 | 4.9 |

| | C-C motif chemokine 26 | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.0311 | 0.0405 | 0.0320 | 0.0436 | 0.0311 | 0.0402 |
| Average | 0.0737 | 0.647 | 0.162 | 0.728 | 0.0500 | 0.737 |
| Stdev | 0.497 | 4.50 | 2.04 | 2.03 | 0.177 | 4.85 |
| p (t-test) | | 0.015 | | 0.23 | | 0.015 |
| Min | 0.00872 | 0.00872 | 0.00872 | 0.00872 | 0.00872 | 0.00872 |
| Max | 9.14 | 42.3 | 42.3 | 7.53 | 2.75 | 42.3 |
| n (Samp) | 383 | 92 | 451 | 20 | 297 | 79 |
| n (Patient) | 383 | 92 | 451 | 20 | 297 | 79 |

-continued

|  | At Enrollment | | |
|---|---|---|---|
|  | sCr or UO | sCr only | UO only |
| AUC | 0.60 | 0.66 | 0.57 |
| SE | 0.034 | 0.068 | 0.037 |
| p | 0.0030 | 0.020 | 0.056 |
| nCohort 1 | 383 | 451 | 297 |
| nCohort 2 | 92 | 20 | 79 |
| Cutoff 1 | 0.0297 | 0.0311 | 0.0291 |
| Sens 1 | 71% | 70% | 76% |
| Spec 1 | 49% | 49% | 45% |
| Cutoff 2 | 0.0236 | 0.0262 | 0.0232 |
| Sens 2 | 80% | 80% | 82% |
| Spec 2 | 45% | 44% | 35% |
| Cutoff 3 | 0.0195 | 0.0232 | 0.0195 |
| Sens 3 | 95% | 90% | 94% |
| Spec 3 | 18% | 35% | 18% |
| Cutoff 4 | 0.0443 | 0.0443 | 0.0443 |
| Sens 4 | 28% | 40% | 25% |
| Spec 4 | 75% | 75% | 72% |
| Cutoff 5 | 0.0486 | 0.0486 | 0.0504 |
| Sens 5 | 24% | 40% | 20% |
| Spec 5 | 80% | 80% | 86% |
| Cutoff 6 | 0.0525 | 0.0525 | 0.0525 |
| Sens 6 | 21% | 30% | 19% |
| Spec 6 | 91% | 90% | 90% |
| OR Quart 2 | 2.3 | 2.0 | 2.6 |
| p Value | 0.031 | 0.42 | 0.017 |
| 95% CI of OR Quart 2 | 1.1 5.0 | 0.36 11 | 1.2 5.7 |
| OR Quart 3 | 3.9 | 3.1 | 3.0 |
| p Value | 3.0E−4 | 0.17 | 0.0047 |
| 95% CI of OR Quart 3 | 1.9 8.1 | 0.61 16 | 1.4 6.6 |
| OR Quart 4 | 2.5 | 4.2 | 1.7 |
| p Value | 0.021 | 0.074 | 0.22 |
| 95% CI of OR Quart 4 | 1.1 5.3 | 0.87 20 | 0.73 3.8 |

| C-C motif chemokine 7 | | | | | | |
|---|---|---|---|---|---|---|
|  | sCr or UO | | sCr only | | UO only | |
|  | Cohort 1 | Cohort 2 | Cohort 1 | Cohort 2 | Cohort 1 | Cohort 2 |
| Median | 0.515 | 0.812 | 0.515 | 1.29 | 0.584 | 0.625 |
| Average | 2.03 | 14.0 | 2.82 | 39.3 | 2.36 | 14.4 |
| Stdev | 8.31 | 60.4 | 15.9 | 110 | 9.29 | 64.5 |
| p (t-test) |  | 2.0E−4 |  | 6.4E−9 |  | 0.0020 |
| Min | 0.146 | 0.146 | 0.146 | 0.188 | 0.146 | 0.146 |
| Max | 125 | 488 | 291 | 488 | 125 | 488 |
| n (Samp) | 385 | 92 | 453 | 20 | 298 | 79 |
| n (Patient) | 385 | 92 | 453 | 20 | 298 | 79 |

|  | At Enrollment | | |
|---|---|---|---|
|  | sCr or UO | sCr only | UO only |
| AUC | 0.62 | 0.76 | 0.56 |
| SE | 0.034 | 0.064 | 0.037 |
| p | 6.5E−4 | 5.6E−5 | 0.11 |
| nCohort 1 | 385 | 453 | 298 |
| nCohort 2 | 92 | 20 | 79 |
| Cutoff 1 | 0.386 | 0.812 | 0.336 |
| Sens 1 | 71% | 70% | 73% |
| Spec 1 | 47% | 65% | 33% |
| Cutoff 2 | 0.320 | 0.584 | 0.319 |
| Sens 2 | 83% | 80% | 84% |
| Spec 2 | 34% | 54% | 26% |
| Cutoff 3 | 0.264 | 0.386 | 0.264 |
| Sens 3 | 92% | 90% | 91% |
| Spec 3 | 15% | 45% | 13% |
| Cutoff 4 | 0.816 | 0.816 | 1.04 |
| Sens 4 | 45% | 60% | 38% |
| Spec 4 | 73% | 70% | 76% |
| Cutoff 5 | 1.07 | 1.11 | 1.15 |
| Sens 5 | 40% | 60% | 24% |
| Spec 5 | 80% | 80% | 82% |

-continued

| | | | |
|---|---|---|---|
| Cutoff 6 | 1.59 | 1.59 | 1.59 |
| Sens 6 | 20% | 40% | 19% |
| Spec 6 | 93% | 92% | 92% |
| OR Quart 2 | 2.1 | 3.1 | 2.0 |
| p Value | 0.052 | 0.34 | 0.072 |
| 95% CI of | 0.99 | 0.31 | 0.94 |
| OR Quart 2 | 4.3 | 30 | 4.1 |
| OR Quart 3 | 1.5 | 4.1 | 1.0 |
| p Value | 0.34 | 0.21 | 1.0 |
| 95% CI of | 0.68 | 0.45 | 0.45 |
| OR Quart 3 | 3.1 | 37 | 2.2 |
| OR Quart 4 | 3.6 | 13 | 2.3 |
| p Value | 2.7E−4 | 0.014 | 0.026 |
| 95% CI of | 1.8 | 1.7 | 1.1 |
| OR Quart 4 | 7.3 | 100 | 4.7 |

Vascular endothelial growth factor receptor 3

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 308 | 354 | 315 | 403 | 308 | 348 |
| Average | 297 | 431 | 322 | 403 | 295 | 437 |
| Stdev | 170 | 381 | 241 | 87.3 | 168 | 412 |
| p (t-test) | | 2.1E−4 | | 0.32 | | 5.1E−4 |
| Min | 1.37 | 1.37 | 1.37 | 308 | 1.37 | 1.37 |
| Max | 942 | 2750 | 2750 | 601 | 942 | 2750 |
| n (Samp) | 196 | 53 | 238 | 9 | 171 | 45 |
| n (Patient) | 196 | 53 | 238 | 9 | 171 | 45 |

| At Enrollment | | | |
|---|---|---|---|
| | sCr or UO | sCr only | UO only |
| AUC | 0.63 | 0.68 | 0.63 |
| SE | 0.045 | 0.10 | 0.049 |
| p | 0.0029 | 0.081 | 0.010 |
| nCohort 1 | 196 | 238 | 171 |
| nCohort 2 | 53 | 9 | 45 |
| Cutoff 1 | 282 | 332 | 273 |
| Sens 1 | 72% | 78% | 71% |
| Spec 1 | 48% | 55% | 46% |
| Cutoff 2 | 229 | 315 | 219 |
| Sens 2 | 81% | 89% | 82% |
| Spec 2 | 37% | 52% | 34% |
| Cutoff 3 | 163 | 295 | 66.4 |
| Sens 3 | 91% | 100% | 96% |
| Spec 3 | 22% | 47% | 11% |
| Cutoff 4 | 397 | 414 | 381 |
| Sens 4 | 49% | 33% | 47% |
| Spec 4 | 72% | 73% | 70% |
| Cutoff 5 | 440 | 445 | 425 |
| Sens 5 | 36% | 11% | 40% |
| Spec 5 | 81% | 81% | 81% |
| Cutoff 6 | 496 | 537 | 486 |
| Sens 6 | 28% | 11% | 33% |
| Spec 6 | 90% | 90% | 90% |
| OR Quart 2 | 1.6 | >1.0 | 1.3 |
| p Value | 0.33 | <1.0 | 0.61 |
| 95% CI of | 0.61 | >0.061 | 0.47 |
| OR Quart 2 | 4.3 | na | 3.6 |
| OR Quart 3 | 1.6 | >6.5 | 1.0 |
| p Value | 0.33 | <0.087 | 1.0 |
| 95% CI of | 0.61 | >0.76 | 0.35 |
| OR Quart 3 | 4.3 | na | 2.9 |
| OR Quart 4 | 3.4 | >2.0 | 3.1 |
| p Value | 0.0087 | <0.57 | 0.017 |
| 95% CI of | 1.4 | >0.18 | 1.2 |
| OR Quart 4 | 8.4 | na | 8.0 |

Insulin-like growth factor-binding protein 5

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.0682 | 0.0682 | nd | nd | 0.0682 | 0.0682 |
| Average | 0.801 | 0.752 | nd | nd | 0.788 | 0.760 |

-continued

| | | | | | | |
|---|---|---|---|---|---|---|
| Stdev | 1.63 | 1.13 | nd | nd | 1.66 | 1.16 |
| p (t-test) | | 0.87 | nd | nd | | 0.93 |
| Min | 0.0116 | 0.0116 | nd | nd | 0.0116 | 0.0116 |
| Max | 10.3 | 3.92 | nd | nd | 10.3 | 3.92 |
| n (Samp) | 138 | 32 | nd | nd | 119 | 30 |
| n (Patient) | 138 | 32 | nd | nd | 119 | 30 |

| | At Enrollment | | |
|---|---|---|---|
| | sCr or UO | sCr only | UO only |
| AUC | 0.49 | nd | 0.49 |
| SE | 0.057 | nd | 0.059 |
| p | 0.86 | nd | 0.86 |
| nCohort 1 | 138 | nd | 119 |
| nCohort 2 | 32 | nd | 30 |
| Cutoff 1 | 0.0116 | nd | 0.0116 |
| Sens 1 | 88% | nd | 87% |
| Spec 1 | 8% | nd | 9% |
| Cutoff 2 | 0.0116 | nd | 0.0116 |
| Sens 2 | 88% | nd | 87% |
| Spec 2 | 8% | nd | 9% |
| Cutoff 3 | 0 | nd | 0 |
| Sens 3 | 100% | nd | 100% |
| Spec 3 | 0% | nd | 0% |
| Cutoff 4 | 0.397 | nd | 0.397 |
| Sens 4 | 34% | nd | 33% |
| Spec 4 | 73% | nd | 75% |
| Cutoff 5 | 1.43 | nd | 1.40 |
| Sens 5 | 19% | nd | 23% |
| Spec 5 | 81% | nd | 81% |
| Cutoff 6 | 3.00 | nd | 3.00 |
| Sens 6 | 6% | nd | 7% |
| Spec 6 | 91% | nd | 92% |
| OR Quart 2 | 0.31 | nd | 0.54 |
| p Value | 0.061 | nd | 0.29 |
| 95% CI of | 0.089 | nd | 0.17 |
| OR Quart 2 | 1.1 | nd | 1.7 |
| OR Quart 3 | 0.57 | nd | 0.34 |
| p Value | 0.29 | nd | 0.094 |
| 95% CI of | 0.20 | nd | 0.096 |
| OR Quart 3 | 1.6 | nd | 1.2 |
| OR Quart 4 | 0.91 | nd | 1.0 |
| p Value | 0.85 | nd | 0.94 |
| 95% CI of | 0.34 | nd | 0.37 |
| OR Quart 4 | 2.4 | nd | 2.9 |

| Immunoglogulin G4 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 180 | 384 | 203 | 460 | 203 | 405 |
| Average | 452 | 829 | 508 | 894 | 476 | 853 |
| Stdev | 664 | 921 | 717 | 977 | 671 | 928 |
| p (t-test) | | 8.8E−6 | | 0.021 | | 6.1E−5 |
| Min | 0.00862 | 0.00996 | 0.00862 | 4.20 | 0.410 | 0.00996 |
| Max | 2400 | 2400 | 2400 | 2400 | 2400 | 2400 |
| n (Samp) | 379 | 92 | 447 | 20 | 292 | 79 |
| n (Patient) | 379 | 92 | 447 | 20 | 292 | 79 |

| | At Enrollment | | |
|---|---|---|---|
| | sCr or UO | sCr only | UO only |
| AUC | 0.62 | 0.60 | 0.62 |
| SE | 0.034 | 0.068 | 0.037 |
| p | 4.7E−4 | 0.15 | 0.0011 |
| nCohort 1 | 379 | 447 | 292 |
| nCohort 2 | 92 | 20 | 79 |
| Cutoff 1 | 132 | 241 | 134 |
| Sens 1 | 71% | 70% | 71% |
| Spec 1 | 42% | 54% | 40% |
| Cutoff 2 | 76.0 | 32.8 | 95.9 |
| Sens 2 | 80% | 80% | 81% |
| Spec 2 | 29% | 15% | 33% |
| Cutoff 3 | 21.3 | 20.5 | 41.4 |
| Sens 3 | 90% | 90% | 91% |

-continued

| | | | |
|---|---|---|---|
| Spec 3 | 13% | 12% | 18% |
| Cutoff 4 | 383 | 431 | 402 |
| Sens 4 | 50% | 50% | 51% |
| Spec 4 | 70% | 70% | 70% |
| Cutoff 5 | 597 | 676 | 663 |
| Sens 5 | 38% | 40% | 35% |
| Spec 5 | 80% | 80% | 80% |
| Cutoff 6 | 1470 | 2150 | 1510 |
| Sens 6 | 26% | 25% | 25% |
| Spec 6 | 90% | 90% | 90% |
| OR Quart 2 | 0.99 | 0 | 1.2 |
| p Value | 0.98 | na | 0.70 |
| 95% CI of | 0.47 | na | 0.52 |
| OR Quart 2 | 2.1 | na | 2.6 |
| OR Quart 3 | 1.5 | 0.82 | 1.9 |
| p Value | 0.23 | 0.75 | 0.10 |
| 95% CI of | 0.76 | 0.24 | 0.88 |
| OR Quart 3 | 3.1 | 2.8 | 4.0 |
| OR Quart 4 | 2.9 | 1.5 | 2.8 |
| p Value | 0.0015 | 0.44 | 0.0067 |
| 95% CI of | 1.5 | 0.53 | 1.3 |
| OR Quart 4 | 5.6 | 4.4 | 5.7 |

Interleukin-21

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 8.33 | 5.94 | 7.99 | 5.73 | 7.44 | 5.97 |
| Average | 11.0 | 8.67 | 10.7 | 7.27 | 10.1 | 8.75 |
| Stdev | 10.9 | 8.64 | 10.7 | 6.70 | 10.1 | 8.81 |
| p (t-test) | | 0.055 | | 0.16 | | 0.28 |
| Min | 0.0122 | 0.00404 | 0.00404 | 0.0219 | 0.0122 | 0.00404 |
| Max | 67.7 | 42.1 | 67.7 | 22.6 | 66.5 | 42.1 |
| n (Samp) | 383 | 92 | 451 | 20 | 297 | 79 |
| n (Patient) | 383 | 92 | 451 | 20 | 297 | 79 |

| | At Enrollment | | |
|---|---|---|---|
| | sCr or UO | sCr only | UO only |
| AUC | 0.43 | 0.42 | 0.46 |
| SE | 0.034 | 0.068 | 0.037 |
| p | 0.051 | 0.22 | 0.24 |
| nCohort 1 | 383 | 451 | 297 |
| nCohort 2 | 92 | 20 | 79 |
| Cutoff 1 | 2.65 | 2.61 | 3.08 |
| Sens 1 | 71% | 70% | 71% |
| Spec 1 | 26% | 26% | 29% |
| Cutoff 2 | 0.596 | 1.78 | 0.586 |
| Sens 2 | 80% | 80% | 81% |
| Spec 2 | 9% | 20% | 10% |
| Cutoff 3 | 0.0247 | 0.0528 | 0.0247 |
| Sens 3 | 92% | 90% | 92% |
| Spec 3 | 3% | 5% | 3% |
| Cutoff 4 | 14.5 | 13.9 | 12.8 |
| Sens 4 | 23% | 20% | 24% |
| Spec 4 | 70% | 70% | 70% |
| Cutoff 5 | 18.0 | 17.5 | 16.9 |
| Sens 5 | 13% | 10% | 15% |
| Spec 5 | 80% | 80% | 80% |
| Cutoff 6 | 24.7 | 24.2 | 22.6 |
| Sens 6 | 5% | 0% | 6% |
| Spec 6 | 90% | 90% | 90% |
| OR Quart 2 | 1.1 | 0.74 | 1.0 |
| p Value | 0.86 | 0.70 | 1.0 |
| 95% CI of | 0.53 | 0.16 | 0.48 |
| OR Quart 2 | 2.2 | 3.4 | 2.1 |
| OR Quart 3 | 1.8 | 1.8 | 1.6 |
| p Value | 0.076 | 0.36 | 0.22 |
| 95% CI of | 0.94 | 0.51 | 0.77 |
| OR Quart 3 | 3.5 | 6.3 | 3.1 |
| OR Quart 4 | 1.6 | 1.5 | 1.3 |
| p Value | 0.17 | 0.51 | 0.47 |
| 95% CI of | 0.82 | 0.42 | 0.64 |
| OR Quart 4 | 3.1 | 5.6 | 2.7 |

-continued

| | Interleukin-23 | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 302 | 96.7 | 268 | 3.63 | 302 | 102 |
| Average | 492 | 329 | 466 | 280 | 487 | 327 |
| Stdev | 691 | 526 | 671 | 497 | 700 | 520 |
| p (t-test) | | 0.035 | | 0.22 | | 0.059 |
| Min | 0.491 | 0.491 | 0.491 | 0.552 | 0.491 | 0.491 |
| Max | 8520 | 3250 | 8520 | 1820 | 8520 | 3250 |
| n (Samp) | 383 | 92 | 451 | 20 | 297 | 79 |
| n (Patient) | 383 | 92 | 451 | 20 | 297 | 79 |

| | At Enrollment | | |
|---|---|---|---|
| | sCr or UO | sCr only | UO only |
| AUC | 0.40 | 0.35 | 0.41 |
| SE | 0.034 | 0.068 | 0.037 |
| p | 0.0044 | 0.028 | 0.011 |
| nCohort 1 | 383 | 451 | 297 |
| nCohort 2 | 92 | 20 | 79 |
| Cutoff 1 | 1.09 | 0.747 | 1.30 |
| Sens 1 | 71% | 70% | 71% |
| Spec 1 | 20% | 12% | 23% |
| Cutoff 2 | 0.844 | 0.708 | 1.01 |
| Sens 2 | 80% | 80% | 81% |
| Spec 2 | 14% | 10% | 17% |
| Cutoff 3 | 0.708 | 0.552 | 0.708 |
| Sens 3 | 90% | 95% | 94% |
| Spec 3 | 10% | 1% | 9% |
| Cutoff 4 | 603 | 553 | 608 |
| Sens 4 | 21% | 20% | 20% |
| Spec 4 | 70% | 70% | 70% |
| Cutoff 5 | 844 | 794 | 813 |
| Sens 5 | 12% | 10% | 13% |
| Spec 5 | 80% | 80% | 80% |
| Cutoff 6 | 1350 | 1180 | 1200 |
| Sens 6 | 5% | 10% | 5% |
| Spec 6 | 90% | 90% | 90% |
| OR Quart 2 | 1.0 | 1.0 | 1.2 |
| p Value | 1.0 | 1.0 | 0.68 |
| 95% CI of | 0.47 | 0.20 | 0.53 |
| OR Quart 2 | 2.1 | 5.1 | 2.6 |
| OR Quart 3 | 2.3 | 1.3 | 2.3 |
| p Value | 0.016 | 0.70 | 0.032 |
| 95% CI of | 1.2 | 0.29 | 1.1 |
| OR Quart 3 | 4.4 | 6.1 | 4.7 |
| OR Quart 4 | 2.1 | 3.6 | 2.4 |
| p Value | 0.031 | 0.058 | 0.021 |
| 95% CI of | 1.1 | 0.96 | 1.1 |
| OR Quart 4 | 4.1 | 13 | 5.0 |

| | Interleukin-28A | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 17.6 | 13.7 | 17.6 | 3.22 | 20.5 | 12.2 |
| Average | 32.5 | 29.4 | 32.3 | 20.4 | 32.6 | 29.5 |
| Stdev | 39.0 | 38.5 | 39.2 | 28.4 | 38.8 | 39.7 |
| p (t-test) | | 0.49 | | 0.18 | | 0.54 |
| Min | 0.0254 | 0.0254 | 0.0254 | 0.0495 | 0.0254 | 0.0254 |
| Max | 197 | 164 | 197 | 91.1 | 197 | 164 |
| n (Samp) | 383 | 92 | 451 | 20 | 297 | 79 |
| n (Patient) | 383 | 92 | 451 | 20 | 297 | 79 |

| | At Enrollment | | |
|---|---|---|---|
| | sCr or UO | sCr only | UO only |
| AUC | 0.47 | 0.38 | 0.47 |
| SE | 0.034 | 0.068 | 0.037 |
| p | 0.43 | 0.076 | 0.38 |
| nCohort 1 | 383 | 451 | 297 |
| nCohort 2 | 92 | 20 | 79 |

-continued

| | | | |
|---|---|---|---|
| Cutoff 1 | 0.194 | 0.0860 | 0.184 |
| Sens 1 | 71% | 70% | 71% |
| Spec 1 | 25% | 13% | 22% |
| Cutoff 2 | 0.137 | 0.0784 | 0.0928 |
| Sens 2 | 80% | 80% | 84% |
| Spec 2 | 19% | 9% | 15% |
| Cutoff 3 | 0.0860 | 0.0775 | 0.0860 |
| Sens 3 | 90% | 90% | 91% |
| Spec 3 | 14% | 6% | 14% |
| Cutoff 4 | 45.8 | 44.0 | 45.8 |
| Sens 4 | 24% | 15% | 24% |
| Spec 4 | 70% | 70% | 70% |
| Cutoff 5 | 59.9 | 59.5 | 59.5 |
| Sens 5 | 17% | 10% | 18% |
| Spec 5 | 80% | 80% | 80% |
| Cutoff 6 | 84.4 | 84.9 | 84.4 |
| Sens 6 | 10% | 5% | 10% |
| Spec 6 | 90% | 90% | 90% |
| OR Quart 2 | 1.3 | 1.7 | 1.3 |
| p Value | 0.41 | 0.48 | 0.47 |
| 95% CI of | 0.69 | 0.40 | 0.64 |
| OR Quart 2 | 2.5 | 7.3 | 2.7 |
| OR Quart 3 | 1.0 | 1.0 | 1.0 |
| p Value | 1.0 | 1.0 | 1.0 |
| 95% CI of | 0.51 | 0.20 | 0.48 |
| OR Quart 3 | 2.0 | 5.1 | 2.1 |
| OR Quart 4 | 1.5 | 3.2 | 1.6 |
| p Value | 0.24 | 0.088 | 0.22 |
| 95% CI of | 0.77 | 0.84 | 0.77 |
| OR Quart 4 | 2.8 | 12 | 3.1 |

| | Interleukin-33 | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 42.8 | 33.3 | 41.5 | 23.7 | 42.8 | 36.0 |
| Average | 55.8 | 41.2 | 53.4 | 33.2 | 55.5 | 42.7 |
| Stdev | 66.2 | 42.0 | 62.6 | 45.0 | 69.4 | 42.9 |
| p (t-test) | | 0.045 | | 0.15 | | 0.12 |
| Min | 0.0232 | 0.0232 | 0.0232 | 0.0372 | 0.0232 | 0.0232 |
| Max | 958 | 227 | 958 | 170 | 958 | 227 |
| n (Samp) | 383 | 92 | 451 | 20 | 297 | 79 |
| n (Patient) | 383 | 92 | 451 | 20 | 297 | 79 |

| | At Enrollment | | |
|---|---|---|---|
| | sCr or UO | sCr only | UO only |
| AUC | 0.42 | 0.35 | 0.43 |
| SE | 0.034 | 0.068 | 0.037 |
| p | 0.015 | 0.025 | 0.049 |
| nCohort 1 | 383 | 451 | 297 |
| nCohort 2 | 92 | 20 | 79 |
| Cutoff 1 | 13.7 | 1.57 | 14.3 |
| Sens 1 | 71% | 70% | 71% |
| Spec 1 | 22% | 14% | 21% |
| Cutoff 2 | 0.0879 | 0.0645 | 0.0879 |
| Sens 2 | 80% | 80% | 81% |
| Spec 2 | 11% | 8% | 9% |
| Cutoff 3 | 0.0538 | 0.0518 | 0.0518 |
| Sens 3 | 90% | 90% | 92% |
| Spec 3 | 4% | 4% | 3% |
| Cutoff 4 | 69.3 | 67.1 | 68.2 |
| Sens 4 | 20% | 15% | 20% |
| Spec 4 | 70% | 70% | 70% |
| Cutoff 5 | 92.2 | 85.1 | 88.8 |
| Sens 5 | 9% | 10% | 9% |
| Spec 5 | 80% | 80% | 80% |
| Cutoff 6 | 120 | 118 | 119 |
| Sens 6 | 7% | 10% | 6% |
| Spec 6 | 90% | 90% | 90% |
| OR Quart 2 | 1.5 | 0.66 | 1.4 |
| p Value | 0.29 | 0.65 | 0.35 |
| 95% CI of | 0.72 | 0.11 | 0.68 |
| OR Quart 2 | 2.9 | 4.0 | 3.0 |
| OR Quart 3 | 1.6 | 2.1 | 1.3 |
| p Value | 0.17 | 0.32 | 0.45 |

-continued

| | | | |
|---|---|---|---|
| 95% CI of OR Quart 3 | 0.81 | 0.50 | 0.63 |
| OR Quart 4 | 3.2 | 8.4 | 2.8 |
| p Value | 2.2 | 3.2 | 1.9 |
| 95% CI of OR Quart 4 | 0.022 | 0.088 | 0.077 |
| | 1.1 | 0.84 | 0.93 |
| | 4.3 | 12 | 3.9 |

| Vascular endothelial growth factor receptor 2 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 488 | 849 | 578 | 751 | 488 | 868 |
| Average | 702 | 1100 | 767 | 1250 | 698 | 1070 |
| Stdev | 724 | 865 | 754 | 1110 | 722 | 806 |
| p (t-test) | | 8.8E-4 | | 0.064 | | 0.0036 |
| Min | 0.218 | 67.0 | 0.218 | 122 | 0.218 | 67.0 |
| Max | 4860 | 3610 | 4860 | 3610 | 4860 | 3460 |
| n (Samp) | 193 | 52 | 235 | 9 | 169 | 44 |
| n (Patient) | 193 | 52 | 235 | 9 | 169 | 44 |

| | At Enrollment | | |
|---|---|---|---|
| | sCr or UO | sCr only | UO only |
| AUC | 0.67 | 0.67 | 0.66 |
| SE | 0.045 | 0.10 | 0.049 |
| p | 1.9E-4 | 0.083 | 7.9E-4 |
| nCohort 1 | 193 | 235 | 169 |
| nCohort 2 | 52 | 9 | 44 |
| Cutoff 1 | 598 | 709 | 578 |
| Sens 1 | 71% | 78% | 70% |
| Spec 1 | 58% | 63% | 55% |
| Cutoff 2 | 414 | 626 | 370 |
| Sens 2 | 81% | 89% | 82% |
| Spec 2 | 45% | 55% | 41% |
| Cutoff 3 | 219 | 106 | 219 |
| Sens 3 | 90% | 100% | 91% |
| Spec 3 | 27% | 17% | 27% |
| Cutoff 4 | 809 | 898 | 801 |
| Sens 4 | 52% | 44% | 55% |
| Spec 4 | 70% | 71% | 70% |
| Cutoff 5 | 1310 | 1370 | 1250 |
| Sens 5 | 33% | 22% | 34% |
| Spec 5 | 80% | 80% | 80% |
| Cutoff 6 | 1680 | 1770 | 1710 |
| Sens 6 | 17% | 22% | 16% |
| Spec 6 | 90% | 90% | 91% |
| OR Quart 2 | 1.6 | 0 | 1.7 |
| p Value | 0.41 | na | 0.38 |
| 95% CI of OR Quart 2 | 0.53 | na | 0.52 |
| | 4.8 | na | 5.6 |
| OR Quart 3 | 4.1 | 6.5 | 3.8 |
| p Value | 0.0054 | 0.087 | 0.017 |
| 95% CI of OR Quart 3 | 1.5 | 0.76 | 1.3 |
| | 11 | 56 | 11 |
| OR Quart 4 | 3.8 | 2.0 | 4.0 |
| p Value | 0.0100 | 0.57 | 0.012 |
| 95% CI of OR Quart 4 | 1.4 | 0.18 | 1.4 |
| | 10 | 23 | 12 |

| Neural cell adhesion molecule 1 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 2390 | 3490 | 2600 | 4140 | 2460 | 3690 |
| Average | 3020 | 5420 | 3300 | 7660 | 3060 | 5620 |
| Stdev | 2320 | 7250 | 3470 | 8830 | 2110 | 7570 |
| p (t-test) | | 8.6E-8 | | 9.1E-7 | | 5.2E-7 |
| Min | 6.83 | 138 | 6.83 | 142 | 173 | 138 |
| Max | 22000 | 55700 | 55700 | 31700 | 15500 | 55700 |
| n (Samp) | 382 | 92 | 450 | 20 | 295 | 79 |
| n (Patient) | 382 | 92 | 450 | 20 | 295 | 79 |

-continued

|  | At Enrollment | | |
|---|---|---|---|
|  | sCr or UO | sCr only | UO only |
| AUC | 0.64 | 0.66 | 0.64 |
| SE | 0.034 | 0.068 | 0.037 |
| p | 3.9E−5 | 0.019 | 1.5E−4 |
| nCohort 1 | 382 | 450 | 295 |
| nCohort 2 | 92 | 20 | 79 |
| Cutoff 1 | 2490 | 2810 | 2670 |
| Sens 1 | 71% | 70% | 71% |
| Spec 1 | 52% | 54% | 53% |
| Cutoff 2 | 1880 | 2200 | 2060 |
| Sens 2 | 80% | 80% | 81% |
| Spec 2 | 36% | 42% | 40% |
| Cutoff 3 | 1210 | 1420 | 1110 |
| Sens 3 | 90% | 90% | 91% |
| Spec 3 | 19% | 23% | 16% |
| Cutoff 4 | 3670 | 3830 | 3790 |
| Sens 4 | 48% | 50% | 47% |
| Spec 4 | 70% | 70% | 70% |
| Cutoff 5 | 4530 | 4660 | 4720 |
| Sens 5 | 33% | 50% | 33% |
| Spec 5 | 80% | 80% | 80% |
| Cutoff 6 | 5740 | 6110 | 5940 |
| Sens 6 | 23% | 30% | 24% |
| Spec 6 | 90% | 90% | 90% |
| OR Quart 2 | 1.3 | 0.99 | 1.7 |
| p Value | 0.57 | 0.99 | 0.22 |
| 95% CI of | 0.57 | 0.20 | 0.73 |
| OR Quart 2 | 2.7 | 5.0 | 4.0 |
| OR Quart 3 | 2.6 | 1.3 | 3.1 |
| p Value | 0.0078 | 0.70 | 0.0063 |
| 95% CI of | 1.3 | 0.29 | 1.4 |
| OR Quart 3 | 5.4 | 6.1 | 6.8 |
| OR Quart 4 | 3.2 | 3.5 | 3.5 |
| p Value | 0.0010 | 0.061 | 0.0018 |
| 95% CI of | 1.6 | 0.94 | 1.6 |
| OR Quart 4 | 6.5 | 13 | 7.8 |

| Platelet-derived growth factor subunit B (dimer) | | | | | | |
|---|---|---|---|---|---|---|
|  | sCr or UO | | sCr only | | UO only | |
|  | Cohort 1 | Cohort 2 | Cohort 1 | Cohort 2 | Cohort 1 | Cohort 2 |
| Median | 1.13 | 1.32 | 1.13 | 2.52 | 1.17 | 1.32 |
| Average | 2.50 | 21.1 | 5.21 | 20.7 | 2.59 | 23.2 |
| Stdev | 6.41 | 120 | 50.9 | 47.9 | 6.55 | 126 |
| p (t-test) |  | 0.0085 |  | 0.28 |  | 0.018 |
| Min | 0.00246 | 0.00705 | 0.00246 | 0.436 | 0.00246 | 0.00705 |
| Max | 67.2 | 935 | 935 | 176 | 67.2 | 935 |
| n (Samp) | 294 | 62 | 340 | 13 | 215 | 56 |
| n (Patient) | 294 | 62 | 340 | 13 | 215 | 56 |

|  | At Enrollment | | |
|---|---|---|---|
|  | sCr or UO | sCr only | UO only |
| AUC | 0.57 | 0.73 | 0.56 |
| SE | 0.041 | 0.081 | 0.044 |
| p | 0.11 | 0.0038 | 0.18 |
| nCohort 1 | 294 | 340 | 215 |
| nCohort 2 | 62 | 13 | 56 |
| Cutoff 1 | 0.708 | 1.39 | 0.648 |
| Sens 1 | 71% | 77% | 71% |
| Spec 1 | 35% | 57% | 34% |
| Cutoff 2 | 0.429 | 0.928 | 0.392 |
| Sens 2 | 81% | 85% | 80% |
| Spec 2 | 27% | 44% | 27% |
| Cutoff 3 | 0.0488 | 0.850 | 0.0144 |
| Sens 3 | 90% | 92% | 91% |
| Spec 3 | 16% | 41% | 11% |
| Cutoff 4 | 2.00 | 2.07 | 2.13 |
| Sens 4 | 42% | 69% | 38% |
| Spec 4 | 70% | 70% | 70% |
| Cutoff 5 | 2.99 | 3.02 | 3.00 |
| Sens 5 | 29% | 46% | 32% |
| Spec 5 | 80% | 80% | 80% |

-continued

| | | | |
|---|---|---|---|
| Cutoff 6 | 4.46 | 4.75 | 4.49 |
| Sens 6 | 19% | 31% | 21% |
| Spec 6 | 90% | 90% | 90% |
| OR Quart 2 | 1.7 | >3.1 | 1.3 |
| p Value | 0.22 | <0.33 | 0.53 |
| 95% CI of | 0.73 | >0.32 | 0.55 |
| OR Quart 2 | 3.8 | na | 3.2 |
| OR Quart 3 | 1.4 | >4.2 | 1.1 |
| p Value | 0.40 | <0.20 | 0.85 |
| 95% CI of | 0.62 | >0.46 | 0.44 |
| OR Quart 3 | 3.3 | na | 2.7 |
| OR Quart 4 | 1.9 | >6.4 | 2.0 |
| p Value | 0.11 | <0.090 | 0.11 |
| 95% CI of | 0.86 | >0.75 | 0.86 |
| OR Quart 4 | 4.3 | na | 4.6 |

Corticotropin

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.00174 | 0.00208 | nd | nd | 0.00174 | 0.00208 |
| Average | 0.00227 | 0.00468 | nd | nd | 0.00252 | 0.00404 |
| Stdev | 0.00351 | 0.00835 | nd | nd | 0.00436 | 0.00776 |
| p (t-test) | | 0.025 | nd | nd | | 0.22 |
| Min | 0.000355 | 0.000388 | nd | nd | 0.000355 | 0.000388 |
| Max | 0.0373 | 0.0377 | nd | nd | 0.0373 | 0.0377 |
| n (Samp) | 111 | 24 | nd | nd | 92 | 22 |
| n (Patient) | 111 | 24 | nd | nd | 92 | 22 |

At Enrollment

| | sCr or UO | sCr only | UO only |
|---|---|---|---|
| AUC | 0.57 | nd | 0.58 |
| SE | 0.066 | nd | 0.070 |
| p | 0.29 | nd | 0.28 |
| nCohort 1 | 111 | nd | 92 |
| nCohort 2 | 24 | nd | 22 |
| Cutoff 1 | 0.00136 | nd | 0.00136 |
| Sens 1 | 71% | nd | 73% |
| Spec 1 | 28% | nd | 28% |
| Cutoff 2 | 0.00106 | nd | 0.00109 |
| Sens 2 | 92% | nd | 82% |
| Spec 2 | 17% | nd | 18% |
| Cutoff 3 | 0.00106 | nd | 0.00106 |
| Sens 3 | 92% | nd | 91% |
| Spec 3 | 17% | nd | 18% |
| Cutoff 4 | 0.00227 | nd | 0.00212 |
| Sens 4 | 42% | nd | 50% |
| Spec 4 | 70% | nd | 71% |
| Cutoff 5 | 0.00282 | nd | 0.00282 |
| Sens 5 | 29% | nd | 27% |
| Spec 5 | 82% | nd | 82% |
| Cutoff 6 | 0.00356 | nd | 0.00362 |
| Sens 6 | 25% | nd | 23% |
| Spec 6 | 90% | nd | 90% |
| OR Quart 2 | 0.36 | nd | 0.42 |
| p Value | 0.17 | nd | 0.26 |
| 95% CI of | 0.084 | nd | 0.095 |
| OR Quart 2 | 1.5 | nd | 1.9 |
| OR Quart 3 | 0.64 | nd | 0.80 |
| p Value | 0.49 | nd | 0.74 |
| 95% CI of | 0.18 | nd | 0.21 |
| OR Quart 3 | 2.3 | nd | 3.0 |
| OR Quart 4 | 1.3 | nd | 1.4 |
| p Value | 0.61 | nd | 0.59 |
| 95% CI of | 0.43 | nd | 0.41 |
| OR Quart 4 | 4.1 | nd | 4.7 |

Thyroxine-binding globulin

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.0625 | 0.225 | 0.0709 | 0.432 | 0.0629 | 0.240 |
| Average | 0.165 | 0.369 | 0.192 | 0.489 | 0.168 | 0.380 |

-continued

| | | | | | | |
|---|---|---|---|---|---|---|
| Stdev | 0.254 | 0.639 | 0.363 | 0.493 | 0.261 | 0.679 |
| p (t-test) | | 0.0035 | | 0.027 | | 0.0084 |
| Min | 0.000478 | 0.00343 | 0.000478 | 0.00635 | 0.000478 | 0.00343 |
| Max | 1.59 | 3.60 | 3.60 | 1.47 | 1.59 | 3.60 |
| n (Samp) | 139 | 35 | 165 | 8 | 112 | 30 |
| n (Patient) | 139 | 35 | 165 | 8 | 112 | 30 |

| | At Enrollment | | |
|---|---|---|---|
| | sCr or UO | sCr only | UO only |
| AUC | 0.63 | 0.69 | 0.64 |
| SE | 0.055 | 0.11 | 0.060 |
| p | 0.016 | 0.080 | 0.019 |
| nCohort 1 | 139 | 165 | 112 |
| nCohort 2 | 35 | 8 | 30 |
| Cutoff 1 | 0.0777 | 0.136 | 0.109 |
| Sens 1 | 71% | 75% | 70% |
| Spec 1 | 56% | 67% | 62% |
| Cutoff 2 | 0.0164 | 0.0115 | 0.0179 |
| Sens 2 | 80% | 88% | 80% |
| Spec 2 | 24% | 17% | 26% |
| Cutoff 3 | 0.00635 | 0.00620 | 0.00767 |
| Sens 3 | 91% | 100% | 90% |
| Spec 3 | 11% | 10% | 11% |
| Cutoff 4 | 0.135 | 0.163 | 0.142 |
| Sens 4 | 60% | 62% | 60% |
| Spec 4 | 71% | 70% | 71% |
| Cutoff 5 | 0.259 | 0.296 | 0.248 |
| Sens 5 | 43% | 50% | 50% |
| Spec 5 | 81% | 81% | 80% |
| Cutoff 6 | 0.466 | 0.486 | 0.466 |
| Sens 6 | 23% | 50% | 20% |
| Spec 6 | 91% | 90% | 90% |
| OR Quart 2 | 0.21 | 0 | 0.44 |
| p Value | 0.057 | na | 0.27 |
| 95% CI of | 0.042 | na | 0.10 |
| OR Quart 2 | 1.0 | na | 1.9 |
| OR Quart 3 | 1.2 | 0.49 | 1.2 |
| p Value | 0.79 | 0.56 | 0.76 |
| 95% CI of | 0.40 | 0.043 | 0.36 |
| OR Quart 3 | 3.4 | 5.6 | 4.0 |
| OR Quart 4 | 2.5 | 2.6 | 3.1 |
| p Value | 0.068 | 0.26 | 0.046 |
| 95% CI of | 0.94 | 0.48 | 1.0 |
| OR Quart 4 | 6.7 | 14 | 9.3 |

Pigment epithelium-derived factor

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 2.47 | 3.75 | 2.62 | 19.9 | 2.76 | 3.80 |
| Average | 18.9 | 28.6 | 19.2 | 51.2 | 21.1 | 29.4 |
| Stdev | 44.7 | 51.4 | 44.0 | 72.0 | 48.8 | 51.8 |
| p (t-test) | | 0.071 | | 0.0021 | | 0.19 |
| Min | 0.000401 | 0.00102 | 0.000401 | 0.0292 | 0.000401 | 0.00102 |
| Max | 391 | 250 | 391 | 250 | 391 | 250 |
| n (Samp) | 383 | 92 | 451 | 20 | 296 | 79 |
| n (Patient) | 383 | 92 | 451 | 20 | 296 | 79 |

| | At Enrollment | | |
|---|---|---|---|
| | sCr or UO | sCr only | UO only |
| AUC | 0.57 | 0.64 | 0.57 |
| SE | 0.034 | 0.068 | 0.037 |
| p | 0.030 | 0.040 | 0.046 |
| nCohort 1 | 383 | 451 | 296 |
| nCohort 2 | 92 | 20 | 79 |
| Cutoff 1 | 1.71 | 3.61 | 1.78 |
| Sens 1 | 71% | 70% | 71% |
| Spec 1 | 42% | 57% | 41% |
| Cutoff 2 | 0.935 | 0.613 | 1.16 |
| Sens 2 | 80% | 80% | 81% |
| Spec 2 | 32% | 22% | 32% |
| Cutoff 3 | 0.293 | 0.155 | 0.346 |
| Sens 3 | 90% | 90% | 91% |

| | | | |
|---|---|---|---|
| Spec 3 | 12% | 5% | 11% |
| Cutoff 4 | 8.12 | 8.68 | 8.83 |
| Sens 4 | 37% | 50% | 39% |
| Spec 4 | 70% | 70% | 70% |
| Cutoff 5 | 21.8 | 21.9 | 23.7 |
| Sens 5 | 30% | 50% | 30% |
| Spec 5 | 80% | 80% | 80% |
| Cutoff 6 | 51.3 | 52.3 | 60.9 |
| Sens 6 | 15% | 25% | 13% |
| Spec 6 | 90% | 90% | 90% |
| OR Quart 2 | 1.5 | 0.19 | 2.0 |
| p Value | 0.23 | 0.13 | 0.072 |
| 95% CI of OR Quart 2 | 0.76 | 0.022 | 0.94 |
|  | 3.1 | 1.7 | 4.2 |
| OR Quart 3 | 1.6 | 0.79 | 1.5 |
| p Value | 0.18 | 0.72 | 0.34 |
| 95% CI of OR Quart 3 | 0.81 | 0.21 | 0.67 |
|  | 3.2 | 3.0 | 3.2 |
| OR Quart 4 | 2.1 | 2.1 | 2.2 |
| p Value | 0.036 | 0.20 | 0.035 |
| 95% CI of OR Quart 4 | 1.0 | 0.69 | 1.1 |
|  | 4.0 | 6.3 | 4.7 |

Tumor necrosis factor receptor superfamily member 8

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 16.9 | 32.3 | 18.6 | 29.0 | 13.2 | 32.9 |
| Average | 22.1 | 65.9 | 30.7 | 56.7 | 20.5 | 73.1 |
| Stdev | 27.0 | 110 | 56.8 | 105 | 26.9 | 117 |
| p (t-test) | | 6.9E−7 | | 0.18 | | 1.7E−7 |
| Min | 0.0493 | 0.0688 | 0.0493 | 0.0688 | 0.0493 | 0.196 |
| Max | 265 | 554 | 554 | 353 | 265 | 554 |
| n (Samp) | 197 | 55 | 240 | 10 | 172 | 47 |
| n (Patient) | 197 | 55 | 240 | 10 | 172 | 47 |

| | At Enrollment | | |
|---|---|---|---|
| | sCr or UO | sCr only | UO only |
| AUC | 0.63 | 0.60 | 0.66 |
| SE | 0.044 | 0.097 | 0.047 |
| p | 0.0023 | 0.28 | 7.0E−4 |
| nCohort 1 | 197 | 240 | 172 |
| nCohort 2 | 55 | 10 | 47 |
| Cutoff 1 | 11.4 | 24.9 | 11.4 |
| Sens 1 | 71% | 70% | 70% |
| Spec 1 | 39% | 63% | 41% |
| Cutoff 2 | 5.14 | 11.4 | 5.09 |
| Sens 2 | 80% | 80% | 81% |
| Spec 2 | 24% | 37% | 26% |
| Cutoff 3 | 1.18 | 7.30 | 1.18 |
| Sens 3 | 91% | 90% | 91% |
| Spec 3 | 15% | 31% | 17% |
| Cutoff 4 | 26.3 | 27.4 | 25.7 |
| Sens 4 | 51% | 50% | 53% |
| Spec 4 | 71% | 71% | 70% |
| Cutoff 5 | 32.6 | 38.9 | 31.4 |
| Sens 5 | 49% | 20% | 51% |
| Spec 5 | 80% | 80% | 80% |
| Cutoff 6 | 46.6 | 62.5 | 42.2 |
| Sens 6 | 31% | 10% | 36% |
| Spec 6 | 90% | 90% | 90% |
| OR Quart 2 | 0.80 | 2.0 | 0.98 |
| p Value | 0.64 | 0.58 | 0.97 |
| 95% CI of OR Quart 2 | 0.32 | 0.18 | 0.36 |
|  | 2.0 | 23 | 2.7 |
| OR Quart 3 | 0.53 | 4.2 | 0.50 |
| p Value | 0.22 | 0.20 | 0.24 |
| 95% CI of OR Quart 3 | 0.19 | 0.46 | 0.16 |
|  | 1.5 | 39 | 1.6 |
| OR Quart 4 | 3.0 | 3.0 | 3.9 |
| p Value | 0.0077 | 0.34 | 0.0029 |
| 95% CI of OR Quart 4 | 1.3 | 0.31 | 1.6 |
|  | 6.7 | 30 | 9.4 |

-continued

| | Alpha-fetoprotein | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.00520 | 0.00660 | nd | nd | 0.00554 | 0.00660 |
| Average | 0.0545 | 0.137 | nd | nd | 0.0561 | 0.135 |
| Stdev | 0.125 | 0.473 | nd | nd | 0.131 | 0.486 |
| p (t-test) | | 0.049 | nd | nd | | 0.083 |
| Min | 0.000463 | 0.000463 | nd | nd | 0.000463 | 0.000463 |
| Max | 0.889 | 2.85 | nd | nd | 0.889 | 2.85 |
| n (Samp) | 169 | 36 | nd | nd | 150 | 34 |
| n (Patient) | 169 | 36 | nd | nd | 150 | 34 |

| | At Enrollment | | |
|---|---|---|---|
| | sCr or UO | sCr only | UO only |
| AUC | 0.57 | nd | 0.55 |
| SE | 0.054 | nd | 0.056 |
| p | 0.21 | nd | 0.33 |
| nCohort 1 | 169 | nd | 150 |
| nCohort 2 | 36 | nd | 34 |
| Cutoff 1 | 0.00483 | nd | 0.00483 |
| Sens 1 | 72% | nd | 71% |
| Spec 1 | 41% | nd | 41% |
| Cutoff 2 | 0.000523 | nd | 0.000523 |
| Sens 2 | 92% | nd | 91% |
| Spec 2 | 12% | nd | 13% |
| Cutoff 3 | 0.000523 | nd | 0.000523 |
| Sens 3 | 92% | nd | 91% |
| Spec 3 | 12% | nd | 13% |
| Cutoff 4 | 0.0444 | nd | 0.0385 |
| Sens 4 | 33% | nd | 32% |
| Spec 4 | 75% | nd | 70% |
| Cutoff 5 | 0.0728 | nd | 0.0671 |
| Sens 5 | 33% | nd | 32% |
| Spec 5 | 83% | nd | 80% |
| Cutoff 6 | 0.162 | nd | 0.162 |
| Sens 6 | 17% | nd | 15% |
| Spec 6 | 91% | nd | 90% |
| OR Quart 2 | 0.72 | nd | 0.62 |
| p Value | 0.57 | nd | 0.40 |
| 95% CI of | 0.23 | nd | 0.20 |
| OR Quart 2 | 2.2 | nd | 1.9 |
| OR Quart 3 | 1.3 | nd | 0.87 |
| p Value | 0.60 | nd | 0.79 |
| 95% CI of | 0.47 | nd | 0.30 |
| OR Quart 3 | 3.6 | nd | 2.5 |
| OR Quart 4 | 1.6 | nd | 1.3 |
| p Value | 0.35 | nd | 0.61 |
| 95% CI of | 0.60 | nd | 0.48 |
| OR Quart 4 | 4.4 | nd | 3.5 |

| | Apolipoprotein (a) | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 1.94 | 3.52 | 2.13 | 4.72 | 2.13 | 3.58 |
| Average | 21.6 | 26.4 | 22.1 | 35.5 | 14.0 | 29.9 |
| Stdev | 106 | 108 | 106 | 137 | 76.5 | 116 |
| p (t-test) | | 0.69 | | 0.58 | | 0.14 |
| Min | 0.00646 | 0.00838 | 0.00646 | 0.00838 | 0.00646 | 0.0122 |
| Max | 1110 | 802 | 1110 | 631 | 1000 | 802 |
| n (Samp) | 400 | 95 | 469 | 21 | 313 | 82 |
| n (Patient) | 400 | 95 | 469 | 21 | 313 | 82 |

| | At Enrollment | | |
|---|---|---|---|
| | sCr or UO | sCr only | UO only |
| AUC | 0.60 | 0.61 | 0.61 |
| SE | 0.033 | 0.067 | 0.036 |
| p | 0.0022 | 0.085 | 0.0025 |
| nCohort 1 | 400 | 469 | 313 |
| nCohort 2 | 95 | 21 | 82 |

-continued

|  |  |  |  |
|---|---|---|---|
| Cutoff 1 | 1.44 | 1.84 | 1.39 |
| Sens 1 | 71% | 71% | 71% |
| Spec 1 | 40% | 48% | 38% |
| Cutoff 2 | 0.995 | 1.39 | 0.977 |
| Sens 2 | 80% | 81% | 80% |
| Spec 2 | 31% | 39% | 29% |
| Cutoff 3 | 0.479 | 0.911 | 0.479 |
| Sens 3 | 92% | 90% | 93% |
| Spec 3 | 18% | 28% | 17% |
| Cutoff 4 | 3.74 | 4.16 | 3.78 |
| Sens 4 | 48% | 52% | 49% |
| Spec 4 | 70% | 70% | 70% |
| Cutoff 5 | 5.82 | 6.54 | 5.56 |
| Sens 5 | 32% | 29% | 35% |
| Spec 5 | 80% | 80% | 80% |
| Cutoff 6 | 13.5 | 16.9 | 10.1 |
| Sens 6 | 16% | 14% | 21% |
| Spec 6 | 90% | 90% | 90% |
| OR Quart 2 | 1.6 | 3.1 | 1.5 |
| p Value | 0.17 | 0.17 | 0.27 |
| 95% CI of OR Quart 2 | 0.81 | 0.61 | 0.72 |
|  | 3.3 | 16 | 3.2 |
| OR Quart 3 | 1.5 | 2.0 | 1.2 |
| p Value | 0.29 | 0.42 | 0.71 |
| 95% CI of OR Quart 3 | 0.72 | 0.37 | 0.53 |
|  | 3.0 | 11 | 2.5 |
| OR Quart 4 | 2.9 | 4.7 | 2.9 |
| p Value | 0.0014 | 0.050 | 0.0034 |
| 95% CI of OR Quart 4 | 1.5 | 1.0 | 1.4 |
|  | 5.7 | 22 | 5.8 |

FIG. 12: Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| | Complement C4-B ||||||
|---|---|---|---|---|---|---|
| | sCr or UO || sCr only || UO only ||
| | Cohort 1 | Cohort 2 | Cohort 1 | Cohort 2 | Cohort 1 | Cohort 2 |
| Median | 66700 | 61400 | nd | nd | 66100 | 60500 |
| Average | 74900 | 70900 | nd | nd | 73000 | 70800 |
| Stdev | 39100 | 44300 | nd | nd | 37800 | 46800 |
| p (t-test) | | 0.65 | nd | nd | | 0.80 |
| Min | 5220 | 9860 | nd | nd | 5220 | 9860 |
| Max | 203000 | 214000 | nd | nd | 170000 | 214000 |
| n (Samp) | 109 | 28 | nd | nd | 98 | 25 |
| n (Patient) | 109 | 28 | nd | nd | 98 | 25 |

| | At Enrollment |||
|---|---|---|---|
| | sCr or UO | sCr only | UO only |
| AUC | 0.47 | nd | 0.47 |
| SE | 0.062 | nd | 0.066 |
| p | 0.62 | nd | 0.63 |
| nCohort 1 | 109 | nd | 98 |
| nCohort 2 | 28 | nd | 25 |
| Cutoff 1 | 48500 | nd | 45900 |
| Sens 1 | 71% | nd | 72% |
| Spec 1 | 26% | nd | 26% |
| Cutoff 2 | 40100 | nd | 40100 |
| Sens 2 | 82% | nd | 80% |
| Spec 2 | 20% | nd | 21% |
| Cutoff 3 | 10700 | nd | 10700 |
| Sens 3 | 93% | nd | 92% |
| Spec 3 | 2% | nd | 2% |
| Cutoff 4 | 90300 | nd | 86600 |
| Sens 4 | 29% | nd | 32% |
| Spec 4 | 71% | nd | 70% |

-continued

| | | | |
|---|---|---|---|
| Cutoff 5 | 114000 | nd | 112000 |
| Sens 5 | 14% | nd | 16% |
| Spec 5 | 81% | nd | 81% |
| Cutoff 6 | 132000 | nd | 132000 |
| Sens 6 | 4% | nd | 4% |
| Spec 6 | 91% | nd | 91% |
| OR Quart 2 | 1.3 | nd | 0.51 |
| p Value | 0.71 | nd | 0.32 |
| 95% CI of | 0.37 | nd | 0.13 |
| OR Quart 2 | 4.2 | nd | 2.0 |
| OR Quart 3 | 1.3 | nd | 1.2 |
| p Value | 0.71 | nd | 0.77 |
| 95% CI of | 0.37 | nd | 0.37 |
| OR Quart 3 | 4.2 | nd | 3.8 |
| OR Quart 4 | 1.5 | nd | 0.86 |
| p Value | 0.51 | nd | 0.81 |
| 95% CI of | 0.46 | nd | 0.25 |
| OR Quart 4 | 4.9 | nd | 2.9 |

C-C motif chemokine 26

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.725 | 1.27 | 0.689 | 4.30 | 0.652 | 1.27 |
| Average | 5.53 | 5.61 | 5.23 | 10.5 | 5.47 | 4.12 |
| Stdev | 12.0 | 10.6 | 11.2 | 18.1 | 12.4 | 5.47 |
| p (t-test) | | 0.98 | | 0.25 | | 0.62 |
| Min | 0.0121 | 0.0121 | 0.0121 | 0.0232 | 0.0121 | 0.0121 |
| Max | 62.5 | 50.9 | 62.5 | 50.9 | 62.5 | 18.3 |
| n (Samp) | 89 | 26 | 108 | 7 | 81 | 22 |
| n (Patient) | 89 | 26 | 108 | 7 | 81 | 22 |

| | At Enrollment | | |
|---|---|---|---|
| | sCr or UO | sCr only | UO only |
| AUC | 0.52 | 0.61 | 0.54 |
| SE | 0.065 | 0.12 | 0.071 |
| p | 0.75 | 0.35 | 0.54 |
| nCohort 1 | 89 | 108 | 81 |
| nCohort 2 | 26 | 7 | 22 |
| Cutoff 1 | 0.0325 | 2.74 | 0.0339 |
| Sens 1 | 77% | 71% | 73% |
| Spec 1 | 18% | 67% | 23% |
| Cutoff 2 | 0.0232 | 0.0325 | 0.0232 |
| Sens 2 | 92% | 86% | 95% |
| Spec 2 | 8% | 19% | 7% |
| Cutoff 3 | 0.0232 | 0.0121 | 0.0232 |
| Sens 3 | 92% | 100% | 95% |
| Spec 3 | 8% | 3% | 7% |
| Cutoff 4 | 3.61 | 4.10 | 3.03 |
| Sens 4 | 42% | 57% | 41% |
| Spec 4 | 71% | 70% | 70% |
| Cutoff 5 | 6.86 | 6.86 | 6.58 |
| Sens 5 | 27% | 29% | 27% |
| Spec 5 | 83% | 81% | 80% |
| Cutoff 6 | 11.9 | 11.9 | 11.6 |
| Sens 6 | 12% | 14% | 9% |
| Spec 6 | 91% | 91% | 90% |
| OR Quart 2 | 0.40 | 0 | 0.58 |
| p Value | 0.18 | na | 0.44 |
| 95% CI of | 0.11 | na | 0.14 |
| OR Quart 2 | 1.5 | na | 2.3 |
| OR Quart 3 | 0.65 | 0.96 | 0.75 |
| p Value | 0.49 | 0.97 | 0.68 |
| 95% CI of | 0.19 | 0.13 | 0.20 |
| OR Quart 3 | 2.2 | 7.4 | 2.9 |
| OR Quart 4 | 0.95 | 1.5 | 1.2 |
| p Value | 0.93 | 0.67 | 0.81 |
| 95% CI of | 0.30 | 0.23 | 0.33 |
| OR Quart 4 | 3.0 | 9.7 | 4.1 |

-continued

| C-C motif chemokine 7 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.512 | 0.804 | 0.620 | 4.45 | 0.512 | 0.804 |
| Average | 7.45 | 31.8 | 8.43 | 82.9 | 7.42 | 36.4 |
| Stdev | 20.8 | 88.6 | 20.4 | 166 | 21.5 | 95.8 |
| p (t-test) | | 0.017 | | 2.0E−5 | | 0.012 |
| Min | 0.193 | 0.193 | 0.193 | 0.308 | 0.193 | 0.193 |
| Max | 166 | 449 | 166 | 449 | 166 | 449 |
| n (Samp) | 90 | 26 | 109 | 7 | 82 | 22 |
| n (Patient) | 90 | 26 | 109 | 7 | 82 | 22 |

| | At Enrollment | | |
|---|---|---|---|
| | sCr or UO | sCr only | UO only |
| AUC | 0.65 | 0.67 | 0.67 |
| SE | 0.064 | 0.12 | 0.069 |
| p | 0.020 | 0.15 | 0.014 |
| nCohort 1 | 90 | 109 | 82 |
| nCohort 2 | 26 | 7 | 22 |
| Cutoff 1 | 0.308 | 0.308 | 0.308 |
| Sens 1 | 81% | 86% | 82% |
| Spec 1 | 38% | 35% | 39% |
| Cutoff 2 | 0.308 | 0.308 | 0.308 |
| Sens 2 | 81% | 86% | 82% |
| Spec 2 | 38% | 35% | 39% |
| Cutoff 3 | 0.193 | 0.193 | 0.193 |
| Sens 3 | 92% | 100% | 91% |
| Spec 3 | 19% | 17% | 21% |
| Cutoff 4 | 0.804 | 2.71 | 0.804 |
| Sens 4 | 46% | 57% | 45% |
| Spec 4 | 71% | 71% | 73% |
| Cutoff 5 | 8.42 | 14.1 | 8.42 |
| Sens 5 | 42% | 43% | 45% |
| Spec 5 | 80% | 81% | 80% |
| Cutoff 6 | 18.4 | 28.9 | 17.1 |
| Sens 6 | 31% | 29% | 32% |
| Spec 6 | 90% | 91% | 90% |
| OR Quart 2 | 1.6 | >3.3 | 0.72 |
| p Value | 0.49 | <0.31 | 0.69 |
| 95% CI of | 0.41 | >0.33 | 0.14 |
| OR Quart 2 | 6.5 | na | 3.6 |
| OR Quart 3 | 1.3 | >1.0 | 1.3 |
| p Value | 0.72 | <0.98 | 0.71 |
| 95% CI of | 0.31 | >0.062 | 0.31 |
| OR Quart 3 | 5.4 | na | 5.6 |
| OR Quart 4 | 3.8 | >3.3 | 3.4 |
| p Value | 0.043 | <0.31 | 0.068 |
| 95% CI of | 1.0 | >0.33 | 0.91 |
| OR Quart 4 | 14 | na | 13 |

| Vascular endothelial growth factor receptor 3 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 5840 | 5630 | 5900 | 5010 | 5670 | 6100 |
| Average | 6920 | 6190 | 6810 | 5980 | 6780 | 6570 |
| Stdev | 4850 | 3230 | 4560 | 4390 | 4900 | 3350 |
| p (t-test) | | 0.47 | | 0.64 | | 0.85 |
| Min | 529 | 1720 | 529 | 1740 | 529 | 1720 |
| Max | 32400 | 14200 | 32400 | 14200 | 32400 | 14200 |
| n (Samp) | 90 | 26 | 109 | 7 | 82 | 22 |
| n (Patient) | 90 | 26 | 109 | 7 | 82 | 22 |

| | At Enrollment | | |
|---|---|---|---|
| | sCr or UO | sCr only | UO only |
| AUC | 0.48 | 0.43 | 0.52 |
| SE | 0.065 | 0.12 | 0.070 |
| p | 0.74 | 0.52 | 0.74 |
| nCohort 1 | 90 | 109 | 82 |
| nCohort 2 | 26 | 7 | 22 |

| | | | |
|---|---|---|---|
| Cutoff 1 | 3700 | 3700 | 4200 |
| Sens 1 | 73% | 71% | 73% |
| Spec 1 | 26% | 26% | 33% |
| Cutoff 2 | 2640 | 2240 | 2640 |
| Sens 2 | 85% | 86% | 86% |
| Spec 2 | 10% | 9% | 10% |
| Cutoff 3 | 2240 | 1720 | 2240 |
| Sens 3 | 92% | 100% | 91% |
| Spec 3 | 10% | 6% | 10% |
| Cutoff 4 | 7860 | 8040 | 7770 |
| Sens 4 | 35% | 29% | 41% |
| Spec 4 | 70% | 71% | 71% |
| Cutoff 5 | 9450 | 9630 | 9320 |
| Sens 5 | 23% | 14% | 32% |
| Spec 5 | 80% | 81% | 80% |
| Cutoff 6 | 12600 | 11600 | 11600 |
| Sens 6 | 4% | 14% | 5% |
| Spec 6 | 90% | 91% | 90% |
| OR Quart 2 | 0.82 | 0 | 0.43 |
| p Value | 0.75 | na | 0.28 |
| 95% CI of | 0.24 | na | 0.096 |
| OR Quart 2 | 2.8 | na | 2.0 |
| OR Quart 3 | 0.82 | 1.6 | 1.0 |
| p Value | 0.75 | 0.64 | 1.0 |
| 95% CI of | 0.24 | 0.24 | 0.28 |
| OR Quart 3 | 2.8 | 10 | 3.6 |
| OR Quart 4 | 1.0 | 1.0 | 1.2 |
| p Value | 1.0 | 1.0 | 0.75 |
| 95% CI of | 0.30 | 0.13 | 0.35 |
| OR Quart 4 | 3.3 | 7.6 | 4.3 |

Insulin-like growth factor-binding protein 5

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 13.1 | 0.422 | nd | nd | 2.58 | 0.488 |
| Average | 36.2 | 16.6 | nd | nd | 32.4 | 17.8 |
| Stdev | 47.9 | 29.9 | nd | nd | 46.8 | 31.3 |
| p (t-test) | | 0.041 | nd | nd | | 0.14 |
| Min | 0.204 | 0.204 | nd | nd | 0.204 | 0.204 |
| Max | 200 | 117 | nd | nd | 200 | 117 |
| n (Samp) | 108 | 28 | nd | nd | 97 | 25 |
| n (Patient) | 108 | 28 | nd | nd | 97 | 25 |

| | At Enrollment | | |
|---|---|---|---|
| | sCr or UO | sCr only | UO only |
| AUC | 0.36 | nd | 0.40 |
| SE | 0.062 | nd | 0.066 |
| p | 0.026 | nd | 0.12 |
| nCohort 1 | 108 | nd | 97 |
| nCohort 2 | 28 | nd | 25 |
| Cutoff 1 | 0.222 | nd | 0.222 |
| Sens 1 | 75% | nd | 72% |
| Spec 1 | 17% | nd | 19% |
| Cutoff 2 | 0.204 | nd | 0.204 |
| Sens 2 | 93% | nd | 92% |
| Spec 2 | 6% | nd | 6% |
| Cutoff 3 | 0.204 | nd | 0.204 |
| Sens 3 | 93% | nd | 92% |
| Spec 3 | 6% | nd | 6% |
| Cutoff 4 | 45.3 | nd | 40.1 |
| Sens 4 | 14% | nd | 16% |
| Spec 4 | 70% | nd | 70% |
| Cutoff 5 | 72.4 | nd | 65.5 |
| Sens 5 | 7% | nd | 8% |
| Spec 5 | 81% | nd | 80% |
| Cutoff 6 | 122 | nd | 98.6 |
| Sens 6 | 0% | nd | 4% |
| Spec 6 | 91% | nd | 91% |
| OR Quart 2 | 1.9 | nd | 2.1 |
| p Value | 0.33 | nd | 0.30 |
| 95% CI of | 0.51 | nd | 0.53 |
| OR Quart 2 | 7.4 | nd | 7.9 |
| OR Quart 3 | 1.6 | nd | 1.6 |
| p Value | 0.50 | nd | 0.49 |

-continued

| | | | |
|---|---|---|---|
| 95% CI of OR Quart 3 | 0.41 6.3 | nd nd | 0.41 6.4 |
| OR Quart 4 | 3.6 | nd | 2.5 |
| p Value | 0.048 | nd | 0.18 |
| 95% CI of OR Quart 4 | 1.0 13 | nd nd | 0.65 9.2 |

Immunoglogulin G4

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 410000 | 219000 | nd | nd | 407000 | 219000 |
| Average | 703000 | 405000 | nd | nd | 637000 | 405000 |
| Stdev | 888000 | 472000 | nd | nd | 737000 | 472000 |
| p (t-test) | | 0.18 | nd | nd | | 0.22 |
| Min | 16100 | 15700 | nd | nd | 16100 | 15700 |
| Max | 5190000 | 1390000 | nd | nd | 3700000 | 1390000 |
| n (Samp) | 81 | 17 | nd | nd | 74 | 17 |
| n (Patient) | 81 | 17 | nd | nd | 74 | 17 |

| | At Enrollment | | |
|---|---|---|---|
| | sCr or UO | sCr only | UO only |
| AUC | 0.37 | nd | 0.38 |
| SE | 0.078 | nd | 0.079 |
| p | 0.092 | nd | 0.12 |
| nCohort 1 | 81 | nd | 74 |
| nCohort 2 | 17 | nd | 17 |
| Cutoff 1 | 162000 | nd | 162000 |
| Sens 1 | 71% | nd | 71% |
| Spec 1 | 25% | nd | 26% |
| Cutoff 2 | 61100 | nd | 61100 |
| Sens 2 | 82% | nd | 82% |
| Spec 2 | 11% | nd | 11% |
| Cutoff 3 | 38600 | nd | 38600 |
| Sens 3 | 94% | nd | 94% |
| Spec 3 | 9% | nd | 8% |
| Cutoff 4 | 767000 | nd | 766000 |
| Sens 4 | 18% | nd | 18% |
| Spec 4 | 70% | nd | 70% |
| Cutoff 5 | 1020000 | nd | 995000 |
| Sens 5 | 18% | nd | 18% |
| Spec 5 | 80% | nd | 81% |
| Cutoff 6 | 1480000 | nd | 1280000 |
| Sens 6 | 0% | nd | 12% |
| Spec 6 | 90% | nd | 91% |
| OR Quart 2 | 0.67 | nd | 0.63 |
| p Value | 0.67 | nd | 0.64 |
| 95% CI of OR Quart 2 | 0.10 4.4 | nd nd | 0.096 4.2 |
| OR Quart 3 | 2.9 | nd | 2.9 |
| p Value | 0.17 | nd | 0.16 |
| 95% CI of OR Quart 3 | 0.64 13 | nd nd | 0.65 13 |
| OR Quart 4 | 1.9 | nd | 2.0 |
| p Value | 0.41 | nd | 0.40 |
| 95% CI of OR Quart 4 | 0.41 9.2 | nd nd | 0.41 9.4 |

Interleukin-21

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.531 | 1.03 | 0.783 | 1.24 | 0.806 | 1.11 |
| Average | 4.02 | 2.04 | 3.61 | 3.11 | 4.36 | 1.69 |
| Stdev | 14.5 | 3.20 | 13.2 | 5.09 | 15.2 | 2.12 |
| p (t-test) | | 0.49 | | 0.92 | | 0.41 |
| Min | 0.0102 | 0.0102 | 0.0102 | 0.0102 | 0.0102 | 0.0102 |
| Max | 132 | 14.3 | 132 | 14.3 | 132 | 8.25 |
| n (Samp) | 90 | 26 | 109 | 7 | 82 | 22 |
| n (Patient) | 90 | 26 | 109 | 7 | 82 | 22 |

-continued

|  | At Enrollment | | |
|---|---|---|---|
|  | sCr or UO | sCr only | UO only |
| AUC | 0.50 | 0.56 | 0.48 |
| SE | 0.065 | 0.12 | 0.070 |
| p | 0.97 | 0.59 | 0.79 |
| nCohort 1 | 90 | 109 | 82 |
| nCohort 2 | 26 | 7 | 22 |
| Cutoff 1 | 0.0182 | 0.632 | 0.0182 |
| Sens 1 | 73% | 71% | 73% |
| Spec 1 | 23% | 50% | 23% |
| Cutoff 2 | 0.0154 | 0.0922 | 0.0154 |
| Sens 2 | 81% | 86% | 82% |
| Spec 2 | 18% | 37% | 17% |
| Cutoff 3 | 0.0102 | 0.0102 | 0.0102 |
| Sens 3 | 92% | 100% | 91% |
| Spec 3 | 4% | 6% | 4% |
| Cutoff 4 | 2.38 | 2.03 | 2.46 |
| Sens 4 | 23% | 29% | 23% |
| Spec 4 | 70% | 71% | 72% |
| Cutoff 5 | 4.32 | 3.40 | 5.00 |
| Sens 5 | 12% | 29% | 9% |
| Spec 5 | 80% | 81% | 80% |
| Cutoff 6 | 7.58 | 7.58 | 8.25 |
| Sens 6 | 8% | 14% | 0% |
| Spec 6 | 90% | 91% | 90% |
| OR Quart 2 | 1.5 | 2.1 | 2.0 |
| p Value | 0.54 | 0.56 | 0.31 |
| 95% CI of | 0.43 | 0.18 | 0.51 |
| OR Quart 2 | 4.9 | 24 | 8.0 |
| OR Quart 3 | 0.80 | 2.1 | 1.3 |
| p Value | 0.74 | 0.56 | 0.71 |
| 95% CI of | 0.21 | 0.18 | 0.31 |
| OR Quart 3 | 3.0 | 24 | 5.6 |
| OR Quart 4 | 1.2 | 2.1 | 1.6 |
| p Value | 0.75 | 0.56 | 0.48 |
| 95% CI of | 0.35 | 0.18 | 0.41 |
| OR Quart 4 | 4.2 | 24 | 6.7 |

| Interleukin-23 | | | | | | |
|---|---|---|---|---|---|---|
|  | sCr or UO | | sCr only | | UO only | |
|  | Cohort 1 | Cohort 2 | Cohort 1 | Cohort 2 | Cohort 1 | Cohort 2 |
| Median | 0.886 | 86.1 | 1.05 | 633 | 1.10 | 51.4 |
| Average | 2790 | 1790 | 2470 | 4040 | 3040 | 1150 |
| Stdev | 15200 | 4450 | 13800 | 7510 | 15900 | 2500 |
| p (t-test) |  | 0.74 |  | 0.77 |  | 0.58 |
| Min | 0.257 | 0.257 | 0.257 | 0.257 | 0.257 | 0.603 |
| Max | 100000 | 20500 | 100000 | 20500 | 100000 | 9140 |
| n (Samp) | 89 | 26 | 108 | 7 | 81 | 22 |
| n (Patient) | 89 | 26 | 108 | 7 | 81 | 22 |

|  | At Enrollment | | |
|---|---|---|---|
|  | sCr or UO | sCr only | UO only |
| AUC | 0.65 | 0.73 | 0.64 |
| SE | 0.064 | 0.11 | 0.070 |
| p | 0.021 | 0.036 | 0.049 |
| nCohort 1 | 89 | 108 | 81 |
| nCohort 2 | 26 | 7 | 22 |
| Cutoff 1 | 0.603 | 72.6 | 0.603 |
| Sens 1 | 88% | 71% | 91% |
| Spec 1 | 30% | 69% | 28% |
| Cutoff 2 | 0.603 | 22.3 | 0.603 |
| Sens 2 | 88% | 86% | 91% |
| Spec 2 | 30% | 66% | 28% |
| Cutoff 3 | 0.257 | 0 | 0.603 |
| Sens 3 | 96% | 100% | 91% |
| Spec 3 | 21% | 0% | 28% |
| Cutoff 4 | 44.5 | 99.6 | 44.5 |
| Sens 4 | 54% | 57% | 50% |
| Spec 4 | 71% | 70% | 70% |
| Cutoff 5 | 306 | 306 | 306 |
| Sens 5 | 31% | 57% | 27% |
| Spec 5 | 81% | 81% | 80% |

-continued

| | | | |
|---|---|---|---|
| Cutoff 6 | 1230 | 1230 | 1040 |
| Sens 6 | 19% | 43% | 18% |
| Spec 6 | 91% | 91% | 90% |
| OR Quart 2 | 4.1 | 0 | 3.4 |
| p Value | 0.096 | na | 0.16 |
| 95% CI of | 0.78 | na | 0.62 |
| OR Quart 2 | 22 | na | 19 |
| OR Quart 3 | 3.4 | 2.0 | 2.7 |
| p Value | 0.16 | 0.58 | 0.26 |
| 95% CI of | 0.62 | 0.17 | 0.48 |
| OR Quart 3 | 18 | 23 | 16 |
| OR Quart 4 | 7.9 | 4.3 | 6.1 |
| p Value | 0.012 | 0.20 | 0.032 |
| 95% CI of | 1.6 | 0.45 | 1.2 |
| OR Quart 4 | 40 | 41 | 32 |

Interleukin-28A

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.265 | 0.230 | 0.195 | 2.92 | 0.195 | 0.195 |
| Average | 4.80 | 18.3 | 5.48 | 44.4 | 4.31 | 10.8 |
| Stdev | 11.6 | 47.5 | 12.7 | 86.6 | 11.2 | 18.5 |
| p (t-test) | | 0.015 | | 4.2E−5 | | 0.042 |
| Min | 0.0727 | 0.0727 | 0.0727 | 0.168 | 0.0727 | 0.0727 |
| Max | 71.6 | 235 | 71.6 | 235 | 71.6 | 62.9 |
| n (Samp) | 89 | 26 | 108 | 7 | 81 | 22 |
| n (Patient) | 89 | 26 | 108 | 7 | 81 | 22 |

At Enrollment

| | sCr or UO | sCr only | UO only |
|---|---|---|---|
| AUC | 0.54 | 0.73 | 0.52 |
| SE | 0.065 | 0.11 | 0.070 |
| p | 0.56 | 0.039 | 0.77 |
| nCohort 1 | 89 | 108 | 81 |
| nCohort 2 | 26 | 7 | 22 |
| Cutoff 1 | 0.0727 | 0.195 | 0.0727 |
| Sens 1 | 77% | 71% | 73% |
| Spec 1 | 13% | 51% | 15% |
| Cutoff 2 | 0 | 0.168 | 0 |
| Sens 2 | 100% | 86% | 100% |
| Spec 2 | 0% | 43% | 0% |
| Cutoff 3 | 0 | 0.148 | 0 |
| Sens 3 | 100% | 100% | 100% |
| Spec 3 | 0% | 35% | 0% |
| Cutoff 4 | 0.265 | 0.265 | 0.265 |
| Sens 4 | 38% | 57% | 36% |
| Spec 4 | 76% | 75% | 78% |
| Cutoff 5 | 6.95 | 9.20 | 3.84 |
| Sens 5 | 35% | 43% | 36% |
| Spec 5 | 82% | 81% | 80% |
| Cutoff 6 | 16.5 | 18.2 | 14.3 |
| Sens 6 | 19% | 29% | 23% |
| Spec 6 | 91% | 91% | 90% |
| OR Quart 2 | 0.78 | >2.1 | 0.75 |
| p Value | 0.70 | <0.56 | 0.68 |
| 95% CI of | 0.23 | >0.18 | 0.20 |
| OR Quart 2 | 2.7 | na | 2.9 |
| OR Quart 3 | 0.48 | >2.1 | 0.41 |
| p Value | 0.29 | <0.56 | 0.25 |
| 95% CI of | 0.12 | >0.18 | 0.091 |
| OR Quart 3 | 1.9 | na | 1.9 |
| OR Quart 4 | 1.3 | >3.2 | 1.4 |
| p Value | 0.61 | <0.32 | 0.59 |
| 95% CI of | 0.42 | >0.32 | 0.41 |
| OR Quart 4 | 4.3 | na | 4.9 |

Interleukin-33

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 0.0981 | 2.43 | 0.0981 | 12.5 | 0.0981 | 2.43 |
| Average | 233 | 89.3 | 202 | 181 | 255 | 64.5 |

-continued

| | | | | | | |
|---|---|---|---|---|---|---|
| Stdev | 1490 | 222 | 1360 | 326 | 1560 | 162 |
| p (t-test) | | 0.63 | | 0.97 | | 0.57 |
| Min | 0.0445 | 0.0455 | 0.0445 | 0.0455 | 0.0445 | 0.0543 |
| Max | 13500 | 892 | 13500 | 892 | 13500 | 730 |
| n (Samp) | 90 | 26 | 109 | 7 | 82 | 22 |
| n (Patient) | 90 | 26 | 109 | 7 | 82 | 22 |

| | At Enrollment | | |
|---|---|---|---|
| | sCr or UO | sCr only | UO only |
| AUC | 0.67 | 0.71 | 0.68 |
| SE | 0.064 | 0.11 | 0.069 |
| p | 0.0084 | 0.057 | 0.0097 |
| nCohort 1 | 90 | 109 | 82 |
| nCohort 2 | 26 | 7 | 22 |
| Cutoff 1 | 0.0981 | 2.03 | 0.0981 |
| Sens 1 | 73% | 71% | 73% |
| Spec 1 | 56% | 65% | 57% |
| Cutoff 2 | 0.0713 | 0.0981 | 0.0713 |
| Sens 2 | 81% | 86% | 82% |
| Spec 2 | 39% | 51% | 39% |
| Cutoff 3 | 0.0494 | 0.0445 | 0.0494 |
| Sens 3 | 96% | 100% | 100% |
| Spec 3 | 26% | 5% | 24% |
| Cutoff 4 | 2.20 | 7.15 | 2.20 |
| Sens 4 | 50% | 57% | 50% |
| Spec 4 | 70% | 72% | 71% |
| Cutoff 5 | 11.1 | 14.9 | 11.1 |
| Sens 5 | 35% | 43% | 32% |
| Spec 5 | 80% | 81% | 80% |
| Cutoff 6 | 41.6 | 65.9 | 41.6 |
| Sens 6 | 23% | 43% | 23% |
| Spec 6 | 90% | 91% | 90% |
| OR Quart 2 | 7.3 | 0 | 6.0 |
| p Value | 0.075 | na | 0.12 |
| 95% CI of | 0.82 | na | 0.64 |
| OR Quart 2 | 65 | na | 55 |
| OR Quart 3 | 15 | 2.1 | 13 |
| p Value | 0.014 | 0.56 | 0.019 |
| 95% CI of | 1.7 | 0.18 | 1.5 |
| OR Quart 3 | 120 | 24 | 110 |
| OR Quart 4 | 13 | 4.5 | 9.2 |
| p Value | 0.021 | 0.19 | 0.046 |
| 95% CI of | 1.5 | 0.47 | 1.0 |
| OR Quart 4 | 110 | 43 | 81 |

| Vascular endothelial growth factor receptor 2 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 7610 | 7540 | 7630 | 5950 | 7750 | 7990 |
| Average | 10700 | 8210 | 10300 | 8400 | 11000 | 8290 |
| Stdev | 17500 | 3210 | 16000 | 3790 | 18300 | 3100 |
| p (t-test) | | 0.47 | | 0.76 | | 0.49 |
| Min | 3730 | 3880 | 3730 | 5120 | 3730 | 3880 |
| Max | 166000 | 14800 | 166000 | 14300 | 166000 | 14800 |
| n (Samp) | 90 | 26 | 109 | 7 | 82 | 22 |
| n (Patient) | 90 | 26 | 109 | 7 | 82 | 22 |

| | At Enrollment | | |
|---|---|---|---|
| | sCr or UO | sCr only | UO only |
| AUC | 0.47 | 0.46 | 0.48 |
| SE | 0.065 | 0.12 | 0.070 |
| p | 0.66 | 0.71 | 0.81 |
| nCohort 1 | 90 | 109 | 82 |
| nCohort 2 | 26 | 7 | 22 |
| Cutoff 1 | 5750 | 5920 | 5750 |
| Sens 1 | 73% | 71% | 73% |
| Spec 1 | 18% | 21% | 16% |
| Cutoff 2 | 5180 | 5700 | 5180 |
| Sens 2 | 81% | 86% | 82% |
| Spec 2 | 10% | 19% | 9% |
| Cutoff 3 | 4850 | 5110 | 4850 |
| Sens 3 | 92% | 100% | 91% |

-continued

| | | | |
|---|---|---|---|
| Spec 3 | 8% | 11% | 6% |
| Cutoff 4 | 9390 | 9460 | 9430 |
| Sens 4 | 35% | 29% | 36% |
| Spec 4 | 70% | 71% | 71% |
| Cutoff 5 | 10600 | 10600 | 10600 |
| Sens 5 | 23% | 29% | 23% |
| Spec 5 | 80% | 81% | 80% |
| Cutoff 6 | 11300 | 11800 | 11800 |
| Sens 6 | 15% | 29% | 14% |
| Spec 6 | 90% | 91% | 90% |
| OR Quart 2 | 0.82 | 0.48 | 1.0 |
| p Value | 0.75 | 0.56 | 1.0 |
| 95% CI of OR Quart 2 | 0.24 | 0.041 | 0.28 |
| | 2.8 | 5.6 | 3.6 |
| OR Quart 3 | 0.23 | 0 | 0.28 |
| p Value | 0.087 | na | 0.14 |
| 95% CI of OR Quart 3 | 0.044 | na | 0.050 |
| | 1.2 | na | 1.5 |
| OR Quart 4 | 1.9 | 2.2 | 1.5 |
| p Value | 0.26 | 0.40 | 0.53 |
| 95% CI of OR Quart 4 | 0.62 | 0.36 | 0.43 |
| | 6.0 | 13 | 5.1 |

Neural cell adhesion molecule 1

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 187000 | 166000 | nd | nd | 182000 | 165000 |
| Average | 190000 | 163000 | nd | nd | 188000 | 158000 |
| Stdev | 69400 | 60900 | nd | nd | 64200 | 58500 |
| p (t-test) | | 0.069 | nd | nd | | 0.040 |
| Min | 69000 | 77400 | nd | nd | 69000 | 77400 |
| Max | 494000 | 331000 | nd | nd | 461000 | 331000 |
| n (Samp) | 109 | 28 | nd | nd | 98 | 25 |
| n (Patient) | 109 | 28 | nd | nd | 98 | 25 |

| | At Enrollment | | |
|---|---|---|---|
| | sCr or UO | sCr only | UO only |
| AUC | 0.38 | nd | 0.35 |
| SE | 0.062 | nd | 0.065 |
| p | 0.044 | nd | 0.021 |
| nCohort 1 | 109 | nd | 98 |
| nCohort 2 | 28 | nd | 25 |
| Cutoff 1 | 114000 | nd | 111000 |
| Sens 1 | 71% | nd | 72% |
| Spec 1 | 13% | nd | 11% |
| Cutoff 2 | 101000 | nd | 101000 |
| Sens 2 | 82% | nd | 80% |
| Spec 2 | 9% | nd | 9% |
| Cutoff 3 | 82600 | nd | 82600 |
| Sens 3 | 93% | nd | 92% |
| Spec 3 | 6% | nd | 5% |
| Cutoff 4 | 216000 | nd | 220000 |
| Sens 4 | 18% | nd | 12% |
| Spec 4 | 71% | nd | 70% |
| Cutoff 5 | 229000 | nd | 230000 |
| Sens 5 | 14% | nd | 8% |
| Spec 5 | 81% | nd | 81% |
| Cutoff 6 | 272000 | nd | 268000 |
| Sens 6 | 4% | nd | 4% |
| Spec 6 | 91% | nd | 91% |
| OR Quart 2 | 1.0 | nd | 1.8 |
| p Value | 0.96 | nd | 0.45 |
| 95% CI of OR Quart 2 | 0.27 | nd | 0.39 |
| | 4.0 | nd | 8.3 |
| OR Quart 3 | 1.8 | nd | 3.2 |
| p Value | 0.33 | nd | 0.11 |
| 95% CI of OR Quart 3 | 0.54 | nd | 0.77 |
| | 6.3 | nd | 14 |
| OR Quart 4 | 2.5 | nd | 4.0 |
| p Value | 0.13 | nd | 0.056 |
| 95% CI of OR Quart 4 | 0.75 | nd | 0.96 |
| | 8.3 | nd | 17 |

-continued

| Platelet-derived growth factor subunit B (dimer) | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 378 | 332 | nd | nd | 337 | 360 |
| Average | 404 | 362 | nd | nd | 380 | 379 |
| Stdev | 251 | 213 | nd | nd | 237 | 221 |
| p (t-test) | | 0.43 | nd | nd | | 0.99 |
| Min | 0.189 | 35.4 | nd | nd | 0.189 | 35.4 |
| Max | 1310 | 766 | nd | nd | 969 | 766 |
| n (Samp) | 104 | 26 | nd | nd | 93 | 23 |
| n (Patient) | 104 | 26 | nd | nd | 93 | 23 |

| | At Enrollment | | |
|---|---|---|---|
| | sCr or UO | sCr only | UO only |
| AUC | 0.46 | nd | 0.51 |
| SE | 0.064 | nd | 0.068 |
| p | 0.54 | nd | 0.89 |
| nCohort 1 | 104 | nd | 93 |
| nCohort 2 | 26 | nd | 23 |
| Cutoff 1 | 202 | nd | 202 |
| Sens 1 | 73% | nd | 74% |
| Spec 1 | 26% | nd | 29% |
| Cutoff 2 | 177 | nd | 155 |
| Sens 2 | 81% | nd | 83% |
| Spec 2 | 22% | nd | 20% |
| Cutoff 3 | 113 | nd | 113 |
| Sens 3 | 92% | nd | 91% |
| Spec 3 | 12% | nd | 14% |
| Cutoff 4 | 527 | nd | 504 |
| Sens 4 | 23% | nd | 30% |
| Spec 4 | 70% | nd | 71% |
| Cutoff 5 | 613 | nd | 575 |
| Sens 5 | 15% | nd | 22% |
| Spec 5 | 81% | nd | 81% |
| Cutoff 6 | 732 | nd | 716 |
| Sens 6 | 8% | nd | 9% |
| Spec 6 | 90% | nd | 90% |
| OR Quart 2 | 0.83 | nd | 0.80 |
| p Value | 0.78 | nd | 0.74 |
| 95% CI of | 0.23 | nd | 0.21 |
| OR Quart 2 | 3.1 | nd | 3.0 |
| OR Quart 3 | 1.7 | nd | 1.0 |
| p Value | 0.38 | nd | 1.0 |
| 95% CI of | 0.52 | nd | 0.28 |
| OR Quart 3 | 5.4 | nd | 3.6 |
| OR Quart 4 | 1.0 | nd | 1.0 |
| p Value | 0.95 | nd | 1.0 |
| 95% CI of | 0.30 | nd | 0.28 |
| OR Quart 4 | 3.6 | nd | 3.6 |

| Corticotropin | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.000700 | 0.00350 | nd | nd | 0.000709 | 0.00277 |
| Average | 0.00668 | 0.00992 | nd | nd | 0.00765 | 0.0108 |
| Stdev | 0.0334 | 0.0200 | nd | nd | 0.0360 | 0.0217 |
| p (t-test) | | 0.68 | nd | nd | | 0.73 |
| Min | 3.38E-6 | 3.38E-6 | nd | nd | 3.38E-6 | 3.38E-6 |
| Max | 0.292 | 0.0908 | nd | nd | 0.292 | 0.0908 |
| n (Samp) | 78 | 20 | nd | nd | 67 | 17 |
| n (Patient) | 78 | 20 | nd | nd | 67 | 17 |

| | At Enrollment | | |
|---|---|---|---|
| | sCr or UO | sCr only | UO only |
| AUC | 0.70 | nd | 0.67 |
| SE | 0.071 | nd | 0.078 |
| p | 0.0042 | nd | 0.035 |
| nCohort 1 | 78 | nd | 67 |
| nCohort 2 | 20 | nd | 17 |

-continued

| | | | |
|---|---|---|---|
| Cutoff 1 | 0.00208 | nd | 0.000539 |
| Sens 1 | 70% | nd | 71% |
| Spec 1 | 71% | nd | 46% |
| Cutoff 2 | 0.000278 | nd | 0.000278 |
| Sens 2 | 90% | nd | 88% |
| Spec 2 | 40% | nd | 39% |
| Cutoff 3 | 0.000278 | nd | 3.38E−6 |
| Sens 3 | 90% | nd | 94% |
| Spec 3 | 40% | nd | 6% |
| Cutoff 4 | 0.00208 | nd | 0.00229 |
| Sens 4 | 70% | nd | 59% |
| Spec 4 | 71% | nd | 70% |
| Cutoff 5 | 0.00381 | nd | 0.00423 |
| Sens 5 | 45% | nd | 47% |
| Spec 5 | 81% | nd | 81% |
| Cutoff 6 | 0.00772 | nd | 0.00914 |
| Sens 6 | 40% | nd | 29% |
| Spec 6 | 91% | nd | 91% |
| OR Quart 2 | 2.1 | nd | 2.2 |
| p Value | 0.42 | nd | 0.39 |
| 95% CI of | 0.35 | nd | 0.36 |
| OR Quart 2 | 13 | nd | 14 |
| OR Quart 3 | 2.9 | nd | 1.6 |
| p Value | 0.23 | nd | 0.64 |
| 95% CI of | 0.50 | nd | 0.24 |
| OR Quart 3 | 17 | nd | 11 |
| OR Quart 4 | 6.2 | nd | 5.8 |
| p Value | 0.032 | nd | 0.042 |
| 95% CI of | 1.2 | nd | 1.1 |
| OR Quart 4 | 33 | nd | 32 |

| Thyroxine-binding globulin | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 34.2 | 30.0 | 33.7 | 28.5 | 33.6 | 30.0 |
| Average | 36.0 | 31.7 | 35.4 | 29.6 | 34.9 | 31.6 |
| Stdev | 10.5 | 11.5 | 10.9 | 7.07 | 10.0 | 11.9 |
| p (t-test) | | 0.032 | | 0.12 | | 0.13 |
| Min | 13.5 | 14.2 | 13.5 | 22.3 | 13.5 | 14.2 |
| Max | 74.3 | 59.5 | 74.3 | 42.5 | 74.3 | 59.5 |
| n (Samp) | 140 | 36 | 166 | 9 | 112 | 31 |
| n (Patient) | 140 | 36 | 166 | 9 | 112 | 31 |

| At Enrollment | | | |
|---|---|---|---|
| | sCr or UO | sCr only | UO only |
| AUC | 0.37 | 0.32 | 0.39 |
| SE | 0.054 | 0.10 | 0.059 |
| p | 0.016 | 0.072 | 0.056 |
| nCohort 1 | 140 | 166 | 112 |
| nCohort 2 | 36 | 9 | 31 |
| Cutoff 1 | 23.9 | 23.3 | 25.7 |
| Sens 1 | 72% | 78% | 71% |
| Spec 1 | 11% | 11% | 14% |
| Cutoff 2 | 21.4 | 22.3 | 19.8 |
| Sens 2 | 81% | 89% | 81% |
| Spec 2 | 6% | 10% | 6% |
| Cutoff 3 | 16.3 | 21.4 | 16.3 |
| Sens 3 | 92% | 100% | 90% |
| Spec 3 | 4% | 10% | 4% |
| Cutoff 4 | 41.5 | 40.9 | 40.0 |
| Sens 4 | 17% | 11% | 23% |
| Spec 4 | 71% | 70% | 71% |
| Cutoff 5 | 44.9 | 44.9 | 43.4 |
| Sens 5 | 14% | 0% | 16% |
| Spec 5 | 80% | 80% | 80% |
| Cutoff 6 | 49.5 | 50.0 | 48.3 |
| Sens 6 | 11% | 0% | 16% |
| Spec 6 | 90% | 90% | 90% |
| OR Quart 2 | 1.0 | 1.0 | 1.0 |
| p Value | 1.0 | 1.0 | 1.0 |
| 95% CI of | 0.30 | 0.061 | 0.26 |
| OR Quart 2 | 3.4 | 17 | 3.8 |
| OR Quart 3 | 1.6 | 4.3 | 2.4 |
| p Value | 0.40 | 0.20 | 0.15 |

-continued

|  | sCr or UO | sCr only | UO only |
|---|---|---|---|
| 95% CI of OR Quart 3 | 0.53 | 0.46 | 0.72 |
|  | 5.0 | 40 | 7.9 |
| OR Quart 4 | 3.3 | 3.2 | 2.8 |
| p Value | 0.029 | 0.32 | 0.084 |
| 95% CI of OR Quart 4 | 1.1 | 0.32 | 0.87 |
|  | 9.5 | 32 | 9.3 |

Pigment epithelium-derived factor

|  | sCr or UO | | sCr only | | UO only | |
|---|---|---|---|---|---|---|
|  | Cohort 1 | Cohort 2 | Cohort 1 | Cohort 2 | Cohort 1 | Cohort 2 |
| Median | 1500 | 1260 | nd | nd | 1490 | 1250 |
| Average | 1690 | 1790 | nd | nd | 1680 | 1760 |
| Stdev | 869 | 1370 | nd | nd | 896 | 1420 |
| p (t-test) |  | 0.64 | nd | nd |  | 0.74 |
| Min | 84.2 | 339 | nd | nd | 84.2 | 339 |
| Max | 4510 | 6200 | nd | nd | 4510 | 6200 |
| n (Samp) | 109 | 28 | nd | nd | 98 | 25 |
| n (Patient) | 109 | 28 | nd | nd | 98 | 25 |

At Enrollment

|  | sCr or UO | sCr only | UO only |
|---|---|---|---|
| AUC | 0.45 | nd | 0.44 |
| SE | 0.062 | nd | 0.066 |
| p | 0.41 | nd | 0.33 |
| nCohort 1 | 109 | nd | 98 |
| nCohort 2 | 28 | nd | 25 |
| Cutoff 1 | 1030 | nd | 1030 |
| Sens 1 | 71% | nd | 72% |
| Spec 1 | 19% | nd | 21% |
| Cutoff 2 | 813 | nd | 950 |
| Sens 2 | 82% | nd | 80% |
| Spec 2 | 10% | nd | 17% |
| Cutoff 3 | 460 | nd | 460 |
| Sens 3 | 93% | nd | 92% |
| Spec 3 | 3% | nd | 3% |
| Cutoff 4 | 1800 | nd | 1770 |
| Sens 4 | 36% | nd | 32% |
| Spec 4 | 71% | nd | 70% |
| Cutoff 5 | 2350 | nd | 2350 |
| Sens 5 | 25% | nd | 20% |
| Spec 5 | 81% | nd | 81% |
| Cutoff 6 | 2870 | nd | 3150 |
| Sens 6 | 14% | nd | 16% |
| Spec 6 | 91% | nd | 91% |
| OR Quart 2 | 0.21 | nd | 0.29 |
| p Value | 0.062 | nd | 0.15 |
| 95% CI of OR Quart 2 | 0.041 | nd | 0.053 |
|  | 1.1 | nd | 1.6 |
| OR Quart 3 | 1.2 | nd | 1.7 |
| p Value | 0.73 | nd | 0.38 |
| 95% CI of OR Quart 3 | 0.41 | nd | 0.52 |
|  | 3.6 | nd | 5.6 |
| OR Quart 4 | 1.2 | nd | 1.5 |
| p Value | 0.73 | nd | 0.50 |
| 95% CI of OR Quart 4 | 0.41 | nd | 0.45 |
|  | 3.6 | nd | 5.0 |

Tumor necrosis factor receptor superfamily member 8

|  | sCr or UO | | sCr only | | UO only | |
|---|---|---|---|---|---|---|
|  | Cohort 1 | Cohort 2 | Cohort 1 | Cohort 2 | Cohort 1 | Cohort 2 |
| Median | 100.0 | 95.1 | 96.5 | 110 | 100.0 | 95.1 |
| Average | 199 | 149 | 192 | 126 | 204 | 152 |
| Stdev | 378 | 136 | 349 | 79.2 | 393 | 143 |
| p (t-test) |  | 0.51 |  | 0.62 |  | 0.55 |
| Min | 12.8 | 36.8 | 12.8 | 54.3 | 12.8 | 36.8 |
| Max | 2700 | 595 | 2700 | 288 | 2700 | 595 |
| n (Samp) | 90 | 26 | 109 | 7 | 82 | 22 |
| n (Patient) | 90 | 26 | 109 | 7 | 82 | 22 |

-continued

|  | At Enrollment | | |
|---|---|---|---|
|  | sCr or UO | sCr only | UO only |
| AUC | 0.51 | 0.53 | 0.51 |
| SE | 0.065 | 0.11 | 0.070 |
| p | 0.87 | 0.81 | 0.86 |
| nCohort 1 | 90 | 109 | 82 |
| nCohort 2 | 26 | 7 | 22 |
| Cutoff 1 | 56.6 | 96.5 | 56.6 |
| Sens 1 | 73% | 71% | 73% |
| Spec 1 | 23% | 50% | 23% |
| Cutoff 2 | 54.3 | 59.2 | 53.7 |
| Sens 2 | 85% | 86% | 86% |
| Spec 2 | 21% | 26% | 21% |
| Cutoff 3 | 37.8 | 53.7 | 37.8 |
| Sens 3 | 92% | 100% | 91% |
| Spec 3 | 14% | 20% | 13% |
| Cutoff 4 | 149 | 156 | 150 |
| Sens 4 | 38% | 14% | 41% |
| Spec 4 | 70% | 71% | 71% |
| Cutoff 5 | 203 | 205 | 203 |
| Sens 5 | 19% | 14% | 18% |
| Spec 5 | 80% | 82% | 80% |
| Cutoff 6 | 277 | 305 | 277 |
| Sens 6 | 15% | 0% | 14% |
| Spec 6 | 90% | 91% | 90% |
| OR Quart 2 | 0.68 | 2.1 | 0.65 |
| p Value | 0.54 | 0.56 | 0.51 |
| 95% CI of | 0.20 | 0.18 | 0.18 |
| OR Quart 2 | 2.3 | 24 | 2.4 |
| OR Quart 3 | 0.68 | 3.2 | 0.65 |
| p Value | 0.54 | 0.32 | 0.51 |
| 95% CI of | 0.20 | 0.32 | 0.18 |
| OR Quart 3 | 2.3 | 33 | 2.4 |
| OR Quart 4 | 0.68 | 1.0 | 0.65 |
| p Value | 0.54 | 1.0 | 0.51 |
| 95% CI of | 0.20 | 0.060 | 0.18 |
| OR Quart 4 | 2.3 | 17 | 2.4 |

| | Alpha-fetoprotein | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 0.316 | 0.438 | nd | nd | 0.317 | 0.438 |
| Average | 0.321 | 0.467 | nd | nd | 0.326 | 0.430 |
| Stdev | 0.281 | 0.409 | nd | nd | 0.306 | 0.396 |
| p (t-test) | | 0.028 | nd | nd | | 0.16 |
| Min | 0.00580 | 0.00580 | nd | nd | 0.00580 | 0.00580 |
| Max | 1.39 | 1.53 | nd | nd | 1.39 | 1.53 |
| n (Samp) | 109 | 28 | nd | nd | 98 | 25 |
| n (Patient) | 109 | 28 | nd | nd | 98 | 25 |

|  | At Enrollment | | |
|---|---|---|---|
|  | sCr or UO | sCr only | UO only |
| AUC | 0.62 | nd | 0.60 |
| SE | 0.062 | nd | 0.066 |
| p | 0.046 | nd | 0.14 |
| nCohort 1 | 109 | nd | 98 |
| nCohort 2 | 28 | nd | 25 |
| Cutoff 1 | 0.225 | nd | 0.00580 |
| Sens 1 | 71% | nd | 92% |
| Spec 1 | 39% | nd | 19% |
| Cutoff 2 | 0.00580 | nd | 0.00580 |
| Sens 2 | 93% | nd | 92% |
| Spec 2 | 17% | nd | 19% |
| Cutoff 3 | 0.00580 | nd | 0.00580 |
| Sens 3 | 93% | nd | 92% |
| Spec 3 | 17% | nd | 19% |
| Cutoff 4 | 0.438 | nd | 0.438 |
| Sens 4 | 46% | nd | 44% |
| Spec 4 | 71% | nd | 70% |
| Cutoff 5 | 0.544 | nd | 0.550 |
| Sens 5 | 39% | nd | 32% |
| Spec 5 | 81% | nd | 81% |

-continued

|  | | | | |
|---|---|---|---|---|
| Cutoff 6 | 0.663 | nd | 0.687 |
| Sens 6 | 25% | nd | 24% |
| Spec 6 | 91% | nd | 91% |
| OR Quart 2 | 0.62 | nd | 2.6 |
| p Value | 0.50 | nd | 0.20 |
| 95% CI of | 0.16 | nd | 0.61 |
| OR Quart 2 | 2.4 | nd | 11 |
| OR Quart 3 | 1.2 | nd | 2.2 |
| p Value | 0.76 | nd | 0.31 |
| 95% CI of | 0.36 | nd | 0.49 |
| OR Quart 3 | 4.1 | nd | 9.6 |
| OR Quart 4 | 2.1 | nd | 3.7 |
| p Value | 0.19 | nd | 0.073 |
| 95% CI of | 0.69 | nd | 0.89 |
| OR Quart 4 | 6.7 | nd | 15 |

| Apolipoprotein(a) | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 55700 | 18600 | nd | nd | 54000 | 17200 |
| Average | 77500 | 43100 | nd | nd | 77800 | 43100 |
| Stdev | 85500 | 62700 | nd | nd | 87900 | 63800 |
| p (t-test) | | 0.037 | nd | nd | | 0.044 |
| Min | 58.7 | 968 | nd | nd | 128 | 968 |
| Max | 411000 | 314000 | nd | nd | 411000 | 314000 |
| n (Samp) | 132 | 31 | nd | nd | 117 | 30 |
| n (Patient) | 132 | 31 | nd | nd | 117 | 30 |

| At Enrollment | | | |
|---|---|---|---|
| | sCr or UO | sCr only | UO only |
| AUC | 0.35 | nd | 0.35 |
| SE | 0.058 | nd | 0.059 |
| p | 0.011 | nd | 0.010 |
| nCohort 1 | 132 | nd | 117 |
| nCohort 2 | 31 | nd | 30 |
| Cutoff 1 | 5630 | nd | 5630 |
| Sens 1 | 71% | nd | 70% |
| Spec 1 | 15% | nd | 15% |
| Cutoff 2 | 4320 | nd | 4320 |
| Sens 2 | 81% | nd | 80% |
| Spec 2 | 11% | nd | 10% |
| Cutoff 3 | 2710 | nd | 2710 |
| Sens 3 | 90% | nd | 90% |
| Spec 3 | 7% | nd | 5% |
| Cutoff 4 | 92400 | nd | 91700 |
| Sens 4 | 16% | nd | 17% |
| Spec 4 | 70% | nd | 70% |
| Cutoff 5 | 112000 | nd | 109000 |
| Sens 5 | 13% | nd | 13% |
| Spec 5 | 80% | nd | 80% |
| Cutoff 6 | 210000 | nd | 227000 |
| Sens 6 | 3% | nd | 3% |
| Spec 6 | 90% | nd | 91% |
| OR Quart 2 | 0.78 | nd | 0.78 |
| p Value | 0.72 | nd | 0.72 |
| 95% CI of | 0.19 | nd | 0.19 |
| OR Quart 2 | 3.1 | nd | 3.2 |
| OR Quart 3 | 2.3 | nd | 2.1 |
| p Value | 0.16 | nd | 0.24 |
| 95% CI of | 0.72 | nd | 0.62 |
| OR Quart 3 | 7.5 | nd | 6.9 |
| OR Quart 4 | 3.1 | nd | 3.2 |
| p Value | 0.056 | nd | 0.051 |
| 95% CI of | 0.97 | nd | 0.99 |
| OR Quart 4 | 9.8 | nd | 10 |

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for evaluating renal status in a subject, comprising:
   (a) performing an assay configured to detect Insulin-like growth factor-binding protein 4 by introducing a body fluid sample obtained from the subject into an assay instrument which (i) contacts all or a portion of the body fluid sample with a binding reagent which specifically binds for detection Insulin-like growth factor-binding protein 4, and (ii) generates one or more assay results indicative of binding of Insulin-like growth factor-binding protein 4 to its binding reagent;
   (b) correlating the assay result(s) to an increased risk of the subject having a RIFLE stage R, I, or F acute kidney injury within 72 hours of the time at which the body fluid sample is obtained when the assay result(s) is above a predetermined threshold; and
   (c) treating the subject determined to be at risk of a RIFLE stage R, I, or F acute kidney injury by one or more of initiating renal replacement therapy, withdrawing delivery of compounds that are known to be damaging to the kidney, delaying procedures that are known to be damaging to the kidney, performing kidney transplant, and modifying diuretic administration.

2. The method according to claim 1, wherein the assay result comprises a measured concentration of Insulin-like growth factor-binding protein 4.

3. The method according to claim 1, wherein a plurality of assay results, one of which is from the assay configured to detect Insulin-like growth factor-binding protein 4, are combined using a function that converts the plurality of assay results into a single composite result.

4. The method according to claim 1, wherein the subject:
   (a) has one or more known risk factors for prerenal, intrinsic renal, or postrenal acute kidney injury;
   (b) has been diagnosed with one or more of congestive heart failure, preeclampsia, eclampsia, diabetes mellitus, hypertension, coronary artery disease, proteinuria, renal insufficiency, glomerular filtration below the normal range, cirrhosis, serum creatinine above the normal range, sepsis, injury to renal function, and reduced renal function;
   (c) has undergone major vascular surgery, coronary artery bypass, or other cardiac surgery; or
   (d) has been exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin.

5. The method according to claim 1, wherein said method further comprises assigning a risk of the future occurrence or nonoccurrence of reduced renal function in said subject.

6. The method according to claim 1, wherein said method further comprises assigning a risk of the future occurrence or nonoccurrence of a need for dialysis in said subject.

7. The method according to claim 1, wherein said method comprises assigning a risk of the future occurrence or nonoccurrence of RIFLE stage F acute kidney injury in said subject.

8. The method according to claim 1, wherein said method further comprises assigning a risk of the future occurrence or nonoccurrence of a need for renal replacement therapy in said subject.

9. The method according to claim 1, wherein said method further comprises assigning a risk of the future occurrence or nonoccurrence of a need for renal transplantation in said subject.

10. The method according to claim 1, wherein the subject is in RIFLE stage 0 or R.

11. The method of claim 1, wherein the subject is in RIFLE stage I.

12. The method of claim 1, wherein the subject is in RIFLE stage R.

13. The method of claim 1, comprising correlating the assay result(s) to an increased risk of the subject having a RIFLE stage F acute kidney injury within 72 hours of the time at which the body fluid sample is obtained from the subject when the assay result(s) is above a predetermined threshold.

14. The method of claim 1, comprising correlating the assay result(s) to an increased risk of the subject having a RIFLE stage I acute kidney injury within 72 hours of the time at which the body fluid sample is obtained from the subject when the assay result(s) is above a predetermined threshold.

15. The method of claim 1, comprising correlating the assay result(s) to an increased risk of the subject having a RIFLE stage R acute kidney injury within 72 hours of the time at which the body fluid sample is obtained from the subject when the assay result(s) is above a predetermined threshold.

16. The method of claim 1, further comprising correlating the assay result(s) to an increased risk of the subject having a RIFLE stage R, I, or F acute kidney injury within 48 hours of the time at which the body fluid sample is obtained from the subject when the assay result(s) is above a predetermined threshold.

17. The method of claim 1, further comprising correlating the assay result(s) to an increased risk of the subject having a RIFLE stage R, I, or F acute kidney injury within 24 hours of the time at which the body fluid sample is obtained from the subject when the assay result(s) is above a predetermined threshold.

18. The method of claim 1, wherein the body fluid sample is a urine sample.

19. A method of detecting insulin-like growth factor-binding protein 4 comprising:
    (a) obtaining a urine sample from a human subject having a RIFLE R acute kidney injury or a RIFLE I acute kidney injury; and
    (b) detecting a level of insulin-like growth factor-binding protein 4 in the urine sample.

* * * * *